United States Patent [19]

Hatanaka et al.

[11] Patent Number: 4,973,354
[45] Date of Patent: Nov. 27, 1990

[54] PYRIMIDINE DERIVATIVES AND HERBICIDE CONTAINING THE SAME

[75] Inventors: Masataka Hatanaka; Junichi Watanabe; Yasuo Kondo, all of Funabashi; Koichi Suzuki, Saitama; Tsutomu Nawamaki, Saitama; Shigeomi Watanabe, Saitama, all of Japan

[73] Assignee: Nissan Chemical Industries, Ltd., Tokyo, Japan

[21] Appl. No.: 442,318

[22] Filed: Nov. 28, 1989

[30] Foreign Application Priority Data

Dec. 1, 1988 [JP] Japan ................................. 63-304450
Jul. 21, 1989 [JP] Japan ................................. 1-190306

[51] Int. Cl.$^5$ .................. A01N 43/54; C07D 239/34; C07D 239/38; C07D 239/42
[52] U.S. Cl. ......................................... 71/92; 544/299; 544/302; 544/309; 544/313; 544/314; 544/315; 544/318
[58] Field of Search ............... 544/299, 302, 309, 313, 544/314, 315, 318; 71/92

[56] References Cited

U.S. PATENT DOCUMENTS 3,974,276  8/1976  Barlow et al. ........................ 71/92
4,427,437  1/1984  Serban et al. ........................ 71/92

OTHER PUBLICATIONS

Serban et al., Chem. Abst., 92-175773f.

*Primary Examiner*—Cecilia Shen
*Attorney, Agent, or Firm*—Oliff & Berridge

[57] ABSTRACT

Disclosed are pyrimidine derivatives of the formula (I) and optical isomers thereof and a herbicide containing one or more of them as an active ingredient.

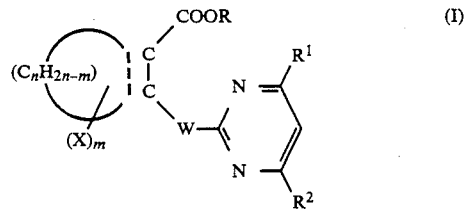

where W is O or S; X is a lower alkyl group or a lower alkoxycarbonyl group; R is H, an optionally substituted lower alkyl group, an optionally substituted lower alkenyl group, an optionally substituted lower alkynyl group, an alkyali metal, an alkaline earth metal or an optionally substituted ammonium cation; $R^1$ and $R^2$ each are a halogen atom, an optionally substituted lower alkyl group or an optionally substituted lower alkoxy group; n is 3 to 5; m is 0 to 2; and $\mathrel{\vcenter{\hbox{---}}}$ is a single bond or a double bond.

2 Claims, No Drawings

PYRIMIDINE DERIVATIVES AND HERBICIDE CONTAINING THE SAME

BACKGROUND OF THE INVENTION

1. Field of the Invention

The present invention relates to novel pyrimidine derivatives and optical isomers thereof as well as to a herbicide containing one or more of the said derivatives as an active ingredient.

2. Description of the Prior Art

Hitherto, it is generally said that the economic cost in the use of a herbicide depends upon the necessary amount of the active ingredient in the herbicide to be applied to a unit area, and therefore, development of a novel herbicide which displays a sufficient herbicidal effect even in a small amount to be used is desired.

It is known that some conventional herbicides would often have a bad influence on crops when applied thereto. Accordingly, studies have been effected for a long period of time for the purpose of obtaining compounds which may display a high herbicidal effect even in a small amount to be used and which may also display a high selectivity between the crops to be protected and the harmful weeds to be destroyed.

For instance, Japanese Patent Laid open No. 54-55729 illustrates a herbicide containing a pyrimidine nucleus-having compound as an active ingredient.

SUMMARY OF THE INVENTION

The present inventors have studied for many years and, as a result, have found that the pyrimidine derivatives of the formula (I) (mentioned below) of the present invention as well as the optical isomers thereof have an extremely higher herbicidal activity than any other known herbicides and additionally have found that some of the pyrimidine derivatives and the optical isomers thereof of the present invention have a selectivity to crops of rice, corn, wheat, soybean, cotton, beet, etc. and therefore are practically useful and that they have an excellent herbicidal activity to harmful weeds of *Echinochoa crus galli, Digitaria adscendens, Cyperus microiria, Solanum nigrum, Galinsoga ciliate, Rorippa indica, Scirpus juncoides, Monochoria vagnalis, Rotala indica, Sagittaria pygmaca*, etc. Accordingly, the inventors have achieved the present invention on the basis of such finding Specifically, where the pyrimidine derivatives and the optical isomers thereof of the present invention are employed as the active ingredient of a herbicide, the amount of the active ingredient to be applied to a unit area may be extremely reduced, as compared with the case of using known herbicidal compounds. Accordingly, the chemical injury of the herbicide of the present invention to crops is extremely smaller than that of the known herbicides; and the economic effect in the use of the herbicide of the present invention is extremely large.

Further, the pyrimidine derivatives and the optical isomers thereof of the present invention are helpful for noticeably reducing the danger of environmental pollution to be caused by application of a large amount of the herbicide to farming lands. In addition, the herbicide containing such derivatives or isomers thereof of the present invention is an epochal herbicide, as it does not remain in the soil and does not have any bad influence on the crops.

Precisely, the present invention provides pyrimidine derivatives of a general formula (I):

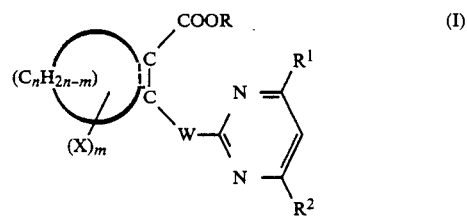

where

W represents an oxygen atom or a sulfur atom;

X represents a lower alkyl group or a lower alkoxycarbonyl group;

R represents a hydrogen atom; a lower alkyl group optionally substituted by substituent(s) selected from a halogen atom, a lower alkoxy group or a lower alkylthio group, or a phenyl group optionally substituted by a halogen atom, a lower alkyl group, a lower alkoxy group or a lower alkylthio group; a lower alkenyl group optionally substituted by substituent(s) selected from a halogen atom, a lower alkoxy group or a lower alkylthio group, or a phenyl group optionally substituted by a halogen aotm, a lower alkyl group, a lower alkoxy group or a lower alkylthio group; a lower alkynyl group optionally substituted by substituent(s) selected from a halogen atom, a lower alkoxy group or a lower alkylthio group, or a phenyl group optionally substituted by a halogen atom, a lower alkyl group, a lower alkoxy group or a lower alkylthio group; an alkali metal; an alkaline earth metal; or an optionally substituted ammonium cation;

$R_1$ and $R_2$ may be same or different and each represents a halogen atom; a lower alkyl group optionally substituted by substituent(s) selected from a halogen atom, a lower alkoxy group or a lower alkylthio group; or a lower alkoxy group optionally substituted by substituent(s) selected from a halogen atom, a lower alkoxy group or a lower alkylthio group;

n represents an integer of from 3 to 5;

m represents an integer of from 0 to 2; and

=== represents a single bond or a double bond;

as well as optical isomers of the said derivatives.

The present invention further provides a herbicide containing one or more of the pyrimidine derivatives and the optical isomers thereof as the active ingredient.

The pyrimidine derivatives and the optical isomers thereof of the present invention are novel compounds which are unknown up to the present and these have an excellent herbicidal acitivity and are useful as a herbicide

BRIEF DESCRIPTION OF THE INVENTION

The pyrimidine derivatives of the formula (I) and the optical isomers thereof of the present invention can be prepared by reacting a cyclic alcohol or cyclic thioalcohol of a general formula (II):

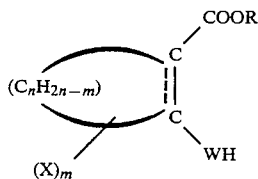

where W, X, R, n, m and ≡≡≡ have the same meanings as defined above, with a pyrimidine compound of a general formula (III)

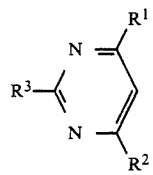

where

R$_3$ represents a halogen atom, an alkylsulfonyl group or an optionally substituted benzylsulfonyl group; and R$_1$ and R$_2$ have the same meanings as defined above, in any desired proportion. Preferably, one mol of the cyclic alochol or cyclic thioalcohol of the formula (II) is blended with one mol of the pyrimidine compound of the formula (III) and these are reacted in a solvent optionally in the presence of a base.

Where the cyclic alcohol or cyclic thioalcohol of the formula (II) has a double bond, it may be in the form of a ketoenol tautomer.

As the solvent usable in the reaction, there are mentioned, for example, hydrocarbon solvents such as benzene, toluene or xylene; halogenated hydrocarbon solvents such as methylene chloride or chloroform; alcohol solvents such as methyl alcohol, ethyl alcohol or isopropyl alcohol; ether solvents such as diethyl ether, diisopropyl ether, tetrahydrofuran or 1,4-dioxane; ketone solvents such as acetone or methyl ethyl ketone; ester solvents such as methyl acetate or ethyl acetate; aprotonic solvents such as dimethylformamide, dimethylacetamide or dimethylsulfoxide; and acetonitrile and water.

As the base also usable in the reaction, there are mentioned, for example, alkali metals such as sodium metal or potassium metal; alkali metal or alkaline earth metal hydrides such as sodium hydride or calcium hydride; carbonates such as sodium carbonate or potassium carbonate; metal hydroxides such as sodium hydroxide or potassium hydroxide; and organic bases such as triethylamine or pyridine.

The reaction may be carried out at any desired temperature falling within the range of from the solidifying point of the sovlent used to the boiling point thereof, preferably from 0° C. to the boiling point of the solvent used. If desired, the reaction may be effected with heating or cooling.

The reaction time may be from several minutes to several hours, preferably from 0.5 to 36 hours.

The pyrimidine derivatives or the optical isomers thereof of the present invention as prepared by the above-mentioned method can optionally be purified by recrystallization or column chromatography, if desired.

The present invention will be explained in more detail by way of the following examples, which, however, are not intended to restrict the scope of the present invention.

EXAMPLE 1

Preparation of Compound No 1

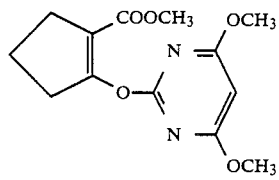

Sodium hydride (5 mmol) was added to 20 ml of hexamethylphosphoric acid triamide solution containing 0.71 g (5 mmol) of methyl 2-oxocyclopentanecarboxylate and stirred for 30 minutes at room temperature.

Next, 1.1 g of 2-methylsulfonyl-4,6-dimethoxypyridine was added thereto and stirred for further 2 hours at 80° C. After cooled, the solvent was removed by distillation under reduced pressure. Water was added to the residue, which was then extracted with ethyl acetate.

The ethyl acetate extract was then washed with water and dried, the solvent was removed by distillation under reduced pressure. Accordignly, a brown oily product was obtained. This was purified by fractionating thin-layer column chromatography to obtain 0.2 g of the above-entitled compound (No. 1) as a pale yellow liquid. The compound had the following physical data: n$_D^{20}$ 1.5303.

$^1$H-NMR [δ Value (ppm), CDCl$_3$] 1.70~2.30(m, 2H), 2.50~2.90 (m, 4H), 3. 57(s, 3H), 3.82 (s, 6H)5.67(s, 1H).

EXAMPLE 2

Preparation of Compound No. 2 (Trans-form):

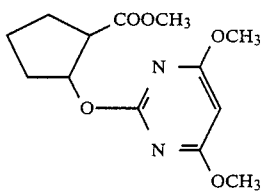

1.4 g (10 mmol) of methyl 2-hydroxycyclopentanecarboxylate and 2.0 g (9.2 mmol) of 2-methanesulfonyl-4,6-dimethoxypyrimidine were dissolved in 50 ml of absolute tetrahydrofuran, and 0.5 g of sodium hydride (50% oily) was added thereto and stirred overnight. The finish of the reaction was confirmed by high-performance liquid chromatography, and the reaction mixture was poured into ice-water. This was extracted with ethyl acetate, the organic layer was dried over anhydrous sodium sulfate, and the solvent was removed by distillation. The resulting residue was purified by column chromatography (silica gel-chloroform), and 2.3 g of a colorless viscous liquid was obtained. Yield: 81.6%. This was subjected to fractionating thin-layer chromatography (Art 5717 manufactured by Merk Co.; kieserite gel 60F$_{254}$), whereupon the liquid was developed with a developer of chloroform/ethyl acetate (10/1) and a fraction having a higher Rf value was fractionated from the eluted two components. Accordingly, 1.2 g of the compound No. 2 of the invention was obtained. This was a colorless viscous liquid and had the following physical data:

$n_D^{20}$ 1.590.

1H-NMR [δ Value (ppm), CDCl3] 1.71~2.36(6H, m) 2.86~3.20(1H,m), 3.66 (3H, s), 3.89(6H, s), 5.65(1H, d,J=3.96 Hz), 5.69(1H, s).

EXAMPLE 3

Preparation of Compound No. 3 (Cis-form):

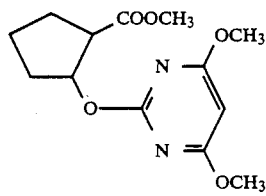

The same process as in Example 2 was carried out, and a fraction having a lower Rf value was fractionated from the two components. Accordingly, 0.91 g of the compound No. 3 of the invention was obtained. This was a colorless viscous liquid and had the following physical data:

$n_D^{20}$ 1.5081.

1H-NMR [δ Value (ppm) CDCl3] 1.42~2.37(6H,m), 2.83~3.11 (1H, m), 3.54 (3H, s), 3.89(6H, s), 5.67(1H, d, J=5.50 Hz), 5.67(1H, s).

EXAMPLE 4

Preparation of Compound No. 4:

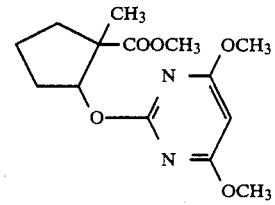

1.6 g (10 mmol) of methyl 1-methyl-2-hydroxycyclopentanecarboxylate and 2.0 g (9.2 mmol) of 2-methanesulfonyl-4,6-dimethoxypyrimidine were dissolved in 50 ml of absolute tetrahydrofuran, and 0.5 g of 50 % oily sodium hydride was added thereto and stirred overnight. The finish of the reaction was confirmed by high-performance liquid chromatography, and the reaction mixture was poured into ice-water. This was extracted with ethyl acetate, the organic layer was dried over anhydrous sodium sulfate, and the solvent was removed by distillation. The resulting residue was purified by column chromatography (silica gel-chloroform) to obtain a viscous liquid. This was subjected to fractionating thin-layer chromatography (Art 5717 manufactured by Merk Co.; kieserite gel 60 F254), whereupon the liquid was developed with a developer of chloroform. Accordingly, 360 g of the compound No. 4 of the invention was obtained This was a colorless viscous liquid and had the following physical data:

$n_D^{19}$ 1.5078.

1H-NMR [δ Value (ppm), CDCl3] 1.25(3H, s), 1.50~2.40 (6H, m), 3/62 (3H s), 3.84 (6H, s), 5.56(1H, s), 5.55~5.80(1H, m).

EXAMPLE 5

Preparation of Compound No. 5:

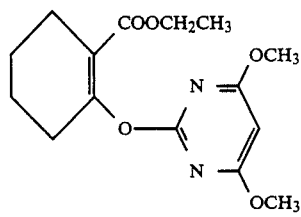

In the same manner as in Example 2 except that 0.85 g (5 mmol) of ethyl 2-oxocyclohexanecarboxylate was used, 0.5 g of the above-entitled compound was obtained as a pale yellow liquid. This had the following physical data:

$n_D^{23.5}$ 1.5126.

1H-NMR [δ Value (ppm) CDCl3] 1.04(t,3H, J=7 Hz), 1.60~2.05 (m, 4H), 2.20~2.65 (m,4H), 3.85(s,6H), 3.97(q, 2H, J=7 Hz), 5.62(s, 1H).

EXAMPLE 6

Preparation of Cis/Trans Mixture:

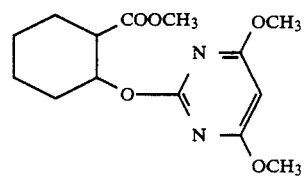

3.2 g of borane/tert-butylamine complex was added to 200 ml of diethyl ether solution containing 15.6 g (0.10 mol) of methyl cyclohexanone-2-carboxylate and stirred overnight at room temperature. An aqueous diluted hydrochloric acid was added thereto to make it weakly acidic, which was then subjected to liquid-liquid separation. The organic layer separated was dried, concentrated and then distilled under reduced pressure to obtain 13.4 g of ethyl 2-hydroxycyclohexanecarboxylate. Yield: 84.8%. b.p. 60° to 62° C. (0.3 mmHg).

1.58 g (10 mmol) of the methyl 2-hydroxycyclohexanecarboxylate and 2.0 g (9.2 mmol) of 2-methanesulfonyl-4,6-dimethoxypyrimidine were dissolved in 50 ml of absolute tetrahydrofuran and then cooled with ice. Next, 0.5 g of 55% oily sodium hydride was added thereto and stirred overnight. The finish of the reaction was confirmed by high-performance liquid chromatography, and the reaction mixture was poured into ice-water. This was then extracted with ethyl acetate and dried over anhydrous sodium sulfate, and the solvent was removed by distillation. The residue was purified by column chromatography to obtain 2.6 g of the above-entitled compound of the invention as a colorless viscous liquid. Yield: 87.6%. This had the following physical data:

1H-NMR [δ Value (ppm), CDCl3] 1.10~2.90 (9H, m), 3.53 (3H, s), 3.82(6H, s), 5.05~5.45 (0.4H, m), 5.52(0.6H, bs), 5.56(1H, s).

EXAMPLE 7

Preparation of Compound No. 6 (Cis/Trans Mixture):

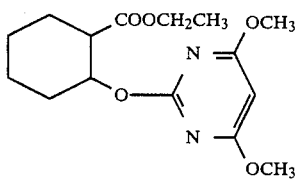

3.2 g of borane/tert-butylamine complex was added to 200 ml of diethyl ether solution containing 17.0 g (0.10 mol) of ethyl cyclohexanone-2-carboxylate and stirred overnight at room temperature. An aqueous diluted hydrochloric acid was added thereto to make it weakly acidic, which was then subjected to liquid-liquid separation. The organic layer thus separated was dried, concentrated and then distilled under reduced pressure to obtain 13.5 g of ethyl 2-hydroxycyclohexanecarboxylate. Yield: 78.5%. b.p. 68° to 71° C. (0.2 mmHg).

1.72 g (10 mmol) of the ethyl 2-hydroxycyclohexanecarboxylate and 2.0 g (9.2 mmol) of 2-methanesulfonyl-4,6-dimethoxypyrimidine were dissolved in 50 ml of absolute tetrahydrofuran and then cooled with ice. Next, 0.5 g of 55% oily sodium hydride was added thereto and stirred overnight. The finish of the reaction was confirmed by high-performance liquid chromatography, and the reaction mixture was poured into ice-water. This was then extracted with ethyl acetate, and dried over anhydrous sodium sulfate, and the solvent was removed by distillation. The residue was purified by column chromatography to obtain 2.6 g of the compound No. 6 of the invention as a colorless viscous liquid Yield: 83.9%

EXAMPLE 8

Preparation of Compound No. 7 (Cis-Form):

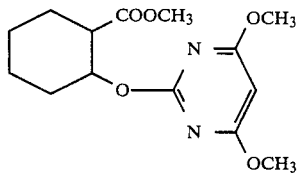

0.80 g (5 mmol) of methyl cis-2-hydroxycyclohexanecarboxylate and sodium hydride (5 mmol) were dissolved in 20 ml of dimethylformamide and stirred for 30 minutes with cooling with ice.

Next, 1.1 g of 2-methylsulfonyl-4,6-dimethoxypyrimidine was added thereto and stirred for 2 hours at 40° to 50° C. After cooled, the sovlent was removed by distillation under reduced pressure. Water was added to the residue, which was then extracted with ethyl acetate.

The ethyl acetate extract was washed with water and dried, and the solvent was removed by distillation under reduced pressure. Accordingly, a pale yellow oily product was obtained. This was purified by silica gel column chromatography to obtain 1.1 g of the compound No. 7 of the invention as a colorless viscous liquid. This had the following physical data:

$n_D^{20}$ 1.5104.

$^1$H—NMR [δ Value (ppm), CDCl$_3$] 1.20~3.00 (m,9H), 3.53(s, 3H), 3.82(s, 6H), 5.52(bs, 1H), 5.54 (s,1H).

EXAMPLE 9

Isolation of Compound No. 9 (Trans-Form):

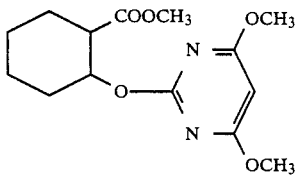

1.0 g of the compound No. 8 of the invention as prepared in Example 6 was subjected to fractionating thin-layer chromatography (Art 5717 manufactured by Merk Co.; kieserite gel 60 F$_{254}$) and developed with a developer of chloroform/ethyl acetate (10/1), whereupon a fraction having a higher Rf value was fractionated from the two components. Accordingly, 300 mg of the compound No. 9 of the invention was obtained. This was a colorless viscous liquid and had the following physical data:

$n_D^{19.5}$ 1.5060.

$^1$H-NMR [δ Value (ppm), CDCl$_3$] 1.10~3.00(9H, m), 3.55(3H, s), 3.87 (6H, s), 5.00~5.45(1H, m), 5.59(1H, s).

EXAMPLE 10

Isolation of Compound No. 8 (Cis-Form):

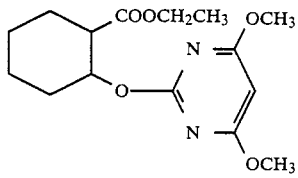

In accordance with the same process as in Example 9, a fraction having a lower Rf value was isolated and 550 g of the compound No. 8 of the invention was obtained from Compound No. 6. This was a colorless viscous liquid and had the following physical data.

$n_D^{19.0}$ 1.5052.

$^1$H-NMR [δValue(ppm), CDCl$_3$] 1.09 (3H, t, J=6.5 Hz), 1.10~2.85 (9H, m), 3.83 (6H, s), 4.00 (2H, q, J=6.5 Hz), 5.56 (1H, s), 5.57 (1H,bs).

EXAMPLE 11

Isolation of Compound No. 10 (Trans-Form):

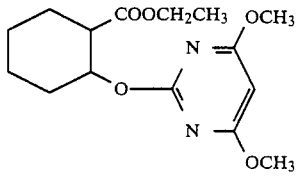

1.0 g of the compound No. 6 of the invention as prepared in Example 7 was fractionated in the same manner as in Example 9, and a fraction having a higher Rf value was isolated. Accordingly, 450 mg of the compound No. 10 of the invention was obtained. This was a colorless viscous liquid and had the following physical data:

$n_D^{19.0}$ 1.5035.

¹H-NMR [δValue (ppm), CDCl₃] 1.11 (3H, t, J=6.5 Hz), 1.10~2.95 (9H, m), 3.84 (6H, s), 3.99 (2H, q, J=6.5 Hz), 4.98~5.57 (1H, m), 5.58 (1H, s).

EXAMPLE 12

Isolation of Compound No. 11 (Cis(+)-Form) and Compound No. 12 (Cis(−)-Form):

Compound No. 11 (Cis(+)-Form):

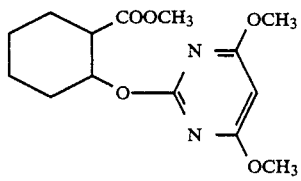

Compound No. 12 (Cis(−)-Form):

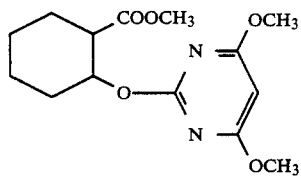

600 mg of the cis-form obtained in Example 8 was subjected to high-performance liquid chromatography (n-hexane/isopropyl alcohol of 50/1, liquid flow rate of 3 ml/min), using an optical active column (Chiral Cell OC, manufactured by Daisel Co.; 25×1 cm) for optical separation.

Accordingly, 300 mg of the first eluate of the cis(−)-form of the compound No. 12 of the invention and 270 mg of the last eluate of the cis(+)-form of the compound No. 11 of the invention were separately obtained.

The cis(−)-form of the compound 12 had the following physical data:

Specific Rotatory Power: $[\alpha]_D^{23.3}$ −7.72 (c=1.165, CHCl₃).

The cis(+)-form of the compound 11 had the following physical data:

Specific Rotatory Power: $[\alpha]_D^{23.3}$ +8.34 (c=1.030, CHCl₃).

EXAMPLE 13

Isolation of Compound No. 13 (Trans(+)-Form) and Compound No. 14 (Trans(−)-Form):

Compound No. 13 (Trans(+)-Form):

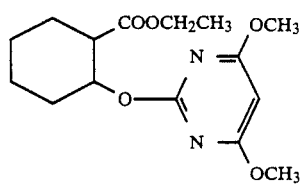

Compound No. 14 (Trans(−)-Form):

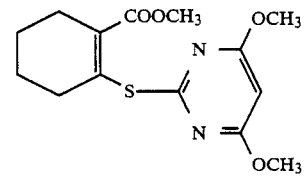

1.0 g of the trans-form obtained in Example 11 was subjected to high-performance liquid chromatography (n-hexane/isopropyl alcohol of 100/1, liquid flow rate of 3 ml/min), using an optical active column (Chiral Cell OC, manufactured by Daisel Co.; 25×1 cm) for optical separation.

Accordingly, 230 mg of the first eluate of the trans(−)-form of the compound No. 14 of the invention and 270 mg of the last eluate of the trans(+)-form of the compound No. 13 of the invention were separately obtained.

The trans(−)-form of the compound No. 14 had the following physical data:

Specific Rotatory Power: $[\alpha]_D^{23.4}$ −22.91 (c=1.008, CHCl₃).

The trans(+)-form of the compound No. 13 had the following physical data:

Specific Rotatory Power: $[\alpha]_D^{23.4}$ +17.94 (c=1.287, CHCl₃).

EXAMPLE 14

Production of Compound No. 15:

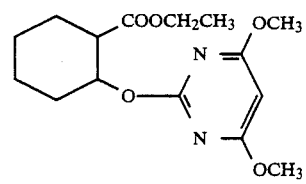

1.6 g (9.3 mmol) of methyl 2-mercaptocyclohexenecarboxylate and 2.0 g (9.2 mmol) of 2-methanesulfonyl-4,6-dimethoxypyrimidine were dissolved in 50 ml of absolute tetrahydrofuran, and 0.5 g of 50% oily sodium hydride was added thereto and stirred overnight. The end point of the reaction was confirmed by high-performance liquid chromatography, and the reaction mixture was poured into ice-water. This was extracted with ethyl acetate, and the organic layer was dried over anhydrous sodium sulfate. The solvent was removed by distillaiton, and the resulting residue was purified by column chromatography (silica gel-chloroform) to obtain 2.3 g of a colorless viscous liquid. Yield: 81.6%. This was developed by fractionating thin-layer chromatography (Art 5717 manufactured by Merk, kieserite gel 60 F₂₅₄), using a developer of chloroform/ethyl acetate (19/1). By fractionating purification, 1.8 g of the compound No. 15 of the invention was obtained. This had the following physical data:

¹H-NMR [δValue (ppm), CDCl₃] 1.05~2.36 (8H, m), 3.81 (6H, s), 3.86 (3H, s), 5.78 (1H, s).

EXAMPLE 15

Preparation of Compound No. 16:

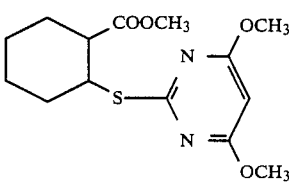

1.6 g (9.2 mmol) of methyl 2-mercaptocyclohexenecarboxylate and 2.0 g (9.2 mmol) of 2-methanesulfonyl-4,6-dimethoxypyrimidine were dissolved in 50 ml of absolute tetrahydrofuran, and 0.5 g of 50% oily sodium hydride was added thereto and stirred overnight. The end point of the reaction was confirmed by high-performance liquid chromatography, and the reaction mixture was poured into ice-water. This was extracted with ethyl acetate, and the organic layer was dried over anhydrous sodium sulfate. The solvent was removed by distillation, and the resulting residue was purified by column chromatography (silica gel-chloroform) to obtain 2.3 g of a colorless viscous liquid. Yield: 81.6%. This was developed by fractionating thin layer chromatography (Art 5717, manufactured by Merk Co.; kieserite gel 60 $F_{254}$), using a developer of chloroform/ethyl acetate (19/1). Accordingly, 0.70 g of the compound No. 16 of the invention was obtained. Yield: 24%. This was a pale yellow viscous liquid and had the following physical data:

$n_D^{21.5}$ 1.5443.

$^1$H-NMR [δValue (ppm), CDCl$_3$] 1.10~2.40 (8H, m), 2.60~3.10 (1H, m), 3.56 (3H, s), 3.83 (6H, s), 4.22~4.51 (1H, m), 5.58 (1H, s).

EXAMPLE 16

Preparation of Compound No. 17 (Cis-Form):

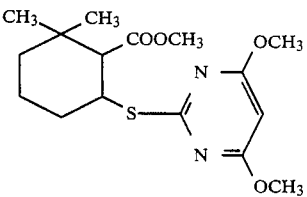

1.8 g (10 mmol) of methyl 2-hydroxy-6,6-dimethylcyclohexanecarboxylate and 2.0 g (9.2 mmol) of 2-methanesulfonyl-4,6-dimethoxypyrimidine were dissolved in 50 ml of absolute tetrahydrofuran, and 0.5 g of 50% oily sodium hydride was added thereto and stirred overnight. The end point of the reaction was confirmed by high-performance liquid chromatography, and the reaction mixture was poured into ice-water. This was extracted with ethyl acetate and the organic layer was dried over anhydrous sodium sulfate. The solvent was removed by distillation and the resulting residue (comprising two components by analysis of high-performance liquid chromatography) was purified by high-performance liquid chromatography, whereupon the latter peak was isolated to obtain 0.55 g of the compound No. 17 of the invention. Yield: 17%. This was a white crystal and had a melting point of 120.0° to 123.0° C. and the following physical data:

$^1$H-NMR [δValue (ppm), CDCl$_3$] 0.92 (3H, s), 1.09 (3H, s), 0.90~2.45 (6H, m), 3.00 (1H, d, J=7 Hz), 3.51 (3H, s), 3.83 (6H, s), 5.00~5.55 (1H, m), 5.57 (1H, s).

EXAMPLE 17

Preparation of Compound No. 18 (Trans-Form):

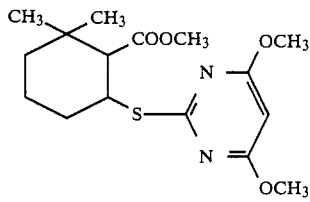

1.8 g (10 mmol) of methyl 2-hydroxy-6,6-dimethylcyclohexanecarboxylate and 2.0 g/(9.2 mmol) of 2-methanesulfonyl-4,6-dimethoxypyrimidine were dissolved in 50 ml of absolute tetrahydrofuran, and 0.5 g of 50% oily sodium hydride was added thereto and stirred overnight. The end point of the reaction was confirmed by high-performance liquid chromatography, and the reaction mixture was poured into ice-water. This was extracted with ethyl acetate, and the organic layer was dried over anhydrous sodium sulfate. The solvent was removed by distillation, and the resulting residue (comprising two components by analysis of high-performance liquid chromatography) was purified by high-performance liquid chromatography, whereupon the former peak was isolated to obtain 0.65 g of the compound No. 18 of the invention. Yield: 20%. This was a white crystal and had a melting point of 82.0° to 84.0° C. and the following physical data:

$^1$H-NMR [δValue (ppm), CDCl$_3$] 1.01 (3H, s), 1.06 (3H, s), 1.40~2.80 (6H, m), 2.62 (1H, d, J=11 Hz), 3.58 (3H, s), 3.83 (6H, s), 5.05~5.80 (1H, m), 5.67 (1H, s).

EXAMPLE 18

Preparation of Compound No. 19:

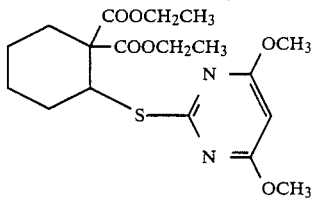

2.4 g (10 mmol) of 2,2-diethoxycarbonylcyclohexyl alcohol and 2.0 g (9.2 mmol) of 2-methanesulfonyl-4,6-dimethoxypyrimidine were dissolved in 50 ml of absolute tetrahydrofuran, and 0.5 g of 50% oily sodium hydride was added thereto and stirred overnight. The end point of the reaction was confirmed by high-performance liquid chromatography, and the reaction mixture was poured into ice-water. This was extracted with ethyl acetate, and the organic layer was dried over anhydrous sodium sulfate. The solvent was removed by distillation, and the residue was purified by high-performance liquid chromatography. Accordingly, 1.6 g of the compound No. 19 of the invention was obtained as a colorless viscous liquid. Yield: 41%. This had the following physical data:

$n_D^{20}$ 1.4955.

$^1$H-NMR [δValue (ppm), CDCl$_3$] 1.05 (3H, t, J=7 Hz), 1.26 (3H, t, J=7 Hz), 1.30~2.45 (8H, m), 3.85 (6H, s), 4.04 (2H, q, J=7 Hz), 4.18 (2H, q, J=7 Hz), 5.58 (1H, s), 5.74~5.89 (1H, m).

EXAMPLE 19

Preparation of Compound No. 22:

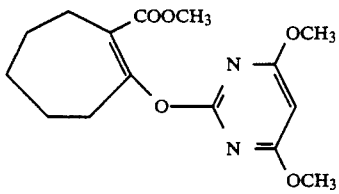

1.7 g (10 mmol) of methyl 2-oxocycloheptanecarboxylate and 2.0 g (9.2 mmol) of 2-methanesulfonyl-4,6-dimethoxypyrimidine were dissolved in 50 ml of absolute tetrahydrofuran, and 0.5 g of 50% oily sodium hydride was added thereto and stirred overnight. The end point of the reaction was confirmed by high-performance liquid chromatography, and the reaction mixture was poured into ice-water. This was extracted with ethyl acetate and the organic layer was dried over anhydrous sodium sulfate. The solvent was removed by distillation, and the resulting residue was purified by column chromatography (silica gel-chloroform) to obtain 1.5 g of a viscous liquid. Yield: 48.7%. This had the following physical data:

$n_D^{20}$ 1.5115.

$^1$H-NMR [$\delta$Value (ppm), CDCl$_3$] 1.20~3.00 (10H, m), 3.51 (3H, s), 3.71 (6H, s), 5.57 (1H, s).

EXAMPLE 20

Preparation of Compound No. 23:

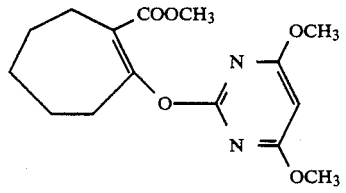

1.7 g (10 mmol) of methyl 2-hydroxycycloheptanecarboxylate and 2.0 g (9.2 mmol) of 2-methanesulfonyl-4,6-dimethoxypyrimidine were dissolved in 50 ml of absolute tetrahydrofuran, and 0.5 g of 50% oily sodium hydride was added thereto and stirred overnight. The end point of the reaction was confirmed by high-performance liquid chromatography, and the reaction mixture was poured into ice-water. This was extracted with ethyl acetate, and the organic layer was dried over anhydrous sodium sulfate. The solvent was removed by distillation, and the resulting residue was purified by column chromatography (silica gel-chloroform) to obtain 1.2 g of a colorless viscous liquid. Yield: 38.7%. This had the following physical data:

$n_D^{20}$ 1.5128.

$^1$H-NMR [$\delta$Value (ppm), CDCl$_3$] 1.30~2.40 (10H, m), 2.70~3.20 (1H, m), 2.55 (3H, s), 3.84 (6H, s), 5.56 (1H, s), 5.30-5.75 (1H, m).

In the same manner as in anyone of the previously mentioned Examples 1 to 20, the compounds of the present invention as shown in Tables 1 to 5 below were obtained.

The structural formulae and the physical data of the compounds obtained in these examples are shown in Table 6 below.

The compound Nos. of the present invention as prepared above are referred to in Composition Examples and Experiment Examples mentioned below.

Where the pyrimidine derivatives or the optical isomers thereof of the present invention are employed as a herbicide, they may be combined with a suitable carrier, for example, a solid carrier such as clay, talc, bentonite or diatomaceous earth or a liquid carrier such as water, alcohols (methanol, ethanol), aromatic hydrocarbons (benzene, toluene, xylene), chlorinated hydrocarbons, ethers, ketones, esters (ethyl acetate) or acid amides (dimethylformamide). If desired, any other additives such as an emulsifier, a dispersing agent, a suspending agent, a wetting agent, a spreader and/or a stabilizer may optionally be added to the herbicidal composition of the present invention. The composition may be in the form of a liquid composition, an emulsion, a wettable powder, a dust, a granular composition, a flowable agent or other various forms for practical use.

The content of the active ingredient of the herbicidal composition is not specifically limited but, in general, is desired to fall within the range of from 0.10 to 90.0% by weight.

If desired, the herbicidal composition of the present invention may further be combined with any other herbicides, various insecticides, fungicides, plant growth regulators and/or synergistic agents, in preparing the composition or in spraying the same for actual use.

For instance, the compounds described in *Farm Chemicals Handbook*, 75th Ed. (1989) are referred to.

The pyrimidine derivatives and the optical isomers thereof of the present invention can be applied not only to upland, paddy fields or fruit farms but also to non-agricultural areas such as playgrounds, vacant lands or railway track spaces for the purpose of killing various weeds therein. The amount of the active ingredient to be applied for such herbicidal purpose is generally from 0.005 to 10 kg/ha or so, though varying in accordance with the place to which the herbicide is applied, the time when the herbicide is applied, the method of applying the herbicide, the kind of weeds to be killed by the herbicide and the kind of the crops to be protected by application of the herbicide.

Next, some examples of herbicidal compositions containing the pyrimidine derivative or the optical isomer thereof of the present invention as the active ingredient will be mentioned below, which, however, are not intended to restrict the scope of the present invention.

Unless otherwise specifically limited, all "parts" are by weight.

Liquid Composition:
Active Ingredient: 5 to 75 parts, preferably 10 to 50 parts, especially preferably 15 to 40 parts
Liquid Carrier: 95 to 25 parts, preferably 88 to 30 parts, especially preferably 82 to 40 parts
Surfactant 1 to 30 parts, preferably 2 to 20 parts Emulsion:
Active Ingredient: 1 to 50 parts, preferably 5 to 45 parts, especially preferably 10 to 40 parts
Surfactant: 1 to 30 parts, preferably 2 to 25 parts, especially preferably 3 to 20 parts
Liquid Carrier: 20 to 95 parts, preferably 30 to 93 parts, especially preferably 57 to 85 parts Dust:

Active Ingredient: 0.5 to 10 parts, especielly preferably 15 to 40 parts
Solid Carrier: 95.5 to 90 parts
Flowable Agent:
Active Ingredient: 5 to 75 parts, preferably 10 to 50 parts
Water: 94 to 25 parts, preferably 90 to 30 parts
Surfactant: 1 to 30 parts, preferably 2 to 20 parts
Wettable Powder:
Active Ingredient: 2.5 to 90 parts, preferably 10 to 80 parts, especially preferably 20 to 75 parts
Surfactant: 0.5 to 20 parts, preferably 1 to 15 parts, especially preferably 2 to 10 parts
Liquid Carrier: 5 to 90 parts, preferably 7.5 to 88 parts, especially preferably 16 to 56 parts
Granular Composition:
Active Ingredient: 0.1 to 30 parts
Solid Carrier: 99.5 to 70 parts The liquid composition and the emulsion are prepared by dissolving an active ingredient into a surfactant-containing liquid carrier. The wettable powder is prepared by blending a surfactant, a solid carrier and an active ingredient and then powdering the resulting blend.

The dust is prepared by blending a surfactant, a solid carrier and an active ingredient and, if desired, further pulverizing the resulting blend.

The flowable agent is prepared by suspending and dispersing an active ingredient in a surfactant-containing aqueous solution.

The granular composition is prepared by blending an active ingredient and the adjuvant.

COMPOSITION EXAMPLE 1

| Wettable Powder: | |
| --- | --- |
| Compound No. 9 of the Invention | 50 parts |
| Zeeklite PFP, (kaolin clay, trade name of Zeeklite Industry Co.) | 43 parts |
| Sorpol 5039 (mixture of nonionic surfactant and anionic surfactant, trade name by Toho Chemical Co.) | 5 parts |
| Carplex (anti-caking agent) (mixture of surfactant and white carbon, trade name of Shionogi Pharmaceutical Co.) | 2 parts |

The above-mentioned ingredients were blended and powdered to obtain a wettable powder. For actual use, the powder is diluted with water to form 1/10 to 1/10,000 and is sprayed in an amount of from 0.005 to 10 kg/ha as the active ingredient.

COMPOSITION EXAMPLE 2

| Emulsion: | |
| --- | --- |
| Compound No. 6 of the Invention | 10 parts |
| Xylene | 70 parts |
| Dimethylformamide | 10 parts |
| Sorpol 2680 (mixture of nonionic surfactant and anionic surfactant, trade name of Toho Chemical Co.) | 10 parts |

The above-mentioned ingredients were uniformly blended to form an emulsion. For actual use, this is diluted to from 1/10 to 1/10,000 and is sprayed in an amount of from 0.005 to 10 kg/ha as the active ingredient.

COMPOSITION EXAMPLE 3

| Granular Composition: | |
| --- | --- |
| Compound No. 13 of the Invention | 5 parts |
| Bentonite | 54 parts |
| Talc | 40 parts |
| Calcium ligninesulfonate | 1 part |

The above-mentioned ingredients were uniformly blended and pulverized, and a small amount of water was added thereto, granulated through a granulating extruder and dried to obtain a granular composition. For actual use, this is applied in an amount of from 0.005 to 10 kg/ha as the active ingredient.

COMPOSITION EXAMPLE 4

| Flowable Agent: | |
| --- | --- |
| Compound No. 9 of the Invention | 25 parts |
| Sorpol 3353 (nonionic surfactant, trade name of Toho Chemical Co.) | 10 parts |
| Lunox 1000 C (anionic surfactant, trade name of Toho Chemical Co.) | 0.5 part |
| 1% Aqueous Xanthan Gum Solution (natural high polymer substance) | 20 parts |
| Water | 44.5 parts |

Sorpol 3353, Lunox 100 C and 1% aqueous Xanthan gum solution were uniformly dissolved in water, and then the compound No. 9 of the invention was added thereto and well stirred. The resulting blend was then wet-powdered with a sand mill to obtain a flowable agent. For practical use, this is diluted to from 1/10 to 1/10,000 and dispersed in an amount of from 0.005 to 10 kg/ha as the active ingredient.

Next, the usefulness of the compounds of the present invention as a herbicide will be explained concretely by way of the following Experiment Examples.

EXPERIMENT EXAMPLE 1

Herbicidal Test in Soil Treatment:

A sterilized farm soil was put in a plastic box having a length of 30 cm, a width of 22 cm and a depth of 6 cm, and *Echinochoa crus galli, Cyperus microiria, Solanum nigrum, Galinosoga ciliate, Rorippa indica* and cotton were seeded. After the seeds were covered with the soil in a depth of about 1.5 cm the above-mentioned liquid composition, wettable powder, emulsion and flowable agent were diluted with water, and each was sprayed over the complete surface of the soil in the box with a small-sized spray, in a determined amount as the active ingredient. Four weeks after the spraying, the herbicidal effect to the weeds was checked in accordance with the evaluation criterion mentioned below.

Herbicidal Effect Evaluation Criterion:

5: Herbicidal effect was 90 % or more. (Almost all were completely killed.)
4: Herbicidal effect was 70 to 90%.
3: Herbicidal effect was 40 to 70%.
2: Herbicidal effect was 20 to 40%.
1: Herbicidal effect was 5 to 20%.

0: Herbicidal effect was less than 5%.(Almost ineffective.)

The herbicidal effect in the above-mentioned evaluation was calculated out from the following equation, on the basis of the weight of the living plants over the soil to which the herbicide was applied and that of the living plants over the soil (control) to which no herbicide was applied.

Herbicidal Effect =

$$\left(1 - \frac{\text{Weight of Living Plants Over the Treated Soil}}{\text{Weight of Living Plants over the Non-Treated Soil}}\right) \times 100$$

The results obtained are shown in Table 7 below.

EXPERIMENT EXAMPLE 2

Herbicidal Test in Foliage Application:

A sterilized farm soil was put in a plastic box having a length of 30 cm, a width of 22 cm and a depth of 6 cm, and *Echinochoa crus galli, Cyperus microiria, Solanum nigrum, Galinsoga ciliate, Rorippa indica,* and rice, cotton and beet were spot-like seeded and were covered with a soil in a depth of about 1.5 cm. After the plant seedlings became two- to three-leaves stage, the above-mentioned liquid composition, wettable powder, emulsion or flowable agent as diluted with water was sprayed over the complete surfaces of the leaves of the weeds and the crops with a small-sized spray, in a determined amount as the active ingredient. Four weeks after the spraying, the herbicidal effect to the weeds was checked in accordance with the same evalaution criterion as in Experiment Example 1. The results obtained are shown in Table 8 below.

TABLE 1

A compound of the general formula:

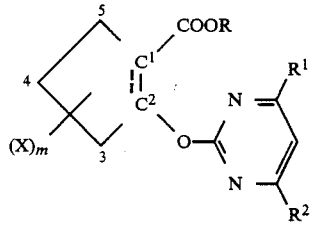

In the below-mentioned table, Me represents methyl group, Et represents ethyl group, Pr represents propyl group, $^i$Pr represents isopropyl group, Bu represents butyl group, $^i$Bu represents isobutyl group, $^s$Bu represents butyl secondary butyl group, $^t$Bu represents tertiary butyl group, cis represents a cis-form, trans represents a trans-form, mix. represents a mixture of a cis-form and a trans-form, 1 represents a single bond and 2 represents a double bond.

| (X)$_m$ | === | R | R$^1$ | R$^2$ |
|---|---|---|---|---|
| — | 1 (cis) | H | Me | Me |
| — | 1 (cis) | Li | Me | Me |
| — | 1 (cis) | Na | Me | Me |
| — | 1 (cis) | K | Me | Me |
| — | 1 (cis) | ½Mg | Me | Me |
| — | 1 (cis) | ½Ca | Me | Me |
| — | 1 (cis) | MeNH$_3$ | Me | Me |
| — | 1 (cis) | EtNH$_3$ | Me | Me |
| — | 1 (cis) | PrNH$_3$ | Me | Me |
| — | 1 (cis) | $^i$PrNH$_3$ | Me | Me |
| — | 1 (cis) | NH$_2$CONH$_3$ | Me | Me |
| — | 1 (cis) | Me | Me | Me |
| — | 1 (cis) | Et | Me | Me |
| — | 1 (cis) | $^i$Pr | Me | Me |
| — | 1 (cis) | Pr | Me | Me |
| — | 1 (cis) | Bu | Me | Me |

TABLE 1-continued

A compound of the general formula:

| (X)$_m$ | === | R | R$^1$ | R$^2$ |
|---|---|---|---|---|
| — | 1 (cis) | $^i$Bu | Me | Me |
| — | 1 (cis) | $^s$Bu | Me | Me |
| — | 1 (cis) | $^t$Bu | Me | Me |
| — | 1 (cis) | —CH$_2$OCH$_3$ | Me | Me |
| — | 1 (cis) | —CH$_2$CH$_2$OCH$_3$ | Me | Me |
| — | 1 (cis) | —CH$_2$SCH$_3$ | Me | Me |
| — | 1 (cis) | —CH$_2$CH=CH$_2$ | Me | Me |
| — | 1 (cis) | —C(CH$_3$)$_2$CH=CH$_2$ | Me | Me |
| — | 1 (cis) | —CH$_2$C≡CH$_2$ | Me | Me |
| — | 1 (cis) | —CH$_2$C$_6$H$_5$ | Me | Me |
| — | 1 (cis) | —CH$_2$C$_6$H$_4$—Cl-2 | Me | Me |
| — | 1 (cis) | —CH$_2$C$_6$H$_4$—Cl-3 | Me | Me |
| — | 1 (cis) | —CH$_2$C$_6$H$_4$—Cl-4 | Me | Me |
| — | 1 (cis) | —CH$_2$C$_6$H$_4$—Me-2 | Me | Me |
| — | 1 (cis) | —CH$_2$C$_6$H$_4$—Me-3 | Me | Me |
| — | 1 (cis) | —CH$_2$C$_6$H$_4$—Me-4 | Me | Me |
| — | 1 (cis) | —CH$_2$C$_6$H$_4$—OMe-2 | Me | Me |
| — | 1 (cis) | —CH$_2$C$_6$H$_4$—OMe-3 | Me | Me |
| — | 1 (cis) | —CH$_2$C$_6$H$_4$—OMe-4 | Me | Me |
| — | 1 (cis) | —CH$_2$CH$_2$C$_6$H$_5$ | Me | Me |
| — | 1 (cis) | H | OMe | Me |
| — | 1 (cis) | Li | OMe | Me |
| — | 1 (cis) | Na | OMe | Me |
| — | 1 (cis) | K | OMe | Me |
| — | 1 (cis) | ½Mg | OMe | Me |
| — | 1 (cis) | ½Ca | OMe | Me |
| — | 1 (cis) | MeNH$_3$ | OMe | Me |
| — | 1 (cis) | EtNH$_3$ | OMe | Me |
| — | 1 (cis) | PrNH$_3$ | OMe | Me |
| — | 1 (cis) | $^i$PrNH$_3$ | OMe | Me |
| — | 1 (cis) | NH$_2$CONH$_3$ | OMe | Me |
| — | 1 (cis) | Me | OMe | Me |
| — | 1 (cis) | Et | OMe | Me |
| — | 1 (cis) | $^i$Pr | OMe | Me |
| — | 1 (cis) | Pr | OMe | Me |
| — | 1 (cis) | Bu | OMe | Me |
| — | 1 (cis) | $^i$Bu | OMe | Me |
| — | 1 (cis) | $^s$Bu | OMe | Me |
| — | 1 (cis) | $^t$Bu | OMe | Me |
| — | 1 (cis) | —CH$_2$OCH$_3$ | OMe | Me |
| — | 1 (cis) | —CH$_2$CH$_2$OCH$_3$ | OMe | Me |
| — | 1 (cis) | —CH$_2$SCH$_3$ | OMe | Me |
| — | 1 (cis) | —CH$_2$CH=CH$_2$ | OMe | Me |
| — | 1 (cis) | —C(CH$_3$)$_2$CH=CH$_2$ | OMe | Me |
| — | 1 (cis) | —CH$_2$C≡CH$_2$ | OMe | Me |
| — | 1 (cis) | —CH$_2$C$_6$H$_5$ | OMe | Me |
| — | 1 (cis) | —CH$_2$C$_6$H$_4$—Cl-2 | OMe | Me |
| — | 1 (cis) | —CH$_2$C$_6$H$_4$—Cl-3 | OMe | Me |
| — | 1 (cis) | —CH$_2$C$_6$H$_4$—Cl-4 | OMe | Me |
| — | 1 (cis) | —CH$_2$C$_6$H$_4$—Me-2 | OMe | Me |
| — | 1 (cis) | —CH$_2$C$_6$H$_4$—Me-3 | OMe | Me |
| — | 1 (cis) | —CH$_2$C$_6$H$_4$—Me-4 | OMe | Me |
| — | 1 (cis) | —CH$_2$C$_6$H$_4$—OMe-2 | OMe | Me |
| — | 1 (cis) | —CH$_2$C$_6$H$_4$—OMe-3 | OMe | Me |
| — | 1 (cis) | —CH$_2$C$_6$H$_4$—OMe-4 | OMe | Me |
| — | 1 (cis) | —CH$_2$CH$_2$C$_6$H$_5$ | OMe | Me |
| — | 1 (cis) | H | OMe | OMe |
| — | 1 (cis) | Li | OMe | OMe |
| — | 1 (cis) | Na | OMe | OMe |
| — | 1 (cis) | K | OMe | OMe |
| — | 1 (cis) | ½Mg | OMe | OMe |

TABLE 1-continued

A compound of the general formula:

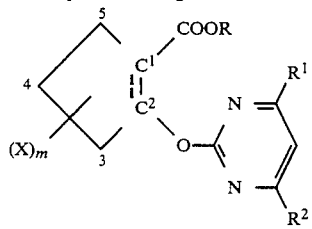

In the below-mentioned table, Me represents methyl group, Et represents ethyl group, Pr represents propyl group, $^i$Pr represents isopropyl group, Bu represents butyl group, $^i$Bu represents isobutyl group, $^s$Bu represents butyl secondary butyl group, $^t$Bu represents tertiary butyl group, cis represents a cis-form, trans represents a trans-form, mix. represents a mixture of a cis-form and a trans-form, 1 represents a single bond and 2 represents a double bond.

| $(X)_m$ | ≡ | R | $R^1$ | $R^2$ |
|---|---|---|---|---|
| — | 1 (cis) | ½Ca | OMe | OMe |
| — | 1 (cis) | MeNH$_3$ | OMe | OMe |
| — | 1 (cis) | EtNH$_3$ | OMe | OMe |
| — | 1 (cis) | PrNH$_3$ | OMe | OMe |
| — | 1 (cis) | $^i$PrNH$_3$ | OMe | OMe |
| — | 1 (cis) | NH$_2$CONH$_3$ | OMe | OMe |
| — | 1 (cis) | Me | OMe | OMe |
| — | 1 (cis) | Et | OMe | OMe |
| — | 1 (cis) | $^i$Pr | OMe | OMe |
| — | 1 (cis) | Pr | OMe | OMe |
| — | 1 (cis) | Bu | OMe | OMe |
| — | 1 (cis) | $^i$Bu | OMe | OMe |
| — | 1 (cis) | $^s$Bu | OMe | OMe |
| — | 1 (cis) | $^t$Bu | OMe | OMe |
| — | 1 (cis) | —CH$_2$OCH$_3$ | OMe | OMe |
| — | 1 (cis) | —CH$_2$CH$_2$OCH$_3$ | OMe | OMe |
| — | 1 (cis) | —CH$_2$SCH$_3$ | OMe | OMe |
| — | 1 (cis) | —CH$_2$CH=CH$_2$ | OMe | OMe |
| — | 1 (cis) | —C(CH$_3$)$_2$CH=CH$_2$ | OMe | OMe |
| — | 1 (cis) | —CH$_2$C≡CH$_2$ | OMe | OMe |
| — | 1 (cis) | —CH$_2$C$_6$H$_5$ | OMe | OMe |
| — | 1 (cis) | —CH$_2$C$_6$H$_4$—Cl-2 | OMe | OMe |
| — | 1 (cis) | —CH$_2$C$_6$H$_4$—Cl-3 | OMe | OMe |
| — | 1 (cis) | —CH$_2$C$_6$H$_4$—Cl-4 | OMe | OMe |
| — | 1 (cis) | —CH$_2$C$_6$H$_4$—Me-2 | OMe | OMe |
| — | 1 (cis) | —CH$_2$C$_6$H$_4$—Me-3 | OMe | OMe |
| — | 1 (cis) | —CH$_2$C$_6$H$_4$—Me-4 | OMe | OMe |
| — | 1 (cis) | —CH$_2$C$_6$H$_4$—OMe-2 | OMe | OMe |
| — | 1 (cis) | —CH$_2$C$_6$H$_4$—OMe-3 | OMe | OMe |
| — | 1 (cis) | —CH$_2$C$_6$H$_4$—OMe-4 | OMe | OMe |
| — | 1 (cis) | —CH$_2$CH$_2$C$_6$H$_5$ | OMe | OMe |
| — | 1 (cis) | H | Cl | Me |
| — | 1 (cis) | Li | Cl | Me |
| — | 1 (cis) | Na | Cl | Me |
| — | 1 (cis) | K | Cl | Me |
| — | 1 (cis) | ½Mg | Cl | Me |
| — | 1 (cis) | ½Ca | Cl | Me |
| — | 1 (cis) | MeNH$_3$ | Cl | Me |
| — | 1 (cis) | EtNH$_3$ | Cl | Me |
| — | 1 (cis) | PrNH$_3$ | Cl | Me |
| — | 1 (cis) | $^i$PrNH$_3$ | Cl | Me |
| — | 1 (cis) | NH$_2$CONH$_3$ | Cl | Me |
| — | 1 (cis) | Me | Cl | Me |
| — | 1 (cis) | Et | Cl | Me |
| — | 1 (cis) | $^i$Pr | Cl | Me |
| — | 1 (cis) | Pr | Cl | Me |
| — | 1 (cis) | Bu | Cl | Me |
| — | 1 (cis) | $^i$Bu | Cl | Me |
| — | 1 (cis) | $^s$Bu | Cl | Me |
| — | 1 (cis) | $^t$Bu | Cl | Me |
| — | 1 (cis) | —CH$_2$OCH$_3$ | Cl | Me |
| — | 1 (cis) | —CH$_2$CH$_2$OCH$_3$ | Cl | Me |
| — | 1 (cis) | —CH$_2$SCH$_3$ | Cl | Me |
| — | 1 (cis) | —CH$_2$CH=CH$_2$ | Cl | Me |
| — | 1 (cis) | —C(CH$_3$)$_2$CH=CH$_2$ | Cl | Me |
| — | 1 (cis) | —CH$_2$C≡CH$_2$ | Cl | Me |
| — | 1 (cis) | —CH$_2$C$_6$H$_5$ | Cl | Me |
| — | 1 (cis) | —CH$_2$C$_6$H$_4$—Cl-2 | Cl | Me |
| — | 1 (cis) | —CH$_2$C$_6$H$_4$—Cl-3 | Cl | Me |
| — | 1 (cis) | —CH$_2$C$_6$H$_4$—Cl-4 | Cl | Me |
| — | 1 (cis) | —CH$_2$C$_6$H$_4$—Me-2 | Cl | Me |
| — | 1 (cis) | —CH$_2$C$_6$H$_4$—Me-3 | Cl | Me |
| — | 1 (cis) | —CH$_2$C$_6$H$_4$—Me-4 | Cl | Me |
| — | 1 (cis) | —CH$_2$C$_6$H$_4$—OMe-2 | Cl | Me |
| — | 1 (cis) | —CH$_2$C$_6$H$_4$—OMe-3 | Cl | Me |
| — | 1 (cis) | —CH$_2$C$_6$H$_4$—OMe-4 | Cl | Me |
| — | 1 (cis) | —CH$_2$CH$_2$C$_6$H$_5$ | Cl | Me |
| — | 1 (cis) | H | Cl | Cl |
| — | 1 (cis) | Li | Cl | Cl |
| — | 1 (cis) | Na | Cl | Cl |
| — | 1 (cis) | K | Cl | Cl |
| — | 1 (cis) | ½Mg | Cl | Cl |
| — | 1 (cis) | ½Ca | Cl | Cl |
| — | 1 (cis) | MeNH$_3$ | Cl | Cl |
| — | 1 (cis) | EtNH$_3$ | Cl | Cl |
| — | 1 (cis) | PrNH$_3$ | Cl | Cl |
| — | 1 (cis) | $^i$PrNH$_3$ | Cl | Cl |
| — | 1 (cis) | NH$_2$CONH$_3$ | Cl | Cl |
| — | 1 (cis) | Me | Cl | Cl |
| — | 1 (cis) | Et | Cl | Cl |
| — | 1 (cis) | $^i$Pr | Cl | Cl |
| — | 1 (cis) | Pr | Cl | Cl |
| — | 1 (cis) | Bu | Cl | Cl |
| — | 1 (cis) | $^i$Bu | Cl | Cl |
| — | 1 (cis) | $^s$Bu | Cl | Cl |
| — | 1 (cis) | $^t$Bu | Cl | Cl |
| — | 1 (cis) | —CH$_2$OCH$_3$ | Cl | Cl |
| — | 1 (cis) | —CH$_2$CH$_2$OCH$_3$ | Cl | Cl |
| — | 1 (cis) | —CH$_2$SCH$_3$ | Cl | Cl |
| — | 1 (cis) | —CH$_2$CH=CH$_2$ | Cl | Cl |
| — | 1 (cis) | —C(CH$_3$)$_2$CH=CH$_2$ | Cl | Cl |
| — | 1 (cis) | —CH$_2$C≡CH$_2$ | Cl | Cl |
| — | 1 (cis) | —CH$_2$C$_6$H$_5$ | Cl | Cl |
| — | 1 (cis) | —CH$_2$C$_6$H$_4$—Cl-2 | Cl | Cl |
| — | 1 (cis) | —CH$_2$C$_6$H$_4$—Cl-3 | Cl | Cl |
| — | 1 (cis) | —CH$_2$C$_6$H$_4$—Cl-4 | Cl | Cl |
| — | 1 (cis) | —CH$_2$C$_6$H$_4$—Me-2 | Cl | Cl |
| — | 1 (cis) | —CH$_2$C$_6$H$_4$—Me-3 | Cl | Cl |
| — | 1 (cis) | —CH$_2$C$_6$H$_4$—Me-4 | Cl | Cl |
| — | 1 (cis) | —CH$_2$C$_6$H$_4$—OMe-2 | Cl | Cl |
| — | 1 (cis) | —CH$_2$C$_6$H$_4$—OMe-3 | Cl | Cl |
| — | 1 (cis) | —CH$_2$C$_6$H$_4$—OMe-4 | Cl | Cl |
| — | 1 (cis) | —CH$_2$CH$_2$C$_6$H$_5$ | Cl | Cl |
| — | 1 (cis) | H | Cl | OMe |
| — | 1 (cis) | Li | Cl | OMe |
| — | 1 (cis) | Na | Cl | OMe |
| — | 1 (cis) | K | Cl | OMe |
| — | 1 (cis) | ½Mg | Cl | OMe |
| — | 1 (cis) | ½Ca | Cl | OMe |
| — | 1 (cis) | MeNH$_3$ | Cl | OMe |
| — | 1 (cis) | EtNH$_3$ | Cl | OMe |
| — | 1 (cis) | PrNH$_3$ | Cl | OMe |
| — | 1 (cis) | $^i$PrNH$_3$ | Cl | OMe |
| — | 1 (cis) | NH$_2$CONH$_3$ | Cl | OMe |
| — | 1 (cis) | Me | Cl | OMe |
| — | 1 (cis) | Et | Cl | OMe |
| — | 1 (cis) | $^i$Pr | Cl | OMe |
| — | 1 (cis) | Pr | Cl | OMe |
| — | 1 (cis) | Bu | Cl | OMe |
| — | 1 (cis) | $^i$Bu | Cl | OMe |
| — | 1 (cis) | $^s$Bu | Cl | OMe |
| — | 1 (cis) | $^t$Bu | Cl | OMe |

TABLE 1-continued

A compound of the general formula:

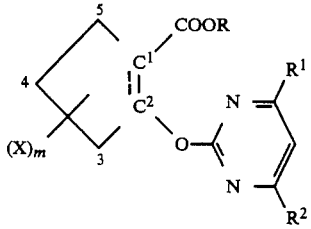

In the below-mentioned table, Me represents methyl group, Et represents ethyl group, Pr represents propyl group, $^i$Pr represents isopropyl group, Bu represents butyl group, $^i$Bu represents isobutyl group, $^s$Bu represents butyl secondary butyl group, $^t$Bu represents tertiary butyl group, cis represents a cis-form, trans represents a trans-form, mix. represents a mixture of a cis-form and a trans-form, 1 represents a single bond and 2 represents a double bond.

| $(X)_m$ | ==== | R | $R^1$ | $R^2$ |
|---|---|---|---|---|
| — | 1 (cis) | —CH$_2$OCH$_3$ | Cl | OMe |
| — | 1 (cis) | —CH$_2$CH$_2$OCH$_3$ | Cl | OMe |
| — | 1 (cis) | —CH$_2$SCH$_3$ | Cl | OMe |
| — | 1 (cis) | —CH$_2$CH=CH$_2$ | Cl | OMe |
| — | 1 (cis) | —C(CH$_3$)$_2$CH=CH$_2$ | Cl | OMe |
| — | 1 (cis) | —CH$_2$C≡CH$_2$ | Cl | OMe |
| — | 1 (cis) | —CH$_2$C$_6$H$_5$ | Cl | OMe |
| — | 1 (cis) | —CH$_2$C$_6$H$_4$—Cl-2 | Cl | OMe |
| — | 1 (cis) | —CH$_2$C$_6$H$_4$—Cl-3 | Cl | OMe |
| — | 1 (cis) | —CH$_2$C$_6$H$_4$—Cl-4 | Cl | OMe |
| — | 1 (cis) | —CH$_2$C$_6$H$_4$—Me-2 | Cl | OMe |
| — | 1 (cis) | —CH$_2$C$_6$H$_4$—Me-3 | Cl | OMe |
| — | 1 (cis) | —CH$_2$C$_6$H$_4$—Me-4 | Cl | OMe |
| — | 1 (cis) | —CH$_2$C$_6$H$_4$—OMe-2 | Cl | OMe |
| — | 1 (cis) | —CH$_2$C$_6$H$_4$—OMe-3 | Cl | OMe |
| — | 1 (cis) | —CH$_2$C$_6$H$_4$—OMe-4 | Cl | OMe |
| — | 1 (cis) | —CH$_2$CH$_2$C$_6$H$_5$ | Cl | OMe |
| — | 1 (cis) | H | Cl | OMe |
| — | 1 (cis) | Li | Cl | OMe |
| — | 1 (cis) | Na | Cl | OMe |
| — | 1 (cis) | K | Cl | OMe |
| — | 1 (cis) | ½Mg | Cl | OMe |
| — | 1 (cis) | ½Ca | Cl | OMe |
| — | 1 (cis) | MeNH$_3$ | Cl | OMe |
| — | 1 (cis) | EtNH$_3$ | Cl | OMe |
| — | 1 (cis) | PrNH$_3$ | Cl | OMe |
| — | 1 (cis) | $^i$PrNH$_3$ | Cl | OMe |
| — | 1 (cis) | NH$_2$CONH$_3$ | Cl | OMe |
| — | 1 (cis) | Me | Cl | OMe |
| — | 1 (cis) | Et | Cl | OMe |
| — | 1 (cis) | $^i$Pr | Cl | OMe |
| — | 1 (cis) | Pr | Cl | OMe |
| — | 1 (cis) | Bu | Cl | OMe |
| — | 1 (cis) | $^i$Bu | Cl | OMe |
| — | 1 (cis) | $^s$Bu | Cl | OMe |
| — | 1 (cis) | $^t$Bu | Cl | OMe |
| — | 1 (cis) | —CH$_2$OCH$_3$ | Cl | OMe |
| — | 1 (cis) | —CH$_2$CH$_2$OCH$_3$ | Cl | OMe |
| — | 1 (cis) | —CH$_2$SCH$_3$ | Cl | OMe |
| — | 1 (cis) | —CH$_2$CH=CH$_2$ | Cl | OMe |
| — | 1 (cis) | —C(CH$_3$)$_2$CH=CH$_2$ | Cl | OMe |
| — | 1 (cis) | —CH$_2$C≡CH$_2$ | Cl | OMe |
| — | 1 (cis) | —CH$_2$C$_6$H$_5$ | Cl | OMe |
| — | 1 (cis) | —CH$_2$C$_6$H$_4$—Cl-2 | Cl | OMe |
| — | 1 (cis) | —CH$_2$C$_6$H$_4$—Cl-3 | Cl | OMe |
| — | 1 (cis) | —CH$_2$C$_6$H$_4$—Cl-4 | Cl | OMe |
| — | 1 (cis) | —CH$_2$C$_6$H$_4$—Me-2 | Cl | OMe |
| — | 1 (cis) | —CH$_2$C$_6$H$_4$—Me-3 | Cl | OMe |
| — | 1 (cis) | —CH$_2$C$_6$H$_4$—Me-4 | Cl | OMe |
| — | 1 (cis) | —CH$_2$C$_6$H$_4$—OMe-2 | Cl | OMe |
| — | 1 (cis) | —CH$_2$C$_6$H$_4$—OMe-3 | Cl | OMe |
| — | 1 (cis) | —CH$_2$C$_6$H$_4$—OMe-4 | Cl | OMe |
| — | 1 (cis) | —CH$_2$CH$_2$C$_6$H$_5$ | Cl | OMe |
| — | 1 (cis) | H | OCHF$_2$ | OMe |
| — | 1 (cis) | Li | OCHF$_2$ | OMe |
| — | 1 (cis) | Na | OCHF$_2$ | OMe |
| — | 1 (cis) | K | OCHF$_2$ | OMe |
| — | 1 (cis) | ½Mg | OCHF$_2$ | OMe |
| — | 1 (cis) | ½Ca | OCHF$_2$ | OMe |
| — | 1 (cis) | MeNH$_3$ | OCHF$_2$ | OMe |
| — | 1 (cis) | EtNH$_3$ | OCHF$_2$ | OMe |

TABLE 1-continued

A compound of the general formula:

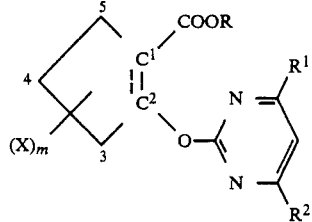

In the below-mentioned table, Me represents methyl group, Et represents ethyl group, Pr represents propyl group, $^i$Pr represents isopropyl group, Bu represents butyl group, $^i$Bu represents isobutyl group, $^s$Bu represents butyl secondary butyl group, $^t$Bu represents tertiary butyl group, cis represents a cis-form, trans represents a trans-form, mix. represents a mixture of a cis-form and a trans-form, 1 represents a single bond and 2 represents a double bond.

| $(X)_m$ | ==== | R | $R^1$ | $R^2$ |
|---|---|---|---|---|
| — | 1 (cis) | PrNH$_3$ | OCHF$_2$ | OMe |
| — | 1 (cis) | $^i$PrNH$_3$ | OCHF$_2$ | OMe |
| — | 1 (cis) | NH$_2$CONH$_3$ | OCHF$_2$ | OMe |
| — | 1 (cis) | Me | OCHF$_2$ | OMe |
| — | 1 (cis) | Et | OCHF$_2$ | OMe |
| — | 1 (cis) | $^i$Pr | OCHF$_2$ | OMe |
| — | 1 (cis) | Pr | OCHF$_2$ | OMe |
| — | 1 (cis) | Bu | OCHF$_2$ | OMe |
| — | 1 (cis) | $^i$Bu | OCHF$_2$ | OMe |
| — | 1 (cis) | $^s$Bu | OCHF$_2$ | OMe |
| — | 1 (cis) | $^t$Bu | OCHF$_2$ | OMe |
| — | 1 (cis) | —CH$_2$OCH$_3$ | OCHF$_2$ | OMe |
| — | 1 (cis) | —CH$_2$CH$_2$OCH$_3$ | OCHF$_2$ | OMe |
| — | 1 (cis) | —CH$_2$SCH$_3$ | OCHF$_2$ | OMe |
| — | 1 (cis) | —CH$_2$CH=CH$_2$ | OCHF$_2$ | OMe |
| — | 1 (cis) | —C(CH$_3$)$_2$CH=CH$_2$ | OCHF$_2$ | OMe |
| — | 1 (cis) | —CH$_2$C≡CH$_2$ | OCHF$_2$ | OMe |
| — | 1 (cis) | —CH$_2$C$_6$H$_5$ | OCHF$_2$ | OMe |
| — | 1 (cis) | —CH$_2$C$_6$H$_4$—Cl-2 | OCHF$_2$ | OMe |
| — | 1 (cis) | —CH$_2$C$_6$H$_4$—Cl-3 | OCHF$_2$ | OMe |
| — | 1 (cis) | —CH$_2$C$_6$H$_4$—Cl-4 | OCHF$_2$ | OMe |
| — | 1 (cis) | —CH$_2$C$_6$H$_4$—Me-2 | OCHF$_2$ | OMe |
| — | 1 (cis) | —CH$_2$C$_6$H$_4$—Me-3 | OCHF$_2$ | OMe |
| — | 1 (cis) | —CH$_2$C$_6$H$_4$—Me-4 | OCHF$_2$ | OMe |
| — | 1 (cis) | —CH$_2$C$_6$H$_4$—OMe-2 | OCHF$_2$ | OMe |
| — | 1 (cis) | —CH$_2$C$_6$H$_4$—OMe-3 | OCHF$_2$ | OMe |
| — | 1 (cis) | —CH$_2$C$_6$H$_4$—OMe-4 | OCHF$_2$ | OMe |
| — | 1 (cis) | —CH$_2$CH$_2$C$_6$H$_5$ | OCHF$_2$ | OMe |
| — | 1 (cis) | H | OCHF$_2$ | OCHF$_2$ |
| — | 1 (cis) | Li | OCHF$_2$ | OCHF$_2$ |
| — | 1 (cis) | Na | OCHF$_2$ | OCHF$_2$ |
| — | 1 (cis) | K | OCHF$_2$ | OCHF$_2$ |
| — | 1 (cis) | ½Mg | OCHF$_2$ | OCHF$_2$ |
| — | 1 (cis) | ½Ca | OCHF$_2$ | OCHF$_2$ |
| — | 1 (cis) | MeNH$_3$ | OCHF$_2$ | OCHF$_2$ |
| — | 1 (cis) | EtNH$_3$ | OCHF$_2$ | OCHF$_2$ |
| — | 1 (cis) | PrNH$_3$ | OCHF$_2$ | OCHF$_2$ |
| — | 1 (cis) | $^i$PrNH$_3$ | OCHF$_2$ | OCHF$_2$ |
| — | 1 (cis) | NH$_2$CONH$_3$ | OCHF$_2$ | OCHF$_2$ |
| — | 1 (cis) | Me | OCHF$_2$ | OCHF$_2$ |
| — | 1 (cis) | Et | OCHF$_2$ | OCHF$_2$ |
| — | 1 (cis) | $^i$Pr | OCHF$_2$ | OCHF$_2$ |
| — | 1 (cis) | Pr | OCHF$_2$ | OCHF$_2$ |
| — | 1 (cis) | Bu | OCHF$_2$ | OCHF$_2$ |
| — | 1 (cis) | $^i$Bu | OCHF$_2$ | OCHF$_2$ |
| — | 1 (cis) | $^s$Bu | OCHF$_2$ | OCHF$_2$ |
| — | 1 (cis) | $^t$Bu | OCHF$_2$ | OCHF$_2$ |
| — | 1 (cis) | —CH$_2$OCH$_3$ | OCHF$_2$ | OCHF$_2$ |
| — | 1 (cis) | —CH$_2$CH$_2$OCH$_3$ | OCHF$_2$ | OCHF$_2$ |
| — | 1 (cis) | —CH$_2$SCH$_3$ | OCHF$_2$ | OCHF$_2$ |
| — | 1 (cis) | —CH$_2$CH=CH$_2$ | OCHF$_2$ | OCHF$_2$ |
| — | 1 (cis) | —C(CH$_3$)$_2$CH=CH$_2$ | OCHF$_2$ | OCHF$_2$ |
| — | 1 (cis) | —CH$_2$C≡CH$_2$ | OCHF$_2$ | OCHF$_2$ |
| — | 1 (cis) | —CH$_2$C$_6$H$_5$ | OCHF$_2$ | OCHF$_2$ |
| — | 1 (cis) | —CH$_2$C$_6$H$_4$—Cl-2 | OCHF$_2$ | OCHF$_2$ |
| — | 1 (cis) | —CH$_2$C$_6$H$_4$—Cl-3 | OCHF$_2$ | OCHF$_2$ |
| — | 1 (cis) | —CH$_2$C$_6$H$_4$—Cl-4 | OCHF$_2$ | OCHF$_2$ |
| — | 1 (cis) | —CH$_2$C$_6$H$_4$—Me-2 | OCHF$_2$ | OCHF$_2$ |
| — | 1 (cis) | —CH$_2$C$_6$H$_4$—Me-3 | OCHF$_2$ | OCHF$_2$ |
| — | 1 (cis) | —CH$_2$C$_6$H$_4$—Me-4 | OCHF$_2$ | OCHF$_2$ |
| — | 1 (cis) | —CH$_2$C$_6$H$_4$—OMe-2 | OCHF$_2$ | OCHF$_2$ |

TABLE 1-continued

A compound of the general formula:


In the below-mentioned table, Me represents methyl group, Et represents ethyl group, Pr represents propyl group, $^i$Pr represents isopropyl group, Bu represents butyl group, $^i$Bu represents isobutyl group, $^s$Bu represents butyl secondary butyl group, $^t$Bu represents tertiary butyl group, cis represents a cis-form, trans represents a trans-form, mix. represents a mixture of a cis-form and a trans-form, 1 represents a single bond and 2 represents a double bond.

| $(X)_m$ | ==== | R | $R^1$ | $R^2$ |
|---|---|---|---|---|
| — | 1 (cis) | —CH$_2$C$_6$H$_4$—OMe-3 | OCHF$_2$ | OCHF$_2$ |
| — | 1 (cis) | —CH$_2$C$_6$H$_4$—OMe-4 | OCHF$_2$ | OCHF$_2$ |
| — | 1 (cis) | —CH$_2$CH$_2$C$_6$H$_5$ | OCHF$_2$ | OCHF$_2$ |
| — | 1 (cis) | H | SMe | OMe |
| — | 1 (cis) | Li | SMe | OMe |
| — | 1 (cis) | Na | SMe | OMe |
| — | 1 (cis) | K | SMe | OMe |
| — | 1 (cis) | ½Mg | SMe | OMe |
| — | 1 (cis) | ½Ca | SMe | OMe |
| — | 1 (cis) | MeNH$_3$ | SMe | OMe |
| — | 1 (cis) | EtNH$_3$ | SMe | OMe |
| — | 1 (cis) | PrNH$_3$ | SMe | OMe |
| — | 1 (cis) | $^i$PrNH$_3$ | SMe | OMe |
| — | 1 (cis) | NH$_2$CONH$_3$ | SMe | OMe |
| — | 1 (cis) | Me | SMe | OMe |
| — | 1 (cis) | Et | SMe | OMe |
| — | 1 (cis) | $^i$Pr | SMe | OMe |
| — | 1 (cis) | Pr | SMe | OMe |
| — | 1 (cis) | Bu | SMe | OMe |
| — | 1 (cis) | $^i$Bu | SMe | OMe |
| — | 1 (cis) | $^s$Bu | SMe | OMe |
| — | 1 (cis) | $^t$Bu | SMe | OMe |
| — | 1 (cis) | —CH$_2$OCH$_3$ | SMe | OMe |
| — | 1 (cis) | —CH$_2$CH$_2$OCH$_3$ | SMe | OMe |
| — | 1 (cis) | —CH$_2$SCH$_3$ | SMe | OMe |
| — | 1 (cis) | —CH$_2$CH=CH$_2$ | SMe | OMe |
| — | 1 (cis) | —C(CH$_3$)$_2$CH=CH$_2$ | SMe | OMe |
| — | 1 (cis) | —CH$_2$C≡CH$_2$ | SMe | OMe |
| — | 1 (cis) | —CH$_2$C$_6$H$_5$ | SMe | OMe |
| — | 1 (cis) | —CH$_2$C$_6$H$_4$—Cl-2 | SMe | OMe |
| — | 1 (cis) | —CH$_2$C$_6$H$_4$—Cl-3 | SMe | OMe |
| — | 1 (cis) | —CH$_2$C$_6$H$_4$—Cl-4 | SMe | OMe |
| — | 1 (cis) | —CH$_2$C$_6$H$_4$—Me-2 | SMe | OMe |
| — | 1 (cis) | —CH$_2$C$_6$H$_4$—Me-3 | SMe | OMe |
| — | 1 (cis) | —CH$_2$C$_6$H$_4$—Me-4 | SMe | OMe |
| — | 1 (cis) | —CH$_2$C$_6$H$_4$—OMe-2 | SMe | OMe |
| — | 1 (cis) | —CH$_2$C$_6$H$_4$—OMe-3 | SMe | OMe |
| — | 1 (cis) | —CH$_2$C$_6$H$_4$—OMe-4 | SMe | OMe |
| — | 1 (cis) | —CH$_2$CH$_2$C$_6$H$_5$ | SMe | OMe |
| — | 1 (cis) | H | SMe | Me |
| — | 1 (cis) | Li | SMe | Me |
| — | 1 (cis) | Na | SMe | Me |
| — | 1 (cis) | K | SMe | Me |
| — | 1 (cis) | ½Mg | SMe | Me |
| — | 1 (cis) | ½Ca | SMe | Me |
| — | 1 (cis) | MeNH$_3$ | SMe | Me |
| — | 1 (cis) | EtNH$_3$ | SMe | Me |
| — | 1 (cis) | PrNH$_3$ | SMe | Me |
| — | 1 (cis) | $^i$PrNH$_3$ | SMe | Me |
| — | 1 (cis) | NH$_2$CONH$_3$ | SMe | Me |
| — | 1 (cis) | Me | SMe | Me |
| — | 1 (cis) | Et | SMe | Me |
| — | 1 (cis) | $^i$Pr | SMe | Me |
| — | 1 (cis) | Pr | SMe | Me |
| — | 1 (cis) | Bu | SMe | Me |
| — | 1 (cis) | $^i$Bu | SMe | Me |
| — | 1 (cis) | $^s$Bu | SMe | Me |
| — | 1 (cis) | $^t$Bu | SMe | Me |
| — | 1 (cis) | —CH$_2$OCH$_3$ | SMe | Me |
| — | 1 (cis) | —CH$_2$CH$_2$OCH$_3$ | SMe | Me |
| — | 1 (cis) | —CH$_2$SCH$_3$ | SMe | Me |
| — | 1 (cis) | —CH$_2$CH=CH$_2$ | SMe | Me |
| — | 1 (cis) | —C(CH$_3$)$_2$CH=CH$_2$ | SMe | Me |
| — | 1 (cis) | —CH$_2$C≡CH$_2$ | SMe | Me |
| — | 1 (cis) | —CH$_2$C$_6$H$_5$ | SMe | Me |
| — | 1 (cis) | —CH$_2$C$_6$H$_4$—Cl-2 | SMe | Me |
| — | 1 (cis) | —CH$_2$C$_6$H$_4$—Cl-3 | SMe | Me |
| — | 1 (cis) | —CH$_2$C$_6$H$_4$—Cl-4 | SMe | Me |
| — | 1 (cis) | —CH$_2$C$_6$H$_4$—Me-2 | SMe | Me |
| — | 1 (cis) | —CH$_2$C$_6$H$_4$—Me-3 | SMe | Me |
| — | 1 (cis) | —CH$_2$C$_6$H$_4$—Me-4 | SMe | Me |
| — | 1 (cis) | —CH$_2$C$_6$H$_4$—OMe-2 | SMe | Me |
| — | 1 (cis) | —CH$_2$C$_6$H$_4$—OMe-3 | SMe | Me |
| — | 1 (cis) | —CH$_2$C$_6$H$_4$—OMe-4 | SMe | Me |
| — | 1 (cis) | —CH$_2$CH$_2$C$_6$H$_5$ | SMe | Me |
| — | 1 (trans) | H | Me | Me |
| — | 1 (trans) | Li | Me | Me |
| — | 1 (trans) | Na | Me | Me |
| — | 1 (trans) | K | Me | Me |
| — | 1 (trans) | ½Mg | Me | Me |
| — | 1 (trans) | ½Ca | Me | Me |
| — | 1 (trans) | MeNH$_3$ | Me | Me |
| — | 1 (trans) | EtNH$_3$ | Me | Me |
| — | 1 (trans) | PrNH$_3$ | Me | Me |
| — | 1 (trans) | $^i$PrNH$_3$ | Me | Me |
| — | 1 (trans) | NH$_2$CONH$_3$ | Me | Me |
| — | 1 (trans) | Me | Me | Me |
| — | 1 (trans) | Et | Me | Me |
| — | 1 (trans) | $^i$Pr | Me | Me |
| — | 1 (trans) | Pr | Me | Me |
| — | 1 (trans) | Bu | Me | Me |
| — | 1 (trans) | $^i$Bu | Me | Me |
| — | 1 (trans) | $^s$Bu | Me | Me |
| — | 1 (trans) | $^t$Bu | Me | Me |
| — | 1 (trans) | —CH$_2$OCH$_3$ | Me | Me |
| — | 1 (trans) | —CH$_2$CH$_2$OCH$_3$ | Me | Me |
| — | 1 (trans) | —CH$_2$SCH$_3$ | Me | Me |
| — | 1 (trans) | —CH$_2$CH=CH$_2$ | Me | Me |
| — | 1 (trans) | —C(CH$_3$)$_2$CH=CH$_2$ | Me | Me |
| — | 1 (trans) | —CH$_2$C≡CH$_2$ | Me | Me |
| — | 1 (trans) | —CH$_2$C$_6$H$_5$ | Me | Me |
| — | 1 (trans) | —CH$_2$C$_6$H$_4$—Cl-2 | Me | Me |
| — | 1 (trans) | —CH$_2$C$_6$H$_4$—Cl-3 | Me | Me |
| — | 1 (trans) | —CH$_2$C$_6$H$_4$—Cl-4 | Me | Me |
| — | 1 (trans) | —CH$_2$C$_6$H$_4$—Me-2 | Me | Me |
| — | 1 (trans) | —CH$_2$C$_6$H$_4$—Me-3 | Me | Me |
| — | 1 (trans) | —CH$_2$C$_6$H$_4$—Me-4 | Me | Me |
| — | 1 (trans) | —CH$_2$C$_6$H$_4$—OMe-2 | Me | Me |
| — | 1 (trans) | —CH$_2$C$_6$H$_4$—OMe-3 | Me | Me |
| — | 1 (trans) | —CH$_2$C$_6$H$_4$—OMe-4 | Me | Me |
| — | 1 (trans) | —CH$_2$CH$_2$C$_6$H$_5$ | Me | Me |
| — | 1 (trans) | H | OMe | Me |
| — | 1 (trans) | Li | OMe | Me |
| — | 1 (trans) | Na | OMe | Me |
| — | 1 (trans) | K | OMe | Me |
| — | 1 (trans) | ½Mg | OMe | Me |
| — | 1 (trans) | ½Ca | OMe | Me |
| — | 1 (trans) | MeNH$_3$ | OMe | Me |
| — | 1 (trans) | EtNH$_3$ | OMe | Me |
| — | 1 (trans) | PrNH$_3$ | OMe | Me |
| — | 1 (trans) | $^i$PrNH$_3$ | OMe | Me |
| — | 1 (trans) | NH$_2$CONH$_3$ | OMe | Me |


TABLE 1-continued

A compound of the general formula:

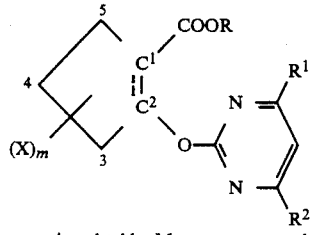

In the below-mentioned table, Me represents methyl group, Et represents ethyl group, Pr represents propyl group, $^i$Pr represents isopropyl group, Bu represents butyl group, $^i$Bu represents isobutyl group, $^s$Bu represents butyl secondary butyl group, $^t$Bu represents tertiary butyl group, cis represents a cis-form, trans represents a trans-form, mix. represents a mixture of a cis-form and a trans-form, 1 represents a single bond and 2 represents a double bond.

| $(X)_m$ | ==== | R | $R^1$ | $R^2$ |
|---|---|---|---|---|
| — | 1 (trans) | Me | OMe | Me |
| — | 1 (trans) | Et | OMe | Me |
| — | 1 (trans) | $^i$Pr | OMe | Me |
| — | 1 (trans) | Pr | OMe | Me |
| — | 1 (trans) | Bu | OMe | Me |
| — | 1 (trans) | $^i$Bu | OMe | Me |
| — | 1 (trans) | $^s$Bu | OMe | Me |
| — | 1 (trans) | $^t$Bu | OMe | Me |
| — | 1 (trans) | —CH$_2$OCH$_3$ | OMe | Me |
| — | 1 (trans) | —CH$_2$CH$_2$OCH$_3$ | OMe | Me |
| — | 1 (trans) | —CH$_2$SCH$_3$ | OMe | Me |
| — | 1 (trans) | —CH$_2$CH=CH$_2$ | OMe | Me |
| — | 1 (trans) | —C(CH$_3$)$_2$CH=CH$_2$ | OMe | Me |
| — | 1 (trans) | —CH$_2$C≡CH$_2$ | OMe | Me |
| — | 1 (trans) | —CH$_2$C$_6$H$_5$ | OMe | Me |
| — | 1 (trans) | —CH$_2$C$_6$H$_4$—Cl-2 | OMe | Me |
| — | 1 (trans) | —CH$_2$C$_6$H$_4$—Cl-3 | OMe | Me |
| — | 1 (trans) | —CH$_2$C$_6$H$_4$—Cl-4 | OMe | Me |
| — | 1 (trans) | —CH$_2$C$_6$H$_4$—Me-2 | OMe | Me |
| — | 1 (trans) | —CH$_2$C$_6$H$_4$—Me-3 | OMe | Me |
| — | 1 (trans) | —CH$_2$C$_6$H$_4$—Me-4 | OMe | Me |
| — | 1 (trans) | —CH$_2$C$_6$H$_4$—OMe-2 | OMe | Me |
| — | 1 (trans) | —CH$_2$C$_6$H$_4$—OMe-3 | OMe | Me |
| — | 1 (trans) | —CH$_2$C$_6$H$_4$—OMe-4 | OMe | Me |
| — | 1 (trans) | —CH$_2$CH$_2$C$_6$H$_5$ | OMe | Me |
| — | 1 (trans) | H | OMe | OMe |
| — | 1 (trans) | Li | OMe | OMe |
| — | 1 (trans) | Na | OMe | OMe |
| — | 1 (trans) | K | OMe | OMe |
| — | 1 (trans) | ½Mg | OMe | OMe |
| — | 1 (trans) | ½Ca | OMe | OMe |
| — | 1 (trans) | MeNH$_3$ | OMe | OMe |
| — | 1 (trans) | EtNH$_3$ | OMe | OMe |
| — | 1 (trans) | PrNH$_3$ | OMe | OMe |
| — | 1 (trans) | $^i$PrNH$_3$ | OMe | OMe |
| — | 1 (trans) | NH$_2$CONH$_3$ | OMe | OMe |
| — | 1 (trans) | Me | OMe | OMe |
| — | 1 (trans) | Et | OMe | OMe |
| — | 1 (trans) | $^i$Pr | OMe | OMe |
| — | 1 (trans) | Pr | OMe | OMe |
| — | 1 (trans) | Bu | OMe | OMe |
| — | 1 (trans) | $^i$Bu | OMe | OMe |
| — | 1 (trans) | $^s$Bu | OMe | OMe |
| — | 1 (trans) | $^t$Bu | OMe | OMe |
| — | 1 (trans) | —CH$_2$OCH$_3$ | OMe | OMe |
| — | 1 (trans) | —CH$_2$CH$_2$OCH$_3$ | OMe | OMe |
| — | 1 (trans) | —CH$_2$SCH$_3$ | OMe | OMe |
| — | 1 (trans) | —CH$_2$CH=CH$_2$ | OMe | OMe |
| — | 1 (trans) | —C(CH$_3$)$_2$CH=CH$_2$ | OMe | OMe |
| — | 1 (trans) | —CH$_2$C≡CH$_2$ | OMe | OMe |
| — | 1 (trans) | —CH$_2$C$_6$H$_5$ | OMe | OMe |
| — | 1 (trans) | —CH$_2$C$_6$H$_4$—Cl-2 | OMe | OMe |
| — | 1 (trans) | —CH$_2$C$_6$H$_4$—Cl-3 | OMe | OMe |
| — | 1 (trans) | —CH$_2$C$_6$H$_4$—Cl-4 | OMe | OMe |
| — | 1 (trans) | —CH$_2$C$_6$H$_4$—Me-2 | OMe | OMe |
| — | 1 (trans) | —CH$_2$C$_6$H$_4$—Me-3 | OMe | OMe |
| — | 1 (trans) | —CH$_2$C$_6$H$_4$—Me-4 | OMe | OMe |
| — | 1 (trans) | —CH$_2$C$_6$H$_4$—OMe-2 | OMe | OMe |
| — | 1 (trans) | —CH$_2$C$_6$H$_4$—OMe-3 | OMe | OMe |
| — | 1 (trans) | —CH$_2$C$_6$H$_4$—OMe-4 | OMe | OMe |
| — | 1 (trans) | —CH$_2$CH$_2$C$_6$H$_5$ | OMe | OMe |

TABLE 1-continued

A compound of the general formula:

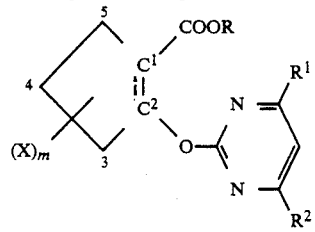

In the below-mentioned table, Me represents methyl group, Et represents ethyl group, Pr represents propyl group, $^i$Pr represents isopropyl group, Bu represents butyl group, $^i$Bu represents isobutyl group, $^s$Bu represents butyl secondary butyl group, $^t$Bu represents tertiary butyl group, cis represents a cis-form, trans represents a trans-form, mix. represents a mixture of a cis-form and a trans-form, 1 represents a single bond and 2 represents a double bond.

| $(X)_m$ | ==== | R | $R^1$ | $R^2$ |
|---|---|---|---|---|
| — | 1 (trans) | H | Cl | Me |
| — | 1 (trans) | Li | Cl | Me |
| — | 1 (trans) | Na | Cl | Me |
| — | 1 (trans) | K | Cl | Me |
| — | 1 (trans) | ½Mg | Cl | Me |
| — | 1 (trans) | ½Ca | Cl | Me |
| — | 1 (trans) | MeNH$_3$ | Cl | Me |
| — | 1 (trans) | EtNH$_3$ | Cl | Me |
| — | 1 (trans) | PrNH$_3$ | Cl | Me |
| — | 1 (trans) | $^i$PrNH$_3$ | Cl | Me |
| — | 1 (trans) | NH$_2$CONH$_3$ | Cl | Me |
| — | 1 (trans) | Me | Cl | Me |
| — | 1 (trans) | Et | Cl | Me |
| — | 1 (trans) | $^i$Pr | Cl | Me |
| — | 1 (trans) | Pr | Cl | Me |
| — | 1 (trans) | Bu | Cl | Me |
| — | 1 (trans) | $^i$Bu | Cl | Me |
| — | 1 (trans) | $^s$Bu | Cl | Me |
| — | 1 (trans) | $^t$Bu | Cl | Me |
| — | 1 (trans) | —CH$_2$OCH$_3$ | Cl | Me |
| — | 1 (trans) | —CH$_2$CH$_2$OCH$_3$ | Cl | Me |
| — | 1 (trans) | —CH$_2$SCH$_3$ | Cl | Me |
| — | 1 (trans) | —CH$_2$CH=CH$_2$ | Cl | Me |
| — | 1 (trans) | —C(CH$_3$)$_2$CH=CH$_2$ | Cl | Me |
| — | 1 (trans) | —CH$_2$C≡CH$_2$ | Cl | Me |
| — | 1 (trans) | —CH$_2$C$_6$H$_5$ | Cl | Me |
| — | 1 (trans) | —CH$_2$C$_6$H$_4$—Cl-2 | Cl | Me |
| — | 1 (trans) | —CH$_2$C$_6$H$_4$—Cl-3 | Cl | Me |
| — | 1 (trans) | —CH$_2$C$_6$H$_4$—Cl-4 | Cl | Me |
| — | 1 (trans) | —CH$_2$C$_6$H$_4$—Me-2 | Cl | Me |
| — | 1 (trans) | —CH$_2$C$_6$H$_4$—Me-3 | Cl | Me |
| — | 1 (trans) | —CH$_2$C$_6$H$_4$—Me-4 | Cl | Me |
| — | 1 (trans) | —CH$_2$C$_6$H$_4$—OMe-2 | Cl | Me |
| — | 1 (trans) | —CH$_2$C$_6$H$_4$—OMe-3 | Cl | Me |
| — | 1 (trans) | —CH$_2$C$_6$H$_4$—OMe-4 | Cl | Me |
| — | 1 (trans) | —CH$_2$CH$_2$C$_6$H$_5$ | Cl | Me |
| — | 1 (trans) | H | Cl | Cl |
| — | 1 (trans) | Li | Cl | Cl |
| — | 1 (trans) | Na | Cl | Cl |
| — | 1 (trans) | K | Cl | Cl |
| — | 1 (trans) | ½Mg | Cl | Cl |
| — | 1 (trans) | ½Ca | Cl | Cl |
| — | 1 (trans) | MeNH$_3$ | Cl | Cl |
| — | 1 (trans) | EtNH$_3$ | Cl | Cl |
| — | 1 (trans) | PrNH$_3$ | Cl | Cl |
| — | 1 (trans) | $^i$PrNH$_3$ | Cl | Cl |
| — | 1 (trans) | NH$_2$CONH$_3$ | Cl | Cl |
| — | 1 (trans) | Me | Cl | Cl |
| — | 1 (trans) | Et | Cl | Cl |
| — | 1 (trans) | $^i$Pr | Cl | Cl |
| — | 1 (trans) | Pr | Cl | Cl |
| — | 1 (trans) | Bu | Cl | Cl |
| — | 1 (trans) | $^i$Bu | Cl | Cl |
| — | 1 (trans) | $^s$Bu | Cl | Cl |
| — | 1 (trans) | $^t$Bu | Cl | Cl |
| — | 1 (trans) | —CH$_2$OCH$_3$ | Cl | Cl |
| — | 1 (trans) | —CH$_2$CH$_2$OCH$_3$ | Cl | Cl |
| — | 1 (trans) | —CH$_2$SCH$_3$ | Cl | Cl |
| — | 1 (trans) | —CH$_2$CH=CH$_2$ | Cl | Cl |
| — | 1 (trans) | —C(CH$_3$)$_2$CH=CH$_2$ | Cl | Cl |
| — | 1 (trans) | —CH$_2$C≡CH$_2$ | Cl | Cl |

TABLE 1-continued

A compound of the general formula:

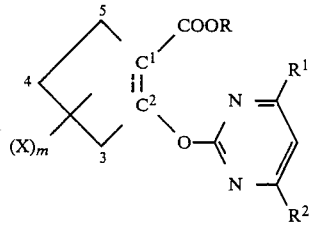

In the below-mentioned table, Me represents methyl group, Et represents ethyl group, Pr represents propyl group, $^i$Pr represents isopropyl group, Bu represents butyl group, $^i$Bu represents isobutyl group, $^s$Bu represents butyl secondary butyl group, $^t$Bu represents tertiary butyl group, cis represents a cis-form, trans represents a trans-form, mix. represents a mixture of a cis-form and a trans-form, 1 represents a single bond and 2 represents a double bond.

| $(X)_m$ | ==== | R | $R^1$ | $R^2$ |
|---|---|---|---|---|
| — | 1 (trans) | —CH$_2$C$_6$H$_5$ | Cl | Cl |
| — | 1 (trans) | —CH$_2$C$_6$H$_4$—Cl-2 | Cl | Cl |
| — | 1 (trans) | —CH$_2$C$_6$H$_4$—Cl-3 | Cl | Cl |
| — | 1 (trans) | —CH$_2$C$_6$H$_4$—Cl-4 | Cl | Cl |
| — | 1 (trans) | —CH$_2$C$_6$H$_4$—Me-2 | Cl | Cl |
| — | 1 (trans) | —CH$_2$C$_6$H$_4$—Me-3 | Cl | Cl |
| — | 1 (trans) | —CH$_2$C$_6$H$_4$—Me-4 | Cl | Cl |
| — | 1 (trans) | —CH$_2$C$_6$H$_4$—OMe-2 | Cl | Cl |
| — | 1 (trans) | —CH$_2$C$_6$H$_4$—OMe-3 | Cl | Cl |
| — | 1 (trans) | —CH$_2$C$_6$H$_4$—OMe-4 | Cl | Cl |
| — | 1 (trans) | —CH$_2$CH$_2$C$_6$H$_5$ | Cl | Cl |
| — | 1 (trans) | H | Cl | OMe |
| — | 1 (trans) | Li | Cl | OMe |
| — | 1 (trans) | Na | Cl | OMe |
| — | 1 (trans) | K | Cl | OMe |
| — | 1 (trans) | ½Mg | Cl | OMe |
| — | 1 (trans) | ½Ca | Cl | OMe |
| — | 1 (trans) | MeNH$_3$ | Cl | OMe |
| — | 1 (trans) | EtNH$_3$ | Cl | OMe |
| — | 1 (trans) | PrNH$_3$ | Cl | OMe |
| — | 1 (trans) | $^i$PrNH$_3$ | Cl | OMe |
| — | 1 (trans) | NH$_2$CONH$_3$ | Cl | OMe |
| — | 1 (trans) | Me | Cl | OMe |
| — | 1 (trans) | Et | Cl | OMe |
| — | 1 (trans) | $^i$Pr | Cl | OMe |
| — | 1 (trans) | Pr | Cl | OMe |
| — | 1 (trans) | Bu | Cl | OMe |
| — | 1 (trans) | $^i$Bu | Cl | OMe |
| — | 1 (trans) | $^s$Bu | Cl | OMe |
| — | 1 (trans) | $^t$Bu | Cl | OMe |
| — | 1 (trans) | —CH$_2$OCH$_3$ | Cl | OMe |
| — | 1 (trans) | —CH$_2$CH$_2$OCH$_3$ | Cl | OMe |
| — | 1 (trans) | —CH$_2$SCH$_3$ | Cl | OMe |
| — | 1 (trans) | —CH$_2$CH=CH$_2$ | Cl | OMe |
| — | 1 (trans) | —C(CH$_3$)$_2$CH=CH$_2$ | Cl | OMe |
| — | 1 (trans) | —CH$_2$C≡CH$_2$ | Cl | OMe |
| — | 1 (trans) | —CH$_2$C$_6$H$_5$ | Cl | OMe |
| — | 1 (trans) | —CH$_2$C$_6$H$_4$—Cl-2 | Cl | OMe |
| — | 1 (trans) | —CH$_2$C$_6$H$_4$—Cl-3 | Cl | OMe |
| — | 1 (trans) | —CH$_2$C$_6$H$_4$—Cl-4 | Cl | OMe |
| — | 1 (trans) | —CH$_2$C$_6$H$_4$—Me-2 | Cl | OMe |
| — | 1 (trans) | —CH$_2$C$_6$H$_4$—Me-3 | Cl | OMe |
| — | 1 (trans) | —CH$_2$C$_6$H$_4$—Me-4 | Cl | OMe |
| — | 1 (trans) | —CH$_2$C$_6$H$_4$—OMe-2 | Cl | OMe |
| — | 1 (trans) | —CH$_2$C$_6$H$_4$—OMe-3 | Cl | OMe |
| — | 1 (trans) | —CH$_2$C$_6$H$_4$—OMe-4 | Cl | OMe |
| — | 1 (trans) | —CH$_2$CH$_2$C$_6$H$_5$ | Cl | OMe |
| — | 1 (trans) | H | OCHF$_2$ | OMe |
| — | 1 (trans) | Li | OCHF$_2$ | OMe |
| — | 1 (trans) | Na | OCHF$_2$ | OMe |
| — | 1 (trans) | K | OCHF$_2$ | OMe |
| — | 1 (trans) | ½Mg | OCHF$_2$ | OMe |
| — | 1 (trans) | ½Ca | OCHF$_2$ | OMe |
| — | 1 (trans) | MeNH$_3$ | OCHF$_2$ | OMe |
| — | 1 (trans) | EtNH$_3$ | OCHF$_2$ | OMe |
| — | 1 (trans) | PrNH$_3$ | OCHF$_2$ | OMe |
| — | 1 (trans) | $^i$PrNH$_3$ | OCHF$_2$ | OMe |
| — | 1 (trans) | NH$_2$CONH$_3$ | OCHF$_2$ | OMe |
| — | 1 (trans) | Me | OCHF$_2$ | OMe |
| — | 1 (trans) | Et | OCHF$_2$ | OMe |
| — | 1 (trans) | $^i$Pr | OCHF$_2$ | OMe |

TABLE 1-continued

A compound of the general formula:

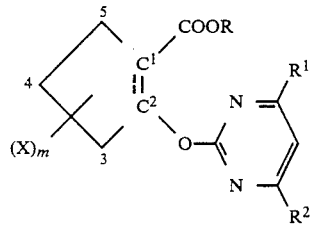

In the below-mentioned table, Me represents methyl group, Et represents ethyl group, Pr represents propyl group, $^i$Pr represents isopropyl group, Bu represents butyl group, $^i$Bu represents isobutyl group, $^s$Bu represents butyl secondary butyl group, $^t$Bu represents tertiary butyl group, cis represents a cis-form, trans represents a trans-form, mix. represents a mixture of a cis-form and a trans-form, 1 represents a single bond and 2 represents a double bond.

| $(X)_m$ | ==== | R | $R^1$ | $R^2$ |
|---|---|---|---|---|
| — | 1 (trans) | Pr | OCHF$_2$ | OMe |
| — | 1 (trans) | Bu | OCHF$_2$ | OMe |
| — | 1 (trans) | $^i$Bu | OCHF$_2$ | OMe |
| — | 1 (trans) | $^s$Bu | OCHF$_2$ | OMe |
| — | 1 (trans) | $^t$Bu | OCHF$_2$ | OMe |
| — | 1 (trans) | —CH$_2$OCH$_3$ | OCHF$_2$ | OMe |
| — | 1 (trans) | —CH$_2$CH$_2$OCH$_3$ | OCHF$_2$ | OMe |
| — | 1 (trans) | —CH$_2$SCH$_3$ | OCHF$_2$ | OMe |
| — | 1 (trans) | —CH$_2$CH=CH$_2$ | OCHF$_2$ | OMe |
| — | 1 (trans) | —C(CH$_3$)$_2$CH=CH$_2$ | OCHF$_2$ | OMe |
| — | 1 (trans) | —CH$_2$C≡CH$_2$ | OCHF$_2$ | OMe |
| — | 1 (trans) | —CH$_2$C$_6$H$_5$ | OCHF$_2$ | OMe |
| — | 1 (trans) | —CH$_2$C$_6$H$_4$—Cl-2 | OCHF$_2$ | OMe |
| — | 1 (trans) | —CH$_2$C$_6$H$_4$—Cl-3 | OCHF$_2$ | OMe |
| — | 1 (trans) | —CH$_2$C$_6$H$_4$—Cl-4 | OCHF$_2$ | OMe |
| — | 1 (trans) | —CH$_2$C$_6$H$_4$—Me-2 | OCHF$_2$ | OMe |
| — | 1 (trans) | —CH$_2$C$_6$H$_4$—Me-3 | OCHF$_2$ | OMe |
| — | 1 (trans) | —CH$_2$C$_6$H$_4$—Me-4 | OCHF$_2$ | OMe |
| — | 1 (trans) | —CH$_2$C$_6$H$_4$—OMe-2 | OCHF$_2$ | OMe |
| — | 1 (trans) | —CH$_2$C$_6$H$_4$—OMe-3 | OCHF$_2$ | OMe |
| — | 1 (trans) | —CH$_2$C$_6$H$_4$—OMe-4 | OCHF$_2$ | OMe |
| — | 1 (trans) | —CH$_2$CH$_2$C$_6$H$_5$ | OCHF$_2$ | OMe |
| — | 1 (trans) | H | OCHF$_2$ | OCHF$_2$ |
| — | 1 (trans) | Li | OCHF$_2$ | OCHF$_2$ |
| — | 1 (trans) | Na | OCHF$_2$ | OCHF$_2$ |
| — | 1 (trans) | K | OCHF$_2$ | OCHF$_2$ |
| — | 1 (trans) | ½Mg | OCHF$_2$ | OCHF$_2$ |
| — | 1 (trans) | ½Ca | OCHF$_2$ | OCHF$_2$ |
| — | 1 (trans) | MeNH$_3$ | OCHF$_2$ | OCHF$_2$ |
| — | 1 (trans) | EtNH$_3$ | OCHF$_2$ | OCHF$_2$ |
| — | 1 (trans) | PrNH$_3$ | OCHF$_2$ | OCHF$_2$ |
| — | 1 (trans) | $^i$PrNH$_3$ | OCHF$_2$ | OCHF$_2$ |
| — | 1 (trans) | NH$_2$CONH$_3$ | OCHF$_2$ | OCHF$_2$ |
| — | 1 (trans) | Me | OCHF$_2$ | OCHF$_2$ |
| — | 1 (trans) | Et | OCHF$_2$ | OCHF$_2$ |
| — | 1 (trans) | $^i$Pr | OCHF$_2$ | OCHF$_2$ |
| — | 1 (trans) | Pr | OCHF$_2$ | OCHF$_2$ |
| — | 1 (trans) | Bu | OCHF$_2$ | OCHF$_2$ |
| — | 1 (trans) | $^i$Bu | OCHF$_2$ | OCHF$_2$ |
| — | 1 (trans) | $^s$Bu | OCHF$_2$ | OCHF$_2$ |
| — | 1 (trans) | $^t$Bu | OCHF$_2$ | OCHF$_2$ |
| — | 1 (trans) | —CH$_2$OCH$_3$ | OCHF$_2$ | OCHF$_2$ |
| — | 1 (trans) | —CH$_2$CH$_2$OCH$_3$ | OCHF$_2$ | OCHF$_2$ |
| — | 1 (trans) | —CH$_2$SCH$_3$ | OCHF$_2$ | OCHF$_2$ |
| — | 1 (trans) | —CH$_2$CH=CH$_2$ | OCHF$_2$ | OCHF$_2$ |
| — | 1 (trans) | —C(CH$_3$)$_2$CH=CH$_2$ | OCHF$_2$ | OCHF$_2$ |
| — | 1 (trans) | —CH$_2$C≡CH$_2$ | OCHF$_2$ | OCHF$_2$ |
| — | 1 (trans) | —CH$_2$C$_6$H$_5$ | OCHF$_2$ | OCHF$_2$ |
| — | 1 (trans) | —CH$_2$C$_6$H$_4$—Cl-2 | OCHF$_2$ | OCHF$_2$ |
| — | 1 (trans) | —CH$_2$C$_6$H$_4$—Cl-3 | OCHF$_2$ | OCHF$_2$ |
| — | 1 (trans) | —CH$_2$C$_6$H$_4$—Cl-4 | OCHF$_2$ | OCHF$_2$ |
| — | 1 (trans) | —CH$_2$C$_6$H$_4$—Me-2 | OCHF$_2$ | OCHF$_2$ |
| — | 1 (trans) | —CH$_2$C$_6$H$_4$—Me-3 | OCHF$_2$ | OCHF$_2$ |
| — | 1 (trans) | —CH$_2$C$_6$H$_4$—Me-4 | OCHF$_2$ | OCHF$_2$ |
| — | 1 (trans) | —CH$_2$C$_6$H$_4$—OMe-2 | OCHF$_2$ | OCHF$_2$ |
| — | 1 (trans) | —CH$_2$C$_6$H$_4$—OMe-3 | OCHF$_2$ | OCHF$_2$ |
| — | 1 (trans) | —CH$_2$C$_6$H$_4$—OMe-4 | OCHF$_2$ | OCHF$_2$ |
| — | 1 (trans) | —CH$_2$CH$_2$C$_6$H$_5$ | OCHF$_2$ | OCHF$_2$ |
| — | 1 (trans) | H | SMe | OMe |
| — | 1 (trans) | Li | SMe | OMe |
| — | 1 (trans) | Na | SMe | OMe |

TABLE 1-continued

A compound of the general formula:

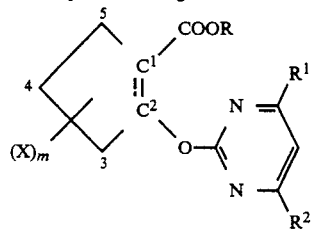

In the below-mentioned table, Me represents methyl group, Et represents ethyl group, Pr represents propyl group, $^i$Pr represents isopropyl group, Bu represents butyl group, $^i$Bu represents isobutyl group, $^s$Bu represents butyl secondary butyl group, $^t$Bu represents tertiary butyl group, cis represents a cis-form, trans represents a trans-form, mix. represents a mixture of a cis-form and a trans-form, 1 represents a single bond and 2 represents a double bond.

| $(X)_m$ | = | R | $R^1$ | $R^2$ |
|---|---|---|---|---|
| — | 1 (trans) | K | SMe | OMe |
| — | 1 (trans) | ½Mg | SMe | OMe |
| — | 1 (trans) | ½Ca | SMe | OMe |
| — | 1 (trans) | MeNH$_3$ | SMe | OMe |
| — | 1 (trans) | EtNH$_3$ | SMe | OMe |
| — | 1 (trans) | PrNH$_3$ | SMe | OMe |
| — | 1 (trans) | $^i$PrNH$_3$ | SMe | OMe |
| — | 1 (trans) | NH$_2$CONH$_3$ | SMe | OMe |
| — | 1 (trans) | Me | SMe | OMe |
| — | 1 (trans) | Et | SMe | OMe |
| — | 1 (trans) | $^i$Pr | SMe | OMe |
| — | 1 (trans) | Pr | SMe | OMe |
| — | 1 (trans) | Bu | SMe | OMe |
| — | 1 (trans) | $^i$Bu | SMe | OMe |
| — | 1 (trans) | $^s$Bu | SMe | OMe |
| — | 1 (trans) | $^t$Bu | SMe | OMe |
| — | 1 (trans) | —CH$_2$OCH$_3$ | SMe | OMe |
| — | 1 (trans) | —CH$_2$CH$_2$OCH$_3$ | SMe | OMe |
| — | 1 (trans) | —CH$_2$SCH$_3$ | SMe | OMe |
| — | 1 (trans) | —CH$_2$CH=CH$_2$ | SMe | OMe |
| — | 1 (trans) | —C(CH$_3$)$_2$CH=CH$_2$ | SMe | OMe |
| — | 1 (trans) | —CH$_2$C≡CH$_2$ | SMe | OMe |
| — | 1 (trans) | —CH$_2$C$_6$H$_5$ | SMe | OMe |
| — | 1 (trans) | —CH$_2$C$_6$H$_4$—Cl-2 | SMe | OMe |
| — | 1 (trans) | —CH$_2$C$_6$H$_4$—Cl-3 | SMe | OMe |
| — | 1 (trans) | —CH$_2$C$_6$H$_4$—Cl-4 | SMe | OMe |
| — | 1 (trans) | —CH$_2$C$_6$H$_4$—Me-2 | SMe | OMe |
| — | 1 (trans) | —CH$_2$C$_6$H$_4$—Me-3 | SMe | OMe |
| — | 1 (trans) | —CH$_2$C$_6$H$_4$—Me-4 | SMe | OMe |
| — | 1 (trans) | —CH$_2$C$_6$H$_4$—OMe-2 | SMe | OMe |
| — | 1 (trans) | —CH$_2$C$_6$H$_4$—OMe-3 | SMe | OMe |
| — | 1 (trans) | —CH$_2$C$_6$H$_4$—OMe-4 | SMe | OMe |
| — | 1 (trans) | —CH$_2$CH$_2$C$_6$H$_5$ | SMe | OMe |
| — | 1 (trans) | H | SMe | Me |
| — | 1 (trans) | Li | SMe | Me |
| — | 1 (trans) | Na | SMe | Me |
| — | 1 (trans) | K | SMe | Me |
| — | 1 (trans) | ½Mg | SMe | Me |
| — | 1 (trans) | ½Ca | SMe | Me |
| — | 1 (trans) | MeNH$_3$ | SMe | Me |
| — | 1 (trans) | EtNH$_3$ | SMe | Me |
| — | 1 (trans) | PrNH$_3$ | SMe | Me |
| — | 1 (trans) | $^i$PrNH$_3$ | SMe | Me |
| — | 1 (trans) | NH$_2$CONH$_3$ | SMe | Me |
| — | 1 (trans) | Me | SMe | Me |
| — | 1 (trans) | Et | SMe | Me |
| — | 1 (trans) | $^i$Pr | SMe | Me |
| — | 1 (trans) | Pr | SMe | Me |
| — | 1 (trans) | Bu | SMe | Me |
| — | 1 (trans) | $^i$Bu | SMe | Me |
| — | 1 (trans) | $^s$Bu | SMe | Me |
| — | 1 (trans) | $^t$Bu | SMe | Me |
| — | 1 (trans) | —CH$_2$OCH$_3$ | SMe | Me |
| — | 1 (trans) | —CH$_2$CH$_2$OCH$_3$ | SMe | Me |
| — | 1 (trans) | —CH$_2$SCH$_3$ | SMe | Me |
| — | 1 (trans) | —CH$_2$CH=CH$_2$ | SMe | Me |
| — | 1 (trans) | —C(CH$_3$)$_2$CH=CH$_2$ | SMe | Me |
| — | 1 (trans) | —CH$_2$C≡CH$_2$ | SMe | Me |
| — | 1 (trans) | —CH$_2$C$_6$H$_5$ | SMe | Me |
| — | 1 (trans) | —CH$_2$C$_6$H$_4$—Cl-2 | SMe | Me |
| — | 1 (trans) | —CH$_2$C$_6$H$_4$—Cl-3 | SMe | Me |

TABLE 1-continued

A compound of the general formula:

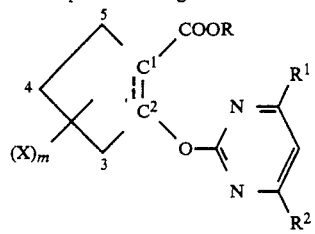

In the below-mentioned table, Me represents methyl group, Et represents ethyl group, Pr represents propyl group, $^i$Pr represents isopropyl group, Bu represents butyl group, $^i$Bu represents isobutyl group, $^s$Bu represents butyl secondary butyl group, $^t$Bu represents tertiary butyl group, cis represents a cis-form, trans represents a trans-form, mix. represents a mixture of a cis-form and a trans-form, 1 represents a single bond and 2 represents a double bond.

| $(X)_m$ | = | R | $R^1$ | $R^2$ |
|---|---|---|---|---|
| — | 1 (trans) | —CH$_2$C$_6$H$_4$—Cl-4 | SMe | Me |
| — | 1 (trans) | —CH$_2$C$_6$H$_4$—Me-2 | SMe | Me |
| — | 1 (trans) | —CH$_2$C$_6$H$_4$—Me-3 | SMe | Me |
| — | 1 (trans) | —CH$_2$C$_6$H$_4$—Me-4 | SMe | Me |
| — | 1 (trans) | —CH$_2$C$_6$H$_4$—OMe-2 | SMe | Me |
| — | 1 (trans) | —CH$_2$C$_6$H$_4$—OMe-3 | SMe | Me |
| — | 1 (trans) | —CH$_2$C$_6$H$_4$—OMe-4 | SMe | Me |
| — | 1 (trans) | —CH$_2$CH$_2$C$_6$H$_5$ | SMe | Me |
| — | 1 (mix.) | H | Me | Me |
| — | 1 (mix.) | Li | Me | Me |
| — | 1 (mix.) | Na | Me | Me |
| — | 1 (mix.) | K | Me | Me |
| — | 1 (mix.) | ½Mg | Me | Me |
| — | 1 (mix.) | ½Ca | Me | Me |
| — | 1 (mix.) | MeNH$_3$ | Me | Me |
| — | 1 (mix.) | EtNH$_3$ | Me | Me |
| — | 1 (mix.) | PrNH$_3$ | Me | Me |
| — | 1 (mix.) | $^i$PrNH$_3$ | Me | Me |
| — | 1 (mix.) | NH$_2$CONH$_3$ | Me | Me |
| — | 1 (mix.) | Me | Me | Me |
| — | 1 (mix.) | Et | Me | Me |
| — | 1 (mix.) | $^i$Pr | Me | Me |
| — | 1 (mix.) | Pr | Me | Me |
| — | 1 (mix.) | Bu | Me | Me |
| — | 1 (mix.) | $^i$Bu | Me | Me |
| — | 1 (mix.) | $^s$Bu | Me | Me |
| — | 1 (mix.) | $^t$Bu | Me | Me |
| — | 1 (mix.) | —CH$_2$OCH$_3$ | Me | Me |
| — | 1 (mix.) | —CH$_2$CH$_2$OCH$_3$ | Me | Me |
| — | 1 (mix.) | —CH$_2$SCH$_3$ | Me | Me |
| — | 1 (mix.) | —CH$_2$CH=CH$_2$ | Me | Me |
| — | 1 (mix.) | —C(CH$_3$)$_2$CH=CH$_2$ | Me | Me |
| — | 1 (mix.) | —CH$_2$C≡CH$_2$ | Me | Me |
| — | 1 (mix.) | —CH$_2$C$_6$H$_5$ | Me | Me |
| — | 1 (mix.) | —CH$_2$C$_6$H$_4$—Cl-2 | Me | Me |
| — | 1 (mix.) | —CH$_2$C$_6$H$_4$—Cl-3 | Me | Me |
| — | 1 (mix.) | —CH$_2$C$_6$H$_4$—Cl-4 | Me | Me |
| — | 1 (mix.) | —CH$_2$C$_6$H$_4$—Me-2 | Me | Me |
| — | 1 (mix.) | —CH$_2$C$_6$H$_4$—Me-3 | Me | Me |
| — | 1 (mix.) | —CH$_2$C$_6$H$_4$—Me-4 | Me | Me |
| — | 1 (mix.) | —CH$_2$C$_6$H$_4$—OMe-2 | Me | Me |
| — | 1 (mix.) | —CH$_2$C$_6$H$_4$—OMe-3 | Me | Me |
| — | 1 (mix.) | —CH$_2$C$_6$H$_4$—OMe-4 | Me | Me |
| — | 1 (mix.) | —CH$_2$CH$_2$C$_6$H$_5$ | Me | Me |
| — | 1 (mix.) | H | OMe | Me |
| — | 1 (mix.) | Li | OMe | Me |
| — | 1 (mix.) | Na | OMe | Me |
| — | 1 (mix.) | K | OMe | Me |
| — | 1 (mix.) | ½Mg | OMe | Me |
| — | 1 (mix.) | ½Ca | OMe | Me |
| — | 1 (mix.) | MeNH$_3$ | OMe | Me |
| — | 1 (mix.) | EtNH$_3$ | OMe | Me |
| — | 1 (mix.) | PrNH$_3$ | OMe | Me |
| — | 1 (mix.) | $^i$PrNH$_3$ | OMe | Me |
| — | 1 (mix.) | NH$_2$CONH$_3$ | OMe | Me |
| — | 1 (mix.) | Me | OMe | Me |
| — | 1 (mix.) | Et | OMe | Me |
| — | 1 (mix.) | $^i$Pr | OMe | Me |
| — | 1 (mix.) | Pr | OMe | Me |
| — | 1 (mix.) | Bu | OMe | Me |
| — | 1 (mix.) | $^i$Bu | OMe | Me |

TABLE 1-continued

A compound of the general formula:

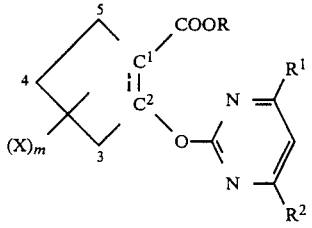

In the below-mentioned table, Me represents methyl group, Et represents ethyl group, Pr represents propyl group, $^i$Pr represents isopropyl group, Bu represents butyl group, $^i$Bu represents isobutyl group, $^s$Bu represents butyl secondary butyl group, $^t$Bu represents tertiary butyl group, cis represents a cis-form, trans represents a trans-form, mix. represents a mixture of a cis-form and a trans-form, 1 represents a single bond and 2 represents a double bond.

| $(X)_m$ | ≡≡≡ | R | $R^1$ | $R^2$ |
|---|---|---|---|---|
| — | 1 (mix.) | $^s$Bu | OMe | Me |
| — | 1 (mix.) | $^t$Bu | OMe | Me |
| — | 1 (mix.) | —CH$_2$OCH$_3$ | OMe | Me |
| — | 1 (mix.) | —CH$_2$CH$_2$OCH$_3$ | OMe | Me |
| — | 1 (mix.) | —CH$_2$SCH$_3$ | OMe | Me |
| — | 1 (mix.) | —CH$_2$CH=CH$_2$ | OMe | Me |
| — | 1 (mix.) | —C(CH$_3$)$_2$CH=CH$_2$ | OMe | Me |
| — | 1 (mix.) | —CH$_2$C≡CH$_2$ | OMe | Me |
| — | 1 (mix.) | —CH$_2$C$_6$H$_5$ | OMe | Me |
| — | 1 (mix.) | —CH$_2$C$_6$H$_4$—Cl-2 | OMe | Me |
| — | 1 (mix.) | —CH$_2$C$_6$H$_4$—Cl-3 | OMe | Me |
| — | 1 (mix.) | —CH$_2$C$_6$H$_4$—Cl-4 | OMe | Me |
| — | 1 (mix.) | —CH$_2$C$_6$H$_4$—Me-2 | OMe | Me |
| — | 1 (mix.) | —CH$_2$C$_6$H$_4$—Me-3 | OMe | Me |
| — | 1 (mix.) | —CH$_2$C$_6$H$_4$—Me-4 | OMe | Me |
| — | 1 (mix.) | —CH$_2$C$_6$H$_4$—OMe-2 | OMe | Me |
| — | 1 (mix.) | —CH$_2$C$_6$H$_4$—OMe-3 | OMe | Me |
| — | 1 (mix.) | —CH$_2$C$_6$H$_4$—OMe-4 | OMe | Me |
| — | 1 (mix.) | —CH$_2$CH$_2$C$_6$H$_5$ | OMe | Me |
| — | 1 (mix.) | H | OMe | OMe |
| — | 1 (mix.) | Li | OMe | OMe |
| — | 1 (mix.) | Na | OMe | OMe |
| — | 1 (mix.) | K | OMe | OMe |
| — | 1 (mix.) | ½Mg | OMe | OMe |
| — | 1 (mix.) | ½Ca | OMe | OMe |
| — | 1 (mix.) | MeNH$_3$ | OMe | OMe |
| — | 1 (mix.) | EtNH$_3$ | OMe | OMe |
| — | 1 (mix.) | PrNH$_3$ | OMe | OMe |
| — | 1 (mix.) | $^i$PrNH$_3$ | OMe | OMe |
| — | 1 (mix.) | NH$_2$CONH$_3$ | OMe | OMe |
| — | 1 (mix.) | Me | OMe | OMe |
| — | 1 (mix.) | Et | OMe | OMe |
| — | 1 (mix.) | $^i$Pr | OMe | OMe |
| — | 1 (mix.) | Pr | OMe | OMe |
| — | 1 (mix.) | Bu | OMe | OMe |
| — | 1 (mix.) | $^i$Bu | OMe | OMe |
| — | 1 (mix.) | $^s$Bu | OMe | OMe |
| — | 1 (mix.) | $^t$Bu | OMe | OMe |
| — | 1 (mix.) | —CH$_2$OCH$_3$ | OMe | OMe |
| — | 1 (mix.) | —CH$_2$CH$_2$OCH$_3$ | OMe | OMe |
| — | 1 (mix.) | —CH$_2$SCH$_3$ | OMe | OMe |
| — | 1 (mix.) | —CH$_2$CH=CH$_2$ | OMe | OMe |
| — | 1 (mix.) | —C(CH$_3$)$_2$CH=CH$_2$ | OMe | OMe |
| — | 1 (mix.) | —CH$_2$C≡CH$_2$ | OMe | OMe |
| — | 1 (mix.) | —CH$_2$C$_6$H$_5$ | OMe | OMe |
| — | 1 (mix.) | —CH$_2$C$_6$H$_4$—Cl-2 | OMe | OMe |
| — | 1 (mix.) | —CH$_2$C$_6$H$_4$—Cl-3 | OMe | OMe |
| — | 1 (mix.) | —CH$_2$C$_6$H$_4$—Cl-4 | OMe | OMe |
| — | 1 (mix.) | —CH$_2$C$_6$H$_4$—Me-2 | OMe | OMe |
| — | 1 (mix.) | —CH$_2$C$_6$H$_4$—Me-3 | OMe | OMe |
| — | 1 (mix.) | —CH$_2$C$_6$H$_4$—Me-4 | OMe | OMe |
| — | 1 (mix.) | —CH$_2$C$_6$H$_4$—OMe-2 | OMe | OMe |
| — | 1 (mix.) | —CH$_2$C$_6$H$_4$—OMe-3 | OMe | OMe |
| — | 1 (mix.) | —CH$_2$C$_6$H$_4$—OMe-4 | OMe | OMe |
| — | 1 (mix.) | —CH$_2$CH$_2$C$_6$H$_5$ | OMe | OMe |
| — | 1 (mix.) | H | Cl | Me |
| — | 1 (mix.) | Li | Cl | Me |
| — | 1 (mix.) | Na | Cl | Me |
| — | 1 (mix.) | K | Cl | Me |
| — | 1 (mix.) | ½Mg | Cl | Me |
| — | 1 (mix.) | ½Ca | Cl | Me |
| — | 1 (mix.) | MeNH$_3$ | Cl | Me |
| — | 1 (mix.) | EtNH$_3$ | Cl | Me |
| — | 1 (mix.) | PrNH$_3$ | Cl | Me |
| — | 1 (mix.) | $^i$PrNH$_3$ | Cl | Me |
| — | 1 (mix.) | NH$_2$CONH$_3$ | Cl | Me |
| — | 1 (mix.) | Me | Cl | Me |
| — | 1 (mix.) | Et | Cl | Me |
| — | 1 (mix.) | $^i$Pr | Cl | Me |
| — | 1 (mix.) | Pr | Cl | Me |
| — | 1 (mix.) | Bu | Cl | Me |
| — | 1 (mix.) | $^i$Bu | Cl | Me |
| — | 1 (mix.) | $^s$Bu | Cl | Me |
| — | 1 (mix.) | $^t$Bu | Cl | Me |
| — | 1 (mix.) | —CH$_2$OCH$_3$ | Cl | Me |
| — | 1 (mix.) | —CH$_2$CH$_2$OCH$_3$ | Cl | Me |
| — | 1 (mix.) | —CH$_2$SCH$_3$ | Cl | Me |
| — | 1 (mix.) | —CH$_2$CH=CH$_2$ | Cl | Me |
| — | 1 (mix.) | —C(CH$_3$)$_2$CH=CH$_2$ | Cl | Me |
| — | 1 (mix.) | —CH$_2$C≡CH$_2$ | Cl | Me |
| — | 1 (mix.) | —CH$_2$C$_6$H$_5$ | Cl | Me |
| — | 1 (mix.) | —CH$_2$C$_6$H$_4$—Cl-2 | Cl | Me |
| — | 1 (mix.) | —CH$_2$C$_6$H$_4$—Cl-3 | Cl | Me |
| — | 1 (mix.) | —CH$_2$C$_6$H$_4$—Cl-4 | Cl | Me |
| — | 1 (mix.) | —CH$_2$C$_6$H$_4$—Me-2 | Cl | Me |
| — | 1 (mix.) | —CH$_2$C$_6$H$_4$—Me-3 | Cl | Me |
| — | 1 (mix.) | —CH$_2$C$_6$H$_4$—Me-4 | Cl | Me |
| — | 1 (mix.) | —CH$_2$C$_6$H$_4$—OMe-2 | Cl | Me |
| — | 1 (mix.) | —CH$_2$C$_6$H$_4$—OMe-3 | Cl | Me |
| — | 1 (mix.) | —CH$_2$C$_6$H$_4$—OMe-4 | Cl | Me |
| — | 1 (mix.) | —CH$_2$CH$_2$C$_6$H$_5$ | Cl | Me |
| — | 1 (mix.) | H | Cl | Cl |
| — | 1 (mix.) | Li | Cl | Cl |
| — | 1 (mix.) | Na | Cl | Cl |
| — | 1 (mix.) | K | Cl | Cl |
| — | 1 (mix.) | ½Mg | Cl | Cl |
| — | 1 (mix.) | ½Ca | Cl | Cl |
| — | 1 (mix.) | MeNH$_3$ | Cl | Cl |
| — | 1 (mix.) | EtNH$_3$ | Cl | Cl |
| — | 1 (mix.) | PrNH$_3$ | Cl | Cl |
| — | 1 (mix.) | $^i$PrNH$_3$ | Cl | Cl |
| — | 1 (mix.) | NH$_2$CONH$_3$ | Cl | Cl |
| — | 1 (mix.) | Me | Cl | Cl |
| — | 1 (mix.) | Et | Cl | Cl |
| — | 1 (mix.) | $^i$Pr | Cl | Cl |
| — | 1 (mix.) | Pr | Cl | Cl |
| — | 1 (mix.) | Bu | Cl | Cl |
| — | 1 (mix.) | $^i$Bu | Cl | Cl |
| — | 1 (mix.) | $^s$Bu | Cl | Cl |
| — | 1 (mix.) | $^t$Bu | Cl | Cl |
| — | 1 (mix.) | —CH$_2$OCH$_3$ | Cl | Cl |
| — | 1 (mix.) | —CH$_2$CH$_2$OCH$_3$ | Cl | Cl |
| — | 1 (mix.) | —CH$_2$SCH$_3$ | Cl | Cl |
| — | 1 (mix.) | —CH$_2$CH=CH$_2$ | Cl | Cl |
| — | 1 (mix.) | —C(CH$_3$)$_2$CH=CH$_2$ | Cl | Cl |
| — | 1 (mix.) | —CH$_2$C≡CH$_2$ | Cl | Cl |
| — | 1 (mix.) | —CH$_2$C$_6$H$_5$ | Cl | Cl |
| — | 1 (mix.) | —CH$_2$C$_6$H$_4$—Cl-2 | Cl | Cl |
| — | 1 (mix.) | —CH$_2$C$_6$H$_4$—Cl-3 | Cl | Cl |
| — | 1 (mix.) | —CH$_2$C$_6$H$_4$—Cl-4 | Cl | Cl |
| — | 1 (mix.) | —CH$_2$C$_6$H$_4$—Me-2 | Cl | Cl |
| — | 1 (mix.) | —CH$_2$C$_6$H$_4$—Me-3 | Cl | Cl |

TABLE 1-continued

A compound of the general formula:

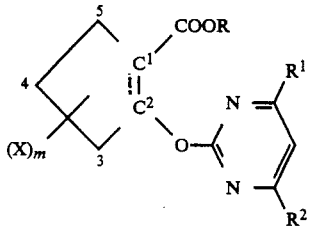

In the below-mentioned table, Me represents methyl group, Et represents ethyl group, Pr represents propyl group, $^i$Pr represents isopropyl group, Bu represents butyl group, $^i$Bu represents isobutyl group, $^s$Bu represents butyl secondary butyl group, $^t$Bu represents tertiary butyl group, cis represents a cis-form, trans represents a trans-form, mix. represents a mixture of a cis-form and a trans-form, 1 represents a single bond and 2 represents a double bond.

| $(X)_m$ | ==== | R | $R^1$ | $R^2$ |
|---|---|---|---|---|
| — | 1 (mix.) | —CH$_2$C$_6$H$_4$—Me-4 | Cl | Cl |
| — | 1 (mix.) | —CH$_2$C$_6$H$_4$—OMe-2 | Cl | Cl |
| — | 1 (mix.) | —CH$_2$C$_6$H$_4$—OMe-3 | Cl | Cl |
| — | 1 (mix.) | —CH$_2$C$_6$H$_4$—OMe-4 | Cl | Cl |
| — | 1 (mix.) | —CH$_2$CH$_2$C$_6$H$_5$ | Cl | Cl |
| — | 1 (mix.) | H | Cl | OMe |
| — | 1 (mix.) | Li | Cl | OMe |
| — | 1 (mix.) | Na | Cl | OMe |
| — | 1 (mix.) | K | Cl | OMe |
| — | 1 (mix.) | ½Mg | Cl | OMe |
| — | 1 (mix.) | ½Ca | Cl | OMe |
| — | 1 (mix.) | MeNH$_3$ | Cl | OMe |
| — | 1 (mix.) | EtNH$_3$ | Cl | OMe |
| — | 1 (mix.) | PrNH$_3$ | Cl | OMe |
| — | 1 (mix.) | $^i$PrNH$_3$ | Cl | OMe |
| — | 1 (mix.) | NH$_2$CONH$_3$ | Cl | OMe |
| — | 1 (mix.) | Me | Cl | OMe |
| — | 1 (mix.) | Et | Cl | OMe |
| — | 1 (mix.) | $^i$Pr | Cl | OMe |
| — | 1 (mix.) | Pr | Cl | OMe |
| — | 1 (mix.) | Bu | Cl | OMe |
| — | 1 (mix.) | $^i$Bu | Cl | OMe |
| — | 1 (mix.) | $^s$Bu | Cl | OMe |
| — | 1 (mix.) | $^t$Bu | Cl | OMe |
| — | 1 (mix.) | —CH$_2$OCH$_3$ | Cl | OMe |
| — | 1 (mix.) | —CH$_2$CH$_2$OCH$_3$ | Cl | OMe |
| — | 1 (mix.) | —CH$_2$SCH$_3$ | Cl | OMe |
| — | 1 (mix.) | —CH$_2$CH=CH$_2$ | Cl | OMe |
| — | 1 (mix.) | —C(CH$_3$)$_2$CH=CH$_2$ | Cl | OMe |
| — | 1 (mix.) | —CH$_2$C≡CH$_2$ | Cl | OMe |
| — | 1 (mix.) | —CH$_2$C$_6$H$_5$ | Cl | OMe |
| — | 1 (mix.) | —CH$_2$C$_6$H$_4$—Cl-2 | Cl | OMe |
| — | 1 (mix.) | —CH$_2$C$_6$H$_4$—Cl-3 | Cl | OMe |
| — | 1 (mix.) | —CH$_2$C$_6$H$_4$—Cl-4 | Cl | OMe |
| — | 1 (mix.) | —CH$_2$C$_6$H$_4$—Me-2 | Cl | OMe |
| — | 1 (mix.) | —CH$_2$C$_6$H$_4$—Me-3 | Cl | OMe |
| — | 1 (mix.) | —CH$_2$C$_6$H$_4$—Me-4 | Cl | OMe |
| — | 1 (mix.) | —CH$_2$C$_6$H$_4$—OMe-2 | Cl | OMe |
| — | 1 (mix.) | —CH$_2$C$_6$H$_4$—OMe-3 | Cl | OMe |
| — | 1 (mix.) | —CH$_2$C$_6$H$_4$—OMe-4 | Cl | OMe |
| — | 1 (mix.) | —CH$_2$CH$_2$C$_6$H$_5$ | Cl | OMe |
| — | 1 (mix.) | H | OCHF$_2$ | OMe |
| — | 1 (mix.) | Li | OCHF$_2$ | OMe |
| — | 1 (mix.) | Na | OCHF$_2$ | OMe |
| — | 1 (mix.) | K | OCHF$_2$ | OMe |
| — | 1 (mix.) | ½Mg | OCHF$_2$ | OMe |
| — | 1 (mix.) | ½Ca | OCHF$_2$ | OMe |
| — | 1 (mix.) | MeNH$_3$ | OCHF$_2$ | OMe |
| — | 1 (mix.) | EtNH$_3$ | OCHF$_2$ | OMe |
| — | 1 (mix.) | PrNH$_3$ | OCHF$_2$ | OMe |
| — | 1 (mix.) | $^i$PrNH$_3$ | OCHF$_2$ | OMe |
| — | 1 (mix.) | NH$_2$CONH$_3$ | OCHF$_2$ | OMe |
| — | 1 (mix.) | Me | OCHF$_2$ | OMe |
| — | 1 (mix.) | Et | OCHF$_2$ | OMe |
| — | 1 (mix.) | $^i$Pr | OCHF$_2$ | OMe |
| — | 1 (mix.) | Pr | OCHF$_2$ | OMe |
| — | 1 (mix.) | Bu | OCHF$_2$ | OMe |
| — | 1 (mix.) | $^i$Bu | OCHF$_2$ | OMe |
| — | 1 (mix.) | $^s$Bu | OCHF$_2$ | OMe |
| — | 1 (mix.) | $^t$Bu | OCHF$_2$ | OMe |
| — | 1 (mix.) | —CH$_2$OCH$_3$ | OCHF$_2$ | OMe |
| — | 1 (mix.) | —CH$_2$CH$_2$OCH$_3$ | OCHF$_2$ | OMe |
| — | 1 (mix.) | —CH$_2$SCH$_3$ | OCHF$_2$ | OMe |
| — | 1 (mix.) | —CH$_2$CH=CH$_2$ | OCHF$_2$ | OMe |
| — | 1 (mix.) | —C(CH$_3$)$_2$CH=CH$_2$ | OCHF$_2$ | OMe |
| — | 1 (mix.) | —CH$_2$C≡CH$_2$ | OCHF$_2$ | OMe |
| — | 1 (mix.) | —CH$_2$C$_6$H$_5$ | OCHF$_2$ | OMe |
| — | 1 (mix.) | —CH$_2$C$_6$H$_4$—Cl-2 | OCHF$_2$ | OMe |
| — | 1 (mix.) | —CH$_2$C$_6$H$_4$—Cl-3 | OCHF$_2$ | OMe |
| — | 1 (mix.) | —CH$_2$C$_6$H$_4$—Cl-4 | OCHF$_2$ | OMe |
| — | 1 (mix.) | —CH$_2$C$_6$H$_4$—Me-2 | OCHF$_2$ | OMe |
| — | 1 (mix.) | —CH$_2$C$_6$H$_4$—Me-3 | OCHF$_2$ | OMe |
| — | 1 (mix.) | —CH$_2$C$_6$H$_4$—Me-4 | OCHF$_2$ | OMe |
| — | 1 (mix.) | —CH$_2$C$_6$H$_4$—OMe-2 | OCHF$_2$ | OMe |
| — | 1 (mix.) | —CH$_2$C$_6$H$_4$—OMe-3 | OCHF$_2$ | OMe |
| — | 1 (mix.) | —CH$_2$C$_6$H$_4$—OMe-4 | OCHF$_2$ | OMe |
| — | 1 (mix.) | —CH$_2$CH$_2$C$_6$H$_5$ | OCHF$_2$ | OMe |
| — | 1 (mix.) | H | OCHF$_2$ | OCHF$_2$ |
| — | 1 (mix.) | Li | OCHF$_2$ | OCHF$_2$ |
| — | 1 (mix.) | Na | OCHF$_2$ | OCHF$_2$ |
| — | 1 (mix.) | K | OCHF$_2$ | OCHF$_2$ |
| — | 1 (mix.) | ½Mg | OCHF$_2$ | OCHF$_2$ |
| — | 1 (mix.) | ½Ca | OCHF$_2$ | OCHF$_2$ |
| — | 1 (mix.) | MeNH$_3$ | OCHF$_2$ | OCHF$_2$ |
| — | 1 (mix.) | EtNH$_3$ | OCHF$_2$ | OCHF$_2$ |
| — | 1 (mix.) | PrNH$_3$ | OCHF$_2$ | OCHF$_2$ |
| — | 1 (mix.) | $^i$PrNH$_3$ | OCHF$_2$ | OCHF$_2$ |
| — | 1 (mix.) | NH$_2$CONH$_3$ | OCHF$_2$ | OCHF$_2$ |
| — | 1 (mix.) | Me | OCHF$_2$ | OCHF$_2$ |
| — | 1 (mix.) | Et | OCHF$_2$ | OCHF$_2$ |
| — | 1 (mix.) | $^i$Pr | OCHF$_2$ | OCHF$_2$ |
| — | 1 (mix.) | Pr | OCHF$_2$ | OCHF$_2$ |
| — | 1 (mix.) | Bu | OCHF$_2$ | OCHF$_2$ |
| — | 1 (mix.) | $^i$Bu | OCHF$_2$ | OCHF$_2$ |
| — | 1 (mix.) | $^s$Bu | OCHF$_2$ | OCHF$_2$ |
| — | 1 (mix.) | $^t$Bu | OCHF$_2$ | OCHF$_2$ |
| — | 1 (mix.) | —CH$_2$OCH$_3$ | OCHF$_2$ | OCHF$_2$ |
| — | 1 (mix.) | —CH$_2$CH$_2$OCH$_3$ | OCHF$_2$ | OCHF$_2$ |
| — | 1 (mix.) | —CH$_2$SCH$_3$ | OCHF$_2$ | OCHF$_2$ |
| — | 1 (mix.) | —CH$_2$CH=CH$_2$ | OCHF$_2$ | OCHF$_2$ |
| — | 1 (mix.) | —C(CH$_3$)$_2$CH=CH$_2$ | OCHF$_2$ | OCHF$_2$ |
| — | 1 (mix.) | —CH$_2$C≡CH$_2$ | OCHF$_2$ | OCHF$_2$ |
| — | 1 (mix.) | —CH$_2$C$_6$H$_5$ | OCHF$_2$ | OCHF$_2$ |
| — | 1 (mix.) | —CH$_2$C$_6$H$_4$—Cl-2 | OCHF$_2$ | OCHF$_2$ |
| — | 1 (mix.) | —CH$_2$C$_6$H$_4$—Cl-3 | OCHF$_2$ | OCHF$_2$ |
| — | 1 (mix.) | —CH$_2$C$_6$H$_4$—Cl-4 | OCHF$_2$ | OCHF$_2$ |
| — | 1 (mix.) | —CH$_2$C$_6$H$_4$—Me-2 | OCHF$_2$ | OCHF$_2$ |
| — | 1 (mix.) | —CH$_2$C$_6$H$_4$—Me-3 | OCHF$_2$ | OCHF$_2$ |
| — | 1 (mix.) | —CH$_2$C$_6$H$_4$—Me-4 | OCHF$_2$ | OCHF$_2$ |
| — | 1 (mix.) | —CH$_2$C$_6$H$_4$—OMe-2 | OCHF$_2$ | OCHF$_2$ |
| — | 1 (mix.) | —CH$_2$C$_6$H$_4$—OMe-3 | OCHF$_2$ | OCHF$_2$ |
| — | 1 (mix.) | —CH$_2$C$_6$H$_4$—OMe-4 | OCHF$_2$ | OCHF$_2$ |
| — | 1 (mix.) | —CH$_2$CH$_2$C$_6$H$_5$ | OCHF$_2$ | OCHF$_2$ |
| — | 1 (mix.) | H | SMe | OMe |
| — | 1 (mix.) | Li | SMe | OMe |
| — | 1 (mix.) | Na | SMe | OMe |
| — | 1 (mix.) | K | SMe | OMe |
| — | 1 (mix.) | ½Mg | SMe | OMe |
| — | 1 (mix.) | ½Ca | SMe | OMe |
| — | 1 (mix.) | MeNH$_3$ | SMe | OMe |
| — | 1 (mix.) | EtNH$_3$ | SMe | OMe |
| — | 1 (mix.) | PrNH$_3$ | SMe | OMe |

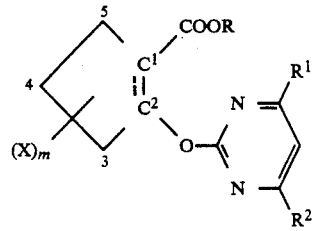

TABLE 1-continued

A compound of the general formula:

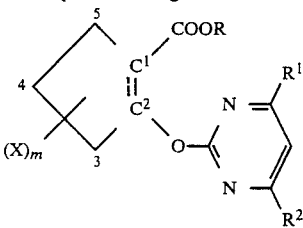

In the below-mentioned table, Me represents methyl group, Et represents ethyl group, Pr represents propyl group, $^i$Pr represents isopropyl group, Bu represents butyl group, $^i$Bu represents isobutyl group, $^s$Bu represents butyl secondary butyl group, $^t$Bu represents tertiary butyl group, cis represents a cis-form, trans represents a trans-form, mix. represents a mixture of a cis-form and a trans-form, 1 represents a single bond and 2 represents a double bond.

| $(X)_m$ | ═ | R | $R^1$ | $R^2$ |
|---|---|---|---|---|
| — | 1 (mix.) | $^i$PrNH$_3$ | SMe | OMe |
| — | 1 (mix.) | NH$_2$CONH$_3$ | SMe | OMe |
| — | 1 (mix.) | Me | SMe | OMe |
| — | 1 (mix.) | Et | SMe | OMe |
| — | 1 (mix.) | $^i$Pr | SMe | OMe |
| — | 1 (mix.) | Pr | SMe | OMe |
| — | 1 (mix.) | Bu | SMe | OMe |
| — | 1 (mix.) | $^i$Bu | SMe | OMe |
| — | 1 (mix.) | $^s$Bu | SMe | OMe |
| — | 1 (mix.) | $^t$Bu | SMe | OMe |
| — | 1 (mix.) | —CH$_2$OCH$_3$ | SMe | OMe |
| — | 1 (mix.) | —CH$_2$CH$_2$OCH$_3$ | SMe | OMe |
| — | 1 (mix.) | —CH$_2$SCH$_3$ | SMe | OMe |
| — | 1 (mix.) | —CH$_2$CH═CH$_2$ | SMe | OMe |
| — | 1 (mix.) | —C(CH$_3$)$_2$CH═CH$_2$ | SMe | OMe |
| — | 1 (mix.) | —CH$_2$C≡CH$_2$ | SMe | OMe |
| — | 1 (mix.) | —CH$_2$C$_6$H$_5$ | SMe | OMe |
| — | 1 (mix.) | —CH$_2$C$_6$H$_4$—Cl-2 | SMe | OMe |
| — | 1 (mix.) | —CH$_2$C$_6$H$_4$—Cl-3 | SMe | OMe |
| — | 1 (mix.) | —CH$_2$C$_6$H$_4$—Cl-4 | SMe | OMe |
| — | 1 (mix.) | —CH$_2$C$_6$H$_4$—Me-2 | SMe | OMe |
| — | 1 (mix.) | —CH$_2$C$_6$H$_4$—Me-3 | SMe | OMe |
| — | 1 (mix.) | —CH$_2$C$_6$H$_4$—Me-4 | SMe | OMe |
| — | 1 (mix.) | —CH$_2$C$_6$H$_4$—OMe-2 | SMe | OMe |
| — | 1 (mix.) | —CH$_2$C$_6$H$_4$—OMe-3 | SMe | OMe |
| — | 1 (mix.) | —CH$_2$C$_6$H$_4$—OMe-4 | SMe | OMe |
| — | 1 (mix.) | —CH$_2$CH$_2$C$_6$H$_5$ | SMe | OMe |
| — | 1 (mix.) | H | SMe | Me |
| — | 1 (mix.) | Li | SMe | Me |
| — | 1 (mix.) | Na | SMe | Me |
| — | 1 (mix.) | K | SMe | Me |
| — | 1 (mix.) | ½Mg | SMe | Me |
| — | 1 (mix.) | ½Ca | SMe | Me |
| — | 1 (mix.) | MeNH$_3$ | SMe | Me |
| — | 1 (mix.) | EtNH$_3$ | SMe | Me |
| — | 1 (mix.) | PrNH$_3$ | SMe | Me |
| — | 1 (mix.) | $^i$PrNH$_3$ | SMe | Me |
| — | 1 (mix.) | NH$_2$CONH$_3$ | SMe | Me |
| — | 1 (mix.) | Me | SMe | Me |
| — | 1 (mix.) | Et | SMe | Me |
| — | 1 (mix.) | $^i$Pr | SMe | Me |
| — | 1 (mix.) | Pr | SMe | Me |
| — | 1 (mix.) | Bu | SMe | Me |
| — | 1 (mix.) | $^i$Bu | SMe | Me |
| — | 1 (mix.) | $^s$Bu | SMe | Me |
| — | 1 (mix.) | $^t$Bu | SMe | Me |
| — | 1 (mix.) | —CH$_2$OCH$_3$ | SMe | Me |
| — | 1 (mix.) | —CH$_2$CH$_2$OCH$_3$ | SMe | Me |
| — | 1 (mix.) | —CH$_2$SCH$_3$ | SMe | Me |
| — | 1 (mix.) | —CH$_2$CH═CH$_2$ | SMe | Me |
| — | 1 (mix.) | —C(CH$_3$)$_2$CH═CH$_2$ | SMe | Me |
| — | 1 (mix.) | —CH$_2$C≡CH$_2$ | SMe | Me |
| — | 1 (mix.) | —CH$_2$C$_6$H$_5$ | SMe | Me |
| — | 1 (mix.) | —CH$_2$C$_6$H$_4$—Cl-2 | SMe | Me |
| — | 1 (mix.) | —CH$_2$C$_6$H$_4$—Cl-3 | SMe | Me |
| — | 1 (mix.) | —CH$_2$C$_6$H$_4$—Cl-4 | SMe | Me |
| — | 1 (mix.) | —CH$_2$C$_6$H$_4$—Me-2 | SMe | Me |
| — | 1 (mix.) | —CH$_2$C$_6$H$_4$—Me-3 | SMe | Me |
| — | 1 (mix.) | —CH$_2$C$_6$H$_4$—Me-4 | SMe | Me |
| — | 1 (mix.) | —CH$_2$C$_6$H$_4$—OMe-2 | SMe | Me |
| — | 1 (mix.) | —CH$_2$C$_6$H$_4$—OMe-3 | SMe | Me |
| — | 1 (mix.) | —CH$_2$C$_6$H$_4$—OMe-4 | SMe | Me |
| — | 1 (mix.) | —CH$_2$CH$_2$C$_6$H$_5$ | SMe | Me |
| — | 2 (—) | H | Me | Me |
| — | 2 (—) | Li | Me | Me |
| — | 2 (—) | Na | Me | Me |
| — | 2 (—) | K | Me | Me |
| — | 2 (—) | ½Mg | Me | Me |
| — | 2 (—) | ½Ca | Me | Me |
| — | 2 (—) | MeNH$_3$ | Me | Me |
| — | 2 (—) | EtNH$_3$ | Me | Me |
| — | 2 (—) | PrNH$_3$ | Me | Me |
| — | 2 (—) | $^i$PrNH$_3$ | Me | Me |
| — | 2 (—) | NH$_2$CONH$_3$ | Me | Me |
| — | 2 (—) | Me | Me | Me |
| — | 2 (—) | Et | Me | Me |
| — | 2 (—) | $^i$Pr | Me | Me |
| — | 2 (—) | Pr | Me | Me |
| — | 2 (—) | Bu | Me | Me |
| — | 2 (—) | $^i$Bu | Me | Me |
| — | 2 (—) | $^s$Bu | Me | Me |
| — | 2 (—) | $^t$Bu | Me | Me |
| — | 2 (—) | —CH$_2$OCH$_3$ | Me | Me |
| — | 2 (—) | —CH$_2$CH$_2$OCH$_3$ | Me | Me |
| — | 2 (—) | —CH$_2$SCH$_3$ | Me | Me |
| — | 2 (—) | —CH$_2$CH═CH$_2$ | Me | Me |
| — | 2 (—) | —C(CH$_3$)$_2$CH═CH$_2$ | Me | Me |
| — | 2 (—) | —CH$_2$C≡CH$_2$ | Me | Me |
| — | 2 (—) | —CH$_2$C$_6$H$_5$ | Me | Me |
| — | 2 (—) | —CH$_2$C$_6$H$_4$—Cl-2 | Me | Me |
| — | 2 (—) | —CH$_2$C$_6$H$_4$—Cl-3 | Me | Me |
| — | 2 (—) | —CH$_2$C$_6$H$_4$—Cl-4 | Me | Me |
| — | 2 (—) | —CH$_2$C$_6$H$_4$—Me-2 | Me | Me |
| — | 2 (—) | —CH$_2$C$_6$H$_4$—Me-3 | Me | Me |
| — | 2 (—) | —CH$_2$C$_6$H$_4$—Me-4 | Me | Me |
| — | 2 (—) | —CH$_2$C$_6$H$_4$—OMe-2 | Me | Me |
| — | 2 (—) | —CH$_2$C$_6$H$_4$—OMe-3 | Me | Me |
| — | 2 (—) | —CH$_2$C$_6$H$_4$—OMe-4 | Me | Me |
| — | 2 (—) | —CH$_2$CH$_2$C$_6$H$_5$ | Me | Me |
| — | 2 (—) | H | OMe | Me |
| — | 2 (—) | Li | OMe | Me |
| — | 2 (—) | Na | OMe | Me |
| — | 2 (—) | K | OMe | Me |
| — | 2 (—) | ½Mg | OMe | Me |
| — | 2 (—) | ½Ca | OMe | Me |
| — | 2 (—) | MeNH$_3$ | OMe | Me |
| — | 2 (—) | EtNH$_3$ | OMe | Me |
| — | 2 (—) | PrNH$_3$ | OMe | Me |
| — | 2 (—) | $^i$PrNH$_3$ | OMe | Me |
| — | 2 (—) | NH$_2$CONH$_3$ | OMe | Me |
| — | 2 (—) | Me | OMe | Me |
| — | 2 (—) | Et | OMe | Me |
| — | 2 (—) | $^i$Pr | OMe | Me |
| — | 2 (—) | Pr | OMe | Me |
| — | 2 (—) | Bu | OMe | Me |
| — | 2 (—) | $^i$Bu | OMe | Me |
| — | 2 (—) | $^s$Bu | OMe | Me |
| — | 2 (—) | $^t$Bu | OMe | Me |
| — | 2 (—) | —CH$_2$OCH$_3$ | OMe | Me |
| — | 2 (—) | —CH$_2$CH$_2$OCH$_3$ | OMe | Me |
| — | 2 (—) | —CH$_2$SCH$_3$ | OMe | Me |
| — | 2 (—) | —CH$_2$CH═CH$_2$ | OMe | Me |

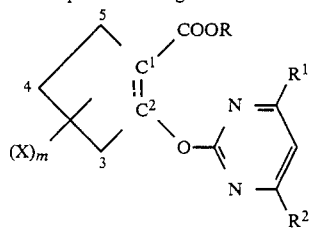

TABLE 1-continued

A compound of the general formula:


In the below-mentioned table, Me represents methyl group, Et represents ethyl group, Pr represents propyl group, $^i$Pr represents isopropyl group, Bu represents butyl group, $^i$Bu represents isobutyl group, $^s$Bu represents butyl secondary butyl group, $^t$Bu represents tertiary butyl group, cis represents a cis-form, trans represents a trans-form, mix. represents a mixture of a cis-form and a trans-form, 1 represents a single bond and 2 represents a double bond.

| $(X)_m$ | ==== | R | $R^1$ | $R^2$ |
|---|---|---|---|---|
| — | 2 (—) | —C(CH$_3$)$_2$CH=CH$_2$ | OMe | Me |
| — | 2 (—) | —CH$_2$C≡CH$_2$ | OMe | Me |
| — | 2 (—) | —CH$_2$C$_6$H$_5$ | OMe | Me |
| — | 2 (—) | —CH$_2$C$_6$H$_4$—Cl-2 | OMe | Me |
| — | 2 (—) | —CH$_2$C$_6$H$_4$—Cl-3 | OMe | Me |
| — | 2 (—) | —CH$_2$C$_6$H$_4$—Cl-4 | OMe | Me |
| — | 2 (—) | —CH$_2$C$_6$H$_4$—Me-2 | OMe | Me |
| — | 2 (—) | —CH$_2$C$_6$H$_4$—Me-3 | OMe | Me |
| — | 2 (—) | —CH$_2$C$_6$H$_4$—Me-4 | OMe | Me |
| — | 2 (—) | —CH$_2$C$_6$H$_4$—OMe-2 | OMe | Me |
| — | 2 (—) | —CH$_2$C$_6$H$_4$—OMe-3 | OMe | Me |
| — | 2 (—) | —CH$_2$C$_6$H$_4$—OMe-4 | OMe | Me |
| — | 2 (—) | —CH$_2$CH$_2$C$_6$H$_5$ | OMe | Me |
| — | 2 (—) | H | OMe | OMe |
| — | 2 (—) | Li | OMe | OMe |
| — | 2 (—) | Na | OMe | OMe |
| — | 2 (—) | K | OMe | OMe |
| — | 2 (—) | ½Mg | OMe | OMe |
| — | 2 (—) | ½Ca | OMe | OMe |
| — | 2 (—) | MeNH$_3$ | OMe | OMe |
| — | 2 (—) | EtNH$_3$ | OMe | OMe |
| — | 2 (—) | PrNH$_3$ | OMe | OMe |
| — | 2 (—) | $^i$PrNH$_3$ | OMe | OMe |
| — | 2 (—) | NH$_2$CONH$_3$ | OMe | OMe |
| — | 2 (—) | Me | OMe | OMe |
| — | 2 (—) | Et | OMe | OMe |
| — | 2 (—) | $^i$Pr | OMe | OMe |
| — | 2 (—) | Pr | OMe | OMe |
| — | 2 (—) | Bu | OMe | OMe |
| — | 2 (—) | $^i$Bu | OMe | OMe |
| — | 2 (—) | $^s$Bu | OMe | OMe |
| — | 2 (—) | $^t$Bu | OMe | OMe |
| — | 2 (—) | —CH$_2$OCH$_3$ | OMe | OMe |
| — | 2 (—) | —CH$_2$CH$_2$OCH$_3$ | OMe | OMe |
| — | 2 (—) | —CH$_2$SCH$_3$ | OMe | OMe |
| — | 2 (—) | —CH$_2$CH=CH$_2$ | OMe | OMe |
| — | 2 (—) | —C(CH$_3$)$_2$CH=CH$_2$ | OMe | OMe |
| — | 2 (—) | —CH$_2$C≡CH$_2$ | OMe | OMe |
| — | 2 (—) | —CH$_2$C$_6$H$_5$ | OMe | OMe |
| — | 2 (—) | —CH$_2$C$_6$H$_4$—Cl-2 | OMe | OMe |
| — | 2 (—) | —CH$_2$C$_6$H$_4$—Cl-3 | OMe | OMe |
| — | 2 (—) | —CH$_2$C$_6$H$_4$—Cl-4 | OMe | OMe |
| — | 2 (—) | —CH$_2$C$_6$H$_4$—Me-2 | OMe | OMe |
| — | 2 (—) | —CH$_2$C$_6$H$_4$—Me-3 | OMe | OMe |
| — | 2 (—) | —CH$_2$C$_6$H$_4$—Me-4 | OMe | OMe |
| — | 2 (—) | —CH$_2$C$_6$H$_4$—OMe-2 | OMe | OMe |
| — | 2 (—) | —CH$_2$C$_6$H$_4$—OMe-3 | OMe | OMe |
| — | 2 (—) | —CH$_2$C$_6$H$_4$—OMe-4 | OMe | OMe |
| — | 2 (—) | —CH$_2$CH$_2$C$_6$H$_5$ | OMe | OMe |
| — | 2 (—) | H | Cl | Me |
| — | 2 (—) | Li | Cl | Me |
| — | 2 (—) | Na | Cl | Me |
| — | 2 (—) | K | Cl | Me |
| — | 2 (—) | ½Mg | Cl | Me |
| — | 2 (—) | ½Ca | Cl | Me |
| — | 2 (—) | MeNH$_3$ | Cl | Me |
| — | 2 (—) | EtNH$_3$ | Cl | Me |
| — | 2 (—) | PrNH$_3$ | Cl | Me |
| — | 2 (—) | $^i$PrNH$_3$ | Cl | Me |
| — | 2 (—) | NH$_2$CONH$_3$ | Cl | Me |
| — | 2 (—) | Me | Cl | Me |
| — | 2 (—) | Et | Cl | Me |
| — | 2 (—) | $^i$Pr | Cl | Me |
| — | 2 (—) | Pr | Cl | Me |
| — | 2 (—) | Bu | Cl | Me |
| — | 2 (—) | $^i$Bu | Cl | Me |
| — | 2 (—) | $^s$Bu | Cl | Me |
| — | 2 (—) | $^t$Bu | Cl | Me |
| — | 2 (—) | —CH$_2$OCH$_3$ | Cl | Me |
| — | 2 (—) | —CH$_2$CH$_2$OCH$_3$ | Cl | Me |
| — | 2 (—) | —CH$_2$SCH$_3$ | Cl | Me |
| — | 2 (—) | —CH$_2$CH=CH$_2$ | Cl | Me |
| — | 2 (—) | —C(CH$_3$)$_2$CH=CH$_2$ | Cl | Me |
| — | 2 (—) | —CH$_2$C≡CH$_2$ | Cl | Me |
| — | 2 (—) | —CH$_2$C$_6$H$_5$ | Cl | Me |
| — | 2 (—) | —CH$_2$C$_6$H$_4$—Cl-2 | Cl | Me |
| — | 2 (—) | —CH$_2$C$_6$H$_4$—Cl-3 | Cl | Me |
| — | 2 (—) | —CH$_2$C$_6$H$_4$—Cl-4 | Cl | Me |
| — | 2 (—) | —CH$_2$C$_6$H$_4$—Me-2 | Cl | Me |
| — | 2 (—) | —CH$_2$C$_6$H$_4$—Me-3 | Cl | Me |
| — | 2 (—) | —CH$_2$C$_6$H$_4$—Me-4 | Cl | Me |
| — | 2 (—) | —CH$_2$C$_6$H$_4$—OMe-2 | Cl | Me |
| — | 2 (—) | —CH$_2$C$_6$H$_4$—OMe-3 | Cl | Me |
| — | 2 (—) | —CH$_2$C$_6$H$_4$—OMe-4 | Cl | Me |
| — | 2 (—) | —CH$_2$CH$_2$C$_6$H$_5$ | Cl | Me |
| — | 2 (—) | H | Cl | Cl |
| — | 2 (—) | Li | Cl | Cl |
| — | 2 (—) | Na | Cl | Cl |
| — | 2 (—) | K | Cl | Cl |
| — | 2 (—) | ½Mg | Cl | Cl |
| — | 2 (—) | ½Ca | Cl | Cl |
| — | 2 (—) | MeNH$_3$ | Cl | Cl |
| — | 2 (—) | EtNH$_3$ | Cl | Cl |
| — | 2 (—) | PrNH$_3$ | Cl | Cl |
| — | 2 (—) | $^i$PrNH$_3$ | Cl | Cl |
| — | 2 (—) | NH$_2$CONH$_3$ | Cl | Cl |
| — | 2 (—) | Me | Cl | Cl |
| — | 2 (—) | Et | Cl | Cl |
| — | 2 (—) | $^i$Pr | Cl | Cl |
| — | 2 (—) | Pr | Cl | Cl |
| — | 2 (—) | Bu | Cl | Cl |
| — | 2 (—) | $^i$Bu | Cl | Cl |
| — | 2 (—) | $^s$Bu | Cl | Cl |
| — | 2 (—) | $^t$Bu | Cl | Cl |
| — | 2 (—) | —CH$_2$OCH$_3$ | Cl | Cl |
| — | 2 (—) | —CH$_2$CH$_2$OCH$_3$ | Cl | Cl |
| — | 2 (—) | —CH$_2$SCH$_3$ | Cl | Cl |
| — | 2 (—) | —CH$_2$CH=CH$_2$ | Cl | Cl |
| — | 2 (—) | —C(CH$_3$)$_2$CH=CH$_2$ | Cl | Cl |
| — | 2 (—) | —CH$_2$C≡CH$_2$ | Cl | Cl |
| — | 2 (—) | —CH$_2$C$_6$H$_5$ | Cl | Cl |
| — | 2 (—) | —CH$_2$C$_6$H$_4$—Cl-2 | Cl | Cl |
| — | 2 (—) | —CH$_2$C$_6$H$_4$—Cl-3 | Cl | Cl |
| — | 2 (—) | —CH$_2$C$_6$H$_4$—Cl-4 | Cl | Cl |
| — | 2 (—) | —CH$_2$C$_6$H$_4$—Me-2 | Cl | Cl |
| — | 2 (—) | —CH$_2$C$_6$H$_4$—Me-3 | Cl | Cl |
| — | 2 (—) | —CH$_2$C$_6$H$_4$—Me-4 | Cl | Cl |
| — | 2 (—) | —CH$_2$C$_6$H$_4$—OMe-2 | Cl | Cl |
| — | 2 (—) | —CH$_2$C$_6$H$_4$—OMe-3 | Cl | Cl |
| — | 2 (—) | —CH$_2$C$_6$H$_4$—OMe-4 | Cl | Cl |
| — | 2 (—) | —CH$_2$CH$_2$C$_6$H$_5$ | Cl | Cl |
| — | 2 (—) | H | Cl | OMe |

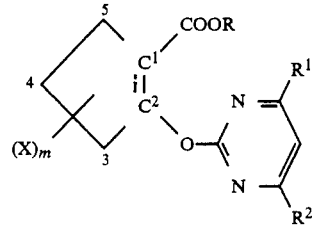

TABLE 1-continued

A compound of the general formula:


In the below-mentioned table, Me represents methyl group, Et represents ethyl group, Pr represents propyl group, $^i$Pr represents isopropyl group, Bu represents butyl group, $^i$Bu represents isobutyl group, $^s$Bu represents butyl secondary butyl group, $^t$Bu represents tertiary butyl group, cis represents a cis-form, trans represents a trans-form, mix. represents a mixture of a cis-form and a trans-form, 1 represents a single bond and 2 represents a double bond.

| $(X)_m$ | ==== | R | $R^1$ | $R^2$ |
|---|---|---|---|---|
| — | 2 (—) | Li | Cl | OMe |
| — | 2 (—) | Na | Cl | OMe |
| — | 2 (—) | K | Cl | OMe |
| — | 2 (—) | ½Mg | Cl | OMe |
| — | 2 (—) | ½Ca | Cl | OMe |
| — | 2 (—) | MeNH$_3$ | Cl | OMe |
| — | 2 (—) | EtNH$_3$ | Cl | OMe |
| — | 2 (—) | PrNH$_3$ | Cl | OMe |
| — | 2 (—) | $^i$PrNH$_3$ | Cl | OMe |
| — | 2 (—) | NH$_2$CONH$_3$ | Cl | OMe |
| — | 2 (—) | Me | Cl | OMe |
| — | 2 (—) | Et | Cl | OMe |
| — | 2 (—) | $^i$Pr | Cl | OMe |
| — | 2 (—) | Pr | Cl | OMe |
| — | 2 (—) | Bu | Cl | OMe |
| — | 2 (—) | $^i$Bu | Cl | OMe |
| — | 2 (—) | $^s$Bu | Cl | OMe |
| — | 2 (—) | $^t$Bu | Cl | OMe |
| — | 2 (—) | —CH$_2$OCH$_3$ | Cl | OMe |
| — | 2 (—) | —CH$_2$CH$_2$OCH$_3$ | Cl | OMe |
| — | 2 (—) | —CH$_2$SCH$_3$ | Cl | OMe |
| — | 2 (—) | —CH$_2$CH=CH$_2$ | Cl | OMe |
| — | 2 (—) | —C(CH$_3$)$_2$CH=CH$_2$ | Cl | OMe |
| — | 2 (—) | —CH$_2$C≡CH$_2$ | Cl | OMe |
| — | 2 (—) | —CH$_2$C$_6$H$_5$ | Cl | OMe |
| — | 2 (—) | —CH$_2$C$_6$H$_4$—Cl-2 | Cl | OMe |
| — | 2 (—) | —CH$_2$C$_6$H$_4$—Cl-3 | Cl | OMe |
| — | 2 (—) | —CH$_2$C$_6$H$_4$—Cl-4 | Cl | OMe |
| — | 2 (—) | —CH$_2$C$_6$H$_4$—Me-2 | Cl | OMe |
| — | 2 (—) | —CH$_2$C$_6$H$_4$—Me-3 | Cl | OMe |
| — | 2 (—) | —CH$_2$C$_6$H$_4$—Me-4 | Cl | OMe |
| — | 2 (—) | —CH$_2$C$_6$H$_4$—OMe-2 | Cl | OMe |
| — | 2 (—) | —CH$_2$C$_6$H$_4$—OMe-3 | Cl | OMe |
| — | 2 (—) | —CH$_2$C$_6$H$_4$—OMe-4 | Cl | OMe |
| — | 2 (—) | —CH$_2$CH$_2$C$_6$H$_5$ | Cl | OMe |
| — | 2 (—) | H | OCHF$_2$ | OMe |
| — | 2 (—) | Li | OCHF$_2$ | OMe |
| — | 2 (—) | Na | OCHF$_2$ | OMe |
| — | 2 (—) | K | OCHF$_2$ | OMe |
| — | 2 (—) | ½Mg | OCHF$_2$ | OMe |
| — | 2 (—) | ½Ca | OCHF$_2$ | OMe |
| — | 2 (—) | MeNH$_3$ | OCHF$_2$ | OMe |
| — | 2 (—) | EtNH$_3$ | OCHF$_2$ | OMe |
| — | 2 (—) | PrNH$_3$ | OCHF$_2$ | OMe |
| — | 2 (—) | $^i$PrNH$_3$ | OCHF$_2$ | OMe |
| — | 2 (—) | NH$_2$CONH$_3$ | OCHF$_2$ | OMe |
| — | 2 (—) | Me | OCHF$_2$ | OMe |
| — | 2 (—) | Et | OCHF$_2$ | OMe |
| — | 2 (—) | $^i$Pr | OCHF$_2$ | OMe |
| — | 2 (—) | Pr | OCHF$_2$ | OMe |
| — | 2 (—) | Bu | OCHF$_2$ | OMe |
| — | 2 (—) | $^i$Bu | OCHF$_2$ | OMe |
| — | 2 (—) | $^s$Bu | OCHF$_2$ | OMe |
| — | 2 (—) | $^t$Bu | OCHF$_2$ | OMe |
| — | 2 (—) | —CH$_2$OCH$_3$ | OCHF$_2$ | OMe |
| — | 2 (—) | —CH$_2$CH$_2$OCH$_3$ | OCHF$_2$ | OMe |
| — | 2 (—) | —CH$_2$SCH$_3$ | OCHF$_2$ | OMe |
| — | 2 (—) | —CH$_2$CH=CH$_2$ | OCHF$_2$ | OMe |
| — | 2 (—) | —C(CH$_3$)$_2$CH=CH$_2$ | OCHF$_2$ | OMe |
| — | 2 (—) | —CH$_2$C≡CH$_2$ | OCHF$_2$ | OMe |
| — | 2 (—) | —CH$_2$C$_6$H$_5$ | OCHF$_2$ | OMe |
| — | 2 (—) | —CH$_2$C$_6$H$_4$—Cl-2 | OCHF$_2$ | OMe |
| — | 2 (—) | —CH$_2$C$_6$H$_4$—Cl-3 | OCHF$_2$ | OMe |
| — | 2 (—) | —CH$_2$C$_6$H$_4$—Cl-4 | OCHF$_2$ | OMe |
| — | 2 (—) | —CH$_2$C$_6$H$_4$—Me-2 | OCHF$_2$ | OMe |
| — | 2 (—) | —CH$_2$C$_6$H$_4$—Me-3 | OCHF$_2$ | OMe |
| — | 2 (—) | —CH$_2$C$_6$H$_4$—Me-4 | OCHF$_2$ | OMe |
| — | 2 (—) | —CH$_2$C$_6$H$_4$—OMe-2 | OCHF$_2$ | OMe |
| — | 2 (—) | —CH$_2$C$_6$H$_4$—OMe-3 | OCHF$_2$ | OMe |
| — | 2 (—) | —CH$_2$C$_6$H$_4$—OMe-4 | OCHF$_2$ | OMe |
| — | 2 (—) | —CH$_2$CH$_2$C$_6$H$_5$ | OCHF$_2$ | OMe |
| — | 2 (—) | H | OCHF$_2$ | OCHF$_2$ |
| — | 2 (—) | Li | OCHF$_2$ | OCHF$_2$ |
| — | 2 (—) | Na | OCHF$_2$ | OCHF$_2$ |
| — | 2 (—) | K | OCHF$_2$ | OCHF$_2$ |
| — | 2 (—) | ½Mg | OCHF$_2$ | OCHF$_2$ |
| — | 2 (—) | ½Ca | OCHF$_2$ | OCHF$_2$ |
| — | 2 (—) | MeNH$_3$ | OCHF$_2$ | OCHF$_2$ |
| — | 2 (—) | EtNH$_3$ | OCHF$_2$ | OCHF$_2$ |
| — | 2 (—) | PrNH$_3$ | OCHF$_2$ | OCHF$_2$ |
| — | 2 (—) | $^i$PrNH$_3$ | OCHF$_2$ | OCHF$_2$ |
| — | 2 (—) | NH$_2$CONH$_3$ | OCHF$_2$ | OCHF$_2$ |
| — | 2 (—) | Me | OCHF$_2$ | OCHF$_2$ |
| — | 2 (—) | Et | OCHF$_2$ | OCHF$_2$ |
| — | 2 (—) | $^i$Pr | OCHF$_2$ | OCHF$_2$ |
| — | 2 (—) | Pr | OCHF$_2$ | OCHF$_2$ |
| — | 2 (—) | Bu | OCHF$_2$ | OCHF$_2$ |
| — | 2 (—) | $^i$Bu | OCHF$_2$ | OCHF$_2$ |
| — | 2 (—) | $^s$Bu | OCHF$_2$ | OCHF$_2$ |
| — | 2 (—) | $^t$Bu | OCHF$_2$ | OCHF$_2$ |
| — | 2 (—) | —CH$_2$OCH$_3$ | OCHF$_2$ | OCHF$_2$ |
| — | 2 (—) | —CH$_2$CH$_2$OCH$_3$ | OCHF$_2$ | OCHF$_2$ |
| — | 2 (—) | —CH$_2$SCH$_3$ | OCHF$_2$ | OCHF$_2$ |
| — | 2 (—) | —CH$_2$CH=CH$_2$ | OCHF$_2$ | OCHF$_2$ |
| — | 2 (—) | —C(CH$_3$)$_2$CH=CH$_2$ | OCHF$_2$ | OCHF$_2$ |
| — | 2 (—) | —CH$_2$C≡CH$_2$ | OCHF$_2$ | OCHF$_2$ |
| — | 2 (—) | —CH$_2$C$_6$H$_5$ | OCHF$_2$ | OCHF$_2$ |
| — | 2 (—) | —CH$_2$C$_6$H$_4$—Cl-2 | OCHF$_2$ | OCHF$_2$ |
| — | 2 (—) | —CH$_2$C$_6$H$_4$—Cl-3 | OCHF$_2$ | OCHF$_2$ |
| — | 2 (—) | —CH$_2$C$_6$H$_4$—Cl-4 | OCHF$_2$ | OCHF$_2$ |
| — | 2 (—) | —CH$_2$C$_6$H$_4$—Me-2 | OCHF$_2$ | OCHF$_2$ |
| — | 2 (—) | —CH$_2$C$_6$H$_4$—Me-3 | OCHF$_2$ | OCHF$_2$ |
| — | 2 (—) | —CH$_2$C$_6$H$_4$—Me-4 | OCHF$_2$ | OCHF$_2$ |
| — | 2 (—) | —CH$_2$C$_6$H$_4$—OMe-2 | OCHF$_2$ | OCHF$_2$ |
| — | 2 (—) | —CH$_2$C$_6$H$_4$—OMe-3 | OCHF$_2$ | OCHF$_2$ |
| — | 2 (—) | —CH$_2$C$_6$H$_4$—OMe-4 | OCHF$_2$ | OCHF$_2$ |
| — | 2 (—) | —CH$_2$CH$_2$C$_6$H$_5$ | OCHF$_2$ | OCHF$_2$ |
| — | 2 (—) | H | SMe | OMe |
| — | 2 (—) | Li | SMe | OMe |
| — | 2 (—) | Na | SMe | OMe |
| — | 2 (—) | K | SMe | OMe |
| — | 2 (—) | ½Mg | SMe | OMe |
| — | 2 (—) | ½Ca | SMe | OMe |
| — | 2 (—) | MeNH$_3$ | SMe | OMe |
| — | 2 (—) | EtNH$_3$ | SMe | OMe |
| — | 2 (—) | PrNH$_3$ | SMe | OMe |
| — | 2 (—) | $^i$PrNH$_3$ | SMe | OMe |
| — | 2 (—) | NH$_2$CONH$_3$ | SMe | OMe |
| — | 2 (—) | Me | SMe | OMe |
| — | 2 (—) | Et | SMe | OMe |
| — | 2 (—) | $^i$Pr | SMe | OMe |
| — | 2 (—) | Pr | SMe | OMe |

TABLE 1-continued

A compound of the general formula:

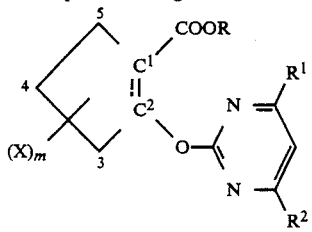

In the below-mentioned table, Me represents methyl group, Et represents ethyl group, Pr represents propyl group, $^i$Pr represents isopropyl group, Bu represents butyl group, $^i$Bu represents isobutyl group, $^s$Bu represents butyl secondary butyl group, $^t$Bu represents tertiary butyl group, cis represents a cis-form, trans represents a trans-form, mix. represents a mixture of a cis-form and a trans-form, 1 represents a single bond and 2 represents a double bond.

| $(X)_m$ | ==== | R | $R^1$ | $R^2$ |
|---|---|---|---|---|
| — | 2 (—) | Bu | SMe | OMe |
| — | 2 (—) | $^i$Bu | SMe | OMe |
| — | 2 (—) | $^s$Bu | SMe | OMe |
| — | 2 (—) | $^t$Bu | SMe | OMe |
| — | 2 (—) | —CH$_2$OCH$_3$ | SMe | OMe |
| — | 2 (—) | —CH$_2$CH$_2$OCH$_3$ | SMe | OMe |
| — | 2 (—) | —CH$_2$SCH$_3$ | SMe | OMe |
| — | 2 (—) | —CH$_2$CH=CH$_2$ | SMe | OMe |
| — | 2 (—) | —C(CH$_3$)$_2$CH=CH$_2$ | SMe | OMe |
| — | 2 (—) | —CH$_2$C≡CH$_2$ | SMe | OMe |
| — | 2 (—) | —CH$_2$C$_6$H$_5$ | SMe | OMe |
| — | 2 (—) | —CH$_2$C$_6$H$_4$—Cl-2 | SMe | OMe |
| — | 2 (—) | —CH$_2$C$_6$H$_4$—Cl-3 | SMe | OMe |
| — | 2 (—) | —CH$_2$C$_6$H$_4$—Cl-4 | SMe | OMe |
| — | 2 (—) | —CH$_2$C$_6$H$_4$—Me-2 | SMe | OMe |
| — | 2 (—) | —CH$_2$C$_6$H$_4$—Me-3 | SMe | OMe |
| — | 2 (—) | —CH$_2$C$_6$H$_4$—Me-4 | SMe | OMe |
| — | 2 (—) | —CH$_2$C$_6$H$_4$—OMe-2 | SMe | OMe |
| — | 2 (—) | —CH$_2$C$_6$H$_4$—OMe-3 | SMe | OMe |
| — | 2 (—) | —CH$_2$C$_6$H$_4$—OMe-4 | SMe | OMe |
| — | 2 (—) | —CH$_2$CH$_2$C$_6$H$_5$ | SMe | OMe |
| — | 2 (—) | H | SMe | Me |
| — | 2 (—) | Li | SMe | Me |
| — | 2 (—) | Na | SMe | Me |
| — | 2 (—) | K | SMe | Me |
| — | 2 (—) | ½Mg | SMe | Me |
| — | 2 (—) | ½Ca | SMe | Me |
| — | 2 (—) | MeNH$_3$ | SMe | Me |
| — | 2 (—) | EtNH$_3$ | SMe | Me |
| — | 2 (—) | PrNH$_3$ | SMe | Me |
| — | 2 (—) | $^i$PrNH$_3$ | SMe | Me |
| — | 2 (—) | NH$_2$CONH$_3$ | SMe | Me |
| — | 2 (—) | Me | SMe | Me |
| — | 2 (—) | Et | SMe | Me |
| — | 2 (—) | $^i$Pr | SMe | Me |
| — | 2 (—) | Pr | SMe | Me |
| — | 2 (—) | Bu | SMe | Me |
| — | 2 (—) | $^i$Bu | SMe | Me |
| — | 2 (—) | $^s$Bu | SMe | Me |
| — | 2 (—) | $^t$Bu | SMe | Me |
| — | 2 (—) | —CH$_2$OCH$_3$ | SMe | Me |
| — | 2 (—) | —CH$_2$CH$_2$OCH$_3$ | SMe | Me |
| — | 2 (—) | —CH$_2$SCH$_3$ | SMe | Me |
| — | 2 (—) | —CH$_2$CH=CH$_2$ | SMe | Me |
| — | 2 (—) | —C(CH$_3$)$_2$CH=CH$_2$ | SMe | Me |
| — | 2 (—) | —CH$_2$C≡CH$_2$ | SMe | Me |
| — | 2 (—) | —CH$_2$C$_6$H$_5$ | SMe | Me |
| — | 2 (—) | —CH$_2$C$_6$H$_4$—Cl-2 | SMe | Me |
| — | 2 (—) | —CH$_2$C$_6$H$_4$—Cl-3 | SMe | Me |
| — | 2 (—) | —CH$_2$C$_6$H$_4$—Cl-4 | SMe | Me |
| — | 2 (—) | —CH$_2$C$_6$H$_4$—Me-2 | SMe | Me |
| — | 2 (—) | —CH$_2$C$_6$H$_4$—Me-3 | SMe | Me |
| — | 2 (—) | —CH$_2$C$_6$H$_4$—Me-4 | SMe | Me |
| — | 2 (—) | —CH$_2$C$_6$H$_4$—OMe-2 | SMe | Me |
| — | 2 (—) | —CH$_2$C$_6$H$_4$—OMe-3 | SMe | Me |
| — | 2 (—) | —CH$_2$C$_6$H$_4$—OMe-4 | SMe | Me |
| — | 2 (—) | —CH$_2$CH$_2$C$_6$H$_5$ | SMe | Me |
| 3-Me | 1 (cis) | H | Me | Me |
| 3-Me | 1 (cis) | Na | Me | Me |
| 3-Me | 1 (cis) | ½Ca | Me | Me |
| 3-Me | 1 (cis) | $^i$PrNH$_3$ | Me | Me |

TABLE 1-continued

A compound of the general formula:

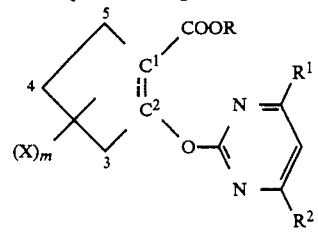

In the below-mentioned table, Me represents methyl group, Et represents ethyl group, Pr represents propyl group, $^i$Pr represents isopropyl group, Bu represents butyl group, $^i$Bu represents isobutyl group, $^s$Bu represents butyl secondary butyl group, $^t$Bu represents tertiary butyl group, cis represents a cis-form, trans represents a trans-form, mix. represents a mixture of a cis-form and a trans-form, 1 represents a single bond and 2 represents a double bond.

| $(X)_m$ | ==== | R | $R^1$ | $R^2$ |
|---|---|---|---|---|
| 3-Me | 1 (cis) | NH$_2$CONH$_3$ | Me | Me |
| 3-Me | 1 (cis) | Me | Me | Me |
| 3-Me | 1 (cis) | Et | Me | Me |
| 3-Me | 1 (cis) | $^i$Pr | Me | Me |
| 3-Me | 1 (cis) | Pr | Me | Me |
| 3-Me | 1 (cis) | Bu | Me | Me |
| 3-Me | 1 (cis) | $^i$Bu | Me | Me |
| 3-Me | 1 (cis) | $^s$Bu | Me | Me |
| 3-Me | 1 (cis) | —CH$_2$OCH$_3$ | Me | Me |
| 3-Me | 1 (cis) | —CH$_2$CH$_2$OCH$_3$ | Me | Me |
| 3-Me | 1 (cis) | —CH$_2$SCH$_3$ | Me | Me |
| 3-Me | 1 (cis) | —CH$_2$CH=CH$_2$ | Me | Me |
| 3-Me | 1 (cis) | —C(CH$_3$)$_2$CH=CH$_2$ | Me | Me |
| 3-Me | 1 (cis) | —CH$_2$C≡CH$_2$ | Me | Me |
| 3-Me | 1 (cis) | —CH$_2$C$_6$H$_5$ | Me | Me |
| 3-Me | 1 (cis) | —CH$_2$C$_6$H$_4$—Cl-2 | Me | Me |
| 3-Me | 1 (cis) | —CH$_2$C$_6$H$_4$—Cl-3 | Me | Me |
| 3-Me | 1 (cis) | —CH$_2$C$_6$H$_4$—Cl-4 | Me | Me |
| 3-Me | 1 (cis) | —CH$_2$C$_6$H$_4$—Me-2 | Me | Me |
| 3-Me | 1 (cis) | —CH$_2$C$_6$H$_4$—Me-3 | Me | Me |
| 3-Me | 1 (cis) | —CH$_2$C$_6$H$_4$—Me-4 | Me | Me |
| 3-Me | 1 (cis) | —CH$_2$C$_6$H$_4$—OMe-2 | Me | Me |
| 3-Me | 1 (cis) | —CH$_2$C$_6$H$_4$—OMe-3 | Me | Me |
| 3-Me | 1 (cis) | —CH$_2$C$_6$H$_4$—OMe-4 | Me | Me |
| 3-Me | 1 (cis) | —CH$_2$CH$_2$C$_6$H$_5$ | Me | Me |
| 3-Me | 1 (cis) | H | OMe | OMe |
| 3-Me | 1 (cis) | Na | OMe | OMe |
| 3-Me | 1 (cis) | ½Ca | OMe | OMe |
| 3-Me | 1 (cis) | $^i$PrNH$_3$ | OMe | OMe |
| 3-Me | 1 (cis) | NH$_2$CONH$_3$ | OMe | OMe |
| 3-Me | 1 (cis) | Me | OMe | OMe |
| 3-Me | 1 (cis) | Et | OMe | OMe |
| 3-Me | 1 (cis) | $^i$Pr | OMe | OMe |
| 3-Me | 1 (cis) | Pr | OMe | OMe |
| 3-Me | 1 (cis) | Bu | OMe | OMe |
| 3-Me | 1 (cis) | $^i$Bu | OMe | OMe |
| 3-Me | 1 (cis) | $^s$Bu | OMe | OMe |
| 3-Me | 1 (cis) | —CH$_2$OCH$_3$ | OMe | OMe |
| 3-Me | 1 (cis) | —CH$_2$CH$_2$OCH$_3$ | OMe | OMe |
| 3-Me | 1 (cis) | —CH$_2$SCH$_3$ | OMe | OMe |
| 3-Me | 1 (cis) | —CH$_2$CH=CH$_2$ | OMe | OMe |
| 3-Me | 1 (cis) | —C(CH$_3$)$_2$CH=CH$_2$ | OMe | OMe |
| 3-Me | 1 (cis) | —CH$_2$C≡CH$_2$ | OMe | OMe |
| 3-Me | 1 (cis) | —CH$_2$C$_6$H$_5$ | OMe | OMe |
| 3-Me | 1 (cis) | —CH$_2$C$_6$H$_4$—Cl-2 | OMe | OMe |
| 3-Me | 1 (cis) | —CH$_2$C$_6$H$_4$—Cl-3 | OMe | OMe |
| 3-Me | 1 (cis) | —CH$_2$C$_6$H$_4$—Cl-4 | OMe | OMe |
| 3-Me | 1 (cis) | —CH$_2$C$_6$H$_4$—Me-2 | OMe | OMe |
| 3-Me | 1 (cis) | —CH$_2$C$_6$H$_4$—Me-3 | OMe | OMe |
| 3-Me | 1 (cis) | —CH$_2$C$_6$H$_4$—Me-4 | OMe | OMe |
| 3-Me | 1 (cis) | —CH$_2$C$_6$H$_4$—OMe-2 | OMe | OMe |
| 3-Me | 1 (cis) | —CH$_2$C$_6$H$_4$—OMe-3 | OMe | OMe |
| 3-Me | 1 (cis) | —CH$_2$C$_6$H$_4$—OMe-4 | OMe | OMe |
| 3-Me | 1 (cis) | —CH$_2$CH$_2$C$_6$H$_5$ | OMe | OMe |
| 3-Me | 1 (trans) | H | Me | Me |
| 3-Me | 1 (trans) | Na | Me | Me |
| 3-Me | 1 (trans) | ½Ca | Me | Me |
| 3-Me | 1 (trans) | $^i$PrNH$_3$ | Me | Me |
| 3-Me | 1 (trans) | NH$_2$CONH$_3$ | Me | Me |
| 3-Me | 1 (trans) | Me | Me | Me |
| 3-Me | 1 (trans) | Et | Me | Me |

TABLE 1-continued

A compound of the general formula:

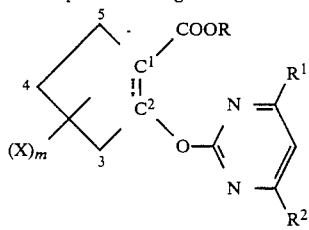 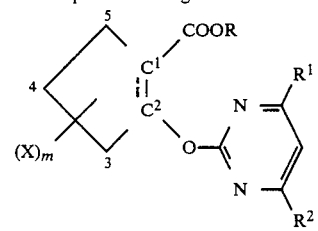

In the below-mentioned table, Me represents methyl group, Et represents ethyl group, Pr represents propyl group, $^i$Pr represents isopropyl group, Bu represents butyl group, $^i$Bu represents isobutyl group, $^s$Bu represents butyl secondary butyl group, $^t$Bu represents tertiary butyl group, cis represents a cis-form, trans represents a trans-form, mix. represents a mixture of a cis-form and a trans-form, 1 represents a single bond and 2 represents a double bond.

| $(X)_m$ | ==== | R | $R^1$ | $R^2$ |
|---|---|---|---|---|
| 3-Me | 1 (trans) | $^i$Pr | Me | Me |
| 3-Me | 1 (trans) | Pr | Me | Me |
| 3-Me | 1 (trans) | Bu | Me | Me |
| 3-Me | 1 (trans) | $^i$Bu | Me | Me |
| 3-Me | 1 (trans) | $^s$Bu | Me | Me |
| 3-Me | 1 (trans) | —CH$_2$OCH$_3$ | Me | Me |
| 3-Me | 1 (trans) | —CH$_2$CH$_2$OCH$_3$ | Me | Me |
| 3-Me | 1 (trans) | —CH$_2$SCH$_3$ | Me | Me |
| 3-Me | 1 (trans) | —CH$_2$CH=CH$_2$ | Me | Me |
| 3-Me | 1 (trans) | —C(CH$_3$)$_2$CH=CH$_2$ | Me | Me |
| 3-Me | 1 (trans) | —CH$_2$C≡CH$_2$ | Me | Me |
| 3-Me | 1 (trans) | —CH$_2$C$_6$H$_5$ | Me | Me |
| 3-Me | 1 (trans) | —CH$_2$C$_6$H$_4$—Cl-2 | Me | Me |
| 3-Me | 1 (trans) | —CH$_2$C$_6$H$_4$—Cl-3 | Me | Me |
| 3-Me | 1 (trans) | —CH$_2$C$_6$H$_4$—Cl-4 | Me | Me |
| 3-Me | 1 (trans) | —CH$_2$C$_6$H$_4$—Me-2 | Me | Me |
| 3-Me | 1 (trans) | —CH$_2$C$_6$H$_4$—Me-3 | Me | Me |
| 3-Me | 1 (trans) | —CH$_2$C$_6$H$_4$—Me-4 | Me | Me |
| 3-Me | 1 (trans) | —CH$_2$C$_6$H$_4$—OMe-2 | Me | Me |
| 3-Me | 1 (trans) | —CH$_2$C$_6$H$_4$—OMe-3 | Me | Me |
| 3-Me | 1 (trans) | —CH$_2$C$_6$H$_4$—OMe-4 | Me | Me |
| 3-Me | 1 (trans) | —CH$_2$CH$_2$C$_6$H$_5$ | Me | Me |
| 3-Me | 1 (trans) | H | OMe | OMe |
| 3-Me | 1 (trans) | Na | OMe | OMe |
| 3-Me | 1 (trans) | ½Ca | OMe | OMe |
| 3-Me | 1 (trans) | $^i$PrNH$_3$ | OMe | OMe |
| 3-Me | 1 (trans) | NH$_2$CONH$_3$ | OMe | OMe |
| 3-Me | 1 (trans) | Me | OMe | OMe |
| 3-Me | 1 (trans) | Et | OMe | OMe |
| 3-Me | 1 (trans) | $^i$Pr | OMe | OMe |
| 3-Me | 1 (trans) | Pr | OMe | OMe |
| 3-Me | 1 (trans) | Bu | OMe | OMe |
| 3-Me | 1 (trans) | $^i$Bu | OMe | OMe |
| 3-Me | 1 (trans) | $^s$Bu | OMe | OMe |
| 3-Me | 1 (trans) | —CH$_2$OCH$_3$ | OMe | OMe |
| 3-Me | 1 (trans) | —CH$_2$CH$_2$OCH$_3$ | OMe | OMe |
| 3-Me | 1 (trans) | —CH$_2$SCH$_3$ | OMe | OMe |
| 3-Me | 1 (trans) | —CH$_2$CH=CH$_2$ | OMe | OMe |
| 3-Me | 1 (trans) | —C(CH$_3$)$_2$CH=CH$_2$ | OMe | OMe |
| 3-Me | 1 (trans) | —CH$_2$C≡CH$_2$ | OMe | OMe |
| 3-Me | 1 (trans) | —CH$_2$C$_6$H$_5$ | OMe | OMe |
| 3-Me | 1 (trans) | —CH$_2$C$_6$H$_4$—Cl-2 | OMe | OMe |
| 3-Me | 1 (trans) | —CH$_2$C$_6$H$_4$—Cl-3 | OMe | OMe |
| 3-Me | 1 (trans) | —CH$_2$C$_6$H$_4$—Cl-4 | OMe | OMe |
| 3-Me | 1 (trans) | —CH$_2$C$_6$H$_4$—Me-2 | OMe | OMe |
| 3-Me | 1 (trans) | —CH$_2$C$_6$H$_4$—Me-3 | OMe | OMe |
| 3-Me | 1 (trans) | —CH$_2$C$_6$H$_4$—Me-4 | OMe | OMe |
| 3-Me | 1 (trans) | —CH$_2$C$_6$H$_4$—OMe-2 | OMe | OMe |
| 3-Me | 1 (trans) | —CH$_2$C$_6$H$_4$—OMe-3 | OMe | OMe |
| 3-Me | 1 (trans) | —CH$_2$C$_6$H$_4$—OMe-4 | OMe | OMe |
| 3-Me | 1 (trans) | —CH$_2$CH$_2$C$_6$H$_5$ | OMe | OMe |
| 3-Me | 1 (mix.) | H | Me | Me |
| 3-Me | 1 (mix.) | Na | Me | Me |
| 3-Me | 1 (mix.) | ½Ca | Me | Me |
| 3-Me | 1 (mix.) | $^i$PrNH$_3$ | Me | Me |
| 3-Me | 1 (mix.) | NH$_2$CONH$_3$ | Me | Me |
| 3-Me | 1 (mix.) | Me | Me | Me |
| 3-Me | 1 (mix.) | Et | Me | Me |
| 3-Me | 1 (mix.) | $^i$Pr | Me | Me |
| 3-Me | 1 (mix.) | Pr | Me | Me |
| 3-Me | 1 (mix.) | Bu | Me | Me |
| 3-Me | 1 (mix.) | $^i$Bu | Me | Me |
| 3-Me | 1 (mix.) | $^s$Bu | Me | Me |
| 3-Me | 1 (mix.) | —CH$_2$OCH$_3$ | Me | Me |
| 3-Me | 1 (mix.) | —CH$_2$CH$_2$OCH$_3$ | Me | Me |
| 3-Me | 1 (mix.) | —CH$_2$SCH$_3$ | Me | Me |
| 3-Me | 1 (mix.) | —CH$_2$CH=CH$_2$ | Me | Me |
| 3-Me | 1 (mix.) | —C(CH$_3$)$_2$CH=CH$_2$ | Me | Me |
| 3-Me | 1 (mix.) | —CH$_2$C≡CH$_2$ | Me | Me |
| 3-Me | 1 (mix.) | —CH$_2$C$_6$H$_5$ | Me | Me |
| 3-Me | 1 (mix.) | —CH$_2$C$_6$H$_4$—Cl-2 | Me | Me |
| 3-Me | 1 (mix.) | —CH$_2$C$_6$H$_4$—Cl-3 | Me | Me |
| 3-Me | 1 (mix.) | —CH$_2$C$_6$H$_4$—Cl-4 | Me | Me |
| 3-Me | 1 (mix.) | —CH$_2$C$_6$H$_4$—Me-2 | Me | Me |
| 3-Me | 1 (mix.) | —CH$_2$C$_6$H$_4$—Me-3 | Me | Me |
| 3-Me | 1 (mix.) | —CH$_2$C$_6$H$_4$—Me-4 | Me | Me |
| 3-Me | 1 (mix.) | —CH$_2$C$_6$H$_4$—OMe-2 | Me | Me |
| 3-Me | 1 (mix.) | —CH$_2$C$_6$H$_4$—OMe-3 | Me | Me |
| 3-Me | 1 (mix.) | —CH$_2$C$_6$H$_4$—OMe-4 | Me | Me |
| 3-Me | 1 (mix.) | —CH$_2$CH$_2$C$_6$H$_5$ | Me | Me |
| 3-Me | 1 (mix.) | H | OMe | OMe |
| 3-Me | 1 (mix.) | Na | OMe | OMe |
| 3-Me | 1 (mix.) | ½Ca | OMe | OMe |
| 3-Me | 1 (mix.) | $^i$PrNH$_3$ | OMe | OMe |
| 3-Me | 1 (mix.) | NH$_2$CONH$_3$ | OMe | OMe |
| 3-Me | 1 (mix.) | Me | OMe | OMe |
| 3-Me | 1 (mix.) | Et | OMe | OMe |
| 3-Me | 1 (mix.) | $^i$Pr | OMe | OMe |
| 3-Me | 1 (mix.) | Pr | OMe | OMe |
| 3-Me | 1 (mix.) | Bu | OMe | OMe |
| 3-Me | 1 (mix.) | $^i$Bu | OMe | OMe |
| 3-Me | 1 (mix.) | $^s$Bu | OMe | OMe |
| 3-Me | 1 (mix.) | —CH$_2$OCH$_3$ | OMe | OMe |
| 3-Me | 1 (mix.) | —CH$_2$CH$_2$OCH$_3$ | OMe | OMe |
| 3-Me | 1 (mix.) | —CH$_2$SCH$_3$ | OMe | OMe |
| 3-Me | 1 (mix.) | —CH$_2$CH=CH$_2$ | OMe | OMe |
| 3-Me | 1 (mix.) | —C(CH$_3$)$_2$CH=CH$_2$ | OMe | OMe |
| 3-Me | 1 (mix.) | —CH$_2$C≡CH$_2$ | OMe | OMe |
| 3-Me | 1 (mix.) | —CH$_2$C$_6$H$_5$ | OMe | OMe |
| 3-Me | 1 (mix.) | —CH$_2$C$_6$H$_4$—Cl-2 | OMe | OMe |
| 3-Me | 1 (mix.) | —CH$_2$C$_6$H$_4$—Cl-3 | OMe | OMe |
| 3-Me | 1 (mix.) | —CH$_2$C$_6$H$_4$—Cl-4 | OMe | OMe |
| 3-Me | 1 (mix.) | —CH$_2$C$_6$H$_4$—Me-2 | OMe | OMe |
| 3-Me | 1 (mix.) | —CH$_2$C$_6$H$_4$—Me-3 | OMe | OMe |
| 3-Me | 1 (mix.) | —CH$_2$C$_6$H$_4$—Me-4 | OMe | OMe |
| 3-Me | 1 (mix.) | —CH$_2$C$_6$H$_4$—OMe-2 | OMe | OMe |
| 3-Me | 1 (mix.) | —CH$_2$C$_6$H$_4$—OMe-3 | OMe | OMe |
| 3-Me | 1 (mix.) | —CH$_2$C$_6$H$_4$—OMe-4 | OMe | OMe |
| 3-Me | 1 (mix.) | —CH$_2$CH$_2$C$_6$H$_5$ | OMe | OMe |
| 3-Me | 2 (—) | H | Me | Me |
| 3-Me | 2 (—) | Na | Me | Me |
| 3-Me | 2 (—) | ½Ca | Me | Me |
| 3-Me | 2 (—) | $^i$PrNH$_3$ | Me | Me |
| 3-Me | 2 (—) | NH$_2$CONH$_3$ | Me | Me |
| 3-Me | 2 (—) | Me | Me | Me |
| 3-Me | 2 (—) | Et | Me | Me |
| 3-Me | 2 (—) | $^i$Pr | Me | Me |
| 3-Me | 2 (—) | Pr | Me | Me |
| 3-Me | 2 (—) | Bu | Me | Me |
| 3-Me | 2 (—) | $^i$Bu | Me | Me |
| 3-Me | 2 (—) | $^s$Bu | Me | Me |
| 3-Me | 2 (—) | —CH$_2$OCH$_3$ | Me | Me |

TABLE 1-continued

A compound of the general formula:

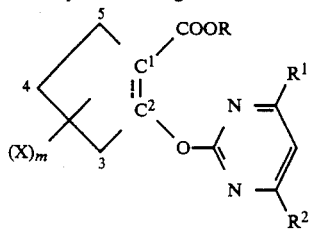

In the below-mentioned table, Me represents methyl group, Et represents ethyl group, Pr represents propyl group, $^i$Pr represents isopropyl group, Bu represents butyl group, $^i$Bu represents isobutyl group, $^s$Bu represents butyl secondary butyl group, $^t$Bu represents tertiary butyl group, cis represents a cis-form, trans represents a trans-form, mix. represents a mixture of a cis-form and a trans-form, 1 represents a single bond and 2 represents a double bond.

| $(X)_m$ | ==== | R | $R^1$ | $R^2$ |
|---|---|---|---|---|
| 3-Me | 2 (—) | —CH$_2$CH$_2$OCH$_3$ | Me | Me |
| 3-Me | 2 (—) | —CH$_2$SCH$_3$ | Me | Me |
| 3-Me | 2 (—) | —CH$_2$CH=CH$_2$ | Me | Me |
| 3-Me | 2 (—) | —C(CH$_3$)$_2$CH=CH$_2$ | Me | Me |
| 3-Me | 2 (—) | —CH$_2$C≡CH$_2$ | Me | Me |
| 3-Me | 2 (—) | —CH$_2$C$_6$H$_5$ | Me | Me |
| 3-Me | 2 (—) | —CH$_2$C$_6$H$_4$—Cl-2 | Me | Me |
| 3-Me | 2 (—) | —CH$_2$C$_6$H$_4$—Cl-3 | Me | Me |
| 3-Me | 2 (—) | —CH$_2$C$_6$H$_4$—Cl-4 | Me | Me |
| 3-Me | 2 (—) | —CH$_2$C$_6$H$_4$—Me-2 | Me | Me |
| 3-Me | 2 (—) | —CH$_2$C$_6$H$_4$—Me-3 | Me | Me |
| 3-Me | 2 (—) | —CH$_2$C$_6$H$_4$—Me-4 | Me | Me |
| 3-Me | 2 (—) | —CH$_2$C$_6$H$_4$—OMe-2 | Me | Me |
| 3-Me | 2 (—) | —CH$_2$C$_6$H$_4$—OMe-3 | Me | Me |
| 3-Me | 2 (—) | —CH$_2$C$_6$H$_4$—OMe-4 | Me | Me |
| 3-Me | 2 (—) | —CH$_2$CH$_2$C$_6$H$_5$ | Me | Me |
| 3-Me | 2 (—) | H | OMe | OMe |
| 3-Me | 2 (—) | Na | OMe | OMe |
| 3-Me | 2 (—) | ½Ca | OMe | OMe |
| 3-Me | 2 (—) | $^i$PrNH$_3$ | OMe | OMe |
| 3-Me | 2 (—) | NH$_2$CONH$_3$ | OMe | OMe |
| 3-Me | 2 (—) | Me | OMe | OMe |
| 3-Me | 2 (—) | Et | OMe | OMe |
| 3-Me | 2 (—) | $^i$Pr | OMe | OMe |
| 3-Me | 2 (—) | Pr | OMe | OMe |
| 3-Me | 2 (—) | Bu | OMe | OMe |
| 3-Me | 2 (—) | $^i$Bu | OMe | OMe |
| 3-Me | 2 (—) | $^s$Bu | OMe | OMe |
| 3-Me | 2 (—) | —CH$_2$OCH$_3$ | OMe | OMe |
| 3-Me | 2 (—) | —CH$_2$CH$_2$OCH$_3$ | OMe | OMe |
| 3-Me | 2 (—) | —CH$_2$SCH$_3$ | OMe | OMe |
| 3-Me | 2 (—) | —CH$_2$CH=CH$_2$ | OMe | OMe |
| 3-Me | 2 (—) | —C(CH$_3$)$_2$CH=CH$_2$ | OMe | OMe |
| 3-Me | 2 (—) | —CH$_2$C≡CH$_2$ | OMe | OMe |
| 3-Me | 2 (—) | —CH$_2$C$_6$H$_5$ | OMe | OMe |
| 3-Me | 2 (—) | —CH$_2$C$_6$H$_4$—Cl-2 | OMe | OMe |
| 3-Me | 2 (—) | —CH$_2$C$_6$H$_4$—Cl-3 | OMe | OMe |
| 3-Me | 2 (—) | —CH$_2$C$_6$H$_4$—Cl-4 | OMe | OMe |
| 3-Me | 2 (—) | —CH$_2$C$_6$H$_4$—Me-2 | OMe | OMe |
| 3-Me | 2 (—) | —CH$_2$C$_6$H$_4$—Me-3 | OMe | OMe |
| 3-Me | 2 (—) | —CH$_2$C$_6$H$_4$—Me-4 | OMe | OMe |
| 3-Me | 2 (—) | —CH$_2$C$_6$H$_4$—OMe-2 | OMe | OMe |
| 3-Me | 2 (—) | —CH$_2$C$_6$H$_4$—OMe-3 | OMe | OMe |
| 3-Me | 2 (—) | —CH$_2$C$_6$H$_4$—OMe-4 | OMe | OMe |
| 3-Me | 2 (—) | —CH$_2$CH$_2$C$_6$H$_5$ | OMe | OMe |
| 4-Me | 1 (cis) | H | Me | Me |
| 4-Me | 1 (cis) | Na | Me | Me |
| 4-Me | 1 (cis) | ½Ca | Me | Me |
| 4-Me | 1 (cis) | $^i$PrNH$_3$ | Me | Me |
| 4-Me | 1 (cis) | NH$_2$CONH$_3$ | Me | Me |
| 4-Me | 1 (cis) | Me | Me | Me |
| 4-Me | 1 (cis) | Et | Me | Me |
| 4-Me | 1 (cis) | $^i$Pr | Me | Me |
| 4-Me | 1 (cis) | Pr | Me | Me |
| 4-Me | 1 (cis) | Bu | Me | Me |
| 4-Me | 1 (cis) | $^i$Bu | Me | Me |
| 4-Me | 1 (cis) | $^s$Bu | Me | Me |
| 4-Me | 1 (cis) | —CH$_2$OCH$_3$ | Me | Me |
| 4-Me | 1 (cis) | —CH$_2$CH$_2$OCH$_3$ | Me | Me |
| 4-Me | 1 (cis) | —CH$_2$SCH$_3$ | Me | Me |
| 4-Me | 1 (cis) | —CH$_2$CH=CH$_2$ | Me | Me |

TABLE 1-continued

A compound of the general formula:

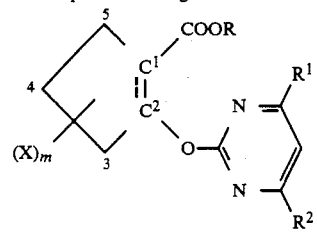

In the below-mentioned table, Me represents methyl group, Et represents ethyl group, Pr represents propyl group, $^i$Pr represents isopropyl group, Bu represents butyl group, $^i$Bu represents isobutyl group, $^s$Bu represents butyl secondary butyl group, $^t$Bu represents tertiary butyl group, cis represents a cis-form, trans represents a trans-form, mix. represents a mixture of a cis-form and a trans-form, 1 represents a single bond.

| $(X)_m$ | ==== | R | $R^1$ | $R^2$ |
|---|---|---|---|---|
| 4-Me | 1 (cis) | —C(CH$_3$)$_2$CH=CH$_2$ | Me | Me |
| 4-Me | 1 (cis) | —CH$_2$C≡CH$_2$ | Me | Me |
| 4-Me | 1 (cis) | —CH$_2$C$_6$H$_5$ | Me | Me |
| 4-Me | 1 (cis) | —CH$_2$C$_6$H$_4$—Cl-2 | Me | Me |
| 4-Me | 1 (cis) | —CH$_2$C$_6$H$_4$—Cl-3 | Me | Me |
| 4-Me | 1 (cis) | —CH$_2$C$_6$H$_4$—Cl-4 | Me | Me |
| 4-Me | 1 (cis) | —CH$_2$C$_6$H$_4$—Me-2 | Me | Me |
| 4-Me | 1 (cis) | —CH$_2$C$_6$H$_4$—Me-3 | Me | Me |
| 4-Me | 1 (cis) | —CH$_2$C$_6$H$_4$—Me-4 | Me | Me |
| 4-Me | 1 (cis) | —CH$_2$C$_6$H$_4$—OMe-2 | Me | Me |
| 4-Me | 1 (cis) | —CH$_2$C$_6$H$_4$—OMe-3 | Me | Me |
| 4-Me | 1 (cis) | —CH$_2$C$_6$H$_4$—OMe-4 | Me | Me |
| 4-Me | 1 (cis) | —CH$_2$CH$_2$C$_6$H$_5$ | Me | Me |
| 4-Me | 1 (cis) | H | OMe | OMe |
| 4-Me | 1 (cis) | Na | OMe | OMe |
| 4-Me | 1 (cis) | ½Ca | OMe | OMe |
| 4-Me | 1 (cis) | $^i$PrNH$_3$ | OMe | OMe |
| 4-Me | 1 (cis) | NH$_2$CONH$_3$ | OMe | OMe |
| 4-Me | 1 (cis) | Me | OMe | OMe |
| 4-Me | 1 (cis) | Et | OMe | OMe |
| 4-Me | 1 (cis) | $^i$Pr | OMe | OMe |
| 4-Me | 1 (cis) | Pr | OMe | OMe |
| 4-Me | 1 (cis) | Bu | OMe | OMe |
| 4-Me | 1 (cis) | $^i$Bu | OMe | OMe |
| 4-Me | 1 (cis) | $^s$Bu | OMe | OMe |
| 4-Me | 1 (cis) | —CH$_2$OCH$_3$ | OMe | OMe |
| 4-Me | 1 (cis) | —CH$_2$CH$_2$OCH$_3$ | OMe | OMe |
| 4-Me | 1 (cis) | —CH$_2$SCH$_3$ | OMe | OMe |
| 4-Me | 1 (cis) | —CH$_2$CH=CH$_2$ | OMe | OMe |
| 4-Me | 1 (cis) | —C(CH$_3$)$_2$CH=CH$_2$ | OMe | OMe |
| 4-Me | 1 (cis) | —CH$_2$C≡CH$_2$ | OMe | OMe |
| 4-Me | 1 (cis) | —CH$_2$C$_6$H$_5$ | OMe | OMe |
| 4-Me | 1 (cis) | —CH$_2$C$_6$H$_4$—Cl-2 | OMe | OMe |
| 4-Me | 1 (cis) | —CH$_2$C$_6$H$_4$—Cl-3 | OMe | OMe |
| 4-Me | 1 (cis) | —CH$_2$C$_6$H$_4$—Cl-4 | OMe | OMe |
| 4-Me | 1 (cis) | —CH$_2$C$_6$H$_4$—Me-2 | OMe | OMe |
| 4-Me | 1 (cis) | —CH$_2$C$_6$H$_4$—Me-3 | OMe | OMe |
| 4-Me | 1 (cis) | —CH$_2$C$_6$H$_4$—Me-4 | OMe | OMe |
| 4-Me | 1 (cis) | —CH$_2$C$_6$H$_4$—OMe-2 | OMe | OMe |
| 4-Me | 1 (cis) | —CH$_2$C$_6$H$_4$—OMe-3 | OMe | OMe |
| 4-Me | 1 (cis) | —CH$_2$C$_6$H$_4$—OMe-4 | OMe | OMe |
| 4-Me | 1 (cis) | —CH$_2$CH$_2$C$_6$H$_5$ | OMe | OMe |
| 4-Me | 1 (trans) | H | Me | Me |
| 4-Me | 1 (trans) | Na | Me | Me |
| 4-Me | 1 (trans) | ½Ca | Me | Me |
| 4-Me | 1 (trans) | $^i$PrNH$_3$ | Me | Me |
| 4-Me | 1 (trans) | NH$_2$CONH$_3$ | Me | Me |
| 4-Me | 1 (trans) | Me | Me | Me |
| 4-Me | 1 (trans) | Et | Me | Me |
| 4-Me | 1 (trans) | $^i$Pr | Me | Me |
| 4-Me | 1 (trans) | Pr | Me | Me |
| 4-Me | 1 (trans) | Bu | Me | Me |
| 4-Me | 1 (trans) | $^i$Bu | Me | Me |
| 4-Me | 1 (trans) | $^s$Bu | Me | Me |
| 4-Me | 1 (trans) | —CH$_2$OCH$_3$ | Me | Me |
| 4-Me | 1 (trans) | —CH$_2$CH$_2$OCH$_3$ | Me | Me |
| 4-Me | 1 (trans) | —CH$_2$SCH$_3$ | Me | Me |
| 4-Me | 1 (trans) | —CH$_2$CH=CH$_2$ | Me | Me |
| 4-Me | 1 (trans) | —C(CH$_3$)$_2$CH=CH$_2$ | Me | Me |
| 4-Me | 1 (trans) | —CH$_2$C≡CH$_2$ | Me | Me |
| 4-Me | 1 (trans) | —CH$_2$C$_6$H$_5$ | Me | Me |

TABLE 1-continued

A compound of the general formula:

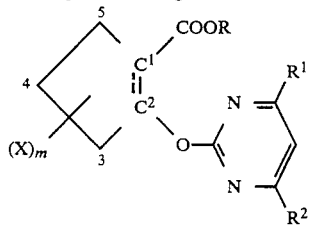

In the below-mentioned table, Me represents methyl group, Et represents ethyl group, Pr represents propyl group, $^i$Pr represents isopropyl group, Bu represents butyl group, $^i$Bu represents isobutyl group, $^s$Bu represents butyl secondary butyl group, $^t$Bu represents tertiary butyl group, cis represents a cis-form, trans represents a trans-form, mix. represents a mixture of a cis-form and a trans-form, 1 represents a single bond and 2 represents a double bond.

| (X)$_m$ | ==== | R | R$^1$ | R$^2$ |
|---|---|---|---|---|
| 4-Me | 1 (trans) | —CH$_2$C$_6$H$_4$—Cl-2 | Me | Me |
| 4-Me | 1 (trans) | —CH$_2$C$_6$H$_4$—Cl-3 | Me | Me |
| 4-Me | 1 (trans) | —CH$_2$C$_6$H$_4$—Cl-4 | Me | Me |
| 4-Me | 1 (trans) | —CH$_2$C$_6$H$_4$—Me-2 | Me | Me |
| 4-Me | 1 (trans) | —CH$_2$C$_6$H$_4$—Me-3 | Me | Me |
| 4-Me | 1 (trans) | —CH$_2$C$_6$H$_4$—Me-4 | Me | Me |
| 4-Me | 1 (trans) | —CH$_2$C$_6$H$_4$—OMe-2 | Me | Me |
| 4-Me | 1 (trans) | —CH$_2$C$_6$H$_4$—OMe-3 | Me | Me |
| 4-Me | 1 (trans) | —CH$_2$C$_6$H$_4$—OMe-4 | Me | Me |
| 4-Me | 1 (trans) | —CH$_2$CH$_2$C$_6$H$_5$ | Me | Me |
| 4-Me | 1 (trans) | H | OMe | OMe |
| 4-Me | 1 (trans) | Na | OMe | OMe |
| 4-Me | 1 (trans) | ½Ca | OMe | OMe |
| 4-Me | 1 (trans) | $^i$PrNH$_3$ | OMe | OMe |
| 4-Me | 1 (trans) | NH$_2$CONH$_3$ | OMe | OMe |
| 4-Me | 1 (trans) | Me | OMe | OMe |
| 4-Me | 1 (trans) | Et | OMe | OMe |
| 4-Me | 1 (trans) | $^i$Pr | OMe | OMe |
| 4-Me | 1 (trans) | Pr | OMe | OMe |
| 4-Me | 1 (trans) | Bu | OMe | OMe |
| 4-Me | 1 (trans) | $^i$Bu | OMe | OMe |
| 4-Me | 1 (trans) | $^s$Bu | OMe | OMe |
| 4-Me | 1 (trans) | —CH$_2$OCH$_3$ | OMe | OMe |
| 4-Me | 1 (trans) | —CH$_2$CH$_2$OCH$_3$ | OMe | OMe |
| 4-Me | 1 (trans) | —CH$_2$SCH$_3$ | OMe | OMe |
| 4-Me | 1 (trans) | —CH$_2$CH=CH$_2$ | OMe | OMe |
| 4-Me | 1 (trans) | —C(CH$_3$)$_2$CH=CH$_2$ | OMe | OMe |
| 4-Me | 1 (trans) | —CH$_2$C≡CH$_2$ | OMe | OMe |
| 4-Me | 1 (trans) | —CH$_2$C$_6$H$_5$ | OMe | OMe |
| 4-Me | 1 (trans) | —CH$_2$C$_6$H$_4$—Cl-2 | OMe | OMe |
| 4-Me | 1 (trans) | —CH$_2$C$_6$H$_4$—Cl-3 | OMe | OMe |
| 4-Me | 1 (trans) | —CH$_2$C$_6$H$_4$—Cl-4 | OMe | OMe |
| 4-Me | 1 (trans) | —CH$_2$C$_6$H$_4$—Me-2 | OMe | OMe |
| 4-Me | 1 (trans) | —CH$_2$C$_6$H$_4$—Me-3 | OMe | OMe |
| 4-Me | 1 (trans) | —CH$_2$C$_6$H$_4$—Me-4 | OMe | OMe |
| 4-Me | 1 (trans) | —CH$_2$C$_6$H$_4$—OMe-2 | OMe | OMe |
| 4-Me | 1 (trans) | —CH$_2$C$_6$H$_4$—OMe-3 | OMe | OMe |
| 4-Me | 1 (trans) | —CH$_2$C$_6$H$_4$—OMe-4 | OMe | OMe |
| 4-Me | 1 (trans) | —CH$_2$CH$_2$C$_6$H$_5$ | OMe | OMe |
| 4-Me | 1 (mix.) | H | Me | Me |
| 4-Me | 1 (mix.) | Na | Me | Me |
| 4-Me | 1 (mix.) | ½Ca | Me | Me |
| 4-Me | 1 (mix.) | $^i$PrNH$_3$ | Me | Me |
| 4-Me | 1 (mix.) | NH$_2$CONH$_3$ | Me | Me |
| 4-Me | 1 (mix.) | Me | Me | Me |
| 4-Me | 1 (mix.) | Et | Me | Me |
| 4-Me | 1 (mix.) | $^i$Pr | Me | Me |
| 4-Me | 1 (mix.) | Pr | Me | Me |
| 4-Me | 1 (mix.) | Bu | Me | Me |
| 4-Me | 1 (mix.) | $^i$Bu | Me | Me |
| 4-Me | 1 (mix.) | $^s$Bu | Me | Me |
| 4-Me | 1 (mix.) | —CH$_2$OCH$_3$ | Me | Me |
| 4-Me | 1 (mix.) | —CH$_2$CH$_2$OCH$_3$ | Me | Me |
| 4-Me | 1 (mix.) | —CH$_2$SCH$_3$ | Me | Me |
| 4-Me | 1 (mix.) | —CH$_2$CH=CH$_2$ | Me | Me |
| 4-Me | 1 (mix.) | —C(CH$_3$)$_2$CH=CH$_2$ | Me | Me |
| 4-Me | 1 (mix.) | —CH$_2$C≡CH$_2$ | Me | Me |
| 4-Me | 1 (mix.) | —CH$_2$C$_6$H$_5$ | Me | Me |
| 4-Me | 1 (mix.) | —CH$_2$C$_6$H$_4$—Cl-2 | Me | Me |
| 4-Me | 1 (mix.) | —CH$_2$C$_6$H$_4$—Cl-3 | Me | Me |
| 4-Me | 1 (mix.) | —CH$_2$C$_6$H$_4$—Cl-4 | Me | Me |
| 4-Me | 1 (mix.) | —CH$_2$C$_6$H$_4$—Me-2 | Me | Me |
| 4-Me | 1 (mix.) | —CH$_2$C$_6$H$_4$—Me-3 | Me | Me |
| 4-Me | 1 (mix.) | —CH$_2$C$_6$H$_4$—Me-4 | Me | Me |
| 4-Me | 1 (mix.) | —CH$_2$C$_6$H$_4$—OMe-2 | Me | Me |
| 4-Me | 1 (mix.) | —CH$_2$C$_6$H$_4$—OMe-3 | Me | Me |
| 4-Me | 1 (mix.) | —CH$_2$C$_6$H$_4$—OMe-4 | Me | Me |
| 4-Me | 1 (mix.) | —CH$_2$CH$_2$C$_6$H$_5$ | Me | Me |
| 4-Me | 1 (mix.) | H | OMe | OMe |
| 4-Me | 1 (mix.) | Na | OMe | OMe |
| 4-Me | 1 (mix.) | ½Ca | OMe | OMe |
| 4-Me | 1 (mix.) | $^i$PrNH$_3$ | OMe | OMe |
| 4-Me | 1 (mix.) | NH$_2$CONH$_3$ | OMe | OMe |
| 4-Me | 1 (mix.) | Me | OMe | OMe |
| 4-Me | 1 (mix.) | Et | OMe | OMe |
| 4-Me | 1 (mix.) | $^i$Pr | OMe | OMe |
| 4-Me | 1 (mix.) | Pr | OMe | OMe |
| 4-Me | 1 (mix.) | Bu | OMe | OMe |
| 4-Me | 1 (mix.) | $^i$Bu | OMe | OMe |
| 4-Me | 1 (mix.) | $^s$Bu | OMe | OMe |
| 4-Me | 1 (mix.) | —CH$_2$OCH$_3$ | OMe | OMe |
| 4-Me | 1 (mix.) | —CH$_2$CH$_2$OCH$_3$ | OMe | OMe |
| 4-Me | 1 (mix.) | —CH$_2$SCH$_3$ | OMe | OMe |
| 4-Me | 1 (mix.) | —CH$_2$CH=CH$_2$ | OMe | OMe |
| 4-Me | 1 (mix.) | —C(CH$_3$)$_2$CH=CH$_2$ | OMe | OMe |
| 4-Me | 1 (mix.) | —CH$_2$C≡CH$_2$ | OMe | OMe |
| 4-Me | 1 (mix.) | —CH$_2$C$_6$H$_5$ | OMe | OMe |
| 4-Me | 1 (mix.) | —CH$_2$C$_6$H$_4$—Cl-2 | OMe | OMe |
| 4-Me | 1 (mix.) | —CH$_2$C$_6$H$_4$—Cl-3 | OMe | OMe |
| 4-Me | 1 (mix.) | —CH$_2$C$_6$H$_4$—Cl-4 | OMe | OMe |
| 4-Me | 1 (mix.) | —CH$_2$C$_6$H$_4$—Me-2 | OMe | OMe |
| 4-Me | 1 (mix.) | —CH$_2$C$_6$H$_4$—Me-3 | OMe | OMe |
| 4-Me | 1 (mix.) | —CH$_2$C$_6$H$_4$—Me-4 | OMe | OMe |
| 4-Me | 1 (mix.) | —CH$_2$C$_6$H$_4$—OMe-2 | OMe | OMe |
| 4-Me | 1 (mix.) | —CH$_2$C$_6$H$_4$—OMe-3 | OMe | OMe |
| 4-Me | 1 (mix.) | —CH$_2$C$_6$H$_4$—OMe-4 | OMe | OMe |
| 4-Me | 1 (mix.) | —CH$_2$CH$_2$C$_6$H$_5$ | OMe | OMe |
| 4-Me | 2 (—) | H | Me | Me |
| 4-Me | 2 (—) | Na | Me | Me |
| 4-Me | 2 (—) | ½Ca | Me | Me |
| 4-Me | 2 (—) | $^i$PrNH$_3$ | Me | Me |
| 4-Me | 2 (—) | NH$_2$CONH$_3$ | Me | Me |
| 4-Me | 2 (—) | Me | Me | Me |
| 4-Me | 2 (—) | Et | Me | Me |
| 4-Me | 2 (—) | $^i$Pr | Me | Me |
| 4-Me | 2 (—) | Pr | Me | Me |
| 4-Me | 2 (—) | Bu | Me | Me |
| 4-Me | 2 (—) | $^i$Bu | Me | Me |
| 4-Me | 2 (—) | $^s$Bu | Me | Me |
| 4-Me | 2 (—) | —CH$_2$OCH$_3$ | Me | Me |
| 4-Me | 2 (—) | —CH$_2$CH$_2$OCH$_3$ | Me | Me |
| 4-Me | 2 (—) | —CH$_2$SCH$_3$ | Me | Me |
| 4-Me | 2 (—) | —CH$_2$CH=CH$_2$ | Me | Me |
| 4-Me | 2 (—) | —C(CH$_3$)$_2$CH=CH$_2$ | Me | Me |
| 4-Me | 2 (—) | —CH$_2$C≡CH$_2$ | Me | Me |
| 4-Me | 2 (—) | —CH$_2$C$_6$H$_5$ | Me | Me |
| 4-Me | 2 (—) | —CH$_2$C$_6$H$_4$—Cl-2 | Me | Me |
| 4-Me | 2 (—) | —CH$_2$C$_6$H$_4$—Cl-3 | Me | Me |
| 4-Me | 2 (—) | —CH$_2$C$_6$H$_4$—Cl-4 | Me | Me |
| 4-Me | 2 (—) | —CH$_2$C$_6$H$_4$—Me-2 | Me | Me |
| 4-Me | 2 (—) | —CH$_2$C$_6$H$_4$—Me-3 | Me | Me |
| 4-Me | 2 (—) | —CH$_2$C$_6$H$_4$—Me-4 | Me | Me |

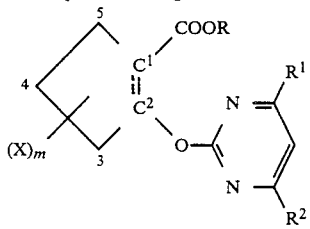

TABLE 1-continued

A compound of the general formula:

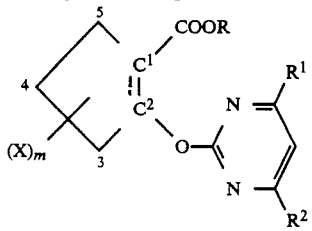

In the below-mentioned table, Me represents methyl group, Et represents ethyl group, Pr represents propyl group, $^i$Pr represents isopropyl group, Bu represents butyl group, $^i$Bu represents isobutyl group, $^s$Bu represents butyl secondary butyl group, $^t$Bu represents tertiary butyl group, cis represents a cis-form, trans represents a trans-form, mix. represents a mixture of a cis-form and a trans-form, 1 represents a single bond and 2 represents a double bond.

| (X)$_m$ | ==== | R | R$^1$ | R$^2$ |
|---|---|---|---|---|
| 4-Me | 2 (—) | —CH$_2$C$_6$H$_4$—OMe-2 | Me | Me |
| 4-Me | 2 (—) | —CH$_2$C$_6$H$_4$—OMe-3 | Me | Me |
| 4-Me | 2 (—) | —CH$_2$C$_6$H$_4$—OMe-4 | Me | Me |
| 4-Me | 2 (—) | —CH$_2$CH$_2$C$_6$H$_5$ | Me | Me |
| 4-Me | 2 (—) | H | OMe | OMe |
| 4-Me | 2 (—) | Na | OMe | OMe |
| 4-Me | 2 (—) | ½Ca | OMe | OMe |
| 4-Me | 2 (—) | $^i$PrNH$_3$ | OMe | OMe |
| 4-Me | 2 (—) | NH$_2$CONH$_3$ | OMe | OMe |
| 4-Me | 2 (—) | Me | OMe | OMe |
| 4-Me | 2 (—) | Et | OMe | OMe |
| 4-Me | 2 (—) | $^i$Pr | OMe | OMe |
| 4-Me | 2 (—) | Pr | OMe | OMe |
| 4-Me | 2 (—) | Bu | OMe | OMe |
| 4-Me | 2 (—) | $^i$Bu | OMe | OMe |
| 4-Me | 2 (—) | $^s$Bu | OMe | OMe |
| 4-Me | 2 (—) | —CH$_2$OCH$_3$ | OMe | OMe |
| 4-Me | 2 (—) | —CH$_2$CH$_2$OCH$_3$ | OMe | OMe |
| 4-Me | 2 (—) | —CH$_2$SCH$_3$ | OMe | OMe |
| 4-Me | 2 (—) | —CH$_2$CH=CH$_2$ | OMe | OMe |
| 4-Me | 2 (—) | —C(CH$_3$)$_2$CH=CH$_2$ | OMe | OMe |
| 4-Me | 2 (—) | —CH$_2$C≡CH$_2$ | OMe | OMe |
| 4-Me | 2 (—) | —CH$_2$C$_6$H$_5$ | OMe | OMe |
| 4-Me | 2 (—) | —CH$_2$C$_6$H$_4$—Cl-2 | OMe | OMe |
| 4-Me | 2 (—) | —CH$_2$C$_6$H$_4$—Cl-3 | OMe | OMe |
| 4-Me | 2 (—) | —CH$_2$C$_6$H$_4$—Cl-4 | OMe | OMe |
| 4-Me | 2 (—) | —CH$_2$C$_6$H$_4$—Me-2 | OMe | OMe |
| 4-Me | 2 (—) | —CH$_2$C$_6$H$_4$—Me-3 | OMe | OMe |
| 4-Me | 2 (—) | —CH$_2$C$_6$H$_4$—Me-4 | OMe | OMe |
| 4-Me | 2 (—) | —CH$_2$C$_6$H$_4$—OMe-2 | OMe | OMe |
| 4-Me | 2 (—) | —CH$_2$C$_6$H$_4$—OMe-3 | OMe | OMe |
| 4-Me | 2 (—) | —CH$_2$C$_6$H$_4$—OMe-4 | OMe | OMe |
| 4-Me | 2 (—) | —CH$_2$CH$_2$C$_6$H$_5$ | OMe | OMe |
| 5-Me | 1 (cis) | H | Me | Me |
| 5-Me | 1 (cis) | Na | Me | Me |
| 5-Me | 1 (cis) | ½Ca | Me | Me |
| 5-Me | 1 (cis) | $^i$PrNH$_3$ | Me | Me |
| 5-Me | 1 (cis) | NH$_2$CONH$_3$ | Me | Me |
| 5-Me | 1 (cis) | Me | Me | Me |
| 5-Me | 1 (cis) | Et | Me | Me |
| 5-Me | 1 (cis) | $^i$Pr | Me | Me |
| 5-Me | 1 (cis) | Pr | Me | Me |
| 5-Me | 1 (cis) | Bu | Me | Me |
| 5-Me | 1 (cis) | $^i$Bu | Me | Me |
| 5-Me | 1 (cis) | $^s$Bu | Me | Me |
| 5-Me | 1 (cis) | —CH$_2$OCH$_3$ | Me | Me |
| 5-Me | 1 (cis) | —CH$_2$CH$_2$OCH$_3$ | Me | Me |
| 5-Me | 1 (cis) | —CH$_2$SCH$_3$ | Me | Me |
| 5-Me | 1 (cis) | —CH$_2$CH=CH$_2$ | Me | Me |
| 5-Me | 1 (cis) | —C(CH$_3$)$_2$CH=CH$_2$ | Me | Me |
| 5-Me | 1 (cis) | —CH$_2$C≡CH$_2$ | Me | Me |
| 5-Me | 1 (cis) | —CH$_2$C$_6$H$_5$ | Me | Me |
| 5-Me | 1 (cis) | —CH$_2$C$_6$H$_4$—Cl-2 | Me | Me |
| 5-Me | 1 (cis) | —CH$_2$C$_6$H$_4$—Cl-3 | Me | Me |
| 5-Me | 1 (cis) | —CH$_2$C$_6$H$_4$—Cl-4 | Me | Me |
| 5-Me | 1 (cis) | —CH$_2$C$_6$H$_4$—Me-2 | Me | Me |
| 5-Me | 1 (cis) | —CH$_2$C$_6$H$_4$—Me-3 | Me | Me |
| 5-Me | 1 (cis) | —CH$_2$C$_6$H$_4$—Me-4 | Me | Me |
| 5-Me | 1 (cis) | —CH$_2$C$_6$H$_4$—OMe-2 | Me | Me |
| 5-Me | 1 (cis) | —CH$_2$C$_6$H$_4$—OMe-3 | Me | Me |
| 5-Me | 1 (cis) | —CH$_2$C$_6$H$_4$—OMe-4 | Me | Me |
| 5-Me | 1 (cis) | —CH$_2$CH$_2$C$_6$H$_5$ | Me | Me |
| 5-Me | 1 (cis) | H | OMe | OMe |
| 5-Me | 1 (cis) | Na | OMe | OMe |
| 5-Me | 1 (cis) | ½Ca | OMe | OMe |
| 5-Me | 1 (cis) | $^i$PrNH$_3$ | OMe | OMe |
| 5-Me | 1 (cis) | NH$_2$CONH$_3$ | OMe | OMe |
| 5-Me | 1 (cis) | Me | OMe | OMe |
| 5-Me | 1 (cis) | Et | OMe | OMe |
| 5-Me | 1 (cis) | $^i$Pr | OMe | OMe |
| 5-Me | 1 (cis) | Pr | OMe | OMe |
| 5-Me | 1 (cis) | Bu | OMe | OMe |
| 5-Me | 1 (cis) | $^i$Bu | OMe | OMe |
| 5-Me | 1 (cis) | $^s$Bu | OMe | OMe |
| 5-Me | 1 (cis) | —CH$_2$OCH$_3$ | OMe | OMe |
| 5-Me | 1 (cis) | —CH$_2$CH$_2$OCH$_3$ | OMe | OMe |
| 5-Me | 1 (cis) | —CH$_2$SCH$_3$ | OMe | OMe |
| 5-Me | 1 (cis) | —CH$_2$CH=CH$_2$ | OMe | OMe |
| 5-Me | 1 (cis) | —C(CH$_3$)$_2$CH=CH$_2$ | OMe | OMe |
| 5-Me | 1 (cis) | —CH$_2$C≡CH$_2$ | OMe | OMe |
| 5-Me | 1 (cis) | —CH$_2$C$_6$H$_5$ | OMe | OMe |
| 5-Me | 1 (cis) | —CH$_2$C$_6$H$_4$—Cl-2 | OMe | OMe |
| 5-Me | 1 (cis) | —CH$_2$C$_6$H$_4$—Cl-3 | OMe | OMe |
| 5-Me | 1 (cis) | —CH$_2$C$_6$H$_4$—Cl-4 | OMe | OMe |
| 5-Me | 1 (cis) | —CH$_2$C$_6$H$_4$—Me-2 | OMe | OMe |
| 5-Me | 1 (cis) | —CH$_2$C$_6$H$_4$—Me-3 | OMe | OMe |
| 5-Me | 1 (cis) | —CH$_2$C$_6$H$_4$—Me-4 | OMe | OMe |
| 5-Me | 1 (cis) | —CH$_2$C$_6$H$_4$—OMe-2 | OMe | OMe |
| 5-Me | 1 (cis) | —CH$_2$C$_6$H$_4$—OMe-3 | OMe | OMe |
| 5-Me | 1 (cis) | —CH$_2$C$_6$H$_4$—OMe-4 | OMe | OMe |
| 5-Me | 1 (cis) | —CH$_2$CH$_2$C$_6$H$_5$ | OMe | OMe |
| 5-Me | 1 (trans) | H | Me | Me |
| 5-Me | 1 (trans) | Na | Me | Me |
| 5-Me | 1 (trans) | ½Ca | Me | Me |
| 5-Me | 1 (trans) | $^i$PrNH$_3$ | Me | Me |
| 5-Me | 1 (trans) | NH$_2$CONH$_3$ | Me | Me |
| 5-Me | 1 (trans) | Me | Me | Me |
| 5-Me | 1 (trans) | Et | Me | Me |
| 5-Me | 1 (trans) | $^i$Pr | Me | Me |
| 5-Me | 1 (trans) | Pr | Me | Me |
| 5-Me | 1 (trans) | Bu | Me | Me |
| 5-Me | 1 (trans) | $^i$Bu | Me | Me |
| 5-Me | 1 (trans) | $^s$Bu | Me | Me |
| 5-Me | 1 (trans) | —CH$_2$OCH$_3$ | Me | Me |
| 5-Me | 1 (trans) | —CH$_2$CH$_2$OCH$_3$ | Me | Me |
| 5-Me | 1 (trans) | —CH$_2$SCH$_3$ | Me | Me |
| 5-Me | 1 (trans) | —CH$_2$CH=CH$_2$ | Me | Me |
| 5-Me | 1 (trans) | —C(CH$_3$)$_2$CH=CH$_2$ | Me | Me |
| 5-Me | 1 (trans) | —CH$_2$C≡CH$_2$ | Me | Me |
| 5-Me | 1 (trans) | —CH$_2$C$_6$H$_5$ | Me | Me |
| 5-Me | 1 (trans) | —CH$_2$C$_6$H$_4$—Cl-2 | Me | Me |
| 5-Me | 1 (trans) | —CH$_2$C$_6$H$_4$—Cl-3 | Me | Me |
| 5-Me | 1 (trans) | —CH$_2$C$_6$H$_4$—Cl-4 | Me | Me |
| 5-Me | 1 (trans) | —CH$_2$C$_6$H$_4$—Me-2 | Me | Me |
| 5-Me | 1 (trans) | —CH$_2$C$_6$H$_4$—Me-3 | Me | Me |
| 5-Me | 1 (trans) | —CH$_2$C$_6$H$_4$—Me-4 | Me | Me |
| 5-Me | 1 (trans) | —CH$_2$C$_6$H$_4$—OMe-2 | Me | Me |
| 5-Me | 1 (trans) | —CH$_2$C$_6$H$_4$—OMe-3 | Me | Me |
| 5-Me | 1 (trans) | —CH$_2$C$_6$H$_4$—OMe-4 | Me | Me |
| 5-Me | 1 (trans) | —CH$_2$CH$_2$C$_6$H$_5$ | Me | Me |
| 5-Me | 1 (trans) | H | OMe | OMe |
| 5-Me | 1 (trans) | Na | OMe | OMe |

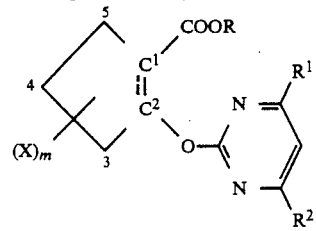

TABLE 1-continued

A compound of the general formula:

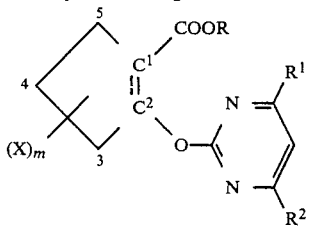

In the below-mentioned table, Me represents methyl group, Et represents ethyl group, Pr represents propyl group, $^i$Pr represents isopropyl group, Bu represents butyl group, $^i$Bu represents isobutyl group, $^s$Bu represents butyl secondary butyl group, $^t$Bu represents tertiary butyl group, cis represents a cis-form, trans represents a trans-form, mix. represents a mixture of a cis-form and a trans-form, 1 represents a single bond and 2 represents a double bond.

| $(X)_m$ | ---- | R | $R^1$ | $R^2$ |
|---|---|---|---|---|
| 5-Me | 1 (trans) | ½Ca | OMe | OMe |
| 5-Me | 1 (trans) | $^i$PrNH$_3$ | OMe | OMe |
| 5-Me | 1 (trans) | NH$_2$CONH$_3$ | OMe | OMe |
| 5-Me | 1 (trans) | Me | OMe | OMe |
| 5-Me | 1 (trans) | Et | OMe | OMe |
| 5-Me | 1 (trans) | $^i$Pr | OMe | OMe |
| 5-Me | 1 (trans) | Pr | OMe | OMe |
| 5-Me | 1 (trans) | Bu | OMe | OMe |
| 5-Me | 1 (trans) | $^i$Bu | OMe | OMe |
| 5-Me | 1 (trans) | $^s$Bu | OMe | OMe |
| 5-Me | 1 (trans) | —CH$_2$OCH$_3$ | OMe | OMe |
| 5-Me | 1 (trans) | —CH$_2$CH$_2$OCH$_3$ | OMe | OMe |
| 5-Me | 1 (trans) | —CH$_2$SCH$_3$ | OMe | OMe |
| 5-Me | 1 (trans) | —CH$_2$CH=CH$_2$ | OMe | OMe |
| 5-Me | 1 (trans) | —C(CH$_3$)$_2$CH=CH$_2$ | OMe | OMe |
| 5-Me | 1 (trans) | —CH$_2$C≡CH$_2$ | OMe | OMe |
| 5-Me | 1 (trans) | —CH$_2$C$_6$H$_5$ | OMe | OMe |
| 5-Me | 1 (trans) | —CH$_2$C$_6$H$_4$—Cl-2 | OMe | OMe |
| 5-Me | 1 (trans) | —CH$_2$C$_6$H$_4$—Cl-3 | OMe | OMe |
| 5-Me | 1 (trans) | —CH$_2$C$_6$H$_4$—Cl-4 | OMe | OMe |
| 5-Me | 1 (trans) | —CH$_2$C$_6$H$_4$—Me-2 | OMe | OMe |
| 5-Me | 1 (trans) | —CH$_2$C$_6$H$_4$—Me-3 | OMe | OMe |
| 5-Me | 1 (trans) | —CH$_2$C$_6$H$_4$—Me-4 | OMe | OMe |
| 5-Me | 1 (trans) | —CH$_2$C$_6$H$_4$—OMe-2 | OMe | OMe |
| 5-Me | 1 (trans) | —CH$_2$C$_6$H$_4$—OMe-3 | OMe | OMe |
| 5-Me | 1 (trans) | —CH$_2$C$_6$H$_4$—OMe-4 | OMe | OMe |
| 5-Me | 1 (trans) | —CH$_2$CH$_2$C$_6$H$_5$ | OMe | OMe |
| 5-Me | 1 (mixt.) | H | Me | Me |
| 5-Me | 1 (mixt.) | Na | Me | Me |
| 5-Me | 1 (mixt.) | ½Ca | Me | Me |
| 5-Me | 1 (mixt.) | $^i$PrNH$_3$ | Me | Me |
| 5-Me | 1 (mixt.) | NH$_2$CONH$_3$ | Me | Me |
| 5-Me | 1 (mixt.) | Me | Me | Me |
| 5-Me | 1 (mixt.) | Et | Me | Me |
| 5-Me | 1 (mixt.) | $^i$Pr | Me | Me |
| 5-Me | 1 (mixt.) | Pr | Me | Me |
| 5-Me | 1 (mixt.) | Bu | Me | Me |
| 5-Me | 1 (mixt.) | $^i$Bu | Me | Me |
| 5-Me | 1 (mixt.) | $^s$Bu | Me | Me |
| 5-Me | 1 (mixt.) | —CH$_2$OCH$_3$ | Me | Me |
| 5-Me | 1 (mixt.) | —CH$_2$CH$_2$OCH$_3$ | Me | Me |
| 5-Me | 1 (mixt.) | —CH$_2$SCH$_3$ | Me | Me |
| 5-Me | 1 (mixt.) | —CH$_2$CH=CH$_2$ | Me | Me |
| 5-Me | 1 (mixt.) | —C(CH$_3$)$_2$CH=CH$_2$ | Me | Me |
| 5-Me | 1 (mixt.) | —CH$_2$C≡CH$_2$ | Me | Me |
| 5-Me | 1 (mixt.) | —CH$_2$C$_6$H$_5$ | Me | Me |
| 5-Me | 1 (mixt.) | —CH$_2$C$_6$H$_4$—Cl-2 | Me | Me |
| 5-Me | 1 (mixt.) | —CH$_2$C$_6$H$_4$—Cl-3 | Me | Me |
| 5-Me | 1 (mixt.) | —CH$_2$C$_6$H$_4$—Cl-4 | Me | Me |
| 5-Me | 1 (mixt.) | —CH$_2$C$_6$H$_4$—Me-2 | Me | Me |
| 5-Me | 1 (mixt.) | —CH$_2$C$_6$H$_4$—Me-3 | Me | Me |
| 5-Me | 1 (mixt.) | —CH$_2$C$_6$H$_4$—Me-4 | Me | Me |
| 5-Me | 1 (mixt.) | —CH$_2$C$_6$H$_4$—OMe-2 | Me | Me |
| 5-Me | 1 (mixt.) | —CH$_2$C$_6$H$_4$—OMe-3 | Me | Me |
| 5-Me | 1 (mixt.) | —CH$_2$C$_6$H$_4$—OMe-4 | Me | Me |
| 5-Me | 1 (mixt.) | —CH$_2$CH$_2$C$_6$H$_5$ | Me | Me |
| 5-Me | 1 (mixt.) | H | OMe | OMe |
| 5-Me | 1 (mixt.) | Na | OMe | OMe |
| 5-Me | 1 (mixt.) | ½Ca | OMe | OMe |
| 5-Me | 1 (mixt.) | $^i$PrNH$_3$ | OMe | OMe |
| 5-Me | 1 (mixt.) | NH$_2$CONH$_3$ | OMe | OMe |
| 5-Me | 1 (mixt.) | Me | OMe | OMe |
| 5-Me | 1 (mixt.) | Et | OMe | OMe |
| 5-Me | 1 (mixt.) | $^i$Pr | OMe | OMe |
| 5-Me | 1 (mixt.) | Pr | OMe | OMe |
| 5-Me | 1 (mixt.) | Bu | OMe | OMe |
| 5-Me | 1 (mixt.) | $^i$Bu | OMe | OMe |
| 5-Me | 1 (mixt.) | $^s$Bu | OMe | OMe |
| 5-Me | 1 (mixt.) | —CH$_2$OCH$_3$ | OMe | OMe |
| 5-Me | 1 (mixt.) | —CH$_2$CH$_2$OCH$_3$ | OMe | OMe |
| 5-Me | 1 (mixt.) | —CH$_2$SCH$_3$ | OMe | OMe |
| 5-Me | 1 (mixt.) | —CH$_2$CH=CH$_2$ | OMe | OMe |
| 5-Me | 1 (mixt.) | —C(CH$_3$)$_2$CH=CH$_2$ | OMe | OMe |
| 5-Me | 1 (mixt.) | —CH$_2$C≡CH$_2$ | OMe | OMe |
| 5-Me | 1 (mixt.) | —CH$_2$C$_6$H$_5$ | OMe | OMe |
| 5-Me | 1 (mixt.) | —CH$_2$C$_6$H$_4$—Cl-2 | OMe | OMe |
| 5-Me | 1 (mixt.) | —CH$_2$C$_6$H$_4$—Cl-3 | OMe | OMe |
| 5-Me | 1 (mixt.) | —CH$_2$C$_6$H$_4$—Cl-4 | OMe | OMe |
| 5-Me | 1 (mixt.) | —CH$_2$C$_6$H$_4$—Me-2 | OMe | OMe |
| 5-Me | 1 (mixt.) | —CH$_2$C$_6$H$_4$—Me-3 | OMe | OMe |
| 5-Me | 1 (mixt.) | —CH$_2$C$_6$H$_4$—Me-4 | OMe | OMe |
| 5-Me | 1 (mixt.) | —CH$_2$C$_6$H$_4$—OMe-2 | OMe | OMe |
| 5-Me | 1 (mixt.) | —CH$_2$C$_6$H$_4$—OMe-3 | OMe | OMe |
| 5-Me | 1 (mixt.) | —CH$_2$C$_6$H$_4$—OMe-4 | OMe | OMe |
| 5-Me | 1 (mixt.) | —CH$_2$CH$_2$C$_6$H$_5$ | OMe | OMe |
| 5-Me | 2 (—) | H | Me | Me |
| 5-Me | 2 (—) | Na | Me | Me |
| 5-Me | 2 (—) | ½Ca | Me | Me |
| 5-Me | 2 (—) | $^i$PrNH$_3$ | Me | Me |
| 5-Me | 2 (—) | NH$_2$CONH$_3$ | Me | Me |
| 5-Me | 2 (—) | Me | Me | Me |
| 5-Me | 2 (—) | Et | Me | Me |
| 5-Me | 2 (—) | $^i$Pr | Me | Me |
| 5-Me | 2 (—) | Pr | Me | Me |
| 5-Me | 2 (—) | Bu | Me | Me |
| 5-Me | 2 (—) | $^i$Bu | Me | Me |
| 5-Me | 2 (—) | $^s$Bu | Me | Me |
| 5-Me | 2 (—) | —CH$_2$OCH$_3$ | Me | Me |
| 5-Me | 2 (—) | —CH$_2$CH$_2$OCH$_3$ | Me | Me |
| 5-Me | 2 (—) | —CH$_2$SCH$_3$ | Me | Me |
| 5-Me | 2 (—) | —CH$_2$CH=CH$_2$ | Me | Me |
| 5-Me | 2 (—) | —C(CH$_3$)$_2$CH=CH$_2$ | Me | Me |
| 5-Me | 2 (—) | —CH$_2$C≡CH$_2$ | Me | Me |
| 5-Me | 2 (—) | —CH$_2$C$_6$H$_5$ | Me | Me |
| 5-Me | 2 (—) | —CH$_2$C$_6$H$_4$—Cl-2 | Me | Me |
| 5-Me | 2 (—) | —CH$_2$C$_6$H$_4$—Cl-3 | Me | Me |
| 5-Me | 2 (—) | —CH$_2$C$_6$H$_4$—Cl-4 | Me | Me |
| 5-Me | 2 (—) | —CH$_2$C$_6$H$_4$—Me-2 | Me | Me |
| 5-Me | 2 (—) | —CH$_2$C$_6$H$_4$—Me-3 | Me | Me |
| 5-Me | 2 (—) | —CH$_2$C$_6$H$_4$—Me-4 | Me | Me |
| 5-Me | 2 (—) | —CH$_2$C$_6$H$_4$—OMe-2 | Me | Me |
| 5-Me | 2 (—) | —CH$_2$C$_6$H$_4$—OMe-3 | Me | Me |
| 5-Me | 2 (—) | —CH$_2$C$_6$H$_4$—OMe-4 | Me | Me |
| 5-Me | 2 (—) | —CH$_2$CH$_2$C$_6$H$_5$ | Me | Me |
| 5-Me | 2 (—) | H | OMe | OMe |
| 5-Me | 2 (—) | Na | OMe | OMe |
| 5-Me | 2 (—) | ½Ca | OMe | OMe |
| 5-Me | 2 (—) | $^i$PrNH$_3$ | OMe | OMe |
| 5-Me | 2 (—) | NH$_2$CONH$_3$ | OMe | OMe |
| 5-Me | 2 (—) | Me | OMe | OMe |
| 5-Me | 2 (—) | Et | OMe | OMe |
| 5-Me | 2 (—) | $^i$Pr | OMe | OMe |

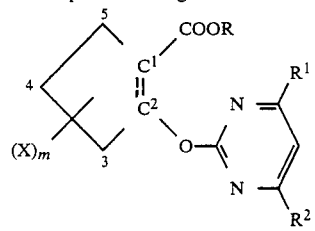

TABLE 1-continued

A compound of the general formula:

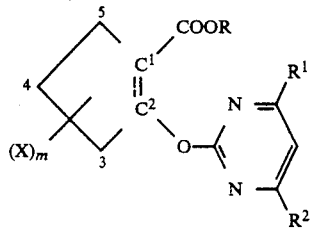

In the below-mentioned table, Me represents methyl group, Et represents ethyl group, Pr represents propyl group, $^i$Pr represents isopropyl group, Bu represents butyl group, $^i$Bu represents isobutyl group, $^s$Bu represents butyl secondary butyl group, $^t$Bu represents tertiary butyl group, cis represents a cis-form, trans represents a trans-form, mix. represents a mixture of a cis-form and a trans-form, 1 represents a single bond and 2 represents a double bond.

| $(X)_m$ | === | R | $R^1$ | $R^2$ |
|---|---|---|---|---|
| 5-Me | 2 (—) | Pr | OMe | OMe |
| 5-Me | 2 (—) | Bu | OMe | OMe |
| 5-Me | 2 (—) | $^i$Bu | OMe | OMe |
| 5-Me | 2 (—) | $^s$Bu | OMe | OMe |
| 5-Me | 2 (—) | —CH$_2$OCH$_3$ | OMe | OMe |
| 5-Me | 2 (—) | —CH$_2$CH$_2$OCH$_3$ | OMe | OMe |
| 5-Me | 2 (—) | —CH$_2$SCH$_3$ | OMe | OMe |
| 5-Me | 2 (—) | —CH$_2$CH=CH$_2$ | OMe | OMe |
| 5-Me | 2 (—) | —C(CH$_3$)$_2$CH=CH$_2$ | OMe | OMe |
| 5-Me | 2 (—) | —CH$_2$C≡CH$_2$ | OMe | OMe |
| 5-Me | 2 (—) | —CH$_2$C$_6$H$_5$ | OMe | OMe |
| 5-Me | 2 (—) | —CH$_2$C$_6$H$_4$—Cl-2 | OMe | OMe |
| 5-Me | 2 (—) | —CH$_2$C$_6$H$_4$—Cl-3 | OMe | OMe |
| 5-Me | 2 (—) | —CH$_2$C$_6$H$_4$—Cl-4 | OMe | OMe |
| 5-Me | 2 (—) | —CH$_2$C$_6$H$_4$—Me-2 | OMe | OMe |
| 5-Me | 2 (—) | —CH$_2$C$_6$H$_4$—Me-3 | OMe | OMe |
| 5-Me | 2 (—) | —CH$_2$C$_6$H$_4$—Me-4 | OMe | OMe |
| 5-Me | 2 (—) | —CH$_2$C$_6$H$_4$—OMe-2 | OMe | OMe |
| 5-Me | 2 (—) | —CH$_2$C$_6$H$_4$—OMe-3 | OMe | OMe |
| 5-Me | 2 (—) | —CH$_2$C$_6$H$_4$—OMe-4 | OMe | OMe |
| 5-Me | 2 (—) | —CH$_2$CH$_2$C$_6$H$_5$ | OMe | OMe |
| 3.3-(Me)$_2$ | 1 (cis) | H | Me | Me |
| 3.3-(Me)$_2$ | 1 (cis) | Na | Me | Me |
| 3.3-(Me)$_2$ | 1 (cis) | ½Ca | Me | Me |
| 3.3-(Me)$_2$ | 1 (cis) | $^i$PrNH$_3$ | Me | Me |
| 3.3-(Me)$_2$ | 1 (cis) | NH$_2$CONH$_3$ | Me | Me |
| 3.3-(Me)$_2$ | 1 (cis) | Me | Me | Me |
| 3.3-(Me)$_2$ | 1 (cis) | Et | Me | Me |
| 3.3-(Me)$_2$ | 1 (cis) | $^i$Pr | Me | Me |
| 3.3-(Me)$_2$ | 1 (cis) | Pr | Me | Me |
| 3.3-(Me)$_2$ | 1 (cis) | Bu | Me | Me |
| 3.3-(Me)$_2$ | 1 (cis) | $^i$Bu | Me | Me |
| 3.3-(Me)$_2$ | 1 (cis) | $^s$Bu | Me | Me |
| 3.3-(Me)$_2$ | 1 (cis) | —CH$_2$OCH$_3$ | Me | Me |
| 3.3-(Me)$_2$ | 1 (cis) | —CH$_2$CH$_2$OCH$_3$ | Me | Me |
| 3.3-(Me)$_2$ | 1 (cis) | —CH$_2$SCH$_3$ | Me | Me |
| 3.3-(Me)$_2$ | 1 (cis) | —CH$_2$CH=CH$_2$ | Me | Me |
| 3.3-(Me)$_2$ | 1 (cis) | —C(CH$_3$)$_2$CH=CH$_2$ | Me | Me |
| 3.3-(Me)$_2$ | 1 (cis) | —CH$_2$C≡CH$_2$ | Me | Me |
| 3.3-(Me)$_2$ | 1 (cis) | —CH$_2$C$_6$H$_5$ | Me | Me |
| 3.3-(Me)$_2$ | 1 (cis) | —CH$_2$C$_6$H$_4$—Cl-2 | Me | Me |
| 3.3-(Me)$_2$ | 1 (cis) | —CH$_2$C$_6$H$_4$—Cl-3 | Me | Me |
| 3.3-(Me)$_2$ | 1 (cis) | —CH$_2$C$_6$H$_4$—Cl-4 | Me | Me |
| 3.3-(Me)$_2$ | 1 (cis) | —CH$_2$C$_6$H$_4$—Me-2 | Me | Me |
| 3.3-(Me)$_2$ | 1 (cis) | —CH$_2$C$_6$H$_4$—Me-3 | Me | Me |
| 3.3-(Me)$_2$ | 1 (cis) | —CH$_2$C$_6$H$_4$—Me-4 | Me | Me |
| 3.3-(Me)$_2$ | 1 (cis) | —CH$_2$C$_6$H$_4$—OMe-2 | Me | Me |
| 3.3-(Me)$_2$ | 1 (cis) | —CH$_2$C$_6$H$_4$—OMe-3 | Me | Me |
| 3.3-(Me)$_2$ | 1 (cis) | —CH$_2$C$_6$H$_4$—OMe-4 | Me | Me |
| 3.3-(Me)$_2$ | 1 (cis) | —CH$_2$CH$_2$C$_6$H$_5$ | Me | Me |
| 3.3-(Me)$_2$ | 1 (cis) | H | OMe | OMe |
| 3.3-(Me)$_2$ | 1 (cis) | Na | OMe | OMe |
| 3.3-(Me)$_2$ | 1 (cis) | ½Ca | OMe | OMe |
| 3.3-(Me)$_2$ | 1 (cis) | $^i$PrNH$_3$ | OMe | OMe |
| 3.3-(Me)$_2$ | 1 (cis) | NH$_2$CONH$_3$ | OMe | OMe |
| 3.3-(Me)$_2$ | 1 (cis) | Me | OMe | OMe |
| 3.3-(Me)$_2$ | 1 (cis) | Et | OMe | OMe |
| 3.3-(Me)$_2$ | 1 (cis) | $^i$Pr | OMe | OMe |
| 3.3-(Me)$_2$ | 1 (cis) | Pr | OMe | OMe |
| 3.3-(Me)$_2$ | 1 (cis) | Bu | OMe | OMe |
| 3.3-(Me)$_2$ | 1 (cis) | $^i$Bu | OMe | OMe |
| 3.3-(Me)$_2$ | 1 (cis) | $^s$Bu | OMe | OMe |
| 3.3-(Me)$_2$ | 1 (cis) | —CH$_2$OCH$_3$ | OMe | OMe |
| 3.3-(Me)$_2$ | 1 (cis) | —CH$_2$CH$_2$OCH$_3$ | OMe | OMe |
| 3.3-(Me)$_2$ | 1 (cis) | —CH$_2$SCH$_3$ | OMe | OMe |
| 3.3-(Me)$_2$ | 1 (cis) | —CH$_2$CH=CH$_2$ | OMe | OMe |
| 3.3-(Me)$_2$ | 1 (cis) | —C(CH$_3$)$_2$CH=CH$_2$ | OMe | OMe |
| 3.3-(Me)$_2$ | 1 (cis) | —CH$_2$C≡CH$_2$ | OMe | OMe |
| 3.3-(Me)$_2$ | 1 (cis) | —CH$_2$C$_6$H$_5$ | OMe | OMe |
| 3.3-(Me)$_2$ | 1 (cis) | —CH$_2$C$_6$H$_4$—Cl-2 | OMe | OMe |
| 3.3-(Me)$_2$ | 1 (cis) | —CH$_2$C$_6$H$_4$—Cl-3 | OMe | OMe |
| 3.3-(Me)$_2$ | 1 (cis) | —CH$_2$C$_6$H$_4$—Cl-4 | OMe | OMe |
| 3.3-(Me)$_2$ | 1 (cis) | —CH$_2$C$_6$H$_4$—Me-2 | OMe | OMe |
| 3.3-(Me)$_2$ | 1 (cis) | —CH$_2$C$_6$H$_4$—Me-3 | OMe | OMe |
| 3.3-(Me)$_2$ | 1 (cis) | —CH$_2$C$_6$H$_4$—Me-4 | OMe | OMe |
| 3.3-(Me)$_2$ | 1 (cis) | —CH$_2$C$_6$H$_4$—OMe-2 | OMe | OMe |
| 3.3-(Me)$_2$ | 1 (cis) | —CH$_2$C$_6$H$_4$—OMe-3 | OMe | OMe |
| 3.3-(Me)$_2$ | 1 (cis) | —CH$_2$C$_6$H$_4$—OMe-4 | OMe | OMe |
| 3.3-(Me)$_2$ | 1 (cis) | —CH$_2$CH$_2$C$_6$H$_5$ | OMe | OMe |
| 3.3-(Me)$_2$ | 1 (trans) | H | Me | Me |
| 3.3-(Me)$_2$ | 1 (trans) | Na | Me | Me |
| 3.3-(Me)$_2$ | 1 (trans) | ½Ca | Me | Me |
| 3.3-(Me)$_2$ | 1 (trans) | $^i$PrNH$_3$ | Me | Me |
| 3.3-(Me)$_2$ | 1 (trans) | NH$_2$CONH$_3$ | Me | Me |
| 3.3-(Me)$_2$ | 1 (trans) | Me | Me | Me |
| 3.3-(Me)$_2$ | 1 (trans) | Et | Me | Me |
| 3.3-(Me)$_2$ | 1 (trans) | $^i$Pr | Me | Me |
| 3.3-(Me)$_2$ | 1 (trans) | Pr | Me | Me |
| 3.3-(Me)$_2$ | 1 (trans) | Bu | Me | Me |
| 3.3-(Me)$_2$ | 1 (trans) | $^i$Bu | Me | Me |
| 3.3-(Me)$_2$ | 1 (trans) | $^s$Bu | Me | Me |
| 3.3-(Me)$_2$ | 1 (trans) | —CH$_2$OCH$_3$ | Me | Me |
| 3.3-(Me)$_2$ | 1 (trans) | —CH$_2$CH$_2$OCH$_3$ | Me | Me |
| 3.3-(Me)$_2$ | 1 (trans) | —CH$_2$SCH$_3$ | Me | Me |
| 3.3-(Me)$_2$ | 1 (trans) | —CH$_2$CH=CH$_2$ | Me | Me |
| 3.3-(Me)$_2$ | 1 (trans) | —C(CH$_3$)$_2$CH=CH$_2$ | Me | Me |
| 3.3-(Me)$_2$ | 1 (trans) | —CH$_2$C≡CH$_2$ | Me | Me |
| 3.3-(Me)$_2$ | 1 (trans) | —CH$_2$C$_6$H$_5$ | Me | Me |
| 3.3-(Me)$_2$ | 1 (trans) | —CH$_2$C$_6$H$_4$—Cl-2 | Me | Me |
| 3.3-(Me)$_2$ | 1 (trans) | —CH$_2$C$_6$H$_4$—Cl-3 | Me | Me |
| 3.3-(Me)$_2$ | 1 (trans) | —CH$_2$C$_6$H$_4$—Cl-4 | Me | Me |
| 3.3-(Me)$_2$ | 1 (trans) | —CH$_2$C$_6$H$_4$—Me-2 | Me | Me |
| 3.3-(Me)$_2$ | 1 (trans) | —CH$_2$C$_6$H$_4$—Me-3 | Me | Me |
| 3.3-(Me)$_2$ | 1 (trans) | —CH$_2$C$_6$H$_4$—Me-4 | Me | Me |
| 3.3-(Me)$_2$ | 1 (trans) | —CH$_2$C$_6$H$_4$—OMe-2 | Me | Me |
| 3.3-(Me)$_2$ | 1 (trans) | —CH$_2$C$_6$H$_4$—OMe-3 | Me | Me |
| 3.3-(Me)$_2$ | 1 (trans) | —CH$_2$C$_6$H$_4$—OMe-4 | Me | Me |
| 3.3-(Me)$_2$ | 1 (trans) | —CH$_2$CH$_2$C$_6$H$_5$ | Me | Me |
| 3.3-(Me)$_2$ | 1 (trans) | H | OMe | OMe |
| 3.3-(Me)$_2$ | 1 (trans) | Na | OMe | OMe |
| 3.3-(Me)$_2$ | 1 (trans) | ½Ca | OMe | OMe |
| 3.3-(Me)$_2$ | 1 (trans) | $^i$PrNH$_3$ | OMe | OMe |
| 3.3-(Me)$_2$ | 1 (trans) | NH$_2$CONH$_3$ | OMe | OMe |
| 3.3-(Me)$_2$ | 1 (trans) | Me | OMe | OMe |
| 3.3-(Me)$_2$ | 1 (trans) | Et | OMe | OMe |
| 3.3-(Me)$_2$ | 1 (trans) | $^i$Pr | OMe | OMe |
| 3.3-(Me)$_2$ | 1 (trans) | Pr | OMe | OMe |
| 3.3-(Me)$_2$ | 1 (trans) | Bu | OMe | OMe |
| 3.3-(Me)$_2$ | 1 (trans) | $^i$Bu | OMe | OMe |
| 3.3-(Me)$_2$ | 1 (trans) | $^s$Bu | OMe | OMe |
| 3.3-(Me)$_2$ | 1 (trans) | —CH$_2$OCH$_3$ | OMe | OMe |
| 3.3-(Me)$_2$ | 1 (trans) | —CH$_2$CH$_2$OCH$_3$ | OMe | OMe |

TABLE 1-continued

A compound of the general formula:

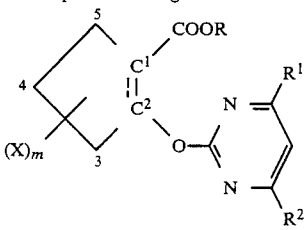
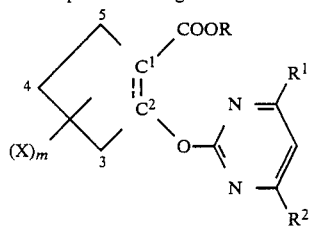

In the below-mentioned table, Me represents methyl group, Et represents ethyl group, Pr represents propyl group, $^i$Pr represents isopropyl group, Bu represents butyl group, $^i$Bu represents isobutyl group, $^s$Bu represents butyl secondary butyl group, $^t$Bu represents tertiary butyl group, cis represents a cis-form, trans represents a trans-form, mix. represents a mixture of a cis-form and a trans-form, 1 represents a single bond and 2 represents a double bond.

| (X)$_m$ | ≡ | R | R$^1$ | R$^2$ |
|---|---|---|---|---|
| 3.3-(Me)$_2$ | 1 (trans) | —CH$_2$SCH$_3$ | OMe | OMe |
| 3.3-(Me)$_2$ | 1 (trans) | —CH$_2$CH=CH$_2$ | OMe | OMe |
| 3.3-(Me)$_2$ | 1 (trans) | —C(CH$_3$)$_2$CH=CH$_2$ | OMe | OMe |
| 3.3-(Me)$_2$ | 1 (trans) | —CH$_2$C≡CH$_2$ | OMe | OMe |
| 3.3-(Me)$_2$ | 1 (trans) | —CH$_2$C$_6$H$_5$ | OMe | OMe |
| 3.3-(Me)$_2$ | 1 (trans) | —CH$_2$C$_6$H$_4$—Cl-2 | OMe | OMe |
| 3.3-(Me)$_2$ | 1 (trans) | —CH$_2$C$_6$H$_4$—Cl-3 | OMe | OMe |
| 3.3-(Me)$_2$ | 1 (trans) | —CH$_2$C$_6$H$_4$—Cl-4 | OMe | OMe |
| 3.3-(Me)$_2$ | 1 (trans) | —CH$_2$C$_6$H$_4$—Me-2 | OMe | OMe |
| 3.3-(Me)$_2$ | 1 (trans) | —CH$_2$C$_6$H$_4$—Me-3 | OMe | OMe |
| 3.3-(Me)$_2$ | 1 (trans) | —CH$_2$C$_6$H$_4$—Me-4 | OMe | OMe |
| 3.3-(Me)$_2$ | 1 (trans) | —CH$_2$C$_6$H$_4$—OMe-2 | OMe | OMe |
| 3.3-(Me)$_2$ | 1 (trans) | —CH$_2$C$_6$H$_4$—OMe-3 | OMe | OMe |
| 3.3-(Me)$_2$ | 1 (trans) | —CH$_2$C$_6$H$_4$—OMe-4 | OMe | OMe |
| 3.3-(Me)$_2$ | 1 (trans) | —CH$_2$CH$_2$C$_6$H$_5$ | OMe | OMe |
| 3.3-(Me)$_2$ | 1 (mix.) | H | Me | Me |
| 3.3-(Me)$_2$ | 1 (mix.) | Na | Me | Me |
| 3.3-(Me)$_2$ | 1 (mix.) | ½Ca | Me | Me |
| 3.3-(Me)$_2$ | 1 (mix.) | $^i$PrNH$_3$ | Me | Me |
| 3.3-(Me)$_2$ | 1 (mix.) | NH$_2$CONH$_3$ | Me | Me |
| 3.3-(Me)$_2$ | 1 (mix.) | Me | Me | Me |
| 3.3-(Me)$_2$ | 1 (mix.) | Et | Me | Me |
| 3.3-(Me)$_2$ | 1 (mix.) | $^i$Pr | Me | Me |
| 3.3-(Me)$_2$ | 1 (mix.) | Pr | Me | Me |
| 3.3-(Me)$_2$ | 1 (mix.) | Bu | Me | Me |
| 3.3-(Me)$_2$ | 1 (mix.) | $^i$Bu | Me | Me |
| 3.3-(Me)$_2$ | 1 (mix.) | $^s$Bu | Me | Me |
| 3.3-(Me)$_2$ | 1 (mix.) | —CH$_2$OCH$_3$ | Me | Me |
| 3.3-(Me)$_2$ | 1 (mix.) | —CH$_2$CH$_2$OCH$_3$ | Me | Me |
| 3.3-(Me)$_2$ | 1 (mix.) | —CH$_2$SCH$_3$ | Me | Me |
| 3.3-(Me)$_2$ | 1 (mix.) | —CH$_2$CH=CH$_2$ | Me | Me |
| 3.3-(Me)$_2$ | 1 (mix.) | —C(CH$_3$)$_2$CH=CH$_2$ | Me | Me |
| 3.3-(Me)$_2$ | 1 (mix.) | —CH$_2$C≡CH$_2$ | Me | Me |
| 3.3-(Me)$_2$ | 1 (mix.) | —CH$_2$C$_6$H$_5$ | Me | Me |
| 3.3-(Me)$_2$ | 1 (mix.) | —CH$_2$C$_6$H$_4$—Cl-2 | Me | Me |
| 3.3-(Me)$_2$ | 1 (mix.) | —CH$_2$C$_6$H$_4$—Cl-3 | Me | Me |
| 3.3-(Me)$_2$ | 1 (mix.) | —CH$_2$C$_6$H$_4$—Cl-4 | Me | Me |
| 3.3-(Me)$_2$ | 1 (mix.) | —CH$_2$C$_6$H$_4$—Me-2 | Me | Me |
| 3.3-(Me)$_2$ | 1 (mix.) | —CH$_2$C$_6$H$_4$—Me-3 | Me | Me |
| 3.3-(Me)$_2$ | 1 (mix.) | —CH$_2$C$_6$H$_4$—Me-4 | Me | Me |
| 3.3-(Me)$_2$ | 1 (mix.) | —CH$_2$C$_6$H$_4$—OMe-2 | Me | Me |
| 3.3-(Me)$_2$ | 1 (mix.) | —CH$_2$C$_6$H$_4$—OMe-3 | Me | Me |
| 3.3-(Me)$_2$ | 1 (mix.) | —CH$_2$C$_6$H$_4$—OMe-4 | Me | Me |
| 3.3-(Me)$_2$ | 1 (mix.) | —CH$_2$CH$_2$C$_6$H$_5$ | Me | Me |
| 3.3-(Me)$_2$ | 1 (mix.) | H | OMe | OMe |
| 3.3-(Me)$_2$ | 1 (mix.) | Na | OMe | OMe |
| 3.3-(Me)$_2$ | 1 (mix.) | ½Ca | OMe | OMe |
| 3.3-(Me)$_2$ | 1 (mix.) | $^i$PrNH$_3$ | OMe | OMe |
| 3.3-(Me)$_2$ | 1 (mix.) | NH$_2$CONH$_3$ | OMe | OMe |
| 3.3-(Me)$_2$ | 1 (mix.) | Me | OMe | OMe |
| 3.3-(Me)$_2$ | 1 (mix.) | Et | OMe | OMe |
| 3.3-(Me)$_2$ | 1 (mix.) | $^i$Pr | OMe | OMe |
| 3.3-(Me)$_2$ | 1 (mix.) | Pr | OMe | OMe |
| 3.3-(Me)$_2$ | 1 (mix.) | Bu | OMe | OMe |
| 3.3-(Me)$_2$ | 1 (mix.) | $^i$Bu | OMe | OMe |
| 3.3-(Me)$_2$ | 1 (mix.) | $^s$Bu | OMe | OMe |
| 3.3-(Me)$_2$ | 1 (mix.) | —CH$_2$OCH$_3$ | OMe | OMe |
| 3.3-(Me)$_2$ | 1 (mix.) | —CH$_2$CH$_2$OCH$_3$ | OMe | OMe |
| 3.3-(Me)$_2$ | 1 (mix.) | —CH$_2$SCH$_3$ | OMe | OMe |
| 3.3-(Me)$_2$ | 1 (mix.) | —CH$_2$CH=CH$_2$ | OMe | OMe |
| 3.3-(Me)$_2$ | 1 (mix.) | —C(CH$_3$)$_2$CH=CH$_2$ | OMe | OMe |
| 3.3-(Me)$_2$ | 1 (mix.) | —CH$_2$C≡CH$_2$ | OMe | OMe |
| 3.3-(Me)$_2$ | 1 (mix.) | —CH$_2$C$_6$H$_5$ | OMe | OMe |
| 3.3-(Me)$_2$ | 1 (mix.) | —CH$_2$C$_6$H$_4$—Cl-2 | OMe | OMe |
| 3.3-(Me)$_2$ | 1 (mix.) | —CH$_2$C$_6$H$_4$—Cl-3 | OMe | OMe |
| 3.3-(Me)$_2$ | 1 (mix.) | —CH$_2$C$_6$H$_4$—Cl-4 | OMe | OMe |
| 3.3-(Me)$_2$ | 1 (mix.) | —CH$_2$C$_6$H$_4$—Me-2 | OMe | OMe |
| 3.3-(Me)$_2$ | 1 (mix.) | —CH$_2$C$_6$H$_4$—Me-3 | OMe | OMe |
| 3.3-(Me)$_2$ | 1 (mix.) | —CH$_2$C$_6$H$_4$—Me-4 | OMe | OMe |
| 3.3-(Me)$_2$ | 1 (mix.) | —CH$_2$C$_6$H$_4$—OMe-2 | OMe | OMe |
| 3.3-(Me)$_2$ | 1 (mix.) | —CH$_2$C$_6$H$_4$—OMe-3 | OMe | OMe |
| 3.3-(Me)$_2$ | 1 (mix.) | —CH$_2$C$_6$H$_4$—OMe-4 | OMe | OMe |
| 3.3-(Me)$_2$ | 1 (mix.) | —CH$_2$CH$_2$C$_6$H$_5$ | OMe | OMe |
| 3.3-(Me)$_2$ | 2 (—) | H | Me | Me |
| 3.3-(Me)$_2$ | 2 (—) | Na | Me | Me |
| 3.3-(Me)$_2$ | 2 (—) | ½Ca | Me | Me |
| 3.3-(Me)$_2$ | 2 (—) | $^i$PrNH$_3$ | Me | Me |
| 3.3-(Me)$_2$ | 2 (—) | NH$_2$CONH$_3$ | Me | Me |
| 3.3-(Me)$_2$ | 2 (—) | Me | Me | Me |
| 3.3-(Me)$_2$ | 2 (—) | Et | Me | Me |
| 3.3-(Me)$_2$ | 2 (—) | $^i$Pr | Me | Me |
| 3.3-(Me)$_2$ | 2 (—) | Pr | Me | Me |
| 3.3-(Me)$_2$ | 2 (—) | Bu | Me | Me |
| 3.3-(Me)$_2$ | 2 (—) | $^i$Bu | Me | Me |
| 3.3-(Me)$_2$ | 2 (—) | $^s$Bu | Me | Me |
| 3.3-(Me)$_2$ | 2 (—) | —CH$_2$OCH$_3$ | Me | Me |
| 3.3-(Me)$_2$ | 2 (—) | —CH$_2$CH$_2$OCH$_3$ | Me | Me |
| 3.3-(Me)$_2$ | 2 (—) | —CH$_2$SCH$_3$ | Me | Me |
| 3.3-(Me)$_2$ | 2 (—) | —CH$_2$CH=CH$_2$ | Me | Me |
| 3.3-(Me)$_2$ | 2 (—) | —C(CH$_3$)$_2$CH=CH$_2$ | Me | Me |
| 3.3-(Me)$_2$ | 2 (—) | —CH$_2$C≡CH$_2$ | Me | Me |
| 3.3-(Me)$_2$ | 2 (—) | —CH$_2$C$_6$H$_5$ | Me | Me |
| 3.3-(Me)$_2$ | 2 (—) | —CH$_2$C$_6$H$_4$—Cl-2 | Me | Me |
| 3.3-(Me)$_2$ | 2 (—) | —CH$_2$C$_6$H$_4$—Cl-3 | Me | Me |
| 3.3-(Me)$_2$ | 2 (—) | —CH$_2$C$_6$H$_4$—Cl-4 | Me | Me |
| 3.3-(Me)$_2$ | 2 (—) | —CH$_2$C$_6$H$_4$—Me-2 | Me | Me |
| 3.3-(Me)$_2$ | 2 (—) | —CH$_2$C$_6$H$_4$—Me-3 | Me | Me |
| 3.3-(Me)$_2$ | 2 (—) | —CH$_2$C$_6$H$_4$—Me-4 | Me | Me |
| 3.3-(Me)$_2$ | 2 (—) | —CH$_2$C$_6$H$_4$—OMe-2 | Me | Me |
| 3.3-(Me)$_2$ | 2 (—) | —CH$_2$C$_6$H$_4$—OMe-3 | Me | Me |
| 3.3-(Me)$_2$ | 2 (—) | —CH$_2$C$_6$H$_4$—OMe-4 | Me | Me |
| 3.3-(Me)$_2$ | 2 (—) | —CH$_2$CH$_2$C$_6$H$_5$ | Me | Me |
| 3.3-(Me)$_2$ | 2 (—) | H | OMe | OMe |
| 3.3-(Me)$_2$ | 2 (—) | Na | OMe | OMe |
| 3.3-(Me)$_2$ | 2 (—) | ½Ca | OMe | OMe |
| 3.3-(Me)$_2$ | 2 (—) | $^i$PrNH$_3$ | OMe | OMe |
| 3.3-(Me)$_2$ | 2 (—) | NH$_2$CONH$_3$ | OMe | OMe |
| 3.3-(Me)$_2$ | 2 (—) | Me | OMe | OMe |
| 3.3-(Me)$_2$ | 2 (—) | Et | OMe | OMe |
| 3.3-(Me)$_2$ | 2 (—) | $^i$Pr | OMe | OMe |
| 3.3-(Me)$_2$ | 2 (—) | Pr | OMe | OMe |
| 3.3-(Me)$_2$ | 2 (—) | Bu | OMe | OMe |
| 3.3-(Me)$_2$ | 2 (—) | $^i$Bu | OMe | OMe |
| 3.3-(Me)$_2$ | 2 (—) | $^s$Bu | OMe | OMe |
| 3.3-(Me)$_2$ | 2 (—) | —CH$_2$OCH$_3$ | OMe | OMe |
| 3.3-(Me)$_2$ | 2 (—) | —CH$_2$CH$_2$OCH$_3$ | OMe | OMe |
| 3.3-(Me)$_2$ | 2 (—) | —CH$_2$SCH$_3$ | OMe | OMe |
| 3.3-(Me)$_2$ | 2 (—) | —CH$_2$CH=CH$_2$ | OMe | OMe |
| 3.3-(Me)$_2$ | 2 (—) | —C(CH$_3$)$_2$CH=CH$_2$ | OMe | OMe |
| 3.3-(Me)$_2$ | 2 (—) | —CH$_2$C≡CH$_2$ | OMe | OMe |
| 3.3-(Me)$_2$ | 2 (—) | —CH$_2$C$_6$H$_5$ | OMe | OMe |
| 3.3-(Me)$_2$ | 2 (—) | —CH$_2$C$_6$H$_4$—Cl-2 | OMe | OMe |

TABLE 1-continued

A compound of the general formula:

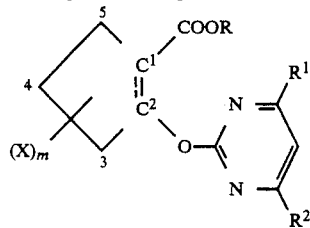 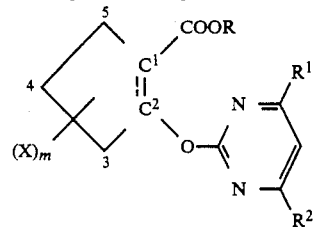

In the below-mentioned table, Me represents methyl group, Et represents ethyl group, Pr represents propyl group, $^i$Pr represents isopropyl group, Bu represents butyl group, $^i$Bu represents isobutyl group, $^s$Bu represents butyl secondary butyl group, $^t$Bu represents tertiary butyl group, cis represents a cis-form, trans represents a trans-form, mix. represents a mixture of a cis-form and a trans-form, 1 represents a single bond and 2 represents a double bond.

| $(X)_m$ | ≡ | R | $R^1$ | $R^2$ |
|---|---|---|---|---|
| 3.3-(Me)$_2$ | 2 (—) | —CH$_2$C$_6$H$_4$—Cl-3 | OMe | OMe |
| 3.3-(Me)$_2$ | 2 (—) | —CH$_2$C$_6$H$_4$—Cl-4 | OMe | OMe |
| 3.3-(Me)$_2$ | 2 (—) | —CH$_2$C$_6$H$_4$—Me-2 | OMe | OMe |
| 3.3-(Me)$_2$ | 2 (—) | —CH$_2$C$_6$H$_4$—Me-3 | OMe | OMe |
| 3.3-(Me)$_2$ | 2 (—) | —CH$_2$C$_6$H$_4$—Me-4 | OMe | OMe |
| 3.3-(Me)$_2$ | 2 (—) | —CH$_2$C$_6$H$_4$—OMe-2 | OMe | OMe |
| 3.3-(Me)$_2$ | 2 (—) | —CH$_2$C$_6$H$_4$—OMe-3 | OMe | OMe |
| 3.3-(Me)$_2$ | 2 (—) | —CH$_2$C$_6$H$_4$—OMe-4 | OMe | OMe |
| 3.3-(Me)$_2$ | 2 (—) | —CH$_2$CH$_2$C$_6$H$_5$ | OMe | OMe |
| 4.4-(Me)$_2$ | 1 (cis) | H | Me | Me |
| 4.4-(Me)$_2$ | 1 (cis) | Na | Me | Me |
| 4.4-(Me)$_2$ | 1 (cis) | ½Ca | Me | Me |
| 4.4-(Me)$_2$ | 1 (cis) | $^i$PrNH$_3$ | Me | Me |
| 4.4-(Me)$_2$ | 1 (cis) | NH$_2$CONH$_3$ | Me | Me |
| 4.4-(Me)$_2$ | 1 (cis) | Me | Me | Me |
| 4.4-(Me)$_2$ | 1 (cis) | Et | Me | Me |
| 4.4-(Me)$_2$ | 1 (cis) | $^i$Pr | Me | Me |
| 4.4-(Me)$_2$ | 1 (cis) | Pr | Me | Me |
| 4.4-(Me)$_2$ | 1 (cis) | Bu | Me | Me |
| 4.4-(Me)$_2$ | 1 (cis) | $^i$Bu | Me | Me |
| 4.4-(Me)$_2$ | 1 (cis) | $^s$Bu | Me | Me |
| 4.4-(Me)$_2$ | 1 (cis) | —CH$_2$OCH$_3$ | Me | Me |
| 4.4-(Me)$_2$ | 1 (cis) | —CH$_2$CH$_2$OCH$_3$ | Me | Me |
| 4.4-(Me)$_2$ | 1 (cis) | —CH$_2$SCH$_3$ | Me | Me |
| 4.4-(Me)$_2$ | 1 (cis) | —CH$_2$CH=CH$_2$ | Me | Me |
| 4.4-(Me)$_2$ | 1 (cis) | —C(CH$_3$)$_2$CH=CH$_2$ | Me | Me |
| 4.4-(Me)$_2$ | 1 (cis) | —CH$_2$C≡CH$_2$ | Me | Me |
| 4.4-(Me)$_2$ | 1 (cis) | —CH$_2$C$_6$H$_5$ | Me | Me |
| 4.4-(Me)$_2$ | 1 (cis) | —CH$_2$C$_6$H$_4$—Cl-2 | Me | Me |
| 4.4-(Me)$_2$ | 1 (cis) | —CH$_2$C$_6$H$_4$—Cl-3 | Me | Me |
| 4.4-(Me)$_2$ | 1 (cis) | —CH$_2$C$_6$H$_4$—Cl-4 | Me | Me |
| 4.4-(Me)$_2$ | 1 (cis) | —CH$_2$C$_6$H$_4$—Me-2 | Me | Me |
| 4.4-(Me)$_2$ | 1 (cis) | —CH$_2$C$_6$H$_4$—Me-3 | Me | Me |
| 4.4-(Me)$_2$ | 1 (cis) | —CH$_2$C$_6$H$_4$—Me-4 | Me | Me |
| 4.4-(Me)$_2$ | 1 (cis) | —CH$_2$C$_6$H$_4$—OMe-2 | Me | Me |
| 4.4-(Me)$_2$ | 1 (cis) | —CH$_2$C$_6$H$_4$—OMe-3 | Me | Me |
| 4.4-(Me)$_2$ | 1 (cis) | —CH$_2$C$_6$H$_4$—OMe-4 | Me | Me |
| 4.4-(Me)$_2$ | 1 (cis) | —CH$_2$CH$_2$C$_6$H$_5$ | Me | Me |
| 4.4-(Me)$_2$ | 1 (cis) | H | OMe | OMe |
| 4.4-(Me)$_2$ | 1 (cis) | Na | OMe | OMe |
| 4.4-(Me)$_2$ | 1 (cis) | ½Ca | OMe | OMe |
| 4.4-(Me)$_2$ | 1 (cis) | $^i$PrNH$_3$ | OMe | OMe |
| 4.4-(Me)$_2$ | 1 (cis) | NH$_2$CONH$_3$ | OMe | OMe |
| 4.4-(Me)$_2$ | 1 (cis) | Me | OMe | OMe |
| 4.4-(Me)$_2$ | 1 (cis) | Et | OMe | OMe |
| 4.4-(Me)$_2$ | 1 (cis) | $^i$Pr | OMe | OMe |
| 4.4-(Me)$_2$ | 1 (cis) | Pr | OMe | OMe |
| 4.4-(Me)$_2$ | 1 (cis) | Bu | OMe | OMe |
| 4.4-(Me)$_2$ | 1 (cis) | $^i$Bu | OMe | OMe |
| 4.4-(Me)$_2$ | 1 (cis) | $^s$Bu | OMe | OMe |
| 4.4-(Me)$_2$ | 1 (cis) | —CH$_2$OCH$_3$ | OMe | OMe |
| 4.4-(Me)$_2$ | 1 (cis) | —CH$_2$CH$_2$OCH$_3$ | OMe | OMe |
| 4.4-(Me)$_2$ | 1 (cis) | —CH$_2$SCH$_3$ | OMe | OMe |
| 4.4-(Me)$_2$ | 1 (cis) | —CH$_2$CH=CH$_2$ | OMe | OMe |
| 4.4-(Me)$_2$ | 1 (cis) | —C(CH$_3$)$_2$CH=CH$_2$ | OMe | OMe |
| 4.4-(Me)$_2$ | 1 (cis) | —CH$_2$C≡CH$_2$ | OMe | OMe |
| 4.4-(Me)$_2$ | 1 (cis) | —CH$_2$C$_6$H$_5$ | OMe | OMe |
| 4.4-(Me)$_2$ | 1 (cis) | —CH$_2$C$_6$H$_4$—Cl-2 | OMe | OMe |
| 4.4-(Me)$_2$ | 1 (cis) | —CH$_2$C$_6$H$_4$—Cl-3 | OMe | OMe |
| 4.4-(Me)$_2$ | 1 (cis) | —CH$_2$C$_6$H$_4$—Cl-4 | OMe | OMe |
| 4.4-(Me)$_2$ | 1 (cis) | —CH$_2$C$_6$H$_4$—Me-2 | OMe | OMe |
| 4.4-(Me)$_2$ | 1 (cis) | —CH$_2$C$_6$H$_4$—Me-3 | OMe | OMe |
| 4.4-(Me)$_2$ | 1 (cis) | —CH$_2$C$_6$H$_4$—Me-4 | OMe | OMe |
| 4.4-(Me)$_2$ | 1 (cis) | —CH$_2$C$_6$H$_4$—OMe-2 | OMe | OMe |
| 4.4-(Me)$_2$ | 1 (cis) | —CH$_2$C$_6$H$_4$—OMe-3 | OMe | OMe |
| 4.4-(Me)$_2$ | 1 (cis) | —CH$_2$C$_6$H$_4$—OMe-4 | OMe | OMe |
| 4.4-(Me)$_2$ | 1 (cis) | —CH$_2$CH$_2$C$_6$H$_5$ | OMe | OMe |
| 4.4-(Me)$_2$ | 1 (trans) | H | Me | Me |
| 4.4-(Me)$_2$ | 1 (trans) | Na | Me | Me |
| 4.4-(Me)$_2$ | 1 (trans) | ½Ca | Me | Me |
| 4.4-(Me)$_2$ | 1 (trans) | $^i$PrNH$_3$ | Me | Me |
| 4.4-(Me)$_2$ | 1 (trans) | NH$_2$CONH$_3$ | Me | Me |
| 4.4-(Me)$_2$ | 1 (trans) | Me | Me | Me |
| 4.4-(Me)$_2$ | 1 (trans) | Et | Me | Me |
| 4.4-(Me)$_2$ | 1 (trans) | $^i$Pr | Me | Me |
| 4.4-(Me)$_2$ | 1 (trans) | Pr | Me | Me |
| 4.4-(Me)$_2$ | 1 (trans) | Bu | Me | Me |
| 4.4-(Me)$_2$ | 1 (trans) | $^i$Bu | Me | Me |
| 4.4-(Me)$_2$ | 1 (trans) | $^s$Bu | Me | Me |
| 4.4-(Me)$_2$ | 1 (trans) | —CH$_2$OCH$_3$ | Me | Me |
| 4.4-(Me)$_2$ | 1 (trans) | —CH$_2$CH$_2$OCH$_3$ | Me | Me |
| 4.4-(Me)$_2$ | 1 (trans) | —CH$_2$SCH$_3$ | Me | Me |
| 4.4-(Me)$_2$ | 1 (trans) | —CH$_2$CH=CH$_2$ | Me | Me |
| 4.4-(Me)$_2$ | 1 (trans) | —C(CH$_3$)$_2$CH=CH$_2$ | Me | Me |
| 4.4-(Me)$_2$ | 1 (trans) | —CH$_2$C≡CH$_2$ | Me | Me |
| 4.4-(Me)$_2$ | 1 (trans) | —CH$_2$C$_6$H$_5$ | Me | Me |
| 4.4-(Me)$_2$ | 1 (trans) | —CH$_2$C$_6$H$_4$—Cl-2 | Me | Me |
| 4.4-(Me)$_2$ | 1 (trans) | —CH$_2$C$_6$H$_4$—Cl-3 | Me | Me |
| 4.4-(Me)$_2$ | 1 (trans) | —CH$_2$C$_6$H$_4$—Cl-4 | Me | Me |
| 4.4-(Me)$_2$ | 1 (trans) | —CH$_2$C$_6$H$_4$—Me-2 | Me | Me |
| 4.4-(Me)$_2$ | 1 (trans) | —CH$_2$C$_6$H$_4$—Me-3 | Me | Me |
| 4.4-(Me)$_2$ | 1 (trans) | —CH$_2$C$_6$H$_4$—Me-4 | Me | Me |
| 4.4-(Me)$_2$ | 1 (trans) | —CH$_2$C$_6$H$_4$—OMe-2 | Me | Me |
| 4.4-(Me)$_2$ | 1 (trans) | —CH$_2$C$_6$H$_4$—OMe-3 | Me | Me |
| 4.4-(Me)$_2$ | 1 (trans) | —CH$_2$C$_6$H$_4$—OMe-4 | Me | Me |
| 4.4-(Me)$_2$ | 1 (trans) | —CH$_2$CH$_2$C$_6$H$_5$ | Me | Me |
| 4.4-(Me)$_2$ | 1 (trans) | H | OMe | OMe |
| 4.4-(Me)$_2$ | 1 (trans) | Na | OMe | OMe |
| 4.4-(Me)$_2$ | 1 (trans) | ½Ca | OMe | OMe |
| 4.4-(Me)$_2$ | 1 (trans) | $^i$PrNH$_3$ | OMe | OMe |
| 4.4-(Me)$_2$ | 1 (trans) | NH$_2$CONH$_3$ | OMe | OMe |
| 4.4-(Me)$_2$ | 1 (trans) | Me | OMe | OMe |
| 4.4-(Me)$_2$ | 1 (trans) | Et | OMe | OMe |
| 4.4-(Me)$_2$ | 1 (trans) | $^i$Pr | OMe | OMe |
| 4.4-(Me)$_2$ | 1 (trans) | Pr | OMe | OMe |
| 4.4-(Me)$_2$ | 1 (trans) | Bu | OMe | OMe |
| 4.4-(Me)$_2$ | 1 (trans) | $^i$Bu | OMe | OMe |
| 4.4-(Me)$_2$ | 1 (trans) | $^s$Bu | OMe | OMe |
| 4.4-(Me)$_2$ | 1 (trans) | —CH$_2$OCH$_3$ | OMe | OMe |
| 4.4-(Me)$_2$ | 1 (trans) | —CH$_2$CH$_2$OCH$_3$ | OMe | OMe |
| 4.4-(Me)$_2$ | 1 (trans) | —CH$_2$SCH$_3$ | OMe | OMe |
| 4.4-(Me)$_2$ | 1 (trans) | —CH$_2$CH=CH$_2$ | OMe | OMe |
| 4.4-(Me)$_2$ | 1 (trans) | —C(CH$_3$)$_2$CH=CH$_2$ | OMe | OMe |
| 4.4-(Me)$_2$ | 1 (trans) | —CH$_2$C≡CH$_2$ | OMe | OMe |
| 4.4-(Me)$_2$ | 1 (trans) | —CH$_2$C$_6$H$_5$ | OMe | OMe |
| 4.4-(Me)$_2$ | 1 (trans) | —CH$_2$C$_6$H$_4$—Cl-2 | OMe | OMe |
| 4.4-(Me)$_2$ | 1 (trans) | —CH$_2$C$_6$H$_4$—Cl-3 | OMe | OMe |
| 4.4-(Me)$_2$ | 1 (trans) | —CH$_2$C$_6$H$_4$—Cl-4 | OMe | OMe |
| 4.4-(Me)$_2$ | 1 (trans) | —CH$_2$C$_6$H$_4$—Me-2 | OMe | OMe |
| 4.4-(Me)$_2$ | 1 (trans) | —CH$_2$C$_6$H$_4$—Me-3 | OMe | OMe |
| 4.4-(Me)$_2$ | 1 (trans) | —CH$_2$C$_6$H$_4$—Me-4 | OMe | OMe |
| 4.4-(Me)$_2$ | 1 (trans) | —CH$_2$C$_6$H$_4$—OMe-2 | OMe | OMe |

TABLE 1-continued

A compound of the general formula:

$$\begin{array}{c} \phantom{X} \\ (X)_m \end{array} \underset{3}{\overset{5}{\underset{4}{\bigg\langle}}} \underset{C^2}{\overset{C^1}{\underset{\|}{\bigg|}}} \underset{O}{\overset{COOR}{\diagdown}} \underset{N}{\overset{R^1}{\diagup}} \underset{R^2}{\overset{}{\diagdown}}$$

In the below-mentioned table, Me represents methyl group, Et represents ethyl group, Pr represents propyl group, $^i$Pr represents isopropyl group, Bu represents butyl group, $^i$Bu represents isobutyl group, $^s$Bu represents butyl secondary butyl group, $^t$Bu represents tertiary butyl group, cis represents a cis-form, trans represents a trans-form, mix. represents a mixture of a cis-form and a trans-form, 1 represents a single bond and 2 represents a double bond.

| (X)$_m$ | ═ | R | R$^1$ | R$^2$ |
|---|---|---|---|---|
| 4.4-(Me)$_2$ | 1 (trans) | —CH$_2$C$_6$H$_4$—OMe-3 | OMe | OMe |
| 4.4-(Me)$_2$ | 1 (trans) | —CH$_2$C$_6$H$_4$—OMe-4 | OMe | OMe |
| 4.4-(Me)$_2$ | 1 (trans) | —CH$_2$CH$_2$C$_6$H$_5$ | OMe | OMe |
| 4.4-(Me)$_2$ | 1 (mix.) | H | Me | Me |
| 4.4-(Me)$_2$ | 1 (mix.) | Na | Me | Me |
| 4.4-(Me)$_2$ | 1 (mix.) | ½Ca | Me | Me |
| 4.4-(Me)$_2$ | 1 (mix.) | $^i$PrNH$_3$ | Me | Me |
| 4.4-(Me)$_2$ | 1 (mix.) | NH$_2$CONH$_3$ | Me | Me |
| 4.4-(Me)$_2$ | 1 (mix.) | Me | Me | Me |
| 4.4-(Me)$_2$ | 1 (mix.) | Et | Me | Me |
| 4.4-(Me)$_2$ | 1 (mix.) | $^i$Pr | Me | Me |
| 4.4-(Me)$_2$ | 1 (mix.) | Pr | Me | Me |
| 4.4-(Me)$_2$ | 1 (mix.) | Bu | Me | Me |
| 4.4-(Me)$_2$ | 1 (mix.) | $^i$Bu | Me | Me |
| 4.4-(Me)$_2$ | 1 (mix.) | $^s$Bu | Me | Me |
| 4.4-(Me)$_2$ | 1 (mix.) | —CH$_2$OCH$_3$ | Me | Me |
| 4.4-(Me)$_2$ | 1 (mix.) | —CH$_2$CH$_2$OCH$_3$ | Me | Me |
| 4.4-(Me)$_2$ | 1 (mix.) | —CH$_2$SCH$_3$ | Me | Me |
| 4.4-(Me)$_2$ | 1 (mix.) | —CH$_2$CH═CH$_2$ | Me | Me |
| 4.4-(Me)$_2$ | 1 (mix.) | —C(CH$_3$)$_2$CH═CH$_2$ | Me | Me |
| 4.4-(Me)$_2$ | 1 (mix.) | —CH$_2$C≡CH$_2$ | Me | Me |
| 4.4-(Me)$_2$ | 1 (mix.) | —CH$_2$C$_6$H$_5$ | Me | Me |
| 4.4-(Me)$_2$ | 1 (mix.) | —CH$_2$C$_6$H$_4$—Cl-2 | Me | Me |
| 4.4-(Me)$_2$ | 1 (mix.) | —CH$_2$C$_6$H$_4$—Cl-3 | Me | Me |
| 4.4-(Me)$_2$ | 1 (mix.) | —CH$_2$C$_6$H$_4$—Cl-4 | Me | Me |
| 4.4-(Me)$_2$ | 1 (mix.) | —CH$_2$C$_6$H$_4$—Me-2 | Me | Me |
| 4.4-(Me)$_2$ | 1 (mix.) | —CH$_2$C$_6$H$_4$—Me-3 | Me | Me |
| 4.4-(Me)$_2$ | 1 (mix.) | —CH$_2$C$_6$H$_4$—Me-4 | Me | Me |
| 4.4-(Me)$_2$ | 1 (mix.) | —CH$_2$C$_6$H$_4$—OMe-2 | Me | Me |
| 4.4-(Me)$_2$ | 1 (mix.) | —CH$_2$C$_6$H$_4$—OMe-3 | Me | Me |
| 4.4-(Me)$_2$ | 1 (mix.) | —CH$_2$C$_6$H$_4$—OMe-4 | Me | Me |
| 4.4-(Me)$_2$ | 1 (mix.) | —CH$_2$CH$_2$C$_6$H$_5$ | Me | Me |
| 4.4-(Me)$_2$ | 1 (mix.) | H | OMe | OMe |
| 4.4-(Me)$_2$ | 1 (mix.) | Na | OMe | OMe |
| 4.4-(Me)$_2$ | 1 (mix.) | ½Ca | OMe | OMe |
| 4.4-(Me)$_2$ | 1 (mix.) | $^i$PrNH$_3$ | OMe | OMe |
| 4.4-(Me)$_2$ | 1 (mix.) | NH$_2$CONH$_3$ | OMe | OMe |
| 4.4-(Me)$_2$ | 1 (mix.) | Me | OMe | OMe |
| 4.4-(Me)$_2$ | 1 (mix.) | Et | OMe | OMe |
| 4.4-(Me)$_2$ | 1 (mix.) | $^i$Pr | OMe | OMe |
| 4.4-(Me)$_2$ | 1 (mix.) | Pr | OMe | OMe |
| 4.4-(Me)$_2$ | 1 (mix.) | Bu | OMe | OMe |
| 4.4-(Me)$_2$ | 1 (mix.) | $^i$Bu | OMe | OMe |
| 4.4-(Me)$_2$ | 1 (mix.) | $^s$Bu | OMe | OMe |
| 4.4-(Me)$_2$ | 1 (mix.) | —CH$_2$OCH$_3$ | OMe | OMe |
| 4.4-(Me)$_2$ | 1 (mix.) | —CH$_2$CH$_2$OCH$_3$ | OMe | OMe |
| 4.4-(Me)$_2$ | 1 (mix.) | —CH$_2$SCH$_3$ | OMe | OMe |
| 4.4-(Me)$_2$ | 1 (mix.) | —CH$_2$CH═CH$_2$ | OMe | OMe |
| 4.4-(Me)$_2$ | 1 (mix.) | —C(CH$_3$)$_2$CH═CH$_2$ | OMe | OMe |
| 4.4-(Me)$_2$ | 1 (mix.) | —CH$_2$C≡CH$_2$ | OMe | OMe |
| 4.4-(Me)$_2$ | 1 (mix.) | —CH$_2$C$_6$H$_5$ | OMe | OMe |
| 4.4-(Me)$_2$ | 1 (mix.) | —CH$_2$C$_6$H$_4$—Cl-2 | OMe | OMe |
| 4.4-(Me)$_2$ | 1 (mix.) | —CH$_2$C$_6$H$_4$—Cl-3 | OMe | OMe |
| 4.4-(Me)$_2$ | 1 (mix.) | —CH$_2$C$_6$H$_4$—Cl-4 | OMe | OMe |
| 4.4-(Me)$_2$ | 1 (mix.) | —CH$_2$C$_6$H$_4$—Me-2 | OMe | OMe |
| 4.4-(Me)$_2$ | 1 (mix.) | —CH$_2$C$_6$H$_4$—Me-3 | OMe | OMe |
| 4.4-(Me)$_2$ | 1 (mix.) | —CH$_2$C$_6$H$_4$—Me-4 | OMe | OMe |
| 4.4-(Me)$_2$ | 1 (mix.) | —CH$_2$C$_6$H$_4$—OMe-2 | OMe | OMe |
| 4.4-(Me)$_2$ | 1 (mix.) | —CH$_2$C$_6$H$_4$—OMe-3 | OMe | OMe |
| 4.4-(Me)$_2$ | 1 (mix.) | —CH$_2$C$_6$H$_4$—OMe-4 | OMe | OMe |
| 4.4-(Me)$_2$ | 1 (mix.) | —CH$_2$CH$_2$C$_6$H$_5$ | OMe | OMe |
| 4.4-(Me)$_2$ | 2 (—) | H | Me | Me |
| 4.4-(Me)$_2$ | 2 (—) | Na | Me | Me |
| 4.4-(Me)$_2$ | 2 (—) | ½Ca | Me | Me |
| 4.4-(Me)$_2$ | 2 (—) | $^i$PrNH$_3$ | Me | Me |
| 4.4-(Me)$_2$ | 2 (—) | NH$_2$CONH$_3$ | Me | Me |
| 4.4-(Me)$_2$ | 2 (—) | Me | Me | Me |
| 4.4-(Me)$_2$ | 2 (—) | Et | Me | Me |
| 4.4-(Me)$_2$ | 2 (—) | $^i$Pr | Me | Me |
| 4.4-(Me)$_2$ | 2 (—) | Pr | Me | Me |
| 4.4-(Me)$_2$ | 2 (—) | Bu | Me | Me |
| 4.4-(Me)$_2$ | 2 (—) | $^i$Bu | Me | Me |
| 4.4-(Me)$_2$ | 2 (—) | $^s$Bu | Me | Me |
| 4.4-(Me)$_2$ | 2 (—) | —CH$_2$OCH$_3$ | Me | Me |
| 4.4-(Me)$_2$ | 2 (—) | —CH$_2$CH$_2$OCH$_3$ | Me | Me |
| 4.4-(Me)$_2$ | 2 (—) | —CH$_2$SCH$_3$ | Me | Me |
| 4.4-(Me)$_2$ | 2 (—) | —CH$_2$CH═CH$_2$ | Me | Me |
| 4.4-(Me)$_2$ | 2 (—) | —C(CH$_3$)$_2$CH═CH$_2$ | Me | Me |
| 4.4-(Me)$_2$ | 2 (—) | —CH$_2$C≡CH$_2$ | Me | Me |
| 4.4-(Me)$_2$ | 2 (—) | —CH$_2$C$_6$H$_5$ | Me | Me |
| 4.4-(Me)$_2$ | 2 (—) | —CH$_2$C$_6$H$_4$—Cl-2 | Me | Me |
| 4.4-(Me)$_2$ | 2 (—) | —CH$_2$C$_6$H$_4$—Cl-3 | Me | Me |
| 4.4-(Me)$_2$ | 2 (—) | —CH$_2$C$_6$H$_4$—Cl-4 | Me | Me |
| 4.4-(Me)$_2$ | 2 (—) | —CH$_2$C$_6$H$_4$—Me-2 | Me | Me |
| 4.4-(Me)$_2$ | 2 (—) | —CH$_2$C$_6$H$_4$—Me-3 | Me | Me |
| 4.4-(Me)$_2$ | 2 (—) | —CH$_2$C$_6$H$_4$—Me-4 | Me | Me |
| 4.4-(Me)$_2$ | 2 (—) | —CH$_2$C$_6$H$_4$—OMe-2 | Me | Me |
| 4.4-(Me)$_2$ | 2 (—) | —CH$_2$C$_6$H$_4$—OMe-3 | Me | Me |
| 4.4-(Me)$_2$ | 2 (—) | —CH$_2$C$_6$H$_4$—OMe-4 | Me | Me |
| 4.4-(Me)$_2$ | 2 (—) | —CH$_2$CH$_2$C$_6$H$_5$ | Me | Me |
| 4.4-(Me)$_2$ | 2 (—) | H | OMe | OMe |
| 4.4-(Me)$_2$ | 2 (—) | Na | OMe | OMe |
| 4.4-(Me)$_2$ | 2 (—) | ½Ca | OMe | OMe |
| 4.4-(Me)$_2$ | 2 (—) | $^i$PrNH$_3$ | OMe | OMe |
| 4.4-(Me)$_2$ | 2 (—) | NH$_2$CONH$_3$ | OMe | OMe |
| 4.4-(Me)$_2$ | 2 (—) | Me | OMe | OMe |
| 4.4-(Me)$_2$ | 2 (—) | Et | OMe | OMe |
| 4.4-(Me)$_2$ | 2 (—) | $^i$Pr | OMe | OMe |
| 4.4-(Me)$_2$ | 2 (—) | Pr | OMe | OMe |
| 4.4-(Me)$_2$ | 2 (—) | Bu | OMe | OMe |
| 4.4-(Me)$_2$ | 2 (—) | $^i$Bu | OMe | OMe |
| 4.4-(Me)$_2$ | 2 (—) | $^s$Bu | OMe | OMe |
| 4.4-(Me)$_2$ | 2 (—) | —CH$_2$OCH$_3$ | OMe | OMe |
| 4.4-(Me)$_2$ | 2 (—) | —CH$_2$CH$_2$OCH$_3$ | OMe | OMe |
| 4.4-(Me)$_2$ | 2 (—) | —CH$_2$SCH$_3$ | OMe | OMe |
| 4.4-(Me)$_2$ | 2 (—) | —CH$_2$CH═CH$_2$ | OMe | OMe |
| 4.4-(Me)$_2$ | 2 (—) | —C(CH$_3$)$_2$CH═CH$_2$ | OMe | OMe |
| 4.4-(Me)$_2$ | 2 (—) | —CH$_2$C≡CH$_2$ | OMe | OMe |
| 4.4-(Me)$_2$ | 2 (—) | —CH$_2$C$_6$H$_5$ | OMe | OMe |
| 4.4-(Me)$_2$ | 2 (—) | —CH$_2$C$_6$H$_4$—Cl-2 | OMe | OMe |
| 4.4-(Me)$_2$ | 2 (—) | —CH$_2$C$_6$H$_4$—Cl-3 | OMe | OMe |
| 4.4-(Me)$_2$ | 2 (—) | —CH$_2$C$_6$H$_4$—Cl-4 | OMe | OMe |
| 4.4-(Me)$_2$ | 2 (—) | —CH$_2$C$_6$H$_4$—Me-2 | OMe | OMe |
| 4.4-(Me)$_2$ | 2 (—) | —CH$_2$C$_6$H$_4$—Me-3 | OMe | OMe |
| 4.4-(Me)$_2$ | 2 (—) | —CH$_2$C$_6$H$_4$—Me-4 | OMe | OMe |
| 4.4-(Me)$_2$ | 2 (—) | —CH$_2$C$_6$H$_4$—OMe-2 | OMe | OMe |
| 4.4-(Me)$_2$ | 2 (—) | —CH$_2$C$_6$H$_4$—OMe-3 | OMe | OMe |
| 4.4-(Me)$_2$ | 2 (—) | —CH$_2$C$_6$H$_4$—OMe-4 | OMe | OMe |
| 4.4-(Me)$_2$ | 2 (—) | —CH$_2$CH$_2$C$_6$H$_5$ | OMe | OMe |
| 4-$^t$Bu | 1 (cis) | H | Me | Me |
| 4-$^t$Bu | 1 (cis) | Na | Me | Me |
| 4-$^t$Bu | 1 (cis) | ½Ca | Me | Me |

TABLE 1-continued

A compound of the general formula:

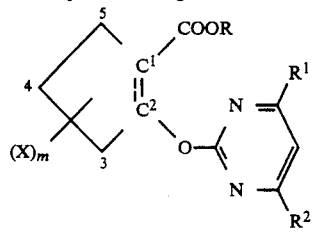

In the below-mentioned table, Me represents methyl group, Et represents ethyl group, Pr represents propyl group, $^i$Pr represents isopropyl group, Bu represents butyl group, $^i$Bu represents isobutyl group, $^s$Bu represents butyl secondary butyl group, $^t$Bu represents tertiary butyl group, cis represents a cis-form, trans represents a trans-form, mix. represents a mixture of a cis-form and a trans-form, 1 represents a single bond and 2 represents a double bond.

| (X)$_m$ | ≡ | R | R$^1$ | R$^2$ |
|---|---|---|---|---|
| 4-$^t$Bu | 1 (cis) | $^i$PrNH$_3$ | Me | Me |
| 4-$^t$Bu | 1 (cis) | NH$_2$CONH$_3$ | Me | Me |
| 4-$^t$Bu | 1 (cis) | Me | Me | Me |
| 4-$^t$Bu | 1 (cis) | Et | Me | Me |
| 4-$^t$Bu | 1 (cis) | $^i$Pr | Me | Me |
| 4-$^t$Bu | 1 (cis) | Pr | Me | Me |
| 4-$^t$Bu | 1 (cis) | Bu | Me | Me |
| 4-$^t$Bu | 1 (cis) | $^i$Bu | Me | Me |
| 4-$^t$Bu | 1 (cis) | $^s$Bu | Me | Me |
| 4-$^t$Bu | 1 (cis) | —CH$_2$OCH$_3$ | Me | Me |
| 4-$^t$Bu | 1 (cis) | —CH$_2$CH$_2$OCH$_3$ | Me | Me |
| 4-$^t$Bu | 1 (cis) | —CH$_2$SCH$_3$ | Me | Me |
| 4-$^t$Bu | 1 (cis) | —CH$_2$CH=CH$_2$ | Me | Me |
| 4-$^t$Bu | 1 (cis) | —C(CH$_3$)$_2$CH=CH$_2$ | Me | Me |
| 4-$^t$Bu | 1 (cis) | —CH$_2$C≡CH$_2$ | Me | Me |
| 4-$^t$Bu | 1 (cis) | —CH$_2$C$_6$H$_5$ | Me | Me |
| 4-$^t$Bu | 1 (cis) | —CH$_2$C$_6$H$_4$—Cl-2 | Me | Me |
| 4-$^t$Bu | 1 (cis) | —CH$_2$C$_6$H$_4$—Cl-3 | Me | Me |
| 4-$^t$Bu | 1 (cis) | —CH$_2$C$_6$H$_4$—Cl-4 | Me | Me |
| 4-$^t$Bu | 1 (cis) | —CH$_2$C$_6$H$_4$—Me-2 | Me | Me |
| 4-$^t$Bu | 1 (cis) | —CH$_2$C$_6$H$_4$—Me-3 | Me | Me |
| 4-$^t$Bu | 1 (cis) | —CH$_2$C$_6$H$_4$—Me-4 | Me | Me |
| 4-$^t$Bu | 1 (cis) | —CH$_2$C$_6$H$_4$—OMe-2 | Me | Me |
| 4-$^t$Bu | 1 (cis) | —CH$_2$C$_6$H$_4$—OMe-3 | Me | Me |
| 4-$^t$Bu | 1 (cis) | —CH$_2$C$_6$H$_4$—OMe-4 | Me | Me |
| 4-$^t$Bu | 1 (cis) | —CH$_2$CH$_2$C$_6$H$_5$ | Me | Me |
| 4-$^t$Bu | 1 (cis) | H | OMe | OMe |
| 4-$^t$Bu | 1 (cis) | Na | OMe | OMe |
| 4-$^t$Bu | 1 (cis) | ½Ca | OMe | OMe |
| 4-$^t$Bu | 1 (cis) | $^i$PrNH$_3$ | OMe | OMe |
| 4-$^t$Bu | 1 (cis) | NH$_2$CONH$_3$ | OMe | OMe |
| 4-$^t$Bu | 1 (cis) | Me | OMe | OMe |
| 4-$^t$Bu | 1 (cis) | Et | OMe | OMe |
| 4-$^t$Bu | 1 (cis) | $^i$Pr | OMe | OMe |
| 4-$^t$Bu | 1 (cis) | Pr | OMe | OMe |
| 4-$^t$Bu | 1 (cis) | Bu | OMe | OMe |
| 4-$^t$Bu | 1 (cis) | $^i$Bu | OMe | OMe |
| 4-$^t$Bu | 1 (cis) | $^s$Bu | OMe | OMe |
| 4-$^t$Bu | 1 (cis) | —CH$_2$OCH$_3$ | OMe | OMe |
| 4-$^t$Bu | 1 (cis) | —CH$_2$CH$_2$OCH$_3$ | OMe | OMe |
| 4-$^t$Bu | 1 (cis) | —CH$_2$SCH$_3$ | OMe | OMe |
| 4-$^t$Bu | 1 (cis) | —CH$_2$CH=CH$_2$ | OMe | OMe |
| 4-$^t$Bu | 1 (cis) | —C(CH$_3$)$_2$CH=CH$_2$ | OMe | OMe |
| 4-$^t$Bu | 1 (cis) | —CH$_2$C≡CH$_2$ | OMe | OMe |
| 4-$^t$Bu | 1 (cis) | —CH$_2$C$_6$H$_5$ | OMe | OMe |
| 4-$^t$Bu | 1 (cis) | —CH$_2$C$_6$H$_4$—Cl-2 | OMe | OMe |
| 4-$^t$Bu | 1 (cis) | —CH$_2$C$_6$H$_4$—Cl-3 | OMe | OMe |
| 4-$^t$Bu | 1 (cis) | —CH$_2$C$_6$H$_4$—Cl-4 | OMe | OMe |
| 4-$^t$Bu | 1 (cis) | —CH$_2$C$_6$H$_4$—Me-2 | OMe | OMe |
| 4-$^t$Bu | 1 (cis) | —CH$_2$C$_6$H$_4$—Me-3 | OMe | OMe |
| 4-$^t$Bu | 1 (cis) | —CH$_2$C$_6$H$_4$—Me-4 | OMe | OMe |
| 4-$^t$Bu | 1 (cis) | —CH$_2$C$_6$H$_4$—OMe-2 | OMe | OMe |
| 4-$^t$Bu | 1 (cis) | —CH$_2$C$_6$H$_4$—OMe-3 | OMe | OMe |
| 4-$^t$Bu | 1 (cis) | —CH$_2$C$_6$H$_4$—OMe-4 | OMe | OMe |
| 4-$^t$Bu | 1 (cis) | —CH$_2$CH$_2$C$_6$H$_5$ | OMe | OMe |
| 4-$^t$Bu | 1 (trans) | H | Me | Me |
| 4-$^t$Bu | 1 (trans) | Na | Me | Me |
| 4-$^t$Bu | 1 (trans) | ½Ca | Me | Me |
| 4-$^t$Bu | 1 (trans) | $^i$PrNH$_3$ | Me | Me |
| 4-$^t$Bu | 1 (trans) | NH$_2$CONH$_3$ | Me | Me |
| 4-$^t$Bu | 1 (trans) | Me | Me | Me |
| 4-$^t$Bu | 1 (trans) | Et | Me | Me |
| 4-$^t$Bu | 1 (trans) | $^i$Pr | Me | Me |
| 4-$^t$Bu | 1 (trans) | Pr | Me | Me |
| 4-$^t$Bu | 1 (trans) | Bu | Me | Me |
| 4-$^t$Bu | 1 (trans) | $^i$Bu | Me | Me |
| 4-$^t$Bu | 1 (trans) | $^s$Bu | Me | Me |
| 4-$^t$Bu | 1 (trans) | —CH$_2$OCH$_3$ | Me | Me |
| 4-$^t$Bu | 1 (trans) | —CH$_2$CH$_2$OCH$_3$ | Me | Me |
| 4-$^t$Bu | 1 (trans) | —CH$_2$SCH$_3$ | Me | Me |
| 4-$^t$Bu | 1 (trans) | —CH$_2$CH=CH$_2$ | Me | Me |
| 4-$^t$Bu | 1 (trans) | —C(CH$_3$)$_2$CH=CH$_2$ | Me | Me |
| 4-$^t$Bu | 1 (trans) | —CH$_2$C≡CH$_2$ | Me | Me |
| 4-$^t$Bu | 1 (trans) | —CH$_2$C$_6$H$_5$ | Me | Me |
| 4-$^t$Bu | 1 (trans) | —CH$_2$C$_6$H$_4$—Cl-2 | Me | Me |
| 4-$^t$Bu | 1 (trans) | —CH$_2$C$_6$H$_4$—Cl-3 | Me | Me |
| 4-$^t$Bu | 1 (trans) | —CH$_2$C$_6$H$_4$—Cl-4 | Me | Me |
| 4-$^t$Bu | 1 (trans) | —CH$_2$C$_6$H$_4$—Me-2 | Me | Me |
| 4-$^t$Bu | 1 (trans) | —CH$_2$C$_6$H$_4$—Me-3 | Me | Me |
| 4-$^t$Bu | 1 (trans) | —CH$_2$C$_6$H$_4$—Me-4 | Me | Me |
| 4-$^t$Bu | 1 (trans) | —CH$_2$C$_6$H$_4$—OMe-2 | Me | Me |
| 4-$^t$Bu | 1 (trans) | —CH$_2$C$_6$H$_4$—OMe-3 | Me | Me |
| 4-$^t$Bu | 1 (trans) | —CH$_2$C$_6$H$_4$—OMe-4 | Me | Me |
| 4-$^t$Bu | 1 (trans) | —CH$_2$CH$_2$C$_6$H$_5$ | Me | Me |
| 4-$^t$Bu | 1 (trans) | H | OMe | OMe |
| 4-$^t$Bu | 1 (trans) | Na | OMe | OMe |
| 4-$^t$Bu | 1 (trans) | ½Ca | OMe | OMe |
| 4-$^t$Bu | 1 (trans) | $^i$PrNH$_3$ | OMe | OMe |
| 4-$^t$Bu | 1 (trans) | NH$_2$CONH$_3$ | OMe | OMe |
| 4-$^t$Bu | 1 (trans) | Me | OMe | OMe |
| 4-$^t$Bu | 1 (trans) | Et | OMe | OMe |
| 4-$^t$Bu | 1 (trans) | $^i$Pr | OMe | OMe |
| 4-$^t$Bu | 1 (trans) | Pr | OMe | OMe |
| 4-$^t$Bu | 1 (trans) | Bu | OMe | OMe |
| 4-$^t$Bu | 1 (trans) | $^i$Bu | OMe | OMe |
| 4-$^t$Bu | 1 (trans) | $^s$Bu | OMe | OMe |
| 4-$^t$Bu | 1 (trans) | —CH$_2$OCH$_3$ | OMe | OMe |
| 4-$^t$Bu | 1 (trans) | —CH$_2$CH$_2$OCH$_3$ | OMe | OMe |
| 4-$^t$Bu | 1 (trans) | —CH$_2$SCH$_3$ | OMe | OMe |
| 4-$^t$Bu | 1 (trans) | —CH$_2$CH=CH$_2$ | OMe | OMe |
| 4-$^t$Bu | 1 (trans) | —C(CH$_3$)$_2$CH=CH$_2$ | OMe | OMe |
| 4-$^t$Bu | 1 (trans) | —CH$_2$C≡CH$_2$ | OMe | OMe |
| 4-$^t$Bu | 1 (trans) | —CH$_2$C$_6$H$_5$ | OMe | OMe |
| 4-$^t$Bu | 1 (trans) | —CH$_2$C$_6$H$_4$—Cl-2 | OMe | OMe |
| 4-$^t$Bu | 1 (trans) | —CH$_2$C$_6$H$_4$—Cl-3 | OMe | OMe |
| 4-$^t$Bu | 1 (trans) | —CH$_2$C$_6$H$_4$—Cl-4 | OMe | OMe |
| 4-$^t$Bu | 1 (trans) | —CH$_2$C$_6$H$_4$—Me-2 | OMe | OMe |
| 4-$^t$Bu | 1 (trans) | —CH$_2$C$_6$H$_4$—Me-3 | OMe | OMe |
| 4-$^t$Bu | 1 (trans) | —CH$_2$C$_6$H$_4$—Me-4 | OMe | OMe |
| 4-$^t$Bu | 1 (trans) | —CH$_2$C$_6$H$_4$—OMe-2 | OMe | OMe |
| 4-$^t$Bu | 1 (trans) | —CH$_2$C$_6$H$_4$—OMe-3 | OMe | OMe |
| 4-$^t$Bu | 1 (trans) | —CH$_2$C$_6$H$_4$—OMe-4 | OMe | OMe |
| 4-$^t$Bu | 1 (trans) | —CH$_2$CH$_2$C$_6$H$_5$ | OMe | OMe |
| 4-$^t$Bu | 1 (mix.) | H | Me | Me |
| 4-$^t$Bu | 1 (mix.) | Na | Me | Me |
| 4-$^t$Bu | 1 (mix.) | ½Ca | Me | Me |
| 4-$^t$Bu | 1 (mix.) | $^i$PrNH$_3$ | Me | Me |
| 4-$^t$Bu | 1 (mix.) | NH$_2$CONH$_3$ | Me | Me |
| 4-$^t$Bu | 1 (mix.) | Me | Me | Me |
| 4-$^t$Bu | 1 (mix.) | Et | Me | Me |
| 4-$^t$Bu | 1 (mix.) | $^i$Pr | Me | Me |
| 4-$^t$Bu | 1 (mix.) | Pr | Me | Me |

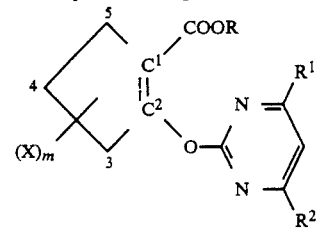

TABLE 1-continued

A compound of the general formula:

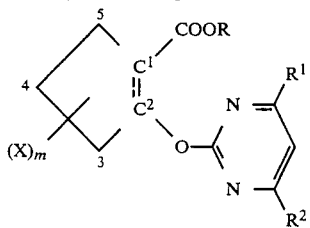

In the below-mentioned table, Me represents methyl group, Et represents ethyl group, Pr represents propyl group, $^i$Pr represents isopropyl group, Bu represents butyl group, $^i$Bu represents isobutyl group, $^s$Bu represents butyl secondary butyl group, $^t$Bu represents tertiary butyl group, cis represents a cis-form, trans represents a trans-form, mix. represents a mixture of a cis-form and a trans-form, 1 represents a single bond and 2 represents a double bond.

| $(X)_m$ | ---- | R | $R^1$ | $R^2$ |
|---|---|---|---|---|
| 4-$^t$Bu | 1 (mix.) | Bu | Me | Me |
| 4-$^t$Bu | 1 (mix.) | $^i$Bu | Me | Me |
| 4-$^t$Bu | 1 (mix.) | $^s$Bu | Me | Me |
| 4-$^t$Bu | 1 (mix.) | —CH$_2$OCH$_3$ | Me | Me |
| 4-$^t$Bu | 1 (mix.) | —CH$_2$CH$_2$OCH$_3$ | Me | Me |
| 4-$^t$Bu | 1 (mix.) | —CH$_2$SCH$_3$ | Me | Me |
| 4-$^t$Bu | 1 (mix.) | —CH$_2$CH=CH$_2$ | Me | Me |
| 4-$^t$Bu | 1 (mix.) | —C(CH$_3$)$_2$CH=CH$_2$ | Me | Me |
| 4-$^t$Bu | 1 (mix.) | —CH$_2$C≡CH$_2$ | Me | Me |
| 4-$^t$Bu | 1 (mix.) | —CH$_2$C$_6$H$_5$ | Me | Me |
| 4-$^t$Bu | 1 (mix.) | —CH$_2$C$_6$H$_4$—Cl-2 | Me | Me |
| 4-$^t$Bu | 1 (mix.) | —CH$_2$C$_6$H$_4$—Cl-3 | Me | Me |
| 4-$^t$Bu | 1 (mix.) | —CH$_2$C$_6$H$_4$—Cl-4 | Me | Me |
| 4-$^t$Bu | 1 (mix.) | —CH$_2$C$_6$H$_4$—Me-2 | Me | Me |
| 4-$^t$Bu | 1 (mix.) | —CH$_2$C$_6$H$_4$—Me-3 | Me | Me |
| 4-$^t$Bu | 1 (mix.) | —CH$_2$C$_6$H$_4$—Me-4 | Me | Me |
| 4-$^t$Bu | 1 (mix.) | —CH$_2$C$_6$H$_4$—OMe-2 | Me | Me |
| 4-$^t$Bu | 1 (mix.) | —CH$_2$C$_6$H$_4$—OMe-3 | Me | Me |
| 4-$^t$Bu | 1 (mix.) | —CH$_2$C$_6$H$_4$—OMe-4 | Me | Me |
| 4-$^t$Bu | 1 (mix.) | —CH$_2$CH$_2$C$_6$H$_5$ | Me | Me |
| 4-$^t$Bu | 1 (mix.) | H | OMe | OMe |
| 4-$^t$Bu | 1 (mix.) | Na | OMe | OMe |
| 4-$^t$Bu | 1 (mix.) | ½Ca | OMe | OMe |
| 4-$^t$Bu | 1 (mix.) | $^i$PrNH$_3$ | OMe | OMe |
| 4-$^t$Bu | 1 (mix.) | NH$_2$CONH$_3$ | OMe | OMe |
| 4-$^t$Bu | 1 (mix.) | Me | OMe | OMe |
| 4-$^t$Bu | 1 (mix.) | Et | OMe | OMe |
| 4-$^t$Bu | 1 (mix.) | $^i$Pr | OMe | OMe |
| 4-$^t$Bu | 1 (mix.) | Pr | OMe | OMe |
| 4-$^t$Bu | 1 (mix.) | Bu | OMe | OMe |
| 4-$^t$Bu | 1 (mix.) | $^i$Bu | OMe | OMe |
| 4-$^t$Bu | 1 (mix.) | $^s$Bu | OMe | OMe |
| 4-$^t$Bu | 1 (mix.) | —CH$_2$OCH$_3$ | OMe | OMe |
| 4-$^t$Bu | 1 (mix.) | —CH$_2$CH$_2$OCH$_3$ | OMe | OMe |
| 4-$^t$Bu | 1 (mix.) | —CH$_2$SCH$_3$ | OMe | OMe |
| 4-$^t$Bu | 1 (mix.) | —CH$_2$CH=CH$_2$ | OMe | OMe |
| 4-$^t$Bu | 1 (mix.) | —C(CH$_3$)$_2$CH=CH$_2$ | OMe | OMe |
| 4-$^t$Bu | 1 (mix.) | —CH$_2$C≡CH$_2$ | OMe | OMe |
| 4-$^t$Bu | 1 (mix.) | —CH$_2$C$_6$H$_5$ | OMe | OMe |
| 4-$^t$Bu | 1 (mix.) | —CH$_2$C$_6$H$_4$—Cl-2 | OMe | OMe |
| 4-$^t$Bu | 1 (mix.) | —CH$_2$C$_6$H$_4$—Cl-3 | OMe | OMe |
| 4-$^t$Bu | 1 (mix.) | —CH$_2$C$_6$H$_4$—Cl-4 | OMe | OMe |
| 4-$^t$Bu | 1 (mix.) | —CH$_2$C$_6$H$_4$—Me-2 | OMe | OMe |
| 4-$^t$Bu | 1 (mix.) | —CH$_2$C$_6$H$_4$—Me-3 | OMe | OMe |
| 4-$^t$Bu | 1 (mix.) | —CH$_2$C$_6$H$_4$—Me-4 | OMe | OMe |
| 4-$^t$Bu | 1 (mix.) | —CH$_2$C$_6$H$_4$—OMe-2 | OMe | OMe |
| 4-$^t$Bu | 1 (mix.) | —CH$_2$C$_6$H$_4$—OMe-3 | OMe | OMe |
| 4-$^t$Bu | 1 (mix.) | —CH$_2$C$_6$H$_4$—OMe-4 | OMe | OMe |
| 4-$^t$Bu | 1 (mix.) | —CH$_2$CH$_2$C$_6$H$_5$ | OMe | OMe |
| 4-$^t$Bu | 2 (—) | H | Me | Me |
| 4-$^t$Bu | 2 (—) | Na | Me | Me |
| 4-$^t$Bu | 2 (—) | ½Ca | Me | Me |
| 4-$^t$Bu | 2 (—) | $^i$PrNH$_3$ | Me | Me |
| 4-$^t$Bu | 2 (—) | NH$_2$CONH$_3$ | Me | Me |

TABLE 1-continued

A compound of the general formula:

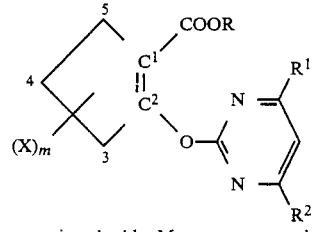

In the below-mentioned table, Me represents methyl group, Et represents ethyl group, Pr represents propyl group, $^i$Pr represents isopropyl group, Bu represents butyl group, $^i$Bu represents isobutyl group, $^s$Bu represents butyl secondary butyl group, $^t$Bu represents tertiary butyl group, cis represents a cis-form, trans represents a trans-form, mix. represents a mixture of a cis-form and a trans-form, 1 represents a single bond and 2 represents a double bond.

| $(X)_m$ | ---- | R | $R^1$ | $R^2$ |
|---|---|---|---|---|
| 4-$^t$Bu | 2 (—) | Me | Me | Me |
| 4-$^t$Bu | 2 (—) | Et | Me | Me |
| 4-$^t$Bu | 2 (—) | $^i$Pr | Me | Me |
| 4-$^t$Bu | 2 (—) | Pr | Me | Me |
| 4-$^t$Bu | 2 (—) | Bu | Me | Me |
| 4-$^t$Bu | 2 (—) | $^i$Bu | Me | Me |
| 4-$^t$Bu | 2 (—) | $^s$Bu | Me | Me |
| 4-$^t$Bu | 2 (—) | —CH$_2$OCH$_3$ | Me | Me |
| 4-$^t$Bu | 2 (—) | —CH$_2$CH$_2$OCH$_3$ | Me | Me |
| 4-$^t$Bu | 2 (—) | —CH$_2$SCH$_3$ | Me | Me |
| 4-$^t$Bu | 2 (—) | —CH$_2$CH=CH$_2$ | Me | Me |
| 4-$^t$Bu | 2 (—) | —C(CH$_3$)$_2$CH=CH$_2$ | Me | Me |
| 4-$^t$Bu | 2 (—) | —CH$_2$C≡CH$_2$ | Me | Me |
| 4-$^t$Bu | 2 (—) | —CH$_2$C$_6$H$_5$ | Me | Me |
| 4-$^t$Bu | 2 (—) | —CH$_2$C$_6$H$_4$—Cl-2 | Me | Me |
| 4-$^t$Bu | 2 (—) | —CH$_2$C$_6$H$_4$—Cl-3 | Me | Me |
| 4-$^t$Bu | 2 (—) | —CH$_2$C$_6$H$_4$—Cl-4 | Me | Me |
| 4-$^t$Bu | 2 (—) | —CH$_2$C$_6$H$_4$—Me-2 | Me | Me |
| 4-$^t$Bu | 2 (—) | —CH$_2$C$_6$H$_4$—Me-3 | Me | Me |
| 4-$^t$Bu | 2 (—) | —CH$_2$C$_6$H$_4$—Me-4 | Me | Me |
| 4-$^t$Bu | 2 (—) | —CH$_2$C$_6$H$_4$—OMe-2 | Me | Me |
| 4-$^t$Bu | 2 (—) | —CH$_2$C$_6$H$_4$—OMe-3 | Me | Me |
| 4-$^t$Bu | 2 (—) | —CH$_2$C$_6$H$_4$—OMe-4 | Me | Me |
| 4-$^t$Bu | 2 (—) | —CH$_2$CH$_2$C$_6$H$_5$ | Me | Me |
| 4-$^t$Bu | 2 (—) | H | OMe | OMe |
| 4-$^t$Bu | 2 (—) | Na | OMe | OMe |
| 4-$^t$Bu | 2 (—) | ½Ca | OMe | OMe |
| 4-$^t$Bu | 2 (—) | $^i$PrNH$_3$ | OMe | OMe |
| 4-$^t$Bu | 2 (—) | NH$_2$CONH$_3$ | OMe | OMe |
| 4-$^t$Bu | 2 (—) | Me | OMe | OMe |
| 4-$^t$Bu | 2 (—) | Et | OMe | OMe |
| 4-$^t$Bu | 2 (—) | $^i$Pr | OMe | OMe |
| 4-$^t$Bu | 2 (—) | Pr | OMe | OMe |
| 4-$^t$Bu | 2 (—) | Bu | OMe | OMe |
| 4-$^t$Bu | 2 (—) | $^i$Bu | OMe | OMe |
| 4-$^t$Bu | 2 (—) | $^s$Bu | OMe | OMe |
| 4-$^t$Bu | 2 (—) | —CH$_2$OCH$_3$ | OMe | OMe |
| 4-$^t$Bu | 2 (—) | —CH$_2$CH$_2$OCH$_3$ | OMe | OMe |
| 4-$^t$Bu | 2 (—) | —CH$_2$SCH$_3$ | OMe | OMe |
| 4-$^t$Bu | 2 (—) | —CH$_2$CH=CH$_2$ | OMe | OMe |
| 4-$^t$Bu | 2 (—) | —C(CH$_3$)$_2$CH=CH$_2$ | OMe | OMe |
| 4-$^t$Bu | 2 (—) | —CH$_2$C≡CH$_2$ | OMe | OMe |
| 4-$^t$Bu | 2 (—) | —CH$_2$C$_6$H$_5$ | OMe | OMe |
| 4-$^t$Bu | 2 (—) | —CH$_2$C$_6$H$_4$—Cl-2 | OMe | OMe |
| 4-$^t$Bu | 2 (—) | —CH$_2$C$_6$H$_4$—Cl-3 | OMe | OMe |
| 4-$^t$Bu | 2 (—) | —CH$_2$C$_6$H$_4$—Cl-4 | OMe | OMe |
| 4-$^t$Bu | 2 (—) | —CH$_2$C$_6$H$_4$—Me-2 | OMe | OMe |
| 4-$^t$Bu | 2 (—) | —CH$_2$C$_6$H$_4$—Me-3 | OMe | OMe |
| 4-$^t$Bu | 2 (—) | —CH$_2$C$_6$H$_4$—Me-4 | OMe | OMe |
| 4-$^t$Bu | 2 (—) | —CH$_2$C$_6$H$_4$—OMe-2 | OMe | OMe |
| 4-$^t$Bu | 2 (—) | —CH$_2$C$_6$H$_4$—OMe-3 | OMe | OMe |
| 4-$^t$Bu | 2 (—) | —CH$_2$C$_6$H$_4$—OMe-4 | OMe | OMe |
| 4-$^t$Bu | 2 (—) | —CH$_2$CH$_2$C$_6$H$_5$ | OMe | OMe |

TABLE

A compound of the general formula:

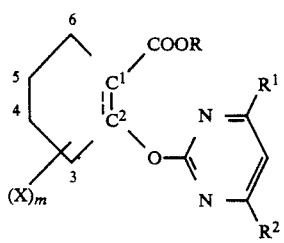

In the below-mentioned table, Me represents methyl group, Et represents ethyl group, Pr represents propyl group, $^i$Pr represents isopropyl group, Bu represents butyl group, $^i$Bu represents isobutyl group, $^s$Bu represents secondary butyl group, $^t$Bu represents tertiary butyl group, cis represents a cis-form, trans represents a trans-form, mix. represents a mixture of a cis-form and a trans-form, 1 represents a single bond and 2 represents a double bond.

| $(X)_m$ | === | R | $R^1$ | $R^2$ |
|---|---|---|---|---|
| — | 1 (cis) | H | Me | Me |
| — | 1 (cis) | Li | Me | Me |
| — | 1 (cis) | Na | Me | Me |
| — | 1 (cis) | K | Me | Me |
| — | 1 (cis) | ½Mg | Me | Me |
| — | 1 (cis) | ½Ca | Me | Me |
| — | 1 (cis) | MeNH$_3$ | Me | Me |
| — | 1 (cis) | EtNH$_3$ | Me | Me |
| — | 1 (cis) | PrNH$_3$ | Me | Me |
| — | 1 (cis) | $^i$PrNH$_3$ | Me | Me |
| — | 1 (cis) | NH$_2$CONH$_3$ | Me | Me |
| — | 1 (cis) | Me | Me | Me |
| — | 1 (cis) | Et | Me | Me |
| — | 1 (cis) | $^i$Pr | Me | Me |
| — | 1 (cis) | Pr | Me | Me |
| — | 1 (cis) | Bu | Me | Me |
| — | 1 (cis) | $^i$Bu | Me | Me |
| — | 1 (cis) | $^s$Bu | Me | Me |
| — | 1 (cis) | $^t$Bu | Me | Me |
| — | 1 (cis) | —CH$_2$OCH$_3$ | Me | Me |
| — | 1 (cis) | —CH$_2$CH$_2$OCH$_3$ | Me | Me |
| — | 1 (cis) | —CH$_2$SCH$_3$ | Me | Me |
| — | 1 (cis) | —CH$_2$CH=CH$_2$ | Me | Me |
| — | 1 (cis) | —C(CH$_3$)$_2$CH=CH$_2$ | Me | Me |
| — | 1 (cis) | —CH$_2$C≡CH$_2$ | Me | Me |
| — | 1 (cis) | —CH$_2$C$_6$H$_5$ | Me | Me |
| — | 1 (cis) | —CH$_2$C$_6$H$_4$—Cl-2 | Me | Me |
| — | 1 (cis) | —CH$_2$C$_6$H$_4$—Cl-3 | Me | Me |
| — | 1 (cis) | —CH$_2$C$_6$H$_4$—Cl-4 | Me | Me |
| — | 1 (cis) | —CH$_2$C$_6$H$_4$—Me-2 | Me | Me |
| — | 1 (cis) | —CH$_2$C$_6$H$_4$—Me-3 | Me | Me |
| — | 1 (cis) | —CH$_2$C$_6$H$_4$—Me-4 | Me | Me |
| — | 1 (cis) | —CH$_2$C$_6$H$_4$—OMe-2 | Me | Me |
| — | 1 (cis) | —CH$_2$C$_6$H$_4$—OMe-3 | Me | Me |
| — | 1 (cis) | —CH$_2$CH$_2$C$_6$H$_5$ | Me | Me |
| — | 1 (cis) | H | OMe | Me |
| — | 1 (cis) | Li | OMe | Me |
| — | 1 (cis) | Na | OMe | Me |
| — | 1 (cis) | K | OMe | Me |
| — | 1 (cis) | ½Mg | OMe | Me |
| — | 1 (cis) | ½Ca | OMe | Me |
| — | 1 (cis) | MeNH$_3$ | OMe | Me |
| — | 1 (cis) | EtNH$_3$ | OMe | Me |
| — | 1 (cis) | PrNH$_3$ | OMe | Me |
| — | 1 (cis) | $^i$PrNH$_3$ | OMe | Me |
| — | 1 (cis) | NH$_2$CONH$_3$ | OMe | Me |
| — | 1 (cis) | Me | OMe | Me |
| — | 1 (cis) | Et | OMe | Me |
| — | 1 (cis) | $^i$Pr | OMe | Me |
| — | 1 (cis) | Pr | OMe | Me |
| — | 1 (cis) | Bu | OMe | Me |
| — | 1 (cis) | $^i$Bu | OMe | Me |
| — | 1 (cis) | $^s$Bu | OMe | Me |
| — | 1 (cis) | $^t$Bu | OMe | Me |
| — | 1 (cis) | —CH$_2$OCH$_3$ | OMe | Me |
| — | 1 (cis) | —CH$_2$CH$_2$OCH$_3$ | OMe | Me |
| — | 1 (cis) | —CH$_2$SCH$_3$ | OMe | Me |

TABLE -continued

A compound of the general formula:

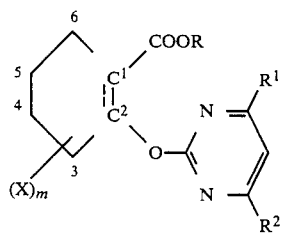

In the below-mentioned table, Me represents methyl group, Et represents ethyl group, Pr represents propyl group, $^i$Pr represents isopropyl group, Bu represents butyl group, $^i$Bu represents isobutyl group, $^s$Bu represents secondary butyl group, $^t$Bu represents tertiary butyl group, cis represents a cis-form, trans represents a trans-form, mix. represents a mixture of a cis-form and a trans-form, 1 represents a single bond and 2 represents a double bond.

| $(X)_m$ | --- | R | $R^1$ | $R^2$ |
|---|---|---|---|---|
| — | 1 (cis) | —CH$_2$CH=CH$_2$ | OMe | Me |
| — | 1 (cis) | —C(CH$_3$)$_2$CH=CH$_2$ | OMe | Me |
| — | 1 (cis) | —CH$_2$C≡CH$_2$ | OMe | Me |
| — | 1 (cis) | —CH$_2$C$_6$H$_5$ | OMe | Me |
| — | 1 (cis) | —CH$_2$C$_6$H$_4$—Cl-2 | OMe | Me |
| — | 1 (cis) | —CH$_2$C$_6$H$_4$—Cl-3 | OMe | Me |
| — | 1 (cis) | —CH$_2$C$_6$H$_4$—Cl-4 | OMe | Me |
| — | 1 (cis) | —CH$_2$C$_6$H$_4$—Me-2 | OMe | Me |
| — | 1 (cis) | —CH$_2$C$_6$H$_4$—Me-3 | OMe | Me |
| — | 1 (cis) | —CH$_2$C$_6$H$_4$—Me-4 | OMe | Me |
| — | 1 (cis) | —CH$_2$C$_6$H$_4$—OMe-2 | OMe | Me |
| — | 1 (cis) | —CH$_2$C$_6$H$_4$—OMe-3 | OMe | Me |
| — | 1 (cis) | —CH$_2$C$_6$H$_4$—OMe-4 | OMe | Me |
| — | 1 (cis) | —CH$_2$CH$_2$C$_6$H$_5$ | OMe | Me |
| — | 1 (cis) | H | OMe | OMe |
| — | 1 (cis) | Li | OMe | OMe |
| — | 1 (cis) | Na | OMe | OMe |
| — | 1 (cis) | K | OMe | OMe |
| — | 1 (cis) | ½Mg | OMe | OMe |
| — | 1 (cis) | ½Ca | OMe | OMe |
| — | 1 (cis) | MeNH$_3$ | OMe | OMe |
| — | 1 (cis) | EtNH$_3$ | OMe | OMe |
| — | 1 (cis) | PrNH$_3$ | OMe | OMe |
| — | 1 (cis) | $^i$PrNH$^3$ | OMe | OMe |
| — | 1 (cis) | NH$_2$CONH$_3$ | OMe | OMe |
| — | 1 (cis) | Me | OMe | OMe |
| — | 1 (cis) | Et | OMe | OMe |
| — | 1 (cis) | $^i$Pr | OMe | OMe |
| — | 1 (cis) | Pr | OMe | OMe |
| — | 1 (cis) | Bu | OMe | OMe |
| — | 1 (cis) | $^i$Bu | OMe | OMe |
| — | 1 (cis) | $^s$Bu | OMe | OMe |
| — | 1 (cis) | $^t$Bu | OMe | OMe |
| — | 1 (cis) | —CH$_2$OCH$_3$ | OMe | OMe |
| — | 1 (cis) | —CH$_2$CH$_2$OCH$_3$ | OMe | OMe |
| — | 1 (cis) | —CH$_2$SCH$_3$ | OMe | OMe |
| — | 1 (cis) | —CH$_2$CH=CH$_2$OMe | OMe | |
| — | 1 (cis) | —C(CH$_3$)$_2$CH=CH$_2$ | OMe | OMe |
| — | 1 (cis) | —CH$_2$C≡CH$_2$ | OMe | OMe |
| — | 1 (cis) | —CH$_2$C$_6$H$_5$ | OMe | OMe |
| — | 1 (cis) | —CH$_2$C$_6$H$_4$—Cl-2 | OMe | OMe |
| — | 1 (cis) | —CH$_2$C$_6$H$_4$—Cl-3 | OMe | OMe |
| — | 1 (cis) | —CH$_2$C$_6$H$_4$—Cl-4 | OMe | OMe |
| — | 1 (cis) | —CH$_2$C$_6$H$_4$—Me-2 | OMe | OMe |
| — | 1 (cis) | —CH$_2$C$_6$H$_4$—Me-3 | OMe | OMe |
| — | 1 (cis) | —CH$_2$C$_6$H$_4$—Me-4 | OMe | OMe |
| — | 1 (cis) | —CH$_2$C$_6$H$_4$—Me-2 | OMe | OMe |
| — | 1 (cis) | —CH$_2$C$_6$H$_4$—Me-3 | OMe | OMe |
| — | 1 (cis) | —CH$_2$C$_6$H$_4$—OMe-4 | OMe | OMe |
| — | 1 (cis) | —CH$_2$CH$_2$C$_6$H$_5$ | OMe | OMe |
| — | 1 (cis) | H | Cl | Me |
| — | 1 (cis) | Li | Cl | Me |
| — | 1 (cis) | Na | Cl | Me |
| — | 1 (cis) | K | Cl | Me |
| — | 1 (cis) | ½Mg | Cl | Me |
| — | 1 (cis) | ½Ca | Cl | Me |
| — | 1 (cis) | MeNH$_3$ | Cl | Me |

TABLE -continued

A compound of the general formula:

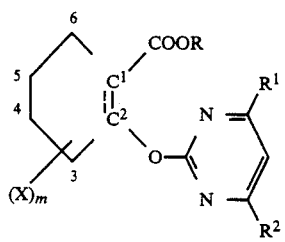

In the below-mentioned table, Me represents methyl group, Et represents ethyl group, Pr represents propyl group, $^i$Pr represents isopropyl group, Bu represents butyl group, $^i$Bu represents isobutyl group, $^s$Bu represents secondary butyl group, $^t$Bu represents tertiary butyl group, cis represents a cis-form, trans represents a trans-form, mix. represents a mixture of a cis-form and a trans-form, 1 represents a single bond and 2 represents a double bond.

| $(X)_m$ | === | R | $R^1$ | $R^2$ |
|---|---|---|---|---|
| — | 1 (cis) | EtNH$_3$ | Cl | Me |
| — | 1 (cis) | PrNH$_3$ | Cl | Me |
| — | 1 (cis) | $^i$PrNH$_3$ | Cl | Me |
| — | 1 (cis) | NH$_2$CONH$_3$ | Cl | Me |
| — | 1 (cis) | Me | Cl | Me |
| — | 1 (cis) | Et | Cl | Me |
| — | 1 (cis) | $^i$Pr | Cl | Me |
| — | 1 (cis) | Pr | Cl | Me |
| — | 1 (cis) | Bu | Cl | Me |
| — | 1 (cis) | $^i$Bu | Cl | Me |
| — | 1 (cis) | $^s$Bu | Cl | Me |
| — | 1 (cis) | $^t$Bu | Cl | Me |
| — | 1 (cis) | —CH$_2$OCH$_3$ | Cl | Me |
| — | 1 (cis) | —CH$_2$CH$_2$OCH$_3$ | Cl | Me |
| — | 1 (cis) | —CH$_2$SCH$_3$ | Cl | Me |
| — | 1 (cis) | —CH$_2$CH=CH$_2$ | Cl | Me |
| — | 1 (cis) | —C(CH$_3$)$_2$CH=CH$_2$ | Cl | Me |
| — | 1 (cis) | —CH$_2$C≡CH$_2$ | Cl | Me |
| — | 1 (cis) | —CH$_2$C$_6$H$_5$ | Cl | Me |
| — | 1 (cis) | —CH$_2$C$_6$H$_4$—Cl-2 | Cl | Me |
| — | 1 (cis) | —CH$_2$C$_6$H$_4$—Cl-3 | Cl | Me |
| — | 1 (cis) | —CH$_2$C$_6$H$_4$—Cl-4 | Cl | Me |
| — | 1 (cis) | —CH$_2$C$_6$H$_4$—Me-2 | Cl | Me |
| — | 1 (cis) | —CH$_2$C$_6$H$_4$—Me-3 | Cl | Me |
| — | 1 (cis) | —CH$_2$C$_6$H$_4$—Me-4 | Cl | Me |
| — | 1 (cis) | —CH$_2$C$_6$H$_4$—OMe-2 | Cl | Me |
| — | 1 (cis) | —CH$_2$C$_6$H$_4$—OMe-3 | Cl | Me |
| — | 1 (cis) | —CH$_2$C$_6$H$_4$—OMe-4 | Cl | Me |
| — | 1 (cis) | —CH$_2$CH$_2$C$_6$H$_5$ | Cl | Me |
| — | 1 (cis) | H | Cl | Cl |
| — | 1 (cis) | Li | Cl | Cl |
| — | 1 (cis) | Na | Cl | Cl |
| — | 1 (cis) | K | Cl | Cl |
| — | 1 (cis) | ½Mg | Cl | Cl |
| — | 1 (cis) | ½Ca | Cl | Cl |
| — | 1 (cis) | MeNH$_3$ | Cl | Cl |
| — | 1 (cis) | EtNH$_3$ | Cl | Cl |
| — | 1 (cis) | PrNH$_3$ | Cl | Cl |
| — | 1 (cis) | $^i$PrNH$_3$ | Cl | Cl |
| — | 1 (cis) | NH$_2$CONH$_3$ | Cl | Cl |
| — | 1 (cis) | Me | Cl | Cl |
| — | 1 (cis) | Et | Cl | Cl |
| — | 1 (cis) | $^i$Pr | Cl | Cl |
| — | 1 (cis) | Pr | Cl | Cl |
| — | 1 (cis) | Bu | Cl | Cl |
| — | 1 (cis) | $^i$Bu | Cl | Cl |
| — | 1 (cis) | $^s$Bu | Cl | Cl |
| — | 1 (cis) | $^t$Bu | Cl | Cl |
| — | 1 (cis) | —CH$_2$OCH$_3$ | Cl | Cl |
| — | 1 (cis) | —CH$_2$CH$_2$OCH$_3$ | Cl | Cl |
| — | 1 (cis) | —CH$_2$SCH$_3$ | Cl | Cl |
| — | 1 (cis) | —CH$_2$CH=CH$_2$ | Cl | Cl |
| — | 1 (cis) | —C(CH$_3$)$_2$CH=CH$_2$ | Cl | Cl |
| — | 1 (cis) | —CH$_2$C≡H$_2$ | Cl | Cl |
| — | 1 (cis) | —CH$_2$C$_6$H$_5$ | Cl | Cl |
| — | 1 (cis) | —CH$_2$C$_6$H$_4$—Cl-2 | Cl | Cl |
| — | 1 (cis) | —CH$_2$C$_6$H$_4$—Cl-3 | Cl | Cl |

TABLE -continued

A compound of the general formula:

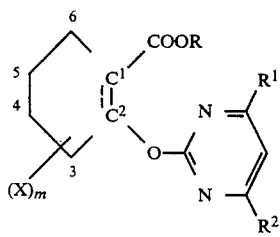

In the below-mentioned table, Me represents methyl group, Et represents ethyl group, Pr represents propyl group, $^i$Pr represents isopropyl group, Bu represents butyl group, $^i$Bu represents isobutyl group, $^s$Bu represents secondary butyl group, $^t$Bu represents tertiary butyl group, cis represents a cis-form, trans represents a trans-form, mix. represents a mixture of a cis-form and a trans-form, 1 represents a single bond and 2 represents a double bond.

| $(X)_m$ | === | R | $R^1$ | $R^2$ |
|---|---|---|---|---|
| — | 1 (cis) | —CH$_2$C$_6$H$_4$—Cl-4 | Cl | Cl |
| — | 1 (cis) | —CH$_2$C$_6$H$_4$—Me-2 | Cl | Cl |
| — | 1 (cis) | —CH$_2$C$_6$H$_4$—Me-3 | Cl | Cl |
| — | 1 (cis) | —CH$_2$C$_6$H$_4$—Me-4 | Cl | Cl |
| — | 1 (cis) | —CH$_2$C$_6$H$_4$—OMe-2 | Cl | Cl |
| — | 1 (cis) | —CH$_2$C$_6$H$_4$—OMe-3 | Cl | Cl |
| — | 1 (cis) | —CH$_2$C$_6$H$_4$—OMe-4 | Cl | Cl |
| — | 1 (cis) | —CH$_2$CH$_2$C$_6$H$_5$ | Cl | Cl |
| — | 1 (cis) | H | Cl | OMe |
| — | 1 (cis) | Li | Cl | OMe |
| — | 1 (cis) | Na | Cl | OMe |
| — | 1 (cis) | K | Cl | OMe |
| — | 1 (cis) | ½Mg | Cl | OMe |
| — | 1 (cis) | ½Ca | Cl | OMe |
| — | 1 (cis) | MeNH$_3$ | Cl | OMe |
| — | 1 (cis) | EtNH$_3$ | Cl | OMe |
| — | 1 (cis) | PrNH$_3$ | Cl | OMe |
| — | 1 (cis) | $^i$PrNH$_3$ | Cl | OMe |
| — | 1 (cis) | NH$_2$CONH$_3$ | Cl | OMe |
| — | 1 (cis) | Me | Cl | OMe |
| — | 1 (cis) | Et | Cl | OMe |
| — | 1 (cis) | $^i$Pr | Cl | OMe |
| — | 1 (cis) | Pr | Cl | OMe |
| — | 1 (cis) | Bu | Cl | OMe |
| — | 1 (cis) | $^i$Bu | Cl | OMe |
| — | 1 (cis) | $^s$Bu | Cl | OMe |
| — | 1 (cis) | $^t$Bu | Cl | OMe |
| — | 1 (cis) | —CH$_2$OCH$_3$ | Cl | OMe |
| — | 1 (cis) | —CH$_2$CH$_2$SCH$_3$ | Cl | OMe |
| — | 1 (cis) | —CH$_2$SCH$_3$ | Cl | OMe |
| — | 1 (cis) | —CH$_2$CH=CH$_2$ | Cl | OMe |
| — | 1 (cis) | —C(CH$_3$)$_2$CH=CH$_2$ | Cl | OMe |
| — | 1 (cis) | —CH$_2$C≡CH$_2$ | Cl | OMe |
| — | 1 (cis) | —CH$_2$C$_6$H$_5$ | Cl | OMe |
| — | 1 (cis) | —CH$_2$C$_6$H$_4$—Cl-2 | Cl | OMe |
| — | 1 (cis) | —CH$_2$C$_6$H$_4$—Cl-3 | Cl | OMe |
| — | 1 (cis) | —CH$_2$C$_6$H$_4$—Cl-4 | Cl | OMe |
| — | 1 (cis) | —CH$_2$C$_6$H$_4$—Me-2 | Cl | OMe |
| — | 1 (cis) | —CH$_2$C$_6$H$_4$—Me-3 | Cl | OMe |
| — | 1 (cis) | —CH$_2$C$_6$H$_4$—Me-4 | Cl | OMe |
| — | 1 (cis) | —CH$_2$C$_6$H$_4$—OMe-2 | Cl | OMe |
| — | 1 (cis) | —CH$_2$C$_6$H$_4$—OMe-3 | Cl | OMe |
| — | 1 (cis) | —CH$_2$C$_6$H$_4$—OMe-4 | Cl | OMe |
| — | 1 (cis) | —CH$_2$C$_6$H$_5$ | Cl | OMe |
| — | 1 (cis) | H | OCHF$_2$ | OMe |
| — | 1 (cis) | Li | OCHF$_2$ | OMe |
| — | 1 (cis) | Na | OCHF$_2$ | OMe |
| — | 1 (cis) | K | OCHF$_2$ | OMe |
| — | 1 (cis) | ½Mg | OCHF$_2$ | OMe |
| — | 1 (cis) | ½Ca | OCHF$_2$ | OMe |
| — | 1 (cis) | MeNH$_3$ | OCHF$_2$ | OMe |
| — | 1 (cis) | EtNH$_3$ | OCHF$_2$ | OMe |
| — | 1 (cis) | PrNH$_3$ | OCHF$_2$ | OMe |
| — | 1 (cis) | $^i$PrNH$_3$ | OCHF$_2$ | OMe |
| — | 1 (cis) | NH$_2$CONH$_3$ | OCHF$_2$ | OMe |
| — | 1 (cis) | Me | OCHF$_2$ | OMe |
| — | 1 (cis) | Et | OCHF$_2$ | OMe |

TABLE -continued

A compound of the general formula:

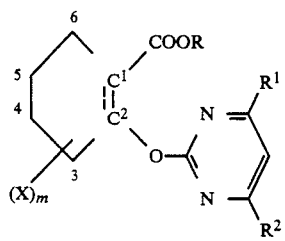

In the below-mentioned table, Me represents methyl group, Et represents ethyl group, Pr represents propyl group, $^i$Pr represents isopropyl group, Bu represents butyl group, $^i$Bu represents isobutyl group, $^s$Bu represents secondary butyl group, $^t$Bu represents tertiary butyl group, cis represents a cis-form, trans represents a trans-form, mix. represents a mixture of a cis-form and a trans-form, 1 represents a single bond and 2 represents a double bond.

| $(X)_m$ | === | R | $R^1$ | $R^2$ |
|---|---|---|---|---|
| — | 1 (cis) | $^i$Pr | $OCHF_2$ | OMe |
| — | 1 (cis) | Pr | $OCHF_2$ | OMe |
| — | 1 (cis) | Bu | $OCHF_2$ | OMe |
| — | 1 (cis) | $^i$Bu | $OCHF_2$ | OMe |
| — | 1 (cis) | $^s$Bu | $OCHF_2$ | OMe |
| — | 1 (cis) | $^t$Bu | $OCHF_2$ | OMe |
| — | 1 (cis) | —$CH_2OCH_3$ | $OCHF_2$ | OMe |
| — | 1 (cis) | —$CH_2CH_2OCH_3$ | $OCHF_2$ | OMe |
| — | 1 (cis) | —$CH_2SCH_3$ | $OCHF_2$ | OMe |
| — | 1 (cis) | —$CH_2CH=CH_2$ | $OCHF_2$ | OMe |
| — | 1 (cis) | —$C(CH_2)_2CH=CH_2$ | $OCHF_2$ | OMe |
| — | 1 (cis) | —$CH_2C\equiv CH_2$ | $OCHF_2$ | OMe |
| — | 1 (cis) | —$CH_2C_6H_5$ | $OCHF_2$ | OMe |
| — | 1 (cis) | —$CH_2C_6H_4$—Cl-2 | $OCHF_2$ | OMe |
| — | 1 (cis) | —$CH_2C_6H_4$—Cl-3 | $OCHF_2$ | OMe |
| — | 1 (cis) | —$CH_2C_6H_4$—Cl-4 | $OCHF_2$ | OMe |
| — | 1 (cis) | —$CH_2C_6H_4$—Me-2 | $OCHF_2$ | OMe |
| — | 1 (cis) | —$CH_2C_6H_4$—Me-3 | $OCHF_2$ | OMe |
| — | 1 (cis) | —$CH_2C_6H_4$—Me-4 | $OCHF_2$ | OMe |
| — | 1 (cis) | —$CH_2C_6H_4$—OMe-2 | $OCHF_2$ | OMe |
| — | 1 (cis) | —$CH_2C_6H_4$—OMe-3 | $OCHF_2$ | OMe |
| — | 1 (cis) | —$CH_2C_6H_4$—OMe-4 | $OCHF_2$ | OMe |
| — | 1 (cis) | —$CH_2CH_2C_6H_5$ | $OCHF_2$ | OMe |
| — | 1 (cis) | H | $OCHF_2$ | $OCHF_2$ |
| — | 1 (cis) | Li | $OCHF_2$ | $OCHF_2$ |
| — | 1 (cis) | Na | $OCHF_2$ | $OCHF_2$ |
| — | 1 (cis) | K | $OCHF_2$ | $OCHF_2$ |
| — | 1 (cis) | ½Mg | $OCHF_2$ | $OCHF_2$ |
| — | 1 (cis) | ½Ca | $OCHF_2$ | $OCHF_2$ |
| — | 1 (cis) | $MeNH_3$ | $OCHF_2$ | $OCHF_2$ |
| — | 1 (cis) | $EtNH_3$ | $OCHF_2$ | $OCHF_2$ |
| — | 1 (cis) | $PrNH_3$ | $OCHF_2$ | $OCHF_2$ |
| — | 1 (cis) | $^i PrNH_3$ | $OCHF_2$ | $OCHF_2$ |
| — | 1 (cis) | $NH_2CONH_3$ | $OCHF_2$ | $OCHF_2$ |
| — | 1 (cis) | Me | $OCHF_2$ | $OCHF_2$ |
| — | 1 (cis) | Et | $OCHF_2$ | $OCHF_2$ |
| — | 1 (cis) | $^i$Pr | $OCHF_2$ | $OCHF_2$ |
| — | 1 (cis) | Pr | $OCHF_2$ | $OCHF_2$ |
| — | 1 (cis) | Bu | $OCHF_2$ | $OCHF_2$ |
| — | 1 (cis) | $^i$Bu | $OCHF_2$ | $OCHF_2$ |
| — | 1 (cis) | $^s$Bu | $OCHF_2$ | $OCHF_2$ |
| — | 1 (cis) | $^t$Bu | $OCHF_2$ | $OCHF_2$ |
| — | 1 (cis) | —$CH_2OCH_3$ | $OCHF_2$ | $OCHF_2$ |
| — | 1 (cis) | —$CH_2CH_2OCH_3$ | $OCHF_2$ | $OCHF_2$ |
| — | 1 (cis) | —$CH_2SCH_3$ | $OCHF_2$ | $OCHF_2$ |
| — | 1 (cis) | —$CH_2CH=CH_2$ | $OCHF_2$ | $OCHF_2$ |
| — | 1 (cis) | —$C(CH_3)_2CH=CH_2$ | $OCHF_2$ | $OCHF_2$ |
| — | 1 (cis) | —$CH_2C\equiv CH_2$ | $OCHF_2$ | $OCHF_2$ |
| — | 1 (cis) | —$CH_2C_6H_5$ | $OCHF_2$ | $OCHF_2$ |
| — | 1 (cis) | —$CH_2C_6H_4$—Cl-2 | $OCHF_2$ | $OCHF_2$ |
| — | 1 (cis) | —$CH_2C_6H_4$—Cl-3 | $OCHF_2$ | $OCHF_2$ |
| — | 1 (cis) | —$CH_2C_6H_4$—Cl-4 | $OCHF_2$ | $OCHF_2$ |
| — | 1 (cis) | —$CH_2C_6H_4$—Me-2 | $OCHF_2$ | $OCHF_2$ |
| — | 1 (cis) | —$CH_2C_6H_4$—Me-3 | $OCHF_2$ | $OCHF_2$ |
| — | 1 (cis) | —$CH_2C_6H_4$—Me-4 | $OCHF_2$ | $OCHF_2$ |
| — | 1 (cis) | —$CH_2C_6H_4$—OMe-2 | $OCHF_2$ | $OCHF_2$ |
| — | 1 (cis) | —$CH_2C_6H_4$—OMe-3 | $OCHF_2$ | $OCHF_2$ |

TABLE -continued

A compound of the general formula:

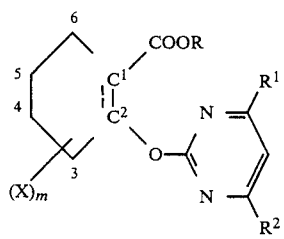

In the below-mentioned table, Me represents methyl group, Et represents ethyl group, Pr represents propyl group, $^i$Pr represents isopropyl group, Bu represents butyl group, $^i$Bu represents isobutyl group, $^s$Bu represents secondary butyl group, $^t$Bu represents tertiary butyl group, cis represents a cis-form, trans represents a trans-form, mix. represents a mixture of a cis-form and a trans-form, 1 represents a single bond and 2 represents a double bond.

| $(X)_m$ | === | R | $R^1$ | $R^2$ |
|---|---|---|---|---|
| — | 1 (cis) | —CH$_2$C$_6$H$_4$—OMe-4 | OCHF$_2$ | OCHF$_2$ |
| — | 1 (cis) | —CH$_2$C$_6$H$_5$ | OCHF$_2$ | OCHF$_2$ |
| — | 1 (cis) | H | SMe | OMe |
| — | 1 (cis) | Li | SMe | OMe |
| — | 1 (cis) | Na | SMe | OMe |
| — | 1 (cis) | K | SMe | OMe |
| — | 1 (cis) | ½Mg | SMe | OMe |
| — | 1 (cis) | ½Ca | SMe | OMe |
| — | 1 (cis) | MeNH$_3$ | SMe | OMe |
| — | 1 (cis) | EtNH$_3$ | SMe | OMe |
| — | 1 (cis) | PrNH$_3$ | SMe | OMe |
| — | 1 (cis) | $^i$PrNH$_3$ | SMe | OMe |
| — | 1 (cis) | NH$_2$CONH$_3$ | SMe | OMe |
| — | 1 (cis) | Me | SMe | OMe |
| — | 1 (cis) | Et | SMe | OMe |
| — | 1 (cis) | $^i$Pr | SMe | OMe |
| — | 1 (cis) | Pr | SMe | OMe |
| — | 1 (cis) | Bu | SMe | OMe |
| — | 1 (cis) | $^i$Bu | SMe | OMe |
| — | 1 (cis) | $^s$Bu | SMe | OMe |
| — | 1 (cis) | $^t$Bu | SMe | OMe |
| — | 1 (cis) | —CH$_2$OCH$_3$ | SMe | OMe |
| — | 1 (cis) | —CH$_2$CH$_2$SCH$_3$ | SMe | OMe |
| — | 1 (cis) | —CH$_2$SCH$_3$ | SMe | OMe |
| — | 1 (cis) | —CH$_2$CH=CH$_2$ | SMe | OMe |
| — | 1 (cis) | —C(CH$_2$)$_2$CH=CH$_2$ | SMe | OMe |
| — | 1 (cis) | —CH$_2$C$_6$H$_5$ | SMe | OMe |
| — | 1 (cis) | —CH$_2$C$_6$H$_4$—Cl-2 | SMe | OMe |
| — | 1 (cis) | —CH$_2$C$_6$H$_4$—Cl-3 | SMe | OMe |
| — | 1 (cis) | —CH$_2$C$_6$H$_4$—Cl-4 | SMe | OMe |
| — | 1 (cis) | —CH$_2$C$_6$H$_4$—Me-2 | SMe | OMe |
| — | 1 (cis) | —CH$_2$C$_6$H$_4$—Me-3 | SMe | OMe |
| — | 1 (cis) | —CH$_2$C$_6$H$_4$—Me-4 | SMe | OMe |
| — | 1 (cis) | —CH$_2$C$_6$H$_4$—OMe-2 | SMe | OMe |
| — | 1 (cis) | —CH$_2$C$_6$H$_4$—OMe-3 | SMe | OMe |
| — | 1 (cis) | —CH$_2$C$_6$H$_4$—OMe-4 | SMe | OMe |
| — | 1 (cis) | —CH$_2$C$_6$H$_5$ | SMe | OMe |
| — | 1 (cis) | H | SMe | Me |
| — | 1 (cis) | Li | SMe | Me |
| — | 1 (cis) | Na | SMe | Me |
| — | 1 (cis) | K | SMe | Me |
| — | 1 (cis) | ½Mg | SMe | Me |
| — | 1 (cis) | ½Ca | SMe | Me |
| — | 1 (cis) | MeNH$_3$ | SMe | Me |
| — | 1 (cis) | EtNH$_3$ | SMe | Me |
| — | 1 (cis) | PrNH$_3$ | SMe | Me |
| — | 1 (cis) | $^i$PrNH$_3$ | SMe | Me |
| — | 1 (cis) | NH$_2$CONH$_3$ | SMe | Me |
| — | 1 (cis) | Me | SMe | Me |
| — | 1 (cis) | Et | SMe | Me |
| — | 1 (cis) | $^i$Pr | SMe | Me |
| — | 1 (cis) | Pr | SMe | Me |
| — | 1 (cis) | Bu | SMe | Me |
| — | 1 (cis) | $^i$Bu | SMe | Me |
| — | 1 (cis) | $^s$Bu | SMe | Me |
| — | 1 (cis) | $^t$Bu | SMe | Me |
| — | 1 (cis) | —CH$_2$OCH$_3$ | SMe | Me |

TABLE -continued

A compound of the general formula:

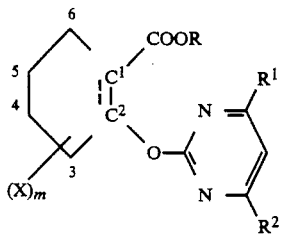

In the below-mentioned table, Me represents methyl group, Et represents ethyl group, Pr represents propyl group, $^i$Pr represents isopropyl group, Bu represents butyl group, $^i$Bu represents isobutyl group, $^s$Bu represents secondary butyl group, $^t$Bu represents tertiary butyl group, cis represents a cis-form, trans represents a trans-form, mix. represents a mixture of a cis-form and a trans-form, 1 represents a single bond and 2 represents a double bond.

| $(X)_m$ | === | R | $R^1$ | $R^2$ |
|---|---|---|---|---|
| — | 1 (cis) | —CH$_2$CH$_2$OCH$_3$ | SMe | Me |
| — | 1 (cis) | —CH$_2$SCH$_3$ | SMe | Me |
| — | 1 (cis) | —CH$_2$CH=CH$_2$ | SMe | Me |
| — | 1 (cis) | —C(CH$_3$)$_2$CH=CH$_2$ | SMe | Me |
| — | 1 (cis) | —CH$_2$C≡CH$_2$ | SMe | Me |
| — | 1 (cis) | —CH$_2$C$_6$H$_5$ | SMe | Me |
| — | 1 (cis) | —CH$_2$C$_6$H$_4$—Cl-2 | SMe | Me |
| — | 1 (cis) | —CH$_2$C$_6$H$_4$—Cl-3 | SMe | Me |
| — | 1 (cis) | —CH$_2$C$_6$H$_4$—Cl-4 | SMe | Me |
| — | 1 (cis) | —CH$_2$C$_6$H$_4$—Me-2 | SMe | Me |
| — | 1 (cis) | —CH$_2$C$_6$H$_4$—Me-3 | SMe | Me |
| — | 1 (cis) | —CH$_2$C$_6$H$_4$—Me-4 | SMe | Me |
| — | 1 (cis) | —CH$_2$C$_6$H$_4$—OMe-2 | SMe | Me |
| — | 1 (cis) | —CH$_2$C$_6$H$_4$—OMe-3 | SMe | Me |
| — | 1 (cis) | —CH$_2$C$_6$H$_4$—OMe-4 | SMe | Me |
| — | 1 (cis) | —CH$_2$C$_6$H$_5$ | SMe | Me |
| — | 1 (trans) | H | Me | Me |
| — | 1 (trans) | Li | Me | Me |
| — | 1 (trans) | Na | Me | Me |
| — | 1 (trans) | K | Me | Me |
| — | 1 (trans) | ½Mg | Me | Me |
| — | 1 (trans) | ½Ca | Me | Me |
| — | 1 (trans) | MeNH$_3$ | Me | Me |
| — | 1 (trans) | EtNH$_3$ | Me | Me |
| — | 1 (trans) | PrNH$_3$ | Me | Me |
| — | 1 (trans) | PrNH$_3$ | OMe | Me |
| — | 1 (trans) | $^i$PrNH$_3$ | OMe | Me |
| — | 1 (trans) | NH$_2$CONH$_3$ | OMe | Me |
| — | 1 (trans) | Me | OMe | Me |
| — | 1 (trans) | Et | OMe | Me |
| — | 1 (trans) | $^i$Pr | OMe | Me |
| — | 1 (trans) | Pr | OMe | Me |
| — | 1 (trans) | Bu | OMe | Me |
| — | 1 (trans) | $^i$Bu | OMe | Me |
| — | 1 (trans) | $^s$Bu | OMe | Me |
| — | 1 (trans) | $^t$Bu | OMe | Me |
| — | 1 (trans) | —CH$_2$OCH$_3$ | OMe | Me |
| — | 1 (trans) | —CH$_2$CH$_2$OCH$_3$ | OMe | Me |
| — | 1 (trans) | —CH$_2$SCH$_3$ | OMe | Me |
| — | 1 (trans) | —CH$_2$CH=CH$_2$ | OMe | Me |
| — | 1 (trans) | —C(CH$_3$)$_2$CH=CH$_2$ | OMe | Me |
| — | 1 (trans) | —CH$_2$C≡CH$_2$ | OMe | Me |
| — | 1 (trans) | —CH$_2$C$_6$H$_5$ | OMe | Me |
| — | 1 (trans) | —CH$_2$C$_6$H$_4$—Cl-2 | OMe | Me |
| — | 1 (trans) | —CH$_2$C$_6$H$_4$—Cl-3 | OMe | Me |
| — | 1 (trans) | —CH$_2$C$_6$H$_4$—Cl-4 | OMe | Me |
| — | 1 (trans) | —CH$_2$C$_6$H$_4$—Me-2 | OMe | Me |
| — | 1 (trans) | —CH$_2$C$_6$H$_4$—Me-3 | OMe | Me |
| — | 1 (trans) | —CH$_2$C$_6$H$_4$—Me-4 | OMe | Me |
| — | 1 (trans) | —CH$_2$C$_6$H$_4$—OMe-2 | OMe | Me |
| — | 1 (trans) | —CH$_2$C$_6$H$_4$—OMe-3 | OMe | Me |
| — | 1 (trans) | —CH$_2$C$_6$H$_4$—OMe-4 | OMe | Me |
| — | 1 (trans) | —CH$_2$C$_6$H$_5$ | OMe | Me |
| — | 1 (trans) | H | OMe | OMe |
| — | 1 (trans) | Li | OMe | OMe |
| — | 1 (trans) | Na | OMe | OMe |
| — | 1 (trans) | K | OMe | OMe |

TABLE -continued

A compound of the general formula:

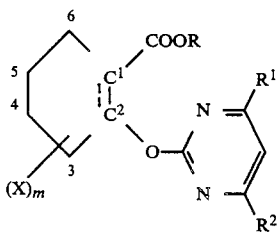

In the below-mentioned table, Me represents methyl group, Et represents ethyl group, Pr represents propyl group, $^i$Pr represents isopropyl group, Bu represents butyl group, $^i$Bu represents isobutyl group, $^s$Bu represents secondary butyl group, $^t$Bu represents tertiary butyl group, cis represents a cis-form, trans represents a trans-form, mix. represents a mixture of a cis-form and a trans-form, 1 represents a single bond and 2 represents a double bond.

| $(X)_m$ | === | R | $R^1$ | $R^2$ |
|---|---|---|---|---|
| — | 1 (trans) | ½Mg | OMe | OMe |
| — | 1 (trans) | ½Ca | OMe | OMe |
| — | 1 (trans) | MeNH$_3$ | OMe | OMe |
| — | 1 (trans) | EtNH$_3$ | OMe | OMe |
| — | 1 (trans) | PrNH$_3$ | OMe | OMe |
| — | 1 (trans) | $^i$PrNH$_3$ | OMe | OMe |
| — | 1 (trans) | NH$_2$CONH$_3$ | OMe | OMe |
| — | 1 (trans) | Me | OMe | OMe |
| — | 1 (trans) | Et | OMe | OMe |
| — | 1 (trans) | $^i$Pr | OMe | OMe |
| — | 1 (trans) | Pr | OMe | OMe |
| — | 1 (trans) | Bu | OMe | OMe |
| — | 1 (trans) | $^i$Bu | OMe | OMe |
| — | 1 (trans) | $^s$Bu | OMe | OMe |
| — | 1 (trans) | $^t$Bu | OMe | OMe |
| — | 1 (trans) | —CH$_2$OCH$_3$ | OMe | OMe |
| — | 1 (trans) | —CH$_2$CH$_2$OCH$_3$ | OMe | OMe |
| — | 1 (trans) | —CH$_2$SCH$_3$ | OMe | OMe |
| — | 1 (trans) | —CH$_2$CH=CH$_2$ | OMe | OMe |
| — | 1 (trans) | —C(CH$_3$)$_2$CH=CH$_2$ | OMe | OMe |
| — | 1 (trans) | —CH$_2$C≡CH$_2$ | OMe | OMe |
| — | 1 (trans) | —CH$_2$C$_6$H$_5$ | OMe | OMe |
| — | 1 (trans) | —CH$_2$C$_6$H$_4$—Cl-2 | OMe | OMe |
| — | 1 (trans) | —CH$_2$C$_6$H$_4$—Cl-3 | OMe | OMe |
| — | 1 (trans) | —CH$_2$C$_6$H$_4$—Cl-4 | OMe | OMe |
| — | 1 (trans) | —CH$_2$C$_6$H$_4$—Me-2 | OMe | OMe |
| — | 1 (trans) | —CH$_2$C$_6$H$_4$—Me-3 | OMe | OMe |
| — | 1 (trans) | —CH$_2$C$_6$H$_4$—Me-4 | OMe | OMe |
| — | 1 (trans) | —CH$_2$C$_6$H$_4$—OMe-2 | OMe | OMe |
| — | 1 (trans) | —CH$_2$C$_6$H$_4$—OMe-3 | OMe | OMe |
| — | 1 (trans) | —CH$_2$C$_6$H$_4$—OMe-4 | OMe | OMe |
| — | 1 (trans) | —CH$_2$CH$_2$C$_6$H$_5$ | OMe | OMe |
| — | 1 (trans) | H | Cl | Me |
| — | 1 (trans) | Li | Cl | Me |
| — | 1 (trans) | Na | Cl | Me |
| — | 1 (trans) | K | Cl | Me |
| — | 1 (trans) | ½Mg | Cl | Me |
| — | 1 (trans) | ½Ca | Cl | Me |
| — | 1 (trans) | MeNH$_3$ | Cl | Me |
| — | 1 (trans) | EtNH$_3$ | Cl | Me |
| — | 1 (trans) | PrNH$_3$ | Cl | Me |
| — | 1 (trans) | $^i$PrNH$_3$ | Cl | Me |
| — | 1 (trans) | NH$_2$CONH$_3$ | Cl | Me |
| — | 1 (trans) | Me | Cl | Me |
| — | 1 (trans) | Et | Cl | Me |
| — | 1 (trans) | $^i$Pr | Cl | Me |
| — | 1 (trans) | Pr | Cl | Me |
| — | 1 (trans) | Bu | Cl | Me |
| — | 1 (trans) | $^i$Bu | Cl | Me |
| — | 1 (trans) | $^s$Bu | Cl | Me |
| — | 1 (trans) | $^t$Bu | Cl | Me |
| — | 1 (trans) | —CH$_2$OCH$_3$ | Cl | Me |
| — | 1 (trans) | —CH$_2$CH$_2$OCH$_3$ | Cl | Me |
| — | 1 (trans) | —CH$_2$SCH$_3$ | Cl | Me |
| — | 1 (trans) | —CH$_2$CH=CH$_2$ | Cl | Me |
| — | 1 (trans) | —C(CH$_3$)$_2$CH=CH$_2$ | Cl | Me |
| — | 1 (trans) | —CH$_2$C≡CH$_2$ | Cl | Me |

TABLE -continued

A compound of the general formula:

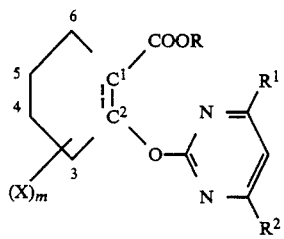

In the below-mentioned table, Me represents methyl group, Et represents ethyl group, Pr represents propyl group, $^i$Pr represents isopropyl group, Bu represents butyl group, $^i$Bu represents isobutyl group, $^s$Bu represents secondary butyl group, $^t$Bu represents tertiary butyl group, cis represents a cis-form, trans represents a trans-form, mix. represents a mixture of a cis-form and a trans-form, 1 represents a single bond and 2 represents a double bond.

| $(X)_m$ | === | R | $R^1$ | $R^2$ |
|---|---|---|---|---|
| — | 1 (trans) | —CH$_2$C$_6$H$_5$ | Cl | Me |
| — | 1 (trans) | —CH$_2$C$_6$H$_4$—Cl-2 | Cl | Me |
| — | 1 (trans) | —CH$_2$C$_6$H$_4$—Cl-3 | Cl | Me |
| — | 1 (trans) | —CH$_2$C$_6$H$_4$—Cl-4 | Cl | Me |
| — | 1 (trans) | —CH$_2$C$_6$H$_4$—Me-2 | Cl | Me |
| — | 1 (trans) | —CH$_2$C$_6$H$_4$—Me-3 | Cl | Me |
| — | 1 (trans) | —CH$_2$C$_6$H$_4$—Me-4 | Cl | Me |
| — | 1 (trans) | —CH$_2$C$_6$H$_4$—OMe-2 | Cl | Me |
| — | 1 (trans) | —CH$_2$C$_6$H$_4$—OMe-3 | Cl | Me |
| — | 1 (trans) | —CH$_2$C$_6$H$_4$—OMe-4 | Cl | Me |
| — | 1 (trans) | —CH$_2$C$_6$H$_5$ | Cl | Me |
| — | 1 (trans) | H | Cl | Cl |
| — | 1 (trans) | Li | Cl | Cl |
| — | 1 (trans) | Na | Cl | Cl |
| — | 1 (trans) | K | Cl | Cl |
| — | 1 (trans) | ½Mg | Cl | Cl |
| — | 1 (trans) | ½Ca | Cl | Cl |
| — | 1 (trans) | MeNH$_3$ | Cl | Cl |
| — | 1 (trans) | EtNH$_3$ | Cl | Cl |
| — | 1 (trans) | PrNH$_3$ | Cl | Cl |
| — | 1 (trans) | $^i$PrNH$_3$ | Cl | Cl |
| — | 1 (trans) | NH$_2$CONH$_3$ | Cl | Cl |
| — | 1 (trans) | Me | Cl | Cl |
| — | 1 (trans) | Et | Cl | Cl |
| — | 1 (trans) | $^i$Pr | Cl | Cl |
| — | 1 (trans) | Pr | Cl | Cl |
| — | 1 (trans) | Bu | Cl | Cl |
| — | 1 (trans) | $^i$Bu | Cl | Cl |
| — | 1 (trans) | $^s$Bu | Cl | Cl |
| — | 1 (trans) | $^t$Bu | Cl | Cl |
| — | 1 (trans) | —CH$_2$OCH$_3$ | Cl | Cl |
| — | 1 (trans) | —CH$_2$CH$_2$OCH$_3$ | Cl | Cl |
| — | 1 (trans) | —CH$_2$SCH$_3$ | Cl | Cl |
| — | 1 (trans) | —CH$_2$CH=CH$_2$ | Cl | Cl |
| — | 1 (trans) | —C(CH$_3$)$_2$CH=CH$_2$ | Cl | Cl |
| — | 1 (trans) | —CH$_2$C≡CH$_2$ | Cl | Cl |
| — | 1 (trans) | —CH$_2$C$_6$H$_5$ | Cl | Cl |
| — | 1 (trans) | —CH$_2$C$_6$H$_4$—Cl-2 | Cl | Cl |
| — | 1 (trans) | —CH$_2$C$_6$H$_4$—Cl-3 | Cl | Cl |
| — | 1 (trans) | —CH$_2$C$_6$H$_4$—Cl-4 | Cl | Cl |
| — | 1 (trans) | —CH$_2$C$_6$H$_4$—Me-2 | Cl | Cl |
| — | 1 (trans) | —CH$_2$C$_6$H$_4$—Me-3 | Cl | Cl |
| — | 1 (trans) | —CH$_2$C$_6$H$_4$—Me-4 | Cl | Cl |
| — | 1 (trans) | —CH$_2$C$_6$H$_4$—OMe-2 | Cl | Cl |
| — | 1 (trans) | —CH$_2$C$_6$H$_4$—OMe-3 | Cl | Cl |
| — | 1 (trans) | —CH$_2$C$_6$H$_4$—OMe-4 | Cl | Cl |
| — | 1 (trans) | —CH$_2$CH$_2$C$_6$H$_5$ | Cl | Cl |
| — | 1 (trans) | H | Cl | OMe |
| — | 1 (trans) | Li | Cl | OMe |
| — | 1 (trans) | Na | Cl | OMe |
| — | 1 (trans) | K | Cl | OMe |
| — | 1 (trans) | ½Mg | Cl | OMe |
| — | 1 (trans) | ½Ca | Cl | OMe |
| — | 1 (trans) | MeNH$_3$ | Cl | OMe |
| — | 1 (trans) | EtNH$_3$ | Cl | OMe |
| — | 1 (trans) | PrNH$_3$ | Cl | OMe |
| — | 1 (trans) | $^i$PrNH$_3$ | Cl | OMe |

TABLE -continued

A compound of the general formula:

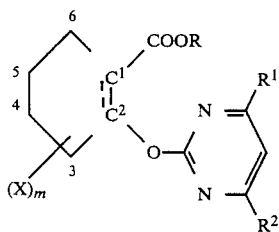

In the below-mentioned table, Me represents methyl group, Et represents ethyl group, Pr represents propyl group, $^i$Pr represents isopropyl group, Bu represents butyl group, $^i$Bu represents isobutyl group, $^s$Bu represents secondary butyl group, $^t$Bu represents tertiary butyl group, cis represents a cis-form, trans represents a trans-form, mix. represents a mixture of a cis-form and a trans-form, 1 represents a single bond and 2 represents a double bond.

| $(X)_m$ | ==== | R | $R^1$ | $R^2$ |
|---|---|---|---|---|
| — | 1 (trans) | $NH_2CONH_3$ | Cl | OMe |
| — | 1 (trans) | Me | Cl | OMe |
| — | 1 (trans) | Et | Cl | OMe |
| — | 1 (trans) | $^i$Pr | Cl | OMe |
| — | 1 (trans) | Pr | Cl | OMe |
| — | 1 (trans) | Bu | Cl | OMe |
| — | 1 (trans) | $^i$Bu | Cl | OMe |
| — | 1 (trans) | $^s$Bu | Cl | OMe |
| — | 1 (trans) | $^t$Bu | Cl | OMe |
| — | 1 (trans) | $-CH_2OCH_3$ | Cl | OMe |
| — | 1 (trans) | $-CH_2CH_2OCH_3$ | Cl | OMe |
| — | 1 (trans) | $-CH_2SCH_3$ | Cl | OMe |
| — | 1 (trans) | $-CH_2CH=CH_2$ | Cl | OMe |
| — | 1 (trans) | $-C(CH_3)_2CH=CH_2$ | Cl | OMe |
| — | 1 (trans) | $-CH_2C\equiv CH_2$ | Cl | OMe |
| — | 1 (trans) | $-CH_2C_6H_5$ | Cl | OMe |
| — | 1 (trans) | $-CH_2C_6H_4-Cl-2$ | Cl | OMe |
| — | 1 (trans) | $-CH_2C_6H_4-Cl-3$ | Cl | OMe |
| — | 1 (trans) | $-CH_2C_6H_4-Cl-4$ | Cl | OMe |
| — | 1 (trans) | $-CH_2C_6H_4-Me-2$ | Cl | OMe |
| — | 1 (trans) | $-CH_2C_6H_4-Me-3$ | Cl | OMe |
| — | 1 (trans) | $-CH_2C_6H_4-Me-4$ | Cl | OMe |
| — | 1 (trans) | $-CH_2C_6H_4-OMe-2$ | Cl | OMe |
| — | 1 (trans) | $-CH_2C_6H_4-OMe-3$ | Cl | OMe |
| — | 1 (trans) | $-CH_2C_6H_4-OMe-4$ | Cl | OMe |
| — | 1 (trans) | $-CH_2CH_2C_6H_5$ | Cl | OMe |
| — | 1 (trans) | H | $OCHF_2$ | OMe |
| — | 1 (trans) | Li | $OCHF_2$ | OMe |
| — | 1 (trans) | Na | $OCHF_3$ | OMe |
| — | 1 (trans) | K | $OCHF_2$ | OMe |
| — | 1 (trans) | ½Mg | $OCHF_2$ | OMe |
| — | 1 (trans) | ½Ca | $OCHF_2$ | OMe |
| — | 1 (trans) | $MeNH_3$ | $OCHF_2$ | OMe |
| — | 1 (trans) | $EtNH_3$ | $OCHF_2$ | OMe |
| — | 1 (trans) | $PrNH_3$ | $OCHF_2$ | OMe |
| — | 1 (trans) | $^iPrNH_3$ | $OCHF_2$ | OMe |
| — | 1 (trans) | $NH_2CONH_3$ | $OCHF_2$ | OMe |
| — | 1 (trans) | Me | $OCHF_2$ | OMe |
| — | 1 (trans) | Et | $OCHF_2$ | OMe |
| — | 1 (trans) | $^i$Pr | $OCHF_2$ | OMe |
| — | 1 (trans) | Pr | $OCHF_2$ | OMe |
| — | 1 (trans) | Bu | $OCHF_2$ | OMe |
| — | 1 (trans) | $^i$Bu | $OCHF_2$ | OMe |
| — | 1 (trans) | $^s$Bu | $OCHF_2$ | OMe |
| — | 1 (trans) | $^t$Bu | $OCHF_2$ | OMe |
| — | 1 (trans) | $-CH_2OCH_3$ | $OCHF_2$ | OMe |
| — | 1 (trans) | $-CH_2CH_2OCH_3$ | $OCHF_2$ | OMe |
| — | 1 (trans) | $-CH_2SCH_3$ | $OCHF_2$ | OMe |
| — | 1 (trans) | $-CH_2CH=CH_2$ | $OCHF_2$ | OMe |
| — | 1 (trans) | $-C(CH_3)_2CH=CH_2$ | $OCHF_2$ | OMe |
| — | 1 (trans) | $-CH_2C\equiv CH_2$ | $OCHF_2$ | OMe |
| — | 1 (trans) | $-CH_2C_6H_5$ | $OCHF_2$ | OMe |
| — | 1 (trans) | $-CH_2C_6H_4-Cl-2$ | $OCHF_2$ | OMe |
| — | 1 (trans) | $-CH_2C_6H_4-Cl-3$ | $OCHF_2$ | OMe |
| — | 1 (trans) | $-CH_2C_6H_4-Me-2$ | $OCHF_2$ | OMe |
| — | 1 (trans) | $-CH_2C_6H_4-Me-3$ | $OCHF_2$ | OMe |
| — | 1 (trans) | $-CH_2C_6H_4-Me-4$ | $OCHF_2$ | OMe |

TABLE -continued

A compound of the general formula:

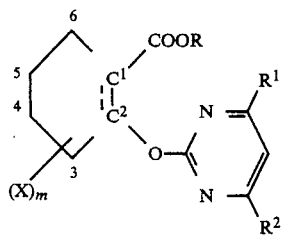

In the below-mentioned table, Me represents methyl group, Et represents ethyl group, Pr represents propyl group, $^i$Pr represents isopropyl group, Bu represents butyl group, $^i$Bu represents isobutyl group, $^s$Bu represents secondary butyl group, $^t$Bu represents tertiary butyl group, cis represents a cis-form, trans represents a trans-form, mix. represents a mixture of a cis-form and a trans-form, 1 represents a single bond and 2 represents a double bond.

| $(X)_m$ | === | R | $R^1$ | $R^2$ |
|---|---|---|---|---|
| — | 1 (trans) | —CH$_2$C$_6$H$_4$—OMe-2 | OCHF$_2$ | OMe |
| — | 1 (trans) | —CH$_2$C$_6$H$_4$—OMe-3 | OCHF$_2$ | OMe |
| — | 1 (trans) | —CH$_2$C$_6$H$_4$—OMe-4 | OCHF$_2$ | OMe |
| — | 1 (trans) | —CH$_2$CH$_2$C$_6$H$_5$ | OCHF$_2$ | OMe |
| — | 1 (trans) | H | OCHF$_2$ | OCHF$_2$ |
| — | 1 (trans) | Li | OCHF$_2$ | OCHF$_2$ |
| — | 1 (trans) | Na | OCHF$_2$ | OCHF$_2$ |
| — | 1 (trans) | K | OCHF$_2$ | OCHF$_2$ |
| — | 1 (trans) | ½Mg | OCHF$_2$ | OCHF$_2$ |
| — | 1 (trans) | ½Ca | OCHF$_2$ | OCHF$_2$ |
| — | 1 (trans) | MeNH$_3$ | OCHF$_2$ | OCHF$_2$ |
| — | 1 (trans) | EtNH$_3$ | OCHF$_2$ | OCHF$_2$ |
| — | 1 (trans) | PrNH$_3$ | OCHF$_2$ | OCHF$_2$ |
| — | 1 (trans) | $^i$PrNH$_3$ | OCHF$_2$ | OCHF$_2$ |
| — | 1 (trans) | NH$_2$CONH$_3$ | OCHF$_2$ | OCHF$_2$ |
| — | 1 (trans) | Me | OCHF$_2$ | OCHF$_2$ |
| — | 1 (trans) | Et | OCHF$_2$ | OCHF$_2$ |
| — | 1 (trans) | $^i$Pr | OCHF$_2$ | OCHF$_2$ |
| — | 1 (trans) | Pr | OCHF$_2$ | OCHF$_2$ |
| — | 1 (trans) | Bu | OCHF$_2$ | OCHF$_2$ |
| — | 1 (trans) | $^i$Bu | OCHF$_2$ | OCHF$_2$ |
| — | 1 (trans) | $^s$Bu | OCHF$_2$ | OCHF$_2$ |
| — | 1 (trans) | $^t$Bu | OCHF$_2$ | OCHF$_2$ |
| — | 1 (trans) | —CH$_2$OCH$_3$ | OCHF$_2$ | OCHF$_2$ |
| — | 1 (trans) | —CH$_2$CH$_2$OCH$_3$ | OCHF$_2$ | OCHF$_2$ |
| — | 1 (trans) | —CH$_2$SCH$_3$ | OCHF$_2$ | OCHF$_2$ |
| — | 1 (trans) | —CH$_2$CH=CH$_2$ | OCHF$_2$ | OCHF$_2$ |
| — | 1 (trans) | —C(CH$_3$)$_2$CH=CH$_2$ | OCHF$_2$ | OCHF$_2$ |
| — | 1 (trans) | —CH$_2$C≡CH$_2$ | OCHF$_2$ | OCHF$_2$ |
| — | 1 (trans) | —CH$_2$C$_6$H$_5$ | OCHF$_2$ | OCHF$_2$ |
| — | 1 (trans) | —CH$_2$C$_6$H$_4$—Cl-2 | OCHF$_2$ | OCHF$_2$ |
| — | 1 (trans) | —CH$_2$C$_6$H$_4$—Cl-3 | OCHF$_2$ | OCHF$_2$ |
| — | 1 (trans) | —CH$_2$C$_6$H$_4$—Cl-4 | OCHF$_2$ | OCHF$_2$ |
| — | 1 (trans) | —CH$_2$C$_6$H$_4$—Me-2 | OCHF$_2$ | OCHF$_2$ |
| — | 1 (trans) | —CH$_2$C$_6$H$_4$—Me-3 | OCHF$_2$ | OCHF$_2$ |
| — | 1 (trans) | —CH$_2$C$_6$H$_4$—Me-4 | OCHF$_2$ | OCHF$_2$ |
| — | 1 (trans) | —CH$_2$C$_6$H$_4$—OMe-2 | OCHF$_2$ | OCHF$_2$ |
| — | 1 (trans) | —CH$_2$C$_6$H$_4$—OMe-3 | OCHF$_2$ | OCHF$_2$ |
| — | 1 (trans) | —CH$_2$C$_6$H$_4$—OMe-4 | OCHF$_2$ | OCHF$_2$ |
| — | 1 (trans) | —CH$_2$CH$_2$C$_6$H$_5$ | OCHF$_2$ | OCHF$_2$ |
| — | 1 (trans) | H | SMe | OMe |
| — | 1 (trans) | Li | SMe | OMe |
| — | 1 (trans) | Na | SMe | OMe |
| — | 1 (trans) | K | SMe | OMe |
| — | 1 (trans) | ½Mg | SMe | OMe |
| — | 1 (trans) | ½Ca | SMe | OMe |
| — | 1 (trans) | MeNH$_3$ | SMe | OMe |
| — | 1 (trans) | EtNH$_3$ | SMe | OMe |
| — | 1 (trans) | PrNH$_3$ | SMe | OMe |
| — | 1 (trans) | $^i$PrNH$_3$ | SMe | OMe |
| — | 1 (trans) | NH$_2$CONH$_3$ | SMe | OMe |
| — | 1 (trans) | Me | SMe | OMe |
| — | 1 (trans) | Et | SMe | OMe |
| — | 1 (trans) | $^i$Pr | SMe | OMe |
| — | 1 (trans) | Pr | SMe | OMe |
| — | 1 (trans) | Bu | SMe | OMe |
| — | 1 (trans) | $^i$Bu | SMe | OMe |

TABLE -continued

A compound of the general formula:

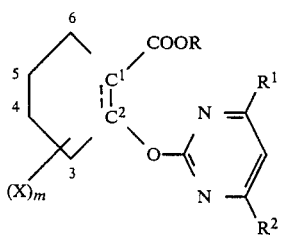

In the below-mentioned table, Me represents methyl group, Et represents ethyl group, Pr represents propyl group, $^i$Pr represents isopropyl group, Bu represents butyl group, $^i$Bu represents isobutyl group, $^s$Bu represents secondary butyl group, $^t$Bu represents tertiary butyl group, cis represents a cis-form, trans represents a trans-form, mix. represents a mixture of a cis-form and a trans-form, 1 represents a single bond and 2 represents a double bond.

| $(X)_m$ | === | R | $R^1$ | $R^2$ |
|---|---|---|---|---|
| — | 1 (trans) | $^s$Bu | SMe | OMe |
| — | 1 (trans) | $^t$Bu | SMe | OMe |
| — | 1 (trans) | —CH$_2$OCH$_3$ | SMe | OMe |
| — | 1 (trans) | —CH$_2$CH$_2$OCH$_3$ | SMe | OMe |
| — | 1 (trans) | —CH$_2$SCH$_3$ | SMe | OMe |
| — | 1 (trans) | —CH$_2$CH=CH$_2$ | SMe | OMe |
| — | 1 (trans) | —C(CH$_3$)$_2$CH=CH$_2$ | SMe | OMe |
| — | 1 (trans) | —CH$_2$C≡CH$_2$ | SMe | OMe |
| — | 1 (trans) | —CH$_2$C$_6$H$_5$ | SMe | OMe |
| — | 1 (trans) | —CH$_2$C$_6$H$_4$—Cl-2 | SMe | OMe |
| — | 1 (trans) | —CH$_2$C$_6$H$_4$—Cl-3 | SMe | OMe |
| — | 1 (trans) | —CH$_2$C$_6$H$_4$—Cl-4 | SMe | OMe |
| — | 1 (trans) | —CH$_2$C$_6$H$_4$—Me-2 | SMe | OMe |
| — | 1 (trans) | —CH$_2$C$_6$H$_4$—Me-3 | SMe | OMe |
| — | 1 (trans) | —CH$_2$C$_6$H$_4$—Me-4 | SMe | OMe |
| — | 1 (trans) | —CH$_2$C$_6$H$_4$—OMe-2 | SMe | OMe |
| — | 1 (trans) | —CH$_2$C$_6$H$_4$—OMe-3 | SMe | OMe |
| — | 1 (trans) | —CH$_2$C$_6$H$_4$—OMe-4 | SMe | OMe |
| — | 1 (trans) | —CH$_2$CH$_2$C$_6$H$_5$ | SMe | OMe |
| — | 1 (trans) | H | SMe | Me |
| — | 1 (trans) | Li | SMe | Me |
| — | 1 (trans) | Na | SMe | Me |
| — | 1 (trans) | K | SMe | Me |
| — | 1 (trans) | ½Mg | SMe | Me |
| — | 1 (trans) | ½Ca | SMe | Me |
| — | 1 (trans) | MeNH$_3$ | SMe | Me |
| — | 1 (trans) | EtNH$_3$ | SMe | Me |
| — | 1 (trans) | PrNH$_3$ | SMe | Me |
| — | 1 (trans) | $^i$PrNH$_3$ | SMe | Me |
| — | 1 (trans) | NH$_2$CONH$_3$ | SMe | Me |
| — | 1 (trans) | Me | SMe | Me |
| — | 1 (trans) | Et | SMe | Me |
| — | 1 (trans) | $^i$Pr | SMe | Me |
| — | 1 (trans) | Pr | SMe | Me |
| — | 1 (trans) | Bu | SMe | Me |
| — | 1 (trans) | $^i$Bu | SMe | Me |
| — | 1 (trans) | $^s$Bu | SMe | Me |
| — | 1 (trans) | $^t$Bu | SMe | Me |
| — | 1 (trans) | —CH$_2$OCH$_3$ | SMe | Me |
| — | 1 (trans) | —CH$_2$CH$_2$OCH$_3$ | SMe | Me |
| — | 1 (trans) | —CH$_2$SCH$_3$ | SMe | Me |
| — | 1 (trans) | —CH$_2$CH=CH$_2$ | SMe | Me |
| — | 1 (trans) | —C(CH$_3$)$_2$CH=CH$_2$ | SMe | Me |
| — | 1 (trans) | —CH$_2$C≡CH$_2$ | SMe | Me |
| — | 1 (trans) | —CH$_2$C$_6$H$_5$ | SMe | Me |
| — | 1 (trans) | —CH$_2$C$_6$H$_4$—Cl-2 | SMe | Me |
| — | 1 (trans) | —CH$_2$C$_6$H$_4$—Cl-3 | SMe | Me |
| — | 1 (trans) | —CH$_2$C$_6$H$_4$—Cl-4 | SMe | Me |
| — | 1 (trans) | —CH$_2$C$_6$H$_4$—Me-2 | SMe | Me |
| — | 1 (trans) | —CH$_2$C$_6$H$_4$—Me-3 | SMe | Me |
| — | 1 (trans) | —CH$_2$C$_6$H$_4$—Me-4 | SMe | Me |
| — | 1 (trans) | —CH$_2$C$_6$H$_4$—OMe-2 | SMe | Me |
| — | 1 (trans) | —CH$_2$C$_6$H$_4$—OMe-3 | SMe | Me |
| — | 1 (trans) | —CH$_2$C$_6$H$_4$—OMe-4 | SMe | Me |
| — | 1 (trans) | —CH$_2$CH$_2$C$_6$H$_5$ | SMe | Me |
| — | 1 (mix.) | H | Me | Me |
| — | 1 (mix.) | Li | Me | Me |

TABLE -continued

A compound of the general formula:

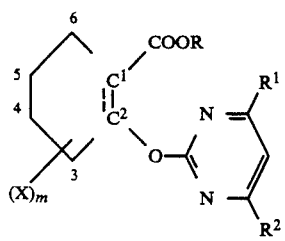

In the below-mentioned table, Me represents methyl group, Et represents ethyl group, Pr represents propyl group, $^i$Pr represents isopropyl group, Bu represents butyl group, $^i$Bu represents isobutyl group, $^s$Bu represents secondary butyl group, $^t$Bu represents tertiary butyl group, cis represents a cis-form, trans represents a trans-form, mix. represents a mixture of a cis-form and a trans-form, 1 represents a single bond and 2 represents a double bond.

| $(X)_m$ | === | R | $R^1$ | $R^2$ |
|---|---|---|---|---|
| — | 1 (mix.) | Na | Me | Me |
| — | 1 (mix.) | K | Me | Me |
| — | 1 (mix.) | ½Mg | Me | Me |
| — | 1 (mix.) | ½Ca | Me | Me |
| — | 1 (mix.) | MeNH$_3$ | Me | Me |
| — | 1 (mix.) | EtNH$_3$ | Me | Me |
| — | 1 (mix.) | PrNH$_3$ | Me | Me |
| — | 1 (mix.) | $^i$PrNH$_3$ | Me | Me |
| — | 1 (mix.) | NH$_2$CONH$_3$ | Me | Me |
| — | 1 (mix.) | Me | Me | Me |
| — | 1 (mix.) | Et | Me | Me |
| — | 1 (mix.) | $^i$Pr | Me | Me |
| — | 1 (mix.) | Pr | Me | Me |
| — | 1 (mix.) | Bu | Me | Me |
| — | 1 (mix.) | $^i$Bu | Me | Me |
| — | 1 (mix.) | $^s$Bu | Me | Me |
| — | 1 (mix.) | $^t$Bu | Me | Me |
| — | 1 (mix.) | —CH$_2$OCH$_3$ | Me | Me |
| — | 1 (mix.) | —CH$_2$CH$_2$OCH$_3$ | Me | Me |
| — | 1 (mix.) | —CH$_2$SCH$_3$ | Me | Me |
| — | 1 (mix.) | —CH$_2$CH=CH$_2$ | Me | Me |
| — | 1 (mix.) | —C(CH$_3$)$_2$CH=CH$_2$ | Me | Me |
| — | 1 (mix.) | —CH$_2$C≡CH$_2$ | Me | Me |
| — | 1 (mix.) | —CH$_2$C$_6$H$_5$ | Me | Me |
| — | 1 (mix.) | —CH$_2$C$_6$H$_4$—Cl-2 | Me | Me |
| — | 1 (mix.) | —CH$_2$C$_6$H$_4$—Cl-3 | Me | Me |
| — | 1 (mix.) | —CH$_2$C$_6$H$_4$—Cl-4 | Me | Me |
| — | 1 (mix.) | —CH$_2$C$_6$H$_4$—Me-2 | Me | Me |
| — | 1 (mix.) | —CH$_2$C$_6$H$_4$—Me-3 | Me | Me |
| — | 1 (mix.) | —CH$_2$C$_6$H$_4$—Me-4 | Me | Me |
| — | 1 (mix.) | —CH$_2$C$_6$H$_4$—OMe-2 | Me | Me |
| — | 1 (mix.) | —CH$_2$C$_6$H$_4$—OMe-3 | Me | Me |
| — | 1 (mix.) | —CH$_2$C$_6$H$_4$—OMe-4 | Me | Me |
| — | 1 (mix.) | —CH$_2$CH$_2$C$_6$H$_5$ | Me | Me |
| — | 1 (mix.) | H | OMe | Me |
| — | 1 (mix.) | Li | OMe | Me |
| — | 1 (mix.) | Na | OMe | Me |
| — | 1 (mix.) | K | OMe | Me |
| — | 1 (mix.) | ½Mg | OMe | Me |
| — | 1 (mix.) | ½Ca | OMe | Me |
| — | 1 (mix.) | MeNH$_3$ | OMe | Me |
| — | 1 (mix.) | EtNH$_3$ | OMe | Me |
| — | 1 (mix.) | PrNH$_3$ | OMe | Me |
| — | 1 (mix.) | $^i$PrNH$_3$ | OMe | Me |
| — | 1 (mix.) | NH$_2$CONH$_3$ | OMe | Me |
| — | 1 (mix.) | Me | OMe | Me |
| — | 1 (mix.) | Et | OMe | Me |
| — | 1 (mix.) | $^i$Pr | OMe | Me |
| — | 1 (mix.) | Pr | OMe | Me |
| — | 1 (mix.) | Bu | OMe | Me |
| — | 1 (mix.) | $^i$Bu | OMe | Me |
| — | 1 (mix.) | $^s$Bu | OMe | Me |
| — | 1 (mix.) | $^t$Bu | OMe | Me |
| — | 1 (mix.) | —CH$_2$OCH$_3$ | OMe | Me |
| — | 1 (mix.) | —CH$_2$CH$_2$OCH$_3$ | OMe | Me |
| — | 1 (mix.) | —CH$_2$SCH$_3$ | OMe | Me |
| — | 1 (mix.) | —CH$_2$CH=CH$_2$ | OMe | Me |

TABLE -continued

A compound of the general formula:

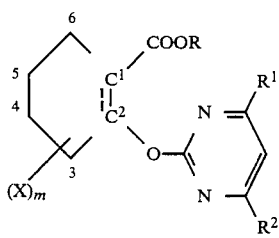

In the below-mentioned table, Me represents methyl group, Et represents ethyl group, Pr represents propyl group, $^i$Pr represents isopropyl group, Bu represents butyl group, $^i$Bu represents isobutyl group, $^s$Bu represents secondary butyl group, $^t$Bu represents tertiary butyl group, cis represents a cis-form, trans represents a trans-form, mix. represents a mixture of a cis-form and a trans-form, 1 represents a single bond and 2 represents a double bond.

| $(X)_m$ | === | R | $R^1$ | $R^2$ |
|---|---|---|---|---|
| — | 1 (mix.) | —C(CH$_3$)$_2$CH=CH$_2$ | OMe | Me |
| — | 1 (mix.) | —CH$_2$C≡CH$_2$ | OMe | Me |
| — | 1 (mix.) | —CH$_2$C$_6$H$_5$ | OMe | Me |
| — | 1 (mix.) | —CH$_2$C$_6$H$_4$—Cl-2 | OMe | Me |
| — | 1 (mix.) | —CH$_2$C$_6$H$_4$—Cl-3 | OMe | Me |
| — | 1 (mix.) | —CH$_2$C$_6$H$_4$—Cl-4 | OMe | Me |
| — | 1 (mix.) | —CH$_2$C$_6$H$_4$—Me-2 | OMe | Me |
| — | 1 (mix.) | —CH$_2$C$_6$H$_4$—Me-3 | OMe | Me |
| — | 1 (mix.) | —CH$_2$C$_6$H$_4$—Me-4 | OMe | Me |
| — | 1 (mix.) | —CH$_2$C$_6$H$_4$—OMe-2 | OMe | Me |
| — | 1 (mix.) | —CH$_2$C$_6$H$_4$—OMe-3 | OMe | Me |
| — | 1 (mix.) | —CH$_2$C$_6$H$_4$—OMe-4 | OMe | Me |
| — | 1 (mix.) | —CH$_2$CH$_2$C$_6$H$_5$ | OMe | Me |
| — | 1 (mix.) | H | OMe | OMe |
| — | 1 (mix.) | Li | OMe | OMe |
| — | 1 (mix.) | Na | OMe | OMe |
| — | 1 (mix.) | K | OMe | OMe |
| — | 1 (mix.) | ½Mg | OMe | OMe |
| — | 1 (mix.) | ½Ca | OMe | OMe |
| — | 1 (mix.) | MeNH$_3$ | OMe | OMe |
| — | 1 (mix.) | EtNH$_3$ | OMe | OMe |
| — | 1 (mix.) | PrNH$_3$ | OMe | OMe |
| — | 1 (mix.) | $^i$PrNH$_3$ | OMe | OMe |
| — | 1 (mix.) | NH$_2$CONH$_3$ | OMe | OMe |
| — | 1 (mix.) | Me | OMe | OMe |
| — | 1 (mix.) | Et | OMe | OMe |
| — | 1 (mix.) | $^i$Pr | OMe | OMe |
| — | 1 (mix.) | Pr | OMe | OMe |
| — | 1 (mix.) | Bu | OMe | OMe |
| — | 1 (mix.) | $^i$Bu | OMe | OMe |
| — | 1 (mix.) | $^s$Bu | OMe | OMe |
| — | 1 (mix.) | $^t$Bu | OMe | OMe |
| — | 1 (mix.) | —CH$_2$OCH$_3$ | OMe | OMe |
| — | 1 (mix.) | —CH$_2$CH$_2$OCH$_3$ | OMe | OMe |
| — | 1 (mix.) | —CH$_2$SCH$_3$ | OMe | OMe |
| — | 1 (mix.) | —CH$_2$CH=CH$_2$ | OMe | OMe |
| — | 1 (mix.) | —C(CH$_3$)$_2$CH=CH$_2$ | OMe | OMe |
| — | 1 (mix.) | —CH$_2$C≡CH$_2$ | OMe | OMe |
| — | 1 (mix.) | —CH$_2$C$_6$H$_5$ | OMe | OMe |
| — | 1 (mix.) | —CH$_2$C$_6$H$_4$—Cl-2 | OMe | OMe |
| — | 1 (mix.) | —CH$_2$C$_6$H$_4$—Cl-3 | OMe | OMe |
| — | 1 (mix.) | —CH$_2$C$_6$H$_4$—Cl-4 | OMe | OMe |
| — | 1 (mix.) | —CH$_2$C$_6$H$_4$—Me-2 | OMe | OMe |
| — | 1 (mix.) | —CH$_2$C$_6$H$_4$—Me-3 | OMe | OMe |
| — | 1 (mix.) | —CH$_2$C$_6$H$_4$—Me-4 | OMe | OMe |
| — | 1 (mix.) | —CH$_2$C$_6$H$_4$—OMe-2 | OMe | OMe |
| — | 1 (mix.) | —CH$_2$C$_6$H$_4$—OMe-3 | OMe | OMe |
| — | 1 (mix.) | —CH$_2$C$_6$H$_4$—OMe-4 | OMe | OMe |
| — | 1 (miX.) | —CH$_2$CH$_2$C$_6$H$_5$ | OMe | OMe |
| — | 1 (mix.) | H | Cl | Me |
| — | 1 (mix.) | Li | Cl | Me |
| — | 1 (mix.) | Na | Cl | Me |
| — | 1 (mix.) | K | Cl | Me |
| — | 1 (mix.) | ½Mg | Cl | Me |
| — | 1 (mix.) | ½Ca | Cl | Me |
| — | 1 (mix.) | MeNH$_3$ | Cl | Me |
| — | 1 (mix.) | EtNH$_3$ | Cl | Me |

TABLE -continued

A compound of the general formula:

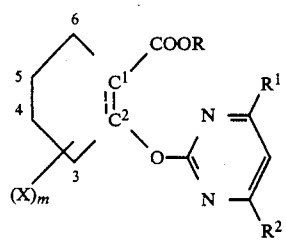

In the below-mentioned table, Me represents methyl group, Et represents ethyl group, Pr represents propyl group, $^i$Pr represents isopropyl group, Bu represents butyl group, $^i$Bu represents isobutyl group, $^s$Bu represents secondary butyl group, $^t$Bu represents tertiary butyl group, cis represents a cis-form, trans represents a trans-form, mix. represents a mixture of a cis-form and a trans-form, 1 represents a single bond and 2 represents a double bond.

| $(X)_m$ | === | R | $R^1$ | $R^2$ |
|---|---|---|---|---|
| — | 1 (mix.) | PrNH$_3$ | Cl | Me |
| — | 1 (mix.) | $^i$PrNH$_3$ | Cl | Me |
| — | 1 (mix.) | NH$_2$CONH$_3$ | Cl | Me |
| — | 1 (mix.) | Me | Cl | Me |
| — | 1 (mix.) | Et | Cl | Me |
| — | 1 (mix.) | $^i$Pr | Cl | Me |
| — | 1 (mix.) | Pr | Cl | Me |
| — | 1 (mix.) | Bu | Cl | Me |
| — | 1 (mix.) | $^i$Bu | Cl | Me |
| — | 1 (mix.) | $^s$Bu | Cl | Me |
| — | 1 (mix.) | $^t$Bu | Cl | Me |
| — | 1 (mix.) | —CH$_2$OCH$_3$ | Cl | Me |
| — | 1 (mix.) | —CH$_2$CH$_2$OCH$_3$ | Cl | Me |
| — | 1 (mix.) | —CH$_2$SCH$_3$ | Cl | Me |
| — | 1 (mix.) | —CH$_2$CH=CH$_2$ | Cl | Me |
| — | 1 (mix.) | —C(CH$_3$)$_2$CH=CH$_2$ | Cl | Me |
| — | 1 (mix.) | —CH$_2$C≡CH$_2$ | Cl | Me |
| — | 1 (mix.) | —CH$_2$C$_6$H$_5$ | Cl | Me |
| — | 1 (mix.) | —CH$_2$C$_6$H$_4$—Cl-2 | Cl | Me |
| — | 1 (mix.) | —CH$_2$C$_6$H$_4$—Cl-3 | Cl | Me |
| — | 1 (mix.) | —CH$_2$C$_6$H$_4$—Cl-4 | Cl | Me |
| — | 1 (mix.) | —CH$_2$C$_6$H$_4$—Me-2 | Cl | Me |
| — | 1 (mix.) | —CH$_2$C$_6$H$_4$—Me-3 | Cl | Me |
| — | 1 (mix.) | —CH$_2$C$_6$H$_4$—Me-4 | Cl | Me |
| — | 1 (mix.) | —CH$_2$C$_6$H$_4$—OMe-2 | Cl | Me |
| — | 1 (mix.) | —CH$_2$C$_6$H$_4$—OMe-3 | Cl | Me |
| — | 1 (mix.) | —CH$_2$C$_6$H$_4$—OMe-4 | Cl | Me |
| — | 1 (mix.) | —CH$_2$CH$_2$C$_6$H$_5$ | Cl | Me |
| — | 1 (mix.) | H | Cl | Cl |
| — | 1 (mix.) | Li | Cl | Cl |
| — | 1 (mix.) | Na | Cl | Cl |
| — | 1 (mix.) | K | Cl | Cl |
| — | 1 (mix.) | ½Mg | Cl | Cl |
| — | 1 (mix.) | ½Ca | Cl | Cl |
| — | 1 (mix.) | MeNH$_3$ | Cl | Cl |
| — | 1 (mix.) | EtNH$_3$ | Cl | Cl |
| — | 1 (mix.) | PrNH$_3$ | Cl | Cl |
| — | 1 (mix.) | $^i$PrNH$_3$ | Cl | Cl |
| — | 1 (mix.) | NH$_2$CONH$_3$ | Cl | Cl |
| — | 1 (mix.) | Me | Cl | Cl |
| — | 1 (mix.) | Et | Cl | Cl |
| — | 1 (mix.) | $^i$Pr | Cl | Cl |
| — | 1 (mix.) | Pr | Cl | Cl |
| — | 1 (mix.) | Bu | Cl | Cl |
| — | 1 (mix.) | $^i$Bu | Cl | Cl |
| — | 1 (mix.) | $^s$Bu | Cl | Cl |
| — | 1 (mix.) | $^t$Bu | Cl | Cl |
| — | 1 (mix.) | —CH$_2$OCH$_3$ | Cl | Cl |
| — | 1 (mix.) | —CH$_2$CH$_2$OCH$_3$ | Cl | Cl |
| — | 1 (mix.) | —CH$_2$SCH$_3$ | Cl | Cl |
| — | 1 (mix.) | —CH$_2$CH=CH$_2$ | Cl | Cl |
| — | 1 (mix.) | —C(CH$_3$)$_2$CH=CH$_2$ | Cl | Cl |
| — | 1 (mix.) | —CH$_2$C≡CH$_2$ | Cl | Cl |
| — | 1 (mix.) | —CH$_2$C$_6$H$_5$ | Cl | Cl |
| — | 1 (mix.) | —CH$_2$C$_6$H$_4$—Cl-2 | Cl | Cl |
| — | 1 (mix.) | —CH$_2$C$_6$H$_4$—Cl-3 | Cl | Cl |
| — | 1 (mix.) | —CH$_2$C$_6$H$_4$—Cl-4 | Cl | Cl |

TABLE -continued

A compound of the general formula:

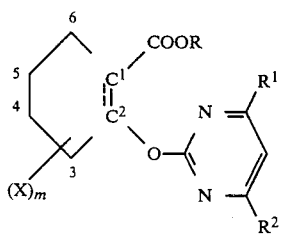

In the below-mentioned table, Me represents methyl group, Et represents ethyl group, Pr represents propyl group, $^i$Pr represents isopropyl group, Bu represents butyl group, $^i$Bu represents isobutyl group, $^s$Bu represents secondary butyl group, $^t$Bu represents tertiary butyl group, cis represents a cis-form, trans represents a trans-form, mix. represents a mixture of a cis-form and a trans-form, 1 represents a single bond and 2 represents a double bond.

| $(X)_m$ | === | R | $R^1$ | $R^2$ |
|---|---|---|---|---|
| — | 1 (mix.) | —CH$_2$C$_6$H$_4$—Me-2 | Cl | Cl |
| — | 1 (mix.) | —CH$_2$C$_6$H$_4$—Me-3 | Cl | Cl |
| — | 1 (mix.) | —CH$_2$C$_6$H$_4$—Me-4 | Cl | Cl |
| — | 1 (mix.) | —CH$_2$C$_6$H$_4$—OMe-2 | Cl | Cl |
| — | 1 (mix.) | —CH$_2$C$_6$H$_4$—OMe-3 | Cl | Cl |
| — | 1 (mix.) | —CH$_2$C$_6$H$_4$—OMe-4 | Cl | Cl |
| — | 1 (mix.) | —CH$_2$CH$_2$C$_6$H$_5$ | Cl | Cl |
| — | 1 (mix.) | H | Cl | OMe |
| — | 1 (mix.) | Li | Cl | OMe |
| — | 1 (mix.) | Na | Cl | OMe |
| — | 1 (mix.) | K | Cl | OMe |
| — | 1 (mix.) | ½Mg | Cl | OMe |
| — | 1 (mix.) | ½Ca | Cl | OMe |
| — | 1 (mix.) | MeNH$_3$ | Cl | OMe |
| — | 1 (mix.) | EtNH$_3$ | Cl | OMe |
| — | 1 (mix.) | PrNH$_3$ | Cl | OMe |
| — | 1 (mix.) | $^i$PrNH$_3$ | Cl | OMe |
| — | 1 (mix.) | NH$_2$CONH$_3$ | Cl | OMe |
| — | 1 (mix.) | Me | Cl | OMe |
| — | 1 (mix.) | Et | Cl | OMe |
| — | 1 (mix.) | $^i$Pr | Cl | OMe |
| — | 1 (mix.) | Pr | Cl | OMe |
| — | 1 (mix.) | Bu | Cl | OMe |
| — | 1 (mix.) | $^i$Bu | Cl | OMe |
| — | 1 (mix.) | $^s$Bu | Cl | OMe |
| — | 1 (mix.) | $^t$Bu | Cl | OMe |
| — | 1 (mix.) | —CH$_2$OCH$_3$ | Cl | OMe |
| — | 1 (mix.) | —CH$_2$CH$_2$OCH$_3$ | Cl | OMe |
| — | 1 (mix.) | —CH$_2$SCH$_3$ | Cl | OMe |
| — | 1 (mix.) | —CH$_2$CH=CH$_2$ | Cl | OMe |
| — | 1 (mix.) | —C(CH$_3$)$_2$CH=CH$_2$ | Cl | OMe |
| — | 1 (mix.) | —CH$_2$C≡CH$_2$ | Cl | OMe |
| — | 1 (mix.) | —CH$_2$C$_6$H$_5$ | Cl | OMe |
| — | 1 (mix.) | —CH$_2$C$_6$H$_4$—Cl-2 | Cl | OMe |
| — | 1 (mix.) | —CH$_2$C$_6$H$_4$—Cl-3 | Cl | OMe |
| — | 1 (mix.) | —CH$_2$C$_6$H$_4$—Cl-4 | Cl | OMe |
| — | 1 (mix.) | —CH$_2$C$_6$H$_4$—Me-2 | Cl | OMe |
| — | 1 (mix.) | —CH$_2$C$_6$H$_4$—Me-3 | Cl | OMe |
| — | 1 (mix.) | —CH$_2$C$_6$H$_4$—Me-4 | Cl | OMe |
| — | 1 (mix.) | —CH$_2$C$_6$H$_4$—OMe-2 | Cl | OMe |
| — | 1 (mix.) | —CH$_2$C$_6$H$_4$—OMe-3 | Cl | OMe |
| — | 1 (mix.) | —CH$_2$C$_6$H$_4$—OMe-4 | Cl | OMe |
| — | 1 (mix.) | —CH$_2$CH$_2$C$_6$H$_5$ | Cl | OMe |
| — | 1 (mix.) | H | OCHF$_2$ | OMe |
| — | 1 (mix.) | Li | OCHF$_2$ | OMe |
| — | 1 (mix.) | Na | OCHF$_2$ | OMe |
| — | 1 (mix.) | K | OCHF$_2$ | OMe |
| — | 1 (mix.) | ½Mg | OCHF$_2$ | OMe |
| — | 1 (mix.) | ½Ca | OCHF$_2$ | OMe |
| — | 1 (mix.) | MeNH$_3$ | OCHF$_2$ | OMe |
| — | 1 (mix.) | EtNH$_3$ | OCHF$_2$ | OMe |
| — | 1 (mix.) | PrNH$_3$ | OCHF$_2$ | OMe |
| — | 1 (mix.) | $^i$PrNH$_3$ | OCHF$_2$ | OMe |
| — | 1 (mix.) | NH$_2$CONH$_3$ | OCHF$_3$ | OMe |
| — | 1 (mix.) | Me | OCHF$_2$ | OMe |
| — | 1 (mix.) | Et | OCHF$_2$ | OMe |
| — | 1 (mix.) | $^i$Pr | OCHF$_2$ | OMe |

TABLE -continued

A compound of the general formula:

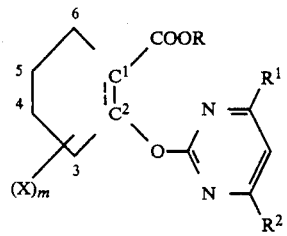

In the below-mentioned table, Me represents methyl group, Et represents ethyl group, Pr represents propyl group, $^i$Pr represents isopropyl group, Bu represents butyl group, $^i$Bu represents isobutyl group, $^s$Bu represents secondary butyl group, $^t$Bu represents tertiary butyl group, cis represents a cis-form, trans represents a trans-form, mix. represents a mixture of a cis-form and a trans-form, 1 represents a single bond and 2 represents a double bond.

| $(X)_m$ | === | R | $R^1$ | $R^2$ |
|---|---|---|---|---|
| — | 1 (mix.) | Pr | $OCHF_2$ | OMe |
| — | 1 (mix.) | Bu | $OCHF_2$ | OMe |
| — | 1 (mix.) | $^i$Bu | $OCHF_2$ | OMe |
| — | 1 (mix.) | $^s$Bu | $OCHF_2$ | OMe |
| — | 1 (mix.) | $^t$Bu | $OCHF_2$ | OMe |
| — | 1 (mix.) | $-CH_2OCH_3$ | $OCHF_2$ | OMe |
| — | 1 (mix.) | $-CH_2CH_2OCH_3$ | $OCHF_2$ | OMe |
| — | 1 (mix.) | $-CH_2SCH_3$ | $OCHF_2$ | OMe |
| — | 1 (mix.) | $-CH_2CH=CH_2$ | $OCHF_2$ | OMe |
| — | 1 (mix.) | $-C(CH_3)_2CH=CH_2$ | $OCHF_2$ | OMe |
| — | 1 (mix.) | $-CH_2C\equiv CH_2$ | $OCHF_2$ | OMe |
| — | 1 (mix.) | $-CH_2C_6H_5$ | $OCHF_2$ | OMe |
| — | 1 (mix.) | $-CH_2C_6H_4-Cl-2$ | $OCHF_2$ | OMe |
| — | 1 (mix.) | $-CH_2C_6H_4-Cl-3$ | $OCHF_2$ | OMe |
| — | 1 (mix.) | $-CH_2C_6H_4-Cl-4$ | $OCHF_2$ | OMe |
| — | 1 (mix.) | $-CH_2C_6H_4-Me-2$ | $OCHF_2$ | OMe |
| — | 1 (mix.) | $-CH_2C_6H_4-Me-3$ | $OCHF_2$ | OMe |
| — | 1 (mix.) | $-CH_2C_6H_4-Me-4$ | $OCHF_2$ | OMe |
| — | 1 (mix.) | $-CH_2C_6H_4-OMe-2$ | $OCHF_2$ | OMe |
| — | 1 (mix.) | $-CH_2C_6H_4-OMe-3$ | $OCHF_2$ | OMe |
| — | 1 (mix.) | $-CH_2C_6H_4-OMe-4$ | $OCHF_2$ | OMe |
| — | 1 (mix.) | $-CH_2CH_2C_6H_5$ | $OCHF_2$ | OMe |
| — | 1 (mix.) | H | $OCHF_2$ | $OCHF_2$ |
| — | 1 (mix.) | Li | $OCHF_2$ | $OCHF_2$ |
| — | 1 (mix.) | Na | $OCHF_2$ | $OCHF_2$ |
| — | 1 (mix.) | K | $OCHF_2$ | $OCHF_2$ |
| — | 1 (mix.) | ½Mg | $OCHF_2$ | $OCHF_2$ |
| — | 1 (mix.) | ½Ca | $OCHF_2$ | $OCHF_2$ |
| — | 1 (mix.) | $MeNH_3$ | $OCHF_2$ | $OCHF_2$ |
| — | 1 (mix.) | $EtNH_3$ | $OCHF_2$ | $OCHF_2$ |
| — | 1 (mix.) | $PrNH_3$ | $OCHF_2$ | $OCHF_2$ |
| — | 1 (mix.) | $^iPrNH_3$ | $OCHF_2$ | $OCHF_2$ |
| — | 1 (mix.) | $NH_2CONH_3$ | $OCHF_2$ | $OCHF_2$ |
| — | 1 (mix.) | Me | $OCHF_2$ | $OCHF_2$ |
| — | 1 (mix.) | Et | $OCHF_2$ | $OCHF_2$ |
| — | 1 (mix.) | $^i$Pr | $OCHF_2$ | $OCHF_2$ |
| — | 1 (mix.) | Pr | $OCHF_2$ | $OCHF_2$ |
| — | 1 (mix.) | Bu | $OCHF_2$ | $OCHF_2$ |
| — | 1 (mix.) | $^i$Bu | $OCHF_2$ | $OCHF_2$ |
| — | 1 (mix.) | $^s$Bu | $OCHF_2$ | $OCHF_2$ |
| — | 1 (mix.) | $^t$Bu | $OCHF_2$ | $OCHF_2$ |
| — | 1 (mix.) | $-CH_2OCH_3$ | $OCHF_2$ | $OCHF_2$ |
| — | 1 (mix.) | $-CH_2CH_2OCH_3$ | $OCHF_2$ | $OCHF_2$ |
| — | 1 (mix.) | $-CH_2SCH_3$ | $OCHF_2$ | $OCHF_2$ |
| — | 1 (mix.) | $-CH_2CH=CH_2$ | $OCHF_2$ | $OCHF_2$ |
| — | 1 (mix.) | $-C(CH_3)_2CH=CH_2$ | $OCHF_2$ | $OCHF_2$ |
| — | 1 (mix.) | $-CH_2C\equiv CH_2$ | $OCHF_2$ | $OCHF_2$ |
| — | 1 (mix.) | $-CH_2C_6H_5$ | $OCHF_2$ | $OCHF_2$ |
| — | 1 (mix.) | $-CH_2C_6H_4-Cl-2$ | $OCHF_2$ | $OCHF_2$ |
| — | 1 (mix.) | $-CH_2C_6H_4-Cl-3$ | $OCHF_2$ | $OCHF_2$ |
| — | 1 (mix.) | $-CH_2C_6H_4-Cl-4$ | $OCHF_2$ | $OCHF_2$ |
| — | 1 (mix.) | $-CH_2C_6H_4-Me-2$ | $OCHF_2$ | $OCHF_2$ |
| — | 1 (mix.) | $-CH_2C_6H_4-Me-3$ | $OCHF_2$ | $OCHF_2$ |
| — | 1 (mix.) | $-CH_2C_6H_4-Me-4$ | $OCHF_2$ | $OCHF_2$ |
| — | 1 (mix.) | $-CH_2C_6H_4-OMe-2$ | $OCHF_2$ | $OCHF_2$ |
| — | 1 (mix.) | $-CH_2C_6H_4-OMe-3$ | $OCHF_2$ | $OCHF_2$ |
| — | 1 (mix.) | $-CH_2C_6H_4-OMe-4$ | $OCHF_2$ | $OCHF_2$ |

TABLE -continued

A compound of the general formula:

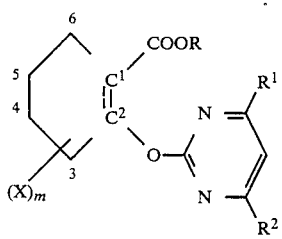

In the below-mentioned table, Me represents methyl group, Et represents ethyl group, Pr represents propyl group, $^i$Pr represents isopropyl group, Bu represents butyl group, $^i$Bu represents isobutyl group, $^s$Bu represents secondary butyl group, $^t$Bu represents tertiary butyl group, cis represents a cis-form, trans represents a trans-form, mix. represents a mixture of a cis-form and a trans-form, 1 represents a single bond and 2 represents a double bond.

| $(X)_m$ | === | R | $R^1$ | $R^2$ |
|---|---|---|---|---|
| — | 1 (mix.) | —CH$_2$CH$_2$C$_6$H$_5$ | OCHF$_2$ | OCHF$_2$ |
| — | 1 (mix.) | H | SMe | OMe |
| — | 1 (mix.) | Li | SMe | OMe |
| — | 1 (mix.) | Na | SMe | OMe |
| — | 1 (mix.) | K | SMe | OMe |
| — | 1 (mix.) | ½Mg | SMe | OMe |
| — | 1 (mix.) | ½Ca | SMe | OMe |
| — | 1 (mix.) | MeNH$_3$ | SMe | OMe |
| — | 1 (mix.) | EtNH$_3$ | SMe | OMe |
| — | 1 (mix.) | PrNH$_3$ | SMe | OMe |
| — | 1 (mix.) | $^i$PrNH$_3$ | SMe | OMe |
| — | 1 (mix.) | NH$_2$CONH$_3$ | SMe | OMe |
| — | 1 (mix.) | Me | SMe | OMe |
| — | 1 (mix.) | Et | SMe | OMe |
| — | 1 (mix.) | $^i$Pr | SMe | OMe |
| — | 1 (mix.) | Pr | SMe | OMe |
| — | 1 (mix.) | Bu | SMe | OMe |
| — | 1 (mix.) | $^i$Bu | SMe | OMe |
| — | 1 (mix.) | $^s$Bu | SMe | OMe |
| — | 1 (mix.) | $^t$Bu | SMe | OMe |
| — | 1 (mix.) | —CH$_2$OCH$_3$ | SMe | OMe |
| — | 1 (mix.) | —CH$_2$CH$_2$OCH$_3$ | SMe | OMe |
| — | 1 (mix.) | —CH$_2$SCH$_3$ | SMe | OMe |
| — | 1 (mix.) | —CH$_2$CH=CH$_2$ | SMe | OMe |
| — | 1 (mix.) | —C(CH$_3$)$_2$CH=CH$_2$ | SMe | OMe |
| — | 1 (mix.) | —CH$_2$C≡CH$_2$ | SMe | OMe |
| — | 1 (mix.) | —CH$_2$C$_6$H$_5$ | SMe | OMe |
| — | 1 (mix.) | —CH$_2$C$_6$H$_4$—Cl-2 | SMe | OMe |
| — | 1 (mix.) | —CH$_2$C$_6$H$_4$—Cl-3 | SMe | OMe |
| — | 1 (mix.) | —CH$_2$C$_6$H$_4$—Cl-4 | SMe | OMe |
| — | 1 (mix.) | —CH$_2$C$_6$H$_4$—Me-2 | SMe | OMe |
| — | 1 (mix.) | —CH$_2$C$_6$H$_4$—Me-3 | SMe | OMe |
| — | 1 (mix.) | —CH$_2$C$_6$H$_4$—Me-4 | SMe | OMe |
| — | 1 (mix.) | —CH$_2$C$_6$H$_4$—OMe-2 | SMe | OMe |
| — | 1 (mix.) | —CH$_2$C$_6$H$_4$—OMe-3 | SMe | OMe |
| — | 1 (mix.) | —CH$_2$C$_6$H$_4$—OMe-4 | SMe | OMe |
| — | 1 (mix.) | —CH$_2$CH$_2$C$_6$H$_5$ | SMe | OMe |
| — | 1 (mix.) | H | SMe | Me |
| — | 1 (mix.) | Li | SMe | Me |
| — | 1 (mix.) | Na | SMe | Me |
| — | 1 (mix.) | K | SMe | Me |
| — | 1 (mix.) | ½Mg | SMe | Me |
| — | 1 (mix.) | ½Ca | SMe | Me |
| — | 1 (mix.) | MeNH$_3$ | SMe | Me |
| — | 1 (mix.) | EtNH$_3$ | SMe | Me |
| — | 1 (mix.) | PrNH$_3$ | SMe | Me |
| — | 1 (mix.) | $^i$PrNH$_3$ | SMe | Me |
| — | 1 (mix.) | NH$_2$CONH$_3$ | SMe | Me |
| — | 1 (mix.) | Me | SMe | Me |
| — | 1 (mix.) | Et | SMe | Me |
| — | 1 (mix.) | $^i$Pr | SMe | Me |
| — | 1 (mix.) | Pr | SMe | Me |
| — | 1 (mix.) | Bu | SMe | Me |
| — | 1 (mix.) | $^i$Bu | SMe | Me |
| — | 1 (mix.) | $^s$Bu | SMe | Me |
| — | 1 (mix.) | $^t$Bu | SMe | Me |
| — | 1 (mix.) | —CH$_2$OCH$_3$ | SMe | Me |

TABLE -continued

A compound of the general formula:

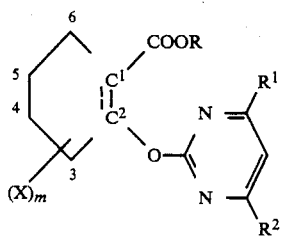

In the below-mentioned table, Me represents methyl group, Et represents ethyl group, Pr represents propyl group, $^i$Pr represents isopropyl group, Bu represents butyl group, $^i$Bu represents isobutyl group, $^s$Bu represents secondary butyl group, $^t$Bu represents tertiary butyl group, cis represents a cis-form, trans represents a trans-form, mix. represents a mixture of a cis-form and a trans-form, 1 represents a single bond and 2 represents a double bond.

| $(X)_m$ | === | R | $R^1$ | $R^2$ |
|---|---|---|---|---|
| — | 1 (mix.) | —CH$_2$CH$_2$OCH$_3$ | SMe | Me |
| — | 1 (mix.) | —CH$_2$SCH$_3$ | SMe | Me |
| — | 1 (mix.) | —CH$_2$CH=CH$_2$ | SMe | Me |
| — | 1 (mix.) | —C(CH$_3$)$_2$CH=CH$_2$ | SMe | Me |
| — | 1 (mix.) | —CH$_2$C≡CH$_2$ | SMe | Me |
| — | 1 (mix.) | —CH$_2$C$_6$H$_5$ | SMe | Me |
| — | 1 (mix.) | —CH$_2$C$_6$H$_4$—Cl-2 | SMe | Me |
| — | 1 (mix.) | —CH$_2$C$_6$H$_4$—Cl-3 | SMe | Me |
| — | 1 (mix.) | —CH$_2$C$_6$H$_4$—Cl-4 | SMe | Me |
| — | 1 (mix.) | —CH$_2$C$_6$H$_4$—Me-2 | SMe | Me |
| — | 1 (mix.) | —CH$_2$C$_6$H$_4$—Me-3 | SMe | Me |
| — | 1 (mix.) | —CH$_2$C$_6$H$_4$—Me-4 | SMe | Me |
| — | 1 (mix.) | —CH$_2$C$_6$H$_4$—OMe-2 | SMe | Me |
| — | 1 (mix.) | —CH$_2$C$_6$H$_4$—OMe-3 | SMe | Me |
| — | 1 (mix.) | —CH$_2$C$_6$H$_4$—OMe-4 | SMe | Me |
| — | 1 (mix.) | —CH$_2$CH$_2$C$_6$H$_5$ | SMe | Me |
| — | 2 (—) | H | Me | Me |
| — | 2 (—) | Li | Me | Me |
| — | 2 (—) | Na | Me | Me |
| — | 2 (—) | K | Me | Me |
| — | 2 (—) | ½Mg | Me | Me |
| — | 2 (—) | ½Ca | Me | Me |
| — | 2 (—) | MeNH$_3$ | Me | Me |
| — | 2 (—) | EtNH$_3$ | Me | Me |
| — | 2 (—) | PrNH$_3$ | Me | Me |
| — | 2 (—) | $^i$PrNH$_3$ | Me | Me |
| — | 2 (—) | NH$_2$CONH$_3$ | Me | Me |
| — | 2 (—) | Me | Me | Me |
| — | 2 (—) | Et | Me | Me |
| — | 2 (—) | $^i$Pr | Me | Me |
| — | 2 (—) | Pr | Me | Me |
| — | 2 (—) | Bu | Me | Me |
| — | 2 (—) | $^i$Bu | Me | Me |
| — | 2 (—) | $^s$Bu | Me | Me |
| — | 2 (—) | $^t$Bu | Me | Me |
| — | 2 (—) | —CH$_2$OCH$_3$ | Me | Me |
| — | 2 (—) | —CH$_2$CH$_2$OCH$_3$ | Me | Me |
| — | 2 (—) | —CH$_2$SCH$_3$ | Me | Me |
| — | 2 (—) | —CH$_2$CH=CH$_2$ | Me | Me |
| — | 2 (—) | —C(CH$_3$)$_2$CH=CH$_2$ | Me | Me |
| — | 2 (—) | —CH$_2$C≡CH$_2$ | Me | Me |
| — | 2 (—) | —CH$_2$C$_6$H$_5$ | Me | Me |
| — | 2 (—) | —CH$_2$C$_6$H$_4$—Cl-2 | Me | Me |
| — | 2 (—) | —CH$_2$C$_6$H$_4$—Cl-3 | Me | Me |
| — | 2 (—) | —CH$_2$C$_6$H$_4$—Cl-4 | Me | Me |
| — | 2 (—) | —CH$_2$C$_6$H$_4$—Me-2 | Me | Me |
| — | 2 (—) | —CH$_2$C$_6$H$_4$—Me-3 | Me | Me |
| — | 2 (—) | —CH$_2$C$_6$H$_4$—Me-4 | Me | Me |
| — | 2 (—) | —CH$_2$C$_6$H$_4$—OMe-2 | Me | Me |
| — | 2 (—) | —CH$_2$C$_6$H$_4$—OMe-3 | Me | Me |
| — | 2 (—) | —CH$_2$C$_6$H$_4$—OMe-4 | Me | Me |
| — | 2 (—) | —CH$_2$CH$_2$C$_6$H$_5$ | Me | Me |
| — | 2 (—) | H | OMe | Me |
| — | 2 (—) | Li | OMe | Me |
| — | 2 (—) | Na | OMe | Me |
| — | 2 (—) | K | OMe | Me |
| — | 2 (—) | ½Mg | OMe | Me |

TABLE -continued

A compound of the general formula:

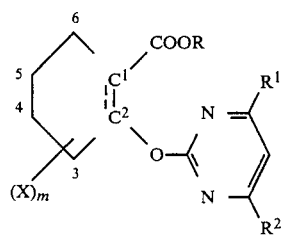

In the below-mentioned table, Me represents methyl group, Et represents ethyl group, Pr represents propyl group, $^i$Pr represents isopropyl group, Bu represents butyl group, $^i$Bu represents isobutyl group, $^s$Bu represents secondary butyl group, $^t$Bu represents tertiary butyl group, cis represents a cis-form, trans represents a trans-form, mix. represents a mixture of a cis-form and a trans-form, 1 represents a single bond and 2 represents a double bond.

| $(X)_m$ | === | R | $R^1$ | $R^2$ |
|---|---|---|---|---|
| — | 2 (—) | ½Ca | OMe | Me |
| — | 2 (—) | MeNH$_3$ | OMe | Me |
| — | 2 (—) | EtNH$_3$ | OMe | Me |
| — | 2 (—) | PrNH$_3$ | OMe | Me |
| — | 2 (—) | $^i$PrNH$_3$ | OMe | Me |
| — | 2 (—) | NH$_2$CONH$_3$ | OMe | Me |
| — | 2 (—) | Me | OMe | Me |
| — | 2 (—) | Et | OMe | Me |
| — | 2 (—) | $^i$Pr | OMe | Me |
| — | 2 (—) | Pr | OMe | Me |
| — | 2 (—) | Bu | OMe | Me |
| — | 2 (—) | $^i$Bu | OMe | Me |
| — | 2 (—) | $^s$Bu | OMe | Me |
| — | 2 (—) | $^t$Bu | OMe | Me |
| — | 2 (—) | —CH$_2$OCH$_3$ | OMe | Me |
| — | 2 (—) | —CH$_2$CH$_2$OCH$_3$ | OMe | Me |
| — | 2 (—) | —CH$_2$SCH$_3$ | OMe | Me |
| — | 2 (—) | —CH$_2$CH=CH$_2$ | OMe | Me |
| — | 2 (—) | —C(CH$_3$)$_2$CH=CH$_2$ | OMe | Me |
| — | 2 (—) | —CH$_2$C≡CH$_2$ | OMe | Me |
| — | 2 (—) | —CH$_2$C$_6$H$_5$ | OMe | Me |
| — | 2 (—) | —CH$_2$C$_6$H$_4$—Cl-2 | OMe | Me |
| — | 2 (—) | —CH$_2$C$_6$H$_4$—Cl-3 | OMe | Me |
| — | 2 (—) | —CH$_2$C$_6$H$_4$—Cl-4 | OMe | Me |
| — | 2 (—) | —CH$_2$C$_6$H$_4$—Me-2 | OMe | Me |
| — | 2 (—) | —CH$_2$C$_6$H$_4$—Me-3 | OMe | Me |
| — | 2 (—) | —CH$_2$C$_6$H$_4$—Me-4 | OMe | Me |
| — | 2 (—) | —CH$_2$C$_6$H$_4$—OMe-2 | OMe | Me |
| — | 2 (—) | —CH$_2$C$_6$H$_4$—OMe-3 | OMe | Me |
| — | 2 (—) | —CH$_2$C$_6$H$_4$—OMe-4 | OMe | Me |
| — | 2 (—) | —CH$_2$CH$_2$C$_6$H$_5$ | OMe | Me |
| — | 2 (—) | H | OMe | OMe |
| — | 2 (—) | Li | OMe | OMe |
| — | 2 (—) | Na | OMe | OMe |
| — | 2 (—) | K | OMe | OMe |
| — | 2 (—) | ½Mg | OMe | OMe |
| — | 2 (—) | ½Ca | OMe | OMe |
| — | 2 (—) | MeNH$_3$ | OMe | OMe |
| — | 2 (—) | EtNH$_3$ | OMe | OMe |
| — | 2 (—) | PrNH$_3$ | OMe | OMe |
| — | 2 (—) | $^i$PrNH$_3$ | OMe | OMe |
| — | 2 (—) | NH$_2$CONH$_3$ | OMe | OMe |
| — | 2 (—) | Me | OMe | OMe |
| — | 2 (—) | Et | OMe | OMe |
| — | 2 (—) | $^i$Pr | OMe | OMe |
| — | 2 (—) | Pr | OMe | OMe |
| — | 2 (—) | Bu | OMe | OMe |
| — | 2 (—) | $^i$Bu | OMe | OMe |
| — | 2 (—) | $^s$Bu | OMe | OMe |
| — | 2 (—) | $^t$Bu | OMe | OMe |
| — | 2 (—) | —CH$_2$OCH$_3$ | OMe | OMe |
| — | 2 (—) | —CH$_2$CH$_2$OCH$_3$ | OMe | OMe |
| — | 2 (—) | —CH$_2$SCH$_3$ | OMe | OMe |

The compound No. 3 of the present invention. 

TABLE -continued

A compound of the general formula:

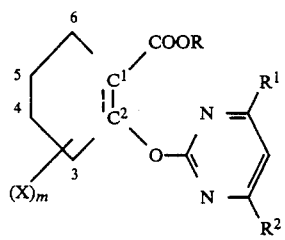

In the below-mentioned table, Me represents methyl group, Et represents ethyl group, Pr represents propyl group, $^i$Pr represents isopropyl group, Bu represents butyl group, $^i$Bu represents isobutyl group, $^s$Bu represents secondary butyl group, $^t$Bu represents tertiary butyl group, cis represents a cis-form, trans represents a trans-form, mix. represents a mixture of a cis-form and a trans-form, 1 represents a single bond and 2 represents a double bond.

| $(X)_m$ | === | R | $R^1$ | $R^2$ |
|---|---|---|---|---|
| — | 2 (—) | —CH$_2$CH=CH$_2$ | OMe | OMe |
| — | 2 (—) | —C(CH$_3$)$_2$CH=CH$_2$ | OMe | OMe |
| — | 2 (—) | —CH$_2$C≡CH$_2$ | OMe | OMe |
| — | 2 (—) | —CH$_2$C$_6$H$_5$ | OMe | OMe |
| — | 2 (—) | —CH$_2$C$_6$H$_4$—Cl-2 | OMe | OMe |
| — | 2 (—) | —CH$_2$C$_6$H$_4$—Cl-3 | OMe | OMe |
| — | 2 (—) | —CH$_2$C$_6$H$_4$—Cl-4 | OMe | OMe |
| — | 2 (—) | —CH$_2$C$_6$H$_4$—Me-2 | OMe | OMe |
| — | 2 (—) | —CH$_2$C$_6$H$_4$—Me-3 | OMe | OMe |
| — | 2 (—) | —CH$_2$C$_6$H$_4$—Me-4 | OMe | OMe |
| — | 2 (—) | —CH$_2$C$_6$H$_4$—OMe-2 | OMe | OMe |
| — | 2 (—) | —CH$_2$C$_6$H$_4$—OMe-3 | OMe | OMe |
| — | 2 (—) | —CH$_2$C$_6$H$_4$—OMe-4 | OMe | OMe |
| — | 2 (—) | —CH$_2$CH$_2$C$_6$H$_5$ | OMe | OMe |
| — | 2 (—) | H | Cl | Me |
| — | 2 (—) | Li | Cl | Me |
| — | 2 (—) | Na | Cl | Me |
| — | 2 (—) | K | Cl | Me |
| — | 2 (—) | ½Mg | Cl | Me |
| — | 2 (—) | ½Ca | Cl | Me |
| — | 2 (—) | MeNH$_3$ | Cl | Me |
| — | 2 (—) | EtNH$_3$ | Cl | Me |
| — | 2 (—) | PrNH$_3$ | Cl | Me |
| — | 2 (—) | $^i$PrNH$_3$ | Cl | Me |
| — | 2 (—) | NH$_2$CONH$_3$ | Cl | Me |
| — | 2 (—) | Me | Cl | Me |
| — | 2 (—) | Et | Cl | Me |
| — | 2 (—) | $^i$Pr | Cl | Me |
| — | 2 (—) | Pr | Cl | Me |
| — | 2 (—) | Bu | Cl | Me |
| — | 2 (—) | $^i$Bu | Cl | Me |
| — | 2 (—) | $^s$Bu | Cl | Me |
| — | 2 (—) | $^t$Bu | Cl | Me |
| — | 2 (—) | —CH$_2$OCH$_3$ | Cl | Me |
| — | 2 (—) | —CH$_2$CH$_2$OCH$_3$ | Cl | Me |
| — | 2 (—) | —CH$_2$SCH$_3$ | Cl | Me |
| — | 2 (—) | —CH$_2$CH=CH$_2$ | Cl | Me |
| — | 2 (—) | —C(CH$_3$)$_2$CH=CH$_2$ | Cl | Me |
| — | 2 (—) | —CH$_2$C≡CH$_2$ | Cl | Me |
| — | 2 (—) | —CH$_2$C$_6$H$_5$ | Cl | Me |
| — | 2 (—) | —CH$_2$C$_6$H$_4$—Cl-2 | Cl | Me |
| — | 2 (—) | —CH$_2$C$_6$H$_4$—Cl-3 | Cl | Me |
| — | 2 (—) | —CH$_2$C$_6$H$_4$—Cl-4 | Cl | Me |
| — | 2 (—) | —CH$_2$C$_6$H$_4$—Me-2 | Cl | Me |
| — | 2 (—) | —CH$_2$C$_6$H$_4$—Me-3 | Cl | Me |
| — | 2 (—) | —CH$_2$C$_6$H$_4$—Me-4 | Cl | Me |
| — | 2 (—) | —CH$_2$C$_6$H$_4$—OMe-2 | Cl | Me |
| — | 2 (—) | —CH$_2$C$_6$H$_4$—OMe-3 | Cl | Me |
| — | 2 (—) | —CH$_2$C$_6$H$_4$—OMe-4 | Cl | Me |
| — | 2 (—) | —CH$_2$CH$_2$C$_6$H$_5$ | Cl | Me |
| — | 2 (—) | H | Cl | Cl |
| — | 2 (—) | Li | Cl | Cl |
| — | 2 (—) | Na | Cl | Cl |
| — | 2 (—) | K | Cl | Cl |
| — | 2 (—) | ½Mg | Cl | Cl |
| — | 2 (—) | ½Ca | Cl | Cl |
| — | 2 (—) | MeNH$_3$ | Cl | Cl |

TABLE -continued

A compound of the general formula:

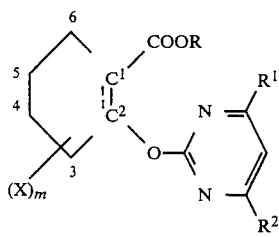

In the below-mentioned table, Me represents methyl group, Et represents ethyl group, Pr represents propyl group, $^i$Pr represents isopropyl group, Bu represents butyl group, $^i$Bu represents isobutyl group, $^s$Bu represents secondary butyl group, $^t$Bu represents tertiary butyl group, cis represents a cis-form, trans represents a trans-form, mix. represents a mixture of a cis-form and a trans-form, 1 represents a single bond and 2 represents a double bond.

| $(X)_m$ | === | R | $R^1$ | $R^2$ |
|---|---|---|---|---|
| — | 2 (—) | EtNH$_3$ | Cl | Cl |
| — | 2 (—) | PrNH$_3$ | Cl | Cl |
| — | 2 (—) | $^i$PrNH$_3$ | Cl | Cl |
| — | 2 (—) | NH$_2$CONH$_3$ | Cl | Cl |
| — | 2 (—) | Me | Cl | Cl |
| — | 2 (—) | Et | Cl | Cl |
| — | 2 (—) | $^i$Pr | Cl | Cl |
| — | 2 (—) | Pr | Cl | Cl |
| — | 2 (—) | Bu | Cl | Cl |
| — | 2 (—) | $^i$Bu | Cl | Cl |
| — | 2 (—) | $^s$Bu | Cl | Cl |
| — | 2 (—) | $^t$Bu | Cl | Cl |
| — | 2 (—) | —CH$_2$OCH$_3$ | Cl | Cl |
| — | 2 (—) | —CH$_2$CH$_2$OCH$_3$ | Cl | Cl |
| — | 2 (—) | —CH$_2$SCH$_3$ | Cl | Cl |
| — | 2 (—) | —CH$_2$CH=CH$_2$ | Cl | Cl |
| — | 2 (—) | —C(CH$_3$)$_2$CH=CH$_2$ | Cl | Cl |
| — | 2 (—) | —CH$_2$C≡CH$_2$ | Cl | Cl |
| — | 2 (—) | —CH$_2$C$_6$H$_5$ | Cl | Cl |
| — | 2 (—) | —CH$_2$C$_6$H$_4$—Cl-2 | Cl | Cl |
| — | 2 (—) | —CH$_2$C$_6$H$_4$—Cl-3 | Cl | Cl |
| — | 2 (—) | —CH$_2$C$_6$H$_4$—Cl-4 | Cl | Cl |
| — | 2 (—) | —CH$_2$C$_6$H$_4$—Me-2 | Cl | Cl |
| — | 2 (—) | —CH$_2$C$_6$H$_4$—Me-3 | Cl | Cl |
| — | 2 (—) | —CH$_2$C$_6$H$_4$—Me-4 | Cl | Cl |
| — | 2 (—) | —CH$_2$C$_6$H$_4$—OMe-2 | Cl | Cl |
| — | 2 (—) | —CH$_2$C$_6$H$_4$—OMe-3 | Cl | Cl |
| — | 2 (—) | —CH$_2$C$_6$H$_4$—OMe-4 | Cl | Cl |
| — | 2 (—) | —CH$_2$CH$_2$C$_6$H$_5$ | Cl | Cl |
| — | 2 (—) | H | Cl | OMe |
| — | 2 (—) | Li | Cl | OMe |
| — | 2 (—) | Na | Cl | OMe |
| — | 2 (—) | K | Cl | OMe |
| — | 2 (—) | ½Mg | Cl | OMe |
| — | 2 (—) | ½Ca | Cl | OMe |
| — | 2 (—) | MeNH$_3$ | Cl | OMe |
| — | 2 (—) | EtNH$_3$ | Cl | OMe |
| — | 2 (—) | PrNH$_3$ | Cl | OMe |
| — | 2 (—) | $^i$PrNH$_3$ | Cl | OMe |
| — | 2 (—) | NH$_2$CONH$_3$ | Cl | OMe |
| — | 2 (—) | Me | Cl | OMe |
| — | 2 (—) | Et | Cl | OMe |
| — | 2 (—) | $^i$Pr | Cl | OMe |
| — | 2 (—) | Pr | Cl | OMe |
| — | 2 (—) | Bu | Cl | OMe |
| — | 2 (—) | $^i$Bu | Cl | OMe |
| — | 2 (—) | $^s$Bu | Cl | OMe |
| — | 2 (—) | $^t$Bu | Cl | OMe |
| — | 2 (—) | —CH$_2$OCH$_3$ | Cl | OMe |
| — | 2 (—) | —CH$_2$CH$_2$OCH$_3$ | Cl | OMe |
| — | 2 (—) | —CH$_2$SCH$_3$ | Cl | OMe |
| — | 2 (—) | —CH$_2$CH=CH$_2$ | Cl | OMe |
| — | 2 (—) | —C(CH$_3$)$_2$CH=CH$_2$ | Cl | OMe |
| — | 2 (—) | —CH$_2$C≡CH$_2$ | Cl | OMe |
| — | 2 (—) | —CH$_2$C$_6$H$_5$ | Cl | OMe |
| — | 2 (—) | —CH$_2$C$_6$H$_4$—Cl-2 | Cl | OMe |
| — | 2 (—) | —CH$_2$C$_6$H$_4$—Cl-3 | Cl | OMe |

TABLE -continued

A compound of the general formula:

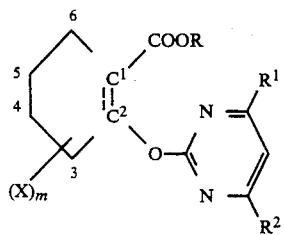

In the below-mentioned table, Me represents methyl group, Et represents ethyl group, Pr represents propyl group, $^i$Pr represents isopropyl group, Bu represents butyl group, $^i$Bu represents isobutyl group, $^s$Bu represents secondary butyl group, $^t$Bu represents tertiary butyl group, cis represents a cis-form, trans represents a trans-form, mix. represents a mixture of a cis-form and a trans-form, 1 represents a single bond and 2 represents a double bond.

| $(X)_m$ | === | R | $R^1$ | $R^2$ |
|---|---|---|---|---|
| — | 2 (—) | —CH$_2$C$_6$H$_4$—Cl-4 | Cl | OMe |
| — | 2 (—) | —CH$_2$C$_6$H$_4$—Me-2 | Cl | OMe |
| — | 2 (—) | —CH$_2$C$_6$H$_4$—Me-3 | Cl | OMe |
| — | 2 (—) | —CH$_2$C$_6$H$_4$—Me-4 | Cl | OMe |
| — | 2 (—) | —CH$_2$C$_6$H$_4$—OMe-2 | Cl | OMe |
| — | 2 (—) | —CH$_2$C$_6$H$_4$—OMe-3 | Cl | OMe |
| — | 2 (—) | —CH$_2$C$_6$H$_4$—OMe-4 | Cl | OMe |
| — | 2 (—) | —CH$_2$CH$_2$C$_6$H$_5$ | Cl | OMe |
| — | 2 (—) | H | OCHF$_2$ | OMe |
| — | 2 (—) | Li | OCHF$_2$ | OMe |
| — | 2 (—) | Na | OCHF$_2$ | OMe |
| — | 2 (—) | K | OCHF$_2$ | OMe |
| — | 2 (—) | ½Mg | OCHF$_2$ | OMe |
| — | 2 (—) | ½Ca | OCHF$_2$ | OMe |
| — | 2 (—) | MeNH$_3$ | OCHF$_2$ | OMe |
| — | 2 (—) | EtNH$_3$ | OCHF$_2$ | OMe |
| — | 2 (—) | PrNH$_3$ | OCHF$_2$ | OMe |
| — | 2 (—) | $^i$PrNH$_3$ | OCHF$_2$ | OMe |
| — | 2 (—) | NH$_2$CONH$_3$ | OCHF$_2$ | OMe |
| — | 2 (—) | Me | OCHF$_2$ | OMe |
| — | 2 (—) | Et | OCHF$_2$ | OMe |
| — | 2 (—) | $^i$Pr | OCHF$_2$ | OMe |
| — | 2 (—) | Pr | OCHF$_2$ | OMe |
| — | 2 (—) | Bu | OCHF$_2$ | OMe |
| — | 2 (—) | $^i$Bu | OCHF$_2$ | OMe |
| — | 2 (—) | $^s$Bu | OCHF$_2$ | OMe |
| — | 2 (—) | $^t$Bu | OCHF$_2$ | OMe |
| — | 2 (—) | —CH$_2$OCH$_3$ | OCHF$_2$ | OMe |
| — | 2 (—) | —CH$_2$CH$_2$OCH$_3$ | OCHF$_2$ | OMe |
| — | 2 (—) | —CH$_2$SCH$_3$ | OCHF$_2$ | OMe |
| — | 2 (—) | —CH$_2$CH=CH$_2$ | OCHF$_2$ | OMe |
| — | 2 (—) | —C(CH$_3$)$_2$CH=CH$_2$ | OCHF$_2$ | OMe |
| — | 2 (—) | —CH$_2$C≡CH$_2$ | OCHF$_2$ | OMe |
| — | 2 (—) | —CH$_2$C$_6$H$_5$ | OCHF$_2$ | OMe |
| — | 2 (—) | —CH$_2$C$_6$H$_4$—Cl-2 | OCHF$_2$ | OMe |
| — | 2 (—) | —CH$_2$C$_6$H$_4$—Cl-3 | OCHF$_2$ | OMe |
| — | 2 (—) | —CH$_2$C$_6$H$_4$—Cl-4 | OCHF$_2$ | OMe |
| — | 2 (—) | —CH$_2$C$_6$H$_4$—Me-2 | OCHF$_2$ | OMe |
| — | 2 (—) | —CH$_2$C$_6$H$_4$—Me-3 | OCHF$_2$ | OMe |
| — | 2 (—) | —CH$_2$C$_6$H$_4$—Me-4 | OCHF$_2$ | OMe |
| — | 2 (—) | —CH$_2$C$_6$H$_4$—OMe-2 | OCHF$_2$ | OMe |
| — | 2 (—) | —CH$_2$C$_6$H$_4$—OMe-3 | OCHF$_2$ | OMe |
| — | 2 (—) | —CH$_2$C$_6$H$_4$—OMe-4 | OCHF$_2$ | OMe |
| — | 2 (—) | —CH$_2$CH$_2$C$_6$H$_5$ | OCHF$_2$ | OMe |
| — | 2 (—) | H | OCHF$_2$ | OCHF$_2$ |
| — | 2 (—) | Li | OCHF$_2$ | OCHF$_2$ |
| — | 2 (—) | Na | OCHF$_2$ | OCHF$_2$ |
| — | 2 (—) | K | OCHF$_2$ | OCHF$_2$ |
| — | 2 (—) | ½Mg | OCHF$_2$ | OCHF$_2$ |
| — | 2 (—) | ½Ca | OCHF$_2$ | OCHF$_2$ |
| — | 2 (—) | MeNH$_3$ | OCHF$_2$ | OCHF$_2$ |
| — | 2 (—) | EtNH$_3$ | OCHF$_2$ | OCHF$_2$ |
| — | 2 (—) | PrNH$_3$ | OCHF$_2$ | OCHF$_2$ |
| — | 2 (—) | $^i$PrNH$_3$ | OCHF$_2$ | OCHF$_2$ |
| — | 2 (—) | NH$_2$CONH$_3$ | OCHF$_2$ | OCHF$_2$ |
| — | 2 (—) | Me | OCHF$_2$ | OCHF$_2$ |
| — | 2 (—) | Et | OCHF$_2$ | OCHF$_2$ |

TABLE -continued

A compound of the general formula:

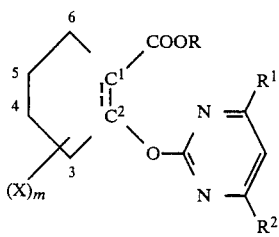

In the below-mentioned table, Me represents methyl group, Et represents ethyl group, Pr represents propyl group, $^i$Pr represents isopropyl group, Bu represents butyl group, $^i$Bu represents isobutyl group, $^s$Bu represents secondary butyl group, $^t$Bu represents tertiary butyl group, cis represents a cis-form, trans represents a trans-form, mix. represents a mixture of a cis-form and a trans-form, 1 represents a single bond and 2 represents a double bond.

| (X)$_m$ | = = = | R | R$^1$ | R$^2$ |
|---|---|---|---|---|
| — | 2 (—) | $^i$Pr | OCHF$_2$ | OCHF$_2$ |
| — | 2 (—) | Pr | OCHF$_2$ | OCHF$_2$ |
| — | 2 (—) | Bu | OCHF$_2$ | OCHF$_2$ |
| — | 2 (—) | $^i$Bu | OCHF$_2$ | OCHF$_2$ |
| — | 2 (—) | $^s$Bu | OCHF$_2$ | OCHF$_2$ |
| — | 2 (—) | $^t$Bu | OCHF$_2$ | OCHF$_2$ |
| — | 2 (—) | —CH$_2$OCH$_3$ | OCHF$_2$ | OCHF$_2$ |
| — | 2 (—) | —CH$_2$CH$_2$OCH$_3$ | OCHF$_2$ | OCHF$_2$ |
| — | 2 (—) | —CH$_2$SCH$_3$ | OCHF$_2$ | OCHF$_2$ |
| — | 2 (—) | —CH$_2$CH=CH$_2$ | OCHF$_2$ | OCHF$_2$ |
| — | 2 (—) | —C(CH$_3$)$_2$CH=CH$_2$ | OCHF$_2$ | OCHF$_2$ |
| — | 2 (—) | —CH$_2$C≡CH$_2$ | OCHF$_2$ | OCHF$_2$ |
| — | 2 (—) | —CH$_2$C$_6$H$_5$ | OCHF$_2$ | OCHF$_2$ |
| — | 2 (—) | —CH$_2$C$_6$H$_4$—Cl-2 | OCHF$_2$ | OCHF$_2$ |
| — | 2 (—) | —CH$_2$C$_6$H$_4$—Cl-3 | OCHF$_2$ | OCHF$_2$ |
| — | 2 (—) | —CH$_2$C$_6$H$_4$—Cl-4 | OCHF$_2$ | OCHF$_2$ |
| — | 2 (—) | —CH$_2$C$_6$H$_4$—Me-2 | OCHF$_2$ | OCHF$_2$ |
| — | 2 (—) | —CH$_2$C$_6$H$_4$—Me-3 | OCHF$_2$ | OCHF$_2$ |
| — | 2 (—) | —CH$_2$C$_6$H$_4$—Me-4 | OCHF$_2$ | OCHF$_2$ |
| — | 2 (—) | —CH$_2$C$_6$H$_4$—OMe-2 | OCHF$_2$ | OCHF$_2$ |
| — | 2 (—) | —CH$_2$C$_6$H$_4$—OMe-3 | OCHF$_2$ | OCHF$_2$ |
| — | 2 (—) | —CH$_2$C$_6$H$_4$—OMe-4 | OCHF$_2$ | OCHF$_2$ |
| — | 2 (—) | —CH$_2$CH$_2$C$_6$H$_5$ | OCHF$_2$ | OCHF$_2$ |
| — | 2 (—) | H | SMe | OMe |
| — | 2 (—) | Li | SMe | OMe |
| — | 2 (—) | Na | SMe | OMe |
| — | 2 (—) | K | SMe | OMe |
| — | 2 (—) | ½ Mg | SMe | OMe |
| — | 2 (—) | ½ Ca | SMe | OMe |
| — | 2 (—) | MeNH$_3$ | SMe | OMe |
| — | 2 (—) | EtNH$_3$ | SMe | OMe |
| — | 2 (—) | PrNH$_3$ | SMe | OMe |
| — | 2 (—) | $^i$PrNH$_3$ | SMe | OMe |
| — | 2 (—) | NH$_2$CONH$_3$ | SMe | OMe |
| — | 2 (—) | Me | SMe | OMe |
| — | 2 (—) | Et | SMe | OMe |
| — | 2 (—) | $^i$Pr | SMe | OMe |
| — | 2 (—) | Pr | SMe | OMe |
| — | 2 (—) | Bu | SMe | OMe |
| — | 2 (—) | $^i$Bu | SMe | OMe |
| — | 2 (—) | $^s$Bu | SMe | OMe |
| — | 2 (—) | $^t$Bu | SMe | OMe |
| — | 2 (—) | —CH$_2$OCH$_3$ | SMe | OMe |
| — | 2 (—) | —CH$_2$CH$_2$OCH$_3$ | SMe | OMe |
| — | 2 (—) | —CH$_2$SCH$_3$ | SMe | OMe |
| — | 2 (—) | —CH$_2$CH=CH$_2$ | SMe | OMe |
| — | 2 (—) | —C(CH$_3$)$_2$CH=CH$_2$ | SMe | OMe |
| — | 2 (—) | —CH$_2$C≡CH$_2$ | SMe | OMe |
| — | 2 (—) | —CH$_2$C$_6$H$_5$ | SMe | OMe |
| — | 2 (—) | —CH$_2$C$_6$H$_4$—Cl-2 | SMe | OMe |
| — | 2 (—) | —CH$_2$C$_6$H$_4$—Cl-3 | SMe | OMe |
| — | 2 (—) | —CH$_2$C$_6$H$_4$—Cl-4 | SMe | OMe |
| — | 2 (—) | —CH$_2$C$_6$H$_4$—Me-2 | SMe | OMe |
| — | 2 (—) | —CH$_2$C$_6$H$_4$—Me-3 | SMe | OMe |
| — | 2 (—) | —CH$_2$C$_6$H$_4$—Me-4 | SMe | OMe |
| — | 2 (—) | —CH$_2$C$_6$H$_4$—OMe-2 | SMe | OMe |
| — | 2 (—) | —CH$_2$C$_6$H$_4$—OMe-3 | SMe | OMe |

TABLE -continued

A compound of the general formula:

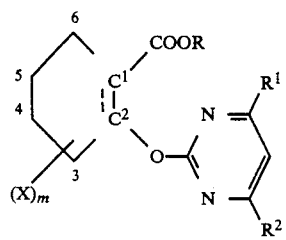

In the below-mentioned table, Me represents methyl group, Et represents ethyl group, Pr represents propyl group, $^i$Pr represents isopropyl group, Bu represents butyl group, $^i$Bu represents isobutyl group, $^s$Bu represents secondary butyl group, $^t$Bu represents tertiary butyl group, cis represents a cis-form, trans represents a trans-form, mix. represents a mixture of a cis-form and a trans-form, 1 represents a single bond and 2 represents a double bond.

| $(X)_m$ | === | R | $R^1$ | $R^2$ |
|---|---|---|---|---|
| — | 2 (—) | —CH$_2$C$_6$H$_4$—OMe-4 | SMe | OMe |
| — | 2 (—) | —CH$_2$CH$_2$C$_6$H$_5$ | SMe | OMe |
| — | 2 (—) | H | SMe | Me |
| — | 2 (—) | Li | SMe | Me |
| — | 2 (—) | Na | SMe | Me |
| — | 2 (—) | K | SMe | Me |
| — | 2 (—) | ½Mg | SMe | Me |
| — | 2 (—) | ½Ca | SMe | Me |
| — | 2 (—) | MeNH$_3$ | SMe | Me |
| — | 2 (—) | EtNH$_3$ | SMe | Me |
| — | 2 (—) | PrNH$_3$ | SMe | Me |
| — | 2 (—) | $^i$PrNH$_3$ | SMe | Me |
| — | 2 (—) | NH$_2$CONH$_3$ | SMe | Me |
| — | 2 (—) | Me | SMe | Me |
| — | 2 (—) | Et | SMe | Me |
| — | 2 (—) | $^i$Pr | SMe | Me |
| — | 2 (—) | Pr | SMe | Me |
| — | 2 (—) | Bu | SMe | Me |
| — | 2 (—) | $^i$Bu | SMe | Me |
| — | 2 (—) | $^s$Bu | SMe | Me |
| — | 2 (—) | $^t$Bu | SMe | Me |
| — | 2 (—) | —CH$_2$OCH$_3$ | SMe | Me |
| — | 2 (—) | —CH$_2$CH$_2$OCH$_3$ | SMe | Me |
| — | 2 (—) | —CH$_2$SCH$_3$ | SMe | Me |
| — | 2 (—) | —CH$_2$CH=CH$_2$ | SMe | Me |
| — | 2 (—) | —C(CH$_3$)$_2$CH=CH$_2$ | SMe | Me |
| — | 2 (—) | —CH$_2$C≡CH$_2$ | Sme | Me |
| — | 2 (—) | —CH$_2$C$_6$H$_5$ | SMe | Me |
| — | 2 (—) | —CH$_2$C$_6$H$_4$—Cl-2 | SMe | Me |
| — | 2 (—) | —CH$_2$C$_6$H$_4$—Cl-3 | SMe | Me |
| — | 2 (—) | —CH$_2$C$_6$H$_4$—Cl-4 | SMe | Me |
| — | 2 (—) | —CH$_2$C$_6$H$_4$—Me-2 | SMe | Me |
| — | 2 (—) | —CH$_2$C$_6$H$_4$—Me-3 | SMe | Me |
| — | 2 (—) | —CH$_2$C$_6$H$_4$—Me-4 | SMe | Me |
| — | 2 (—) | —CH$_2$C$_6$H$_4$—OMe-2 | SMe | Me |
| — | 2 (—) | —CH$_2$C$_6$H$_4$—OMe-3 | SMe | Me |
| — | 2 (—) | —CH$_2$C$_6$H$_4$—OMe-4 | SMe | Me |
| — | 2 (—) | —CH$_2$CH$_2$C$_6$H$_5$ | SMe | Me |
| 3-Me | 1 (cis) | H | Me | Me |
| 3-Me | 1 (cis) | Na | Me | Me |
| 3-Me | 1 (cis) | ½Ca | Me | Me |
| 3-Me | 1 (cis) | $^i$PrNH$_3$ | Me | Me |
| 3-Me | 1 (cis) | NH$_2$CONH$_3$ | Me | Me |
| 3-Me | 1 (cis) | Me | Me | Me |
| 3-Me | 1 (cis) | Et | Me | Me |
| 3-Me | 1 (cis) | $^i$Pr | Me | Me |
| 3-Me | 1 (cis) | Pr | Me | Me |
| 3-Me | 1 (cis) | Bu | Me | Me |
| 3-Me | 1 (cis) | $^i$Bu | Me | Me |
| 3-Me | 1 (cis) | $^s$Bu | Me | Me |
| 3-Me | 1 (cis) | —CH$_2$OCH$_3$ | Me | Me |
| 3-Me | 1 (cis) | —CH$_2$CH$_2$OCH$_3$ | Me | Me |
| 3-Me | 1 (cis) | —CH$_2$SCH$_3$ | Me | Me |
| 3-Me | 1 (cis) | —CH$_2$CH=CH$_2$ | Me | Me |
| 3-Me | 1 (cis) | —C(CH$_3$)$_2$CH=CH$_2$ | Me | Me |
| 3-Me | 1 (cis) | —CH$_2$C≡CH$_2$ | Me | Me |
| 3-Me | 1 (cis) | —CH$_2$C$_6$H$_5$ | Me | Me |

TABLE -continued

A compound of the general formula:

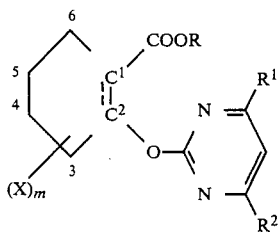

In the below-mentioned table, Me represents methyl group, Et represents ethyl group, Pr represents propyl group, $^i$Pr represents isopropyl group, Bu represents butyl group, $^i$Bu represents isobutyl group, $^s$Bu represents secondary butyl group, $^t$Bu represents tertiary butyl group, cis represents a cis-form, trans represents a trans-form, mix. represents a mixture of a cis-form and a trans-form, 1 represents a single bond and 2 represents a double bond.

| $(X)_m$ | === | R | $R^1$ | $R^2$ |
|---|---|---|---|---|
| 3-Me | 1 (cis) | —CH$_2$C$_6$H$_4$—Cl-2 | Me | Me |
| 3-Me | 1 (cis) | —CH$_2$C$_6$H$_4$—Cl-3 | Me | Me |
| 3-Me | 1 (cis) | —CH$_2$C$_6$H$_4$—Cl-4 | Me | Me |
| 3-Me | 1 (cis) | —CH$_2$C$_6$H$_4$—Me-2 | Me | Me |
| 3-Me | 1 (cis) | —CH$_2$C$_6$H$_4$—Me-3 | Me | Me |
| 3-Me | 1 (cis) | —CH$_2$C$_6$H$_4$—Me-4 | Me | Me |
| 3-Me | 1 (cis) | —CH$_2$C$_6$H$_4$—OMe-2 | Me | Me |
| 3-Me | 1 (cis) | —CH$_2$C$_6$H$_4$—OMe-3 | Me | Me |
| 3-Me | 1 (cis) | —CH$_2$C$_6$H$_4$—OMe-4 | Me | Me |
| 3-Me | 1 (cis) | —CH$_2$CH$_2$C$_6$H$_5$ | Me | Me |
| 3-Me | 1 (cis) | H | OMe | OMe |
| 3-Me | 1 (cis) | Na | OMe | OMe |
| 3-Me | 1 (cis) | ½Ca | OMe | OMe |
| 3-Me | 1 (cis) | $^i$PrNH$_3$ | OMe | OMe |
| 3-Me | 1 (cis) | NH$_2$CONH$_3$ | OMe | OMe |
| 3-Me | 1 (cis) | Me | OMe | OMe |
| 3-Me | 1 (cis) | Et | OMe | OMe |
| 3-Me | 1 (cis) | $^i$Pr | OMe | OMe |
| 3-Me | 1 (cis) | Pr | OMe | OMe |
| 3-Me | 1 (cis) | Bu | OMe | OMe |
| 3-Me | 1 (cis) | $^i$Bu | OMe | OMe |
| 3-Me | 1 (cis) | $^s$Bu | OMe | OMe |
| 3-Me | 1 (cis) | —CH$_2$OCH$_3$ | OMe | OMe |
| 3-Me | 1 (cis) | —CH$_2$CH$_2$OCH$_3$ | OMe | OMe |
| 3-Me | 1 (cis) | —CH$_2$SCH$_3$ | OMe | OMe |
| 3-Me | 1 (cis) | —CH$_2$CH=CH$_2$ | OMe | OMe |
| 3-Me | 1 (cis) | —C(CH$_3$)$_2$CH=CH$_2$ | OMe | OMe |
| 3-Me | 1 (cis) | —CH$_2$C≡CH$_2$ | OMe | OMe |
| 3-Me | 1 (cis) | —CH$_2$C$_6$H$_5$ | OMe | OMe |
| 3-Me | 1 (cis) | —CH$_2$C$_6$H$_4$—Cl-2 | OMe | OMe |
| 3-Me | 1 (cis) | —CH$_2$C$_6$H$_4$—Cl-3 | OMe | OMe |
| 3-Me | 1 (cis) | —CH$_2$C$_6$H$_4$—Cl-4 | OMe | OMe |
| 3-Me | 1 (cis) | —CH$_2$C$_6$H$_4$—Me-2 | OMe | OMe |
| 3-Me | 1 (cis) | —CH$_2$C$_6$H$_4$—Me-3 | OMe | OMe |
| 3-Me | 1 (cis) | —CH$_2$C$_6$H$_4$—Me-4 | OMe | OMe |
| 3-Me | 1 (cis) | —CH$_2$C$_6$H$_4$—OMe-2 | OMe | OMe |
| 3-Me | 1 (cis) | —CH$_2$C$_6$H$_4$—OMe-3 | OMe | OMe |
| 3-Me | 1 (cis) | —CH$_2$C$_6$H$_4$—OMe-4 | OMe | OMe |
| 3-Me | 1 (cis) | —CH$_2$CH$_2$C$_6$H$_5$ | OMe | OMe |
| 3-Me | 1 (trans) | H | Me | Me |
| 3-Me | 1 (trans) | Na | Me | Me |
| 3-Me | 1 (trans) | ½Ca | Me | Me |
| 3-Me | 1 (trans) | $^i$PrNH$_3$ | Me | Me |
| 3-Me | 1 (trans) | NH$_2$CONH$_3$ | Me | Me |
| 3-Me | 1 (trans) | Me | Me | Me |
| 3-Me | 1 (trans) | Et | Me | Me |
| 3-Me | 1 (trans) | $^i$Pr | Me | Me |
| 3-Me | 1 (trans) | Pr | Me | Me |
| 3-Me | 1 (trans) | Bu | Me | Me |
| 3-Me | 1 (trans) | $^i$Bu | Me | Me |
| 3-Me | 1 (trans) | $^s$Bu | Me | Me |
| 3-Me | 1 (trans) | —CH$_2$OCH$_3$ | Me | Me |
| 3-Me | 1 (trans) | —CH$_2$CH$_2$OCH$_3$ | Me | Me |
| 3-Me | 1 (trans) | —CH$_2$SCH$_3$ | Me | Me |
| 3-Me | 1 (trans) | —CH$_2$CH=CH$_2$ | Me | Me |
| 3-Me | 1 (trans) | —C(CH$_3$)$_2$CH=CH$_2$ | Me | Me |
| 3-Me | 1 (trans) | —CH$_2$C≡CH$_2$ | Me | Me |

TABLE -continued

A compound of the general formula:

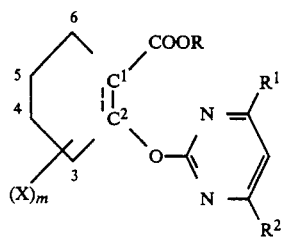

In the below-mentioned table, Me represents methyl group, Et represents ethyl group, Pr represents propyl group, $^i$Pr represents isopropyl group, Bu represents butyl group, $^i$Bu represents isobutyl group, $^s$Bu represents secondary butyl group, $^t$Bu represents tertiary butyl group, cis represents a cis-form, trans represents a trans-form, mix. represents a mixture of a cis-form and a trans-form, 1 represents a single bond and 2 represents a double bond.

| $(X)_m$ | ─── | R | $R^1$ | $R^2$ |
|---|---|---|---|---|
| 3-Me | 1 (trans) | —CH$_2$C$_6$H$_5$ | Me | Me |
| 3-Me | 1 (trans) | —CH$_2$C$_6$H$_4$—Cl-2 | Me | Me |
| 3-Me | 1 (trans) | —CH$_2$C$_6$H$_4$—Cl-3 | Me | Me |
| 3-Me | 1 (trans) | —CH$_2$C$_6$H$_4$—Cl-4 | Me | Me |
| 3-Me | 1 (trans) | —CH$_2$C$_6$H$_4$—Me-2 | Me | Me |
| 3-Me | 1 (trans) | —CH$_2$C$_6$H$_4$—Me-3 | Me | Me |
| 3-Me | 1 (trans) | —CH$_2$C$_6$H$_4$—Me-4 | Me | Me |
| 3-Me | 1 (trans) | —CH$_2$C$_6$H$_4$—OMe-2 | Me | Me |
| 3-Me | 1 (trans) | —CH$_2$C$_6$H$_4$—OMe-3 | Me | Me |
| 3-Me | 1 (trans) | —CH$_2$C$_6$H$_4$—OMe-4 | Me | Me |
| 3-Me | 1 (trans) | —CH$_2$CH$_2$C$_6$H$_5$ | Me | Me |
| 3-Me | 1 (trans) | H | OMe | OMe |
| 3-Me | 1 (trans) | Na | OMe | OMe |
| 3-Me | 1 (trans) | ½Ca | OMe | OMe |
| 3-Me | 1 (trans) | $^i$PrNH$_3$ | OMe | OMe |
| 3-Me | 1 (trans) | NH$_2$CONH$_3$ | OMe | OMe |
| 3-Me | 1 (trans) | Me | OMe | OMe |
| 3-Me | 1 (trans) | Et | OMe | OMe |
| 3-Me | 1 (trans) | $^i$Pr | OMe | OMe |
| 3-Me | 1 (trans) | Pr | OMe | OMe |
| 3-Me | 1 (trans) | Bu | OMe | OMe |
| 3-Me | 1 (trans) | $^i$Bu | OMe | OMe |
| 3-Me | 1 (trans) | $^s$Bu | OMe | OMe |
| 3-Me | 1 (trans) | —CH$_2$OCH$_3$ | OMe | OMe |
| 3-Me | 1 (trans) | —CH$_2$CH$_2$OCH$_3$ | OMe | OMe |
| 3-Me | 1 (trans) | —CH$_2$SCH$_3$ | OMe | OMe |
| 3-Me | 1 (trans) | —CH$_2$CH=CH$_2$ | OMe | OMe |
| 3-Me | 1 (trans) | —C(CH$_3$)$_2$CH=CH$_2$ | OMe | OMe |
| 3-Me | 1 (trans) | —CH$_2$C≡CH$_2$ | OMe | OMe |
| 3-Me | 1 (trans) | —CH$_2$C$_6$H$_5$ | OMe | OMe |
| 3-Me | 1 (trans) | —CH$_2$C$_6$H$_4$—Cl-2 | OMe | OMe |
| 3-Me | 1 (trans) | —CH$_2$C$_6$H$_4$—Cl-3 | OMe | OMe |
| 3-Me | 1 (trans) | —CH$_2$C$_6$H$_4$—Cl-4 | OMe | OMe |
| 3-Me | 1 (trans) | —CH$_2$C$_6$H$_4$—Me-2 | OMe | OMe |
| 3-Me | 1 (trans) | —CH$_2$C$_6$H$_4$—Me-3 | OMe | OMe |
| 3-Me | 1 (trans) | —CH$_2$C$_6$H$_4$—Me-4 | OMe | OMe |
| 3-Me | 1 (trans) | —CH$_2$C$_6$H$_4$—OMe-2 | OMe | OMe |
| 3-Me | 1 (trans) | —CH$_2$C$_6$H$_4$—OMe-3 | OMe | OMe |
| 3-Me | 1 (trans) | —CH$_2$C$_6$H$_4$—OMe-4 | OMe | OMe |
| 3-Me | 1 (trans) | —CH$_2$CH$_2$C$_6$H$_5$ | OMe | OMe |
| 3-Me | 1 (mixt.) | H | Me | Me |
| 3-Me | 1 (mixt.) | Na | Me | Me |
| 3-Me | 1 (mixt.) | ½Ca | Me | Me |
| 3-Me | 1 (mixt.) | $^i$PrNH$_3$ | Me | Me |
| 3-Me | 1 (mixt.) | NH$_2$CONH$_3$ | Me | Me |
| 3-Me | 1 (mixt.) | Me | Me | Me |
| 3-Me | 1 (mixt.) | Et | Me | Me |
| 3-Me | 1 (mixt.) | $^i$Pr | Me | Me |
| 3-Me | 1 (mixt.) | Pr | Me | Me |
| 3-Me | 1 (mixt.) | Bu | Me | Me |
| 3-Me | 1 (mixt.) | $^i$Bu | Me | Me |
| 3-Me | 1 (mixt.) | $^s$Bu | Me | Me |
| 3-Me | 1 (mixt.) | —CH$_2$OCH$_3$ | Me | Me |
| 3-Me | 1 (mixt.) | —CH$_2$CH$_2$OCH$_3$ | Me | Me |
| 3-Me | 1 (mixt.) | —CH$_2$SCH$_3$ | Me | Me |
| 3-Me | 1 (mixt.) | —CH$_2$CH=CH$_2$ | Me | Me |
| 3-Me | 1 (mixt.) | —C(CH$_3$)$_2$CH=CH$_2$ | Me | Me |

TABLE -continued

A compound of the general formula:

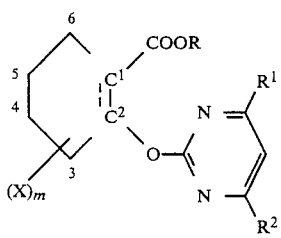

In the below-mentioned table, Me represents methyl group, Et represents ethyl group, Pr represents propyl group, $^i$Pr represents isopropyl group, Bu represents butyl group, $^i$Bu represents isobutyl group, $^s$Bu represents secondary butyl group, $^t$Bu represents tertiary butyl group, cis represents a cis-form, trans represents a trans-form, mix. represents a mixture of a cis-form and a trans-form, 1 represents a single bond and 2 represents a double bond.

| $(X)_m$ | === | R | $R^1$ | $R^2$ |
|---|---|---|---|---|
| 3-Me | 1 (mixt.) | —CH$_2$C≡CH$_2$ | Me | Me |
| 3-Me | 1 (mixt.) | —CH$_2$C$_6$H$_5$ | Me | Me |
| 3-Me | 1 (mixt.) | —CH$_2$C$_6$H$_4$—Cl-2 | Me | Me |
| 3-Me | 1 (mixt.) | —CH$_2$C$_6$H$_4$—Cl-3 | Me | Me |
| 3-Me | 1 (mixt.) | —CH$_2$C$_6$H$_4$—Cl-4 | Me | Me |
| 3-Me | 1 (mixt.) | —CH$_2$C$_6$H$_4$—Me-2 | Me | Me |
| 3-Me | 1 (mixt.) | —CH$_2$C$_6$H$_4$—Me-3 | Me | Me |
| 3-Me | 1 (mixt.) | —CH$_2$C$_6$H$_4$—Me-4 | Me | Me |
| 3-Me | 1 (mixt.) | —CH$_2$C$_6$H$_4$—OMe-2 | Me | Me |
| 3-Me | 1 (mixt.) | —CH$_2$C$_6$H$_4$—OMe-3 | Me | Me |
| 3-Me | 1 (mixt.) | —CH$_2$C$_6$H$_4$—OMe-4 | Me | Me |
| 3-Me | 1 (mixt.) | —CH$_2$CH$_2$C$_6$H$_5$ | Me | Me |
| 3-Me | 1 (mixt.) | H | OMe | OMe |
| 3-Me | 1 (mixt.) | Na | OMe | OMe |
| 3-Me | 1 (mixt.) | ½Ca | OMe | OMe |
| 3-Me | 1 (mixt.) | $^i$PrNH$_3$ | OMe | OMe |
| 3-Me | 1 (mixt.) | NH$_2$CONH$_3$ | OMe | OMe |
| 3-Me | 1 (mixt.) | Me | OMe | OMe |
| 3-Me | 1 (mixt.) | Et | OMe | OMe |
| 3-Me | 1 (mixt.) | $^i$Pr | OMe | OMe |
| 3-Me | 1 (mixt.) | Pr | OMe | OMe |
| 3-Me | 1 (mixt.) | Bu | OMe | OMe |
| 3-Me | 1 (mixt.) | $^i$Bu | OMe | OMe |
| 3-Me | 1 (mixt.) | $^s$Bu | OMe | OMe |
| 3-Me | 1 (mixt.) | —CH$_2$OCH$_3$ | OMe | OMe |
| 3-Me | 1 (mixt.) | —CH$_2$CH$_2$OCH$_3$ | OMe | OMe |
| 3-Me | 1 (mixt.) | —CH$_2$SCH$_3$ | OMe | OMe |
| 3-Me | 1 (mixt.) | —CH$_2$CH=CH$_2$ | OMe | OMe |
| 3-Me | 1 (mixt.) | —C(CH$_3$)$_2$CH=CH$_2$ | OMe | OMe |
| 3-Me | 1 (mixt.) | —CH$_2$C≡CH$_2$ | OMe | OMe |
| 3-Me | 1 (mixt.) | —CH$_2$C$_6$H$_5$ | OMe | OMe |
| 3-Me | 1 (mixt.) | —CH$_2$C$_6$H$_4$—Cl-2 | OMe | OMe |
| 3-Me | 1 (mixt.) | —CH$_2$C$_6$H$_4$—Cl-3 | OMe | OMe |
| 3-Me | 1 (mixt.) | —CH$_2$C$_6$H$_4$—Cl-4 | OMe | OMe |
| 3-Me | 1 (mixt.) | —CH$_2$C$_6$H$_4$—Me-2 | OMe | OMe |
| 3-Me | 1 (mixt.) | —CH$_2$C$_6$H$_4$—Me-3 | OMe | OMe |
| 3-Me | 1 (mixt.) | —CH$_2$C$_6$H$_4$—Me-4 | OMe | OMe |
| 3-Me | 1 (mixt.) | —CH$_2$C$_6$H$_4$—OMe-2 | OMe | OMe |
| 3-Me | 1 (mixt.) | —CH$_2$C$_6$H$_4$—OMe-3 | OMe | OMe |
| 3-Me | 1 (mixt.) | —CH$_2$C$_6$H$_4$—OMe-4 | OMe | OMe |
| 3-Me | 1 (mixt.) | —CH$_2$CH$_2$C$_6$H$_5$ | OMe | OMe |
| 3-Me | 2 (—) | H | Me | Me |
| 3-Me | 2 (—) | Na | Me | Me |
| 3-Me | 2 (—) | ½Ca | Me | Me |
| 3-Me | 2 (—) | $^i$PrNH$_3$ | Me | Me |
| 3-Me | 2 (—) | NH$_2$CONH$_3$ | Me | Me |
| 3-Me | 2 (—) | Me | Me | Me |
| 3-Me | 2 (—) | Et | Me | Me |
| 3-Me | 2 (—) | $^i$Pr | Me | Me |
| 3-Me | 2 (—) | Pr | Me | Me |
| 3-Me | 2 (—) | Bu | Me | Me |
| 3-Me | 2 (—) | $^i$Bu | Me | Me |
| 3-Me | 2 (—) | $^s$Bu | Me | Me |
| 3-Me | 2 (—) | —CH$_2$OCH$_3$ | Me | Me |
| 3-Me | 2 (—) | —CH$_2$CH$_2$OCH$_3$ | Me | Me |
| 3-Me | 2 (—) | —CH$_2$SCH$_3$ | Me | Me |
| 3-Me | 2 (—) | —CH$_2$CH=CH$_2$ | Me | Me |

TABLE -continued

A compound of the general formula:

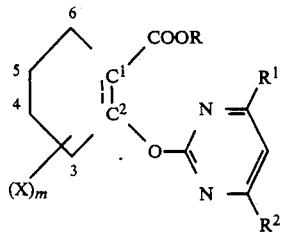

In the below-mentioned table, Me represents methyl group, Et represents ethyl group, Pr represents propyl group, $^i$Pr represents isopropyl group, Bu represents butyl group, $^i$Bu represents isobutyl group, $^s$Bu represents secondary butyl group, $^t$Bu represents tertiary butyl group, cis represents a cis-form, trans represents a trans-form, mix. represents a mixture of a cis-form and a trans-form, 1 represents a single bond and 2 represents a double bond.

| $(X)_m$ | === | R | $R^1$ | $R^2$ |
|---|---|---|---|---|
| 3-Me | 2 (—) | —C(CH$_3$)$_2$CH=CH$_2$ | Me | Me |
| 3-Me | 2 (—) | —CH$_2$C≡CH$_2$ | Me | Me |
| 3-Me | 2 (—) | —CH$_2$C$_6$H$_5$ | Me | Me |
| 3-Me | 2 (—) | —CH$_2$C$_6$H$_4$—Cl-2 | Me | Me |
| 3-Me | 2 (—) | —CH$_2$C$_6$H$_4$—Cl-3 | Me | Me |
| 3-Me | 2 (—) | —CH$_2$C$_6$H$_4$—Cl-4 | Me | Me |
| 3-Me | 2 (—) | —CH$_2$C$_6$H$_4$—Me-2 | Me | Me |
| 3-Me | 2 (—) | —CH$_2$C$_6$H$_4$—Me-3 | Me | Me |
| 3-Me | 2 (—) | —CH$_2$C$_6$H$_4$—Me-4 | Me | Me |
| 3-Me | 2 (—) | —CH$_2$C$_6$H$_4$—OMe-2 | Me | Me |
| 3-Me | 2 (—) | —CH$_2$C$_6$H$_4$—OMe-3 | Me | Me |
| 3-Me | 2 (—) | —CH$_2$C$_6$H$_4$—OMe-4 | Me | Me |
| 3-Me | 2 (—) | —CH$_2$CH$_2$C$_6$H$_5$ | Me | Me |
| 3-Me | 2 (—) | H | OMe | OMe |
| 3-Me | 2 (—) | Na | OMe | OMe |
| 3-Me | 2 (—) | ½Ca | OMe | OMe |
| 3-Me | 2 (—) | $^i$PrNH$_3$ | OMe | OMe |
| 3-Me | 2 (—) | NH$_2$CONH$_3$ | OMe | OMe |
| 3-Me | 2 (—) | Me | OMe | OMe |
| 3-Me | 2 (—) | Et | OMe | OMe |
| 3-Me | 2 (—) | $^i$Pr | OMe | OMe |
| 3-Me | 2 (—) | Pr | OMe | OMe |
| 3-Me | 2 (—) | Bu | OMe | OMe |
| 3-Me | 2 (—) | $^i$Bu | OMe | OMe |
| 3-Me | 2 (—) | $^s$Bu | OMe | OMe |
| 3-Me | 2 (—) | —CH$_2$OCH$_3$ | OMe | OMe |
| 3-Me | 2 (—) | —CH$_2$CH$_2$OCH$_3$ | OMe | OMe |
| 3-Me | 2 (—) | —CH$_2$SCH$_3$ | OMe | OMe |
| 3-Me | 2 (—) | —CH$_2$CH=CH$_2$ | OMe | OMe |
| 3-Me | 2 (—) | —C(CH$_3$)$_2$CH=CH$_2$ | OMe | OMe |
| 3-Me | 2 (—) | —CH$_2$C≡CH$_2$ | OMe | OMe |
| 3-Me | 2 (—) | —CH$_2$C$_6$H$_5$ | OMe | OMe |
| 3-Me | 2 (—) | —CH$_2$C$_6$H$_4$—Cl-2 | OMe | OMe |
| 3-Me | 2 (—) | —CH$_2$C$_6$H$_4$—Cl-3 | OMe | OMe |
| 3-Me | 2 (—) | —CH$_2$C$_6$H$_4$—Cl-4 | OMe | OMe |
| 3-Me | 2 (—) | —CH$_2$C$_6$H$_4$—Me-2 | OMe | OMe |
| 3-Me | 2 (—) | —CH$_2$C$_6$H$_4$—Me-3 | OMe | OMe |
| 3-Me | 2 (—) | —CH$_2$C$_6$H$_4$—Me-4 | OMe | OMe |
| 3-Me | 2 (—) | —CH$_2$C$_6$H$_4$—OMe-2 | OMe | OMe |
| 3-Me | 2 (—) | —CH$_2$C$_6$H$_4$—OMe-3 | OMe | OMe |
| 3-Me | 2 (—) | —CH$_2$C$_6$H$_4$—OMe-4 | OMe | OMe |
| 3-Me | 2 (—) | —CH$_2$CH$_2$C$_6$H$_5$ | OMe | OMe |
| 4-Me | 1 (cis) | H | Me | Me |
| 4-Me | 1 (cis) | Na | Me | Me |
| 4-Me | 1 (cis) | ½Ca | Me | Me |
| 4-Me | 1 (cis) | $^i$PrNH$_3$ | Me | Me |
| 4-Me | 1 (cis) | NH$_2$CONH$_3$ | Me | Me |
| 4-Me | 1 (cis) | Me | Me | Me |
| 4-Me | 1 (cis) | Et | Me | Me |
| 4-Me | 1 (cis) | $^i$Pr | Me | Me |
| 4-Me | 1 (cis) | Pr | Me | Me |
| 4-Me | 1 (cis) | Bu | Me | Me |
| 4-Me | 1 (cis) | $^i$Bu | Me | Me |
| 4-Me | 1 (cis) | $^s$Bu | Me | Me |
| 4-Me | 1 (cis) | —CH$_2$OCH$_3$ | Me | Me |
| 4-Me | 1 (cis) | —CH$_2$CH$_2$OCH$_3$ | Me | Me |
| 4-Me | 1 (cis) | —CH$_2$SCH$_3$ | Me | Me |

TABLE -continued

A compound of the general formula:

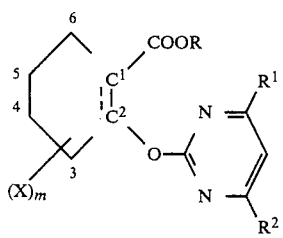

In the below-mentioned table, Me represents methyl group, Et represents ethyl group, Pr represents propyl group, $^{i}$Pr represents isopropyl group, Bu represents butyl group, $^{i}$Bu represents isobutyl group, $^{s}$Bu represents secondary butyl group, $^{t}$Bu represents tertiary butyl group, cis represents a cis-form, trans represents a trans-form, mix. represents a mixture of a cis-form and a trans-form, 1 represents a single bond and 2 represents a double bond.

| $(X)_m$ | === | R | $R^1$ | $R^2$ |
|---|---|---|---|---|
| 4-Me | 1 (cis) | —$CH_2CH=CH_2$ | Me | Me |
| 4-Me | 1 (cis) | —$C(CH_3)_2CH=CH_2$ | Me | Me |
| 4-Me | 1 (cis) | —$CH_2C\equiv CH_2$ | Me | Me |
| 4-Me | 1 (cis) | —$CH_2C_6H_5$ | Me | Me |
| 4-Me | 1 (cis) | —$CH_2C_6H_4$—Cl-2 | Me | Me |
| 4-Me | 1 (cis) | —$CH_2C_6H_4$—Cl-3 | Me | Me |
| 4-Me | 1 (cis) | —$CH_2C_6H_4$—Cl-4 | Me | Me |
| 4-Me | 1 (cis) | —$CH_2C_6H_4$—Me-2 | Me | Me |
| 4-Me | 1 (cis) | —$CH_2C_6H_4$—Me-3 | Me | Me |
| 4-Me | 1 (cis) | —$CH_2C_6H_4$—Me-4 | Me | Me |
| 4-Me | 1 (cis) | —$CH_2C_6H_4$—OMe-2 | Me | Me |
| 4-Me | 1 (cis) | —$CH_2C_6H_4$—OMe-3 | Me | Me |
| 4-Me | 1 (cis) | —$CH_2C_6H_4$—OMe-4 | Me | Me |
| 4-Me | 1 (cis) | —$CH_2CH_2C_6H_5$ | Me | Me |
| 4-Me | 1 (cis) | H | OMe | OMe |
| 4-Me | 1 (cis) | Na | OMe | OMe |
| 4-Me | 1 (cis) | ½Ca | OMe | OMe |
| 4-Me | 1 (cis) | $^{i}PrNH_3$ | OMe | OMe |
| 4-Me | 1 (cis) | $NH_2CONH_3$ | OMe | OMe |
| 4-Me | 1 (cis) | Me | OMe | OMe |
| 4-Me | 1 (cis) | Et | OMe | OMe |
| 4-Me | 1 (cis) | $^{i}$Pr | OMe | OMe |
| 4-Me | 1 (cis) | Pr | OMe | OMe |
| 4-Me | 1 (cis) | Bu | OMe | OMe |
| 4-Me | 1 (cis) | $^{i}$Bu | OMe | OMe |
| 4-Me | 1 (cis) | $^{s}$Bu | OMe | OMe |
| 4-Me | 1 (cis) | —$CH_2OCH_3$ | OMe | OMe |
| 4-Me | 1 (cis) | —$CH_2CH_2OCH_3$ | OMe | OMe |
| 4-Me | 1 (cis) | —$CH_2SCH_3$ | OMe | OMe |
| 4-Me | 1 (cis) | —$CH_2CH=CH_2$ | OMe | OMe |
| 4-Me | 1 (cis) | —$C(CH_3)_2CH=CH_2$ | OMe | OMe |
| 4-Me | 1 (cis) | —$CH_2C\equiv CH_2$ | OMe | OMe |
| 4-Me | 1 (cis) | —$CH_2C_6H_5$ | OMe | OMe |
| 4-Me | 1 (cis) | —$CH_2C_6H_4$—Cl-2 | OMe | OMe |
| 4-Me | 1 (cis) | —$CH_2C_6H_4$—Cl-3 | OMe | OMe |
| 4-Me | 1 (cis) | —$CH_2C_6H_4$—Cl-4 | OMe | OMe |
| 4-Me | 1 (cis) | —$CH_2C_6H_4$—Me-2 | OMe | OMe |
| 4-Me | 1 (cis) | —$CH_2C_6H_4$—Me-3 | OMe | OMe |
| 4-Me | 1 (cis) | —$CH_2C_6H_4$—Me-4 | OMe | OMe |
| 4-Me | 1 (cis) | —$CH_2C_6H_4$—OMe-2 | OMe | OMe |
| 4-Me | 1 (cis) | —$CH_2C_6H_4$—OMe-3 | OMe | OMe |
| 4-Me | 1 (cis) | —$CH_2C_6H_4$—OMe-4 | OMe | OMe |
| 4-Me | 1 (cis) | —$CH_2CH_2C_6H_5$ | OMe | OMe |
| 4-Me | 1 (trans) | H | Me | Me |
| 4-Me | 1 (trans) | Na | Me | Me |
| 4-Me | 1 (trans) | ½Ca | Me | Me |
| 4-Me | 1 (trans) | $^{i}PrNH_3$ | Me | Me |
| 4-Me | 1 (trans) | $NH_2CONH_3$ | Me | Me |
| 4-Me | 1 (trans) | Me | Me | Me |
| 4-Me | 1 (trans) | Et | Me | Me |
| 4-Me | 1 (trans) | $^{i}$Pr | Me | Me |
| 4-Me | 1 (trans) | Pr | Me | Me |
| 4-Me | 1 (trans) | Bu | Me | Me |
| 4-Me | 1 (trans) | $^{i}$Bu | Me | Me |
| 4-Me | 1 (trans) | $^{s}$Bu | Me | Me |
| 4-Me | 1 (trans) | —$CH_2OCH_3$ | Me | Me |
| 4-Me | 1 (trans) | —$CH_2CH_2OCH_3$ | Me | Me |

TABLE -continued

A compound of the general formula:

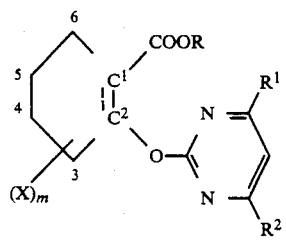

In the below-mentioned table, Me represents methyl group, Et represents ethyl group, Pr represents propyl group, $^i$Pr represents isopropyl group, Bu represents butyl group, $^i$Bu represents isobutyl group, $^s$Bu represents secondary butyl group, $^t$Bu represents tertiary butyl group, cis represents a cis-form, trans represents a trans-form, mix. represents a mixture of a cis-form and a trans-form, 1 represents a single bond and 2 represents a double bond.

| $(X)_m$ | === | R | $R^1$ | $R^2$ |
|---|---|---|---|---|
| 4-Me | 1 (trans) | —CH$_2$SCH$_3$ | Me | Me |
| 4-Me | 1 (trans) | —CH$_2$CH=CH$_2$ | Me | Me |
| 4-Me | 1 (trans) | —C(CH$_3$)$_2$CH=CH$_2$ | Me | Me |
| 4-Me | 1 (trans) | —CH$_2$C≡CH$_2$ | Me | Me |
| 4-Me | 1 (trans) | —CH$_2$C$_6$H$_5$ | Me | Me |
| 4-Me | 1 (trans) | —CH$_2$C$_6$H$_4$—Cl-2 | Me | Me |
| 4-Me | 1 (trans) | —CH$_2$C$_6$H$_4$—Cl-3 | Me | Me |
| 4-Me | 1 (trans) | —CH$_2$C$_6$H$_4$—Cl-4 | Me | Me |
| 4-Me | 1 (trans) | —CH$_2$C$_6$H$_4$—Me-2 | Me | Me |
| 4-Me | 1 (trans) | —CH$_2$C$_6$H$_4$—Me-3 | Me | Me |
| 4-Me | 1 (trans) | —CH$_2$C$_6$H$_4$—Me-4 | Me | Me |
| 4-Me | 1 (trans) | —CH$_2$C$_6$H$_4$—OMe-2 | Me | Me |
| 4-Me | 1 (trans) | —CH$_2$C$_6$H$_4$—OMe-3 | Me | Me |
| 4-Me | 1 (trans) | —CH$_2$C$_6$H$_4$—OMe-4 | Me | Me |
| 4-Me | 1 (trans) | —CH$_2$CH$_2$C$_6$H$_5$ | Me | Me |
| 4-Me | 1 (trans) | H | OMe | OMe |
| 4-Me | 1 (trans) | Na | OMe | OMe |
| 4-Me | 1 (trans) | ½Ca | OMe | OMe |
| 4-Me | 1 (trans) | $^i$PrNH$_3$ | OMe | OMe |
| 4-Me | 1 (trans) | NH$_2$CONH$_3$ | OMe | OMe |
| 4-Me | 1 (trans) | Me | OMe | OMe |
| 4-Me | 1 (trans) | Et | OMe | OMe |
| 4-Me | 1 (trans) | $^i$Pr | OMe | OMe |
| 4-Me | 1 (trans) | Pr | OMe | OMe |
| 4-Me | 1 (trans) | Bu | OMe | OMe |
| 4-Me | 1 (trans) | $^i$Bu | OMe | OMe |
| 4-Me | 1 (trans) | $^s$Bu | OMe | OMe |
| 4-Me | 1 (trans) | —CH$_2$OCH$_3$ | OMe | OMe |
| 4-Me | 1 (trans) | —CH$_2$CH$_2$OCH$_3$ | OMe | OMe |
| 4-Me | 1 (trans) | —CH$_2$SCH$_3$ | OMe | OMe |
| 4-Me | 1 (trans) | —CH$_2$CH=CH$_2$ | OMe | OMe |
| 4-Me | 1 (trans) | —C(CH$_3$)$_2$CH=CH$_2$ | OMe | OMe |
| 4-Me | 1 (trans) | —CH$_2$C≡CH$_2$ | OMe | OMe |
| 4-Me | 1 (trans) | —CH$_2$C$_6$H$_5$ | OMe | OMe |
| 4-Me | 1 (trans) | —CH$_2$C$_6$H$_4$—Cl-2 | OMe | OMe |
| 4-Me | 1 (trans) | —CH$_2$C$_6$H$_4$—Cl-3 | OMe | OMe |
| 4-Me | 1 (trans) | —CH$_2$C$_6$H$_4$—Cl-4 | OMe | OMe |
| 4-Me | 1 (trans) | —CH$_2$C$_6$H$_4$—Me-2 | OMe | OMe |
| 4-Me | 1 (trans) | —CH$_2$C$_6$H$_4$—Me-3 | OMe | OMe |
| 4-Me | 1 (trans) | —CH$_2$C$_6$H$_4$—Me-4 | OMe | OMe |
| 4-Me | 1 (trans) | —CH$_2$C$_6$H$_4$—OMe-2 | OMe | OMe |
| 4-Me | 1 (trans) | —CH$_2$C$_6$H$_4$—OMe-3 | OMe | OMe |
| 4-Me | 1 (trans) | —CH$_2$C$_6$H$_4$—OMe-4 | OMe | OMe |
| 4-Me | 1 (trans) | —CH$_2$CH$_2$C$_6$H$_5$ | OMe | OMe |
| 4-Me | 1 (mixt.) | H | Me | Me |
| 4-Me | 1 (mixt.) | Na | Me | Me |
| 4-Me | 1 (mixt.) | ½Ca | Me | Me |
| 4-Me | 1 (mixt.) | $^i$PrNH$_3$ | Me | Me |
| 4-Me | 1 (mixt.) | NH$_2$CONH$_3$ | Me | Me |
| 4-Me | 1 (mixt.) | Me | Me | Me |
| 4-Me | 1 (mixt.) | Et | Me | Me |
| 4-Me | 1 (mixt.) | $^i$Pr | Me | Me |
| 4-Me | 1 (mixt.) | Pr | Me | Me |
| 4-Me | 1 (mixt.) | Bu | Me | Me |
| 4-Me | 1 (mixt.) | $^i$Bu | Me | Me |
| 4-Me | 1 (mixt.) | $^s$Bu | Me | Me |
| 4-Me | 1 (mixt.) | —CH$_2$OCH$_3$ | Me | Me |

TABLE -continued

A compound of the general formula:

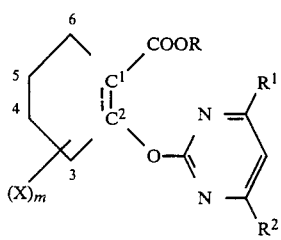

In the below-mentioned table, Me represents methyl group, Et represents ethyl group, Pr represents propyl group, $^i$Pr represents isopropyl group, Bu represents butyl group, $^i$Bu represents isobutyl group, $^s$Bu represents secondary butyl group, $^t$Bu represents tertiary butyl group, cis represents a cis-form, trans represents a trans-form, mix. represents a mixture of a cis-form and a trans-form, 1 represents a single bond and 2 represents a double bond.

| (X)$_m$ | === | R | R$^1$ | R$^2$ |
|---|---|---|---|---|
| 4-Me | 1 (mixt.) | —CH$_2$CH$_2$OCH$_3$ | Me | Me |
| 4-Me | 1 (mixt.) | —CH$_2$SCH$_3$ | Me | Me |
| 4-Me | 1 (mixt.) | —CH$_2$CH=CH$_2$ | Me | Me |
| 4-Me | 1 (mixt.) | —C(CH$_3$)$_2$CH=CH$_2$ | Me | Me |
| 4-Me | 1 (mixt.) | —CH$_2$C≡CH$_2$ | Me | Me |
| 4-Me | 1 (mixt.) | —CH$_2$C$_6$H$_5$ | Me | Me |
| 4-Me | 1 (mixt.) | —CH$_2$C$_6$H$_4$—Cl-2 | Me | Me |
| 4-Me | 1 (mixt.) | —CH$_2$C$_6$H$_4$—Cl-3 | Me | Me |
| 4-Me | 1 (mixt.) | —CH$_2$C$_6$H$_4$—Cl-4 | Me | Me |
| 4-Me | 1 (mixt.) | —CH$_2$C$_6$H$_4$—Me-2 | Me | Me |
| 4-Me | 1 (mixt.) | —CH$_2$C$_6$H$_4$—Me-3 | Me | Me |
| 4-Me | 1 (mixt.) | —CH$_2$C$_6$H$_4$—Me-4 | Me | Me |
| 4-Me | 1 (mixt.) | —CH$_2$C$_6$H$_4$—OMe-2 | Me | Me |
| 4-Me | 1 (mixt.) | —CH$_2$C$_6$H$_4$—OMe-3 | Me | Me |
| 4-Me | 1 (mixt.) | —CH$_2$C$_6$H$_4$—OMe-4 | Me | Me |
| 4-Me | 1 (mixt.) | —CH$_2$CH$_2$C$_6$H$_5$ | Me | Me |
| 4-Me | 1 (mixt.) | H | OMe | OMe |
| 4-Me | 1 (mixt.) | Na | OMe | OMe |
| 4-Me | 1 (mixt.) | ½Ca | OMe | OMe |
| 4-Me | 1 (mixt.) | $^i$PrNH$_3$ | OMe | OMe |
| 4-Me | 1 (mixt.) | NH$_2$CONH$_3$ | OMe | OMe |
| 4-Me | 1 (mixt.) | Me | OMe | OMe |
| 4-Me | 1 (mixt.) | Et | OMe | OMe |
| 4-Me | 1 (mixt.) | $^i$Pr | OMe | OMe |
| 4-Me | 1 (mixt.) | Pr | OMe | OMe |
| 4-Me | 1 (mixt.) | Bu | OMe | OMe |
| 4-Me | 1 (mixt.) | $^i$Bu | OMe | OMe |
| 4-Me | 1 (mixt.) | $^s$Bu | OMe | OMe |
| 4-Me | 1 (mixt.) | —CH$_2$OCH$_3$ | OMe | OMe |
| 4-Me | 1 (mixt.) | —CH$_2$CH$_2$OCH$_3$ | OMe | OMe |
| 4-Me | 1 (mixt.) | —CH$_2$SCH$_3$ | OMe | OMe |
| 4-Me | 1 (mixt.) | —CH$_2$CH=CH$_2$ | OMe | OMe |
| 4-Me | 1 (mixt.) | —C(CH$_3$)$_2$CH=CH$_2$ | OMe | OMe |
| 4-Me | 1 (mixt.) | —CH$_2$C≡CH$_2$ | OMe | OMe |
| 4-Me | 1 (mixt.) | —CH$_2$C$_6$H$_5$ | OMe | OMe |
| 4-Me | 1 (mixt.) | —CH$_2$C$_6$H$_4$—Cl-2 | OMe | OMe |
| 4-Me | 1 (mixt.) | —CH$_2$C$_6$H$_4$—Cl-3 | OMe | OMe |
| 4-Me | 1 (mixt.) | —CH$_2$C$_6$H$_4$—Cl-4 | OMe | OMe |
| 4-Me | 1 (mixt.) | —CH$_2$C$_6$H$_4$—Me-2 | OMe | OMe |
| 4-Me | 1 (mixt.) | —CH$_2$C$_6$H$_4$—Me-3 | OMe | OMe |
| 4-Me | 1 (mixt.) | —CH$_2$C$_6$H$_4$—Me-4 | OMe | OMe |
| 4-Me | 1 (mixt.) | —CH$_2$C$_6$H$_4$—OMe-2 | OMe | OMe |
| 4-Me | 1 (mixt.) | —CH$_2$C$_6$H$_4$—OMe-3 | OMe | OMe |
| 4-Me | 1 (mixt.) | —CH$_2$C$_6$H$_4$—OMe-4 | OMe | OMe |
| 4-Me | 1 (mixt.) | —CH$_2$CH$_2$C$_6$H$_5$ | OMe | OMe |
| 4-Me | 2 (—) | H | Me | Me |
| 4-Me | 2 (—) | Na | Me | Me |
| 4-Me | 2 (—) | ½Ca | Me | Me |
| 4-Me | 2 (—) | $^i$PrNH$_3$ | Me | Me |
| 4-Me | 2 (—) | NH$_2$CONH$_3$ | Me | Me |
| 4-Me | 2 (—) | Me | Me | Me |
| 4-Me | 2 (—) | Et | Me | Me |
| 4-Me | 2 (—) | $^i$Pr | Me | Me |
| 4-Me | 2 (—) | Pr | Me | Me |
| 4-Me | 2 (—) | Bu | Me | Me |
| 4-Me | 2 (—) | $^i$Bu | Me | Me |
| 4-Me | 2 (—) | $^s$Bu | Me | Me |

TABLE -continued

A compound of the general formula:

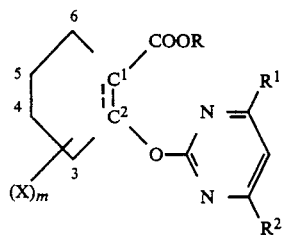

In the below-mentioned table, Me represents methyl group, Et represents ethyl group, Pr represents propyl group, $^i$Pr represents isopropyl group, Bu represents butyl group, $^i$Bu represents isobutyl group, $^s$Bu represents secondary butyl group, $^t$Bu represents tertiary butyl group, cis represents a cis-form, trans represents a trans-form, mix. represents a mixture of a cis-form and a trans-form, 1 represents a single bond and 2 represents a double bond.

| (X)$_m$ | ⚌ | R | R$^1$ | R$^2$ |
|---|---|---|---|---|
| 4-Me | 2 (—) | —CH$_2$OCH$_3$ | Me | Me |
| 4-Me | 2 (—) | —CH$_2$CH$_2$OCH$_3$ | Me | Me |
| 4-Me | 2 (—) | —CH$_2$SCH$_3$ | Me | Me |
| 4-Me | 2 (—) | —CH$_2$CH=CH$_2$ | Me | Me |
| 4-Me | 2 (—) | —C(CH$_3$)$_2$CH=CH$_2$ | Me | Me |
| 4-Me | 2 (—) | —CH$_2$C≡CH$_2$ | Me | Me |
| 4-Me | 2 (—) | —CH$_2$C$_6$H$_5$ | Me | Me |
| 4-Me | 2 (—) | —CH$_2$C$_6$H$_4$—Cl-2 | Me | Me |
| 4-Me | 2 (—) | —CH$_2$C$_6$H$_4$—Cl-3 | Me | Me |
| 4-Me | 2 (—) | —CH$_2$C$_6$H$_4$—Cl-4 | Me | Me |
| 4-Me | 2 (—) | —CH$_2$C$_6$H$_4$—Me-2 | Me | Me |
| 4-Me | 2 (—) | —CH$_2$C$_6$H$_4$—Me-3 | Me | Me |
| 4-Me | 2 (—) | —CH$_2$C$_6$H$_4$—Me-4 | Me | Me |
| 4-Me | 2 (—) | —CH$_2$C$_6$H$_4$—OMe-2 | Me | Me |
| 4-Me | 2 (—) | —CH$_2$C$_6$H$_4$—OMe-3 | Me | Me |
| 4-Me | 2 (—) | —CH$_2$C$_6$H$_4$—OMe-4 | Me | Me |
| 4-Me | 2 (—) | —CH$_2$CH$_2$C$_6$H$_5$ | Me | Me |
| 4-Me | 2 (—) | H | OMe | OMe |
| 4-Me | 2 (—) | Na | OMe | OMe |
| 4-Me | 2 (—) | ½Ca | OMe | OMe |
| 4-Me | 2 (—) | $^i$PrNH$_3$ | OMe | OMe |
| 4-Me | 2 (—) | NH$_2$CONH$_3$ | OMe | OMe |
| 4-Me | 2 (—) | Me | OMe | OMe |
| 4-Me | 2 (—) | Et | OMe | OMe |
| 4-Me | 2 (—) | $^i$Pr | OMe | OMe |
| 4-Me | 2 (—) | Pr | OMe | OMe |
| 4-Me | 2 (—) | Bu | OMe | OMe |
| 4-Me | 2 (—) | $^i$Bu | OMe | OMe |
| 4-Me | 2 (—) | $^s$Bu | OMe | OMe |
| 4-Me | 2 (—) | —CH$_2$OCH$_3$ | OMe | OMe |
| 4-Me | 2 (—) | —CH$_2$CH$_2$OCH$_3$ | OMe | OMe |
| 4-Me | 2 (—) | —CH$_2$SCH$_3$ | OMe | OMe |
| 4-Me | 2 (—) | —CH$_2$CH=CH$_2$ | OMe | OMe |
| 4-Me | 2 (—) | —C(CH$_3$)$_2$CH=CH$_2$ | OMe | OMe |
| 4-Me | 2 (—) | —CH$_2$C≡CH$_2$ | OMe | OMe |
| 4-Me | 2 (—) | —CH$_2$C$_6$H$_5$ | OMe | OMe |
| 4-Me | 2 (—) | —CH$_2$C$_6$H$_4$—Cl-2 | OMe | OMe |
| 4-Me | 2 (—) | —CH$_2$C$_6$H$_4$—Cl-3 | OMe | OMe |
| 4-Me | 2 (—) | —CH$_2$C$_6$H$_4$—Cl-4 | OMe | OMe |
| 4-Me | 2 (—) | —CH$_2$C$_6$H$_4$—Me-2 | OMe | OMe |
| 4-Me | 2 (—) | —CH$_2$C$_6$H$_4$—Me-3 | OMe | OMe |
| 4-Me | 2 (—) | —CH$_2$C$_6$H$_4$—Me-4 | OMe | OMe |
| 4-Me | 2 (—) | —CH$_2$C$_6$H$_4$—OMe-2 | OMe | OMe |
| 4-Me | 2 (—) | —CH$_2$C$_6$H$_4$—OMe-3 | OMe | OMe |
| 4-Me | 2 (—) | —CH$_2$C$_6$H$_4$—OMe-4 | OMe | OMe |
| 4-Me | 2 (—) | —CH$_2$CH$_2$C$_6$H$_5$ | OMe | OMe |
| 5-Me | 1 (cis) | H | Me | Me |
| 5-Me | 1 (cis) | Na | Me | Me |
| 5-Me | 1 (cis) | ½Ca | Me | Me |
| 5-Me | 1 (cis) | $^i$PrNH$_3$ | Me | Me |
| 5-Me | 1 (cis) | NH$_2$CONH$_3$ | Me | Me |
| 5-Me | 1 (cis) | Me | Me | Me |
| 5-Me | 1 (cis) | Et | Me | Me |
| 5-Me | 1 (cis) | $^i$Pr | Me | Me |
| 5-Me | 1 (cis) | Pr | Me | Me |
| 5-Me | 1 (cis) | Bu | Me | Me |
| 5-Me | 1 (cis) | $^i$Bu | Me | Me |

TABLE -continued

A compound of the general formula:

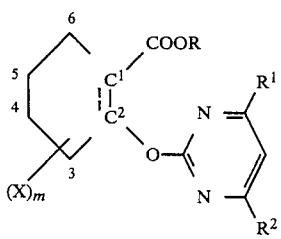

In the below-mentioned table, Me represents methyl group, Et represents ethyl group, Pr represents propyl group, $^i$Pr represents isopropyl group, Bu represents butyl group, $^i$Bu represents isobutyl group, $^s$Bu represents secondary butyl group, $^t$Bu represents tertiary butyl group, cis represents a cis-form, trans represents a trans-form, mix. represents a mixture of a cis-form and a trans-form, 1 represents a single bond and 2 represents a double bond.

| $(X)_m$ | === | R | $R^1$ | $R^2$ |
|---|---|---|---|---|
| 5-Me | 1 (cis) | $^s$Bu | Me | Me |
| 5-Me | 1 (cis) | —CH$_2$OCH$_3$ | Me | Me |
| 5-Me | 1 (cis) | —CH$_2$CH$_2$OCH$_3$ | Me | Me |
| 5-Me | 1 (cis) | —CH$_2$SCH$_3$ | Me | Me |
| 5-Me | 1 (cis) | —CH$_2$CH=CH$_2$ | Me | Me |
| 5-Me | 1 (cis) | —C(CH$_3$)$_2$CH=CH$_2$ | Me | Me |
| 5-Me | 1 (cis) | —CH$_2$C≡CH$_2$ | Me | Me |
| 5-Me | 1 (cis) | —CH$_2$C$_6$H$_5$ | Me | Me |
| 5-Me | 1 (cis) | —CH$_2$C$_6$H$_4$—Cl-2 | Me | Me |
| 5-Me | 1 (cis) | —CH$_2$C$_6$H$_4$—Cl-3 | Me | Me |
| 5-Me | 1 (cis) | —CH$_2$C$_6$H$_4$—Cl-4 | Me | Me |
| 5-Me | 1 (cis) | —CH$_2$C$_6$H$_4$—Me-2 | Me | Me |
| 5-Me | 1 (cis) | —CH$_2$C$_6$H$_4$—Me-3 | Me | Me |
| 5-Me | 1 (cis) | —CH$_2$C$_6$H$_4$—Me-4 | Me | Me |
| 5-Me | 1 (cis) | —CH$_2$C$_6$H$_4$—OMe-2 | Me | Me |
| 5-Me | 1 (cis) | —CH$_2$C$_6$H$_4$—OMe-3 | Me | Me |
| 5-Me | 1 (cis) | —CH$_2$C$_6$H$_4$—OMe-4 | Me | Me |
| 5-Me | 1 (cis) | —CH$_2$CH$_2$C$_6$H$_5$ | Me | Me |
| 5-Me | 1 (cis) | H | OMe | OMe |
| 5-Me | 1 (cis) | Na | OMe | OMe |
| 5-Me | 1 (cis) | ½Ca | OMe | OMe |
| 5-Me | 1 (cis) | $^i$PrNH$_3$ | OMe | OMe |
| 5-Me | 1 (cis) | NH$_2$CONH$_3$ | OMe | OMe |
| 5-Me | 1 (cis) | Me | OMe | OMe |
| 5-Me | 1 (cis) | Et | OMe | OMe |
| 5-Me | 1 (cis) | $^i$Pr | OMe | OMe |
| 5-Me | 1 (cis) | Pr | OMe | OMe |
| 5-Me | 1 (cis) | Bu | OMe | OMe |
| 5-Me | 1 (cis) | $^i$Bu | OMe | OMe |
| 5-Me | 1 (cis) | $^s$Bu | OMe | OMe |
| 5-Me | 1 (cis) | —CH$_2$OCH$_3$ | OMe | OMe |
| 5-Me | 1 (cis) | —CH$_2$CH$_2$OCH$_3$ | OMe | OMe |
| 5-Me | 1 (cis) | —CH$_2$SCH$_3$ | OMe | OMe |
| 5-Me | 1 (cis) | —CH$_2$CH=CH$_2$ | OMe | OMe |
| 5-Me | 1 (cis) | —C(CH$_3$)$_2$CH=CH$_2$ | OMe | OMe |
| 5-Me | 1 (cis) | —CH$_2$C≡CH$_2$ | OMe | OMe |
| 5-Me | 1 (cis) | —CH$_2$C$_6$H$_5$ | OMe | OMe |
| 5-Me | 1 (cis) | —CH$_2$C$_6$H$_4$—Cl-2 | OMe | OMe |
| 5-Me | 1 (cis) | —CH$_2$C$_6$H$_4$—Cl-3 | OMe | OMe |
| 5-Me | 1 (cis) | —CH$_2$C$_6$H$_4$—Cl-4 | OMe | OMe |
| 5-Me | 1 (cis) | —CH$_2$C$_6$H$_4$—Me-2 | OMe | OMe |
| 5-Me | 1 (cis) | —CH$_2$C$_6$H$_4$—Me-3 | OMe | OMe |
| 5-Me | 1 (cis) | —CH$_2$C$_6$H$_4$—Me-4 | OMe | OMe |
| 5-Me | 1 (cis) | —CH$_2$C$_6$H$_4$—OMe-2 | OMe | OMe |
| 5-Me | 1 (cis) | —CH$_2$C$_6$H$_4$—OMe-3 | OMe | OMe |
| 5-Me | 1 (cis) | —CH$_2$C$_6$H$_4$—OMe-4 | OMe | OMe |
| 5-Me | 1 (cis) | —CH$_2$CH$_2$C$_6$H$_5$ | OMe | OMe |
| 5-Me | 1 (trans) | H | Me | Me |
| 5-Me | 1 (trans) | Na | Me | Me |
| 5-Me | 1 (trans) | ½Ca | Me | Me |
| 5-Me | 1 (trans) | $^i$PrNH$_3$ | Me | Me |
| 5-Me | 1 (trans) | NH$_2$CONH$_3$ | Me | Me |
| 5-Me | 1 (trans) | Me | Me | Me |
| 5-Me | 1 (trans) | Et | Me | Me |
| 5-Me | 1 (trans) | $^i$Pr | Me | Me |
| 5-Me | 1 (trans) | Pr | Me | Me |
| 5-Me | 1 (trans) | Bu | Me | Me |

TABLE -continued

A compound of the general formula:

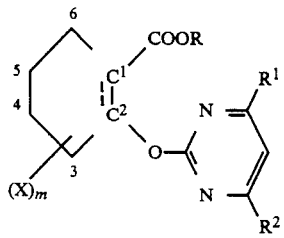

In the below-mentioned table, Me represents methyl group, Et represents ethyl group, Pr represents propyl group, $^i$Pr represents isopropyl group, Bu represents butyl group, $^i$Bu represents isobutyl group, $^s$Bu represents secondary butyl group, $^t$Bu represents tertiary butyl group, cis represents a cis-form, trans represents a trans-form, mix. represents a mixture of a cis-form and a trans-form, 1 represents a single bond and 2 represents a double bond.

| $(X)_m$ | === | R | $R^1$ | $R^2$ |
|---|---|---|---|---|
| 5-Me | 1 (trans) | $^i$Bu | Me | Me |
| 5-Me | 1 (trans) | $^s$Bu | Me | Me |
| 5-Me | 1 (trans) | —CH$_2$OCH$_3$ | Me | Me |
| 5-Me | 1 (trans) | —CH$_2$CH$_2$OCH$_3$ | Me | Me |
| 5-Me | 1 (trans) | —CH$_2$SCH$_3$ | Me | Me |
| 5-Me | 1 (trans) | —CH$_2$CH=CH$_2$ | Me | Me |
| 5-Me | 1 (trans) | —C(CH$_3$)$_2$CH=CH$_2$ | Me | Me |
| 5-Me | 1 (trans) | —CH$_2$C≡CH$_2$ | Me | Me |
| 5-Me | 1 (trans) | —CH$_2$C$_6$H$_5$ | Me | Me |
| 5-Me | 1 (trans) | —CH$_2$C$_6$H$_4$—Cl-2 | Me | Me |
| 5-Me | 1 (trans) | —CH$_2$C$_6$H$_4$—Cl-3 | Me | Me |
| 5-Me | 1 (trans) | —CH$_2$C$_6$H$_4$—Cl-4 | Me | Me |
| 5-Me | 1 (trans) | —CH$_2$C$_6$H$_4$—Me-2 | Me | Me |
| 5-Me | 1 (trans) | —CH$_2$C$_6$H$_4$—Me-3 | Me | Me |
| 5-Me | 1 (trans) | —CH$_2$C$_6$H$_4$—Me-4 | Me | Me |
| 5-Me | 1 (trans) | —CH$_2$C$_6$H$_4$—OMe-2 | Me | Me |
| 5-Me | 1 (trans) | —CH$_2$C$_6$H$_4$—OMe-3 | Me | Me |
| 5-Me | 1 (trans) | —CH$_2$C$_6$H$_4$—OMe-4 | Me | Me |
| 5-Me | 1 (trans) | —CH$_2$CH$_2$C$_6$H$_5$ | Me | Me |
| 5-Me | 1 (trans) | H | OMe | OMe |
| 5-Me | 1 (trans) | Na | OMe | OMe |
| 5-Me | 1 (trans) | ½Ca | OMe | OMe |
| 5-Me | 1 (trans) | $^i$PrNH$_3$ | OMe | OMe |
| 5-Me | 1 (trans) | NH$_2$CONH$_3$ | OMe | OMe |
| 5-Me | 1 (trans) | Me | OMe | OMe |
| 5-Me | 1 (trans) | Et | OMe | OMe |
| 5-Me | 1 (trans) | $^i$Pr | OMe | OMe |
| 5-Me | 1 (trans) | Pr | OMe | OMe |
| 5-Me | 1 (trans) | Bu | OMe | OMe |
| 5-Me | 1 (trans) | $^i$Bu | OMe | OMe |
| 5-Me | 1 (trans) | $^s$Bu | OMe | OMe |
| 5-Me | 1 (trans) | —CH$_2$OCH$_3$ | OMe | OMe |
| 5-Me | 1 (trans) | —CH$_2$CH$_2$OCH$_3$ | OMe | OMe |
| 5-Me | 1 (trans) | —CH$_2$SCH$_3$ | OMe | OMe |
| 5-Me | 1 (trans) | —CH$_2$CH=CH$_2$ | OMe | OMe |
| 5-Me | 1 (trans) | —C(CH$_3$)$_2$CH=CH$_2$ | OMe | OMe |
| 5-Me | 1 (trans) | —CH$_2$C≡CH$_2$ | OMe | OMe |
| 5-Me | 1 (trans) | —CH$_2$C$_6$H$_5$ | OMe | OMe |
| 5-Me | 1 (trans) | —CH$_2$C$_6$H$_4$—Cl-2 | OMe | OMe |
| 5-Me | 1 (trans) | —CH$_2$C$_6$H$_4$—Cl-3 | OMe | OMe |
| 5-Me | 1 (trans) | —CH$_2$C$_6$H$_4$—Cl-4 | OMe | OMe |
| 5-Me | 1 (trans) | —CH$_2$C$_6$H$_4$—Me-2 | OMe | OMe |
| 5-Me | 1 (trans) | —CH$_2$C$_6$H$_4$—Me-3 | OMe | OMe |
| 5-Me | 1 (trans) | —CH$_2$C$_6$H$_4$—Me-4 | OMe | OMe |
| 5-Me | 1 (trans) | —CH$_2$C$_6$H$_4$—OMe-2 | OMe | OMe |
| 5-Me | 1 (trans) | —CH$_2$C$_6$H$_4$—OMe-3 | OMe | OMe |
| 5-Me | 1 (trans) | —CH$_2$C$_6$H$_4$—OMe-4 | OMe | OMe |
| 5-Me | 1 (trans) | —CH$_2$CH$_2$C$_6$H$_5$ | OMe | OMe |
| 5-Me | 1 (mixt.) | H | Me | Me |
| 5-Me | 1 (mixt.) | Na | Me | Me |
| 5-Me | 1 (mixt.) | ½Ca | Me | Me |
| 5-Me | 1 (mixt.) | $^i$PrNH$_3$ | Me | Me |
| 5-Me | 1 (mixt.) | NH$_2$CONH$_3$ | Me | Me |
| 5-Me | 1 (mixt.) | Me | Me | Me |
| 5-Me | 1 (mixt.) | Et | Me | Me |
| 5-Me | 1 (mixt.) | $^i$Pr | Me | Me |
| 5-Me | 1 (mixt.) | Pr | Me | Me |

TABLE -continued

A compound of the general formula:

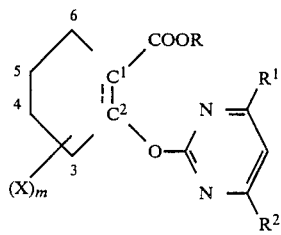

In the below-mentioned table, Me represents methyl group, Et represents ethyl group, Pr represents propyl group, $^i$Pr represents isopropyl group, Bu represents butyl group, $^i$Bu represents isobutyl group, $^s$Bu represents secondary butyl group, $^t$Bu represents tertiary butyl group, cis represents a cis-form, trans represents a trans-form, mix. represents a mixture of a cis-form and a trans-form, 1 represents a single bond and 2 represents a double bond.

| $(X)_m$ | === | R | $R^1$ | $R^2$ |
|---|---|---|---|---|
| 5-Me | 1 (mixt.) | Bu | Me | Me |
| 5-Me | 1 (mixt.) | $^i$Bu | Me | Me |
| 5-Me | 1 (mixt.) | $^s$Bu | Me | Me |
| 5-Me | 1 (mixt.) | —CH$_2$OCH$_3$ | Me | Me |
| 5-Me | 1 (mixt.) | —CH$_2$CH$_2$OCH$_3$ | Me | Me |
| 5-Me | 1 (mixt.) | —CH$_2$SCH$_3$ | Me | Me |
| 5-Me | 1 (mixt.) | —CH$_2$CH=CH$_2$ | Me | Me |
| 5-Me | 1 (mixt.) | —C(CH$_3$)$_2$CH=CH$_2$ | Me | Me |
| 5-Me | 1 (mixt.) | —CH$_2$C≡CH$_2$ | Me | Me |
| 5-Me | 1 (mixt.) | —CH$_2$C$_6$H$_5$ | Me | Me |
| 5-Me | 1 (mixt.) | —CH$_2$C$_6$H$_4$—Cl-2 | Me | Me |
| 5-Me | 1 (mixt.) | —CH$_2$C$_6$H$_4$—Cl-3 | Me | Me |
| 5-Me | 1 (mixt.) | —CH$_2$C$_6$H$_4$—Cl-4 | Me | Me |
| 5-Me | 1 (mixt.) | —CH$_2$C$_6$H$_4$—Me-2 | Me | Me |
| 5-Me | 1 (mixt.) | —CH$_2$C$_6$H$_4$—Me-3 | Me | Me |
| 5-Me | 1 (mixt.) | —CH$_2$C$_6$H$_4$—Me-4 | Me | Me |
| 5-Me | 1 (mixt.) | —CH$_2$C$_6$H$_4$—OMe-2 | Me | Me |
| 5-Me | 1 (mixt.) | —CH$_2$C$_6$H$_4$—OMe-3 | Me | Me |
| 5-Me | 1 (mixt.) | —CH$_2$C$_6$H$_4$—OMe-4 | Me | Me |
| 5-Me | 1 (mixt.) | —CH$_2$CH$_2$C$_6$H$_5$ | Me | Me |
| 5-Me | 1 (mixt.) | H | OMe | OMe |
| 5-Me | 1 (mixt.) | Na | OMe | OMe |
| 5-Me | 1 (mixt.) | ½Ca | OMe | OMe |
| 5-Me | 1 (mixt.) | $^i$PrNH$_3$ | OMe | OMe |
| 5-Me | 1 (mixt.) | NH$_2$CONH$_3$ | OMe | OMe |
| 5-Me | 1 (mixt.) | Me | OMe | OMe |
| 5-Me | 1 (mixt.) | Et | OMe | OMe |
| 5-Me | 1 (mixt.) | $^i$Pr | OMe | OMe |
| 5-Me | 1 (mixt.) | Pr | OMe | OMe |
| 5-Me | 1 (mixt.) | Bu | OMe | OMe |
| 5-Me | 1 (mixt.) | $^i$Bu | OMe | OMe |
| 5-Me | 1 (mixt.) | $^s$Bu | OMe | OMe |
| 5-Me | 1 (mixt.) | —CH$_2$OCH$_3$ | OMe | OMe |
| 5-Me | 1 (mixt.) | —CH$_2$CH$_2$OCH$_3$ | OMe | OMe |
| 5-Me | 1 (mixt.) | —CH$_2$SCH$_3$ | OMe | OMe |
| 5-Me | 1 (mixt.) | —CH$_2$CH=CH$_2$ | OMe | OMe |
| 5-Me | 1 (mixt.) | —C(CH$_3$)$_2$CH=CH$_2$ | OMe | OMe |
| 5-Me | 1 (mixt.) | —CH$_2$C≡CH$_2$ | OMe | OMe |
| 5-Me | 1 (mixt.) | —CH$_2$C$_6$H$_5$ | OMe | OMe |
| 5-Me | 1 (mixt.) | —CH$_2$C$_6$H$_4$—Cl-2 | OMe | OMe |
| 5-Me | 1 (mixt.) | —CH$_2$C$_6$H$_4$—Cl-3 | OMe | OMe |
| 5-Me | 1 (mixt.) | —CH$_2$C$_6$H$_4$—Cl-4 | OMe | OMe |
| 5-Me | 1 (mixt.) | —CH$_2$C$_6$H$_4$—Me-2 | OMe | OMe |
| 5-Me | 1 (mixt.) | —CH$_2$C$_6$H$_4$—Me-3 | OMe | OMe |
| 5-Me | 1 (mixt.) | —CH$_2$C$_6$H$_4$—Me-4 | OMe | OMe |
| 5-Me | 1 (mixt.) | —CH$_2$C$_6$H$_4$—OMe-2 | OMe | OMe |
| 5-Me | 1 (mixt.) | —CH$_2$C$_6$H$_4$—OMe-3 | OMe | OMe |
| 5-Me | 1 (mixt.) | —CH$_2$C$_6$H$_4$—OMe-4 | OMe | OMe |
| 5-Me | 1 (mixt.) | —CH$_2$CH$_2$C$_6$H$_5$ | OMe | OMe |
| 5-Me | 2 (—) | H | Me | Me |
| 5-Me | 2 (—) | Na | Me | Me |
| 5-Me | 2 (—) | ½Ca | Me | Me |
| 5-Me | 2 (—) | $^i$PrNH$_3$ | Me | Me |
| 5-Me | 2 (—) | NH$_2$CONH$_3$ | Me | Me |
| 5-Me | 2 (—) | Me | Me | Me |
| 5-Me | 2 (—) | Et | Me | Me |
| 5-Me | 2 (—) | $^i$Pr | Me | Me |

TABLE -continued

A compound of the general formula:

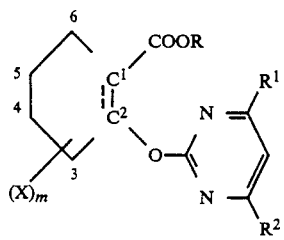

In the below-mentioned table, Me represents methyl group, Et represents ethyl group, Pr represents propyl group, $^i$Pr represents isopropyl group, Bu represents butyl group, $^i$Bu represents isobutyl group, $^s$Bu represents secondary butyl group, $^t$Bu represents tertiary butyl group, cis represents a cis-form, trans represents a trans-form, mix. represents a mixture of a cis-form and a trans-form, 1 represents a single bond and 2 represents a double bond.

| (X)$_m$ | === | R | R$^1$ | R$^2$ |
|---|---|---|---|---|
| 5-Me | 2 (—) | Pr | Me | Me |
| 5-Me | 2 (—) | Bu | Me | Me |
| 5-Me | 2 (—) | $^i$Bu | Me | Me |
| 5-Me | 2 (—) | $^s$Bu | Me | Me |
| 5-Me | 2 (—) | —CH$_2$OCH$_3$ | Me | Me |
| 5-Me | 2 (—) | —CH$_2$CH$_2$OCH$_3$ | Me | Me |
| 5-Me | 2 (—) | —CH$_2$SCH$_3$ | Me | Me |
| 5-Me | 2 (—) | —CH$_2$CH=CH$_2$ | Me | Me |
| 5-Me | 2 (—) | —C(CH$_3$)$_2$CH=CH$_2$ | Me | Me |
| 5-Me | 2 (—) | —CH$_2$C≡CH$_2$ | Me | Me |
| 5-Me | 2 (—) | —CH$_2$C$_6$H$_5$ | Me | Me |
| 5-Me | 2 (—) | —CH$_2$C$_6$H$_4$—Cl-2 | Me | Me |
| 5-Me | 2 (—) | —CH$_2$C$_6$H$_4$—Cl-3 | Me | Me |
| 5-Me | 2 (—) | —CH$_2$C$_6$H$_4$—Cl-4 | Me | Me |
| 5-Me | 2 (—) | —CH$_2$C$_6$H$_4$—Me-2 | Me | Me |
| 5-Me | 2 (—) | —CH$_2$C$_6$H$_4$—Me-3 | Me | Me |
| 5-Me | 2 (—) | —CH$_2$C$_6$H$_4$—Me-4 | Me | Me |
| 5-Me | 2 (—) | —CH$_2$C$_6$H$_4$—OMe-2 | Me | Me |
| 5-Me | 2 (—) | —CH$_2$C$_6$H$_4$—OMe-3 | Me | Me |
| 5-Me | 2 (—) | —CH$_2$C$_6$H$_4$—OMe-4 | Me | Me |
| 5-Me | 2 (—) | —CH$_2$CH$_2$C$_6$H$_5$ | Me | Me |
| 5-Me | 2 (—) | H | OMe | OMe |
| 5-Me | 2 (—) | Na | OMe | OMe |
| 5-Me | 2 (—) | ½Ca | OMe | OMe |
| 5-Me | 2 (—) | $^i$PrNH$_3$ | OMe | PMe |
| 5-Me | 2 (—) | NH$_2$CONH$_3$ | OMe | OMe |
| 5-Me | 2 (—) | Me | OMe | OMe |
| 5-Me | 2 (—) | Et | OMe | OMe |
| 5-Me | 2 (—) | $^i$Pr | OMe | OMe |
| 5-Me | 2 (—) | Pr | OMe | OMe |
| 5-Me | 2 (—) | Bu | OMe | OMe |
| 5-Me | 2 (—) | $^i$Bu | OMe | OMe |
| 5-Me | 2 (—) | $^s$Bu | OMe | OMe |
| 5-Me | 2 (—) | —CH$_2$OCH$_3$ | OMe | OMe |
| 5-Me | 2 (—) | —CH$_2$CH$_2$OCH$_3$ | OMe | OMe |
| 5-Me | 2 (—) | —CH$_2$SCH$_3$ | OMe | OMe |
| 5-Me | 2 (—) | —CH$_2$CH=CH$_2$ | OMe | OMe |
| 5-Me | 2 (—) | —C(CH$_3$)$_2$CH=CH$_2$ | OMe | OMe |
| 5-Me | 2 (—) | —CH$_2$C≡CH$_2$ | OMe | OMe |
| 5-Me | 2 (—) | —CH$_2$C$_6$H$_5$ | OMe | OMe |
| 5-Me | 2 (—) | —CH$_2$C$_6$H$_4$—Cl-2 | OMe | OMe |
| 5-Me | 2 (—) | —CH$_2$C$_6$H$_4$—Cl-3 | OMe | OMe |
| 5-Me | 2 (—) | —CH$_2$C$_6$H$_4$—Cl-4 | OMe | OMe |
| 5-Me | 2 (—) | —CH$_2$C$_6$H$_4$—Me-2 | OMe | OMe |
| 5-Me | 2 (—) | —CH$_2$C$_6$H$_4$—Me-3 | OMe | OMe |
| 5-Me | 2 (—) | —CH$_2$C$_6$H$_4$—Me-4 | OMe | OMe |
| 5-Me | 2 (—) | —CH$_2$C$_6$H$_4$—OMe-2 | OMe | OMe |
| 5-Me | 2 (—) | —CH$_2$C$_6$H$_4$—OMe-3 | OMe | OMe |
| 5-Me | 2 (—) | —CH$_2$C$_6$H$_4$—OMe-4 | OMe | OMe |
| 5-Me | 2 (—) | —CH$_2$CH$_2$C$_6$H$_5$ | OMe | OMe |
| 3.3-(Me)$_2$ | 1 (cis) | H | Me | Me |
| 3.3-(Me)$_2$ | 1 (cis) | Na | Me | Me |
| 3.3-(Me)$_2$ | 1 (cis) | ½Ca | Me | Me |
| 3.3-(Me)$_2$ | 1 (cis) | $^i$PrNH$_3$ | Me | Me |
| 3.3-(Me)$_2$ | 1 (cis) | NH$_2$CONH$_3$ | Me | Me |
| 3.3-(Me)$_2$ | 1 (cis) | Me | Me | Me |
| 3.3-(Me)$_2$ | 1 (cis) | Et | Me | Me |

TABLE -continued

A compound of the general formula:

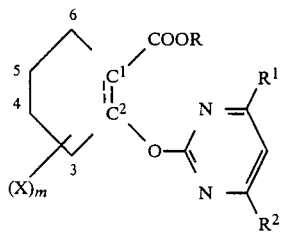

In the below-mentioned table, Me represents methyl group, Et represents ethyl group, Pr represents propyl group, $^i$Pr represents isopropyl group, Bu represents butyl group, $^i$Bu represents isobutyl group, $^s$Bu represents secondary butyl group, $^t$Bu represents tertiary butyl group, cis represents a cis-form, trans represents a trans-form, mix. represents a mixture of a cis-form and a trans-form, 1 represents a single bond and 2 represents a double bond.

| $(X)_m$ | --- | R | $R^1$ | $R^2$ |
|---|---|---|---|---|
| 3.3-(Me)$_2$ | 1 (cis) | $^i$Pr | Me | Me |
| 3.3-(Me)$_2$ | 1 (cis) | Pr | Me | Me |
| 3.3-(Me)$_2$ | 1 (cis) | Bu | Me | Me |
| 3.3-(Me)$_2$ | 1 (cis) | $^i$Bu | Me | Me |
| 3.3-(Me)$_2$ | 1 (cis) | $^s$Bu | Me | Me |
| 3.3-(Me)$_2$ | 1 (cis) | —CH$_2$OCH$_3$ | Me | Me |
| 3.3-(Me)$_2$ | 1 (cis) | —CH$_2$CH$_2$OCH$_3$ | Me | Me |
| 3.3-(Me)$_2$ | 1 (cis) | —CH$_2$SCH$_3$ | Me | Me |
| 3.3-(Me)$_2$ | 1 (cis) | —CH$_2$CH=CH$_2$ | Me | Me |
| 3.3-(Me)$_2$ | 1 (cis) | —C(CH$_3$)$_2$CH=CH$_2$ | Me | Me |
| 3.3-(Me)$_2$ | 1 (cis) | —CH$_2$C≡CH$_2$ | Me | Me |
| 3.3-(Me)$_2$ | 1 (cis) | —CH$_2$C$_6$H$_5$ | Me | Me |
| 3.3-(Me)$_2$ | 1 (cis) | —CH$_2$C$_6$H$_4$—Cl-2 | Me | Me |
| 3.3-(Me)$_2$ | 1 (cis) | —CH$_2$C$_6$H$_4$—Cl-3 | Me | Me |
| 3.3-(Me)$_2$ | 1 (cis) | —CH$_2$C$_6$H$_4$—Cl-4 | Me | Me |
| 3.3-(Me)$_2$ | 1 (cis) | —CH$_2$C$_6$H$_4$—Me-2 | Me | Me |
| 3.3-(Me)$_2$ | 1 (cis) | —CH$_2$C$_6$H$_4$—Me-3 | Me | Me |
| 3.3-(Me)$_2$ | 1 (cis) | —CH$_2$C$_6$H$_4$—Me-4 | Me | Me |
| 3.3-(Me)$_2$ | 1 (cis) | —CH$_2$C$_6$H$_4$—OMe-2 | Me | Me |
| 3.3-(Me)$_2$ | 1 (cis) | —CH$_2$C$_6$H$_4$—OMe-3 | Me | Me |
| 3.3-(Me)$_2$ | 1 (cis) | —CH$_2$C$_6$H$_4$—OMe-4 | Me | Me |
| 3.3-(Me)$_2$ | 1 (cis) | —CH$_2$CH$_2$C$_6$H$_5$ | Me | Me |
| 3.3-(Me)$_2$ | 1 (cis) | H | OMe | OMe |
| 3.3-(Me)$_2$ | 1 (cis) | Na | OMe | OMe |
| 3.3-(Me)$_2$ | 1 (cis) | ½Ca | OMe | OMe |
| 3.3-(Me)$_2$ | 1 (cis) | $^i$PrNH$_3$ | OMe | OMe |
| 3.3-(Me)$_2$ | 1 (cis) | NH$_2$CONH$_3$ | OMe | OMe |
| 3.3-(Me)$_2$ | 1 (cis) | Me | OMe | OMe |
| 3.3-(Me)$_2$ | 1 (cis) | Et | OMe | OMe |
| 3.3-(Me)$_2$ | 1 (cis) | $^i$Pr | OMe | OMe |
| 3.3-(Me)$_2$ | 1 (cis) | Pr | OMe | OMe |
| 3.3-(Me)$_2$ | 1 (cis) | Bu | OMe | OMe |
| 3.3-(Me)$_2$ | 1 (cis) | $^i$Bu | OMe | OMe |
| 3.3-(Me)$_2$ | 1 (cis) | $^s$Bu | OMe | OMe |
| 3.3-(Me)$_2$ | 1 (cis) | —CH$_2$OCH$_3$ | OMe | OMe |
| 3.3-(Me)$_2$ | 1 (cis) | —CH$_2$CH$_2$OCH$_3$ | OMe | OMe |
| 3.3-(Me)$_2$ | 1 (cis) | —CH$_2$SCH$_3$ | OMe | OMe |
| 3.3-(Me)$_2$ | 1 (cis) | —CH$_2$CH=CH$_2$ | OMe | OMe |
| 3.3-(Me)$_2$ | 1 (cis) | —C(CH$_3$)$_2$CH=CH$_2$ | OMe | OMe |
| 3.3-(Me)$_2$ | 1 (cis) | —CH$_2$C≡CH$_2$ | OMe | OMe |
| 3.3-(Me)$_2$ | 1 (cis) | —CH$_2$C$_6$H$_5$ | OMe | OMe |
| 3.3-(Me)$_2$ | 1 (cis) | —CH$_2$C$_6$H$_4$—Cl-2 | OMe | OMe |
| 3.3-(Me)$_2$ | 1 (cis) | —CH$_2$C$_6$H$_4$—Cl-3 | OMe | OMe |
| 3.3-(Me)$_2$ | 1 (cis) | —CH$_2$C$_6$H$_4$—Cl-4 | OMe | OMe |
| 3.3-(Me)$_2$ | 1 (cis) | —CH$_2$C$_6$H$_4$—Me-2 | OMe | OMe |
| 3.3-(Me)$_2$ | 1 (cis) | —CH$_2$C$_6$H$_4$—Me-3 | OMe | OMe |
| 3.3-(Me)$_2$ | 1 (cis) | —CH$_2$C$_6$H$_4$—Me-4 | OMe | OMe |
| 3.3-(Me)$_2$ | 1 (cis) | —CH$_2$C$_6$H$_4$—OMe-2 | OMe | OMe |
| 3.3-(Me)$_2$ | 1 (cis) | —CH$_2$C$_6$H$_4$—OMe-3 | OMe | OMe |
| 3.3-(Me)$_2$ | 1 (cis) | —CH$_2$C$_6$H$_4$—OMe-4 | OMe | OMe |
| 3.3-(Me)$_2$ | 1 (cis) | —CH$_2$CH$_2$C$_6$H$_5$ | OMe | OMe |
| 3.3-(Me)$_2$ | 1 (trans) | H | Me | Me |
| 3.3-(Me)$_2$ | 1 (trans) | Na | Me | Me |
| 3.3-(Me)$_2$ | 1 (trans) | ½Ca | Me | Me |
| 3.3-(Me)$_2$ | 1 (trans) | $^i$PrNH$_3$ | Me | Me |
| 3.3-(Me)$_2$ | 1 (trans) | NH$_2$CONH$_3$ | Me | Me |
| 3.3-(Me)$_2$ | 1 (trans) | Me | Me | Me |

TABLE -continued

A compound of the general formula:

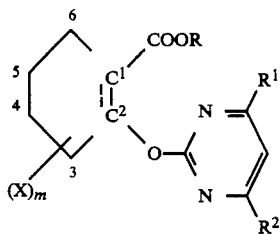

In the below-mentioned table, Me represents methyl group, Et represents ethyl group, Pr represents propyl group, $^i$Pr represents isopropyl group, Bu represents butyl group, $^i$Bu represents isobutyl group, $^s$Bu represents secondary butyl group, $^t$Bu represents tertiary butyl group, cis represents a cis-form, trans represents a trans-form, mix. represents a mixture of a cis-form and a trans-form, 1 represents a single bond and 2 represents a double bond.

| $(X)_m$ | === | R | $R^1$ | $R^2$ |
|---|---|---|---|---|
| 3,3-(Me)$_2$ | 1 (trans) | Et | Me | Me |
| 3,3-(Me)$_2$ | 1 (trans) | $^i$Pr | Me | Me |
| 3,3-(Me)$_2$ | 1 (trans) | Pr | Me | Me |
| 3,3-(Me)$_2$ | 1 (trans) | Bu | Me | Me |
| 3,3-(Me)$_2$ | 1 (trans) | $^i$Bu | Me | Me |
| 3,3-(Me)$_2$ | 1 (trans) | $^s$Bu | Me | Me |
| 3,3-(Me)$_2$ | 1 (trans) | —CH$_2$OCH$_3$ | Me | Me |
| 3,3-(Me)$_2$ | 1 (trans) | —CH$_2$CH$_2$OCH$_3$ | Me | Me |
| 3,3-(Me)$_2$ | 1 (trans) | —CH$_2$SCH$_3$ | Me | Me |
| 3,3-(Me)$_2$ | 1 (trans) | —CH$_2$CH=CH$_2$ | Me | Me |
| 3,3-(Me)$_2$ | 1 (trans) | —C(CH$_3$)$_2$CH=CH$_2$ | Me | Me |
| 3,3-(Me)$_2$ | 1 (trans) | —CH$_2$C≡CH$_2$ | Me | Me |
| 3,3-(Me)$_2$ | 1 (trans) | —CH$_2$C$_6$H$_5$ | Me | Me |
| 3,3-(Me)$_2$ | 1 (trans) | —CH$_2$C$_6$H$_4$—Cl-2 | Me | Me |
| 3,3-(Me)$_2$ | 1 (trans) | —CH$_2$C$_6$H$_4$—Cl-3 | Me | Me |
| 3,3-(Me)$_2$ | 1 (trans) | —CH$_2$C$_6$H$_4$—Cl-4 | Me | Me |
| 3,3-(Me)$_2$ | 1 (trans) | —CH$_2$C$_6$H$_4$—Me-2 | Me | Me |
| 3,3-(Me)$_2$ | 1 (trans) | —CH$_2$C$_6$H$_4$—Me-3 | Me | Me |
| 3,3-(Me)$_2$ | 1 (trans) | —CH$_2$C$_6$H$_4$—Me-4 | Me | Me |
| 3,3-(Me)$_2$ | 1 (trans) | —CH$_2$C$_6$H$_4$—OMe-2 | Me | Me |
| 3,3-(Me)$_2$ | 1 (trans) | —CH$_2$C$_6$H$_4$—OMe-3 | Me | Me |
| 3,3-(Me)$_2$ | 1 (trans) | —CH$_2$C$_6$H$_4$—OMe-4 | Me | Me |
| 3,3-(Me)$_2$ | 1 (trans) | —CH$_2$CH$_2$C$_6$H$_5$ | Me | Me |
| 3,3-(Me)$_2$ | 1 (trans) | H | OMe | OMe |
| 3,3-(Me)$_2$ | 1 (trans) | Na | OMe | OMe |
| 3,3-(Me)$_2$ | 1 (trans) | ½Ca | OMe | OMe |
| 3,3-(Me)$_2$ | 1 (trans) | $^i$PrNH$_3$ | OMe | OMe |
| 3,3-(Me)$_2$ | 1 (trans) | NH$_2$CONH$_3$ | OMe | OMe |
| 3,3-(Me)$_2$ | 1 (trans) | Me | OMe | OMe |
| 3,3-(Me)$_2$ | 1 (trans) | Et | OMe | OMe |
| 3,3-(Me)$_2$ | 1 (trans) | $^i$Pr | OMe | OMe |
| 3,3-(Me)$_2$ | 1 (trans) | Pr | OMe | OMe |
| 3,3-(Me)$_2$ | 1 (trans) | Bu | OMe | OMe |
| 3,3-(Me)$_2$ | 1 (trans) | $^i$Bu | OMe | OMe |
| 3,3-(Me)$_2$ | 1 (trans) | $^s$Bu | OMe | OMe |
| 3,3-(Me)$_2$ | 1 (trans) | —CH$_2$OCH$_3$ | OMe | OMe |
| 3,3-(Me)$_2$ | 1 (trans) | —CH$_2$CH$_2$OCH$_3$ | OMe | OMe |
| 3,3-(Me)$_2$ | 1 (trans) | —CH$_2$SCH$_3$ | OMe | OMe |
| 3,3-(Me)$_2$ | 1 (trans) | —CH$_2$CH=CH$_2$ | OMe | OMe |
| 3,3-(Me)$_2$ | 1 (trans) | —C(CH$_3$)$_2$CH=CH$_2$ | OMe | OMe |
| 3,3-(Me)$_2$ | 1 (trans) | —CH$_2$C≡CH$_2$ | OMe | OMe |
| 3,3-(Me)$_2$ | 1 (trans) | —CH$_2$C$_6$H$_5$ | OMe | OMe |
| 3,3-(Me)$_2$ | 1 (trans) | —CH$_2$C$_6$H$_4$—Cl-2 | OMe | OMe |
| 3,3-(Me)$_2$ | 1 (trans) | —CH$_2$C$_6$H$_4$—Cl-3 | OMe | OMe |
| 3,3-(Me)$_2$ | 1 (trans) | —CH$_2$C$_6$H$_4$—Cl-4 | OMe | OMe |
| 3,3-(Me)$_2$ | 1 (trans) | —CH$_2$C$_6$H$_4$—Me-2 | OMe | OMe |
| 3,3-(Me)$_2$ | 1 (trans) | —CH$_2$C$_6$H$_4$—Me-3 | OMe | OMe |
| 3,3-(Me)$_2$ | 1 (trans) | —CH$_2$C$_6$H$_4$—Me-4 | OMe | OMe |
| 3,3-(Me)$_2$ | 1 (trans) | —CH$_2$C$_6$H$_4$—OMe-2 | OMe | OMe |
| 3,3-(Me)$_2$ | 1 (trans) | —CH$_2$C$_6$H$_4$—OMe-3 | OMe | OMe |
| 3,3-(Me)$_2$ | 1 (trans) | —CH$_2$C$_6$H$_4$—OMe-4 | OMe | OMe |
| 3,3-(Me)$_2$ | 1 (trans) | —CH$_2$CH$_2$C$_6$H$_5$ | OMe | OMe |
| 3,3-(Me)$_2$ | 1 (mixt.) | H | Me | Me |
| 3,3-(Me)$_2$ | 1 (mixt.) | Na | Me | Me |
| 3,3-(Me)$_2$ | 1 (mixt.) | ½Ca | Me | Me |
| 3,3-(Me)$_2$ | 1 (mixt.) | $^i$PrNH$_3$ | Me | Me |
| 3,3-(Me)$_2$ | 1 (mixt.) | NH$_2$CONH$_3$ | Me | Me |

TABLE -continued

A compound of the general formula:

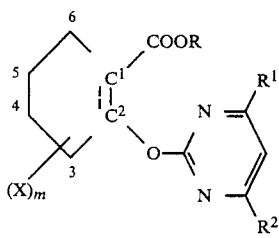

In the below-mentioned table, Me represents methyl group, Et represents ethyl group, Pr represents propyl group, $^i$Pr represents isopropyl group, Bu represents butyl group, $^i$Bu represents isobutyl group, $^s$Bu represents secondary butyl group, $^t$Bu represents tertiary butyl group, cis represents a cis-form, trans represents a trans-form, mix. represents a mixture of a cis-form and a trans-form, 1 represents a single bond and 2 represents a double bond.

| (X)$_m$ | === | R | R$^1$ | R$^2$ |
|---|---|---|---|---|
| 3.3-(Me)$_2$ | 1 (mixt.) | Me | Me | Me |
| 3.3-(Me)$_2$ | 1 (mixt.) | Et | Me | Me |
| 3.3-(Me)$_2$ | 1 (mixt.) | $^i$Pr | Me | Me |
| 3.3-(Me)$_2$ | 1 (mixt.) | Pr | Me | Me |
| 3.3-(Me)$_2$ | 1 (mixt.) | Bu | Me | Me |
| 3.3-(Me)$_2$ | 1 (mixt.) | $^i$Bu | Me | Me |
| 3.3-(Me)$_2$ | 1 (mixt.) | $^s$Bu | Me | Me |
| 3.3-(Me)$_2$ | 1 (mixt.) | —CH$_2$OCH$_3$ | Me | Me |
| 3.3-(Me)$_2$ | 1 (mixt.) | —CH$_2$CH$_2$OCH$_3$ | Me | Me |
| 3.3-(Me)$_2$ | 1 (mixt.) | —CH$_2$SCH$_3$ | Me | Me |
| 3.3-(Me)$_2$ | 1 (mixt.) | —CH$_2$CH=CH$_2$ | Me | Me |
| 3.3-(Me)$_2$ | 1 (mixt.) | —C(CH$_3$)$_2$CH=CH$_2$ | Me | Me |
| 3.3-(Me)$_2$ | 1 (mixt.) | —CH$_2$C≡CH$_2$ | Me | Me |
| 3.3-(Me)$_2$ | 1 (mixt.) | —CH$_2$C$_6$H$_5$ | Me | Me |
| 3.3-(Me)$_2$ | 1 (mixt.) | —CH$_2$C$_6$H$_4$—Cl-2 | Me | Me |
| 3.3-(Me)$_2$ | 1 (mixt.) | —CH$_2$C$_6$H$_4$—Cl-3 | Me | Me |
| 3.3-(Me)$_2$ | 1 (mixt.) | —CH$_2$C$_6$H$_4$—Cl-4 | Me | Me |
| 3.3-(Me)$_2$ | 1 (mixt.) | —CH$_2$C$_6$H$_4$—Me-2 | Me | Me |
| 3.3-(Me)$_2$ | 1 (mixt.) | —CH$_2$C$_6$H$_4$—Me-3 | Me | Me |
| 3.3-(Me)$_2$ | 1 (mixt.) | —CH$_2$C$_6$H$_4$—Me-4 | Me | Me |
| 3.3-(Me)$_2$ | 1 (mixt.) | —CH$_2$C$_6$H$_4$—OMe-2 | Me | Me |
| 3.3-(Me)$_2$ | 1 (mixt.) | —CH$_2$C$_6$H$_4$—OMe-3 | Me | Me |
| 3.3-(Me)$_2$ | 1 (mixt.) | —CH$_2$C$_6$H$_4$—OMe-4 | Me | Me |
| 3.3-(Me)$_2$ | 1 (mixt.) | —CH$_2$CH$_2$C$_6$H$_5$ | Me | Me |
| 3.3-(Me)$_2$ | 1 (mixt.) | H | OMe | OMe |
| 3.3-(Me)$_2$ | 1 (mixt.) | Na | OMe | OMe |
| 3.3-(Me)$_2$ | 1 (mixt.) | ½Ca | OMe | OMe |
| 3.3-(Me)$_2$ | 1 (mixt.) | $^i$PrNH$_3$ | OMe | OMe |
| 3.3-(Me)$_2$ | 1 (mixt.) | NH$_2$CONH$_3$ | OMe | OMe |
| 3.3-(Me)$_2$ | 1 (mixt.) | Me | OMe | OMe |
| 3.3-(Me)$_2$ | 1 (mixt.) | Et | OMe | OMe |
| 3.3-(Me)$_2$ | 1 (mixt.) | $^i$Pr | OMe | OMe |
| 3.3-(Me)$_2$ | 1 (mixt.) | Pr | OMe | OMe |
| 3.3-(Me)$_2$ | 1 (mixt.) | Bu | OMe | OMe |
| 3.3-(Me)$_2$ | 1 (mixt.) | $^i$Bu | OMe | OMe |
| 3.3-(Me)$_2$ | 1 (mixt.) | $^s$Bu | OMe | OMe |
| 3.3-(Me)$_2$ | 1 (mixt.) | —CH$_2$OCH$_3$ | OMe | OMe |
| 3.3-(Me)$_2$ | 1 (mixt.) | —CH$_2$CH$_2$OCH$_3$ | OMe | OMe |
| 3.3-(Me)$_2$ | 1 (mixt.) | —CH$_2$SCH$_3$ | OMe | OMe |
| 3.3-(Me)$_2$ | 1 (mixt.) | —CH$_2$CH=CH$_2$ | OMe | OMe |
| 3.3-(Me)$_2$ | 1 (mixt.) | —C(CH$_3$)$_2$CH=CH$_2$ | OMe | OMe |
| 3.3-(Me)$_2$ | 1 (mixt.) | —CH$_2$C≡CH$_2$ | OMe | OMe |
| 3.3-(Me)$_2$ | 1 (mixt.) | —CH$_2$C$_6$H$_5$ | OMe | OMe |
| 3.3-(Me)$_2$ | 1 (mixt.) | —CH$_2$C$_6$H$_4$—Cl-2 | OMe | OMe |
| 3.3-(Me)$_2$ | 1 (mixt.) | —CH$_2$C$_6$H$_4$—Cl-3 | OMe | OMe |
| 3.3-(Me)$_2$ | 1 (mixt.) | —CH$_2$C$_6$H$_4$—Cl-4 | OMe | OMe |
| 3.3-(Me)$_2$ | 1 (mixt.) | —CH$_2$C$_6$H$_4$—Me-2 | OMe | OMe |
| 3.3-(Me)$_2$ | 1 (mixt.) | —CH$_2$C$_6$H$_4$—Me-3 | OMe | OMe |
| 3.3-(Me)$_2$ | 1 (mixt.) | —CH$_2$C$_6$H$_4$—Me-4 | OMe | OMe |
| 3.3-(Me)$_2$ | 1 (mixt.) | —CH$_2$C$_6$H$_4$—OMe-2 | OMe | OMe |
| 3.3-(Me)$_2$ | 1 (mixt.) | —CH$_2$C$_6$H$_4$—OMe-3 | OMe | OMe |
| 3.3-(Me)$_2$ | 1 (mixt.) | —CH$_2$C$_6$H$_4$—OMe-4 | OMe | OMe |
| 3.3-(Me)$_2$ | 1 (mixt.) | —CH$_2$CH$_2$C$_6$H$_5$ | OMe | OMe |
| 3.3-(Me)$_2$ | 2 (—) | H | Me | Me |
| 3.3-(Me)$_2$ | 2 (—) | Na | Me | Me |
| 3.3-(Me)$_2$ | 2 (—) | ½Ca | Me | Me |
| 3.3-(Me)$_2$ | 2 (—) | $^i$PrNH$_3$ | Me | Me |

TABLE -continued

A compound of the general formula:

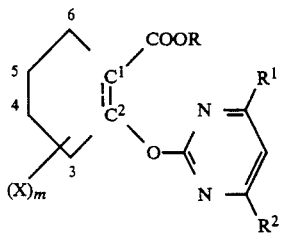

In the below-mentioned table, Me represents methyl group, Et represents ethyl group, Pr represents propyl group, $^i$Pr represents isopropyl group, Bu represents butyl group, $^i$Bu represents isobutyl group, $^s$Bu represents secondary butyl group, $^t$Bu represents tertiary butyl group, cis represents a cis-form, trans represents a trans-form, mix. represents a mixture of a cis-form and a trans-form, 1 represents a single bond and 2 represents a double bond.

| $(X)_m$ | === | R | $R^1$ | $R^2$ |
|---|---|---|---|---|
| 3.3-(Me)$_2$ | 2 (—) | NH$_2$CONH$_3$ | Me | Me |
| 3.3-(Me)$_2$ | 2 (—) | Me | Me | Me |
| 3.3-(Me)$_2$ | 2 (—) | Et | Me | Me |
| 3.3-(Me)$_2$ | 2 (—) | $^i$Pr | Me | Me |
| 3.3-(Me)$_2$ | 2 (—) | Pr | Me | Me |
| 3.3-(Me)$_2$ | 2 (—) | Bu | Me | Me |
| 3.3-(Me)$_2$ | 2 (—) | $^i$Bu | Me | Me |
| 3.3-(Me)$_2$ | 2 (—) | $^s$Bu | Me | Me |
| 3.3-(Me)$_2$ | 2 (—) | —CH$_2$OCH$_3$ | Me | Me |
| 3.3-(Me)$_2$ | 2 (—) | —CH$_2$CH$_2$OCH$_3$ | Me | Me |
| 3.3-(Me)$_2$ | 2 (—) | —CH$_2$SCH$_3$ | Me | Me |
| 3.3-(Me)$_2$ | 2 (—) | —CH$_2$CH=CH$_2$ | Me | Me |
| 3.3-(Me)$_2$ | 2 (—) | —C(CH$_3$)$_2$CH=CH$_2$ | Me | Me |
| 3.3-(Me)$_2$ | 2 (—) | —CH$_2$C≡CH$_2$ | Me | Me |
| 3.3-(Me)$_2$ | 2 (—) | —CH$_2$C$_6$H$_5$ | Me | Me |
| 3.3-(Me)$_2$ | 2 (—) | —CH$_2$C$_6$H$_4$—Cl-2 | Me | Me |
| 3.3-(Me)$_2$ | 2 (—) | —CH$_2$C$_6$H$_4$—Cl-3 | Me | Me |
| 3.3-(Me)$_2$ | 2 (—) | —CH$_2$C$_6$H$_4$—Cl-4 | Me | Me |
| 3.3-(Me)$_2$ | 2 (—) | —CH$_2$C$_6$H$_4$—Me-2 | Me | Me |
| 3.3-(Me)$_2$ | 2 (—) | —CH$_2$C$_6$H$_4$—Me-3 | Me | Me |
| 3.3-(Me)$_2$ | 2 (—) | —CH$_2$C$_6$H$_4$—Me-4 | Me | Me |
| 3.3-(Me)$_2$ | 2 (—) | —CH$_2$C$_6$H$_4$—OMe-2 | Me | Me |
| 3.3-(Me)$_2$ | 2 (—) | —CH$_2$C$_6$H$_4$—OMe-3 | Me | Me |
| 3.3-(Me)$_2$ | 2 (—) | —CH$_2$C$_6$H$_4$—OMe-4 | Me | Me |
| 3.3-(Me)$_2$ | 2 (—) | —CH$_2$CH$_2$C$_6$H$_5$ | Me | Me |
| 3.3-(Me)$_2$ | 2 (—) | H | OMe | OMe |
| 3.3-(Me)$_2$ | 2 (—) | Na | OMe | OMe |
| 3.3-(Me)$_2$ | 2 (—) | ½Ca | OMe | OMe |
| 3.3-(Me)$_2$ | 2 (—) | $^i$PrNH$_3$ | OMe | OMe |
| 3.3-(Me)$_2$ | 2 (—) | NH$_2$CONH$_3$ | OMe | OMe |
| 3.3-(Me)$_2$ | 2 (—) | Me | OMe | OMe |
| 3.3-(Me)$_2$ | 2 (—) | Et | OMe | OMe |
| 3.3-(Me)$_2$ | 2 (—) | $^i$Pr | OMe | OMe |
| 3.3-(Me)$_2$ | 2 (—) | Pr | OMe | OMe |
| 3.3-(Me)$_2$ | 2 (—) | Bu | OMe | OMe |
| 3.3-(Me)$_2$ | 2 (—) | $^i$Bu | OMe | OMe |
| 3.3-(Me)$_2$ | 2 (—) | $^s$Bu | OMe | OMe |
| 3.3-(Me)$_2$ | 2 (—) | —CH$_2$OCH$_3$ | OMe | OMe |
| 3.3-(Me)$_2$ | 2 (—) | —CH$_2$CH$_2$OCH$_3$ | OMe | OMe |
| 3.3-(Me)$_2$ | 2 (—) | —CH$_2$SCH$_3$ | OMe | OMe |
| 3.3-(Me)$_2$ | 2 (—) | —CH$_2$CH=CH$_2$ | OMe | OMe |
| 3.3-(Me)$_2$ | 2 (—) | —C(CH$_3$)$_2$CH=CH$_2$ | OMe | OMe |
| 3.3-(Me)$_2$ | 2 (—) | —CH$_2$C≡CH$_2$ | OMe | OMe |
| 3.3-(Me)$_2$ | 2 (—) | —CH$_2$C$_6$H$_5$ | OMe | OMe |
| 3.3-(Me)$_2$ | 2 (—) | —CH$_2$C$_6$H$_4$—Cl-2 | OMe | OMe |
| 3.3-(Me)$_2$ | 2 (—) | —CH$_2$C$_6$H$_4$—Cl-3 | OMe | OMe |
| 3.3-(Me)$_2$ | 2 (—) | —CH$_2$C$_6$H$_4$—Cl-4 | OMe | OMe |
| 3.3-(Me)$_2$ | 2 (—) | —CH$_2$C$_6$H$_4$—Me-2 | OMe | OMe |
| 3.3-(Me)$_2$ | 2 (—) | —CH$_2$C$_6$H$_4$—Me-3 | OMe | OMe |
| 3.3-(Me)$_2$ | 2 (—) | —CH$_2$C$_6$H$_4$—Me-4 | OMe | OMe |
| 3.3-(Me)$_2$ | 2 (—) | —CH$_2$C$_6$H$_4$—OMe-2 | OMe | OMe |
| 3.3-(Me)$_2$ | 2 (—) | —CH$_2$C$_6$H$_4$—OMe-3 | OMe | OMe |
| 3.3-(Me)$_2$ | 2 (—) | —CH$_2$C$_6$H$_4$—OMe-4 | OMe | OMe |
| 3.3-(Me)$_2$ | 2 (—) | —CH$_2$CH$_2$C$_6$H$_5$ | OMe | OMe |
| 4.4-(Me)$_2$ | 1 (cis) | H | Me | Me |
| 4.4-(Me)$_2$ | 1 (cis) | Na | Me | Me |
| 4.4-(Me)$_2$ | 1 (cis) | ½Ca | Me | Me |

TABLE -continued

A compound of the general formula:

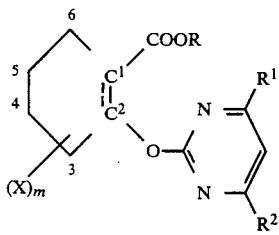

In the below-mentioned table, Me represents methyl group, Et represents ethyl group, Pr represents propyl group, $^i$Pr represents isopropyl group, Bu represents butyl group, $^i$Bu represents isobutyl group, $^s$Bu represents secondary butyl group, $^t$Bu represents tertiary butyl group, cis represents a cis-form, trans represents a trans-form, mix. represents a mixture of a cis-form and a trans-form, 1 represents a single bond and 2 represents a double bond.

| $(X)_m$ | === | R | $R^1$ | $R^2$ |
|---|---|---|---|---|
| 4.4-(Me)$_2$ | 1 (cis) | $^i$PrNH$_3$ | Me | Me |
| 4.4-(Me)$_2$ | 1 (cis) | NH$_2$CONH$_3$ | Me | Me |
| 4.4-(Me)$_2$ | 1 (cis) | Me | Me | Me |
| 4.4-(Me)$_2$ | 1 (cis) | Et | Me | Me |
| 4.4-(Me)$_2$ | 1 (cis) | $^i$Pr | Me | Me |
| 4.4-(Me)$_2$ | 1 (cis) | Pr | Me | Me |
| 4.4-(Me)$_2$ | 1 (cis) | Bu | Me | Me |
| 4.4-(Me)$_2$ | 1 (cis) | $^i$Bu | Me | Me |
| 4.4-(Me)$_2$ | 1 (cis) | $^s$Bu | Me | Me |
| 4.4-(Me)$_2$ | 1 (cis) | —CH$_2$OCH$_3$ | Me | Me |
| 4.4-(Me)$_2$ | 1 (cis) | —CH$_2$CH$_2$OCH$_3$ | Me | Me |
| 4.4-(Me)$_2$ | 1 (cis) | —CH$_2$SCH$_3$ | Me | Me |
| 4.4-(Me)$_2$ | 1 (cis) | —CH$_2$CH=CH$_2$ | Me | Me |
| 4.4-(Me)$_2$ | 1 (cis) | —C(CH$_3$)$_2$CH=CH$_2$ | Me | Me |
| 4.4-(Me)$_2$ | 1 (cis) | —CH$_2$C≡CH$_2$ | Me | Me |
| 4.4-(Me)$_2$ | 1 (cis) | —CH$_2$C$_6$H$_5$ | Me | Me |
| 4.4-(Me)$_2$ | 1 (cis) | —CH$_2$C$_6$H$_4$—Cl-2 | Me | Me |
| 4.4-(Me)$_2$ | 1 (cis) | —CH$_2$C$_6$H$_4$—Cl-3 | Me | Me |
| 4.4-(Me)$_2$ | 1 (cis) | —CH$_2$C$_6$H$_4$—Cl-4 | Me | Me |
| 4.4-(Me)$_2$ | 1 (cis) | —CH$_2$C$_6$H$_4$—Me-2 | Me | Me |
| 4.4-(Me)$_2$ | 1 (cis) | —CH$_2$C$_6$H$_4$—Me-3 | Me | Me |
| 4.4-(Me)$_2$ | 1 (cis) | —CH$_2$C$_6$H$_4$—Me-4 | Me | Me |
| 4.4-(Me)$_2$ | 1 (cis) | —CH$_2$C$_6$H$_4$—OMe-2 | Me | Me |
| 4.4-(Me)$_2$ | 1 (cis) | —CH$_2$C$_6$H$_4$—OMe-3 | Me | Me |
| 4.4-(Me)$_2$ | 1 (cis) | —CH$_2$C$_6$H$_4$—OMe-4 | Me | Me |
| 4.4-(Me)$_2$ | 1 (cis) | —CH$_2$CH$_2$C$_6$H$_5$ | Me | Me |
| 4.4-(Me)$_2$ | 1 (cis) | H | OMe | OMe |
| 4.4-(Me)$_2$ | 1 (cis) | Na | OMe | OMe |
| 4.4-(Me)$_2$ | 1 (cis) | ½Ca | OMe | OMe |
| 4.4-(Me)$_2$ | 1 (cis) | $^i$PrNH$_3$ | OMe | OMe |
| 4.4-(Me)$_2$ | 1 (cis) | NH$_2$CONH$_3$ | OMe | OMe |
| 4.4-(Me)$_2$ | 1 (cis) | Me | OMe | OMe |
| 4.4-(Me)$_2$ | 1 (cis) | Et | OMe | OMe |
| 4.4-(Me)$_2$ | 1 (cis) | $^i$Pr | OMe | OMe |
| 4.4-(Me)$_2$ | 1 (cis) | Pr | OMe | OMe |
| 4.4-(Me)$_2$ | 1 (cis) | Bu | OMe | OMe |
| 4.4-(Me)$_2$ | 1 (cis) | $^i$Bu | OMe | OMe |
| 4.4-(Me)$_2$ | 1 (cis) | $^s$Bu | OMe | OMe |
| 4.4-(Me)$_2$ | 1 (cis) | —CH$_2$OCH$_3$ | OMe | OMe |
| 4.4-(Me)$_2$ | 1 (cis) | —CH$_2$CH$_2$OCH$_3$ | OMe | OMe |
| 4.4-(Me)$_2$ | 1 (cis) | —CH$_2$SCH$_3$ | OMe | OMe |
| 4.4-(Me)$_2$ | 1 (cis) | —CH$_2$CH=CH$_2$ | OMe | OMe |
| 4.4-(Me)$_2$ | 1 (cis) | —C(CH$_3$)$_2$CH=CH$_2$ | OMe | OMe |
| 4.4-(Me)$_2$ | 1 (cis) | —CH$_2$C≡CH$_2$ | OMe | OMe |
| 4.4-(Me)$_2$ | 1 (cis) | —CH$_2$C$_6$H$_5$ | OMe | OMe |
| 4.4-(Me)$_2$ | 1 (cis) | —CH$_2$C$_6$H$_4$—Cl-2 | OMe | OMe |
| 4.4-(Me)$_2$ | 1 (cis) | —CH$_2$C$_6$H$_4$—Cl-3 | OMe | OMe |
| 4.4-(Me)$_2$ | 1 (cis) | —CH$_2$C$_6$H$_4$—Cl-4 | OMe | OMe |
| 4.4-(Me)$_2$ | 1 (cis) | —CH$_2$C$_6$H$_4$—Me-2 | OMe | OMe |
| 4.4-(Me)$_2$ | 1 (cis) | —CH$_2$C$_6$H$_4$—Me-3 | OMe | OMe |
| 4.4-(Me)$_2$ | 1 (cis) | —CH$_2$C$_6$H$_4$—Me-4 | OMe | OMe |
| 4.4-(Me)$_2$ | 1 (cis) | —CH$_2$C$_6$H$_4$—OMe-2 | OMe | OMe |
| 4.4-(Me)$_2$ | 1 (cis) | —CH$_2$C$_6$H$_4$—OMe-3 | OMe | OMe |
| 4.4-(Me)$_2$ | 1 (cis) | —CH$_2$C$_6$H$_4$—OMe-4 | OMe | OMe |
| 4.4-(Me)$_2$ | 1 (cis) | —CH$_2$CH$_2$C$_6$H$_5$ | OMe | OMe |
| 4.4-(Me)$_2$ | 1 (trans) | H | Me | Me |
| 4.4-(Me)$_2$ | 1 (trans) | Na | Me | Me |

TABLE -continued

A compound of the general formula:

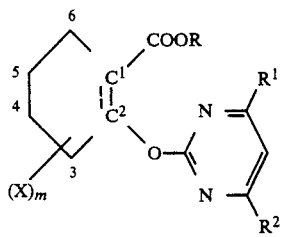

In the below-mentioned table, Me represents methyl group, Et represents ethyl group, Pr represents propyl group, $^i$Pr represents isopropyl group, Bu represents butyl group, $^i$Bu represents isobutyl group, $^s$Bu represents secondary butyl group, $^t$Bu represents tertiary butyl group, cis represents a cis-form, trans represents a trans-form, mix. represents a mixture of a cis-form and a trans-form, 1 represents a single bond and 2 represents a double bond.

| $(X)_m$ | === | R | $R^1$ | $R^2$ |
|---|---|---|---|---|
| 4.4-(Me)$_2$ | 1 (trans) | ½Ca | Me | Me |
| 4.4-(Me)$_2$ | 1 (trans) | $^i$PrNH$_3$ | Me | Me |
| 4.4-(Me)$_2$ | 1 (trans) | NH$_2$CONH$_3$ | Me | Me |
| 4.4-(Me)$_2$ | 1 (trans) | Me | Me | Me |
| 4.4-(Me)$_2$ | 1 (trans) | Et | Me | Me |
| 4.4-(Me)$_2$ | 1 (trans) | $^i$Pr | Me | Me |
| 4.4-(Me)$_2$ | 1 (trans) | Pr | Me | Me |
| 4.4-(Me)$_2$ | 1 (trans) | Bu | Me | Me |
| 4.4-(Me)$_2$ | 1 (trans) | $^i$Bu | Me | Me |
| 4.4-(Me)$_2$ | 1 (trans) | $^s$Bu | Me | Me |
| 4.4-(Me)$_2$ | 1 (trans) | —CH$_2$OCH$_3$ | Me | Me |
| 4.4-(Me)$_2$ | 1 (trans) | —CH$_2$CH$_2$OCH$_3$ | Me | Me |
| 4.4-(Me)$_2$ | 1 (trans) | —CH$_2$SCH$_3$ | Me | Me |
| 4.4-(Me)$_2$ | 1 (trans) | —CH$_2$CH=CH$_2$ | Me | Me |
| 4.4-(Me)$_2$ | 1 (trans) | —C(CH$_3$)$_2$CH=CH$_2$ | Me | Me |
| 4.4-(Me)$_2$ | 1 (trans) | —CH$_2$C≡CH$_2$ | Me | Me |
| 4.4-(Me)$_2$ | 1 (trans) | —CH$_2$C$_6$H$_5$ | Me | Me |
| 4.4-(Me)$_2$ | 1 (trans) | —CH$_2$C$_6$H$_4$—Cl-2 | Me | Me |
| 4.4-(Me)$_2$ | 1 (trans) | —CH$_2$C$_6$H$_4$—Cl-3 | Me | Me |
| 4.4-(Me)$_2$ | 1 (trans) | —CH$_2$C$_6$H$_4$—Cl-4 | Me | Me |
| 4.4-(Me)$_2$ | 1 (trans) | —CH$_2$C$_6$H$_4$—Me-2 | Me | Me |
| 4.4-(Me)$_2$ | 1 (trans) | —CH$_2$C$_6$H$_4$—Me-3 | Me | Me |
| 4.4-(Me)$_2$ | 1 (trans) | —CH$_2$C$_6$H$_4$—Me-4 | Me | Me |
| 4.4-(Me)$_2$ | 1 (trans) | —CH$_2$C$_6$H$_4$—OMe-2 | Me | Me |
| 4.4-(Me)$_2$ | 1 (trans) | —CH$_2$C$_6$H$_4$—OMe-3 | Me | Me |
| 4.4-(Me)$_2$ | 1 (trans) | —CH$_2$C$_6$H$_4$—OMe-4 | Me | Me |
| 4.4-(Me)$_2$ | 1 (trans) | —CH$_2$CH$_2$C$_6$H$_5$ | Me | Me |
| 4.4-(Me)$_2$ | 1 (trans) | H | OMe | OMe |
| 4.4-(Me)$_2$ | 1 (trans) | Na | OMe | OMe |
| 4.4-(Me)$_2$ | 1 (trans) | ½Ca | OMe | OMe |
| 4.4-(Me)$_2$ | 1 (trans) | $^i$PrNH$_3$ | OMe | OMe |
| 4.4-(Me)$_2$ | 1 (trans) | NH$_2$CONH$_3$ | OMe | OMe |
| 4.4-(Me)$_2$ | 1 (trans) | Me | OMe | OMe |
| 4.4-(Me)$_2$ | 1 (trans) | Et | OMe | OMe |
| 4.4-(Me)$_2$ | 1 (trans) | $^i$Pr | OMe | OMe |
| 4.4-(Me)$_2$ | 1 (trans) | Pr | OMe | OMe |
| 4.4-(Me)$_2$ | 1 (trans) | Bu | OMe | OMe |
| 4.4-(Me)$_2$ | 1 (trans) | $^i$Bu | OMe | OMe |
| 4.4-(Me)$_2$ | 1 (trans) | $^s$Bu | OMe | OMe |
| 4.4-(Me)$_2$ | 1 (trans) | —CH$_2$OCH$_3$ | OMe | OMe |
| 4.4-(Me)$_2$ | 1 (trans) | —CH$_2$CH$_2$OCH$_3$ | OMe | OMe |
| 4.4-(Me)$_2$ | 1 (trans) | —CH$_2$SCH$_3$ | OMe | OMe |
| 4.4-(Me)$_2$ | 1 (trans) | —CH$_2$CH=CH$_2$ | OMe | OMe |
| 4.4-(Me)$_2$ | 1 (trans) | —C(CH$_3$)$_2$CH=CH$_2$ | OMe | OMe |
| 4.4-(Me)$_2$ | 1 (trans) | —CH$_2$C≡CH$_2$ | OMe | OMe |
| 4.4-(Me)$_2$ | 1 (trans) | —CH$_2$C$_6$H$_5$ | OMe | OMe |
| 4.4-(Me)$_2$ | 1 (trans) | —CH$_2$C$_6$H$_4$—Cl-2 | OMe | OMe |
| 4.4-(Me)$_2$ | 1 (trans) | —CH$_2$C$_6$H$_4$—Cl-3 | OMe | OMe |
| 4.4-(Me)$_2$ | 1 (trans) | —CH$_2$C$_6$H$_4$—Cl-4 | OMe | OMe |
| 4.4-(Me)$_2$ | 1 (trans) | —CH$_2$C$_6$H$_4$—Me-2 | OMe | OMe |
| 4.4-(Me)$_2$ | 1 (trans) | —CH$_2$C$_6$H$_4$—Me-3 | OMe | OMe |
| 4.4-(Me)$_2$ | 1 (trans) | —CH$_2$C$_6$H$_4$—Me-4 | OMe | OMe |
| 4.4-(Me)$_2$ | 1 (trans) | —CH$_2$C$_6$H$_4$—OMe-2 | OMe | OMe |
| 4.4-(Me)$_2$ | 1 (trans) | —CH$_2$C$_6$H$_4$—OMe-3 | OMe | OMe |
| 4.4-(Me)$_2$ | 1 (trans) | —CH$_2$C$_6$H$_4$—OMe-4 | OMe | OMe |
| 4.4-(Me)$_2$ | 1 (trans) | —CH$_2$CH$_2$C$_6$H$_5$ | OMe | OMe |
| 4.4-(Me)$_2$ | 1 (mixt.) | H | Me | Me |

TABLE -continued

A compound of the general formula:

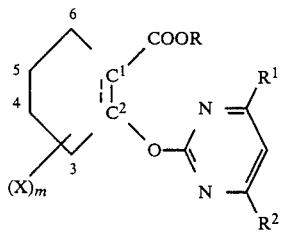

In the below-mentioned table, Me represents methyl
group, Et represents ethyl group, Pr represents propyl
group, $^i$Pr represents isopropyl group, Bu represents butyl
group, $^i$Bu represents isobutyl group, $^s$Bu represents
secondary butyl group, $^t$Bu represents tertiary butyl
group, cis represents a cis-form, trans represents a
trans-form, mix. represents a mixture of a cis-form and
a trans-form, 1 represents a single bond and 2 represents
a double bond.

| $(X)_m$ | --- | R | $R^1$ | $R^2$ |
|---|---|---|---|---|
| 4,4-(Me)$_2$ | 1 (mixt.) | Na | Me | Me |
| 4,4-(Me)$_2$ | 1 (mixt.) | ½Ca | Me | Me |
| 4,4-(Me)$_2$ | 1 (mixt.) | $^i$PrNH$_3$ | Me | Me |
| 4,4-(Me)$_2$ | 1 (mixt.) | NH$_2$CONH$_3$ | Me | Me |
| 4,4-(Me)$_2$ | 1 (mixt.) | Me | Me | Me |
| 4,4-(Me)$_2$ | 1 (mixt.) | Et | Me | Me |
| 4,4-(Me)$_2$ | 1 (mixt.) | $^i$Pr | Me | Me |
| 4,4-(Me)$_2$ | 1 (mixt.) | Pr | Me | Me |
| 4,4-(Me)$_2$ | 1 (mixt.) | Bu | Me | Me |
| 4,4-(Me)$_2$ | 1 (mixt.) | $^i$Bu | Me | Me |
| 4,4-(Me)$_2$ | 1 (mixt.) | $^s$Bu | Me | Me |
| 4,4-(Me)$_2$ | 1 (mixt.) | —CH$_2$OCH$_3$ | Me | Me |
| 4,4-(Me)$_2$ | 1 (mixt.) | —CH$_2$CH$_2$OCH$_3$ | Me | Me |
| 4,4-(Me)$_2$ | 1 (mixt.) | —CH$_2$SCH$_3$ | Me | Me |
| 4,4-(Me)$_2$ | 1 (mixt.) | —CH$_2$CH=CH$_2$ | Me | Me |
| 4,4-(Me)$_2$ | 1 (mixt.) | —C(CH$_3$)$_2$CH=CH$_2$ | Me | Me |
| 4,4-(Me)$_2$ | 1 (mixt.) | —CH$_2$C≡CH$_2$ | Me | Me |
| 4,4-(Me)$_2$ | 1 (mixt.) | —CH$_2$C$_6$H$_5$ | Me | Me |
| 4,4-(Me)$_2$ | 1 (mixt.) | —CH$_2$C$_6$H$_4$—Cl-2 | Me | Me |
| 4,4-(Me)$_2$ | 1 (mixt.) | —CH$_2$C$_6$H$_4$—Cl-3 | Me | Me |
| 4,4-(Me)$_2$ | 1 (mixt.) | —CH$_2$C$_6$H$_4$—Cl-4 | Me | Me |
| 4,4-(Me)$_2$ | 1 (mixt.) | —CH$_2$C$_6$H$_4$—Me-2 | Me | Me |
| 4,4-(Me)$_2$ | 1 (mixt.) | —CH$_2$C$_6$H$_4$—Me-3 | Me | Me |
| 4,4-(Me)$_2$ | 1 (mixt.) | —CH$_2$C$_6$H$_4$—Me-4 | Me | Me |
| 4,4-(Me)$_2$ | 1 (mixt.) | —CH$_2$C$_6$H$_4$—OMe-2 | Me | Me |
| 4,4-(Me)$_2$ | 1 (mixt.) | —CH$_2$C$_6$H$_4$—OMe-3 | Me | Me |
| 4,4-(Me)$_2$ | 1 (mixt.) | —CH$_2$C$_6$H$_4$—OMe-4 | Me | Me |
| 4,4-(Me)$_2$ | 1 (mixt.) | —CH$_2$CH$_2$C$_6$H$_5$ | Me | Me |
| 4,4-(Me)$_2$ | 1 (mixt.) | H | OMe | OMe |
| 4,4-(Me)$_2$ | 1 (mixt.) | Na | OMe | OMe |
| 4,4-(Me)$_2$ | 1 (mixt.) | ½Ca | OMe | OMe |
| 4,4-(Me)$_2$ | 1 (mixt.) | $^i$PrNH$_3$ | OMe | OMe |
| 4,4-(Me)$_2$ | 1 (mixt.) | NH$_2$CONH$_3$ | OMe | OMe |
| 4,4-(Me)$_2$ | 1 (mixt.) | Me | OMe | OMe |
| 4,4-(Me)$_2$ | 1 (mixt.) | Et | OMe | OMe |
| 4,4-(Me)$_2$ | 1 (mixt.) | $^i$Pr | OMe | OMe |
| 4,4-(Me)$_2$ | 1 (mixt.) | Pr | OMe | OMe |
| 4,4-(Me)$_2$ | 1 (mixt.) | Bu | OMe | OMe |
| 4,4-(Me)$_2$ | 1 (mixt.) | $^i$Bu | OMe | OMe |
| 4,4-(Me)$_2$ | 1 (mixt.) | $^s$Bu | OMe | OMe |
| 4,4-(Me)$_2$ | 1 (mixt.) | —CH$_2$OCH$_3$ | OMe | OMe |
| 4,4-(Me)$_2$ | 1 (mixt.) | —CH$_2$CH$_2$OCH$_3$ | OMe | OMe |
| 4,4-(Me)$_2$ | 1 (mixt.) | —CH$_2$SCH$_3$ | OMe | OMe |
| 4,4-(Me)$_2$ | 1 (mixt.) | —CH$_2$CH=CH$_2$ | OMe | OMe |
| 4,4-(Me)$_2$ | 1 (mixt.) | —C(CH$_3$)$_2$CH=CH$_2$ | OMe | OMe |
| 4,4-(Me)$_2$ | 1 (mixt.) | —CH$_2$C≡CH$_2$ | OMe | OMe |
| 4,4-(Me)$_2$ | 1 (mixt.) | —CH$_2$C$_6$H$_5$ | OMe | OMe |
| 4,4-(Me)$_2$ | 1 (mixt.) | —CH$_2$C$_6$H$_4$—Cl-2 | OMe | OMe |
| 4,4-(Me)$_2$ | 1 (mixt.) | —CH$_2$C$_6$H$_4$—Cl-3 | OMe | OMe |
| 4,4-(Me)$_2$ | 1 (mixt.) | —CH$_2$C$_6$H$_4$—Cl-4 | OMe | OMe |
| 4,4-(Me)$_2$ | 1 (mixt.) | —CH$_2$C$_6$H$_4$—Me-2 | OMe | OMe |
| 4,4-(Me)$_2$ | 1 (mixt.) | —CH$_2$C$_6$H$_4$—Me-3 | OMe | OMe |
| 4,4-(Me)$_2$ | 1 (mixt.) | —CH$_2$C$_6$H$_4$—Me-4 | OMe | OMe |
| 4,4-(Me)$_2$ | 1 (mixt.) | —CH$_2$C$_6$H$_4$—OMe-2 | OMe | OMe |
| 4,4-(Me)$_2$ | 1 (mixt.) | —CH$_2$C$_6$H$_4$—OMe-3 | OMe | OMe |
| 4,4-(Me)$_2$ | 1 (mixt.) | —CH$_2$C$_6$H$_4$—OMe-4 | OMe | OMe |
| 4,4-(Me)$_2$ | 1 (mixt.) | —CH$_2$CH$_2$C$_6$H$_5$ | OMe | OMe |

TABLE -continued

A compound of the general formula:

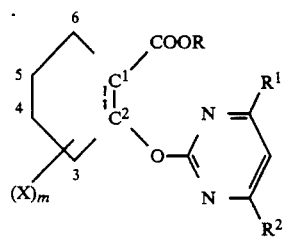

In the below-mentioned table, Me represents methyl group, Et represents ethyl group, Pr represents propyl group, $^i$Pr represents isopropyl group, Bu represents butyl group, $^i$Bu represents isobutyl group, $^s$Bu represents secondary butyl group, $^t$Bu represents tertiary butyl group, cis represents a cis-form, trans represents a trans-form, mix. represents a mixture of a cis-form and a trans-form, 1 represents a single bond and 2 represents a double bond.

| (X)$_m$ | === | R | R$^1$ | R$^2$ |
|---|---|---|---|---|
| 4.4-(Me)$_2$ | 2 (—) | H | Me | Me |
| 4.4-(Me)$_2$ | 2 (—) | Na | Me | Me |
| 4.4-(Me)$_2$ | 2 (—) | ½Ca | Me | Me |
| 4.4-(Me)$_2$ | 2 (—) | $^i$PrNH$_3$ | Me | Me |
| 4.4-(Me)$_2$ | 2 (—) | NH$_2$CONH$_3$ | Me | Me |
| 4.4-(Me)$_2$ | 2 (—) | Me | Me | Me |
| 4.4-(Me)$_2$ | 2 (—) | Et | Me | Me |
| 4.4-(Me)$_2$ | 2 (—) | $^i$Pr | Me | Me |
| 4.4-(Me)$_2$ | 2 (—) | Pr | Me | Me |
| 4.4-(Me)$_2$ | 2 (—) | Bu | Me | Me |
| 4.4-(Me)$_2$ | 2 (—) | $^i$Bu | Me | Me |
| 4.4-(Me)$_2$ | 2 (—) | $^s$Bu | Me | Me |
| 4.4-(Me)$_2$ | 2 (—) | —CH$_2$OCH$_3$ | Me | Me |
| 4.4-(Me)$_2$ | 2 (—) | —CH$_2$CH$_2$OCH$_3$ | Me | Me |
| 4.4-(Me)$_2$ | 2 (—) | —CH$_2$SCH$_3$ | Me | Me |
| 4.4-(Me)$_2$ | 2 (—) | —CH$_2$CH=CH$_2$ | Me | Me |
| 4.4-(Me)$_2$ | 2 (—) | —C(CH$_3$)$_2$CH=CH$_2$ | Me | Me |
| 4.4-(Me)$_2$ | 2 (—) | —CH$_2$C≡CH$_2$ | Me | Me |
| 4.4-(Me)$_2$ | 2 (—) | —CH$_2$C$_6$H$_5$ | Me | Me |
| 4.4-(Me)$_2$ | 2 (—) | —CH$_2$C$_6$H$_4$—Cl-2 | Me | Me |
| 4.4-(Me)$_2$ | 2 (—) | —CH$_2$C$_6$H$_4$—Cl-3 | Me | Me |
| 4.4-(Me)$_2$ | 2 (—) | —CH$_2$C$_6$H$_4$—Cl-4 | Me | Me |
| 4.4-(Me)$_2$ | 2 (—) | —CH$_2$C$_6$H$_4$—Me-2 | Me | Me |
| 4.4-(Me)$_2$ | 2 (—) | —CH$_2$C$_6$H$_4$—Me-3 | Me | Me |
| 4.4-(Me)$_2$ | 2 (—) | —CH$_2$C$_6$H$_4$—Me-4 | Me | Me |
| 4.4-(Me)$_2$ | 2 (—) | —CH$_2$C$_6$H$_4$—OMe-2 | Me | Me |
| 4.4-(Me)$_2$ | 2 (—) | —CH$_2$C$_6$H$_4$—OMe-3 | Me | Me |
| 4.4-(Me)$_2$ | 2 (—) | —CH$_2$C$_6$H$_4$—OMe-4 | Me | Me |
| 4.4-(Me)$_2$ | 2 (—) | —CH$_2$CH$_2$C$_6$H$_5$ | Me | Me |
| 4.4-(Me)$_2$ | 2 (—) | H | OMe | OMe |
| 4.4-(Me)$_2$ | 2 (—) | Na | OMe | OMe |
| 4.4-(Me)$_2$ | 2 (—) | ½Ca | OMe | OMe |
| 4.4-(Me)$_2$ | 2 (—) | $^i$PrNH$_3$ | OMe | OMe |
| 4.4-(Me)$_2$ | 2 (—) | NH$_2$CONH$_3$ | OMe | OMe |
| 4.4-(Me)$_2$ | 2 (—) | Me | OMe | OMe |
| 4.4-(Me)$_2$ | 2 (—) | Et | OMe | OMe |
| 4.4-(Me)$_2$ | 2 (—) | $^i$Pr | OMe | OMe |
| 4.4-(Me)$_2$ | 2 (—) | Pr | OMe | OMe |
| 4.4-(Me)$_2$ | 2 (—) | Bu | OMe | OMe |
| 4.4-(Me)$_2$ | 2 (—) | $^i$Bu | OMe | OMe |
| 4.4-(Me)$_2$ | 2 (—) | $^s$Bu | OMe | OMe |
| 4.4-(Me)$_2$ | 2 (—) | —CH$_2$OCH$_3$ | OMe | OMe |
| 4.4-(Me)$_2$ | 2 (—) | —CH$_2$CH$_2$OCH$_3$ | OMe | OMe |
| 4.4-(Me)$_2$ | 2 (—) | —CH$_2$SCH$_3$ | OMe | OMe |
| 4.4-(Me)$_2$ | 2 (—) | —CH$_2$CH=CH$_2$ | OMe | OMe |
| 4.4-(Me)$_2$ | 2 (—) | —C(CH$_3$)$_2$CH=CH$_2$ | OMe | OMe |
| 4.4-(Me)$_2$ | 2 (—) | —CH$_2$C≡CH$_2$ | OMe | OMe |
| 4.4-(Me)$_2$ | 2 (—) | —CH$_2$C$_6$H$_5$ | OMe | OMe |
| 4.4-(Me)$_2$ | 2 (—) | —CH$_2$C$_6$H$_4$—Cl-2 | OMe | OMe |
| 4.4-(Me)$_2$ | 2 (—) | —CH$_2$C$_6$H$_4$—Cl-3 | OMe | OMe |
| 4.4-(Me)$_2$ | 2 (—) | —CH$_2$C$_6$H$_4$—Cl-4 | OMe | OMe |
| 4.4-(Me)$_2$ | 2 (—) | —CH$_2$C$_6$H$_4$—Me-2 | OMe | OMe |
| 4.4-(Me)$_2$ | 2 (—) | —CH$_2$C$_6$H$_4$—Me-3 | OMe | OMe |
| 4.4-(Me)$_2$ | 2 (—) | —CH$_2$C$_6$H$_4$—Me-4 | OMe | OMe |
| 4.4-(Me)$_2$ | 2 (—) | —CH$_2$C$_6$H$_4$—OMe-2 | OMe | OMe |
| 4.4-(Me)$_2$ | 2 (—) | —CH$_2$C$_6$H$_4$—OMe-3 | OMe | OMe |
| 4.4-(Me)$_2$ | 2 (—) | —CH$_2$C$_6$H$_4$—OMe-4 | OMe | OMe |

TABLE -continued

A compound of the general formula:

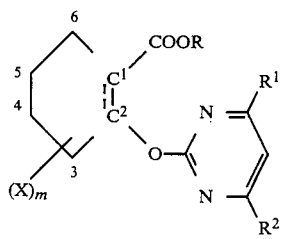

In the below-mentioned table, Me represents methyl group, Et represents ethyl group, Pr represents propyl group, $^i$Pr represents isopropyl group, Bu represents butyl group, $^i$Bu represents isobutyl group, $^s$Bu represents secondary butyl group, $^t$Bu represents tertiary butyl group, cis represents a cis-form, trans represents a trans-form, mix. represents a mixture of a cis-form and a trans-form, 1 represents a single bond and 2 represents a double bond.

| $(X)_m$ | === | R | $R^1$ | $R^2$ |
|---|---|---|---|---|
| 4.4-(Me)$_2$ | 2 (—) | —CH$_2$CH$_2$C$_6$H$_5$ | OMe | OMe |
| 5.5-(Me)$_2$ | 1 (cis) | H | Me | Me |
| 5.5-(Me)$_2$ | 1 (cis) | Na | Me | Me |
| 5.5-(Me)$_2$ | 1 (cis) | ½Ca | Me | Me |
| 5.5-(Me)$_2$ | 1 (cis) | $^i$PrNH$_3$ | Me | Me |
| 5.5-(Me)$_2$ | 1 (cis) | NH$_2$CONH$_3$ | Me | Me |
| 5.5-(Me)$_2$ | 1 (cis) | Me | Me | Me |
| 5.5-(Me)$_2$ | 1 (cis) | Et | Me | Me |
| 5.5-(Me)$_2$ | 1 (cis) | $^i$Pr | Me | Me |
| 5.5-(Me)$_2$ | 1 (cis) | Pr | Me | Me |
| 5.5-(Me)$_2$ | 1 (cis) | Bu | Me | Me |
| 5.5-(Me)$_2$ | 1 (cis) | $^i$Bu | Me | Me |
| 5.5-(Me)$_2$ | 1 (cis) | $^s$Bu | Me | Me |
| 5.5-(Me)$_2$ | 1 (cis) | —CH$_2$OCH$_3$ | Me | Me |
| 5.5-(Me)$_2$ | 1 (cis) | —CH$_2$CH$_2$OCH$_3$ | Me | Me |
| 5.5-(Me)$_2$ | 1 (cis) | —CH$_2$SCH$_3$ | Me | Me |
| 5.5-(Me)$_2$ | 1 (cis) | —CH$_2$CH=CH$_2$ | Me | Me |
| 5.5-(Me)$_2$ | 1 (cis) | —C(CH$_3$)$_2$CH=CH$_2$ | Me | Me |
| 5.5-(Me)$_2$ | 1 (cis) | —CH$_2$C≡CH$_2$ | Me | Me |
| 5.5-(Me)$_2$ | 1 (cis) | —CH$_2$C$_6$H$_5$ | Me | Me |
| 5.5-(Me)$_2$ | 1 (cis) | —CH$_2$C$_6$H$_4$—Cl-2 | Me | Me |
| 5.5-(Me)$_2$ | 1 (cis) | —CH$_2$C$_6$H$_4$—Cl-3 | Me | Me |
| 5.5-(Me)$_2$ | 1 (cis) | —CH$_2$C$_6$H$_4$—Cl-4 | Me | Me |
| 5.5-(Me)$_2$ | 1 (cis) | —CH$_2$C$_6$H$_4$—Me-2 | Me | Me |
| 5.5-(Me)$_2$ | 1 (cis) | —CH$_2$C$_6$H$_4$—Me-3 | Me | Me |
| 5.5-(Me)$_2$ | 1 (cis) | —CH$_2$C$_6$H$_4$—Me-4 | Me | Me |
| 5.5-(Me)$_2$ | 1 (cis) | —CH$_2$C$_6$H$_4$—OMe-2 | Me | Me |
| 5.5-(Me)$_2$ | 1 (cis) | —CH$_2$C$_6$H$_4$—OMe-3 | Me | Me |
| 5.5-(Me)$_2$ | 1 (cis) | —CH$_2$C$_6$H$_4$—OMe-4 | Me | Me |
| 5.5-(Me)$_2$ | 1 (cis) | —CH$_2$CH$_2$C$_6$H$_5$ | Me | Me |
| 5.5-(Me)$_2$ | 1 (cis) | H | OMe | OMe |
| 5.5-(Me)$_2$ | 1 (cis) | Na | OMe | OMe |
| 5.5-(Me)$_2$ | 1 (cis) | ½Ca | OMe | OMe |
| 5.5-(Me)$_2$ | 1 (cis) | $^i$PrNH$_3$ | OMe | OMe |
| 5.5-(Me)$_2$ | 1 (cis) | NH$_2$CONH$_3$ | OMe | OMe |
| 5.5-(Me)$_2$ | 1 (cis) | Me | OMe | OMe |
| 5.5-(Me)$_2$ | 1 (cis) | Et | OMe | OMe |
| 5.5-(Me)$_2$ | 1 (cis) | $^i$Pr | OMe | OMe |
| 5.5-(Me)$_2$ | 1 (cis) | Pr | OMe | OMe |
| 5.5-(Me)$_2$ | 1 (cis) | Bu | OMe | OMe |
| 5.5-(Me)$_2$ | 1 (cis) | $^i$Bu | OMe | OMe |
| 5.5-(Me)$_2$ | 1 (cis) | $^s$Bu | OMe | OMe |
| 5.5-(Me)$_2$ | 1 (cis) | —CH$_2$OCH$_3$ | OMe | OMe |
| 5.5-(Me)$_2$ | 1 (cis) | —CH$_2$CH$_2$OCH$_3$ | OMe | OMe |
| 5.5-(Me)$_2$ | 1 (cis) | —CH$_2$SCH$_3$ | OMe | OMe |
| 5.5-(Me)$_2$ | 1 (cis) | —CH$_2$CH=CH$_2$ | OMe | OMe |
| 5.5-(Me)$_2$ | 1 (cis) | —C(CH$_3$)$_2$CH=CH$_2$ | OMe | OMe |
| 5.5-(Me)$_2$ | 1 (cis) | —CH$_2$C≡CH$_2$ | Ome | Ome |
| 5.5-(Me)$_2$ | 1 (cis) | —CH$_2$C$_6$H$_5$ | OMe | OMe |
| 5.5-(Me)$_2$ | 1 (cis) | —CH$_2$C$_6$H$_4$—Cl-2 | OMe | OMe |
| 5.5-(Me)$_2$ | 1 (cis) | —CH$_2$C$_6$H$_4$—Cl-3 | OMe | OMe |
| 5.5-(Me)$_2$ | 1 (cis) | —CH$_2$C$_6$H$_4$—Cl-4 | OMe | OMe |
| 5.5-(Me)$_2$ | 1 (cis) | —CH$_2$C$_6$H$_4$—Me-2 | OMe | OMe |
| 5.5-(Me)$_2$ | 1 (cis) | —CH$_2$C$_6$H$_4$—Me-3 | OMe | OMe |
| 5.5-(Me)$_2$ | 1 (cis) | —CH$_2$C$_6$H$_4$—Me-4 | OMe | OMe |
| 5.5-(Me)$_2$ | 1 (cis) | —CH$_2$C$_6$H$_4$—OMe-2 | OMe | OMe |
| 5.5-(Me)$_2$ | 1 (cis) | —CH$_2$C$_6$H$_4$—OMe-3 | OMe | OMe |

TABLE -continued

A compound of the general formula:

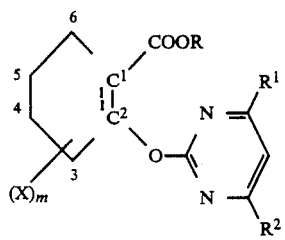

In the below-mentioned table, Me represents methyl group, Et represents ethyl group, Pr represents propyl group, $^i$Pr represents isopropyl group, Bu represents butyl group, $^i$Bu represents isobutyl group, $^s$Bu represents secondary butyl group, $^t$Bu represents tertiary butyl group, cis represents a cis-form, trans represents a trans-form, mix. represents a mixture of a cis-form and a trans-form, 1 represents a single bond and 2 represents a double bond.

| $(X)_m$ | === | R | $R^1$ | $R^2$ |
|---|---|---|---|---|
| 5.5-(Me)$_2$ | 1 (cis) | —CH$_2$C$_6$H$_4$—OMe-4 | OMe | OMe |
| 5.5-(Me)$_2$ | 1 (cis) | —CH$_2$CH$_2$C$_6$H$_5$ | OMe | OMe |
| 5.5-(Me)$_2$ | 1 (trans) | H | Me | Me |
| 5.5-(Me)$_2$ | 1 (trans) | Na | Me | Me |
| 5.5-(Me)$_2$ | 1 (trans) | ½Ca | Me | Me |
| 5.5-(Me)$_2$ | 1 (trans) | $^i$PrNH$_3$ | Me | Me |
| 5.5-(Me)$_2$ | 1 (trans) | NH$_2$CONH$_3$ | Me | Me |
| 5.5-(Me)$_2$ | 1 (trans) | Me | Me | Me |
| 5.5-(Me)$_2$ | 1 (trans) | Et | Me | Me |
| 5.5-(Me)$_2$ | 1 (trans) | $^i$Pr | Me | Me |
| 5.5-(Me)$_2$ | 1 (trans) | Pr | Me | Me |
| 5.5-(Me)$_2$ | 1 (trans) | Bu | Me | Me |
| 5.5-(Me)$_2$ | 1 (trans) | $^i$Bu | Me | Me |
| 5.5-(Me)$_2$ | 1 (trans) | $^s$Bu | Me | Me |
| 5.5-(Me)$_2$ | 1 (trans) | —CH$_2$OCH$_3$ | Me | Me |
| 5.5-(Me)$_2$ | 1 (trans) | —CH$_2$CH$_2$OCH$_3$ | Me | Me |
| 5.5-(Me)$_2$ | 1 (trans) | —CH$_2$SCH$_3$ | Me | Me |
| 5.5-(Me)$_2$ | 1 (trans) | —CH$_2$CH=CH$_2$ | Me | Me |
| 5.5-(Me)$_2$ | 1 (trans) | —C(CH$_3$)$_2$CH=CH$_2$ | Me | Me |
| 5.5-(Me)$_2$ | 1 (trans) | —CH$_2$C≡CH$_2$ | Me | Me |
| 5.5-(Me)$_2$ | 1 (trans) | —CH$_2$C$_6$H$_5$ | Me | Me |
| 5.5-(Me)$_2$ | 1 (trans) | —CH$_2$C$_6$H$_4$—Cl-2 | Me | Me |
| 5.5-(Me)$_2$ | 1 (trans) | —CH$_2$C$_6$H$_4$—Cl-3 | Me | Me |
| 5.5-(Me)$_2$ | 1 (trans) | —CH$_2$C$_6$H$_4$—Cl-4 | Me | Me |
| 5.5-(Me)$_2$ | 1 (trans) | —CH$_2$C$_6$H$_4$—Me-2 | Me | Me |
| 5.5-(Me)$_2$ | 1 (trans) | —CH$_2$C$_6$H$_4$—Me-3 | Me | Me |
| 5.5-(Me)$_2$ | 1 (trans) | —CH$_2$C$_6$H$_4$—Me-4 | Me | Me |
| 5.5-(Me)$_2$ | 1 (trans) | —CH$_2$C$_6$H$_4$—OMe-2 | Me | Me |
| 5.5-(Me)$_2$ | 1 (trans) | —CH$_2$C$_6$H$_4$—OMe-3 | Me | Me |
| 5.5-(Me)$_2$ | 1 (trans) | —CH$_2$C$_6$H$_4$—OMe-4 | Me | Me |
| 5.5-(Me)$_2$ | 1 (trans) | —CH$_2$CH$_2$C$_6$H$_5$ | Me | Me |
| 5.5-(Me)$_2$ | 1 (trans) | H | OMe | OMe |
| 5.5-(Me)$_2$ | 1 (trans) | Na | OMe | OMe |
| 5.5-(Me)$_2$ | 1 (trans) | ½Ca | OMe | OMe |
| 5.5-(Me)$_2$ | 1 (trans) | $^i$PrNH$_3$ | OMe | OMe |
| 5.5-(Me)$_2$ | 1 (trans) | NH$_2$CONH$_3$ | OMe | OMe |
| 5.5-(Me)$_2$ | 1 (trans) | Me | OMe | OMe |
| 5.5-(Me)$_2$ | 1 (trans) | Et | OMe | OMe |
| 5.5-(Me)$_2$ | 1 (trans) | $^i$Pr | OMe | OMe |
| 5.5-(Me)$_2$ | 1 (trans) | Pr | OMe | OMe |
| 5.5-(Me)$_2$ | 1 (trans) | Bu | OMe | OMe |
| 5.5-(Me)$_2$ | 1 (trans) | $^i$Bu | OMe | OMe |
| 5.5-(Me)$_2$ | 1 (trans) | $^s$Bu | OMe | OMe |
| 5.5-(Me)$_2$ | 1 (trans) | —CH$_2$OCH$_3$ | OMe | OMe |
| 5.5-(Me)$_2$ | 1 (trans) | —CH$_2$CH$_2$OCH$_3$ | OMe | OMe |
| 5.5-(Me)$_2$ | 1 (trans) | —CH$_2$SCH$_3$ | OMe | OMe |
| 5.5-(Me)$_2$ | 1 (trans) | —CH$_2$CH=CH$_2$ | OMe | OMe |
| 5.5-(Me)$_2$ | 1 (trans) | —C(CH$_3$)$_2$CH=CH$_2$ | OMe | OMe |
| 5.5-(Me)$_2$ | 1 (trans) | —CH$_2$C≡CH$_2$ | OMe | OMe |
| 5.5-(Me)$_2$ | 1 (trans) | —CH$_2$C$_6$H$_5$ | OMe | OMe |
| 5.5-(Me)$_2$ | 1 (trans) | —CH$_2$C$_6$H$_4$—Cl-2 | OMe | OMe |
| 5.5-(Me)$_2$ | 1 (trans) | —CH$_2$C$_6$H$_4$—Cl-3 | OMe | OMe |
| 5.5-(Me)$_2$ | 1 (trans) | —CH$_2$C$_6$H$_4$—Cl-4 | OMe | OMe |
| 5.5-(Me)$_2$ | 1 (trans) | —CH$_2$C$_6$H$_4$—Me-2 | OMe | OMe |
| 5.5-(Me)$_2$ | 1 (trans) | —CH$_2$C$_6$H$_4$—Me-3 | OMe | OMe |
| 5.5-(Me)$_2$ | 1 (trans) | —CH$_2$C$_6$H$_4$—Me-4 | OMe | OMe |
| 5.5-(Me)$_2$ | 1 (trans) | —CH$_2$C$_6$H$_4$—OMe-2 | OMe | OMe |

TABLE-continued

A compound of the general formula:

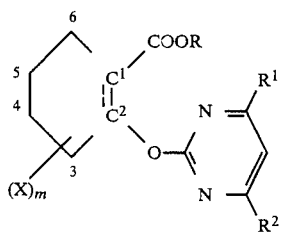

In the below-mentioned table, Me represents methyl group, Et represents ethyl group, Pr represents propyl group, $^i$Pr represents isopropyl group, Bu represents butyl group, $^i$Bu represents isobutyl group, $^s$Bu represents secondary butyl group, $^t$Bu represents tertiary butyl group, cis represents a cis-form, trans represents a trans-form, mix. represents a mixture of a cis-form and a trans-form, 1 represents a single bond and 2 represents a double bond.

| $(X)_m$ | === | R | $R^1$ | $R^2$ |
|---|---|---|---|---|
| 5.5-(Me)$_2$ | 1 (trans) | —CH$_2$C$_6$H$_4$—OMe-3 | OMe | OMe |
| 5.5-(Me)$_2$ | 1 (trans) | —CH$_2$C$_6$H$_4$—OMe-4 | OMe | OMe |
| 5.5-(Me)$_2$ | 1 (trans) | —CH$_2$CH$_2$C$_6$H$_5$ | OMe | OMe |
| 5.5-(Me)$_2$ | 1 (mixt.) | H | Me | Me |
| 5.5-(Me)$_2$ | 1 (mixt.) | Na | Me | Me |
| 5.5-(Me)$_2$ | 1 (mixt.) | ½Ca | Me | Me |
| 5.5-(Me)$_2$ | 1 (mixt.) | $^i$PrNH$_3$ | Me | Me |
| 5.5-(Me)$_2$ | 1 (mixt.) | NH$_2$CONH$_3$ | Me | Me |
| 5.5-(Me)$_2$ | 1 (mixt.) | Me | Me | Me |
| 5.5-(Me)$_2$ | 1 (mixt.) | Et | Me | Me |
| 5.5-(Me)$_2$ | 1 (mixt.) | $^i$Pr | Me | Me |
| 5.5-(Me)$_2$ | 1 (mixt.) | Pr | Me | Me |
| 5.5-(Me)$_2$ | 1 (mixt.) | Bu | Me | Me |
| 5.5-(Me)$_2$ | 1 (mixt.) | $^i$Bu | Me | Me |
| 5.5-(Me)$_2$ | 1 (mixt.) | $^s$Bu | Me | Me |
| 5.5-(Me)$_2$ | 1 (mixt.) | —CH$_2$OCH$_3$ | Me | Me |
| 5.5-(Me)$_2$ | 1 (mixt.) | —CH$_2$CH$_2$OCH$_3$ | Me | Me |
| 5.5-(Me)$_2$ | 1 (mixt.) | —CH$_2$SCH$_3$ | Me | Me |
| 5.5-(Me)$_2$ | 1 (mixt.) | —CH$_2$CH=CH$_2$ | Me | Me |
| 5.5-(Me)$_2$ | 1 (mixt.) | —C(CH$_3$)$_2$CH=CH$_2$ | Me | Me |
| 5.5-(Me)$_2$ | 1 (mixt.) | —CH$_2$C≡CH$_2$ | Me | Me |
| 5.5-(Me)$_2$ | 1 (mixt.) | —CH$_2$C$_6$H$_5$ | Me | Me |
| 5.5-(Me)$_2$ | 1 (mixt.) | —CH$_2$C$_6$H$_4$—Cl-2 | Me | Me |
| 5.5-(Me)$_2$ | 1 (mixt.) | —CH$_2$C$_6$H$_4$—Cl-3 | Me | Me |
| 5.5-(Me)$_2$ | 1 (mixt.) | —CH$_2$C$_6$H$_4$—Cl-4 | Me | Me |
| 5.5-(Me)$_2$ | 1 (mixt.) | —CH$_2$C$_6$H$_4$—Me-2 | Me | Me |
| 5.5-(Me)$_2$ | 1 (mixt.) | —CH$_2$C$_6$H$_4$—Me-3 | Me | Me |
| 5.5-(Me)$_2$ | 1 (mixt.) | —CH$_2$C$_6$H$_4$—Me-4 | Me | Me |
| 5.5-(Me)$_2$ | 1 (mixt.) | —CH$_2$C$_6$H$_4$—OMe-2 | Me | Me |
| 5.5-(Me)$_2$ | 1 (mixt.) | —CH$_2$C$_6$H$_4$—OMe-3 | Me | Me |
| 5.5-(Me)$_2$ | 1 (mixt.) | —CH$_2$C$_6$H$_4$—OMe-4 | Me | Me |
| 5.5-(Me)$_2$ | 1 (mixt.) | —CH$_2$CH$_2$C$_6$H$_5$ | Me | Me |
| 5.5-(Me)$_2$ | 1 (mixt.) | H | OMe | OMe |
| 5.5-(Me)$_2$ | 1 (mixt.) | Na | OMe | OMe |
| 5.5-(Me)$_2$ | 1 (mixt.) | ½Ca | OMe | OMe |
| 5.5-(Me)$_2$ | 1 (mixt.) | $^i$PrNH$_3$ | OMe | OMe |
| 5.5-(Me)$_2$ | 1 (mixt.) | NH$_2$CONH$_3$ | OMe | OMe |
| 5.5-(Me)$_2$ | 1 (mixt.) | Me | OMe | OMe |
| 5.5-(Me)$_2$ | 1 (mixt.) | Et | OMe | OMe |
| 5.5-(Me)$_2$ | 1 (mixt.) | $^i$Pr | OMe | OMe |
| 5.5-(Me)$_2$ | 1 (mixt.) | Pr | OMe | OMe |
| 5.5-(Me)$_2$ | 1 (mixt.) | Bu | OMe | OMe |
| 5.5-(Me)$_2$ | 1 (mixt.) | $^i$Bu | OMe | OMe |
| 5.5-(Me)$_2$ | 1 (mixt.) | $^s$Bu | OMe | OMe |
| 5.5-(Me)$_2$ | 1 (mixt.) | —CH$_2$OCH$_3$ | OMe | OMe |
| 5.5-(Me)$_2$ | 1 (mixt.) | —CH$_2$CH$_2$OCH$_3$ | OMe | OMe |
| 5.5-(Me)$_2$ | 1 (mixt.) | —CH$_2$SCH$_3$ | OMe | OMe |
| 5.5-(Me)$_2$ | 1 (mixt.) | —CH$_2$CH=CH$_2$ | OMe | OMe |
| 5.5-(Me)$_2$ | 1 (mixt.) | —C(CH$_3$)$_2$CH=CH$_2$ | OMe | OMe |
| 5.5-(Me)$_2$ | 1 (mixt.) | —CH$_2$C≡CH$_2$ | OMe | OMe |
| 5.5-(Me)$_2$ | 1 (mixt.) | —CH$_2$C$_6$H$_5$ | OMe | OMe |
| 5.5-(Me)$_2$ | 1 (mixt.) | —CH$_2$C$_6$H$_4$—Cl-2 | OMe | OMe |
| 5.5-(Me)$_2$ | 1 (mixt.) | —CH$_2$C$_6$H$_4$—Cl-3 | OMe | OMe |
| 5.5-(Me)$_2$ | 1 (mixt.) | —CH$_2$C$_6$H$_4$—Cl-4 | OMe | OMe |
| 5.5-(Me)$_2$ | 1 (mixt.) | —CH$_2$C$_6$H$_4$—Me-2 | OMe | OMe |
| 5.5-(Me)$_2$ | 1 (mixt.) | —CH$_2$C$_6$H$_4$—Me-3 | OMe | OMe |
| 5.5-(Me)$_2$ | 1 (mixt.) | —CH$_2$C$_6$H$_4$—Me-4 | OMe | OMe |

TABLE -continued

A compound of the general formula:

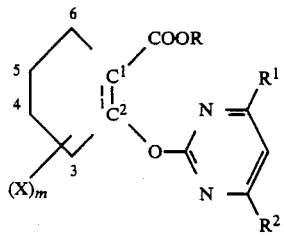

In the below-mentioned table, Me represents methyl group, Et represents ethyl group, Pr represents propyl group, $^i$Pr represents isopropyl group, Bu represents butyl group, $^i$Bu represents isobutyl group, $^s$Bu represents secondary butyl group, $^t$Bu represents tertiary butyl group, cis represents a cis-form, trans represents a trans-form, mix. represents a mixture of a cis-form and a trans-form, 1 represents a single bond and 2 represents a double bond.

| $(X)_m$ | === | R | $R^1$ | $R^2$ |
|---|---|---|---|---|
| 5.5-(Me)$_2$ | 1 (mixt.) | —CH$_2$C$_6$H$_4$—OMe-2 | OMe | OMe |
| 5.5-(Me)$_2$ | 1 (mixt.) | —CH$_2$C$_6$H$_4$—OMe-3 | OMe | OMe |
| 5.5-(Me)$_2$ | 1 (mixt.) | —CH$_2$C$_6$H$_4$—OMe-4 | OMe | OMe |
| 5.5-(Me)$_2$ | 1 (mixt.) | —CH$_2$CH$_2$C$_6$H$_5$ | OMe | OMe |
| 5.5-(Me)$_2$ | 2 (—) | H | Me | Me |
| 5.5-(Me)$_2$ | 2 (—) | Na | Me | Me |
| 5.5-(Me)$_2$ | 2 (—) | ½Ca | Me | Me |
| 5.5-(Me)$_2$ | 2 (—) | $^i$PrNH$_3$ | Me | Me |
| 5.5-(Me)$_2$ | 2 (—) | NH$_2$CONH$_3$ | Me | Me |
| 5.5-(Me)$_2$ | 2 (—) | Me | Me | Me |
| 5.5-(Me)$_2$ | 2 (—) | Et | Me | Me |
| 5.5-(Me)$_2$ | 2 (—) | $^i$Pr | Me | Me |
| 5.5-(Me)$_2$ | 2 (—) | Pr | Me | Me |
| 5.5-(Me)$_2$ | 2 (—) | Bu | Me | Me |
| 5.5-(Me)$_2$ | 2 (—) | $^i$Bu | Me | Me |
| 5.5-(Me)$_2$ | 2 (—) | $^s$Bu | Me | Me |
| 5.5-(Me)$_2$ | 2 (—) | —CH$_2$OCH$_3$ | Me | Me |
| 5.5-(Me)$_2$ | 2 (—) | —CH$_2$CH$_2$OCH$_3$ | Me | Me |
| 5.5-(Me)$_2$ | 2 (—) | —CH$_2$SCH$_3$ | Me | Me |
| 5.5-(Me)$_2$ | 2 (—) | —CH$_2$CH=CH$_2$ | Me | Me |
| 5.5-(Me)$_2$ | 2 (—) | —C(CH$_3$)$_2$CH=CH$_2$ | Me | Me |
| 5.5-(Me)$_2$ | 2 (—) | —CH$_2$C≡CH$_2$ | Me | Me |
| 5.5-(Me)$_2$ | 2 (—) | —CH$_2$C$_6$H$_5$ | Me | Me |
| 5.5-(Me)$_2$ | 2 (—) | —CH$_2$C$_6$H$_4$—Cl-2 | Me | Me |
| 5.5-(Me)$_2$ | 2 (—) | —CH$_2$C$_6$H$_4$—Cl-3 | Me | Me |
| 5.5-(Me)$_2$ | 2 (—) | —CH$_2$C$_6$H$_4$—Cl-4 | Me | Me |
| 5.5-(Me)$_2$ | 2 (—) | —CH$_2$C$_6$H$_4$—Me-2 | Me | Me |
| 5.5-(Me)$_2$ | 2 (—) | —CH$_2$C$_6$H$_4$—Me-3 | Me | Me |
| 5.5-(Me)$_2$ | 2 (—) | —CH$_2$C$_6$H$_4$—Me-4 | Me | Me |
| 5.5-(Me)$_2$ | 2 (—) | —CH$_2$C$_6$H$_4$—OMe-2 | Me | Me |
| 5.5-(Me)$_2$ | 2 (—) | —CH$_2$C$_6$H$_4$—OMe-3 | Me | Me |
| 5.5-(Me)$_2$ | 2 (—) | —CH$_2$C$_6$H$_4$—OMe-4 | Me | Me |
| 5.5-(Me)$_2$ | 2 (—) | —CH$_2$CH$_2$C$_6$H$_5$ | Me | Me |
| 5.5-(Me)$_2$ | 2 (—) | H | OMe | OMe |
| 5.5-(Me)$_2$ | 2 (—) | Na | OMe | OMe |
| 5.5-(Me)$_2$ | 2 (—) | ½Ca | OMe | OMe |
| 5.5-(Me)$_2$ | 2 (—) | $^i$PrNH$_3$ | OMe | OMe |
| 5.5-(Me)$_2$ | 2 (—) | NH$_2$CONH$_3$ | OMe | OMe |
| 5.5-(Me)$_2$ | 2 (—) | Me | OMe | OMe |
| 5.5-(Me)$_2$ | 2 (—) | Et | OMe | OMe |
| 5.5-(Me)$_2$ | 2 (—) | $^i$Pr | OMe | OMe |
| 5.5-(Me)$_2$ | 2 (—) | Pr | OMe | OMe |
| 5.5-(Me)$_2$ | 2 (—) | Bu | OMe | OMe |
| 5.5-(Me)$_2$ | 2 (—) | $^i$Bu | OMe | OMe |
| 5.5-(Me)$_2$ | 2 (—) | $^s$Bu | OMe | OMe |
| 5.5-(Me)$_2$ | 2 (—) | —CH$_2$OCH$_3$ | OMe | OMe |
| 5.5-(Me)$_2$ | 2 (—) | —CH$_2$CH$_2$OCH$_3$ | OMe | OMe |
| 5.5-(Me)$_2$ | 2 (—) | —CH$_2$SCH$_3$ | OMe | OMe |
| 5.5-(Me)$_2$ | 2 (—) | —CH$_2$CH=CH$_2$ | OMe | OMe |
| 5.5-(Me)$_2$ | 2 (—) | —C(CH$_3$)$_2$CH=CH$_2$ | OMe | OMe |
| 5.5-(Me)$_2$ | 2 (—) | —CH$_2$C≡CH$_2$ | OMe | OMe |
| 5.5-(Me)$_2$ | 2 (—) | —CH$_2$C$_6$H$_5$ | OMe | OMe |
| 5.5-(Me)$_2$ | 2 (—) | —CH$_2$C$_6$H$_4$—Cl-2 | OMe | OMe |
| 5.5-(Me)$_2$ | 2 (—) | —CH$_2$C$_6$H$_4$—Cl-3 | OMe | OMe |
| 5.5-(Me)$_2$ | 2 (—) | —CH$_2$C$_6$H$_4$—Cl-4 | OMe | OMe |
| 5.5-(Me)$_2$ | 2 (—) | —CH$_2$C$_6$H$_4$—Me-2 | OMe | OMe |
| 5.5-(Me)$_2$ | 2 (—) | —CH$_2$C$_6$H$_4$—Me-3 | OMe | OMe |

TABLE -continued

A compound of the general formula:

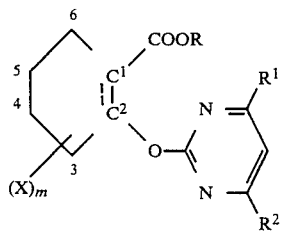

In the below-mentioned table, Me represents methyl group, Et represents ethyl group, Pr represents propyl group, $^i$Pr represents isopropyl group, Bu represents butyl group, $^i$Bu represents isobutyl group, $^s$Bu represents secondary butyl group, $^t$Bu represents tertiary butyl group, cis represents a cis-form, trans represents a trans-form, mix. represents a mixture of a cis-form and a trans-form, 1 represents a single bond and 2 represents a double bond.

| $(X)_m$ | === | R | $R^1$ | $R^2$ |
|---|---|---|---|---|
| 5.5-(Me)$_2$ | 2 (—) | —CH$_2$C$_6$H$_4$—Me-4 | OMe | OMe |
| 5.5-(Me)$_2$ | 2 (—) | —CH$_2$C$_6$H$_4$—OMe-2 | OMe | OMe |
| 5.5-(Me)$_2$ | 2 (—) | —CH$_2$C$_6$H$_4$—OMe-3 | OMe | OMe |
| 5.5-(Me)$_2$ | 2 (—) | —CH$_2$C$_6$H$_4$—OMe-4 | OMe | OMe |
| 5.5-(Me)$_2$ | 2 (—) | —CH$_2$CH$_2$C$_6$H$_5$ | OMe | OMe |
| 4.5-(Me)$_2$ | 1 (cis) | H | Me | Me |
| 4.5-(Me)$_2$ | 1 (cis) | Na | Me | Me |
| 4.5-(Me)$_2$ | 1 (cis) | ½Ca | Me | Me |
| 4.5-(Me)$_2$ | 1 (cis) | $^i$PrNH$_3$ | Me | Me |
| 4.5-(Me)$_2$ | 1 (cis) | NH$_2$CONH$_3$ | Me | Me |
| 4.5-(Me)$_2$ | 1 (cis) | Me | Me | Me |
| 4.5-(Me)$_2$ | 1 (cis) | Et | Me | Me |
| 4.5-(Me)$_2$ | 1 (cis) | $^i$Pr | Me | Me |
| 4.5-(Me)$_2$ | 1 (cis) | Pr | Me | Me |
| 4.5-(Me)$_2$ | 1 (cis) | Bu | Me | Me |
| 4.5-(Me)$_2$ | 1 (cis) | $^i$Bu | Me | Me |
| 4.5-(Me)$_2$ | 1 (cis) | $^s$Bu | Me | Me |
| 4.5-(Me)$_2$ | 1 (cis) | —CH$_2$OCH$_3$ | Me | Me |
| 4.5-(Me)$_2$ | 1 (cis) | —CH$_2$CH$_2$OCH$_3$ | Me | Me |
| 4.5-(Me)$_2$ | 1 (cis) | —CH$_2$SCH$_3$ | Me | Me |
| 4.5-(Me)$_2$ | 1 (cis) | —CH$_2$CH=CH$_2$ | Me | Me |
| 4.5-(Me)$_2$ | 1 (cis) | —C(CH$_3$)$_2$CH=CH$_2$ | Me | Me |
| 4.5-(Me)$_2$ | 1 (cis) | —CH$_2$C≡CH$_2$ | Me | Me |
| 4.5-(Me)$_2$ | 1 (cis) | —CH$_2$C$_6$H$_5$ | Me | Me |
| 4.5-(Me)$_2$ | 1 (cis) | —CH$_2$C$_6$H$_4$—Cl-2 | Me | Me |
| 4.5-(Me)$_2$ | 1 (cis) | —CH$_2$C$_6$H$_4$—Cl-3 | Me | Me |
| 4.5-(Me)$_2$ | 1 (cis) | —CH$_2$C$_6$H$_4$—Cl-4 | Me | Me |
| 4.5-(Me)$_2$ | 1 (cis) | —CH$_2$C$_6$H$_4$—Me-2 | Me | Me |
| 4.5-(Me)$_2$ | 1 (cis) | —CH$_2$C$_6$H$_4$—Me-3 | Me | Me |
| 4.5-(Me)$_2$ | 1 (cis) | —CH$_2$C$_6$H$_4$—Me-4 | Me | Me |
| 4.5-(Me)$_2$ | 1 (cis) | —CH$_2$C$_6$H$_4$—OMe-2 | Me | Me |
| 4.5-(Me)$_2$ | 1 (cis) | —CH$_2$C$_6$H$_4$—OMe-3 | Me | Me |
| 4.5-(Me)$_2$ | 1 (cis) | —CH$_2$C$_6$H$_4$—OMe-4 | Me | Me |
| 4.5-(Me)$_2$ | 1 (cis) | —CH$_2$CH$_2$C$_6$H$_5$ | Me | Me |
| 4.5-(Me)$_2$ | 1 (cis) | H | OMe | OMe |
| 4.5-(Me)$_2$ | 1 (cis) | Na | OMe | OMe |
| 4.5-(Me)$_2$ | 1 (cis) | ½Ca | OMe | OMe |
| 4.5-(Me)$_2$ | 1 (cis) | $^i$PrNH$_3$ | OMe | OMe |
| 4.5-(Me)$_2$ | 1 (cis) | NH$_2$CONH$_3$ | OMe | OMe |
| 4.5-(Me)$_2$ | 1 (cis) | Me | OMe | OMe |
| 4.5-(Me)$_2$ | 1 (cis) | Et | OMe | OMe |
| 4.5-(Me)$_2$ | 1 (cis) | $^i$Pr | OMe | OMe |
| 4.5-(Me)$_2$ | 1 (cis) | Pr | OMe | OMe |
| 4.5-(Me)$_2$ | 1 (cis) | Bu | OMe | OMe |
| 4.5-(Me)$_2$ | 1 (cis) | $^i$Bu | OMe | OMe |
| 4.5-(Me)$_2$ | 1 (cis) | $^s$Bu | OMe | OMe |
| 4.5-(Me)$_2$ | 1 (cis) | —CH$_2$OCH$_3$ | OMe | OMe |
| 4.5-(Me)$_2$ | 1 (cis) | —CH$_2$CH$_2$OCH$_3$ | OMe | OMe |
| 4.5-(Me)$_2$ | 1 (cis) | —CH$_2$SCH$_3$ | OMe | OMe |
| 4.5-(Me)$_2$ | 1 (cis) | —CH$_2$CH=CH$_2$ | OMe | OMe |
| 4.5-(Me)$_2$ | 1 (cis) | —C(CH$_3$)$_2$CH=CH$_2$ | OMe | OMe |
| 4.5-(Me)$_2$ | 1 (cis) | —CH$_2$C≡CH$_2$ | OMe | OMe |
| 4.5-(Me)$_2$ | 1 (cis) | —CH$_2$C$_6$H$_5$ | OMe | OMe |
| 4.5-(Me)$_2$ | 1 (cis) | —CH$_2$C$_6$H$_4$—Cl-2 | OMe | OMe |
| 4.5-(Me)$_2$ | 1 (cis) | —CH$_2$C$_6$H$_4$—Cl-3 | OMe | OMe |
| 4.5-(Me)$_2$ | 1 (cis) | —CH$_2$C$_6$H$_4$—Cl-4 | OMe | OMe |
| 4.5-(Me)$_2$ | 1 (cis) | —CH$_2$C$_6$H$_4$—Me-2 | OMe | OMe |

TABLE -continued

A compound of the general formula:

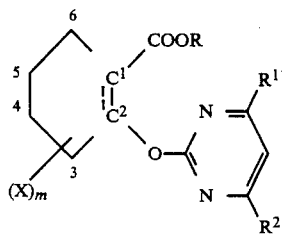

In the below-mentioned table, Me represents methyl group, Et represents ethyl group, Pr represents propyl group, $^i$Pr represents isopropyl group, Bu represents butyl group, $^i$Bu represents isobutyl group, $^s$Bu represents secondary butyl group, $^t$Bu represents tertiary butyl group, cis represents a cis-form, trans represents a trans-form, mix. represents a mixture of a cis-form and a trans-form, 1 represents a single bond and 2 represents a double bond.

| $(X)_m$ | === | R | $R^1$ | $R^2$ |
|---|---|---|---|---|
| 4.5-(Me)$_2$ | 1 (cis) | —CH$_2$C$_6$H$_4$—Me-3 | OMe | OMe |
| 4.5-(Me)$_2$ | 1 (cis) | —CH$_2$C$_6$H$_4$—Me-4 | OMe | OMe |
| 4.5-(Me)$_2$ | 1 (cis) | —CH$_2$C$_6$H$_4$—OMe-2 | OMe | OMe |
| 4.5-(Me)$_2$ | 1 (cis) | —CH$_2$C$_6$H$_4$—OMe-3 | OMe | OMe |
| 4.5-(Me)$_2$ | 1 (cis) | —CH$_2$C$_6$H$_4$—OMe-4 | OMe | OMe |
| 4.5-(Me)$_2$ | 1 (cis) | —CH$_2$CH$_2$C$_6$H$_5$ | OMe | OMe |
| 4.5-(Me)$_2$ | 1 (trans) | H | Me | Me |
| 4.5-(Me)$_2$ | 1 (trans) | Na | Me | Me |
| 4.5-(Me)$_2$ | 1 (trans) | ½Ca | Me | Me |
| 4.5-(Me)$_2$ | 1 (trans) | $^i$PrNH$_3$ | Me | Me |
| 4.5-(Me)$_2$ | 1 (trans) | NH$_2$CONH$_3$ | Me | Me |
| 4.5-(Me)$_2$ | 1 (trans) | Me | Me | Me |
| 4.5-(Me)$_2$ | 1 (trans) | Et | Me | Me |
| 4.5-(Me)$_2$ | 1 (trans) | $^i$Pr | Me | Me |
| 4.5-(Me)$_2$ | 1 (trans) | Pr | Me | Me |
| 4.5-(Me)$_2$ | 1 (trans) | Bu | Me | Me |
| 4.5-(Me)$_2$ | 1 (trans) | $^i$Bu | Me | Me |
| 4.5-(Me)$_2$ | 1 (trans) | $^s$Bu | Me | Me |
| 4.5-(Me)$_2$ | 1 (trans) | —CH$_2$OCH$_3$ | Me | Me |
| 4.5-(Me)$_2$ | 1 (trans) | —CH$_2$CH$_2$OCH$_3$ | Me | Me |
| 4.5-(Me)$_2$ | 1 (trans) | —CH$_2$SCH$_3$ | Me | Me |
| 4.5-(Me)$_2$ | 1 (trans) | —CH$_2$CH=CH$_2$ | Me | Me |
| 4.5-(Me)$_2$ | 1 (trans) | —C(CH$_3$)$_2$CH=CH$_2$ | Me | Me |
| 4.5-(Me)$_2$ | 1 (trans) | —CH$_2$C≡CH$_2$ | Me | Me |
| 4.5-(Me)$_2$ | 1 (trans) | —CH$_2$C$_6$H$_5$ | Me | Me |
| 4.5-(Me)$_2$ | 1 (trans) | —CH$_2$C$_6$H$_4$—Cl-2 | Me | Me |
| 4.5-(Me)$_2$ | 1 (trans) | —CH$_2$C$_6$H$_4$—Cl-3 | Me | Me |
| 4.5-(Me)$_2$ | 1 (trans) | —CH$_2$C$_6$H$_4$—Cl-4 | Me | Me |
| 4.5-(Me)$_2$ | 1 (trans) | —CH$_2$C$_6$H$_4$—Me-2 | Me | Me |
| 4.5-(Me)$_2$ | 1 (trans) | —CH$_2$C$_6$H$_4$—Me-3 | Me | Me |
| 4.5-(Me)$_2$ | 1 (trans) | —CH$_2$C$_6$H$_4$—Me-4 | Me | Me |
| 4.5-(Me)$_2$ | 1 (trans) | —CH$_2$C$_6$H$_4$—OMe-2 | Me | Me |
| 4.5-(Me)$_2$ | 1 (trans) | —CH$_2$C$_6$H$_4$—OMe-3 | Me | Me |
| 4.5-(Me)$_2$ | 1 (trans) | —CH$_2$C$_6$H$_4$—OMe-4 | Me | Me |
| 4.5-(Me)$_2$ | 1 (trans) | —CH$_2$CH$_2$C$_6$H$_5$ | Me | Me |
| 4.5-(Me)$_2$ | 1 (trans) | H | OMe | OMe |
| 4.5-(Me)$_2$ | 1 (trans) | Na | OMe | OMe |
| 4.5-(Me)$_2$ | 1 (trans) | ½Ca | OMe | OMe |
| 4.5-(Me)$_2$ | 1 (trans) | $^i$PrNH$_3$ | OMe | OMe |
| 4.5-(Me)$_2$ | 1 (trans) | NH$_2$CONH$_3$ | OMe | OMe |
| 4.5-(Me)$_2$ | 1 (trans) | Me | OMe | OMe |
| 4.5-(Me)$_2$ | 1 (trans) | Et | OMe | OMe |
| 4.5-(Me)$_2$ | 1 (trans) | $^i$Pr | OMe | OMe |
| 4.5-(Me)$_2$ | 1 (trans) | Pr | OMe | OMe |
| 4.5-(Me)$_2$ | 1 (trans) | Bu | OMe | OMe |
| 4.5-(Me)$_2$ | 1 (trans) | $^i$Bu | OMe | OMe |
| 4.5-(Me)$_2$ | 1 (trans) | $^s$Bu | OMe | OMe |
| 4.5-(Me)$_2$ | 1 (trans) | —CH$_2$OCH$_3$ | OMe | OMe |
| 4.5-(Me)$_2$ | 1 (trans) | —CH$_2$CH$_2$OCH$_3$ | OMe | OMe |
| 4.5-(Me)$_2$ | 1 (trans) | —CH$_2$SCH$_3$ | OMe | OMe |
| 4.5-(Me)$_2$ | 1 (trans) | —CH$_2$CH=CH$_2$ | OMe | OMe |
| 4.5-(Me)$_2$ | 1 (trans) | —C(CH$_3$)$_2$CH=CH$_2$ | OMe | OMe |
| 4.5-(Me)$_2$ | 1 (trans) | —CH$_2$C≡CH$_2$ | OMe | OMe |
| 4.5-(Me)$_2$ | 1 (trans) | —CH$_2$C$_6$H$_5$ | OMe | OMe |
| 4.5-(Me)$_2$ | 1 (trans) | —CH$_2$C$_6$H$_4$—Cl-2 | OMe | OMe |
| 4.5-(Me)$_2$ | 1 (trans) | —CH$_2$C$_6$H$_4$—Cl-3 | OMe | OMe |
| 4.5-(Me)$_2$ | 1 (trans) | —CH$_2$C$_6$H$_4$—Cl-4 | OMe | OMe |

TABLE -continued

A compound of the general formula:

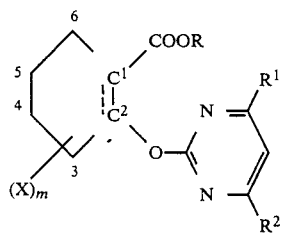

In the below-mentioned table, Me represents methyl group, Et represents ethyl group, Pr represents propyl group, $^i$Pr represents isopropyl group, Bu represents butyl group, $^i$Bu represents isobutyl group, $^s$Bu represents secondary butyl group, $^t$Bu represents tertiary butyl group, cis represents a cis-form, trans represents a trans-form, mix. represents a mixture of a cis-form and a trans-form, 1 represents a single bond and 2 represents a double bond.

| $(X)_m$ | === | R | $R^1$ | $R^2$ |
|---|---|---|---|---|
| 4.5-(Me)$_2$ | 1 (trans) | —CH$_2$C$_6$H$_4$—Me-2 | OMe | OMe |
| 4.5-(Me)$_2$ | 1 (trans) | —CH$_2$C$_6$H$_4$—Me-3 | OMe | OMe |
| 4.5-(Me)$_2$ | 1 (trans) | —CH$_2$C$_6$H$_4$—Me-4 | OMe | OMe |
| 4.5-(Me)$_2$ | 1 (trans) | —CH$_2$C$_6$H$_4$—OMe-2 | OMe | OMe |
| 4.5-(Me)$_2$ | 1 (trans) | —CH$_2$C$_6$H$_4$—OMe-3 | OMe | OMe |
| 4.5-(Me)$_2$ | 1 (trans) | —CH$_2$C$_6$H$_4$—OMe-4 | OMe | OMe |
| 4.5-(Me)$_2$ | 1 (trans) | —CH$_2$CH$_2$C$_6$H$_5$ | OMe | OMe |
| 4.5-(Me)$_2$ | 1 (mixt.) | H | Me | Me |
| 4.5-(Me)$_2$ | 1 (mixt.) | Na | Me | Me |
| 4.5-(Me)$_2$ | 1 (mixt.) | ½Ca | Me | Me |
| 4.5-(Me)$_2$ | 1 (mixt.) | $^i$PrNH$_3$ | Me | Me |
| 4.5-(Me)$_2$ | 1 (mixt.) | NH$_2$CONH$_3$ | Me | Me |
| 4.5-(Me)$_2$ | 1 (mixt.) | Me | Me | Me |
| 4.5-(Me)$_2$ | 1 (mixt.) | Et | Me | Me |
| 4.5-(Me)$_2$ | 1 (mixt.) | $^i$Pr | Me | Me |
| 4.5-(Me)$_2$ | 1 (mixt.) | Pr | Me | Me |
| 4.5-(Me)$_2$ | 1 (mixt.) | Bu | Me | Me |
| 4.5-(Me)$_2$ | 1 (mixt.) | $^i$Bu | Me | Me |
| 4.5-(Me)$_2$ | 1 (mixt.) | $^s$Bu | Me | Me |
| 4.5-(Me)$_2$ | 1 (mixt.) | —CH$_2$OCH$_3$ | Me | Me |
| 4.5-(Me)$_2$ | 1 (mixt.) | —CH$_2$CH$_2$OCH$_3$ | Me | Me |
| 4.5-(Me)$_2$ | 1 (mixt.) | —CH$_2$SCH$_3$ | Me | Me |
| 4.5-(Me)$_2$ | 1 (mixt.) | —CH$_2$CH=CH$_2$ | Me | Me |
| 4.5-(Me)$_2$ | 1 (mixt.) | —C(CH$_3$)$_2$CH=CH$_2$ | Me | Me |
| 4.5-(Me)$_2$ | 1 (mixt.) | —CH$_2$C≡CH$_2$ | Me | Me |
| 4.5-(Me)$_2$ | 1 (mixt.) | —CH$_2$C$_6$H$_5$ | Me | Me |
| 4.5-(Me)$_2$ | 1 (mixt.) | —CH$_2$C$_6$H$_4$—Cl-2 | Me | Me |
| 4.5-(Me)$_2$ | 1 (mixt.) | —CH$_2$C$_6$H$_4$—Cl-3 | Me | Me |
| 4.5-(Me)$_2$ | 1 (mixt.) | —CH$_2$C$_6$H$_4$—Cl-4 | Me | Me |
| 4.5-(Me)$_2$ | 1 (mixt.) | —CH$_2$C$_6$H$_4$—Me-2 | Me | Me |
| 4.5-(Me)$_2$ | 1 (mixt.) | —CH$_2$C$_6$H$_4$—Me-3 | Me | Me |
| 4.5-(Me)$_2$ | 1 (mixt.) | —CH$_2$C$_6$H$_4$—Me-4 | Me | Me |
| 4.5-(Me)$_2$ | 1 (mixt.) | —CH$_2$C$_6$H$_4$—OMe-2 | Me | Me |
| 4.5-(Me)$_2$ | 1 (mixt.) | —CH$_2$C$_6$H$_4$—OMe-3 | Me | Me |
| 4.5-(Me)$_2$ | 1 (mixt.) | —CH$_2$C$_6$H$_4$—OMe-4 | Me | Me |
| 4.5-(Me)$_2$ | 1 (mixt.) | —CH$_2$CH$_2$C$_6$H$_5$ | Me | Me |
| 4.5-(Me)$_2$ | 1 (mixt.) | H | OMe | OMe |
| 4.5-(Me)$_2$ | 1 (mixt.) | Na | OMe | OMe |
| 4.5-(Me)$_2$ | 1 (mixt.) | ½Ca | OMe | OMe |
| 4.5-(Me)$_2$ | 1 (mixt.) | $^i$PrNH$_3$ | OMe | OMe |
| 4.5-(Me)$_2$ | 1 (mixt.) | NH$_2$CONH$_3$ | OMe | OMe |
| 4.5-(Me)$_2$ | 1 (mixt.) | Me | OMe | OMe |
| 4.5-(Me)$_2$ | 1 (mixt.) | Et | OMe | OMe |
| 4.5-(Me)$_2$ | 1 (mixt.) | $^i$Pr | OMe | OMe |
| 4.5-(Me)$_2$ | 1 (mixt.) | Pr | OMe | OMe |
| 4.5-(Me)$_2$ | 1 (mixt.) | Bu | OMe | OMe |
| 4.5-(Me)$_2$ | 1 (mixt.) | $^i$Bu | OMe | OMe |
| 4.5-(Me)$_2$ | 1 (mixt.) | $^s$Bu | OMe | OMe |
| 4.5-(Me)$_2$ | 1 (mixt.) | —CH$_2$OCH$_3$ | OMe | OMe |
| 4.5-(Me)$_2$ | 1 (mixt.) | —CH$_2$CH$_2$OCH$_3$ | OMe | OMe |
| 4.5-(Me)$_2$ | 1 (mixt.) | —CH$_2$SCH$_3$ | OMe | OMe |
| 4.5-(Me)$_2$ | 1 (mixt.) | —CH$_2$CH=CH$_2$ | OMe | OMe |
| 4.5-(Me)$_2$ | 1 (mixt.) | —C(CH$_3$)$_2$CH=CH$_2$ | OMe | OMe |
| 4.5-(Me)$_2$ | 1 (mixt.) | —CH$_2$C≡CH$_2$ | OMe | OMe |
| 4.5-(Me)$_2$ | 1 (mixt.) | —CH$_2$C$_6$H$_5$ | OMe | OMe |
| 4.5-(Me)$_2$ | 1 (mixt.) | —CH$_2$C$_6$H$_4$—Cl-2 | OMe | OMe |
| 4.5-(Me)$_2$ | 1 (mixt.) | —CH$_2$C$_6$H$_4$—Cl-3 | OMe | OMe |

TABLE -continued

A compound of the general formula:

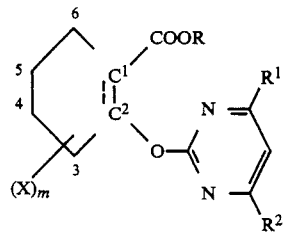

In the below-mentioned table, Me represents methyl group, Et represents ethyl group, Pr represents propyl group, $^i$Pr represents isopropyl group, Bu represents butyl group, $^i$Bu represents isobutyl group, $^s$Bu represents secondary butyl group, $^t$Bu represents tertiary butyl group, cis represents a cis-form, trans represents a trans-form, mix. represents a mixture of a cis-form and a trans-form, 1 represents a single bond and 2 represents a double bond.

| (X)$_m$ | === | R | R$^1$ | R$^2$ |
|---|---|---|---|---|
| 4.5-(Me)$_2$ | 1 (mixt.) | —CH$_2$C$_6$H$_4$—Cl-4 | OMe | OMe |
| 4.5-(Me)$_2$ | 1 (mixt.) | —CH$_2$C$_6$H$_4$—Me-2 | OMe | OMe |
| 4.5-(Me)$_2$ | 1 (mixt.) | —CH$_2$C$_6$H$_4$—Me-3 | OMe | OMe |
| 4.5-(Me)$_2$ | 1 (mixt.) | —CH$_2$C$_6$H$_4$—Me-4 | OMe | OMe |
| 4.5-(Me)$_2$ | 1 (mixt.) | —CH$_2$C$_6$H$_4$—OMe-2 | OMe | OMe |
| 4.5-(Me)$_2$ | 1 (mixt.) | —CH$_2$C$_6$H$_4$—OMe-3 | OMe | OMe |
| 4.5-(Me)$_2$ | 1 (mixt.) | —CH$_2$C$_6$H$_4$—OMe-4 | OMe | OMe |
| 4.5-(Me)$_2$ | 1 (mixt.) | —CH$_2$CH$_2$C$_6$H$_5$ | OMe | OMe |
| 4.5-(Me)$_2$ | 2 (—) | H | Me | Me |
| 4.5-(Me)$_2$ | 2 (—) | Na | Me | Me |
| 4.5-(Me)$_2$ | 2 (—) | ½Ca | Me | Me |
| 4.5-(Me)$_2$ | 2 (—) | $^i$PrNH$_3$ | Me | Me |
| 4.5-(Me)$_2$ | 2 (—) | NH$_2$CONH$_3$ | Me | Me |
| 4.5-(Me)$_2$ | 2 (—) | Me | Me | Me |
| 4.5-(Me)$_2$ | 2 (—) | Et | Me | Me |
| 4.5-(Me)$_2$ | 2 (—) | $^i$Pr | Me | Me |
| 4.5-(Me)$_2$ | 2 (—) | Pr | Me | Me |
| 4.5-(Me)$_2$ | 2 (—) | Bu | Me | Me |
| 4.5-(Me)$_2$ | 2 (—) | $^i$Bu | Me | Me |
| 4.5-(Me)$_2$ | 2 (—) | $^s$Bu | Me | Me |
| 4.5-(Me)$_2$ | 2 (—) | —CH$_2$OCH$_3$ | Me | Me |
| 4.5-(Me)$_2$ | 2 (—) | —CH$_2$CH$_2$OCH$_3$ | Me | Me |
| 4.5-(Me)$_2$ | 2 (—) | —CH$_2$SCH$_3$ | Me | Me |
| 4.5-(Me)$_2$ | 2 (—) | —CH$_2$CH=CH$_2$ | Me | Me |
| 4.5-(Me)$_2$ | 2 (—) | —C(CH$_3$)$_2$CH=CH$_2$ | Me | Me |
| 4.5-(Me)$_2$ | 2 (—) | —CH$_2$C≡CH$_2$ | Me | Me |
| 4.5-(Me)$_2$ | 2 (—) | —CH$_2$C$_6$H$_5$ | Me | Me |
| 4.5-(Me)$_2$ | 2 (—) | —CH$_2$C$_6$H$_4$—Cl-2 | Me | Me |
| 4.5-(Me)$_2$ | 2 (—) | —CH$_2$C$_6$H$_4$—Cl-3 | Me | Me |
| 4.5-(Me)$_2$ | 2 (—) | —CH$_2$C$_6$H$_4$—Cl-4 | Me | Me |
| 4.5-(Me)$_2$ | 2 (—) | —CH$_2$C$_6$H$_4$—Me-2 | Me | Me |
| 4.5-(Me)$_2$ | 2 (—) | —CH$_2$C$_6$H$_4$—Me-3 | Me | Me |
| 4.5-(Me)$_2$ | 2 (—) | —CH$_2$C$_6$H$_4$—Me-4 | Me | Me |
| 4.5-(Me)$_2$ | 2 (—) | —CH$_2$C$_6$H$_4$—OMe-2 | Me | Me |
| 4.5-(Me)$_2$ | 2 (—) | —CH$_2$C$_6$H$_4$—OMe-3 | Me | Me |
| 4.5-(Me)$_2$ | 2 (—) | —CH$_2$C$_6$H$_4$—OMe-4 | Me | Me |
| 4.5-(Me)$_2$ | 2 (—) | —CH$_2$CH$_2$C$_6$H$_5$ | Me | Me |
| 4.5-(Me)$_2$ | 2 (—) | H | OMe | OMe |
| 4.5-(Me)$_2$ | 2 (—) | Na | OMe | OMe |
| 4.5-(Me)$_2$ | 2 (—) | ½Ca | OMe | OMe |
| 4.5-(Me)$_2$ | 2 (—) | $^i$PrNH$_3$ | OMe | OMe |
| 4.5-(Me)$_2$ | 2 (—) | NH$_2$CONH$_3$ | OMe | OMe |
| 4.5-(Me)$_2$ | 2 (—) | Me | OMe | OMe |
| 4.5-(Me)$_2$ | 2 (—) | Et | OMe | OMe |
| 4.5-(Me)$_2$ | 2 (—) | $^i$Pr | OMe | OMe |
| 4.5-(Me)$_2$ | 2 (—) | Pr | OMe | OMe |
| 4.5-(Me)$_2$ | 2 (—) | Bu | OMe | OMe |
| 4.5-(Me)$_2$ | 2 (—) | $^i$Bu | OMe | OMe |
| 4.5-(Me)$_2$ | 2 (—) | $^s$Bu | OMe | OMe |
| 4.5-(Me)$_2$ | 2 (—) | —CH$_2$OCH$_3$ | OMe | OMe |
| 4.5-(Me)$_2$ | 2 (—) | —CH$_2$CH$_2$OCH$_3$ | OMe | OMe |
| 4.5-(Me)$_2$ | 2 (—) | —CH$_2$SCH$_3$ | OMe | OMe |
| 4.5-(Me)$_2$ | 2 (—) | —CH$_2$CH=CH$_2$ | OMe | OMe |
| 4.5-(Me)$_2$ | 2 (—) | —C(CH$_3$)$_2$CH=CH$_2$ | OMe | OMe |
| 4.5-(Me)$_2$ | 2 (—) | —CH$_2$C≡CH$_2$ | OMe | OMe |
| 4.5-(Me)$_2$ | 2 (—) | —CH$_2$C$_6$H$_5$ | OMe | OMe |
| 4.5-(Me)$_2$ | 2 (—) | —CH$_2$C$_6$H$_4$—Cl-2 | OMe | OMe |

TABLE -continued

A compound of the general formula:

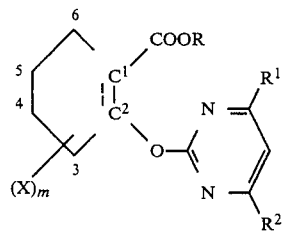

In the below-mentioned table, Me represents methyl group, Et represents ethyl group, Pr represents propyl group, $^i$Pr represents isopropyl group, Bu represents butyl group, $^i$Bu represents isobutyl group, $^s$Bu represents secondary butyl group, $^t$Bu represents tertiary butyl group, cis represents a cis-form, trans represents a trans-form, mix. represents a mixture of a cis-form and a trans-form, 1 represents a single bond and 2 represents a double bond.

| $(X)_m$ | === | R | $R^1$ | $R^2$ |
|---|---|---|---|---|
| 4.5-(Me)$_2$ | 2 (—) | —CH$_2$C$_6$H$_4$—Cl-3 | OMe | OMe |
| 4.5-(Me)$_2$ | 2 (—) | —CH$_2$C$_6$H$_4$—Cl-4 | OMe | OMe |
| 4.5-(Me)$_2$ | 2 (—) | —CH$_2$C$_6$H$_4$—Me-2 | OMe | OMe |
| 4.5-(Me)$_2$ | 2 (—) | —CH$_2$C$_6$H$_4$—Me-3 | OMe | OMe |
| 4.5-(Me)$_2$ | 2 (—) | —CH$_2$C$_6$H$_4$—Me-4 | OMe | OMe |
| 4.5-(Me)$_2$ | 2 (—) | —CH$_2$C$_6$H$_4$—OMe-2 | OMe | OMe |
| 4.5-(Me)$_2$ | 2 (—) | —CH$_2$C$_6$H$_4$—OMe-3 | OMe | OMe |
| 4.5-(Me)$_2$ | 2 (—) | —CH$_2$C$_6$H$_4$—OMe-4 | OMe | OMe |
| 4.5-(Me)$_2$ | 2 (—) | —CH$_2$CH$_2$C$_6$H$_5$ | OMe | OMe |
| 4-Et | 1 (cis) | H | Me | Me |
| 4-Et | 1 (cis) | Na | Me | Me |
| 4-Et | 1 (cis) | ½Ca | Me | Me |
| 4-Et | 1 (cis) | $^i$PrNH$_3$ | Me | Me |
| 4-Et | 1 (cis) | NH$_2$CONH$_3$ | Me | Me |
| 4-Et | 1 (cis) | Me | Me | Me |
| 4-Et | 1 (cis) | Et | Me | Me |
| 4-Et | 1 (cis) | $^i$Pr | Me | Me |
| 4-Et | 1 (cis) | Pr | Me | Me |
| 4-Et | 1 (cis) | Bu | Me | Me |
| 4-Et | 1 (cis) | $^i$Bu | Me | Me |
| 4-Et | 1 (cis) | $^s$Bu | Me | Me |
| 4-Et | 1 (cis) | —CH$_2$OCH$_3$ | Me | Me |
| 4-Et | 1 (cis) | —CH$_2$CH$_2$OCH$_3$ | Me | Me |
| 4-Et | 1 (cis) | —CH$_2$SCH$_3$ | Me | Me |
| 4-Et | 1 (cis) | —CH$_2$CH=CH$_2$ | Me | Me |
| 4-Et | 1 (cis) | —C(CH$_3$)$_2$CH=CH$_2$ | Me | Me |
| 4-Et | 1 (cis) | —CH$_2$C≡CH$_2$ | Me | Me |
| 4-Et | 1 (cis) | —CH$_2$C$_6$H$_5$ | Me | Me |
| 4-Et | 1 (cis) | —CH$_2$C$_6$H$_4$—Cl-2 | Me | Me |
| 4-Et | 1 (cis) | —CH$_2$C$_6$H$_4$—Cl-3 | Me | Me |
| 4-Et | 1 (cis) | —CH$_2$C$_6$H$_4$—Cl-4 | Me | Me |
| 4-Et | 1 (cis) | —CH$_2$C$_6$H$_4$—Me-2 | Me | Me |
| 4-Et | 1 (cis) | —CH$_2$C$_6$H$_4$—Me-3 | Me | Me |
| 4-Et | 1 (cis) | —CH$_2$C$_6$H$_4$—Me-4 | Me | Me |
| 4-Et | 1 (cis) | —CH$_2$C$_6$H$_4$—OMe-2 | Me | Me |
| 4-Et | 1 (cis) | —CH$_2$C$_6$H$_4$—OMe-3 | Me | Me |
| 4-Et | 1 (cis) | —CH$_2$C$_6$H$_4$—OMe-4 | Me | Me |
| 4-Et | 1 (cis) | —CH$_2$CH$_2$C$_6$H$_5$ | Me | Me |
| 4-Et | 1 (cis) | H | OMe | OMe |
| 4-Et | 1 (cis) | Na | OMe | OMe |
| 4-Et | 1 (cis) | ½Ca | OMe | OMe |
| 4-Et | 1 (cis) | $^i$PrNH$_3$ | OMe | OMe |
| 4-Et | 1 (cis) | NH$_2$CONH$_3$ | OMe | OMe |
| 4-Et | 1 (cis) | Me | OMe | OMe |
| 4-Et | 1 (cis) | Et | OMe | OMe |
| 4-Et | 1 (cis) | $^i$Pr | OMe | OMe |
| 4-Et | 1 (cis) | Pr | OMe | OMe |
| 4-Et | 1 (cis) | Bu | OMe | OMe |
| 4-Et | 1 (cis) | $^i$Bu | OMe | OMe |
| 4-Et | 1 (cis) | $^s$Bu | OMe | OMe |
| 4-Et | 1 (cis) | —CH$_2$OCH$_3$ | OMe | OMe |
| 4-Et | 1 (cis) | —CH$_2$CH$_2$OCH$_3$ | OMe | OMe |
| 4-Et | 1 (cis) | —CH$_2$SCH$_3$ | OMe | OMe |
| 4-Et | 1 (cis) | —CH$_2$CH=CH$_2$ | OMe | OMe |
| 4-Et | 1 (cis) | —C(CH$_3$)$_2$CH=CH$_2$ | OMe | OMe |
| 4-Et | 1 (cis) | —CH$_2$C≡CH$_2$ | OMe | OMe |
| 4-Et | 1 (cis) | —CH$_2$C$_6$H$_5$ | OMe | OMe |

TABLE -continued

A compound of the general formula:

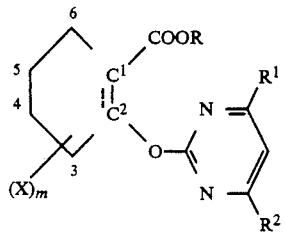

In the below-mentioned table, Me represents methyl group, Et represents ethyl group, Pr represents propyl group, $^i$Pr represents isopropyl group, Bu represents butyl group, $^i$Bu represents isobutyl group, $^s$Bu represents secondary butyl group, $^t$Bu represents tertiary butyl group, cis represents a cis-form, trans represents a trans-form, mix. represents a mixture of a cis-form and a trans-form, 1 represents a single bond and 2 represents a double bond.

| $(X)_m$ | === | R | $R^1$ | $R^2$ |
|---|---|---|---|---|
| 4-Et | 1 (cis) | —CH$_2$C$_6$H$_4$—Cl-2 | OMe | OMe |
| 4-Et | 1 (cis) | —CH$_2$C$_6$H$_4$—Cl-3 | OMe | OMe |
| 4-Et | 1 (cis) | —CH$_2$C$_6$H$_4$—Cl-4 | OMe | OMe |
| 4-Et | 1 (cis) | —CH$_2$C$_6$H$_4$—Me-2 | OMe | OMe |
| 4-Et | 1 (cis) | —CH$_2$C$_6$H$_4$—Me-3 | OMe | OMe |
| 4-Et | 1 (cis) | —CH$_2$C$_6$H$_4$—Me-4 | OMe | OMe |
| 4-Et | 1 (cis) | —CH$_2$C$_6$H$_4$—OMe-2 | OMe | OMe |
| 4-Et | 1 (cis) | —CH$_2$C$_6$H$_4$—OMe-3 | OMe | OMe |
| 4-Et | 1 (cis) | —CH$_2$C$_6$H$_4$—OMe-4 | OMe | OMe |
| 4-Et | 1 (cis) | —CH$_2$CH$_2$C$_6$H$_5$ | OMe | OMe |
| 4-Et | 1 (trans) | H | Me | Me |
| 4-Et | 1 (trans) | Na | Me | Me |
| 4-Et | 1 (trans) | ½Ca | Me | Me |
| 4-Et | 1 (trans) | $^i$PrNH$_3$ | Me | Me |
| 4-Et | 1 (trans) | NH$_2$CONH$_3$ | Me | Me |
| 4-Et | 1 (trans) | Me | Me | Me |
| 4-Et | 1 (trans) | Et | Me | Me |
| 4-Et | 1 (trans) | $^i$Pr | Me | Me |
| 4-Et | 1 (trans) | Pr | Me | Me |
| 4-Et | 1 (trans) | Bu | Me | Me |
| 4-Et | 1 (trans) | $^i$Bu | Me | Me |
| 4-Et | 1 (trans) | $^s$Bu | Me | Me |
| 4-Et | 1 (trans) | —CH$_2$OCH$_3$ | Me | Me |
| 4-Et | 1 (trans) | —CH$_2$CH$_2$OCH$_3$ | Me | Me |
| 4-Et | 1 (trans) | —CH$_2$SCH$_3$ | Me | Me |
| 4-Et | 1 (trans) | —CH$_2$CH=CH$_2$ | Me | Me |
| 4-Et | 1 (trans) | —C(CH$_3$)$_2$CH=CH$_2$ | Me | Me |
| 4-Et | 1 (trans) | —CH$_2$C≡CH$_2$ | Me | Me |
| 4-Et | 1 (trans) | —CH$_2$C$_6$H$_5$ | Me | Me |
| 4-Et | 1 (trans) | —CH$_2$C$_6$H$_4$—Cl-2 | Me | Me |
| 4-Et | 1 (trans) | —CH$_2$C$_6$H$_4$—Cl-3 | Me | Me |
| 4-Et | 1 (trans) | —CH$_2$C$_6$H$_4$—Cl-4 | Me | Me |
| 4-Et | 1 (trans) | —CH$_2$C$_6$H$_4$—Me-2 | Me | Me |
| 4-Et | 1 (trans) | —CH$_2$C$_6$H$_4$—Me-3 | Me | Me |
| 4-Et | 1 (trans) | —CH$_2$C$_6$H$_4$—Me-4 | Me | Me |
| 4-Et | 1 (trans) | —CH$_2$C$_6$H$_4$—OMe-2 | Me | Me |
| 4-Et | 1 (trans) | —CH$_2$C$_6$H$_4$—OMe-3 | Me | Me |
| 4-Et | 1 (trans) | —CH$_2$C$_6$H$_4$—OMe-4 | Me | Me |
| 4-Et | 1 (trans) | —CH$_2$CH$_2$C$_6$H$_5$ | Me | Me |
| 4-Et | 1 (trans) | H | OMe | OMe |
| 4-Et | 1 (trans) | Na | OMe | OMe |
| 4-Et | 1 (trans) | ½Ca | OMe | OMe |
| 4-Et | 1 (trans) | $^i$PrNH$_3$ | OMe | OMe |
| 4-Et | 1 (trans) | NH$_2$CONH$_3$ | OMe | OMe |
| 4-Et | 1 (trans) | Me | OMe | OMe |
| 4-Et | 1 (trans) | Et | OMe | OMe |
| 4-Et | 1 (trans) | $^i$Pr | OMe | OMe |
| 4-Et | 1 (trans) | Pr | OMe | OMe |
| 4-Et | 1 (trans) | Bu | OMe | OMe |
| 4-Et | 1 (trans) | $^i$Bu | OMe | OMe |
| 4-Et | 1 (trans) | $^s$Bu | OMe | OMe |
| 4-Et | 1 (trans) | —CH$_2$OCH$_3$ | OMe | OMe |
| 4-Et | 1 (trans) | —CH$_2$CH$_2$OCH$_3$ | OMe | OMe |
| 4-Et | 1 (trans) | —CH$_2$SCH$_3$ | OMe | OMe |
| 4-Et | 1 (trans) | —CH$_2$CH=CH$_2$ | OMe | OMe |
| 4-Et | 1 (trans) | —C(CH$_3$)$_2$CH=CH$_2$ | OMe | OMe |
| 4-Et | 1 (trans) | —CH$_2$C≡CH$_2$ | OMe | OMe |

TABLE -continued

A compound of the general formula:

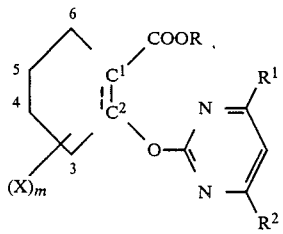

In the below-mentioned table, Me represents methyl group, Et represents ethyl group, Pr represents propyl group, $^i$Pr represents isopropyl group, Bu represents butyl group, $^i$Bu represents isobutyl group, $^s$Bu represents secondary butyl group, $^t$Bu represents tertiary butyl group, cis represents a cis-form, trans represents a trans-form, mix. represents a mixture of a cis-form and a trans-form, 1 represents a single bond and 2 represents a double bond.

| $(X)_m$ | === | R | $R^1$ | $R^2$ |
|---|---|---|---|---|
| 4-Et | 1 (trans) | —CH$_2$C$_6$H$_5$ | OMe | OMe |
| 4-Et | 1 (trans) | —CH$_2$C$_6$H$_4$—Cl-2 | OMe | OMe |
| 4-Et | 1 (trans) | —CH$_2$C$_6$H$_4$—Cl-3 | OMe | OMe |
| 4-Et | 1 (trans) | —CH$_2$C$_6$H$_4$—Cl-4 | OMe | OMe |
| 4-Et | 1 (trans) | —CH$_2$C$_6$H$_4$—Me-2 | OMe | OMe |
| 4-Et | 1 (trans) | —CH$_2$C$_6$H$_4$—Me-3 | OMe | OMe |
| 4-Et | 1 (trans) | —CH$_2$C$_6$H$_4$—Me-4 | OMe | OMe |
| 4-Et | 1 (trans) | —CH$_2$C$_6$H$_4$—OMe-2 | OMe | OMe |
| 4-Et | 1 (trans) | —CH$_2$C$_6$H$_4$—OMe-3 | OMe | OMe |
| 4-Et | 1 (trans) | —CH$_2$C$_6$H$_4$—OMe-4 | OMe | OMe |
| 4-Et | 1 (trans) | —CH$_2$CH$_2$C$_6$H$_5$ | OMe | OMe |
| 4-Et | 1 (mixt.) | H | Me | Me |
| 4-Et | 1 (mixt.) | Na | Me | Me |
| 4-Et | 1 (mixt.) | ½Ca | Me | Me |
| 4-Et | 1 (mixt.) | $^i$PrNH$_3$ | Me | Me |
| 4-Et | 1 (mixt.) | NH$_2$CONH$_3$ | Me | Me |
| 4-Et | 1 (mixt.) | Me | Me | Me |
| 4-Et | 1 (mixt.) | Et | Me | Me |
| 4-Et | 1 (mixt.) | $^i$Pr | Me | Me |
| 4-Et | 1 (mixt.) | Pr | Me | Me |
| 4-Et | 1 (mixt.) | Bu | Me | Me |
| 4-Et | 1 (mixt.) | $^i$Bu | Me | Me |
| 4-Et | 1 (mixt.) | $^s$Bu | Me | Me |
| 4-Et | 1 (mixt.) | —CH$_2$OCH$_3$ | Me | Me |
| 4-Et | 1 (mixt.) | —CH$_2$CH$_2$OCH$_3$ | Me | Me |
| 4-Et | 1 (mixt.) | —CH$_2$SCH$_3$ | Me | Me |
| 4-Et | 1 (mixt.) | —CH$_2$CH=CH$_2$ | Me | Me |
| 4-Et | 1 (mixt.) | —C(CH$_3$)$_2$CH=CH$_2$ | Me | Me |
| 4-Et | 1 (mixt.) | —CH$_2$C≡CH$_2$ | Me | Me |
| 4-Et | 1 (mixt.) | —CH$_2$C$_6$H$_5$ | Me | Me |
| 4-Et | 1 (mixt.) | —CH$_2$C$_6$H$_4$—Cl-2 | Me | Me |
| 4-Et | 1 (mixt.) | —CH$_2$C$_6$H$_4$—Cl-3 | Me | Me |
| 4-Et | 1 (mixt.) | —CH$_2$C$_6$H$_4$—Cl-4 | Me | Me |
| 4-Et | 1 (mixt.) | —CH$_2$C$_6$H$_4$—Me-2 | Me | Me |
| 4-Et | 1 (mixt.) | —CH$_2$C$_6$H$_4$—Me-3 | Me | Me |
| 4-Et | 1 (mixt.) | —CH$_2$C$_6$H$_4$—Me-4 | Me | Me |
| 4-Et | 1 (mixt.) | —CH$_2$C$_6$H$_4$—OMe-2 | Me | Me |
| 4-Et | 1 (mixt.) | —CH$_2$C$_6$H$_4$—OMe-3 | Me | Me |
| 4-Et | 1 (mixt.) | —CH$_2$C$_6$H$_4$—OMe-4 | Me | Me |
| 4-Et | 1 (mixt.) | —CH$_2$CH$_2$C$_6$H$_5$ | Me | Me |
| 4-Et | 1 (mixt.) | H | OMe | OMe |
| 4-Et | 1 (mixt.) | Na | OMe | OMe |
| 4-Et | 1 (mixt.) | ½Ca | OMe | OMe |
| 4-Et | 1 (mixt.) | $^i$PrNH$_3$ | OMe | OMe |
| 4-Et | 1 (mixt.) | NH$_2$CONH$_3$ | OMe | OMe |
| 4-Et | 1 (mixt.) | Me | OMe | OMe |
| 4-Et | 1 (mixt.) | Et | OMe | OMe |
| 4-Et | 1 (mixt.) | $^i$Pr | OMe | OMe |
| 4-Et | 1 (mixt.) | Pr | OMe | OMe |
| 4-Et | 1 (mixt.) | Bu | OMe | OMe |
| 4-Et | 1 (mixt.) | $^i$Bu | OMe | OMe |
| 4-Et | 1 (mixt.) | $^s$Bu | OMe | OMe |
| 4-Et | 1 (mixt.) | —CH$_2$OCH$_3$ | OMe | OMe |
| 4-Et | 1 (mixt.) | —CH$_2$CH$_2$OCH$_3$ | OMe | OMe |
| 4-Et | 1 (mixt.) | —CH$_2$SCH$_3$ | OMe | OMe |
| 4-Et | 1 (mixt.) | —CH$_2$CH=CH$_2$ | OMe | OMe |
| 4-Et | 1 (mixt.) | —C(CH$_3$)$_2$CH=CH$_2$ | OMe | OMe |

TABLE -continued

A compound of the general formula:

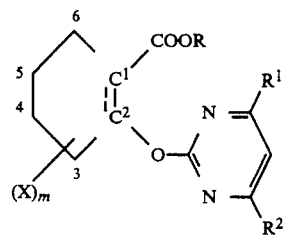

In the below-mentioned table, Me represents methyl group, Et represents ethyl group, Pr represents propyl group, $^i$Pr represents isopropyl group, Bu represents butyl group, $^i$Bu represents isobutyl group, $^s$Bu represents secondary butyl group, $^t$Bu represents tertiary butyl group, cis represents a cis-form, trans represents a trans-form, mix. represents a mixture of a cis-form and a trans-form, 1 represents a single bond and 2 represents a double bond.

| (X)$_m$ | === | R | R$^1$ | R$^2$ |
|---|---|---|---|---|
| 4-Et | 1 (mixt.) | —CH$_2$C≡CH$_2$ | OMe | OMe |
| 4-Et | 1 (mixt.) | —CH$_2$C$_6$H$_5$ | OMe | OMe |
| 4-Et | 1 (mixt.) | —CH$_2$C$_6$H$_4$—Cl-2 | OMe | OMe |
| 4-Et | 1 (mixt.) | —CH$_2$C$_6$H$_4$—Cl-3 | OMe | OMe |
| 4-Et | 1 (mixt.) | —CH$_2$C$_6$H$_4$—Cl-4 | OMe | OMe |
| 4-Et | 1 (mixt.) | —CH$_2$C$_6$H$_4$—Me-2 | OMe | OMe |
| 4-Et | 1 (mixt.) | —CH$_2$C$_6$H$_4$—Me-3 | OMe | OMe |
| 4-Et | 1 (mixt.) | —CH$_2$C$_6$H$_4$—Me-4 | OMe | OMe |
| 4-Et | 1 (mixt.) | —CH$_2$C$_6$H$_4$—OMe-2 | OMe | OMe |
| 4-Et | 1 (mixt.) | —CH$_2$C$_6$H$_4$—OMe-3 | OMe | OMe |
| 4-Et | 1 (mixt.) | —CH$_2$C$_6$H$_4$—OMe-4 | OMe | OMe |
| 4-Et | 1 (mixt.) | —CH$_2$CH$_2$C$_6$H$_5$ | OMe | OMe |
| 4-Et | 2 (—) | H | Me | Me |
| 4-Et | 2 (—) | Na | Me | Me |
| 4-Et | 2 (—) | ½Ca | Me | Me |
| 4-Et | 2 (—) | $^i$PrNH$_3$ | Me | Me |
| 4-Et | 2 (—) | NH$_2$CONH$_3$ | Me | Me |
| 4-Et | 2 (—) | Me | Me | Me |
| 4-Et | 2 (—) | Et | Me | Me |
| 4-Et | 2 (—) | $^i$Pr | Me | Me |
| 4-Et | 2 (—) | Pr | Me | Me |
| 4-Et | 2 (—) | Bu | Me | Me |
| 4-Et | 2 (—) | $^i$Bu | Me | Me |
| 4-Et | 2 (—) | $^s$Bu | Me | Me |
| 4-Et | 2 (—) | —CH$_2$OCH$_3$ | Me | Me |
| 4-Et | 2 (—) | —CH$_2$CH$_2$OCH$_3$ | Me | Me |
| 4-Et | 2 (—) | —CH$_2$SCH$_3$ | Me | Me |
| 4-Et | 2 (—) | —CH$_2$CH=CH$_2$ | Me | Me |
| 4-Et | 2 (—) | —C(CH$_3$)$_2$CH=CH$_2$ | Me | Me |
| 4-Et | 2 (—) | —CH$_2$C≡CH$_2$ | Me | Me |
| 4-Et | 2 (—) | —CH$_2$C$_6$H$_5$ | Me | Me |
| 4-Et | 2 (—) | —CH$_2$C$_6$H$_4$—Cl-2 | Me | Me |
| 4-Et | 2 (—) | —CH$_2$C$_6$H$_4$—Cl-3 | Me | Me |
| 4-Et | 2 (—) | —CH$_2$C$_6$H$_4$—Cl-4 | Me | Me |
| 4-Et | 2 (—) | —CH$_2$C$_6$H$_4$—Me-2 | Me | Me |
| 4-Et | 2 (—) | —CH$_2$C$_6$H$_4$—Me-3 | Me | Me |
| 4-Et | 2 (—) | —CH$_2$C$_6$H$_4$—Me-4 | Me | Me |
| 4-Et | 2 (—) | —CH$_2$C$_6$H$_4$—OMe-2 | Me | Me |
| 4-Et | 2 (—) | —CH$_2$C$_6$H$_4$—OMe-3 | Me | Me |
| 4-Et | 2 (—) | —CH$_2$C$_6$H$_4$—OMe-4 | Me | Me |
| 4-Et | 2 (—) | —CH$_2$CH$_2$C$_6$H$_5$ | Me | Me |
| 4-Et | 2 (—) | H | OMe | OMe |
| 4-Et | 2 (—) | Na | OMe | OMe |
| 4-Et | 2 (—) | ½Ca | OMe | OMe |
| 4-Et | 2 (—) | $^i$PrNH$_3$ | OMe | OMe |
| 4-Et | 2 (—) | NH$_2$CONH$_3$ | OMe | OMe |
| 4-Et | 2 (—) | Me | OMe | OMe |
| 4-Et | 2 (—) | Et | OMe | OMe |
| 4-Et | 2 (—) | $^i$Pr | OMe | OMe |
| 4-Et | 2 (—) | Pr | OMe | OMe |
| 4-Et | 2 (—) | Bu | OMe | OMe |
| 4-Et | 2 (—) | $^i$Bu | OMe | OMe |
| 4-Et | 2 (—) | $^s$Bu | OMe | OMe |
| 4-Et | 2 (—) | —CH$_2$OCH$_3$ | OMe | OMe |
| 4-Et | 2 (—) | —CH$_2$CH$_2$OCH$_3$ | OMe | OMe |
| 4-Et | 2 (—) | —CH$_2$SCH$_3$ | OMe | OMe |
| 4-Et | 2 (—) | —CH$_2$CH=CH$_2$ | OMe | OMe |

TABLE -continued

A compound of the general formula:

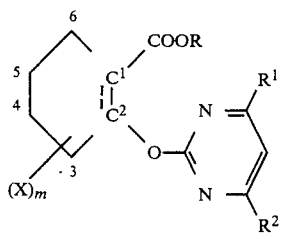

In the below-mentioned table, Me represents methyl group, Et represents ethyl group, Pr represents propyl group, $^i$Pr represents isopropyl group, Bu represents butyl group, $^i$Bu represents isobutyl group, $^s$Bu represents secondary butyl group, $^t$Bu represents tertiary butyl group, cis represents a cis-form, trans represents a trans-form, mix. represents a mixture of a cis-form and a trans-form, 1 represents a single bond and 2 represents a double bond.

| $(X)_m$ | === | R | $R^1$ | $R^2$ |
|---|---|---|---|---|
| 4-Et | 2 (—) | —C(CH$_3$)$_2$CH=CH$_2$ | OMe | OMe |
| 4-Et | 2 (—) | —CH$_2$C≡CH | OMe | OMe |
| 4-Et | 2 (—) | —CH$_2$C$_6$H$_5$ | OMe | OMe |
| 4-Et | 2 (—) | —CH$_2$C$_6$H$_4$—Cl-2 | OMe | OMe |
| 4-Et | 2 (—) | —CH$_2$C$_6$H$_4$—Cl-3 | OMe | OMe |
| 4-Et | 2 (—) | —CH$_2$C$_6$H$_4$—Cl-4 | OMe | OMe |
| 4-Et | 2 (—) | —CH$_2$C$_6$H$_4$—Me-2 | OMe | OMe |
| 4-Et | 2 (—) | —CH$_2$C$_6$H$_4$—Me-3 | OMe | OMe |
| 4-Et | 2 (—) | —CH$_2$C$_6$H$_4$—Me-4 | OMe | OMe |
| 4-Et | 2 (—) | —CH$_2$C$_6$H$_4$—OMe-2 | OMe | OMe |
| 4-Et | 2 (—) | —CH$_2$C$_6$H$_4$—OMe-3 | OMe | OMe |
| 4-Et | 2 (—) | —CH$_2$C$_6$H$_4$—OMe-4 | OMe | OMe |
| 4-Et | 2 (—) | —CH$_2$CH$_2$C$_6$H$_5$ | OMe | OMe |
| 4-$^i$Pr | 1 (cis) | H | Me | Me |
| 4-$^i$Pr | 1 (cis) | Na | Me | Me |
| 4-$^i$Pr | 1 (cis) | ½Ca | Me | Me |
| 4-$^i$Pr | 1 (cis) | $^i$PrNH$_3$ | Me | Me |
| 4-$^i$Pr | 1 (cis) | NH$_2$CONH$_3$ | Me | Me |
| 4-$^i$Pr | 1 (cis) | Me | Me | Me |
| 4-$^i$Pr | 1 (cis) | Et | Me | Me |
| 4-$^i$Pr | 1 (cis) | $^i$Pr | Me | Me |
| 4-$^i$Pr | 1 (cis) | Pr | Me | Me |
| 4-$^i$Pr | 1 (cis) | Bu | Me | Me |
| 4-$^i$Pr | 1 (cis) | $^i$Bu | Me | Me |
| 4-$^i$Pr | 1 (cis) | $^s$Bu | Me | Me |
| 4-$^i$Pr | 1 (cis) | —CH$_2$OCH$_3$ | Me | Me |
| 4-$^i$Pr | 1 (cis) | —CH$_2$CH$_2$OCH$_3$ | Me | Me |
| 4-$^i$Pr | 1 (cis) | —CH$_2$SCH$_3$ | Me | Me |
| 4-$^i$Pr | 1 (cis) | —CH$_2$CH=CH$_2$ | Me | Me |
| 4-$^i$Pr | 1 (cis) | —C(CH$_3$)$_2$CH=CH$_2$ | Me | Me |
| 4-$^i$Pr | 1 (cis) | —CH$_2$C≡CH | Me | Me |
| 4-$^i$Pr | 1 (cis) | —CH$_2$C$_6$H$_5$ | Me | Me |
| 4-$^i$Pr | 1 (cis) | —CH$_2$C$_6$H$_4$—Cl-2 | Me | Me |
| 4-$^i$Pr | 1 (cis) | —CH$_2$C$_6$H$_4$—Cl-3 | Me | Me |
| 4-$^i$Pr | 1 (cis) | —CH$_2$C$_6$H$_4$—Cl-4 | Me | Me |
| 4-$^i$Pr | 1 (cis) | —CH$_2$C$_6$H$_4$—Me-2 | Me | Me |
| 4-$^i$Pr | 1 (cis) | —CH$_2$C$_6$H$_4$—Me-3 | Me | Me |
| 4-$^i$Pr | 1 (cis) | —CH$_2$C$_6$H$_4$—Me-4 | Me | Me |
| 4-$^i$Pr | 1 (cis) | —CH$_2$C$_6$H$_4$—OMe-2 | Me | Me |
| 4-$^i$Pr | 1 (cis) | —CH$_2$C$_6$H$_4$—OMe-3 | Me | Me |
| 4-$^i$Pr | 1 (cis) | —CH$_2$C$_6$H$_4$—OMe-4 | Me | Me |
| 4-$^i$Pr | 1 (cis) | —CH$_2$CH$_2$C$_6$H$_5$ | Me | Me |
| 4-$^i$Pr | 1 (cis) | H | OMe | OMe |
| 4-$^i$Pr | 1 (cis) | Na | OMe | OMe |
| 4-$^i$Pr | 1 (cis) | ½Ca | OMe | OMe |
| 4-$^i$Pr | 1 (cis) | $^i$PrNH$_3$ | OMe | OMe |
| 4-$^i$Pr | 1 (cis) | NH$_2$CONH$_3$ | OMe | OMe |
| 4-$^i$Pr | 1 (cis) | Me | OMe | OMe |
| 4-$^i$Pr | 1 (cis) | Et | OMe | OMe |
| 4-$^i$Pr | 1 (cis) | $^i$Pr | OMe | OMe |
| 4-$^i$Pr | 1 (cis) | Pr | OMe | OMe |
| 4-$^i$Pr | 1 (cis) | Bu | OMe | OMe |
| 4-$^i$Pr | 1 (cis) | $^i$Bu | OMe | OMe |
| 4-$^i$Pr | 1 (cis) | $^s$Bu | OMe | OMe |
| 4-$^i$Pr | 1 (cis) | —CH$_2$OCH$_3$ | OMe | OMe |
| 4-$^i$Pr | 1 (cis) | —CH$_2$CH$_2$OCH$_3$ | OMe | OMe |
| 4-$^i$Pr | 1 (cis) | —CH$_2$SCH$_3$ | OMe | OMe |

TABLE -continued

A compound of the general formula:

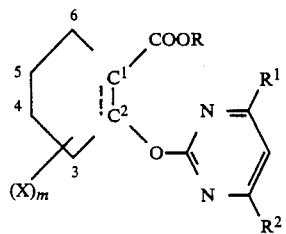

In the below-mentioned table, Me represents methyl group, Et represents ethyl group, Pr represents propyl group, $^i$Pr represents isopropyl group, Bu represents butyl group, $^i$Bu represents isobutyl group, $^s$Bu represents secondary butyl group, $^t$Bu represents tertiary butyl group, cis represents a cis-form, trans represents a trans-form, mix. represents a mixture of a cis-form and a trans-form, 1 represents a single bond and 2 represents a double bond.

| $(X)_m$ | === | R | $R^1$ | $R^2$ |
|---|---|---|---|---|
| 4-$^i$Pr | 1 (cis) | —CH$_2$CH=CH$_2$ | OMe | OMe |
| 4-$^i$Pr | 1 (cis) | —C(CH$_3$)$_2$CH=CH$_2$ | OMe | OMe |
| 4-$^i$Pr | 1 (cis) | —CH$_2$C≡CH$_2$ | OMe | OMe |
| 4-$^i$Pr | 1 (cis) | —CH$_2$C$_6$H$_5$ | OMe | OMe |
| 4-$^i$Pr | 1 (cis) | —CH$_2$C$_6$H$_4$—Cl-2 | OMe | OMe |
| 4-$^i$Pr | 1 (cis) | —CH$_2$C$_6$H$_4$—Cl-3 | OMe | OMe |
| 4-$^i$Pr | 1 (cis) | —CH$_2$C$_6$H$_4$—Cl-4 | OMe | OMe |
| 4-$^i$Pr | 1 (cis) | —CH$_2$C$_6$H$_4$—Me-2 | OMe | OMe |
| 4-$^i$Pr | 1 (cis) | —CH$_2$C$_6$H$_4$—Me-3 | OMe | OMe |
| 4-$^i$Pr | 1 (cis) | —CH$_2$C$_6$H$_4$—Me-4 | OMe | OMe |
| 4-$^i$Pr | 1 (cis) | —CH$_2$C$_6$H$_4$—OMe-2 | OMe | OMe |
| 4-$^i$Pr | 1 (cis) | —CH$_2$C$_6$H$_4$—OMe-3 | OMe | OMe |
| 4-$^i$Pr | 1 (cis) | —CH$_2$C$_6$H$_4$—OMe-4 | OMe | OMe |
| 4-$^i$Pr | 1 (cis) | —CH$_2$CH$_2$C$_6$H$_5$ | OMe | OMe |
| 4-$^i$Pr | 1 (trans) | H | Me | Me |
| 4-$^i$Pr | 1 (trans) | Na | Me | Me |
| 4-$^i$Pr | 1 (trans) | ½Ca | Me | Me |
| 4-$^i$Pr | 1 (trans) | $^i$PrNH$_3$ | Me | Me |
| 4-$^i$Pr | 1 (trans) | NH$_2$CONH$_3$ | Me | Me |
| 4-$^i$Pr | 1 (trans) | Me | Me | Me |
| 4-$^i$Pr | 1 (trans) | Et | Me | Me |
| 4-$^i$Pr | 1 (trans) | $^i$Pr | Me | Me |
| 4-$^i$Pr | 1 (trans) | Pr | Me | Me |
| 4-$^i$Pr | 1 (trans) | Bu | Me | Me |
| 4-$^i$Pr | 1 (trans) | $^i$Bu | Me | Me |
| 4-$^i$Pr | 1 (trans) | $^s$Bu | Me | Me |
| 4-$^i$Pr | 1 (trans) | —CH$_2$OCH$_3$ | Me | Me |
| 4-$^i$Pr | 1 (trans) | —CH$_2$CH$_2$OCH$_3$ | Me | Me |
| 4-$^i$Pr | 1 (trans) | —CH$_2$SCH$_3$ | Me | Me |
| 4-$^i$Pr | 1 (trans) | —CH$_2$CH=CH$_2$ | Me | Me |
| 4-$^i$Pr | 1 (trans) | —C(CH$_3$)$_2$CH=CH$_2$ | Me | Me |
| 4-$^i$Pr | 1 (trans) | —CH$_2$C≡CH$_2$ | Me | Me |
| 4-$^i$Pr | 1 (trans) | —CH$_2$C$_6$H$_5$ | Me | Me |
| 4-$^i$Pr | 1 (trans) | —CH$_2$C$_6$H$_4$—Cl-2 | Me | Me |
| 4-$^i$Pr | 1 (trans) | —CH$_2$C$_6$H$_4$—Cl-3 | Me | Me |
| 4-$^i$Pr | 1 (trans) | —CH$_2$C$_6$H$_4$—Cl-4 | Me | Me |
| 4-$^i$Pr | 1 (trans) | —CH$_2$C$_6$H$_4$—Me-2 | Me | Me |
| 4-$^i$Pr | 1 (trans) | —CH$_2$C$_6$H$_4$—Me-3 | Me | Me |
| 4-$^i$Pr | 1 (trans) | —CH$_2$C$_6$H$_4$—Me-4 | Me | Me |
| 4-$^i$Pr | 1 (trans) | —CH$_2$C$_6$H$_4$—OMe-2 | Me | Me |
| 4-$^i$Pr | 1 (trans) | —CH$_2$C$_6$H$_4$—OMe-3 | Me | Me |
| 4-$^i$Pr | 1 (trans) | —CH$_2$C$_6$H$_4$—OMe-4 | Me | Me |
| 4-$^i$Pr | 1 (trans) | —CH$_2$CH$_2$C$_6$H$_5$ | Me | Me |
| 4-$^i$Pr | 1 (trans) | H | OMe | OMe |
| 4-$^i$Pr | 1 (trans) | Na | OMe | OMe |
| 4-$^i$Pr | 1 (trans) | ½Ca | OMe | OMe |
| 4-$^i$Pr | 1 (trans) | $^i$PrNH$_3$ | OMe | OMe |
| 4-$^i$Pr | 1 (trans) | NH$_2$CONH$_3$ | OMe | OMe |
| 4-$^i$Pr | 1 (trans) | Me | OMe | OMe |
| 4-$^i$Pr | 1 (trans) | Et | OMe | OMe |
| 4-$^i$Pr | 1 (trans) | $^i$Pr | OMe | OMe |
| 4-$^i$Pr | 1 (trans) | Pr | OMe | OMe |
| 4-$^i$Pr | 1 (trans) | Bu | OMe | OMe |
| 4-$^i$Pr | 1 (trans) | $^i$Bu | OMe | OMe |
| 4-$^i$Pr | 1 (trans) | $^s$Bu | OMe | OMe |
| 4-$^i$Pr | 1 (trans) | —CH$_2$OCH$_3$ | OMe | OMe |
| 4-$^i$Pr | 1 (trans) | —CH$_2$CH$_2$OCH$_3$ | OMe | OMe |

TABLE -continued

A compound of the general formula:

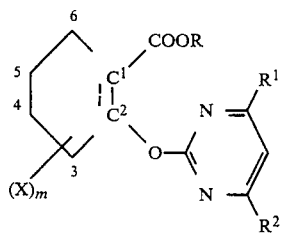

In the below-mentioned table, Me represents methyl group, Et represents ethyl group, Pr represents propyl group, $^i$Pr represents isopropyl group, Bu represents butyl group, $^i$Bu represents isobutyl group, $^s$Bu represents secondary butyl group, $^t$Bu represents tertiary butyl group, cis represents a cis-form, trans represents a trans-form, mix. represents a mixture of a cis-form and a trans-form, 1 represents a single bond and 2 represents a double bond.

| $(X)_m$ | === | R | $R^1$ | $R^2$ |
|---|---|---|---|---|
| 4-$^i$Pr | 1 (trans) | —CH$_2$SCH$_3$ | OMe | OMe |
| 4-$^i$Pr | 1 (trans) | —CH$_2$CH=CH$_2$ | OMe | OMe |
| 4-$^i$Pr | 1 (trans) | —C(CH$_3$)$_2$CH=CH$_2$ | OMe | OMe |
| 4-$^i$Pr | 1 (trans) | —CH$_2$C≡CH$_2$ | OMe | OMe |
| 4-$^i$Pr | 1 (trans) | —CH$_2$C$_6$H$_5$ | OMe | OMe |
| 4-$^i$Pr | 1 (trans) | —CH$_2$C$_6$H$_4$—Cl-2 | OMe | OMe |
| 4-$^i$Pr | 1 (trans) | —CH$_2$C$_6$H$_4$—Cl-3 | OMe | OMe |
| 4-$^i$Pr | 1 (trans) | —CH$_2$C$_6$H$_4$—Cl-4 | OMe | OMe |
| 4-$^i$Pr | 1 (trans) | —CH$_2$C$_6$H$_4$—Me-2 | OMe | OMe |
| 4-$^i$Pr | 1 (trans) | —CH$_2$C$_6$H$_4$—Me-3 | OMe | OMe |
| 4-$^i$Pr | 1 (trans) | —CH$_2$C$_6$H$_4$—Me-4 | OMe | OMe |
| 4-$^i$Pr | 1 (trans) | —CH$_2$C$_6$H$_4$—OMe-2 | OMe | OMe |
| 4-$^i$Pr | 1 (trans) | —CH$_2$C$_6$H$_4$—OMe-3 | OMe | OMe |
| 4-$^i$Pr | 1 (trans) | —CH$_2$C$_6$H$_4$—OMe-4 | OMe | OMe |
| 4-$^i$Pr | 1 (trans) | —CH$_2$CH$_2$C$_6$H$_5$ | OMe | OMe |
| 4-$^i$Pr | 1 (mixt.) | H | Me | Me |
| 4-$^i$Pr | 1 (mixt.) | Na | Me | Me |
| 4-$^i$Pr | 1 (mixt.) | ½Ca | Me | Me |
| 4-$^i$Pr | 1 (mixt.) | $^i$PrNH$_3$ | Me | Me |
| 4-$^i$Pr | 1 (mixt.) | NH$_2$CONH$_3$ | Me | Me |
| 4-$^i$Pr | 1 (mixt.) | Me | Me | Me |
| 4-$^i$Pr | 1 (mixt.) | Et | Me | Me |
| 4-$^i$Pr | 1 (mixt.) | $^i$Pr | Me | Me |
| 4-$^i$Pr | 1 (mixt.) | Pr | Me | Me |
| 4-$^i$Pr | 1 (mixt.) | Bu | Me | Me |
| 4-$^i$Pr | 1 (mixt.) | $^i$Bu | Me | Me |
| 4-$^i$Pr | 1 (mixt.) | $^s$Bu | Me | Me |
| 4-$^i$Pr | 1 (mixt.) | —CH$_2$OCH$_3$ | Me | Me |
| 4-$^i$Pr | 1 (mixt.) | —CH$_2$CH$_2$OCH$_3$ | Me | Me |
| 4-$^i$Pr | 1 (mixt.) | —CH$_2$SCH$_3$ | Me | Me |
| 4-$^i$Pr | 1 (mixt.) | —CH$_2$CH=CH$_2$ | Me | Me |
| 4-$^i$Pr | 1 (mixt.) | —C(CH$_3$)$_2$CH=CH$_2$ | Me | Me |
| 4-$^i$Pr | 1 (mixt.) | —CH$_2$C≡CH$_2$ | Me | Me |
| 4-$^i$Pr | 1 (mixt.) | —CH$_2$C$_6$H$_5$ | Me | Me |
| 4-$^i$Pr | 1 (mixt.) | —CH$_2$C$_6$H$_4$—Cl-2 | Me | Me |
| 4-$^i$Pr | 1 (mixt.) | —CH$_2$C$_6$H$_4$—Cl-3 | Me | Me |
| 4-$^i$Pr | 1 (mixt.) | —CH$_2$C$_6$H$_4$—Cl-4 | Me | Me |
| 4-$^i$Pr | 1 (mixt.) | —CH$_2$C$_6$H$_4$—Me-2 | Me | Me |
| 4-$^i$Pr | 1 (mixt.) | —CH$_2$C$_6$H$_4$—Me-3 | Me | Me |
| 4-$^i$Pr | 1 (mixt.) | —CH$_2$C$_6$H$_4$—Me-4 | Me | Me |
| 4-$^i$Pr | 1 (mixt.) | —CH$_2$C$_6$H$_4$—OMe-2 | Me | Me |
| 4-$^i$Pr | 1 (mixt.) | —CH$_2$C$_6$H$_4$—OMe-3 | Me | Me |
| 4-$^i$Pr | 1 (mixt.) | —CH$_2$C$_6$H$_4$—OMe-4 | Me | Me |
| 4-$^i$Pr | 1 (mixt.) | —CH$_2$CH$_2$C$_6$H$_5$ | Me | Me |
| 4-$^i$Pr | 1 (mixt.) | H | OMe | OMe |
| 4-$^i$Pr | 1 (mixt.) | Na | OMe | OMe |
| 4-$^i$Pr | 1 (mixt.) | ½Ca | OMe | OMe |
| 4-$^i$Pr | 1 (mixt.) | $^i$PrNH$_3$ | OMe | OMe |
| 4-$^i$Pr | 1 (mixt.) | NH$_2$CONH$_3$ | OMe | OMe |
| 4-$^i$Pr | 1 (mixt.) | Me | OMe | OMe |
| 4-$^i$Pr | 1 (mixt.) | Et | OMe | OMe |
| 4-$^i$Pr | 1 (mixt.) | $^i$Pr | OMe | OMe |
| 4-$^i$Pr | 1 (mixt.) | Pr | OMe | OMe |
| 4-$^i$Pr | 1 (mixt.) | Bu | OMe | OMe |
| 4-$^i$Pr | 1 (mixt.) | $^i$Bu | OMe | OMe |
| 4-$^i$Pr | 1 (mixt.) | $^s$Bu | OMe | OMe |
| 4-$^i$Pr | 1 (mixt.) | —CH$_2$OCH$_3$ | OMe | OMe |

TABLE -continued

A compound of the general formula:

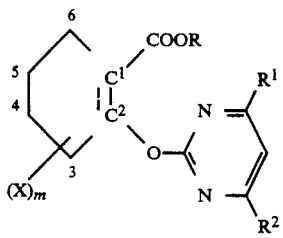

In the below-mentioned table, Me represents methyl group, Et represents ethyl group, Pr represents propyl group, $^i$Pr represents isopropyl group, Bu represents butyl group, $^i$Bu represents isobutyl group, $^s$Bu represents secondary butyl group, $^t$Bu represents tertiary butyl group, cis represents a cis-form, trans represents a trans-form, mix. represents a mixture of a cis-form and a trans-form, 1 represents a single bond and 2 represents a double bond.

| (X)$_m$ | === | R | R$^1$ | R$^2$ |
|---|---|---|---|---|
| 4-$^i$Pr | 1 (mixt.) | —CH$_2$CH$_2$OCH$_3$ | OMe | OMe |
| 4-$^i$Pr | 1 (mixt.) | —CH$_2$SCH$_3$ | OMe | OMe |
| 4-$^i$Pr | 1 (mixt.) | —CH$_2$CH=CH$_2$ | OMe | OMe |
| 4-$^i$Pr | 1 (mixt.) | —C(CH$_3$)$_2$CH=CH$_2$ | OMe | OMe |
| 4-$^i$Pr | 1 (mixt.) | —CH$_2$C≡CH$_2$ | OMe | OMe |
| 4-$^i$Pr | 1 (mixt.) | —CH$_2$C$_6$H$_5$ | OMe | OMe |
| 4-$^i$Pr | 1 (mixt.) | —CH$_2$C$_6$H$_4$—Cl-2 | OMe | OMe |
| 4-$^i$Pr | 1 (mixt.) | —CH$_2$C$_6$H$_4$—Cl-3 | OMe | OMe |
| 4-$^i$Pr | 1 (mixt.) | —CH$_2$C$_6$H$_4$—Cl-4 | OMe | OMe |
| 4-$^i$Pr | 1 (mixt.) | —CH$_2$C$_6$H$_4$—Me-2 | OMe | OMe |
| 4-$^i$Pr | 1 (mixt.) | —CH$_2$C$_6$H$_4$—Me-3 | OMe | OMe |
| 4-$^i$Pr | 1 (mixt.) | —CH$_2$C$_6$H$_4$—Me-4 | OMe | OMe |
| 4-$^i$Pr | 1 (mixt.) | —CH$_2$C$_6$H$_4$—OMe-2 | OMe | OMe |
| 4-$^i$Pr | 1 (mixt.) | —CH$_2$C$_6$H$_4$—OMe-3 | OMe | OMe |
| 4-$^i$Pr | 1 (mixt.) | —CH$_2$C$_6$H$_4$—OMe-4 | OMe | OMe |
| 4-$^i$Pr | 1 (mixt.) | —CH$_2$CH$_2$C$_6$H$_5$ | OMe | OMe |
| 4-$^i$Pr | 2 (—) | H | Me | Me |
| 4-$^i$Pr | 2 (—) | Na | Me | Me |
| 4-$^i$Pr | 2 (—) | ½Ca | Me | Me |
| 4-$^i$Pr | 2 (—) | $^i$PrNH$_3$ | Me | Me |
| 4-$^i$Pr | 2 (—) | NH$_2$CONH$_3$ | Me | Me |
| 4-$^i$Pr | 2 (—) | Me | Me | Me |
| 4-$^i$Pr | 2 (—) | Et | Me | Me |
| 4-$^i$Pr | 2 (—) | $^i$Pr | Me | Me |
| 4-$^i$Pr | 2 (—) | Pr | Me | Me |
| 4-$^i$Pr | 2 (—) | Bu | Me | Me |
| 4-$^i$Pr | 2 (—) | $^i$Bu | Me | Me |
| 4-$^i$Pr | 2 (—) | $^s$Bu | Me | Me |
| 4-$^i$Pr | 2 (—) | —CH$_2$OCH$_3$ | Me | Me |
| 4-$^i$Pr | 2 (—) | —CH$_2$CH$_2$OCH$_3$ | Me | Me |
| 4-$^i$Pr | 2 (—) | —CH$_2$SCH$_3$ | Me | Me |
| 4-$^i$Pr | 2 (—) | —CH$_2$CH=CH$_2$ | Me | Me |
| 4-$^i$Pr | 2 (—) | —C(CH$_3$)$_2$CH=CH$_2$ | Me | Me |
| 4-$^i$Pr | 2 (—) | —CH$_2$C≡CH$_2$ | Me | Me |
| 4-$^i$Pr | 2 (—) | —CH$_2$C$_6$H$_5$ | Me | Me |
| 4-$^i$Pr | 2 (—) | —CH$_2$C$_6$H$_4$—Cl-2 | Me | Me |
| 4-$^i$Pr | 2 (—) | —CH$_2$C$_6$H$_4$—Cl-3 | Me | Me |
| 4-$^i$Pr | 2 (—) | —CH$_2$C$_6$H$_4$—Cl-4 | Me | Me |
| 4-$^i$Pr | 2 (—) | —CH$_2$C$_6$H$_4$—Me-2 | Me | Me |
| 4-$^i$Pr | 2 (—) | —CH$_2$C$_6$H$_4$—Me-3 | Me | Me |
| 4-$^i$Pr | 2 (—) | —CH$_2$C$_6$H$_4$—Me-4 | Me | Me |
| 4-$^i$Pr | 2 (—) | —CH$_2$C$_6$H$_4$—OMe-2 | Me | Me |
| 4-$^i$Pr | 2 (—) | —CH$_2$C$_6$H$_4$—OMe-3 | Me | Me |
| 4-$^i$Pr | 2 (—) | —CH$_2$C$_6$H$_4$—OMe-4 | Me | Me |
| 4-$^i$Pr | 2 (—) | —CH$_2$CH$_2$C$_6$H$_5$ | Me | Me |
| 4-$^i$Pr | 2 (—) | H | OMe | OMe |
| 4-$^i$Pr | 2 (—) | Na | OMe | OMe |
| 4-$^i$Pr | 2 (—) | ½Ca | OMe | OMe |
| 4-$^i$Pr | 2 (—) | $^i$PrNH$_3$ | OMe | OMe |
| 4-$^i$Pr | 2 (—) | NH$_2$CONH$_3$ | OMe | OMe |
| 4-$^i$Pr | 2 (—) | Me | OMe | OMe |
| 4-$^i$Pr | 2 (—) | Et | OMe | OMe |
| 4-$^i$Pr | 2 (—) | $^i$Pr | OMe | OMe |
| 4-$^i$Pr | 2 (—) | Pr | OMe | OMe |
| 4-$^i$Pr | 2 (—) | Bu | OMe | OMe |
| 4-$^i$Pr | 2 (—) | $^i$Bu | OMe | OMe |
| 4-$^i$Pr | 2 (—) | $^s$Bu | OMe | OMe |

TABLE -continued

A compound of the general formula:

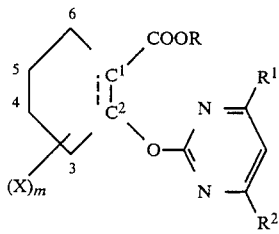

In the below-mentioned table, Me represents methyl group, Et represents ethyl group, Pr represents propyl group, $^i$Pr represents isopropyl group, Bu represents butyl group, $^i$Bu represents isobutyl group, $^s$Bu represents secondary butyl group, $^t$Bu represents tertiary butyl group, cis represents a cis-form, trans represents a trans-form, mix. represents a mixture of a cis-form and a trans-form, 1 represents a single bond and 2 represents a double bond.

| $(X)_m$ | === | R | $R^1$ | $R^2$ |
|---|---|---|---|---|
| 4-$^i$Pr | 2 (—) | —CH$_2$OCH$_3$ | OMe | OMe |
| 4-$^i$Pr | 2 (—) | —CH$_2$CH$_2$OCH$_3$ | OMe | OMe |
| 4-$^i$Pr | 2 (—) | —CH$_2$SCH$_3$ | OMe | OMe |
| 4-$^i$Pr | 2 (—) | —CH$_2$CH=CH$_2$ | OMe | OMe |
| 4-$^i$Pr | 2 (—) | —C(CH$_3$)$_2$CH=CH$_2$ | OMe | OMe |
| 4-$^i$Pr | 2 (—) | —CH$_2$C≡CH$_2$ | OMe | OMe |
| 4-$^i$Pr | 2 (—) | —CH$_2$C$_6$H$_5$ | OMe | OMe |
| 4-$^i$Pr | 2 (—) | —CH$_2$C$_6$H$_4$—Cl-2 | OMe | OMe |
| 4-$^i$Pr | 2 (—) | —CH$_2$C$_6$H$_4$—Cl-3 | OMe | OMe |
| 4-$^i$Pr | 2 (—) | —CH$_2$C$_6$H$_4$—Cl-4 | OMe | OMe |
| 4-$^i$Pr | 2 (—) | —CH$_2$C$_6$H$_4$—Me-2 | OMe | OMe |
| 4-$^i$Pr | 2 (—) | —CH$_2$C$_6$H$_4$—Me-3 | OMe | OMe |
| 4-$^i$Pr | 2 (—) | —CH$_2$C$_6$H$_4$—Me-4 | OMe | OMe |
| 4-$^i$Pr | 2 (—) | —CH$_2$C$_6$H$_4$—OMe-2 | OMe | OMe |
| 4-$^i$Pr | 2 (—) | —CH$_2$C$_6$H$_4$—OMe-3 | OMe | OMe |
| 4-$^i$Pr | 2 (—) | —CH$_2$C$_6$H$_4$—OMe-4 | OMe | OMe |
| 4-$^i$Pr | 2 (—) | —CH$_2$CH$_2$C$_6$H$_5$ | OMe | OMe |
| 4-$^t$Bt | 1 (cis) | H | Me | Me |
| 4-$^t$Bt | 1 (cis) | Na | Me | Me |
| 4-$^t$Bt | 1 (cis) | ½Ca | Me | Me |
| 4-$^t$Bt | 1 (cis) | $^i$PrNH$_3$ | Me | Me |
| 4-$^t$Bt | 1 (cis) | NH$_2$CONH$_3$ | Me | Me |
| 4-$^t$Bt | 1 (cis) | Me | Me | Me |
| 4-$^t$Bt | 1 (cis) | Et | Me | Me |
| 4-$^t$Bt | 1 (cis) | $^i$Pr | Me | Me |
| 4-$^t$Bt | 1 (cis) | Pr | Me | Me |
| 4-$^t$Bt | 1 (cis) | Bu | Me | Me |
| 4-$^t$Bt | 1 (cis) | $^i$Bu | Me | Me |
| 4-$^t$Bt | 1 (cis) | $^s$Bu | Me | Me |
| 4-$^t$Bt | 1 (cis) | —CH$_2$OCH$_3$ | Me | Me |
| 4-$^t$Bt | 1 (cis) | —CH$_2$CH$_2$OCH$_3$ | Me | Me |
| 4-$^t$Bt | 1 (cis) | —CH$_2$SCH$_3$ | Me | Me |
| 4-$^t$Bt | 1 (cis) | —CH$_2$CH=CH$_2$ | Me | Me |
| 4-$^t$Bt | 1 (cis) | —C(CH$_3$)$_2$CH=CH$_2$ | Me | Me |
| 4-$^t$Bt | 1 (cis) | —CH$_2$C≡CH$_2$ | Me | Me |
| 4-$^t$Bt | 1 (cis) | —CH$_2$C$_6$H$_5$ | Me | Me |
| 4-$^t$Bt | 1 (cis) | —CH$_2$C$_6$H$_4$—Cl-2 | Me | Me |
| 4-$^t$Bt | 1 (cis) | —CH$_2$C$_6$H$_4$—Cl-3 | Me | Me |
| 4-$^t$Bt | 1 (cis) | —CH$_2$C$_6$H$_4$—Cl-4 | Me | Me |
| 4-$^t$Bt | 1 (cis) | —CH$_2$C$_6$H$_4$—Me-2 | Me | Me |
| 4-$^t$Bt | 1 (cis) | —CH$_2$C$_6$H$_4$—Me-3 | Me | Me |
| 4-$^t$Bt | 1 (cis) | —CH$_2$C$_6$H$_4$—Me-4 | Me | Me |
| 4-$^t$Bt | 1 (cis) | —CH$_2$C$_6$H$_4$—OMe-2 | Me | Me |
| 4-$^t$Bt | 1 (cis) | —CH$_2$C$_6$H$_4$—OMe-3 | Me | Me |
| 4-$^t$Bt | 1 (cis) | —CH$_2$C$_6$H$_4$—OMe-4 | Me | Me |
| 4-$^t$Bt | 1 (cis) | —CH$_2$CH$_2$C$_6$H$_5$ | Me | Me |
| 4-$^t$Bt | 1 (cis) | H | OMe | OMe |
| 4-$^t$Bt | 1 (cis) | Na | OMe | OMe |
| 4-$^t$Bt | 1 (cis) | ½Ca | OMe | OMe |
| 4-$^t$Bt | 1 (cis) | $^i$PrNH$_3$ | OMe | OMe |
| 4-$^t$Bt | 1 (cis) | NH$_2$CONH$_3$ | OMe | OMe |
| 4-$^t$Bt | 1 (cis) | Me | OMe | OMe |
| 4-$^t$Bt | 1 (cis) | Et | OMe | OMe |
| 4-$^t$Bt | 1 (cis) | $^i$Pr | OMe | OMe |
| 4-$^t$Bt | 1 (cis) | Bt | OMe | OMe |
| 4-$^t$Bt | 1 (cis) | Bu | OMe | OMe |
| 4-$^t$Bt | 1 (cis) | $^i$Bu | OMe | OMe |

TABLE -continued

A compound of the general formula:

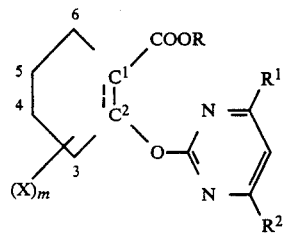

In the below-mentioned table, Me represents methyl group, Et represents ethyl group, Pr represents propyl group, $^i$Pr represents isopropyl group, Bu represents butyl group, $^i$Bu represents isobutyl group, $^s$Bu represents secondary butyl group, $^t$Bu represents tertiary butyl group, cis represents a cis-form, trans represents a trans-form, mix. represents a mixture of a cis-form and a trans-form, 1 represents a single bond and 2 represents a double bond.

| $(X)_m$ | ═══ | R | $R^1$ | $R^2$ |
|---|---|---|---|---|
| 4-$^t$Bt | 1 (cis) | $^s$Bu | OMe | OMe |
| 4-$^t$Bt | 1 (cis) | —CH$_2$OCH$_3$ | OMe | OMe |
| 4-$^t$Bt | 1 (cis) | —CH$_2$CH$_2$OCH$_3$ | OMe | OMe |
| 4-$^t$Bt | 1 (cis) | —CH$_2$SCH$_3$ | OMe | OMe |
| 4-$^t$Bt | 1 (cis) | —CH$_2$CH=CH$_2$ | OMe | OMe |
| 4-$^t$Bt | 1 (cis) | —C(CH$_3$)$_2$CH=CH$_2$ | OMe | OMe |
| 4-$^t$Bt | 1 (cis) | —CH$_2$C≡CH$_2$ | OMe | OMe |
| 4-$^t$Bt | 1 (cis) | —CH$_2$C$_6$H$_5$ | OMe | OMe |
| 4-$^t$Bt | 1 (cis) | —CH$_2$C$_6$H$_4$—Cl-2 | OMe | OMe |
| 4-$^t$Bt | 1 (cis) | —CH$_2$C$_6$H$_4$—Cl-3 | OMe | OMe |
| 4-$^t$Bt | 1 (cis) | —CH$_2$C$_6$H$_4$—Cl-4 | OMe | OMe |
| 4-$^t$Bt | 1 (cis) | —CH$_2$C$_6$H$_4$—Me-2 | OMe | OMe |
| 4-$^t$Bt | 1 (cis) | —CH$_2$C$_6$H$_4$—Me-3 | OMe | OMe |
| 4-$^t$Bt | 1 (cis) | —CH$_2$C$_6$H$_4$—Me-4 | OMe | OMe |
| 4-$^t$Bt | 1 (cis) | —CH$_2$C$_6$H$_4$—OMe-2 | OMe | OMe |
| 4-$^t$Bt | 1 (cis) | —CH$_2$C$_6$H$_4$—OMe-3 | OMe | OMe |
| 4-$^t$Bt | 1 (cis) | —CH$_2$C$_6$H$_4$—OMe-4 | OMe | OMe |
| 4-$^t$Bt | 1 (cis) | —CH$_2$CH$_2$C$_6$H$_5$ | OMe | OMe |
| 4-$^t$Bt | 1 (trans) | H | Me | Me |
| 4-$^t$Bt | 1 (trans) | Na | Me | Me |
| 4-$^t$Bt | 1 (trans) | ½Ca | Me | Me |
| 4-$^t$Bt | 1 (trans) | $^i$PrNH$_3$ | Me | Me |
| 4-$^t$Bt | 1 (trans) | NH$_2$CONH$_3$ | Me | Me |
| 4-$^t$Bt | 1 (trans) | Me | Me | Me |
| 4-$^t$Bt | 1 (trans) | Et | Me | Me |
| 4-$^t$Bt | 1 (trans) | $^i$Pr | Me | Me |
| 4-$^t$Bt | 1 (trans) | Pr | Me | Me |
| 4-$^t$Bt | 1 (trans) | Bu | Me | Me |
| 4-$^t$Bt | 1 (trans) | $^i$Bu | Me | Me |
| 4-$^t$Bt | 1 (trans) | $^s$Bu | Me | Me |
| 4-$^t$Bt | 1 (trans) | —CH$_2$OCH$_3$ | Me | Me |
| 4-$^t$Bt | 1 (trans) | —CH$_2$CH$_2$OCH$_3$ | Me | Me |
| 4-$^t$Bt | 1 (trans) | —CH$_2$SCH$_3$ | Me | Me |
| 4-$^t$Bt | 1 (trans) | —CH$_2$CH=CH$_2$ | Me | Me |
| 4-$^t$Bt | 1 (trans) | —C(CH$_3$)$_2$CH=CH$_2$ | Me | Me |
| 4-$^t$Bt | 1 (trans) | —CH$_2$C≡CH$_2$ | Me | Me |
| 4-$^t$Bt | 1 (trans) | —CH$_2$C$_6$H$_5$ | Me | Me |
| 4-$^t$Bt | 1 (trans) | —CH$_2$C$_6$H$_4$—Cl-2 | Me | Me |
| 4-$^t$Bt | 1 (trans) | —CH$_2$C$_6$H$_4$—Cl-3 | Me | Me |
| 4-$^t$Bt | 1 (trans) | —CH$_2$C$_6$H$_4$—Cl-4 | Me | Me |
| 4-$^t$Bt | 1 (trans) | —CH$_2$C$_6$H$_4$—Me-2 | Me | Me |
| 4-$^t$Bt | 1 (trans) | —CH$_2$C$_6$H$_4$—Me-3 | Me | Me |
| 4-$^t$Bt | 1 (trans) | —CH$_2$C$_6$H$_4$—Me-4 | Me | Me |
| 4-$^t$Bt | 1 (trans) | —CH$_2$C$_6$H$_4$—OMe-2 | Me | Me |
| 4-$^t$Bt | 1 (trans) | —CH$_2$C$_6$H$_4$—OMe-3 | Me | Me |
| 4-$^t$Bt | 1 (trans) | —CH$_2$C$_6$H$_4$—OMe-4 | Me | Me |
| 4-$^t$Bt | 1 (trans) | —CH$_2$CH$_2$C$_6$H$_5$ | Me | Me |
| 4-$^t$Bt | 1 (trans) | H | OMe | OMe |
| 4-$^t$Bt | 1 (trans) | Na | OMe | OMe |
| 4-$^t$Bt | 1 (trans) | ½Ca | OMe | OMe |
| 4-$^t$Bt | 1 (trans) | $^i$PrNH$_3$ | OMe | OMe |
| 4-$^t$Bt | 1 (trans) | NH$_2$CONH$_3$ | OMe | OMe |
| 4-$^t$Bt | 1 (trans) | Me | OMe | OMe |
| 4-$^t$Bt | 1 (trans) | Et | OMe | OMe |
| 4-$^t$Bt | 1 (trans) | $^i$Pr | OMe | OMe |
| 4-$^t$Bt | 1 (trans) | Pr | OMe | OMe |
| 4-$^t$Bt | 1 (trans) | Bu | OMe | OMe |

TABLE -continued

A compound of the general formula:

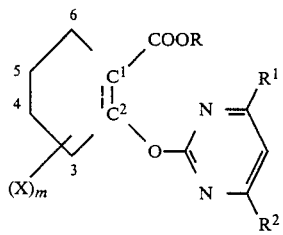

In the below-mentioned table, Me represents methyl group, Et represents ethyl group, Pr represents propyl group, $^i$Pr represents isopropyl group, Bu represents butyl group, $^i$Bu represents isobutyl group, $^s$Bu represents secondary butyl group, $^t$Bu represents tertiary butyl group, cis represents a cis-form, trans represents a trans-form, mix. represents a mixture of a cis-form and a trans-form, 1 represents a single bond and 2 represents a double bond.

| $(X)_m$ | === | R | $R^1$ | $R^2$ |
|---|---|---|---|---|
| 4-$^t$Bt | 1 (trans) | $^t$Bu | OMe | OMe |
| 4-$^t$Bt | 1 (trans) | $^s$Bu | OMe | OMe |
| 4-$^t$Bt | 1 (trans) | —CH$_2$OCH$_3$ | OMe | OMe |
| 4-$^t$Bt | 1 (trans) | —CH$_2$CH$_2$OCH$_3$ | OMe | OMe |
| 4-$^t$Bt | 1 (trans) | —CH$_2$SCH$_3$ | OMe | OMe |
| 4-$^t$Bt | 1 (trans) | —CH$_2$CH=CH$_2$ | OMe | OMe |
| 4-$^t$Bt | 1 (trans) | —C(CH$_3$)$_2$CH=CH$_2$ | OMe | OMe |
| 4-$^t$Bt | 1 (trans) | —CH$_2$C≡CH$_2$ | OMe | OMe |
| 4-$^t$Bt | 1 (trans) | —CH$_2$C$_6$H$_5$ | OMe | OMe |
| 4-$^t$Bt | 1 (trans) | —CH$_2$C$_6$H$_4$—Cl-2 | OMe | OMe |
| 4-$^t$Bt | 1 (trans) | —CH$_2$C$_6$H$_4$—Cl-3 | OMe | OMe |
| 4-$^t$Bt | 1 (trans) | —CH$_2$C$_6$H$_4$—Cl-4 | OMe | OMe |
| 4-$^t$Bt | 1 (trans) | —CH$_2$C$_6$H$_4$—Me-2 | OMe | OMe |
| 4-$^t$Bt | 1 (trans) | —CH$_2$C$_6$H$_4$—Me-3 | OMe | OMe |
| 4-$^t$Bt | 1 (trans) | —CH$_2$C$_6$H$_4$—Me-4 | OMe | OMe |
| 4-$^t$Bt | 1 (trans) | —CH$_2$C$_6$H$_4$—OMe-2 | OMe | OMe |
| 4-$^t$Bt | 1 (trans) | —CH$_2$C$_6$H$_4$—OMe-3 | OMe | OMe |
| 4-$^t$Bt | 1 (trans) | —CH$_2$C$_6$H$_4$—OMe-4 | OMe | OMe |
| 4-$^t$Bt | 1 (trans) | —CH$_2$CH$_2$C$_6$H$_5$ | OMe | OMe |
| 4-$^t$Bt | 1 (mixt.) | H | Me | Me |
| 4-$^t$Bt | 1 (mixt.) | Na | Me | Me |
| 4-$^t$Bt | 1 (mixt.) | ½Ca | Me | Me |
| 4-$^t$Bt | 1 (mixt.) | $^i$PrNH$_3$ | Me | Me |
| 4-$^t$Bt | 1 (mixt.) | NH$_2$CONH$_3$ | Me | Me |
| 4-$^t$Bt | 1 (mixt.) | Me | Me | Me |
| 4-$^t$Bt | 1 (mixt.) | Et | Me | Me |
| 4-$^t$Bt | 1 (mixt.) | $^i$Pr | Me | Me |
| 4-$^t$Bt | 1 (mixt.) | Pr | Me | Me |
| 4-$^t$Bt | 1 (mixt.) | Bu | Me | Me |
| 4-$^t$Bt | 1 (mixt.) | $^i$Bu | Me | Me |
| 4-$^t$Bt | 1 (mixt.) | $^s$Bu | Me | Me |
| 4-$^t$Bt | 1 (mixt.) | —CH$_2$OCH$_3$ | Me | Me |
| 4-$^t$Bt | 1 (mixt.) | —CH$_2$CH$_2$OCH$_3$ | Me | Me |
| 4-$^t$Bt | 1 (mixt.) | —CH$_2$SCH$_3$ | Me | Me |
| 4-$^t$Bt | 1 (mixt.) | —CH$_2$CH=CH$_2$ | Me | Me |
| 4-$^t$Bt | 1 (mixt.) | —C(CH$_3$)$_2$CH=CH$_2$ | Me | Me |
| 4-$^t$Bt | 1 (mixt.) | —CH$_2$C≡CH$_2$ | Me | Me |
| 4-$^t$Bt | 1 (mixt.) | —CH$_2$C$_6$H$_5$ | Me | Me |
| 4-$^t$Bt | 1 (mixt.) | —CH$_2$C$_6$H$_4$—Cl-2 | Me | Me |
| 4-$^t$Bt | 1 (mixt.) | —CH$_2$C$_6$H$_4$—Cl-3 | Me | Me |
| 4-$^t$Bt | 1 (mixt.) | —CH$_2$C$_6$H$_4$—Cl-4 | Me | Me |
| 4-$^t$Bt | 1 (mixt.) | —CH$_2$C$_6$H$_4$—Me-2 | Me | Me |
| 4-$^t$Bt | 1 (mixt.) | —CH$_2$C$_6$H$_4$—Me-3 | Me | Me |
| 4-$^t$Bt | 1 (mixt.) | —CH$_2$C$_6$H$_4$—Me-4 | Me | Me |
| 4-$^t$Bt | 1 (mixt.) | —CH$_2$C$_6$H$_4$—OMe-2 | Me | Me |
| 4-$^t$Bt | 1 (mixt.) | —CH$_2$C$_6$H$_4$—OMe-3 | Me | Me |
| 4-$^t$Bt | 1 (mixt.) | —CH$_2$C$_6$H$_4$—OMe-4 | Me | Me |
| 4-$^t$Bt | 1 (mixt.) | —CH$_2$CH$_2$C$_6$H$_5$ | Me | Me |
| 4-$^t$Bt | 1 (mixt.) | H | OMe | OMe |
| 4-$^t$Bt | 1 (mixt.) | Na | OMe | OMe |
| 4-$^t$Bt | 1 (mixt.) | ½Ca | OMe | OMe |
| 4-$^t$Bt | 1 (mixt.) | $^i$PrNH$_3$ | OMe | OMe |
| 4-$^t$Bt | 1 (mixt.) | NH$_2$CONH$_3$ | OMe | OMe |
| 4-$^t$Bt | 1 (mixt.) | Me | OMe | OMe |
| 4-$^t$Bt | 1 (mixt.) | Et | OMe | OMe |
| 4-$^t$Bt | 1 (mixt.) | $^i$Pr | OMe | OMe |
| 4-$^t$Bt | 1 (mixt.) | Pr | OMe | OMe |

TABLE -continued

A compound of the general formula:

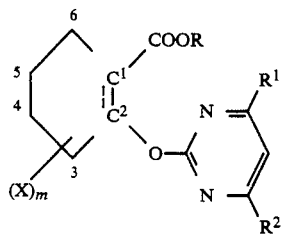

In the below-mentioned table, Me represents methyl
group, Et represents ethyl group, Pr represents propyl
group, $^i$Pr represents isopropyl group, Bu represents butyl
group, $^i$Bu represents isobutyl group, $^s$Bu represents
secondary butyl group, $^t$Bu represents tertiary butyl
group, cis represents a cis-form, trans represents a
trans-form, mix. represents a mixture of a cis-form and
a trans-form, 1 represents a single bond and 2 represents
a double bond.

| $(X)_m$ | === | R | $R^1$ | $R^2$ |
|---|---|---|---|---|
| 4-$^t$Bt | 1 (mixt.) | Bu | OMe | OMe |
| 4-$^t$Bt | 1 (mixt.) | $^i$Bu | OMe | OMe |
| 4-$^t$Bt | 1 (mixt.) | $^s$Bu | OMe | OMe |
| 4-$^t$Bt | 1 (mixt.) | —CH$_2$OCH$_3$ | OMe | OMe |
| 4-$^t$Bt | 1 (mixt.) | —CH$_2$CH$_2$OCH$_3$ | OMe | OMe |
| 4-$^t$Bt | 1 (mixt.) | —CH$_2$SCH$_3$ | OMe | OMe |
| 4-$^t$Bt | 1 (mixt.) | —CH$_2$CH=CH$_2$ | OMe | OMe |
| 4-$^t$Bt | 1 (mixt.) | —C(CH$_3$)$_2$CH=CH$_2$ | OMe | OMe |
| 4-$^t$Bt | 1 (mixt.) | —CH$_2$C≡CH$_2$ | OMe | OMe |
| 4-$^t$Bt | 1 (mixt.) | —CH$_2$C$_6$H$_5$ | OMe | OMe |
| 4-$^t$Bt | 1 (mixt.) | —CH$_2$C$_6$H$_4$—Cl-2 | OMe | OMe |
| 4-$^t$Bt | 1 (mixt.) | —CH$_2$C$_6$H$_4$—Cl-3 | OMe | OMe |
| 4-$^t$Bt | 1 (mixt.) | —CH$_2$C$_6$H$_4$—Cl-4 | OMe | OMe |
| 4-$^t$Bt | 1 (mixt.) | —CH$_2$C$_6$H$_4$—Me-2 | OMe | OMe |
| 4-$^t$Bt | 1 (mixt.) | —CH$_2$C$_6$H$_4$—Me-3 | OMe | OMe |
| 4-$^t$Bt | 1 (mixt.) | —CH$_2$C$_6$H$_4$—Me-4 | OMe | OMe |
| 4-$^t$Bt | 1 (mixt.) | —CH$_2$C$_6$H$_4$—OMe-2 | OMe | OMe |
| 4-$^t$Bt | 1 (mixt.) | —CH$_2$C$_6$H$_4$—OMe-3 | OMe | OMe |
| 4-$^t$Bt | 1 (mixt.) | —CH$_2$C$_6$H$_4$—OMe-4 | OMe | OMe |
| 4-$^t$Bt | 1 (mixt.) | —CH$_2$CH$_2$C$_6$H$_5$ | OMe | OMe |
| 4-$^t$Bt | 2 (—) | H | Me | Me |
| 4-$^t$Bt | 2 (—) | Na | Me | Me |
| 4-$^t$Bt | 2 (—) | ½Ca | Me | Me |
| 4-$^t$Bt | 2 (—) | $^i$PrNH$_3$ | Me | Me |
| 4-$^t$Bt | 2 (—) | NH$_2$CONH$_3$ | Me | Me |
| 4-$^t$Bt | 2 (—) | Me | Me | Me |
| 4-$^t$Bt | 2 (—) | Et | Me | Me |
| 4-$^t$Bt | 2 (—) | $^i$Pr | Me | Me |
| 4-$^t$Bt | 2 (—) | Bt | Me | Me |
| 4-$^t$Bt | 2 (—) | Bu | Me | Me |
| 4-$^t$Bt | 2 (—) | $^i$Bu | Me | Me |
| 4-$^t$Bt | 2 (—) | $^s$Bu | Me | Me |
| 4-$^t$Bt | 2 (—) | —CH$_2$OCH$_3$ | Me | Me |
| 4-$^t$Bt | 2 (—) | —CH$_2$CH$_2$OCH$_3$ | Me | Me |
| 4-$^t$Bt | 2 (—) | —CH$_2$SCH$_3$ | Me | Me |
| 4-$^t$Bt | 2 (—) | —CH$_2$CH=CH$_2$ | Me | Me |
| 4-$^t$Bt | 2 (—) | —C(CH$_3$)$_2$CH=CH$_2$ | Me | Me |
| 4-$^t$Bt | 2 (—) | —CH$_2$C≡CH$_2$ | Me | Me |
| 4-$^t$Bt | 2 (—) | —CH$_2$C$_6$H$_5$ | Me | Me |
| 4-$^t$Bt | 2 (—) | —CH$_2$C$_6$H$_4$—Cl-2 | Me | Me |
| 4-$^t$Bt | 2 (—) | —CH$_2$C$_6$H$_4$—Cl-3 | Me | Me |
| 4-$^t$Bt | 2 (—) | —CH$_2$C$_6$H$_4$—Cl-4 | Me | Me |
| 4-$^t$Bt | 2 (—) | —CH$_2$C$_6$H$_4$—Me-2 | Me | Me |
| 4-$^t$Bt | 2 (—) | —CH$_2$C$_6$H$_4$—Me-3 | Me | Me |
| 4-$^t$Bt | 2 (—) | —CH$_2$C$_6$H$_4$—Me-4 | Me | Me |
| 4-$^t$Bt | 2 (—) | —CH$_2$C$_6$H$_4$—OMe-2 | Me | Me |
| 4-$^t$Bt | 2 (—) | —CH$_2$C$_6$H$_4$—OMe-3 | Me | Me |
| 4-$^t$Bt | 2 (—) | —CH$_2$C$_6$H$_4$—OMe-4 | Me | Me |
| 4-$^t$Bt | 2 (—) | —CH$_2$CH$_2$C$_6$H$_5$ | Me | Me |
| 4-$^t$Bt | 2 (—) | H | OMe | OMe |
| 4-$^t$Bt | 2 (—) | Na | OMe | OMe |
| 4-$^t$Bt | 2 (—) | ½Ca | OMe | OMe |
| 4-$^t$Bt | 2 (—) | $^i$PrNH$_3$ | OMe | OMe |
| 4-$^t$Bt | 2 (—) | NH$_2$CONH$_3$ | OMe | OMe |
| 4-$^t$Bt | 2 (—) | Me | OMe | OMe |
| 4-$^t$Bt | 2 (—) | Et | OMe | OMe |
| 4-$^t$Bt | 2 (—) | $^i$Pr | OMe | OMe |

TABLE -continued

A compound of the general formula:

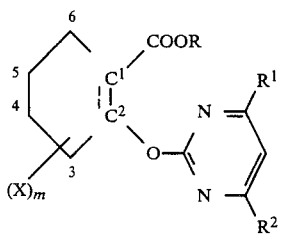

In the below-mentioned table, Me represents methyl group, Et represents ethyl group, Pr represents propyl group, $^i$Pr represents isopropyl group, Bu represents butyl group, $^i$Bu represents isobutyl group, $^s$Bu represents secondary butyl group, $^t$Bu represents tertiary butyl group, cis represents a cis-form, trans represents a trans-form, mix. represents a mixture of a cis-form and a trans-form, 1 represents a single bond and 2 represents a double bond.

| $(X)_m$ | === | R | $R^1$ | $R^2$ |
|---|---|---|---|---|
| 4-$^t$Bt | 2 (—) | Pr | OMe | OMe |
| 4-$^t$Bt | 2 (—) | Bu | OMe | OMe |
| 4-$^t$Bt | 2 (—) | $^i$Bu | OMe | OMe |
| 4-$^t$Bt | 2 (—) | $^s$Bu | OMe | OMe |
| 4-$^t$Bt | 2 (—) | —CH$_2$OCH$_3$ | OMe | OMe |
| 4-$^t$Bt | 2 (—) | —CH$_2$CH$_2$OCH$_3$ | OMe | OMe |
| 4-$^t$Bt | 2 (—) | —CH$_2$SCH$_3$ | OMe | OMe |
| 4-$^t$Bt | 2 (—) | —CH$_2$CH=CH$_2$ | OMe | OMe |
| 4-$^t$Bt | 2 (—) | —C(CH$_3$)$_2$CH=CH$_2$ | OMe | OMe |
| 4-$^t$Bt | 2 (—) | —CH$_2$C≡CH$_2$ | OMe | OMe |
| 4-$^t$Bt | 2 (—) | —CH$_2$C$_6$H$_5$ | OMe | OMe |
| 4-$^t$Bt | 2 (—) | —CH$_2$C$_6$H$_4$—Cl-2 | OMe | OMe |
| 4-$^t$Bt | 2 (—) | —CH$_2$C$_6$H$_4$—Cl-3 | OMe | OMe |
| 4-$^t$Bt | 2 (—) | —CH$_2$C$_6$H$_4$—Cl-4 | OMe | OMe |
| 4-$^t$Bt | 2 (—) | —CH$_2$C$_6$H$_4$—Me-2 | OMe | OMe |
| 4-$^t$Bt | 2 (—) | —CH$_2$C$_6$H$_4$—Me-3 | OMe | OMe |
| 4-$^t$Bt | 2 (—) | —CH$_2$C$_6$H$_4$—Me-4 | OMe | OMe |
| 4-$^t$Bt | 2 (—) | —CH$_2$C$_6$H$_4$—OMe-2 | OMe | OMe |
| 4-$^t$Bt | 2 (—) | —CH$_2$C$_6$H$_4$—OMe-3 | OMe | OMe |
| 4-$^t$Bt | 2 (—) | —CH$_2$C$_6$H$_4$—OMe-4 | OMe | OMe |
| 4-$^t$Bt | 2 (—) | —CH$_2$CH$_2$C$_6$H$_5$ | OMe | OMe |
| 5-$^t$Bt | 1 (cis) | H | Me | Me |
| 5-$^t$Bt | 1 (cis) | Na | Me | Me |
| 5-$^t$Bt | 1 (cis) | ½Ca | Me | Me |
| 5-$^t$Bt | 1 (cis) | $^i$PrNH$_3$ | Me | Me |
| 5-$^t$Bt | 1 (cis) | NH$_2$CONH$_3$ | Me | Me |
| 5-$^t$Bt | 1 (cis) | Me | Me | Me |
| 5-$^t$Bt | 1 (cis) | Et | Me | Me |
| 5-$^t$Bt | 1 (cis) | $^i$Pr | Me | Me |
| 5-$^t$Bt | 1 (cis) | Pr | Me | Me |
| 5-$^t$Bt | 1 (cis) | Bu | Me | Me |
| 5-$^t$Bt | 1 (cis) | $^i$Bu | Me | Me |
| 5-$^t$Bt | 1 (cis) | $^s$Bu | Me | Me |
| 5-$^t$Bt | 1 (cis) | —CH$_2$OCH$_3$ | Me | Me |
| 5-$^t$Bt | 1 (cis) | —CH$_2$CH$_2$OCH$_3$ | Me | Me |
| 5-$^t$Bt | 1 (cis) | —CH$_2$SCH$_3$ | Me | Me |
| 5-$^t$Bt | 1 (cis) | —CH$_2$CH=CH$_2$ | Me | Me |
| 5-$^t$Bt | 1 (cis) | —C(CH$_3$)$_2$CH=CH$_2$ | Me | Me |
| 5-$^t$Bt | 1 (cis) | —CH$_2$C≡CH$_2$ | Me | Me |
| 5-$^t$Bt | 1 (cis) | —CH$_2$C$_6$H$_5$ | Me | Me |
| 5-$^t$Bt | 1 (cis) | —CH$_2$C$_6$H$_4$—Cl-2 | Me | Me |
| 5-$^t$Bt | 1 (cis) | —CH$_2$C$_6$H$_4$—Cl-3 | Me | Me |
| 5-$^t$Bt | 1 (cis) | —CH$_2$C$_6$H$_4$—Cl-4 | Me | Me |
| 5-$^t$Bt | 1 (cis) | —CH$_2$C$_6$H$_4$—Me-2 | Me | Me |
| 5-$^t$Bt | 1 (cis) | —CH$_2$C$_6$H$_4$—Me-3 | Me | Me |
| 5-$^t$Bt | 1 (cis) | —CH$_2$C$_6$H$_4$—Me-4 | Me | Me |
| 5-$^t$Bt | 1 (cis) | —CH$_2$C$_6$H$_4$—OMe-2 | Me | Me |
| 5-$^t$Bt | 1 (cis) | —CH$_2$C$_6$H$_4$—OMe-3 | Me | Me |
| 5-$^t$Bt | 1 (cis) | —CH$_2$C$_6$H$_4$—OMe-4 | Me | Me |
| 5-$^t$Bt | 1 (cis) | —CH$_2$CH$_2$C$_6$H$_5$ | Me | Me |
| 5-$^t$Bt | 1 (cis) | H | OMe | OMe |
| 5-$^t$Bt | 1 (cis) | Na | OMe | OMe |
| 5-$^t$Bt | 1 (cis) | ½Ca | OMe | OMe |
| 5-$^t$Bt | 1 (cis) | $^i$PrNH$_3$ | OMe | OMe |
| 5-$^t$Bt | 1 (cis) | NH$_2$CONH$_3$ | OMe | OMe |
| 5-$^t$Bt | 1 (cis) | Me | OMe | OMe |
| 5-$^t$Bt | 1 (cis) | Et | OMe | OMe |

TABLE -continued

A compound of the general formula:

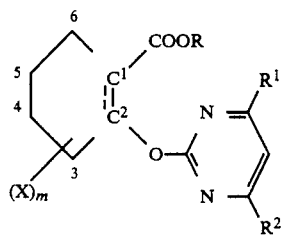

In the below-mentioned table, Me represents methyl group, Et represents ethyl group, Pr represents propyl group, $^i$Pr represents isopropyl group, Bu represents butyl group, $^i$Bu represents isobutyl group, $^s$Bu represents secondary butyl group, $^t$Bu represents tertiary butyl group, cis represents a cis-form, trans represents a trans-form, mix. represents a mixture of a cis-form and a trans-form, 1 represents a single bond and 2 represents a double bond.

| $(X)_m$ | === | R | $R^1$ | $R^2$ |
|---|---|---|---|---|
| 5-$^t$Bt | 1 (cis) | $^i$Pr | OMe | OMe |
| 5-$^t$Bt | 1 (cis) | Pr | OMe | OMe |
| 5-$^t$Bt | 1 (cis) | Bu | OMe | OMe |
| 5-$^t$Bt | 1 (cis) | $^i$Bu | OMe | OMe |
| 5-$^t$Bt | 1 (cis) | $^s$Bu | OMe | OMe |
| 5-$^t$Bt | 1 (cis) | —CH$_2$OCH$_3$ | OMe | OMe |
| 5-$^t$Bt | 1 (cis) | —CH$_2$CH$_2$OCH$_3$ | OMe | OMe |
| 5-$^t$Bt | 1 (cis) | —CH$_2$SCH$_3$ | OMe | OMe |
| 5-$^t$Bt | 1 (cis) | —CH$_2$CH=CH$_2$ | OMe | OMe |
| 5-$^t$Bt | 1 (cis) | —C(CH$_3$)$_2$CH=CH$_2$ | OMe | OMe |
| 5-$^t$Bt | 1 (cis) | —CH$_2$C≡CH$_2$ | OMe | OMe |
| 5-$^t$Bt | 1 (cis) | —CH$_2$C$_6$H$_5$ | OMe | OMe |
| 5-$^t$Bt | 1 (cis) | —CH$_2$C$_6$H$_4$—Cl-2 | OMe | OMe |
| 5-$^t$Bt | 1 (cis) | —CH$_2$C$_6$H$_4$—Cl-3 | OMe | OMe |
| 5-$^t$Bt | 1 (cis) | —CH$_2$C$_6$H$_4$—Cl-4 | OMe | OMe |
| 5-$^t$Bt | 1 (cis) | —CH$_2$C$_6$H$_4$—Me-2 | OMe | OMe |
| 5-$^t$Bt | 1 (cis) | —CH$_2$C$_6$H$_4$—Me-3 | OMe | OMe |
| 5-$^t$Bt | 1 (cis) | —CH$_2$C$_6$H$_4$—Me-4 | OMe | OMe |
| 5-$^t$Bt | 1 (cis) | —CH$_2$C$_6$H$_4$—OMe-2 | OMe | OMe |
| 5-$^t$Bt | 1 (cis) | —CH$_2$C$_6$H$_4$—OMe-3 | OMe | OMe |
| 5-$^t$Bt | 1 (cis) | —CH$_2$C$_6$H$_4$—OMe-4 | OMe | OMe |
| 5-$^t$Bt | 1 (cis) | —CH$_2$CH$_2$C$_6$H$_5$ | OMe | OMe |
| 5-$^t$Bt | 1 (trans) | H | Me | Me |
| 5-$^t$Bt | 1 (trans) | Na | Me | Me |
| 5-$^t$Bt | 1 (trans) | ½Ca | Me | Me |
| 5-$^t$Bt | 1 (trans) | $^i$PrNH$_3$ | Me | Me |
| 5-$^t$Bt | 1 (trans) | NH$_2$CONH$_3$ | Me | Me |
| 5-$^t$Bt | 1 (trans) | Me | Me | Me |
| 5-$^t$Bt | 1 (trans) | Et | Me | Me |
| 5-$^t$Bt | 1 (trans) | $^i$Pr | Me | Me |
| 5-$^t$Bt | 1 (trans) | Pr | Me | Me |
| 5-$^t$Bt | 1 (trans) | Bu | Me | Me |
| 5-$^t$Bt | 1 (trans) | $^i$Bu | Me | Me |
| 5-$^t$Bt | 1 (trans) | $^s$Bu | Me | Me |
| 5-$^t$Bt | 1 (trans) | —CH$_2$OCH$_3$ | Me | Me |
| 5-$^t$Bt | 1 (trans) | —CH$_2$CH$_2$OCH$_3$ | Me | Me |
| 5-$^t$Bt | 1 (trans) | —CH$_2$SCH$_3$ | Me | Me |
| 5-$^t$Bt | 1 (trans) | —CH$_2$CH=CH$_2$ | Me | Me |
| 5-$^t$Bt | 1 (trans) | —C(CH$_3$)$_2$CH=CH$_2$ | Me | Me |
| 5-$^t$Bt | 1 (trans) | —CH$_2$C≡CH$_2$ | Me | Me |
| 5-$^t$Bt | 1 (trans) | —CH$_2$C$_6$H$_5$ | Me | Me |
| 5-$^t$Bt | 1 (trans) | —CH$_2$C$_6$H$_4$—Cl-2 | Me | Me |
| 5-$^t$Bt | 1 (trans) | —CH$_2$C$_6$H$_4$—Cl-3 | Me | Me |
| 5-$^t$Bt | 1 (trans) | —CH$_2$C$_6$H$_4$—Cl-4 | Me | Me |
| 5-$^t$Bt | 1 (trans) | —CH$_2$C$_6$H$_4$—Me-2 | Me | Me |
| 5-$^t$Bt | 1 (trans) | —CH$_2$C$_6$H$_4$—Me-3 | Me | Me |
| 5-$^t$Bt | 1 (trans) | —CH$_2$C$_6$H$_4$—Me-4 | Me | Me |
| 5-$^t$Bt | 1 (trans) | —CH$_2$C$_6$H$_4$—OMe-2 | Me | Me |
| 5-$^t$Bt | 1 (trans) | —CH$_2$C$_6$H$_4$—OMe-3 | Me | Me |
| 5-$^t$Bt | 1 (trans) | —CH$_2$C$_6$H$_4$—OMe-4 | Me | Me |
| 5-$^t$Bt | 1 (trans) | —CH$_2$CH$_2$C$_6$H$_5$ | Me | Me |
| 5-$^t$Bt | 1 (trans) | H | OMe | OMe |
| 5-$^t$Bt | 1 (trans) | Na | OMe | OMe |
| 5-$^t$Bt | 1 (trans) | ½Ca | OMe | OMe |
| 5-$^t$Bt | 1 (trans) | $^i$PrNH$_3$ | OMe | OMe |
| 5-$^t$Bt | 1 (trans) | NH$_2$CONH$_3$ | OMe | OMe |
| 5-$^t$Bt | 1 (trans) | Me | OMe | OMe |

TABLE -continued

A compound of the general formula:

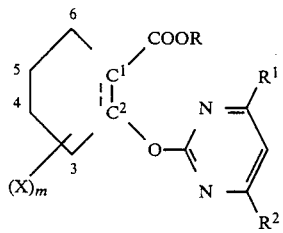

In the below-mentioned table, Me represents methyl group, Et represents ethyl group, Pr represents propyl group, $^i$Pr represents isopropyl group, Bu represents butyl group, $^i$Bu represents isobutyl group, $^s$Bu represents secondary butyl group, $^t$Bu represents tertiary butyl group, cis represents a cis-form, trans represents a trans-form, mix. represents a mixture of a cis-form and a trans-form, 1 represents a single bond and 2 represents a double bond.

| $(X)_m$ | === | R | $R^1$ | $R^2$ |
|---|---|---|---|---|
| 5-$^t$Bt | 1 (trans) | Et | OMe | OMe |
| 5-$^t$Bt | 1 (trans) | $^i$Pr | OMe | OMe |
| 5-$^t$Bt | 1 (trans) | Pr | OMe | OMe |
| 5-$^t$Bt | 1 (trans) | Bu | OMe | OMe |
| 5-$^t$Bt | 1 (trans) | $^i$Bu | OMe | OMe |
| 5-$^t$Bt | 1 (trans) | $^s$Bu | OMe | OMe |
| 5-$^t$Bt | 1 (trans) | —CH$_2$OCH$_3$ | OMe | OMe |
| 5-$^t$Bt | 1 (trans) | —CH$_2$CH$_2$OCH$_3$ | OMe | OMe |
| 5-$^t$Bt | 1 (trans) | —CH$_2$SCH$_3$ | OMe | OMe |
| 5-$^t$Bt | 1 (trans) | —CH$_2$CH=CH$_2$ | OMe | OMe |
| 5-$^t$Bt | 1 (trans) | —C(CH$_3$)$_2$CH=CH$_2$ | OMe | OMe |
| 5-$^t$Bt | 1 (trans) | —CH$_2$C≡CH$_2$ | OMe | OMe |
| 5-$^t$Bt | 1 (trans) | —CH$_2$C$_6$H$_5$ | OMe | OMe |
| 5-$^t$Bt | 1 (trans) | —CH$_2$C$_6$H$_4$—Cl-2 | OMe | OMe |
| 5-$^t$Bt | 1 (trans) | —CH$_2$C$_6$H$_4$—Cl-3 | OMe | OMe |
| 5-$^t$Bt | 1 (trans) | —CH$_2$C$_6$H$_4$—Cl-4 | OMe | OMe |
| 5-$^t$Bt | 1 (trans) | —CH$_2$C$_6$H$_4$—Me-2 | OMe | OMe |
| 5-$^t$Bt | 1 (trans) | —CH$_2$C$_6$H$_4$—Me-3 | OMe | OMe |
| 5-$^t$Bt | 1 (trans) | —CH$_2$C$_6$H$_4$—Me-4 | OMe | OMe |
| 5-$^t$Bt | 1 (trans) | —CH$_2$C$_6$H$_4$—OMe-2 | OMe | OMe |
| 5-$^t$Bt | 1 (trans) | —CH$_2$C$_6$H$_4$—OMe-3 | OMe | OMe |
| 5-$^t$Bt | 1 (trans) | —CH$_2$C$_6$H$_4$—OMe-4 | OMe | OMe |
| 5-$^t$Bt | 1 (trans) | —CH$_2$CH$_2$C$_6$H$_5$ | OMe | OMe |
| 5-$^t$Bt | 1 (mixt.) | H | Me | Me |
| 5-$^t$Bt | 1 (mixt.) | Na | Me | Me |
| 5-$^t$Bt | 1 (mixt.) | ½Ca | Me | Me |
| 5-$^t$Bt | 1 (mixt.) | $^i$PrNH$_3$ | Me | Me |
| 5-$^t$Bt | 1 (mixt.) | NH$_2$CONH$_3$ | Me | Me |
| 5-$^t$Bt | 1 (mixt.) | Me | Me | Me |
| 5-$^t$Bt | 1 (mixt.) | Et | Me | Me |
| 5-$^t$Bt | 1 (mixt.) | $^i$Pr | Me | Me |
| 5-$^t$Bt | 1 (mixt.) | Pr | Me | Me |
| 5-$^t$Bt | 1 (mixt.) | Bu | Me | Me |
| 5-$^t$Bt | 1 (mixt.) | $^i$Bu | Me | Me |
| 5-$^t$Bt | 1 (mixt.) | $^s$Bu | Me | Me |
| 5-$^t$Bt | 1 (mixt.) | —CH$_2$OCH$_3$ | Me | Me |
| 5-$^t$Bt | 1 (mixt.) | —CH$_2$CH$_2$OCH$_3$ | Me | Me |
| 5-$^t$Bt | 1 (mixt.) | —CH$_2$SCH$_3$ | Me | Me |
| 5-$^t$Bt | 1 (mixt.) | —CH$_2$CH=CH$_2$ | Me | Me |
| 5-$^t$Bt | 1 (mixt.) | —C(CH$_3$)$_2$CH=CH$_2$ | Me | Me |
| 5-$^t$Bt | 1 (mixt.) | —CH$_2$C≡CH$_2$ | Me | Me |
| 5-$^t$Bt | 1 (mixt.) | —CH$_2$C$_6$H$_5$ | Me | Me |
| 5-$^t$Bt | 1 (mixt.) | —CH$_2$C$_6$H$_4$—Cl-2 | Me | Me |
| 5-$^t$Bt | 1 (mixt.) | —CH$_2$C$_6$H$_4$—Cl-3 | Me | Me |
| 5-$^t$Bt | 1 (mixt.) | —CH$_2$C$_6$H$_4$—Cl-4 | Me | Me |
| 5-$^t$Bt | 1 (mixt.) | —CH$_2$C$_6$H$_4$—Me-2 | Me | Me |
| 5-$^t$Bt | 1 (mixt.) | —CH$_2$C$_6$H$_4$—Me-3 | Me | Me |
| 5-$^t$Bt | 1 (mixt.) | —CH$_2$C$_6$H$_4$—Me-4 | Me | Me |
| 5-$^t$Bt | 1 (mixt.) | —CH$_2$C$_6$H$_4$—OMe-2 | Me | Me |
| 5-$^t$Bt | 1 (mixt.) | —CH$_2$C$_6$H$_4$—OMe-3 | Me | Me |
| 5-$^t$Bt | 1 (mixt.) | —CH$_2$C$_6$H$_4$—OMe-4 | Me | Me |
| 5-$^t$Bt | 1 (mixt.) | —CH$_2$CH$_2$C$_6$H$_5$ | Me | Me |
| 5-$^t$Bt | 1 (mixt.) | H | OMe | OMe |
| 5-$^t$Bt | 1 (mixt.) | Na | OMe | OMe |
| 5-$^t$Bt | 1 (mixt.) | ½Ca | OMe | OMe |
| 5-$^t$Bt | 1 (mixt.) | $^i$PrNH$_3$ | OMe | OMe |
| 5-$^t$Bt | 1 (mixt.) | NH$_2$CONH$_3$ | OMe | OMe |

TABLE -continued

A compound of the general formula:

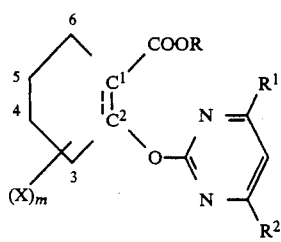

In the below-mentioned table, Me represents methyl group, Et represents ethyl group, Pr represents propyl group, $^i$Pr represents isopropyl group, Bu represents butyl group, $^i$Bu represents isobutyl group, $^s$Bu represents secondary butyl group, $^t$Bu represents tertiary butyl group, cis represents a cis-form, trans represents a trans-form, mix. represents a mixture of a cis-form and a trans-form, 1 represents a single bond and 2 represents a double bond.

| $(X)_m$ | === | R | $R^1$ | $R^2$ |
|---|---|---|---|---|
| 5-$^t$Bt | 1 (mixt.) | Me | OMe | OMe |
| 5-$^t$Bt | 1 (mixt.) | Et | OMe | OMe |
| 5-$^t$Bt | 1 (mixt.) | $^i$Pr | OMe | OMe |
| 5-$^t$Bt | 1 (mixt.) | Pr | OMe | OMe |
| 5-$^t$Bt | 1 (mixt.) | Bu | OMe | OMe |
| 5-$^t$Bt | 1 (mixt.) | $^i$Bu | OMe | OMe |
| 5-$^t$Bt | 1 (mixt.) | $^s$Bu | OMe | OMe |
| 5-$^t$Bt | 1 (mixt.) | —CH$_2$OCH$_3$ | OMe | OMe |
| 5-$^t$Bt | 1 (mixt.) | —CH$_2$CH$_2$OCH$_3$ | OMe | OMe |
| 5-$^t$Bt | 1 (mixt.) | —CH$_2$SCH$_3$ | OMe | OMe |
| 5-$^t$Bt | 1 (mixt.) | —CH$_2$CH=CH$_2$ | OMe | OMe |
| 5-$^t$Bt | 1 (mixt.) | —C(CH$_3$)$_2$CH=CH$_2$ | OMe | OMe |
| 5-$^t$Bt | 1 (mixt.) | —CH$_2$C≡CH$_2$ | OMe | OMe |
| 5-$^t$Bt | 1 (mixt.) | —CH$_2$C$_6$H$_5$ | OMe | OMe |
| 5-$^t$Bt | 1 (mixt.) | —CH$_2$C$_6$H$_4$—Cl-2 | OMe | OMe |
| 5-$^t$Bt | 1 (mixt.) | —CH$_2$C$_6$H$_4$—Cl-3 | OMe | OMe |
| 5-$^t$Bt | 1 (mixt.) | —CH$_2$C$_6$H$_4$—Cl-4 | OMe | OMe |
| 5-$^t$Bt | 1 (mixt.) | —CH$_2$C$_6$H$_4$—Me-2 | OMe | OMe |
| 5-$^t$Bt | 1 (mixt.) | —CH$_2$C$_6$H$_4$—Me-3 | OMe | OMe |
| 5-$^t$Bt | 1 (mixt.) | —CH$_2$C$_6$H$_4$—Me-4 | OMe | OMe |
| 5-$^t$Bt | 1 (mixt.) | —CH$_2$C$_6$H$_4$—OMe-2 | OMe | OMe |
| 5-$^t$Bt | 1 (mixt.) | —CH$_2$C$_6$H$_4$—OMe-3 | OMe | OMe |
| 5-$^t$Bt | 1 (mixt.) | —CH$_2$C$_6$H$_4$—OMe-4 | OMe | OMe |
| 5-$^t$Bt | 1 (mixt.) | —CH$_2$CH$_2$C$_6$H$_5$ | OMe | OMe |
| 5-$^t$Bt | 2 (—) | H | Me | Me |
| 5-$^t$Bt | 2 (—) | Na | Me | Me |
| 5-$^t$Bt | 2 (—) | ½Ca | Me | Me |
| 5-$^t$Bt | 2 (—) | $^i$PrNH$_3$ | Me | Me |
| 5-$^t$Bt | 2 (—) | NH$_2$CONH$_3$ | Me | Me |
| 5-$^t$Bt | 2 (—) | Me | Me | Me |
| 5-$^t$Bt | 2 (—) | Et | Me | Me |
| 5-$^t$Bt | 2 (—) | $^i$Pr | Me | Me |
| 5-$^t$Bt | 2 (—) | Pr | Me | Me |
| 5-$^t$Bt | 2 (—) | Bu | Me | Me |
| 5-$^t$Bt | 2 (—) | $^i$Bu | Me | Me |
| 5-$^t$Bt | 2 (—) | $^s$Bu | Me | Me |
| 5-$^t$Bt | 2 (—) | —CH$_2$OCH$_3$ | Me | Me |
| 5-$^t$Bt | 2 (—) | —CH$_2$CH$_2$OCH$_3$ | Me | Me |
| 5-$^t$Bt | 2 (—) | —CH$_2$SCH$_3$ | Me | Me |
| 5-$^t$Bt | 2 (—) | —CH$_2$CH=CH$_2$ | Me | Me |
| 5-$^t$Bt | 2 (—) | —C(CH$_3$)$_2$CH=CH$_2$ | Me | Me |
| 5-$^t$Bt | 2 (—) | —CH$_2$C≡CH$_2$ | Me | Me |
| 5-$^t$Bt | 2 (—) | —CH$_2$C$_6$H$_5$ | Me | Me |
| 5-$^t$Bt | 2 (—) | —CH$_2$C$_6$H$_4$—Cl-2 | Me | Me |
| 5-$^t$Bt | 2 (—) | —CH$_2$C$_6$H$_4$—Cl-3 | Me | Me |
| 5-$^t$Bt | 2 (—) | —CH$_2$C$_6$H$_4$—Cl-4 | Me | Me |
| 5-$^t$Bt | 2 (—) | —CH$_2$C$_6$H$_4$—Me-2 | Me | Me |
| 5-$^t$Bt | 2 (—) | —CH$_2$C$_6$H$_4$—Me-3 | Me | Me |
| 5-$^t$Bt | 2 (—) | —CH$_2$C$_6$H$_4$—Me-4 | Me | Me |
| 5-$^t$Bt | 2 (—) | —CH$_2$C$_6$H$_4$—OMe-2 | Me | Me |
| 5-$^t$Bt | 2 (—) | —CH$_2$C$_6$H$_4$—OMe-3 | Me | Me |
| 5-$^t$Bt | 2 (—) | —CH$_2$C$_6$H$_4$—OMe-4 | Me | Me |
| 5-$^t$Bt | 2 (—) | —CH$_2$CH$_2$C$_6$H$_5$ | Me | Me |
| 5-$^t$Bt | 2 (—) | H | OMe | OMe |
| 5-$^t$Bt | 2 (—) | Na | OMe | OMe |
| 5-$^t$Bt | 2 (—) | ½Ca | OMe | OMe |
| 5-$^t$Bt | 2 (—) | $^i$PrNH$_3$ | OMe | OMe |

TABLE -continued

A compound of the general formula:

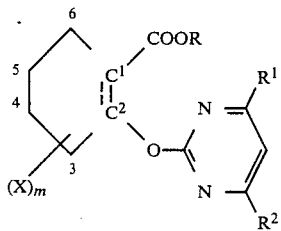

In the below-mentioned table, Me represents methyl group, Et represents ethyl group, Pr represents propyl group, $^i$Pr represents isopropyl group, Bu represents butyl group, $^i$Bu represents isobutyl group, $^s$Bu represents secondary butyl group, $^t$Bu represents tertiary butyl group, cis represents a cis-form, trans represents a trans-form, mix. represents a mixture of a cis-form and a trans-form, 1 represents a single bond and 2 represents a double bond.

| $(X)_m$ | --- | R | $R^1$ | $R^2$ |
|---|---|---|---|---|
| 5-$^t$Bt | 2 (—) | $NH_2CONH_3$ | OMe | OMe |
| 5-$^t$Bt | 2 (—) | Me | OMe | OMe |
| 5-$^t$Bt | 2 (—) | Et | OMe | OMe |
| 5-$^t$Bt | 2 (—) | $^i$Pr | OMe | OMe |
| 5-$^t$Bt | 2 (—) | Pr | OMe | OMe |
| 5-$^t$Bt | 2 (—) | Bu | OMe | OMe |
| 5-$^t$Bt | 2 (—) | $^i$Bu | OMe | OMe |
| 5-$^t$Bt | 2 (—) | $^s$Bu | OMe | OMe |
| 5-$^t$Bt | 2 (—) | $-CH_2OCH_3$ | OMe | OMe |
| 5-$^t$Bt | 2 (—) | $-CH_2CH_2OCH_3$ | OMe | OMe |
| 5-$^t$Bt | 2 (—) | $-CH_2SCH_3$ | OMe | OMe |
| 5-$^t$Bt | 2 (—) | $-CH_2CH=CH_2$ | OMe | OMe |
| 5-$^t$Bt | 2 (—) | $-C(CH_3)_2CH=CH_2$ | OMe | OMe |
| 5-$^t$Bt | 2 (—) | $-CH_2C\equiv CH_2$ | OMe | OMe |
| 5-$^t$Bt | 2 (—) | $-CH_2C_6H_5$ | OMe | OMe |
| 5-$^t$Bt | 2 (—) | $-CH_2C_6H_4-Cl-2$ | OMe | OMe |
| 5-$^t$Bt | 2 (—) | $-CH_2C_6H_4-Cl-3$ | OMe | OMe |
| 5-$^t$Bt | 2 (—) | $-CH_2C_6H_4-Cl-4$ | OMe | OMe |
| 5-$^t$Bt | 2 (—) | $-CH_2C_6H_4-Me-2$ | OMe | OMe |
| 5-$^t$Bt | 2 (—) | $-CH_2C_6H_4-Me-3$ | OMe | OMe |
| 5-$^t$Bt | 2 (—) | $-CH_2C_6H_4-Me-4$ | OMe | OMe |
| 5-$^t$Bt | 2 (—) | $-CH_2C_6H_4-OMe-2$ | OMe | OMe |
| 5-$^t$Bt | 2 (—) | $-CH_2C_6H_4-OMe-3$ | OMe | OMe |
| 5-$^t$Bt | 2 (—) | $-CH_2C_6H_4-OMe-4$ | OMe | OMe |
| 5-$^t$Bt | 2 (—) | $-CH_2CH_2C_6H_5$ | OMe | OMe |
| 3-Me-6-$^i$Pr | 1 (cis) | H | OMe | OMe |
| 3-Me-6-$^i$Pr | 1 (cis) | Na | OMe | OMe |
| 3-Me-6-$^i$Pr | 1 (cis) | ½Ca | OMe | OMe |
| 3-Me-6-$^i$Pr | 1 (cis) | $^i$PrNH$_3$ | OMe | OMe |
| 3-Me-6-$^i$Pr | 1 (cis) | $NH_2CONH_3$ | OMe | OMe |
| 3-Me-6-$^i$Pr | 1 (cis) | Me | OMe | OMe |
| 3-Me-6-$^i$Pr | 1 (cis) | Et | OMe | OMe |
| 3-Me-6-$^i$Pr | 1 (cis) | $^i$Pr | OMe | OMe |
| 3-Me-6-$^i$Pr | 1 (cis) | Pr | OMe | OMe |
| 3-Me-6-$^i$Pr | 1 (cis) | Bu | OMe | OMe |
| 3-Me-6-$^i$Pr | 1 (cis) | $^i$Bu | OMe | OMe |
| 3-Me-6-$^i$Pr | 1 (cis) | $^s$Bu | OMe | OMe |
| 3-Me-6-$^i$Pr | 1 (cis) | $-CH_2OCH_3$ | OMe | OMe |
| 3-Me-6-$^i$Pr | 1 (cis) | $-CH_2CH_2OCH_3$ | OMe | OMe |
| 3-Me-6-$^i$Pr | 1 (cis) | $-CH_2SCH_3$ | OMe | OMe |
| 3-Me-6-$^i$Pr | 1 (cis) | $-CH_2CH=CH_2$ | OMe | OMe |
| 3-Me-6-$^i$Pr | 1 (cis) | $-C(CH_3)_2CH=CH_2$ | OMe | OMe |
| 3-Me-6-$^i$Pr | 1 (cis) | $-CH_2C\equiv CH_2$ | OMe | OMe |
| 3-Me-6-$^i$Pr | 1 (cis) | $-CH_2C_6H_5$ | OMe | OMe |
| 3-Me-6-$^i$Pr | 1 (cis) | $-CH_2C_6H_4-Cl-2$ | OMe | OMe |
| 3-Me-6-$^i$Pr | 1 (cis) | $-CH_2C_6H_4-Cl-3$ | OMe | OMe |
| 3-Me-6-$^i$Pr | 1 (cis) | $-CH_2C_6H_4-Cl-4$ | OMe | OMe |
| 3-Me-6-$^i$Pr | 1 (cis) | $-CH_2C_6H_4-Me-2$ | OMe | OMe |
| 3-Me-6-$^i$Pr | 1 (cis) | $-CH_2C_6H_4-Me-3$ | OMe | OMe |
| 3-Me-6-$^i$Pr | 1 (cis) | $-CH_2C_6H_4-Me-4$ | OMe | OMe |
| 3-Me-6-$^i$Pr | 1 (cis) | $-CH_2C_6H_4-OMe-2$ | OMe | OMe |
| 3-Me-6-$^i$Pr | 1 (cis) | $-CH_2C_6H_4-OMe-3$ | OMe | OMe |
| 3-Me-6-$^i$Pr | 1 (cis) | $-CH_2C_6H_4-OMe-4$ | OMe | OMe |
| 3-Me-6-$^i$Pr | 1 (cis) | $-CH_2CH_2C_6H_5$ | OMe | OMe |
| 3-Me-6-$^i$Pr | 1 (trans) | H | OMe | OMe |
| 3-Me-6-$^i$Pr | 1 (trans) | Na | OMe | OMe |
| 3-Me-6-$^i$Pr | 1 (trans) | ½Ca | OMe | OMe |

TABLE -continued

A compound of the general formula:

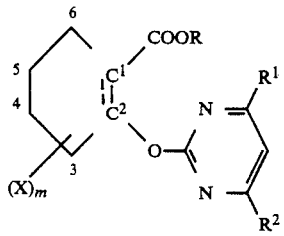

In the below-mentioned table, Me represents methyl group, Et represents ethyl group, Pr represents propyl group, $^i$Pr represents isopropyl group, Bu represents butyl group, $^i$Bu represents isobutyl group, $^s$Bu represents secondary butyl group, $^t$Bu represents tertiary butyl group, cis represents a cis-form, trans represents a trans-form, mix. represents a mixture of a cis-form and a trans-form, 1 represents a single bond and 2 represents a double bond.

| $(X)_m$ | === | R | $R^1$ | $R^2$ |
|---|---|---|---|---|
| 3-Me-6-$^i$Pr | 1 (trans) | $^i$PrNH$_3$ | OMe | OMe |
| 3-Me-6-$^i$Pr | 1 (trans) | NH$_2$CONH$_3$ | OMe | OMe |
| 3-Me-6-$^i$Pr | 1 (trans) | Me | OMe | OMe |
| 3-Me-6-$^i$Pr | 1 (trans) | Et | OMe | OMe |
| 3-Me-6-$^i$Pr | 1 (trans) | $^i$Pr | OMe | OMe |
| 3-Me-6-$^i$Pr | 1 (trans) | Pr | OMe | OMe |
| 3-Me-6-$^i$Pr | 1 (trans) | Bu | OMe | OMe |
| 3-Me-6-$^i$Pr | 1 (trans) | $^i$Bu | OMe | OMe |
| 3-Me-6-$^i$Pr | 1 (trans) | $^s$Bu | OMe | OMe |
| 3-Me-6-$^i$Pr | 1 (trans) | —CH$_2$OCH$_3$ | OMe | OMe |
| 3-Me-6-$^i$Pr | 1 (trans) | —CH$_2$CH$_2$OCH$_3$ | OMe | OMe |
| 3-Me-6-$^i$Pr | 1 (trans) | —CH$_2$SCH$_3$ | OMe | OMe |
| 3-Me-6-$^i$Pr | 1 (trans) | —CH$_2$CH=CH$_2$ | OMe | OMe |
| 3-Me-6-$^i$Pr | 1 (trans) | —C(CH$_3$)$_2$CH=CH$_2$ | OMe | OMe |
| 3-Me-6-$^i$Pr | 1 (trans) | —CH$_2$C≡CH$_2$ | OMe | OMe |
| 3-Me-6-$^i$Pr | 1 (trans) | —CH$_2$C$_6$H$_5$ | OMe | OMe |
| 3-Me-6-$^i$Pr | 1 (trans) | —CH$_2$C$_6$H$_4$—Cl-2 | OMe | OMe |
| 3-Me-6-$^i$Pr | 1 (trans) | —CH$_2$C$_6$H$_4$—Cl-3 | OMe | OMe |
| 3-Me-6-$^i$Pr | 1 (trans) | —CH$_2$C$_6$H$_4$—Cl-4 | OMe | OMe |
| 3-Me-6-$^i$Pr | 1 (trans) | —CH$_2$C$_6$H$_4$—Me-2 | OMe | OMe |
| 3-Me-6-$^i$Pr | 1 (trans) | —CH$_2$C$_6$H$_4$—Me-3 | OMe | OMe |
| 3-Me-6-$^i$Pr | 1 (trans) | —CH$_2$C$_6$H$_4$—Me-4 | OMe | OMe |
| 3-Me-6-$^i$Pr | 1 (trans) | —CH$_2$C$_6$H$_4$—OMe-2 | OMe | OMe |
| 3-Me-6-$^i$Pr | 1 (trans) | —CH$_2$C$_6$H$_4$—OMe-3 | OMe | OMe |
| 3-Me-6-$^i$Pr | 1 (trans) | —CH$_2$C$_6$H$_4$—OMe-4 | OMe | OMe |
| 3-Me-6-$^i$Pr | 1 (trans) | —CH$_2$CH$_2$C$_6$H$_5$ | OMe | OMe |
| 3-Me-6-$^i$Pr | 1 (mixt.) | H | OMe | OMe |
| 3-Me-6-$^i$Pr | 1 (mixt.) | Na | OMe | OMe |
| 3-Me-6-$^i$Pr | 1 (mixt.) | ½Ca | OMe | OMe |
| 3-Me-6-$^i$Pr | 1 (mixt.) | $^i$PrNH$_3$ | OMe | OMe |
| 3-Me-6-$^i$Pr | 1 (mixt.) | NH$_2$CONH$_3$ | OMe | OMe |
| 3-Me-6-$^i$Pr | 1 (mixt.) | Me | OMe | OMe |
| 3-Me-6-$^i$Pr | 1 (mixt.) | Et | OMe | OMe |
| 3-Me-6-$^i$Pr | 1 (mixt.) | $^i$Pr | OMe | OMe |
| 3-Me-6-$^i$Pr | 1 (mixt.) | Pr | OMe | OMe |
| 3-Me-6-$^i$Pr | 1 (mixt.) | Bu | OMe | OMe |
| 3-Me-6-$^i$Pr | 1 (mixt.) | $^i$Bu | OMe | OMe |
| 3-Me-6-$^i$Pr | 1 (mixt.) | $^s$Bu | OMe | OMe |
| 3-Me-6-$^i$Pr | 1 (mixt.) | —CH$_2$OCH$_3$ | OMe | OMe |
| 3-Me-6-$^i$Pr | 1 (mixt.) | —CH$_2$CH$_2$OCH$_3$ | OMe | OMe |
| 3-Me-6-$^i$Pr | 1 (mixt.) | —CH$_2$SCH$_3$ | OMe | OMe |
| 3-Me-6-$^i$Pr | 1 (mixt.) | —CH$_2$CH=CH$_2$ | OMe | OMe |
| 3-Me-6-$^i$Pr | 1 (mixt.) | —C(CH$_3$)$_2$CH=CH$_2$ | OMe | OMe |
| 3-Me-6-$^i$Pr | 1 (mixt.) | —CH$_2$C≡CH$_2$ | OMe | OMe |
| 3-Me-6-$^i$Pr | 1 (mixt.) | —CH$_2$C$_6$H$_5$ | OMe | OMe |
| 3-Me-6-$^i$Pr | 1 (mixt.) | —CH$_2$C$_6$H$_4$—Cl-2 | OMe | OMe |
| 3-Me-6-$^i$Pr | 1 (mixt.) | —CH$_2$C$_6$H$_4$—Cl-3 | OMe | OMe |
| 3-Me-6-$^i$Pr | 1 (mixt.) | —CH$_2$C$_6$H$_4$—Cl-4 | OMe | OMe |
| 3-Me-6-$^i$Pr | 1 (mixt.) | —CH$_2$C$_6$H$_4$—Me-2 | OMe | OMe |
| 3-Me-6-$^i$Pr | 1 (mixt.) | —CH$_2$C$_6$H$_4$—Me-3 | OMe | OMe |
| 3-Me-6-$^i$Pr | 1 (mixt.) | —CH$_2$C$_6$H$_4$—Me-4 | OMe | OMe |
| 3-Me-6-$^i$Pr | 1 (mixt.) | —CH$_2$C$_6$H$_4$—OMe-2 | OMe | OMe |
| 3-Me-6-$^i$Pr | 1 (mixt.) | —CH$_2$C$_6$H$_4$—OMe-3 | OMe | OMe |
| 3-Me-6-$^i$Pr | 1 (mixt.) | —CH$_2$C$_6$H$_4$—OMe-4 | OMe | OMe |
| 3-Me-6-$^i$Pr | 1 (mixt.) | —CH$_2$CH$_2$C$_6$H$_5$ | OMe | OMe |
| 3-Me-6-$^i$Pr | 2 (—) | H | OMe | OMe |
| 3-Me-6-$^i$Pr | 2 (—) | Na | OMe | OMe |

TABLE -continued

A compound of the general formula:

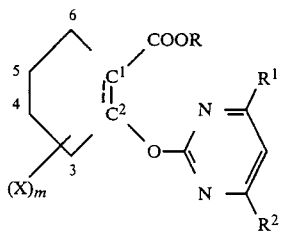

In the below-mentioned table, Me represents methyl group, Et represents ethyl group, Pr represents propyl group, $^i$Pr represents isopropyl group, Bu represents butyl group, $^i$Bu represents isobutyl group, $^s$Bu represents secondary butyl group, $^t$Bu represents tertiary butyl group, cis represents a cis-form, trans represents a trans-form, mix. represents a mixture of a cis-form and a trans-form, 1 represents a single bond and 2 represents a double bond.

| $(X)_m$ | === | R | $R^1$ | $R^2$ |
|---|---|---|---|---|
| 3-Me-6-$^i$Pr | 2 (—) | $\frac{1}{2}$Ca | OMe | OMe |
| 3-Me-6-$^i$Pr | 2 (—) | $^i$PrNH$_3$ | OMe | OMe |
| 3-Me-6-$^i$Pr | 2 (—) | NH$_2$CONH$_3$ | OMe | OMe |
| 3-Me-6-$^i$Pr | 2 (—) | Me | OMe | OMe |
| 3-Me-6-$^i$Pr | 2 (—) | Et | OMe | OMe |
| 3-Me-6-$^i$Pr | 2 (—) | $^i$Pr | OMe | OMe |
| 3-Me-6-$^i$Pr | 2 (—) | Pr | OMe | OMe |
| 3-Me-6-$^i$Pr | 2 (—) | Bu | OMe | OMe |
| 3-Me-6-$^i$Pr | 2 (—) | $^i$Bu | OMe | OMe |
| 3-Me-6-$^i$Pr | 2 (—) | $^s$Bu | OMe | OMe |
| 3-Me-6-$^i$Pr | 2 (—) | —CH$_2$OCH$_3$ | OMe | OMe |
| 3-Me-6-$^i$Pr | 2 (—) | —CH$_2$CH$_2$OCH$_3$ | OMe | OMe |
| 3-Me-6-$^i$Pr | 2 (—) | —CH$_2$SCH$_3$ | OMe | OMe |
| 3-Me-6-$^i$Pr | 2 (—) | —CH$_2$CH=CH$_2$ | OMe | OMe |
| 3-Me-6-$^i$Pr | 2 (—) | —C(CH$_3$)$_2$CH=CH$_2$ | OMe | OMe |
| 3-Me-6-$^i$Pr | 2 (—) | —CH$_2$C≡CH$_2$ | OMe | OMe |
| 3-Me-6-$^i$Pr | 2 (—) | —CH$_2$C$_6$H$_5$' | OMe | OMe |
| 3-Me-6-$^i$Pr | 2 (—) | —CH$_2$C$_6$H$_4$—Cl-2 | OMe | OMe |
| 3-Me-6-$^i$Pr | 2 (—) | —CH$_2$C$_6$H$_4$—Cl-3 | OMe | OMe |
| 3-Me-6-$^i$Pr | 2 (—) | —CH$_2$C$_6$H$_4$—Cl-4 | OMe | OMe |
| 3-Me-6-$^i$Pr | 2 (—) | —CH$_2$C$_6$H$_4$—Me-2 | OMe | OMe |
| 3-Me-6-$^i$Pr | 2 (—) | —CH$_2$C$_6$H$_4$—Me-3 | OMe | OMe |
| 3-Me-6-$^i$Pr | 2 (—) | —CH$_2$C$_6$H$_4$—Me-4 | OMe | OMe |
| 3-Me-6-$^i$Pr | 2 (—) | —CH$_2$C$_6$H$_4$—OMe-2 | OMe | OMe |
| 3-Me-6-$^i$Pr | 2 (—) | —CH$_2$C$_6$H$_4$—OMe-3 | OMe | OMe |
| 3-Me-6-$^i$Pr | 2 (—) | —CH$_2$C$_6$H$_4$—OMe-4 | OMe | OMe |
| 3-Me-6-$^i$Pr | 2 (—) | —CH$_2$CH$_2$C$_6$H$_5$ | OMe | OMe |
| 3-$^i$Pr-6-Me | 1 (cis) | H | OMe | OMe |
| 3-$^i$Pr-6-Me | 1 (cis) | Na | OMe | OMe |
| 3-$^i$Pr-6-Me | 1 (cis) | $\frac{1}{2}$Ca | OMe | OMe |
| 3-$^i$Pr-6-Me | 1 (cis) | $^i$PrNH$_3$ | OMe | OMe |
| 3-$^i$Pr-6-Me | 1 (cis) | NH$_2$CONH$_3$ | OMe | OMe |
| 3-$^i$Pr-6-Me | 1 (cis) | Me | OMe | OMe |
| 3-$^i$Pr-6-Me | 1 (cis) | Et | OMe | OMe |
| 3-$^i$Pr-6-Me | 1 (cis) | $^i$Pr | OMe | OMe |
| 3-$^i$Pr-6-Me | 1 (cis) | Pr | OMe | OMe |
| 3-$^i$Pr-6-Me | 1 (cis) | Bu | OMe | OMe |
| 3-$^i$Pr-6-Me | 1 (cis) | $^i$Bu | OMe | OMe |
| 3-$^i$Pr-6-Me | 1 (cis) | $^s$Bu | OMe | OMe |
| 3-$^i$Pr-6-Me | 1 (cis) | —CH$_2$OCH$_3$ | OMe | OMe |
| 3-$^i$Pr-6-Me | 1 (cis) | —CH$_2$CH$_2$OCH$_3$ | OMe | OMe |
| 3-$^i$Pr-6-Me | 1 (cis) | —CH$_2$SCH$_3$ | OMe | OMe |
| 3-$^i$Pr-6-Me | 1 (cis) | —CH$_2$CH=CH$_2$ | OMe | OMe |
| 3-$^i$Pr-6-Me | 1 (cis) | —C(CH$_3$)$_2$CH=CH$_2$ | OMe | OMe |
| 3-$^i$Pr-6-Me | 1 (cis) | —CH$_2$C≡CH$_2$ | OMe | OMe |
| 3-$^i$Pr-6-Me | 1 (cis) | —CH$_2$C$_6$H$_5$ | OMe | OMe |
| 3-$^i$Pr-6-Me | 1 (cis) | —CH$_2$C$_6$H$_4$—Cl-2 | OMe | OMe |
| 3-$^i$Pr-6-Me | 1 (cis) | —CH$_2$C$_6$H$_4$—Cl-3 | OMe | OMe |
| 3-$^i$Pr-6-Me | 1 (cis) | —CH$_2$C$_6$H$_4$—Cl-4 | OMe | OMe |
| 3-$^i$Pr-6-Me | 1 (cis) | —CH$_2$C$_6$H$_4$—Me-2 | OMe | OMe |
| 3-$^i$Pr-6-Me | 1 (cis) | —CH$_2$C$_6$H$_4$—Me-3 | OMe | OMe |
| 3-$^i$Pr-6-Me | 1 (cis) | —CH$_2$C$_6$H$_4$—Me-4 | OMe | OMe |
| 3-$^i$Pr-6-Me | 1 (cis) | —CH$_2$C$_6$H$_4$—OMe-2 | OMe | OMe |
| 3-$^i$Pr-6-Me | 1 (cis) | —CH$_2$C$_6$H$_4$—OMe-3 | OMe | OMe |
| 3-$^i$Pr-6-Me | 1 (cis) | —CH$_2$C$_6$H$_4$—OMe-4 | OMe | OMe |
| 3-$^i$Pr-6-Me | 1 (cis) | —CH$_2$CH$_2$C$_6$H$_5$ | OMe | OMe |
| 3-$^i$Pr-6-Me | 1 (trans) | H | OMe | OMe |

TABLE -continued

A compound of the general formula:

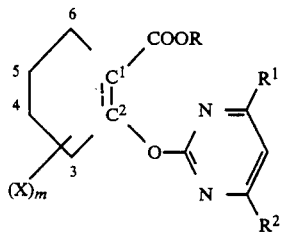

In the below-mentioned table, Me represents methyl group, Et represents ethyl group, Pr represents propyl group, $^i$Pr represents isopropyl group, Bu represents butyl group, $^i$Bu represents isobutyl group, $^s$Bu represents secondary butyl group, $^t$Bu represents tertiary butyl group, cis represents a cis-form, trans represents a trans-form, mix. represents a mixture of a cis-form and a trans-form, 1 represents a single bond and 2 represents a double bond.

| $(X)_m$ | --- | R | $R^1$ | $R^2$ |
|---|---|---|---|---|
| 3-$^i$Pr-6-Me | 1 (trans) | Na | OMe | OMe |
| 3-$^i$Pr-6-Me | 1 (trans) | ½Ca | OMe | OMe |
| 3-$^i$Pr-6-Me | 1 (trans) | $^i$PrNH$_3$ | OMe | OMe |
| 3-$^i$Pr-6-Me | 1 (trans) | NH$_2$CONH$_3$ | OMe | OMe |
| 3-$^i$Pr-6-Me | 1 (trans) | Me | OMe | OMe |
| 3-$^i$Pr-6-Me | 1 (trans) | Et | OMe | OMe |
| 3-$^i$Pr-6-Me | 1 (trans) | $^i$Pr | OMe | OMe |
| 3-$^i$Pr-6-Me | 1 (trans) | Pr | OMe | OMe |
| 3-$^i$Pr-6-Me | 1 (trans) | Bu | OMe | OMe |
| 3-$^i$Pr-6-Me | 1 (trans) | $^i$Bu | OMe | OMe |
| 3-$^i$Pr-6-Me | 1 (trans) | $^s$Bu | OMe | OMe |
| 3-$^i$Pr-6-Me | 1 (trans) | —CH$_2$OCH$_3$ | OMe | OMe |
| 3-$^i$Pr-6-Me | 1 (trans) | —CH$_2$CH$_2$OCH$_3$ | OMe | OMe |
| 3-$^i$Pr-6-Me | 1 (trans) | —CH$_2$SCH$_3$ | OMe | OMe |
| 3-$^i$Pr-6-Me | 1 (trans) | —CH$_2$CH=CH$_2$ | OMe | OMe |
| 3-$^i$Pr-6-Me | 1 (trans) | —C(CH$_3$)$_2$CH=CH$_2$ | OMe | OMe |
| 3-$^i$Pr-6-Me | 1 (trans) | —CH$_2$C≡CH$_2$ | OMe | OMe |
| 3-$^i$Pr-6-Me | 1 (trans) | —CH$_2$C$_6$H$_5$ | OMe | OMe |
| 3-$^i$Pr-6-Me | 1 (trans) | —CH$_2$C$_6$H$_4$—Cl-2 | OMe | OMe |
| 3-$^i$Pr-6-Me | 1 (trans) | —CH$_2$C$_6$H$_4$—Cl-3 | OMe | OMe |
| 3-$^i$Pr-6-Me | 1 (trans) | —CH$_2$C$_6$H$_4$—Cl-4 | OMe | OMe |
| 3-$^i$Pr-6-Me | 1 (trans) | —CH$_2$C$_6$H$_4$—Me-2 | OMe | OMe |
| 3-$^i$Pr-6-Me | 1 (trans) | —CH$_2$C$_6$H$_4$—Me-3 | OMe | OMe |
| 3-$^i$Pr-6-Me | 1 (trans) | —CH$_2$C$_6$H$_4$—Me-4 | OMe | OMe |
| 3-$^i$Pr-6-Me | 1 (trans) | —CH$_2$C$_6$H$_4$—OMe-2 | OMe | OMe |
| 3-$^i$Pr-6-Me | 1 (trans) | —CH$_2$C$_6$H$_4$—OMe-3 | OMe | OMe |
| 3-$^i$Pr-6-Me | 1 (trans) | —CH$_2$C$_6$H$_4$—OMe-4 | OMe | OMe |
| 3-$^i$Pr-6-Me | 1 (trans) | —CH$_2$CH$_2$C$_6$H$_5$ | OMe | OMe |
| 3-$^i$Pr-6-Me | 1 (mixt.) | H | OMe | OMe |
| 3-$^i$Pr-6-Me | 1 (mixt.) | Na | OMe | OMe |
| 3-$^i$Pr-6-Me | 1 (mixt.) | ½Ca | OMe | OMe |
| 3-$^i$Pr-6-Me | 1 (mixt.) | $^i$PrNH$_3$ | OMe | OMe |
| 3-$^i$Pr-6-Me | 1 (mixt.) | NH$_2$CONH$_3$ | OMe | OMe |
| 3-$^i$Pr-6-Me | 1 (mixt.) | Me | OMe | OMe |
| 3-$^i$Pr-6-Me | 1 (mixt.) | Et | OMe | OMe |
| 3-$^i$Pr-6-Me | 1 (mixt.) | $^i$Pr | OMe | OMe |
| 3-$^i$Pr-6-Me | 1 (mixt.) | Pr | OMe | OMe |
| 3-$^i$Pr-6-Me | 1 (mixt.) | Bu | OMe | OMe |
| 3-$^i$Pr-6-Me | 1 (mixt.) | $^i$Bu | OMe | OMe |
| 3-$^i$Pr-6-Me | 1 (mixt.) | $^s$Bu | OMe | OMe |
| 3-$^i$Pr-6-Me | 1 (mixt.) | —CH$_2$OCH$_3$ | OMe | OMe |
| 3-$^i$Pr-6-Me | 1 (mixt.) | —CH$_2$CH$_2$OCH$_3$ | OMe | OMe |
| 3-$^i$Pr-6-Me | 1 (mixt.) | —CH$_2$SCH$_3$ | OMe | OMe |
| 3-$^i$Pr-6-Me | 1 (mixt.) | —CH$_2$CH=CH$_2$ | OMe | OMe |
| 3-$^i$Pr-6-Me | 1 (mixt.) | —C(CH$_3$)$_2$CH=CH$_2$ | OMe | OMe |
| 3-$^i$Pr-6-Me | 1 (mixt.) | —CH$_2$C≡CH$_2$ | OMe | OMe |
| 3-$^i$Pr-6-Me | 1 (mixt.) | —CH$_2$C$_6$H$_5$ | OMe | OMe |
| 3-$^i$Pr-6-Me | 1 (mixt.) | —CH$_2$C$_6$H$_4$—Cl-2 | OMe | OMe |
| 3-$^i$Pr-6-Me | 1 (mixt.) | —CH$_2$C$_6$H$_4$—Cl-3 | OMe | OMe |
| 3-$^i$Pr-6-Me | 1 (mixt.) | —CH$_2$C$_6$H$_4$—Cl-4 | OMe | OMe |
| 3-$^i$Pr-6-Me | 1 (mixt.) | —CH$_2$C$_6$H$_4$—Me-2 | OMe | OMe |
| 3-$^i$Pr-6-Me | 1 (mixt.) | —CH$_2$C$_6$H$_4$—Me-3 | OMe | OMe |
| 3-$^i$Pr-6-Me | 1 (mixt.) | —CH$_2$C$_6$H$_4$—Me-4 | OMe | OMe |
| 3-$^i$Pr-6-Me | 1 (mixt.) | —CH$_2$C$_6$H$_4$—OMe-2 | OMe | OMe |
| 3-$^i$Pr-6-Me | 1 (mixt.) | —CH$_2$C$_6$H$_4$—OMe-3 | OMe | OMe |
| 3-$^i$Pr-6-Me | 1 (mixt.) | —CH$_2$C$_6$H$_4$—OMe-4 | OMe | OMe |
| 3-$^i$Pr-6-Me | 1 (mixt.) | —CH$_2$CH$_2$C$_6$H$_5$ | OMe | OMe |

TABLE -continued

A compound of the general formula:

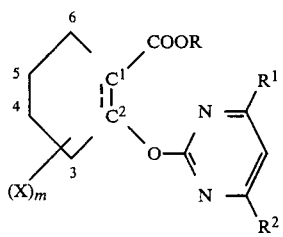

In the below-mentioned table, Me represents methyl group, Et represents ethyl group, Pr represents propyl group, $^i$Pr represents isopropyl group, Bu represents butyl group, $^i$Bu represents isobutyl group, $^s$Bu represents secondary butyl group, $^t$Bu represents tertiary butyl group, cis represents a cis-form, trans represents a trans-form, mix. represents a mixture of a cis-form and a trans-form, 1 represents a single bond and 2 represents a double bond.

| $(X)_m$ | $===$ | R | $R^1$ | $R^2$ |
|---|---|---|---|---|
| 3-$^i$Pr-6-Me | 2 (—) | H | OMe | OMe |
| 3-$^i$Pr-6-Me | 2 (—) | Na | OMe | OMe |
| 3-$^i$Pr-6-Me | 2 (—) | ½Ca | OMe | OMe |
| 3-$^i$Pr-6-Me | 2 (—) | $^i$PrNH$_3$ | OMe | OMe |
| 3-$^i$Pr-6-Me | 2 (—) | NH$_2$CONH$_3$ | OMe | OMe |
| 3-$^i$Pr-6-Me | 2 (—) | Me | OMe | OMe |
| 3-$^i$Pr-6-Me | 2 (—) | Et | OMe | OMe |
| 3-$^i$Pr-6-Me | 2 (—) | $^i$Pr | OMe | OMe |
| 3-$^i$Pr-6-Me | 2 (—) | Pr | OMe | OMe |
| 3-$^i$Pr-6-Me | 2 (—) | Bu | OMe | OMe |
| 3-$^i$Pr-6-Me | 2 (—) | $^i$Bu | OMe | OMe |
| 3-$^i$Pr-6-Me | 2 (—) | $^s$Bu | OMe | OMe |
| 3-$^i$Pr-6-Me | 2 (—) | —CH$_2$OCH$_3$ | OMe | OMe |
| 3-$^i$Pr-6-Me | 2 (—) | —CH$_2$CH$_2$OCH$_3$ | OMe | OMe |
| 3-$^i$Pr-6-Me | 2 (—) | —CH$_2$SCH$_3$ | OMe | OMe |
| 3-$^i$Pr-6-Me | 2 (—) | —CH$_2$CH=CH$_2$ | OMe | OMe |
| 3-$^i$Pr-6-Me | 2 (—) | —C(CH$_3$)$_2$CH=CH$_2$ | OMe | OMe |
| 3-$^i$Pr-6-Me | 2 (—) | —CH$_2$C≡CH$_2$ | OMe | OMe |
| 3-$^i$Pr-6-Me | 2 (—) | —CH$_2$C$_6$H$_5$ | OMe | OMe |
| 3-$^i$Pr-6-Me | 2 (—) | —CH$_2$C$_6$H$_4$—Cl-2 | OMe | OMe |
| 3-$^i$Pr-6-Me | 2 (—) | —CH$_2$C$_6$H$_4$—Cl-3 | OMe | OMe |
| 3-$^i$Pr-6-Me | 2 (—) | —CH$_2$C$_6$H$_4$—Cl-4 | OMe | OMe |
| 3-$^i$Pr-6-Me | 2 (—) | —CH$_2$C$_6$H$_4$—Me-2 | OMe | OMe |
| 3-$^i$Pr-6-Me | 2 (—) | —CH$_2$C$_6$H$_4$—Me-3 | OMe | OMe |
| 3-$^i$Pr-6-Me | 2 (—) | —CH$_2$C$_6$H$_4$—Me-4 | OMe | OMe |
| 3-$^i$Pr-6-Me | 2 (—) | —CH$_2$C$_6$H$_4$—OMe-2 | OMe | OMe |
| 3-$^i$Pr-6-Me | 2 (—) | —CH$_2$C$_6$H$_4$—OMe-3 | OMe | OMe |
| 3-$^i$Pr-6-Me | 2 (—) | —CH$_2$C$_6$H$_4$—OMe-4 | OMe | OMe |
| 3-$^i$Pr-6-Me | 2 (—) | —CH$_2$CH$_2$C$_6$H$_5$ | OMe | OMe |

TABLE 3

A compound of the general formula:

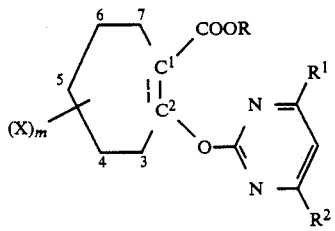

In the below-mentioned table, Me represents methyl group, Et represents ethyl group, Pr represents propyl group, $^i$Pr represents isopropyl group, Bu represents butyl group, $^i$Bu represents isobutyl group, $^s$Bu represents secondary butyl group, $^t$Bu represents tertiary butyl group, cis represents a cis-form, trans represents a trans-form, mix. represents a mixture of a cis-form and a trans-form, 1 represents a single bond and 2 represents a double bond

| $(X)_m$ | — | R | $R^1$ | $R^2$ |
|---|---|---|---|---|
| — | 1 (cis) | H | Me | Me |
| — | 1 (cis) | Li | Me | Me |
| — | 1 (cis) | Na | Me | Me |
| — | 1 (cis) | K | Me | Me |
| — | 1 (cis) | ½Mg | Me | Me |
| — | 1 (cis) | ½Ca | Me | Me |
| — | 1 (cis) | MeNH$_3$ | Me | Me |
| — | 1 (cis) | EtNH$_3$ | Me | Me |
| — | 1 (cis) | PrNH$_3$ | Me | Me |
| — | 1 (cis) | $^i$PrNH$_3$ | Me | Me |
| — | 1 (cis) | NH$_2$CONH$_3$ | Me | Me |
| — | 1 (cis) | Me | Me | Me |
| — | 1 (cis) | Et | Me | Me |
| — | 1 (cis) | $^i$Pr | Me | Me |
| — | 1 (cis) | Pr | Me | Me |
| — | 1 (cis) | Bu | Me | Me |
| — | 1 (cis) | $^i$Bu | Me | Me |
| — | 1 (cis) | $^s$Bu | Me | Me |
| — | 1 (cis) | $^t$Bu | Me | Me |
| — | 1 (cis) | —CH$_2$OCH$_3$ | Me | Me |
| — | 1 (cis) | —CH$_2$CH$_2$OCH$_3$ | Me | Me |
| — | 1 (cis) | —CH$_2$SCH$_3$ | Me | Me |
| — | 1 (cis) | —CH$_2$CH=CH$_2$ | Me | Me |
| — | 1 (cis) | —C(CH$_3$)$_2$CH=CH$_2$ | Me | Me |
| — | 1 (cis) | —CH$_2$C≡CH$_2$ | Me | Me |
| — | 1 (cis) | —CH$_2$C$_6$H$_5$ | Me | Me |
| — | 1 (cis) | —CH$_2$C$_6$H$_4$—Cl-2 | Me | Me |
| — | 1 (cis) | —CH$_2$C$_6$H$_4$—Cl-3 | Me | Me |
| — | 1 (cis) | —CH$_2$C$_6$H$_4$—Cl-4 | Me | Me |
| — | 1 (cis) | —CH$_2$C$_6$H$_4$—Me-2 | Me | Me |
| — | 1 (cis) | —CH$_2$C$_6$H$_4$—Me-3 | Me | Me |
| — | 1 (cis) | —CH$_2$C$_6$H$_4$—Me-4 | Me | Me |
| — | 1 (cis) | —CH$_2$C$_6$H$_4$—OMe-2 | Me | Me |
| — | 1 (cis) | —CH$_2$C$_6$H$_4$—OMe-3 | Me | Me |
| — | 1 (cis) | —CH$_2$C$_6$H$_4$—OMe-4 | Me | Me |
| — | 1 (cis) | —CH$_2$CH$_2$C$_6$H$_5$ | Me | Me |
| — | 1 (cis) | H | OMe | Me |
| — | 1 (cis) | Li | OMe | Me |
| — | 1 (cis) | Na | OMe | Me |
| — | 1 (cis) | K | OMe | Me |
| — | 1 (cis) | ½Mg | OMe | Me |
| — | 1 (cis) | ½Ca | OMe | Me |
| — | 1 (cis) | MeNH$_3$ | OMe | Me |
| — | 1 (cis) | EtNH$_3$ | OMe | Me |
| — | 1 (cis) | PrNH$_3$ | OMe | Me |
| — | 1 (cis) | $^i$PrNH$_3$ | OMe | Me |
| — | 1 (cis) | NH$_2$CONH$_3$ | OMe | Me |
| — | 1 (cis) | Me | OMe | Me |
| — | 1 (cis) | Et | OMe | Me |
| — | 1 (cis) | $^i$Pr | OMe | Me |
| — | 1 (cis) | Pr | OMe | Me |
| — | 1 (cis) | Bu | OMe | Me |
| — | 1 (cis) | $^i$Bu | OMe | Me |
| — | 1 (cis) | $^s$Bu | OMe | Me |
| — | 1 (cis) | $^t$Bu | OMe | Me |
| — | 1 (cis) | —CH$_2$OCH$_3$ | OMe | Me |
| — | 1 (cis) | —CH$_2$CH$_2$OCH$_3$ | OMe | Me |
| — | 1 (cis) | —CH$_2$SCH$_3$ | OMe | Me |
| — | 1 (cis) | —CH$_2$CH=CH$_2$ | OMe | Me |
| — | 1 (cis) | —C(CH$_3$)$_2$CH=CH$_2$ | OMe | Me |
| — | 1 (cis) | —CH$_2$C≡CH$_2$ | OMe | Me |
| — | 1 (cis) | —CH$_2$C$_6$H$_5$ | OMe | Me |
| — | 1 (cis) | —CH$_2$C$_6$H$_4$—Cl-2 | OMe | Me |
| — | 1 (cis) | —CH$_2$C$_6$H$_4$—Cl-3 | OMe | Me |
| — | 1 (cis) | —CH$_2$C$_6$H$_4$—Cl-4 | OMe | Me |
| — | 1 (cis) | —CH$_2$C$_6$H$_4$—Me-2 | OMe | Me |
| — | 1 (cis) | —CH$_2$C$_6$H$_4$—Me-3 | OMe | Me |
| — | 1 (cis) | —CH$_2$C$_6$H$_4$—Me-4 | OMe | Me |
| — | 1 (cis) | —CH$_2$C$_6$H$_4$—OMe-2 | OMe | Me |
| — | 1 (cis) | —CH$_2$C$_6$H$_4$—OMe-3 | OMe | Me |
| — | 1 (cis) | —CH$_2$C$_6$H$_4$—OMe-4 | OMe | Me |
| — | 1 (cis) | —CH$_2$CH$_2$C$_6$H$_5$ | OMe | Me |
| — | 1 (cis) | H | OMe | OMe |
| — | 1 (cis) | Li | OMe | OMe |
| — | 1 (cis) | Na | OMe | OMe |
| — | 1 (cis) | K | OMe | OMe |
| — | 1 (cis) | ½Mg | OMe | OMe |
| — | 1 (cis) | ½Ca | OMe | OMe |
| — | 1 (cis) | MeNH$_3$ | OMe | OMe |
| — | 1 (cis) | EtNH$_3$ | OMe | OMe |
| — | 1 (cis) | PrNH$_3$ | OMe | OMe |
| — | 1 (cis) | $^i$PrNH$_3$ | OMe | OMe |
| — | 1 (cis) | NH$_2$CONH$_3$ | OMe | OMe |
| — | 1 (cis) | Me | OMe | OMe |
| — | 1 (cis) | Et | OMe | OMe |
| — | 1 (cis) | $^i$Pr | OMe | OMe |
| — | 1 (cis) | Pr | OMe | OMe |
| — | 1 (cis) | Bu | OMe | OMe |
| — | 1 (cis) | $^i$Bu | OMe | OMe |
| — | 1 (cis) | $^s$Bu | OMe | OMe |
| — | 1 (cis) | $^t$Bu | OMe | OMe |
| — | 1 (cis) | —CH$_2$OCH$_3$ | OMe | OMe |
| — | 1 (cis) | —CH$_2$CH$_2$OCH$_3$ | OMe | OMe |
| — | 1 (cis) | —CH$_2$SCH$_3$ | OMe | OMe |
| — | 1 (cis) | —CH$_2$CH=CH$_2$ | OMe | OMe |
| — | 1 (cis) | —C(CH$_3$)$_2$CH=CH$_2$ | OMe | OMe |
| — | 1 (cis) | —CH$_2$C≡CH$_2$ | OMe | OMe |
| — | 1 (cis) | —CH$_2$C$_6$H$_5$ | OMe | OMe |
| — | 1 (cis) | —CH$_2$C$_6$H$_4$—Cl-2 | OMe | OMe |
| — | 1 (cis) | —CH$_2$C$_6$H$_4$—Cl-3 | OMe | OMe |
| — | 1 (cis) | —CH$_2$C$_6$H$_4$—Cl-4 | OMe | OMe |
| — | 1 (cis) | —CH$_2$C$_6$H$_4$—Me-2 | OMe | OMe |
| — | 1 (cis) | —CH$_2$C$_6$H$_4$—Me-3 | OMe | OMe |
| — | 1 (cis) | —CH$_2$C$_6$H$_4$—Me-4 | OMe | OMe |
| — | 1 (cis) | —CH$_2$C$_6$H$_4$—OMe-2 | OMe | OMe |
| — | 1 (cis) | —CH$_2$C$_6$H$_4$—OMe-3 | OMe | OMe |
| — | 1 (cis) | —CH$_2$C$_6$H$_4$—OMe-4 | OMe | OMe |
| — | 1 (cis) | —CH$_2$CH$_2$C$_6$H$_5$ | OMe | OMe |
| — | 1 (cis) | H | Cl | Me |
| — | 1 (cis) | Li | Cl | Me |
| — | 1 (cis) | Na | Cl | Me |
| — | 1 (cis) | K | Cl | Me |
| — | 1 (cis) | ½Mg | Cl | Me |
| — | 1 (cis) | ½Ca | Cl | Me |
| — | 1 (cis) | MeNH$_3$ | Cl | Me |
| — | 1 (cis) | EtNH$_3$ | Cl | Me |

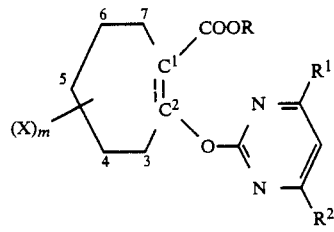

TABLE 3-continued

A compound of the general formula:

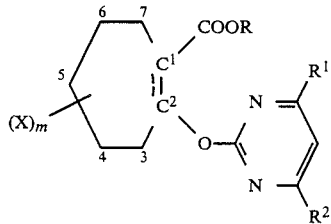

In the below-mentioned table, Me represents methyl group, Et represents ethyl group, Pr represents propyl group, $^i$Pr represents isopropyl group, Bu represents butyl group, $^i$Bu represents isobutyl group, $^s$Bu represents secondary butyl group, $^t$Bu represents tertiary butyl group, cis represents a cis-form, trans represents a trans-form, mix. represents a mixture of a cis-form and a trans-form, 1 represents a single bond and 2 represents a double bond

| $(X)_m$ | — | R | $R^1$ | $R^2$ |
|---|---|---|---|---|
| — | 1 (cis) | PrNH$_3$ | Cl | Me |
| — | 1 (cis) | $^i$PrNH$_3$ | Cl | Me |
| — | 1 (cis) | NH$_2$CONH$_3$ | Cl | Me |
| — | 1 (cis) | Me | Cl | Me |
| — | 1 (cis) | Et | Cl | Me |
| — | 1 (cis) | $^i$Pr | Cl | Me |
| — | 1 (cis) | Pr | Cl | Me |
| — | 1 (cis) | Bu | Cl | Me |
| — | 1 (cis) | $^i$Bu | Cl | Me |
| — | 1 (cis) | $^s$Bu | Cl | Me |
| — | 1 (cis) | $^t$Bu | Cl | Me |
| — | 1 (cis) | —CH$_2$OCH$_3$ | Cl | Me |
| — | 1 (cis) | —CH$_2$CH$_2$OCH$_3$ | Cl | Me |
| — | 1 (cis) | —CH$_2$SCH$_3$ | Cl | Me |
| — | 1 (cis) | —CH$_2$CH=CH$_2$ | Cl | Me |
| — | 1 (cis) | —C(CH$_3$)$_2$CH=CH$_2$ | Cl | Me |
| — | 1 (cis) | —CH$_2$C≡CH$_2$ | Cl | Me |
| — | 1 (cis) | —CH$_2$C$_6$H$_5$ | Cl | Me |
| — | 1 (cis) | —CH$_2$C$_6$H$_4$—Cl-2 | Cl | Me |
| — | 1 (cis) | —CH$_2$C$_6$H$_4$—Cl-3 | Cl | Me |
| — | 1 (cis) | —CH$_2$C$_6$H$_4$—Cl-4 | Cl | Me |
| — | 1 (cis) | —CH$_2$C$_6$H$_4$—Me-2 | Cl | Me |
| — | 1 (cis) | —CH$_2$C$_6$H$_4$—Me-3 | Cl | Me |
| — | 1 (cis) | —CH$_2$C$_6$H$_4$—Me-4 | Cl | Me |
| — | 1 (cis) | —CH$_2$C$_6$H$_4$—OMe-2 | Cl | Me |
| — | 1 (cis) | —CH$_2$C$_6$H$_4$—OMe-3 | Cl | Me |
| — | 1 (cis) | —CH$_2$C$_6$H$_4$—OMe-4 | Cl | Me |
| — | 1 (cis) | —CH$_2$CH$_2$C$_6$H$_5$ | Cl | Me |
| — | 1 (cis) | H | Cl | Cl |
| — | 1 (cis) | Li | Cl | Cl |
| — | 1 (cis) | Na | Cl | Cl |
| — | 1 (cis) | K | Cl | Cl |
| — | 1 (cis) | ½Mg | Cl | Cl |
| — | 1 (cis) | ½Ca | Cl | Cl |
| — | 1 (cis) | MeNH$_3$ | Cl | Cl |
| — | 1 (cis) | EtNH$_3$ | Cl | Cl |
| — | 1 (cis) | PrNH$_3$ | Cl | Cl |
| — | 1 (cis) | $^i$PrNH$_3$ | Cl | Cl |
| — | 1 (cis) | NH$_2$CONH$_3$ | Cl | Cl |
| — | 1 (cis) | Me | Cl | Cl |
| — | 1 (cis) | Et | Cl | Cl |
| — | 1 (cis) | $^i$Pr | Cl | Cl |
| — | 1 (cis) | Pr | Cl | Cl |
| — | 1 (cis) | Bu | Cl | Cl |
| — | 1 (cis) | $^i$Bu | Cl | Cl |
| — | 1 (cis) | $^s$Bu | Cl | Cl |
| — | 1 (cis) | $^t$Bu | Cl | Cl |
| — | 1 (cis) | —CH$_2$OCH$_3$ | Cl | Cl |
| — | 1 (cis) | —CH$_2$CH$_2$OCH$_3$ | Cl | Cl |
| — | 1 (cis) | —CH$_2$SCH$_3$ | Cl | Cl |
| — | 1 (cis) | —CH$_2$CH=CH$_2$ | Cl | Cl |
| — | 1 (cis) | —C(CH$_3$)$_2$CH=CH$_2$ | Cl | Cl |
| — | 1 (cis) | —CH$_2$C≡CH$_2$ | Cl | Cl |
| — | 1 (cis) | —CH$_2$C$_6$H$_5$ | Cl | Cl |
| — | 1 (cis) | —CH$_2$C$_6$H$_4$—Cl-2 | Cl | Cl |
| — | 1 (cis) | —CH$_2$C$_6$H$_4$—Cl-3 | Cl | Cl |
| — | 1 (cis) | —CH$_2$C$_6$H$_4$—Cl-4 | Cl | Cl |
| — | 1 (cis) | —CH$_2$C$_6$H$_4$—Me-2 | Cl | Cl |
| — | 1 (cis) | —CH$_2$C$_6$H$_4$—Me-3 | Cl | Cl |
| — | 1 (cis) | —CH$_2$C$_6$H$_4$—Me-4 | Cl | Cl |
| — | 1 (cis) | —CH$_2$C$_6$H$_4$—OMe-2 | Cl | Cl |
| — | 1 (cis) | —CH$_2$C$_6$H$_4$—OMe-3 | Cl | Cl |
| — | 1 (cis) | —CH$_2$C$_6$H$_4$—OMe-4 | Cl | Cl |
| — | 1 (cis) | —CH$_2$CH$_2$C$_6$H$_5$ | Cl | Cl |
| — | 1 (cis) | H | Cl | OMe |
| — | 1 (cis) | Li | Cl | OMe |
| — | 1 (cis) | Na | Cl | OMe |
| — | 1 (cis) | K | Cl | OMe |
| — | 1 (cis) | ½Mg | Cl | OMe |
| — | 1 (cis) | ½Ca | Cl | OMe |
| — | 1 (cis) | MeNH$_3$ | Cl | OMe |
| — | 1 (cis) | EtNH$_3$ | Cl | OMe |
| — | 1 (cis) | PrNH$_3$ | Cl | OMe |
| — | 1 (cis) | $^i$PrNH$_3$ | Cl | OMe |
| — | 1 (cis) | NH$_2$CONH$_3$ | Cl | OMe |
| — | 1 (cis) | Me | Cl | OMe |
| — | 1 (cis) | Et | Cl | OMe |
| — | 1 (cis) | $^i$Pr | Cl | OMe |
| — | 1 (cis) | Pr | Cl | OMe |
| — | 1 (cis) | Bu | Cl | OMe |
| — | 1 (cis) | $^i$Bu | Cl | OMe |
| — | 1 (cis) | $^s$Bu | Cl | OMe |
| — | 1 (cis) | $^t$Bu | Cl | OMe |
| — | 1 (cis) | —CH$_2$OCH$_3$ | Cl | OMe |
| — | 1 (cis) | —CH$_2$CH$_2$OCH$_3$ | Cl | OMe |
| — | 1 (cis) | —CH$_2$SCH$_3$ | Cl | OMe |
| — | 1 (cis) | —CH$_2$CH=CH$_2$ | Cl | OMe |
| — | 1 (cis) | —C(CH$_3$)$_2$CH=CH$_2$ | Cl | OMe |
| — | 1 (cis) | —CH$_2$C≡CH$_2$ | Cl | OMe |
| — | 1 (cis) | —CH$_2$C$_6$H$_5$ | Cl | OMe |
| — | 1 (cis) | —CH$_2$C$_6$H$_4$—Cl-2 | Cl | OMe |
| — | 1 (cis) | —CH$_2$C$_6$H$_4$—Cl-3 | Cl | OMe |
| — | 1 (cis) | —CH$_2$C$_6$H$_4$—Cl-4 | Cl | OMe |
| — | 1 (cis) | —CH$_2$C$_6$H$_4$—Me-2 | Cl | OMe |
| — | 1 (cis) | —CH$_2$C$_6$H$_4$—Me-3 | Cl | OMe |
| — | 1 (cis) | —CH$_2$C$_6$H$_4$—Me-4 | Cl | OMe |
| — | 1 (cis) | —CH$_2$C$_6$H$_4$—OMe-2 | Cl | OMe |
| — | 1 (cis) | —CH$_2$C$_6$H$_4$—OMe-3 | Cl | OMe |
| — | 1 (cis) | —CH$_2$C$_6$H$_4$—OMe-4 | Cl | OMe |
| — | 1 (cis) | —CH$_2$CH$_2$C$_6$H$_5$ | Cl | OMe |
| — | 1 (cis) | H | OCHF$_2$ | OMe |
| — | 1 (cis) | Li | OCHF$_2$ | OMe |
| — | 1 (cis) | Na | OCHF$_2$ | OMe |
| — | 1 (cis) | K | OCHF$_2$ | OMe |
| — | 1 (cis) | ½Mg | OCHF$_2$ | OMe |
| — | 1 (cis) | ½Ca | OCHF$_2$ | OMe |
| — | 1 (cis) | MeNH$_3$ | OCHF$_2$ | OMe |
| — | 1 (cis) | EtNH$_3$ | OCHF$_2$ | OMe |
| — | 1 (cis) | PrNH$_3$ | OCHF$_2$ | OMe |
| — | 1 (cis) | $^i$PrNH$_3$ | OCHF$_2$ | OMe |
| — | 1 (cis) | NH$_2$CONH$_3$ | OCHF$_2$ | OMe |
| — | 1 (cis) | Me | OCHF$_2$ | OMe |
| — | 1 (cis) | Et | OCHF$_2$ | OMe |
| — | 1 (cis) | $^i$Pr | OCHF$_2$ | OMe |
| — | 1 (cis) | Pr | OCHF$_2$ | OMe |
| — | 1 (cis) | Bu | OCHF$_2$ | OMe |

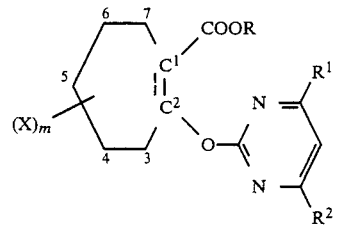

TABLE 3-continued

A compound of the general formula:

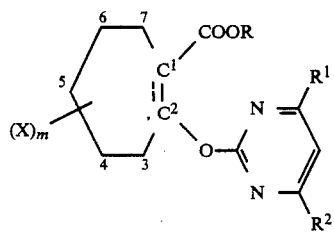 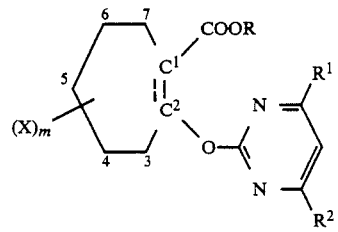

In the below-mentioned table, Me represents methyl group, Et represents ethyl group, Pr represents propyl group, $^i$Pr represents isopropyl group, Bu represents butyl group, $^i$Bu represents isobutyl group, $^s$Bu represents secondary butyl group, $^t$Bu represents tertiary butyl group, cis represents a cis-form, trans represents a trans-form, mix. represents a mixture of a cis-form and a trans-form, 1 represents a single bond and 2 represents a double bond

| $(X)_m$ | — | R | $R^1$ | $R^2$ |
|---|---|---|---|---|
| — | 1 (cis) | $^i$Bu | $OCHF_2$ | OMe |
| — | 1 (cis) | $^s$Bu | $OCHF_2$ | OMe |
| — | 1 (cis) | $^t$Bu | $OCHF_2$ | OMe |
| — | 1 (cis) | —$CH_2OCH_3$ | $OCHF_2$ | OMe |
| — | 1 (cis) | —$CH_2CH_2OCH_3$ | $OCHF_2$ | OMe |
| — | 1 (cis) | —$CH_2SCH_3$ | $OCHF_2$ | OMe |
| — | 1 (cis) | —$CH_2CH=CH_2$ | $OCHF_2$ | OMe |
| — | 1 (cis) | —$C(CH_3)_2CH=CH_2$ | $OCHF_2$ | OMe |
| — | 1 (cis) | —$CH_2C\equiv CH_2$ | $OCHF_2$ | OMe |
| — | 1 (cis) | —$CH_2C_6H_5$ | $OCHF_2$ | OMe |
| — | 1 (cis) | —$CH_2C_6H_4$—Cl-2 | $OCHF_2$ | OMe |
| — | 1 (cis) | —$CH_2C_6H_4$—Cl-3 | $OCHF_2$ | OMe |
| — | 1 (cis) | —$CH_2C_6H_4$—Cl-4 | $OCHF_2$ | OMe |
| — | 1 (cis) | —$CH_2C_6H_4$—Me-2 | $OCHF_2$ | OMe |
| — | 1 (cis) | —$CH_2C_6H_4$—Me-3 | $OCHF_2$ | OMe |
| — | 1 (cis) | —$CH_2C_6H_4$—Me-4 | $OCHF_2$ | OMe |
| — | 1 (cis) | —$CH_2C_6H_4$—OMe-2 | $OCHF_2$ | OMe |
| — | 1 (cis) | —$CH_2C_6H_4$—OMe-3 | $OCHF_2$ | OMe |
| — | 1 (cis) | —$CH_2C_6H_4$—OMe-4 | $OCHF_2$ | OMe |
| — | 1 (cis) | —$CH_2CH_2C_6H_5$ | $OCHF_2$ | OMe |
| — | 1 (cis) | H | $OCHF_2$ | $OCHF_2$ |
| — | 1 (cis) | Li | $OCHF_2$ | $OCHF_2$ |
| — | 1 (cis) | Na | $OCHF_2$ | $OCHF_2$ |
| — | 1 (cis) | K | $OCHF_2$ | $OCHF_2$ |
| — | 1 (cis) | ½Mg | $OCHF_2$ | $OCHF_2$ |
| — | 1 (cis) | ½Ca | $OCHF_2$ | $OCHF_2$ |
| — | 1 (cis) | $MeNH_3$ | $OCHF_2$ | $OCHF_2$ |
| — | 1 (cis) | $EtNH_3$ | $OCHF_2$ | $OCHF_2$ |
| — | 1 (cis) | $PrNH_3$ | $OCHF_2$ | $OCHF_2$ |
| — | 1 (cis) | $^iPrNH_3$ | $OCHF_2$ | $OCHF_2$ |
| — | 1 (cis) | $NH_2CONH_3$ | $OCHF_2$ | $OCHF_2$ |
| — | 1 (cis) | Me | $OCHF_2$ | $OCHF_2$ |
| — | 1 (cis) | Et | $OCHF_2$ | $OCHF_2$ |
| — | 1 (cis) | $^i$Pr | $OCHF_2$ | $OCHF_2$ |
| — | 1 (cis) | Pr | $OCHF_2$ | $OCHF_2$ |
| — | 1 (cis) | Bu | $OCHF_2$ | $OCHF_2$ |
| — | 1 (cis) | $^i$Bu | $OCHF_2$ | $OCHF_2$ |
| — | 1 (cis) | $^s$Bu | $OCHF_2$ | $OCHF_2$ |
| — | 1 (cis) | $^t$Bu | $OCHF_2$ | $OCHF_2$ |
| — | 1 (cis) | —$CH_2OCH_3$ | $OCHF_2$ | $OCHF_2$ |
| — | 1 (cis) | —$CH_2CH_2OCH_3$ | $OCHF_2$ | $OCHF_2$ |
| — | 1 (cis) | —$CH_2SCH_3$ | $OCHF_2$ | $OCHF_2$ |
| — | 1 (cis) | —$CH_2CH=CH_2$ | $OCHF_2$ | $OCHF_2$ |
| — | 1 (cis) | —$C(CH_3)_2CH=CH_2$ | $OCHF_2$ | $OCHF_2$ |
| — | 1 (cis) | —$CH_2C\equiv CH_2$ | $OCHF_2$ | $OCHF_2$ |
| — | 1 (cis) | —$CH_2C_6H_5$ | $OCHF_2$ | $OCHF_2$ |
| — | 1 (cis) | —$CH_2C_6H_4$—Cl-2 | $OCHF_2$ | $OCHF_2$ |
| — | 1 (cis) | —$CH_2C_6H_4$—Cl-3 | $OCHF_2$ | $OCHF_2$ |
| — | 1 (cis) | —$CH_2C_6H_4$—Cl-4 | $OCHF_2$ | $OCHF_2$ |
| — | 1 (cis) | —$CH_2C_6H_4$—Me-2 | $OCHF_2$ | $OCHF_2$ |
| — | 1 (cis) | —$CH_2C_6H_4$—Me-3 | $OCHF_2$ | $OCHF_2$ |
| — | 1 (cis) | —$CH_2C_6H_4$—Me-4 | $OCHF_2$ | $OCHF_2$ |
| — | 1 (cis) | —$CH_2C_6H_4$—OMe-2 | $OCHF_2$ | $OCHF_2$ |
| — | 1 (cis) | —$CH_2C_6H_4$—OMe-3 | $OCHF_2$ | $OCHF_2$ |
| — | 1 (cis) | —$CH_2C_6H_4$—OMe-4 | $OCHF_2$ | $OCHF_2$ |
| — | 1 (cis) | —$CH_2CH_2C_6H_5$ | $OCHF_2$ | $OCHF_2$ |
| — | 1 (cis) | H | SMe | OMe |
| — | 1 (cis) | Li | SMe | OMe |
| — | 1 (cis) | Na | SMe | OMe |
| — | 1 (cis) | K | SMe | OMe |
| — | 1 (cis) | ½Mg | SMe | OMe |
| — | 1 (cis) | ½Ca | SMe | OMe |
| — | 1 (cis) | $MeNH_3$ | SMe | OMe |
| — | 1 (cis) | $EtNH_3$ | SMe | OMe |
| — | 1 (cis) | $PrNH_3$ | SMe | OMe |
| — | 1 (cis) | $^iPrNH_3$ | SMe | OMe |
| — | 1 (cis) | $NH_2CONH_3$ | SMe | OMe |
| — | 1 (cis) | Me | SMe | OMe |
| — | 1 (cis) | Et | SMe | OMe |
| — | 1 (cis) | $^i$Pr | SMe | OMe |
| — | 1 (cis) | Pr | SMe | OMe |
| — | 1 (cis) | Bu | SMe | OMe |
| — | 1 (cis) | $^i$Bu | SMe | OMe |
| — | 1 (cis) | $^s$Bu | SMe | OMe |
| — | 1 (cis) | $^t$Bu | SMe | OMe |
| — | 1 (cis) | —$CH_2OCH_3$ | SMe | OMe |
| — | 1 (cis) | —$CH_2CH_2OCH_3$ | SMe | OMe |
| — | 1 (cis) | —$CH_2SCH_3$ | SMe | OMe |
| — | 1 (cis) | —$CH_2CH=CH_2$ | SMe | OMe |
| — | 1 (cis) | —$C(CH_3)_2CH=CH_2$ | SMe | OMe |
| — | 1 (cis) | —$CH_2C\equiv CH_2$ | SMe | OMe |
| — | 1 (cis) | —$CH_2C_6H_5$ | SMe | OMe |
| — | 1 (cis) | —$CH_2C_6H_4$—Cl-2 | SMe | OMe |
| — | 1 (cis) | —$CH_2C_6H_4$—Cl-3 | SMe | OMe |
| — | 1 (cis) | —$CH_2C_6H_4$—Cl-4 | SMe | OMe |
| — | 1 (cis) | —$CH_2C_6H_4$—Me-2 | SMe | OMe |
| — | 1 (cis) | —$CH_2C_6H_4$—Me-3 | SMe | OMe |
| — | 1 (cis) | —$CH_2C_6H_4$—Me-4 | SMe | OMe |
| — | 1 (cis) | —$CH_2C_6H_4$—OMe-2 | SMe | OMe |
| — | 1 (cis) | —$CH_2C_6H_4$—OMe-3 | SMe | OMe |
| — | 1 (cis) | —$CH_2C_6H_4$—OMe-4 | SMe | OMe |
| — | 1 (cis) | —$CH_2CH_2C_6H_5$ | SMe | OMe |
| — | 1 (cis) | H | SMe | Me |
| — | 1 (cis) | Li | SMe | Me |
| — | 1 (cis) | Na | SMe | Me |
| — | 1 (cis) | K | SMe | Me |
| — | 1 (cis) | ½Mg | SMe | Me |
| — | 1 (cis) | ½Ca | SMe | Me |
| — | 1 (cis) | $MeNH_3$ | SMe | Me |
| — | 1 (cis) | $EtNH_3$ | SMe | Me |
| — | 1 (cis) | $PrNH_3$ | SMe | Me |
| — | 1 (cis) | $^iPrNH_3$ | SMe | Me |
| — | 1 (cis) | $NH_2CONH_3$ | SMe | Me |
| — | 1 (cis) | Me | SMe | Me |
| — | 1 (cis) | Et | SMe | Me |
| — | 1 (cis) | $^i$Pr | SMe | Me |
| — | 1 (cis) | Pr | SMe | Me |
| — | 1 (cis) | Bu | SMe | Me |
| — | 1 (cis) | $^i$Bu | SMe | Me |
| — | 1 (cis) | $^s$Bu | SMe | Me |
| — | 1 (cis) | $^t$Bu | SMe | Me |
| — | 1 (cis) | —$CH_2OCH_3$ | SMe | Me |
| — | 1 (cis) | —$CH_2CH_2OCH_3$ | SMe | Me |
| — | 1 (cis) | —$CH_2SCH_3$ | SMe | Me |
| — | 1 (cis) | —$CH_2CH=CH_2$ | SMe | Me |
| — | 1 (cis) | —$C(CH_3)_2CH=CH_2$ | SMe | Me |

TABLE 3-continued

A compound of the general formula:

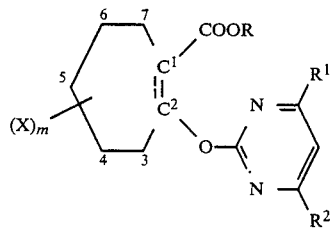

In the below-mentioned table, Me represents methyl group, Et represents ethyl group, Pr represents propyl group, $^i$Pr represents isopropyl group, Bu represents butyl group, $^i$Bu represents isobutyl group, $^s$Bu represents secondary butyl group, $^t$Bu represents tertiary butyl group, cis represents a cis-form, trans represents a trans-form, mix. represents a mixture of a cis-form and a trans-form, 1 represents a single bond and 2 represents a double bond

| $(X)_m$ | — | R | $R^1$ | $R^2$ |
|---|---|---|---|---|
| — | 1 (cis) | —CH$_2$C≡CH$_2$ | SMe | Me |
| — | 1 (cis) | —CH$_2$C$_6$H$_5$ | SMe | Me |
| — | 1 (cis) | —CH$_2$C$_6$H$_4$—Cl-2 | SMe | Me |
| — | 1 (cis) | —CH$_2$C$_6$H$_4$—Cl-3 | SMe | Me |
| — | 1 (cis) | —CH$_2$C$_6$H$_4$—Cl-4 | SMe | Me |
| — | 1 (cis) | —CH$_2$C$_6$H$_4$—Me-2 | SMe | Me |
| — | 1 (cis) | —CH$_2$C$_6$H$_4$—Me-3 | SMe | Me |
| — | 1 (cis) | —CH$_2$C$_6$H$_4$—Me-4 | SMe | Me |
| — | 1 (cis) | —CH$_2$C$_6$H$_4$—OMe-2 | SMe | Me |
| — | 1 (cis) | —CH$_2$C$_6$H$_4$—OMe-3 | SMe | Me |
| — | 1 (cis) | —CH$_2$C$_6$H$_4$—OMe-4 | SMe | Me |
| — | 1 (cis) | —CH$_2$CH$_2$C$_6$H$_5$ | SMe | Me |
| — | 1 (trans) | H | Me | Me |
| — | 1 (trans) | Li | Me | Me |
| — | 1 (trans) | Na | Me | Me |
| — | 1 (trans) | K | Me | Me |
| — | 1 (trans) | ½Mg | Me | Me |
| — | 1 (trans) | ½Ca | Me | Me |
| — | 1 (trans) | MeNH$_3$ | Me | Me |
| — | 1 (trans) | EtNH$_3$ | Me | Me |
| — | 1 (trans) | PrNH$_3$ | Me | Me |
| — | 1 (trans) | $^i$PrNH$_3$ | Me | Me |
| — | 1 (trans) | NH$_2$CONH$_3$ | Me | Me |
| — | 1 (trans) | Me | Me | Me |
| — | 1 (trans) | Et | Me | Me |
| — | 1 (trans) | $^i$Pr | Me | Me |
| — | 1 (trans) | Pr | Me | Me |
| — | 1 (trans) | Bu | Me | Me |
| — | 1 (trans) | $^i$Bu | Me | Me |
| — | 1 (trans) | $^s$Bu | Me | Me |
| — | 1 (trans) | $^t$Bu | Me | Me |
| — | 1 (trans) | —CH$_2$OCH$_3$ | Me | Me |
| — | 1 (trans) | —CH$_2$CH$_2$OCH$_3$ | Me | Me |
| — | 1 (trans) | —CH$_2$SCH$_3$ | Me | Me |
| — | 1 (trans) | —CH$_2$CH=CH$_2$ | Me | Me |
| — | 1 (trans) | —C(CH$_3$)$_2$CH=CH$_2$ | Me | Me |
| — | 1 (trans) | —CH$_2$C≡CH$_2$ | Me | Me |
| — | 1 (trans) | —CH$_2$C$_6$H$_5$ | Me | Me |
| — | 1 (trans) | —CH$_2$C$_6$H$_4$—Cl-2 | Me | Me |
| — | 1 (trans) | —CH$_2$C$_6$H$_4$—Cl-3 | Me | Me |
| — | 1 (trans) | —CH$_2$C$_6$H$_4$—Cl-4 | Me | Me |
| — | 1 (trans) | —CH$_2$C$_6$H$_4$—Me-2 | Me | Me |
| — | 1 (trans) | —CH$_2$C$_6$H$_4$—Me-3 | Me | Me |
| — | 1 (trans) | —CH$_2$C$_6$H$_4$—Me-4 | Me | Me |
| — | 1 (trans) | —CH$_2$C$_6$H$_4$—OMe-2 | Me | Me |
| — | 1 (trans) | —CH$_2$C$_6$H$_4$—OMe-3 | Me | Me |
| — | 1 (trans) | —CH$_2$C$_6$H$_4$—OMe-4 | Me | Me |
| — | 1 (trans) | —CH$_2$CH$_2$C$_6$H$_5$ | Me | Me |
| — | 1 (trans) | H | OMe | Me |
| — | 1 (trans) | Li | OMe | Me |
| — | 1 (trans) | Na | OMe | Me |
| — | 1 (trans) | K | OMe | Me |
| — | 1 (trans) | ½Mg | OMe | Me |
| — | 1 (trans) | ½Ca | OMe | Me |
| — | 1 (trans) | MeNH$_3$ | OMe | Me |
| — | 1 (trans) | EtNH$_3$ | OMe | Me |
| — | 1 (trans) | PrNH$_3$ | OMe | Me |
| — | 1 (trans) | $^i$PrNH$_3$ | OMe | Me |
| — | 1 (trans) | NH$_2$CONH$_3$ | OMe | Me |
| — | 1 (trans) | Me | OMe | Me |
| — | 1 (trans) | Et | OMe | Me |
| — | 1 (trans) | $^i$Pr | OMe | Me |
| — | 1 (trans) | Pr | OMe | Me |
| — | 1 (trans) | Bu | OMe | Me |
| — | 1 (trans) | $^i$Bu | OMe | Me |
| — | 1 (trans) | $^s$Bu | OMe | Me |
| — | 1 (trans) | $^t$Bu | OMe | Me |
| — | 1 (trans) | —CH$_2$OCH$_3$ | OMe | Me |
| — | 1 (trans) | —CH$_2$CH$_2$OCH$_3$ | OMe | Me |
| — | 1 (trans) | —CH$_2$SCH$_3$ | OMe | Me |
| — | 1 (trans) | —CH$_2$CH=CH$_2$ | OMe | Me |
| — | 1 (trans) | —C(CH$_3$)$_2$CH=CH$_2$ | OMe | Me |
| — | 1 (trans) | —CH$_2$C≡CH$_2$ | OMe | Me |
| — | 1 (trans) | —CH$_2$C$_6$H$_5$ | OMe | Me |
| — | 1 (trans) | —CH$_2$C$_6$H$_4$—Cl-2 | OMe | Me |
| — | 1 (trans) | —CH$_2$C$_6$H$_4$—Cl-3 | OMe | Me |
| — | 1 (trans) | —CH$_2$C$_6$H$_4$—Cl-4 | OMe | Me |
| — | 1 (trans) | —CH$_2$C$_6$H$_4$—Me-2 | OMe | Me |
| — | 1 (trans) | —CH$_2$C$_6$H$_4$—Me-3 | OMe | Me |
| — | 1 (trans) | —CH$_2$C$_6$H$_4$—Me-4 | OMe | Me |
| — | 1 (trans) | —CH$_2$C$_6$H$_4$—OMe-2 | OMe | Me |
| — | 1 (trans) | —CH$_2$C$_6$H$_4$—OMe-3 | OMe | Me |
| — | 1 (trans) | —CH$_2$C$_6$H$_4$—OMe-4 | OMe | Me |
| — | 1 (trans) | —CH$_2$CH$_2$C$_6$H$_5$ | OMe | Me |
| — | 1 (trans) | H | OMe | OMe |
| — | 1 (trans) | Li | OMe | OMe |
| — | 1 (trans) | Na | OMe | OMe |
| — | 1 (trans) | K | OMe | OMe |
| — | 1 (trans) | ½Mg | OMe | OMe |
| — | 1 (trans) | ½Ca | OMe | OMe |
| — | 1 (trans) | MeNH$_3$ | OMe | OMe |
| — | 1 (trans) | EtNH$_3$ | OMe | OMe |
| — | 1 (trans) | PrNH$_3$ | OMe | OMe |
| — | 1 (trans) | $^i$PrNH$_3$ | OMe | OMe |
| — | 1 (trans) | NH$_2$CONH$_3$ | OMe | OMe |
| — | 1 (trans) | Me | OMe | Ome |
| — | 1 (trans) | Et | OMe | OMe |
| — | 1 (trans) | $^i$Pr | OMe | OMe |
| — | 1 (trans) | Pr | OMe | OMe |
| — | 1 (trans) | Bu | OMe | OMe |
| — | 1 (trans) | $^i$Bu | OMe | OMe |
| — | 1 (trans) | $^s$Bu | OMe | OMe |
| — | 1 (trans) | $^t$Bu | OMe | OMe |
| — | 1 (trans) | —CH$_2$OCH$_3$ | OMe | OMe |
| — | 1 (trans) | —CH$_2$CH$_2$OCH$_3$ | OMe | OMe |
| — | 1 (trans) | —CH$_2$SCH$_3$ | OMe | OMe |
| — | 1 (trans) | —CH$_2$CH=CH$_2$ | OMe | OMe |
| — | 1 (trans) | —C(CH$_3$)$_2$CH=CH$_2$ | OMe | OMe |
| — | 1 (trans) | —CH$_2$C≡CH$_2$ | OMe | OMe |
| — | 1 (trans) | —CH$_2$C$_6$H$_5$ | OMe | OMe |
| — | 1 (trans) | —CH$_2$C$_6$H$_4$—Cl-2 | OMe | OMe |
| — | 1 (trans) | —CH$_2$C$_6$H$_4$—Cl-3 | OMe | OMe |
| — | 1 (trans) | —CH$_2$C$_6$H$_4$—Cl-4 | OMe | OMe |
| — | 1 (trans) | —CH$_2$C$_6$H$_4$—Me-2 | OMe | OMe |
| — | 1 (trans) | —CH$_2$C$_6$H$_4$—Me-3 | OMe | OMe |
| — | 1 (trans) | —CH$_2$C$_6$H$_4$—Me-4 | OMe | OMe |

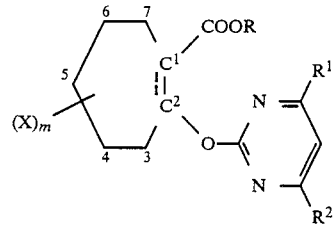

TABLE 3-continued

A compound of the general formula:

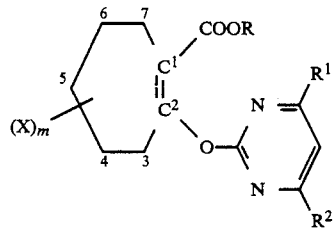

In the below-mentioned table, Me represents methyl group, Et represents ethyl group, Pr represents propyl group, $^i$Pr represents isopropyl group, Bu represents butyl group, $^i$Bu represents isobutyl group, $^s$Bu represents secondary butyl group, $^t$Bu represents tertiary butyl group, cis represents a cis-form, trans represents a trans-form, mix. represents a mixture of a cis-form and a trans-form, 1 represents a single bond and 2 represents a double bond

| $(X)_m$ | — | R | $R^1$ | $R^2$ |
|---|---|---|---|---|
| — | 1 (trans) | —CH$_2$C$_6$H$_4$—OMe-2 | OMe | OMe |
| — | 1 (trans) | —CH$_2$C$_6$H$_4$—OMe-3 | OMe | OMe |
| — | 1 (trans) | —CH$_2$C$_6$H$_4$—OMe-4 | OMe | OMe |
| — | 1 (trans) | —CH$_2$CH$_2$C$_6$H$_5$ | OMe | OMe |
| — | 1 (trans) | H | Cl | Me |
| — | 1 (trans) | Li | Cl | Me |
| — | 1 (trans) | Na | Cl | Me |
| — | 1 (trans) | K | Cl | Me |
| — | 1 (trans) | ½Mg | Cl | Me |
| — | 1 (trans) | ½Ca | Cl | Me |
| — | 1 (trans) | MeNH$_3$ | Cl | Me |
| — | 1 (trans) | EtNH$_3$ | Cl | Me |
| — | 1 (trans) | PrNH$_3$ | Cl | Me |
| — | 1 (trans) | $^i$PrNH$_3$ | Cl | Me |
| — | 1 (trans) | NH$_2$CONH$_3$ | Cl | Me |
| — | 1 (trans) | Me | Cl | Me |
| — | 1 (trans) | Et | Cl | Me |
| — | 1 (trans) | $^i$Pr | Cl | Me |
| — | 1 (trans) | Pr | Cl | Me |
| — | 1 (trans) | Bu | Cl | Me |
| — | 1 (trans) | $^i$Bu | Cl | Me |
| — | 1 (trans) | $^s$Bu | Cl | Me |
| — | 1 (trans) | $^t$Bu | Cl | Me |
| — | 1 (trans) | —CH$_2$OCH$_3$ | Cl | Me |
| — | 1 (trans) | —CH$_2$CH$_2$OCH$_3$ | Cl | Me |
| — | 1 (trans) | —CH$_2$SCH$_3$ | Cl | Me |
| — | 1 (trans) | —CH$_2$CH=CH$_2$ | Cl | Me |
| — | 1 (trans) | —C(CH$_3$)$_2$CH=CH$_2$ | Cl | Me |
| — | 1 (trans) | —CH$_2$C≡CH$_2$ | Cl | Me |
| — | 1 (trans) | —CH$_2$C$_6$H$_5$ | Cl | Me |
| — | 1 (trans) | —CH$_2$C$_6$H$_4$—Cl-2 | Cl | Me |
| — | 1 (trans) | —CH$_2$C$_6$H$_4$—Cl-3 | Cl | Me |
| — | 1 (trans) | —CH$_2$C$_6$H$_4$—Cl-4 | Cl | Me |
| — | 1 (trans) | —CH$_2$C$_6$H$_4$—Me-2 | Cl | Me |
| — | 1 (trans) | —CH$_2$C$_6$H$_4$—Me-3 | Cl | Me |
| — | 1 (trans) | —CH$_2$C$_6$H$_4$—Me-4 | Cl | Me |
| — | 1 (trans) | —CH$_2$C$_6$H$_4$—OMe-2 | Cl | Me |
| — | 1 (trans) | —CH$_2$C$_6$H$_4$—OMe-3 | Cl | Me |
| — | 1 (trans) | —CH$_2$C$_6$H$_4$—OMe-4 | Cl | Me |
| — | 1 (trans) | —CH$_2$CH$_2$C$_6$H$_5$ | Cl | Me |
| — | 1 (trans) | H | Cl | Cl |
| — | 1 (trans) | Li | Cl | Cl |
| — | 1 (trans) | Na | Cl | Cl |
| — | 1 (trans) | K | Cl | Cl |
| — | 1 (trans) | ½Mg | Cl | Cl |
| — | 1 (trans) | ½Ca | Cl | Cl |
| — | 1 (trans) | MeNH$_3$ | Cl | Cl |
| — | 1 (trans) | EtNH$_3$ | Cl | Cl |
| — | 1 (trans) | PrNH$_3$ | Cl | Cl |
| — | 1 (trans) | $^i$PrNH$_3$ | Cl | Cl |
| — | 1 (trans) | NH$_2$CONH$_3$ | Cl | Cl |
| — | 1 (trans) | Me | Cl | Cl |
| — | 1 (trans) | Et | Cl | Cl |
| — | 1 (trans) | $^i$Pr | Cl | Cl |
| — | 1 (trans) | Pr | Cl | Cl |
| — | 1 (trans) | Bu | Cl | Cl |
| — | 1 (trans) | $^i$Bu | Cl | Cl |
| — | 1 (trans) | $^s$Bu | Cl | Cl |

TABLE 3-continued

A compound of the general formula:

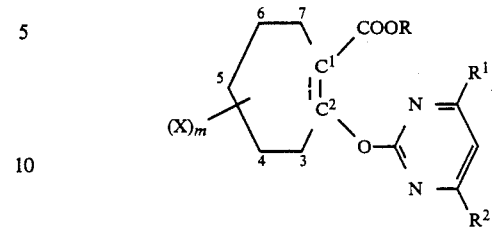

In the below-mentioned table, Me represents methyl group, Et represents ethyl group, Pr represents propyl group, $^i$Pr represents isopropyl group, Bu represents butyl group, $^i$Bu represents isobutyl group, $^s$Bu represents secondary butyl group, $^t$Bu represents tertiary butyl group, cis represents a cis-form, trans represents a trans-form, mix. represents a mixture of a cis-form and a trans-form, 1 represents a single bond and 2 represents a double bond

| $(X)_m$ | — | R | $R^1$ | $R^2$ |
|---|---|---|---|---|
| — | 1 (trans) | $^t$Bu | Cl | Cl |
| — | 1 (trans) | —CH$_2$OCH$_3$ | Cl | Cl |
| — | 1 (trans) | —CH$_2$CH$_2$OCH$_3$ | Cl | Cl |
| — | 1 (trans) | —CH$_2$SCH$_3$ | Cl | Cl |
| — | 1 (trans) | —CH$_2$CH=CH$_2$ | Cl | Cl |
| — | 1 (trans) | —C(CH$_3$)$_2$CH=CH$_2$ | Cl | Cl |
| — | 1 (trans) | —CH$_2$C≡CH$_2$ | Cl | Cl |
| — | 1 (trans) | —CH$_2$C$_6$H$_5$ | Cl | Cl |
| — | 1 (trans) | —CH$_2$C$_6$H$_4$—Cl-2 | Cl | Cl |
| — | 1 (trans) | —CH$_2$C$_6$H$_4$—Cl-3 | Cl | Cl |
| — | 1 (trans) | —CH$_2$C$_6$H$_4$—Cl-4 | Cl | Cl |
| — | 1 (trans) | —CH$_2$C$_6$H$_4$—Me-2 | Cl | Cl |
| — | 1 (trans) | —CH$_2$C$_6$H$_4$—Me-3 | Cl | Cl |
| — | 1 (trans) | —CH$_2$C$_6$H$_4$—Me-4 | Cl | Cl |
| — | 1 (trans) | —CH$_2$C$_6$H$_4$—OMe-2 | Cl | Cl |
| — | 1 (trans) | —CH$_2$C$_6$H$_4$—OMe-3 | Cl | Cl |
| — | 1 (trans) | —CH$_2$C$_6$H$_4$—OMe-4 | Cl | Cl |
| — | 1 (trans) | —CH$_2$CH$_2$C$_6$H$_5$ | Cl | Cl |
| — | 1 (trans) | H | Cl | OMe |
| — | 1 (trans) | Li | Cl | OMe |
| — | 1 (trans) | Na | Cl | OMe |
| — | 1 (trans) | K | Cl | OMe |
| — | 1 (trans) | ½Mg | Cl | OMe |
| — | 1 (trans) | ½Ca | Cl | OMe |
| — | 1 (trans) | MeNH$_3$ | Cl | OMe |
| — | 1 (trans) | EtNH$_3$ | Cl | OMe |
| — | 1 (trans) | PrNH$_3$ | Cl | OMe |
| — | 1 (trans) | $^i$PrNH$_3$ | Cl | OMe |
| — | 1 (trans) | NH$_2$CONH$_3$ | Cl | OMe |
| — | 1 (trans) | Me | Cl | OMe |
| — | 1 (trans) | Et | Cl | OMe |
| — | 1 (trans) | $^i$Pr | Cl | OMe |
| — | 1 (trans) | Pr | Cl | OMe |
| — | 1 (trans) | Bu | Cl | OMe |
| — | 1 (trans) | $^i$Bu | Cl | OMe |
| — | 1 (trans) | $^s$Bu | Cl | OMe |
| — | 1 (trans) | $^t$Bu | Cl | OMe |
| — | 1 (trans) | —CH$_2$OCH$_3$ | Cl | OMe |
| — | 1 (trans) | —CH$_2$CH$_2$OCH$_3$ | Cl | OMe |
| — | 1 (trans) | —CH$_2$SCH$_3$ | Cl | OMe |
| — | 1 (trans) | —CH$_2$CH=CH$_2$ | Cl | OMe |
| — | 1 (trans) | —C(CH$_3$)$_2$CH=CH$_2$ | Cl | OMe |
| — | 1 (trans) | —CH$_2$C≡CH$_2$ | Cl | OMe |
| — | 1 (trans) | —CH$_2$C$_6$H$_5$ | Cl | OMe |
| — | 1 (trans) | —CH$_2$C$_6$H$_4$—Cl-2 | Cl | OMe |
| — | 1 (trans) | —CH$_2$C$_6$H$_4$—Cl-3 | Cl | OMe |
| — | 1 (trans) | —CH$_2$C$_6$H$_4$—Cl-4 | Cl | OMe |
| — | 1 (trans) | —CH$_2$C$_6$H$_4$—Me-2 | Cl | OMe |
| — | 1 (trans) | —CH$_2$C$_6$H$_4$—Me-3 | Cl | OMe |
| — | 1 (trans) | —CH$_2$C$_6$H$_4$—Me-4 | Cl | OMe |
| — | 1 (trans) | —CH$_2$C$_6$H$_4$—OMe-2 | Cl | OMe |
| — | 1 (trans) | —CH$_2$C$_6$H$_4$—OMe-3 | Cl | OMe |
| — | 1 (trans) | —CH$_2$C$_6$H$_4$—OMe-4 | Cl | OMe |
| — | 1 (trans) | —CH$_2$CH$_2$C$_6$H$_5$ | Cl | OMe |
| — | 1 (trans) | H | OCHF$_2$ | OMe |
| — | 1 (trans) | Li | OCHF$_2$ | OMe |
| — | 1 (trans) | Na | OCHF$_2$ | OMe |
| — | 1 (trans) | K | OCHF$_2$ | OMe |

TABLE 3-continued

A compound of the general formula:

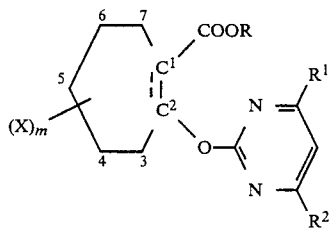

In the below-mentioned table, Me represents methyl group, Et represents ethyl group, Pr represents propyl group, $^i$Pr represents isopropyl group, Bu represents butyl group, $^i$Bu represents isobutyl group, $^s$Bu represents secondary butyl group, $^t$Bu represents tertiary butyl group, cis represents a cis-form, trans represents a trans-form, mix. represents a mixture of a cis-form and a trans-form, 1 represents a single bond and 2 represents a double bond

| $(X)_m$ | | R | $R^1$ | $R^2$ |
|---|---|---|---|---|
| — | 1 (trans) | $\frac{1}{2}$Mg | $OCHF_2$ | OMe |
| — | 1 (trans) | $\frac{1}{2}$Ca | $OCHF_2$ | OMe |
| — | 1 (trans) | $MeNH_3$ | $OCHF_2$ | OMe |
| — | 1 (trans) | $EtNH_3$ | $OCHF_2$ | OMe |
| — | 1 (trans) | $PrNH_3$ | $OCHF_2$ | OMe |
| — | 1 (trans) | $^iPrNH_3$ | $OCHF_2$ | OMe |
| — | 1 (trans) | $NH_2CONH_3$ | $OCHF_2$ | OMe |
| — | 1 (trans) | Me | $OCHF_2$ | OMe |
| — | 1 (trans) | Et | $OCHF_2$ | OMe |
| — | 1 (trans) | $^iPr$ | $OCHF_2$ | OMe |
| — | 1 (trans) | Pr | $OCHF_2$ | OMe |
| — | 1 (trans) | Bu | $OCHF_2$ | OMe |
| — | 1 (trans) | $^iBu$ | $OCHF_2$ | OMe |
| — | 1 (trans) | $^sBu$ | $OCHF_2$ | OMe |
| — | 1 (trans) | $^tBu$ | $OCHF_2$ | OMe |
| — | 1 (trans) | $-CH_2OCH_3$ | $OCHF_2$ | OMe |
| — | 1 (trans) | $-CH_2CH_2OCH_3$ | $OCHF_2$ | OMe |
| — | 1 (trans) | $-CH_2SCH_3$ | $OCHF_2$ | OMe |
| — | 1 (trans) | $-CH_2CH=CH_2$ | $OCHF_2$ | OMe |
| — | 1 (trans) | $-C(CH_3)_2CH=CH_2$ | $OCHF_2$ | OMe |
| — | 1 (trans) | $-CH_2C\equiv CH_2$ | $OCHF_2$ | OMe |
| — | 1 (trans) | $-CH_2C_6H_5$ | $OCHF_2$ | OMe |
| — | 1 (trans) | $-CH_2C_6H_4-Cl-2$ | $OCHF_2$ | OMe |
| — | 1 (trans) | $-CH_2C_6H_4-Cl-3$ | $OCHF_2$ | OMe |
| — | 1 (trans) | $-CH_2C_6H_4-Cl-4$ | $OCHF_2$ | OMe |
| — | 1 (trans) | $-CH_2C_6H_4-Me-2$ | $OCHF_2$ | OMe |
| — | 1 (trans) | $-CH_2C_6H_4-Me-3$ | $OCHF_2$ | OMe |
| — | 1 (trans) | $-CH_2C_6H_4-Me-4$ | $OCHF_2$ | OMe |
| — | 1 (trans) | $-CH_2C_6H_4-OMe-2$ | $OCHF_2$ | OMe |
| — | 1 (trans) | $-CH_2C_6H_4-OMe-3$ | $OCHF_2$ | OMe |
| — | 1 (trans) | $-CH_2C_6H_4-OMe-4$ | $OCHF_2$ | OMe |
| — | 1 (trans) | $-CH_2CH_2C_6H_5$ | $OCHF_2$ | OMe |
| — | 1 (trans) | H | $OCHF_2$ | $OCHF_2$ |
| — | 1 (trans) | Li | $OCHF_2$ | $OCHF_2$ |
| — | 1 (trans) | Na | $OCHF_2$ | $OCHF_2$ |
| — | 1 (trans) | K | $OCHF_2$ | $OCHF_2$ |
| — | 1 (trans) | $\frac{1}{2}$Mg | $OCHF_2$ | $OCHF_2$ |
| — | 1 (trans) | $\frac{1}{2}$Ca | $OCHF_2$ | $OCHF_2$ |
| — | 1 (trans) | $MeNH_3$ | $OCHF_2$ | $OCHF_2$ |
| — | 1 (trans) | $EtNH_3$ | $OCHF_2$ | $OCHF_2$ |
| — | 1 (trans) | $PrNH_3$ | $OCHF_2$ | $OCHF_2$ |
| — | 1 (trans) | $^iPrNH_3$ | $OCHF_2$ | $OCHF_2$ |
| — | 1 (trans) | $NH_2CONH_3$ | $OCHF_2$ | $OCHF_2$ |
| — | 1 (trans) | Me | $OCHF_2$ | $OCHF_2$ |
| — | 1 (trans) | Et | $OCHF_2$ | $OCHF_2$ |
| — | 1 (trans) | $^iPr$ | $OCHF_2$ | $OCHF_2$ |
| — | 1 (trans) | Pr | $OCHF_2$ | $OCHF_2$ |
| — | 1 (trans) | Bu | $OCHF_2$ | $OCHF_2$ |
| — | 1 (trans) | $^iBu$ | $OCHF_2$ | $OCHF_2$ |
| — | 1 (trans) | $^sBu$ | $OCHF_2$ | $OCHF_2$ |
| — | 1 (trans) | $^tBu$ | $OCHF_2$ | $OCHF_2$ |
| — | 1 (trans) | $-CH_2OCH_3$ | $OCHF_2$ | $OCHF_2$ |
| — | 1 (trans) | $-CH_2CH_2OCH_3$ | $OCHF_2$ | $OCHF_2$ |
| — | 1 (trans) | $-CH_2SCH_3$ | $OCHF_2$ | $OCHF_2$ |
| — | 1 (trans) | $-CH_2CH=CH_2$ | $OCHF_2$ | $OCHF_2$ |
| — | 1 (trans) | $-C(CH_3)_2CH=CH_2$ | $OCHF_2$ | $OCHF_2$ |
| — | 1 (trans) | $-CH_2C\equiv CH_2$ | $OCHF_2$ | $OCHF_2$ |
| — | 1 (trans) | $-CH_2C_6H_5$ | $OCHF_2$ | $OCHF_2$ |

TABLE 3-continued

A compound of the general formula:

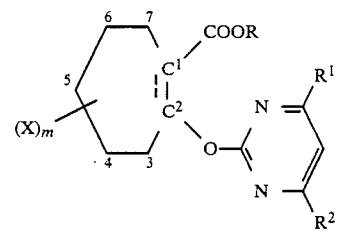

In the below-mentioned table, Me represents methyl group, Et represents ethyl group, Pr represents propyl group, $^i$Pr represents isopropyl group, Bu represents butyl group, $^i$Bu represents isobutyl group, $^s$Bu represents secondary butyl group, $^t$Bu represents tertiary butyl group, cis represents a cis-form, trans represents a trans-form, mix. represents a mixture of a cis-form and a trans-form, 1 represents a single bond and 2 represents a double bond

| $(X)_m$ | | R | $R^1$ | $R^2$ |
|---|---|---|---|---|
| — | 1 (trans) | $-CH_2C_6H_4-Cl-2$ | $OCHF_2$ | $OCHF_2$ |
| — | 1 (trans) | $-CH_2C_6H_4-Cl-3$ | $OCHF_2$ | $OCHF_2$ |
| — | 1 (trans) | $-CH_2C_6H_4-Cl-4$ | $OCHF_2$ | $OCHF_2$ |
| — | 1 (trans) | $-CH_2C_6H_4-Me-2$ | $OCHF_2$ | $OCHF_2$ |
| — | 1 (trans) | $-CH_2C_6H_4-Me-3$ | $OCHF_2$ | $OCHF_2$ |
| — | 1 (trans) | $-CH_2C_6H_4-Me-4$ | $OCHF_2$ | $OCHF_2$ |
| — | 1 (trans) | $-CH_2C_6H_4-OMe-2$ | $OCHF_2$ | $OCHF_2$ |
| — | 1 (trans) | $-CH_2C_6H_4-OMe-3$ | $OCHF_2$ | $OCHF_2$ |
| — | 1 (trans) | $-CH_2C_6H_4-OMe-4$ | $OCHF_2$ | $OCHF_2$ |
| — | 1 (trans) | $-CH_2CH_2C_6H_5$ | $OCHF_2$ | $OCHF_2$ |
| — | 1 (trans) | H | SMe | OMe |
| — | 1 (trans) | Li | SMe | OMe |
| — | 1 (trans) | Na | SMe | OMe |
| — | 1 (trans) | K | SMe | OMe |
| — | 1 (trans) | $\frac{1}{2}$Mg | SMe | OMe |
| — | 1 (trans) | $\frac{1}{2}$Ca | SMe | OMe |
| — | 1 (trans) | $MeNH_3$ | SMe | OMe |
| — | 1 (trans) | $EtNH_3$ | SMe | OMe |
| — | 1 (trans) | $PrNH_3$ | SMe | OMe |
| — | 1 (trans) | $^iPrNH_3$ | SMe | OMe |
| — | 1 (trans) | $NH_2CONH_3$ | SMe | OMe |
| — | 1 (trans) | Me | SMe | OMe |
| — | 1 (trans) | Et | SMe | OMe |
| — | 1 (trans) | $^iPr$ | SMe | OMe |
| — | 1 (trans) | Pr | SMe | OMe |
| — | 1 (trans) | Bu | SMe | OMe |
| — | 1 (trans) | $^iBu$ | SMe | OMe |
| — | 1 (trans) | $^sBu$ | SMe | OMe |
| — | 1 (trans) | $^tBu$ | SMe | OMe |
| — | 1 (trans) | $-CH_2OCH_3$ | SMe | OMe |
| — | 1 (trans) | $-CH_2CH_2OCH_3$ | SMe | OMe |
| — | 1 (trans) | $-CH_2SCH_3$ | SMe | OMe |
| — | 1 (trans) | $-CH_2CH=CH_2$ | SMe | OMe |
| — | 1 (trans) | $-C(CH_3)_2CH=CH_2$ | SMe | OMe |
| — | 1 (trans) | $-CH_2C\equiv CH_2$ | SMe | OMe |
| — | 1 (trans) | $-CH_2C_6H_5$ | SMe | OMe |
| — | 1 (trans) | $-CH_2C_6H_4-Cl-2$ | SMe | OMe |
| — | 1 (trans) | $-CH_2C_6H_4-Cl-3$ | SMe | OMe |
| — | 1 (trans) | $-CH_2C_6H_4-Cl-4$ | SMe | OMe |
| — | 1 (trans) | $-CH_2C_6H_4-Me-2$ | SMe | OMe |
| — | 1 (trans) | $-CH_2C_6H_4-Me-3$ | SMe | OMe |
| — | 1 (trans) | $-CH_2C_6H_4-Me-4$ | SMe | OMe |
| — | 1 (trans) | $-CH_2C_6H_4-OMe-2$ | SMe | OMe |
| — | 1 (trans) | $-CH_2C_6H_4-OMe-3$ | SMe | OMe |
| — | 1 (trans) | $-CH_2C_6H_4-OMe-4$ | SMe | OMe |
| — | 1 (trans) | $-CH_2CH_2CH_2C_6H_5$ | SMe | OMe |
| — | 1 (trans) | H | SMe | Me |
| — | 1 (trans) | Li | SMe | Me |
| — | 1 (trans) | Na | SMe | Me |
| — | 1 (trans) | K | SMe | Me |
| — | 1 (trans) | $\frac{1}{2}$Mg | SMe | Me |
| — | 1 (trans) | $\frac{1}{2}$Ca | SMe | Me |
| — | 1 (trans) | $MeNH_3$ | SMe | Me |
| — | 1 (trans) | $EtNH_3$ | SMe | Me |
| — | 1 (trans) | $PrNH_3$ | SMe | Me |
| — | 1 (trans) | $^iPrNH_3$ | SMe | Me |
| — | 1 (trans) | $NH_2CONH_3$ | SMe | Me |
| — | 1 (trans) | Me | SMe | Me |

TABLE 3-continued

A compound of the general formula:

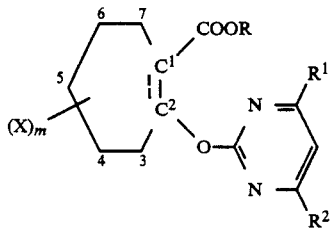

In the below-mentioned table, Me represents methyl group, Et represents ethyl group, Pr represents propyl group, $^i$Pr represents isopropyl group, Bu represents butyl group, $^i$Bu represents isobutyl group, $^s$Bu represents secondary butyl group, $^t$Bu represents tertiary butyl group, cis represents a cis-form, trans represents a trans-form, mix. represents a mixture of a cis-form and a trans-form, 1 represents a single bond and 2 represents a double bond

| $(X)_m$ | — | R | $R^1$ | $R^2$ |
|---|---|---|---|---|
| — | 1 (trans) | Et | SMe | Me |
| — | 1 (trans) | $^i$Pr | SMe | Me |
| — | 1 (trans) | Pr | SMe | Me |
| — | 1 (trans) | Bu | SMe | Me |
| — | 1 (trans) | $^i$Bu | SMe | Me |
| — | 1 (trans) | $^s$Bu | SMe | Me |
| — | 1 (trans) | $^t$Bu | SMe | Me |
| — | 1 (trans) | —CH$_2$OCH$_3$ | SMe | Me |
| — | 1 (trans) | —CH$_2$CH$_2$OCH$_3$ | SMe | Me |
| — | 1 (trans) | —CH$_2$SCH$_3$ | SMe | Me |
| — | 1 (trans) | —CH$_2$CH=CH$_2$ | SMe | Me |
| — | 1 (trans) | —C(CH$_3$)$_2$CH=CH$_2$ | SMe | Me |
| — | 1 (trans) | —CH$_2$C≡CH$_2$ | SMe | Me |
| — | 1 (trans) | —CH$_2$C$_6$H$_5$ | SMe | Me |
| — | 1 (trans) | —CH$_2$C$_6$H$_4$—Cl-2 | SMe | Me |
| — | 1 (trans) | —CH$_2$C$_6$H$_4$—Cl-3 | SMe | Me |
| — | 1 (trans) | —CH$_2$C$_6$H$_4$—Cl-4 | SMe | Me |
| — | 1 (trans) | —CH$_2$C$_6$H$_4$—Me-2 | SMe | Me |
| — | 1 (trans) | —CH$_2$C$_6$H$_4$—Me-3 | SMe | Me |
| — | 1 (trans) | —CH$_2$C$_6$H$_4$—Me-4 | SMe | Me |
| — | 1 (trans) | —CH$_2$C$_6$H$_4$—OMe-2 | SMe | Me |
| — | 1 (trans) | —CH$_2$C$_6$H$_4$—OMe-3 | SMe | Me |
| — | 1 (trans) | —CH$_2$C$_6$H$_4$—OMe-4 | SMe | Me |
| — | 1 (trans) | —CH$_2$CH$_2$C$_6$H$_5$ | SMe | Me |
| — | 1 (mixt.) | H | Me | Me |
| — | 1 (mixt.) | Li | Me | Me |
| — | 1 (mixt.) | Na | Me | Me |
| — | 1 (mixt.) | K | Me | Me |
| — | 1 (mixt.) | ½Mg | Me | Me |
| — | 1 (mixt.) | ½Ca | Me | Me |
| — | 1 (mixt.) | MeNH$_3$ | Me | Me |
| — | 1 (mixt.) | EtNH$_3$ | Me | Me |
| — | 1 (mixt.) | PrNH$_3$ | Me | Me |
| — | 1 (mixt.) | $^i$PrNH$_3$ | Me | Me |
| — | 1 (mixt.) | NH$_2$CONH$_3$ | Me | Me |
| — | 1 (mixt.) | Me | Me | Me |
| — | 1 (mixt.) | Et | Me | Me |
| — | 1 (mixt.) | $^i$Pr | Me | Me |
| — | 1 (mixt.) | Pr | Me | Me |
| — | 1 (mixt.) | Bu | Me | Me |
| — | 1 (mixt.) | $^i$Bu | Me | Me |
| — | 1 (mixt.) | $^s$Bu | Me | Me |
| — | 1 (mixt.) | $^t$Bu | Me | Me |
| — | 1 (mixt.) | —CH$_2$OCH$_3$ | Me | Me |
| — | 1 (mixt.) | —CH$_2$CH$_2$OCH$_3$ | Me | Me |
| — | 1 (mixt.) | —CH$_2$SCH$_3$ | Me | Me |
| — | 1 (mixt.) | —CH$_2$CH=CH$_2$ | Me | Me |
| — | 1 (mixt.) | —C(CH$_3$)$_2$CH=CH$_2$ | Me | Me |
| — | 1 (mixt.) | —CH$_2$C≡CH$_2$ | Me | Me |
| — | 1 (mixt.) | —CH$_2$C$_6$H$_5$ | Me | Me |
| — | 1 (mixt.) | —CH$_2$C$_6$H$_4$—Cl-2 | Me | Me |
| — | 1 (mixt.) | —CH$_2$C$_6$H$_4$—Cl-3 | Me | Me |
| — | 1 (mixt.) | —CH$_2$C$_6$H$_4$—Cl-4 | Me | Me |
| — | 1 (mixt.) | —CH$_2$C$_6$H$_4$—Me-2 | Me | Me |
| — | 1 (mixt.) | —CH$_2$C$_6$H$_4$—Me-3 | Me | Me |
| — | 1 (mixt.) | —CH$_2$C$_6$H$_4$—Me-4 | Me | Me |
| — | 1 (mixt.) | —CH$_2$C$_6$H$_4$—OMe-2 | Me | Me |
| — | 1 (mixt.) | —CH$_2$C$_6$H$_4$—OMe-3 | Me | Me |
| — | 1 (mixt.) | —CH$_2$C$_6$H$_4$—OMe-4 | Me | Me |
| — | 1 (mixt.) | —CH$_2$CH$_2$C$_6$H$_5$ | Me | Me |
| — | 1 (mixt.) | H | OMe | Me |
| — | 1 (mixt.) | Li | OMe | Me |
| — | 1 (mixt.) | Na | OMe | Me |
| — | 1 (mixt.) | K | OMe | Me |
| — | 1 (mixt.) | ½Mg | OMe | Me |
| — | 1 (mixt.) | ½Ca | OMe | Me |
| — | 1 (mixt.) | MeNH$_3$ | OMe | Me |
| — | 1 (mixt.) | EtNH$_3$ | OMe | Me |
| — | 1 (mixt.) | PrNH$_3$ | OMe | Me |
| — | 1 (mixt.) | $^i$PrNH$_3$ | OMe | Me |
| — | 1 (mixt.) | NH$_2$CONH$_3$ | OMe | Me |
| — | 1 (mixt.) | Me | OMe | Me |
| — | 1 (mixt.) | Et | OMe | Me |
| — | 1 (mixt.) | $^i$Pr | OMe | Me |
| — | 1 (mixt.) | Pr | OMe | Me |
| — | 1 (mixt.) | Bu | OMe | Me |
| — | 1 (mixt.) | $^i$Bu | OMe | Me |
| — | 1 (mixt.) | $^s$Bu | OMe | Me |
| — | 1 (mixt.) | $^t$Bu | OMe | Me |
| — | 1 (mixt.) | —CH$_2$OCH$_3$ | OMe | Me |
| — | 1 (mixt.) | —CH$_2$CH$_2$OCH$_3$ | OMe | Me |
| — | 1 (mixt.) | —CH$_2$SCH$_3$ | OMe | Me |
| — | 1 (mixt.) | —CH$_2$CH=CH$_2$ | OMe | Me |
| — | 1 (mixt.) | —C(CH$_3$)$_2$CH=CH$_2$ | OMe | Me |
| — | 1 (mixt.) | —CH$_2$C≡CH$_2$ | OMe | Me |
| — | 1 (mixt.) | —CH$_2$C$_6$H$_5$ | OMe | Me |
| — | 1 (mixt.) | —CH$_2$C$_6$H$_4$—Cl-2 | OMe | Me |
| — | 1 (mixt.) | —CH$_2$C$_6$H$_4$—Cl-3 | OMe | Me |
| — | 1 (mixt.) | —CH$_2$C$_6$H$_4$—Cl-4 | OMe | Me |
| — | 1 (mixt.) | —CH$_2$C$_6$H$_4$—Me-2 | OMe | Me |
| — | 1 (mixt.) | —CH$_2$C$_6$H$_4$—Me-3 | OMe | Me |
| — | 1 (mixt.) | —CH$_2$C$_6$H$_4$—Me-4 | OMe | Me |
| — | 1 (mixt.) | —CH$_2$C$_6$H$_4$—OMe-2 | OMe | Me |
| — | 1 (mixt.) | —CH$_2$C$_6$H$_4$—OMe-3 | OMe | Me |
| — | 1 (mixt.) | —CH$_2$C$_6$H$_4$—OMe-4 | OMe | Me |
| — | 1 (mixt.) | —CH$_2$CH$_2$C$_6$H$_5$ | OMe | Me |
| — | 1 (mixt.) | H | OMe | OMe |
| — | 1 (mixt.) | Li | OMe | OMe |
| — | 1 (mixt.) | Na | OMe | OMe |
| — | 1 (mixt.) | K | OMe | OMe |
| — | 1 (mixt.) | ½Mg | OMe | OMe |
| — | 1 (mixt.) | ½Ca | OMe | OMe |
| — | 1 (mixt.) | MeNH$_3$ | OMe | OMe |
| — | 1 (mixt.) | EtNH$_3$ | OMe | OMe |
| — | 1 (mixt.) | PrNH$_3$ | OMe | OMe |
| — | 1 (mixt.) | $^i$PrNH$_3$ | OMe | OMe |
| — | 1 (mixt.) | NH$_2$CONH$_3$ | OMe | OMe |
| — | 1 (mixt.) | Me | OMe | OMe |
| — | 1 (mixt.) | Et | OMe | OMe |
| — | 1 (mixt.) | $^i$Pr | OMe | OMe |
| — | 1 (mixt.) | Pr | OMe | OMe |
| — | 1 (mixt.) | Bu | OMe | OMe |
| — | 1 (mixt.) | $^i$Bu | OMe | OMe |
| — | 1 (mixt.) | $^s$Bu | OMe | OMe |
| — | 1 (mixt.) | $^t$Bu | OMe | OMe |
| — | 1 (mixt.) | —CH$_2$OCH$_3$ | OMe | OMe |

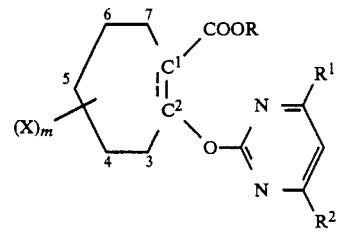

TABLE 3-continued

A compound of the general formula:

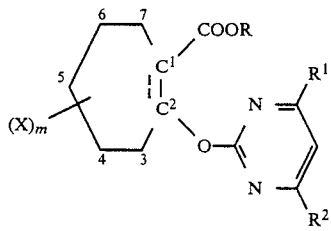

In the below-mentioned table, Me represents methyl group, Et represents ethyl group, Pr represents propyl group, $^i$Pr represents isopropyl group, Bu represents butyl group, $^i$Bu represents isobutyl group, $^s$Bu represents secondary butyl group, $^t$Bu represents tertiary butyl group, cis represents a cis-form, trans represents a trans-form, mix. represents a mixture of a cis-form and a trans-form, 1 represents a single bond and 2 represents a double bond

| $(X)_m$ | — | R | $R^1$ | $R^2$ |
|---|---|---|---|---|
| — | 1 (mixt.) | —CH$_2$CH$_2$OCH$_3$ | OMe | OMe |
| — | 1 (mixt.) | —CH$_2$SCH$_3$ | OMe | OMe |
| — | 1 (mixt.) | —CH$_2$CH=CH$_2$ | OMe | OMe |
| — | 1 (mixt.) | —C(CH$_3$)$_2$CH=CH$_2$ | OMe | OMe |
| — | 1 (mixt.) | —CH$_2$C≡CH$_2$ | OMe | OMe |
| — | 1 (mixt.) | —CH$_2$C$_6$H$_5$ | OMe | OMe |
| — | 1 (mixt.) | —CH$_2$C$_6$H$_4$—Cl-2 | OMe | OMe |
| — | 1 (mixt.) | —CH$_2$C$_6$H$_4$—Cl-3 | OMe | OMe |
| — | 1 (mixt.) | —CH$_2$C$_6$H$_4$—Cl-4 | OMe | OMe |
| — | 1 (mixt.) | —CH$_2$C$_6$H$_4$—Me-2 | OMe | OMe |
| — | 1 (mixt.) | —CH$_2$C$_6$H$_4$—Me-3 | OMe | OMe |
| — | 1 (mixt.) | —CH$_2$C$_6$H$_4$—Me-4 | OMe | OMe |
| — | 1 (mixt.) | —CH$_2$C$_6$H$_4$—OMe-2 | OMe | OMe |
| — | 1 (mixt.) | —CH$_2$C$_6$H$_4$—OMe-3 | OMe | OMe |
| — | 1 (mixt.) | —CH$_2$C$_6$H$_4$—OMe-4 | OMe | OMe |
| — | 1 (mixt.) | —CH$_2$CH$_2$C$_6$H$_5$ | OMe | OMe |
| — | 1 (mixt.) | H | Cl | Me |
| — | 1 (mixt.) | Li | Cl | Me |
| — | 1 (mixt.) | Na | Cl | Me |
| — | 1 (mixt.) | K | Cl | Me |
| — | 1 (mixt.) | ½Mg | Cl | Me |
| — | 1 (mixt.) | ½Ca | Cl | Me |
| — | 1 (mixt.) | MeNH$_3$ | Cl | Me |
| — | 1 (mixt.) | EtNH$_3$ | Cl | Me |
| — | 1 (mixt.) | PrNH$_3$ | Cl | Me |
| — | 1 (mixt.) | $^i$PrNH$_3$ | Cl | Me |
| — | 1 (mixt.) | NH$_2$CONH$_3$ | Cl | Me |
| — | 1 (mixt.) | Me | Cl | Me |
| — | 1 (mixt.) | Et | Cl | Me |
| — | 1 (mixt.) | $^i$Pr | Cl | Me |
| — | 1 (mixt.) | Pr | Cl | Me |
| — | 1 (mixt.) | Bu | Cl | Me |
| — | 1 (mixt.) | $^i$Bu | Cl | Me |
| — | 1 (mixt.) | $^s$Bu | Cl | Me |
| — | 1 (mixt.) | $^t$Bu | Cl | Me |
| — | 1 (mixt.) | —CH$_2$OCH$_3$ | Cl | Me |
| — | 1 (mixt.) | —CH$_2$CH$_2$OCH$_3$ | Cl | Me |
| — | 1 (mixt.) | —CH$_2$SCH$_3$ | Cl | Me |
| — | 1 (mixt.) | —CH$_2$CH=CH$_2$ | Cl | Me |
| — | 1 (mixt.) | —C(CH$_3$)$_2$CH=CH$_2$ | Cl | Me |
| — | 1 (mixt.) | —CH$_2$C≡CH$_2$ | Cl | Me |
| — | 1 (mixt.) | —CH$_2$C$_6$H$_5$ | Cl | Me |
| — | 1 (mixt.) | —CH$_2$C$_6$H$_4$—Cl-2 | Cl | Me |
| — | 1 (mixt.) | —CH$_2$C$_6$H$_4$—Cl-3 | Cl | Me |
| — | 1 (mixt.) | —CH$_2$C$_6$H$_4$—Cl-4 | Cl | Me |
| — | 1 (mixt.) | —CH$_2$C$_6$H$_4$—Me-2 | Cl | Me |
| — | 1 (mixt.) | —CH$_2$C$_6$H$_4$—Me-3 | Cl | Me |
| — | 1 (mixt.) | —CH$_2$C$_6$H$_4$—Me-4 | Cl | Me |
| — | 1 (mixt.) | —CH$_2$C$_6$H$_4$—OMe-2 | Cl | Me |
| — | 1 (mixt.) | —CH$_2$C$_6$H$_4$—OMe-3 | Cl | Me |
| — | 1 (mixt.) | —CH$_2$C$_6$H$_4$—OMe-4 | Cl | Me |
| — | 1 (mixt.) | —CH$_2$CH$_2$C$_6$H$_5$ | Cl | Me |
| — | 1 (mixt.) | H | Cl | Cl |
| — | 1 (mixt.) | Li | Cl | Cl |
| — | 1 (mixt.) | Na | Cl | Cl |
| — | 1 (mixt.) | K | Cl | Cl |
| — | 1 (mixt.) | ½Mg | Cl | Cl |
| — | 1 (mixt.) | ½Ca | Cl | Cl |

TABLE 3-continued

A compound of the general formula:

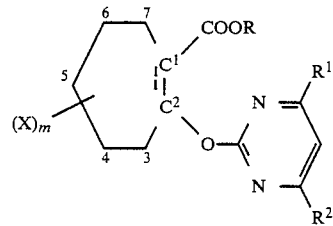

In the below-mentioned table, Me represents methyl group, Et represents ethyl group, Pr represents propyl group, $^i$Pr represents isopropyl group, Bu represents butyl group, $^i$Bu represents isobutyl group, $^s$Bu represents secondary butyl group, $^t$Bu represents tertiary butyl group, cis represents a cis-form, trans represents a trans-form, mix. represents a mixture of a cis-form and a trans-form, 1 represents a single bond and 2 represents a double bond

| $(X)_m$ | — | R | $R^1$ | $R^2$ |
|---|---|---|---|---|
| — | 1 (mixt.) | MeNH$_3$ | Cl | Cl |
| — | 1 (mixt.) | EtNH$_3$ | Cl | Cl |
| — | 1 (mixt.) | PrNH$_3$ | Cl | Cl |
| — | 1 (mixt.) | $^i$PrNH$_3$ | Cl | Cl |
| — | 1 (mixt.) | NH$_2$CONH$_3$ | Cl | Cl |
| — | 1 (mixt.) | Me | Cl | Cl |
| — | 1 (mixt.) | Et | Cl | Cl |
| — | 1 (mixt.) | $^i$Pr | Cl | Cl |
| — | 1 (mixt.) | Pr | Cl | Cl |
| — | 1 (mixt.) | Bu | Cl | Cl |
| — | 1 (mixt.) | $^i$Bu | Cl | Cl |
| — | 1 (mixt.) | $^s$Bu | Cl | Cl |
| — | 1 (mixt.) | $^t$Bu | Cl | Cl |
| — | 1 (mixt.) | —CH$_2$OCH$_3$ | Cl | Cl |
| — | 1 (mixt.) | —CH$_2$CH$_2$OCH$_3$ | Cl | Cl |
| — | 1 (mixt.) | —CH$_2$SCH$_3$ | Cl | Cl |
| — | 1 (mixt.) | —CH$_2$CH=CH$_2$ | Cl | Cl |
| — | 1 (mixt.) | —C(CH$_3$)$_2$CH=CH$_2$ | Cl | Cl |
| — | 1 (mixt.) | —CH$_2$C≡CH$_2$ | Cl | Cl |
| — | 1 (mixt.) | —CH$_2$C$_6$H$_5$ | Cl | Cl |
| — | 1 (mixt.) | —CH$_2$C$_6$H$_4$—Cl-2 | Cl | Cl |
| — | 1 (mixt.) | —CH$_2$C$_6$H$_4$—Cl-3 | Cl | Cl |
| — | 1 (mixt.) | —CH$_2$C$_6$H$_4$—Cl-4 | Cl | Cl |
| — | 1 (mixt.) | —CH$_2$C$_6$H$_4$—Me-2 | Cl | Cl |
| — | 1 (mixt.) | —CH$_2$C$_6$H$_4$—Me-3 | Cl | Cl |
| — | 1 (mixt.) | —CH$_2$C$_6$H$_4$—Me-4 | Cl | Cl |
| — | 1 (mixt.) | —CH$_2$C$_6$H$_4$—OMe-2 | Cl | Cl |
| — | 1 (mixt.) | —CH$_2$C$_6$H$_4$—OMe-3 | Cl | Cl |
| — | 1 (mixt.) | —CH$_2$C$_6$H$_4$—OMe-4 | Cl | Cl |
| — | 1 (mixt.) | —CH$_2$CH$_2$C$_6$H$_5$ | Cl | Cl |
| — | 1 (mixt.) | H | Cl | OMe |
| — | 1 (mixt.) | Li | Cl | OMe |
| — | 1 (mixt.) | Na | Cl | OMe |
| — | 1 (mixt.) | K | Cl | OMe |
| — | 1 (mixt.) | ½Mg | Cl | OMe |
| — | 1 (mixt.) | ½Ca | Cl | OMe |
| — | 1 (mixt.) | MeNH$_3$ | Cl | OMe |
| — | 1 (mixt.) | EtNH$_3$ | Cl | OMe |
| — | 1 (mixt.) | PrNH$_3$ | Cl | OMe |
| — | 1 (mixt.) | $^i$PrNH$_3$ | Cl | OMe |
| — | 1 (mixt.) | NH$_2$CONH$_3$ | Cl | OMe |
| — | 1 (mixt.) | Me | Cl | OMe |
| — | 1 (mixt.) | Et | Cl | OMe |
| — | 1 (mixt.) | $^i$Pr | Cl | OMe |
| — | 1 (mixt.) | Pr | Cl | OMe |
| — | 1 (mixt.) | Bu | Cl | OMe |
| — | 1 (mixt.) | $^i$Bu | Cl | OMe |
| — | 1 (mixt.) | $^s$Bu | Cl | OMe |
| — | 1 (mixt.) | $^t$Bu | Cl | OMe |
| — | 1 (mixt.) | —CH$_2$OCH$_3$ | Cl | OMe |
| — | 1 (mixt.) | —CH$_2$CH$_2$OCH$_3$ | Cl | OMe |
| — | 1 (mixt.) | —CH$_2$SCH$_3$ | Cl | OMe |
| — | 1 (mixt.) | —CH$_2$CH=CH$_2$ | Cl | OMe |
| — | 1 (mixt.) | —C(CH$_3$)$_2$CH=CH$_2$ | Cl | OMe |
| — | 1 (mixt.) | —CH$_2$C≡CH$_2$ | Cl | OMe |
| — | 1 (mixt.) | —CH$_2$C$_6$H$_5$ | Cl | OMe |
| — | 1 (mixt.) | —CH$_2$C$_6$H$_4$—Cl-2 | Cl | OMe |
| — | 1 (mixt.) | —CH$_2$C$_6$H$_4$—Cl-3 | Cl | OMe |

TABLE 3-continued

A compound of the general formula:

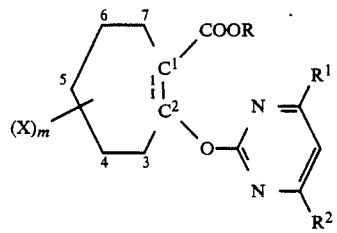

In the below-mentioned table, Me represents methyl group, Et represents ethyl group, Pr represents propyl group, $^{i}$Pr represents isopropyl group, Bu represents butyl group, $^{i}$Bu represents isobutyl group, $^{s}$Bu represents secondary butyl group, $^{t}$Bu represents tertiary butyl group, cis represents a cis-form, trans represents a trans-form, mix. represents a mixture of a cis-form and a trans-form, 1 represents a single bond and 2 represents a double bond

| $(X)_m$ | — | R | $R^1$ | $R^2$ |
|---|---|---|---|---|
| — | 1 (mixt.) | —CH$_2$C$_6$H$_4$—Cl-4 | Cl | OMe |
| — | 1 (mixt.) | —CH$_2$C$_6$H$_4$—Me-2 | Cl | OMe |
| — | 1 (mixt.) | —CH$_2$C$_6$H$_4$—Me-3 | Cl | OMe |
| — | 1 (mixt.) | —CH$_2$C$_6$H$_4$—Me-4 | Cl | OMe |
| — | 1 (mixt.) | —CH$_2$C$_6$H$_4$—OMe-2 | Cl | OMe |
| — | 1 (mixt.) | —CH$_2$C$_6$H$_4$—OMe-3 | Cl | OMe |
| — | 1 (mixt.) | —CH$_2$C$_6$H$_4$—OMe-4 | Cl | OMe |
| — | 1 (mixt.) | —CH$_2$CH$_2$C$_6$H$_5$ | Cl | OMe |
| — | 1 (mixt.) | H | OCHF$_2$ | OMe |
| — | 1 (mixt.) | Li | OCHF$_2$ | OMe |
| — | 1 (mixt.) | Na | OCHF$_2$ | OMe |
| — | 1 (mixt.) | K | OCHF$_2$ | OMe |
| — | 1 (mixt.) | ½Mg | OCHF$_2$ | OMe |
| — | 1 (mixt.) | ½Ca | OCHF$_2$ | OMe |
| — | 1 (mixt.) | MeNH$_3$ | OCHF$_2$ | OMe |
| — | 1 (mixt.) | EtNH$_3$ | OCHF$_2$ | OMe |
| — | 1 (mixt.) | PrNH$_3$ | OCHF$_2$ | OMe |
| — | 1 (mixt.) | $^{i}$PrNH$_3$ | OCHF$_2$ | OMe |
| — | 1 (mixt.) | NH$_2$CONH$_3$ | OCHF$_2$ | OMe |
| — | 1 (mixt.) | Me | OCHF$_2$ | OMe |
| — | 1 (mixt.) | Et | OCHF$_2$ | OMe |
| — | 1 (mixt.) | $^{i}$Pr | OCHF$_2$ | OMe |
| — | 1 (mixt.) | Pr | OCHF$_2$ | OMe |
| — | 1 (mixt.) | Bu | OCHF$_2$ | OMe |
| — | 1 (mixt.) | $^{i}$Bu | OCHF$_2$ | OMe |
| — | 1 (mixt.) | $^{s}$Bu | OCHF$_2$ | OMe |
| — | 1 (mixt.) | $^{t}$Bu | OCHF$_2$ | OMe |
| — | 1 (mixt.) | —CH$_2$OCH$_3$ | OCHF$_2$ | OMe |
| — | 1 (mixt.) | —CH$_2$CH$_2$OCH$_3$ | OCHF$_2$ | OMe |
| — | 1 (mixt.) | —CH$_2$SCH$_3$ | OCHF$_2$ | OMe |
| — | 1 (mixt.) | —CH$_2$CH=CH$_2$ | OCHF$_2$ | OMe |
| — | 1 (mixt.) | —C(CH$_3$)$_2$CH=CH$_2$ | OCHF$_2$ | OMe |
| — | 1 (mixt.) | —CH$_2$C≡CH$_2$ | OCHF$_2$ | OMe |
| — | 1 (mixt.) | —CH$_2$C$_6$H$_5$ | OCHF$_2$ | OMe |
| — | 1 (mixt.) | —CH$_2$C$_6$H$_4$—Cl-2 | OCHF$_2$ | OMe |
| — | 1 (mixt.) | —CH$_2$C$_6$H$_4$—Cl-3 | OCHF$_2$ | OMe |
| — | 1 (mixt.) | —CH$_2$C$_6$H$_4$—Cl-4 | OCHF$_2$ | OMe |
| — | 1 (mixt.) | —CH$_2$C$_6$H$_4$—Me-2 | OCHF$_2$ | OMe |
| — | 1 (mixt.) | —CH$_2$C$_6$H$_4$—Me-3 | OCHF$_2$ | OMe |
| — | 1 (mixt.) | —CH$_2$C$_6$H$_4$—Me-4 | OCHF$_2$ | OMe |
| — | 1 (mixt.) | —CH$_2$C$_6$H$_4$—OMe-2 | OCHF$_2$ | OMe |
| — | 1 (mixt.) | —CH$_2$C$_6$H$_4$—OMe-3 | OCHF$_2$ | OMe |
| — | 1 (mixt.) | —CH$_2$C$_6$H$_4$—OMe-4 | OCHF$_2$ | OMe |
| — | 1 (mixt.) | CH$_2$CH$_2$C$_6$H$_5$ | OCHF$_2$ | OMe |
| — | 1 (mixt.) | H | OCHF$_2$ | OCHF$_2$ |
| — | 1 (mixt.) | Li | OCHF$_2$ | OCHF$_2$ |
| — | 1 (mixt.) | Na | OCHF$_2$ | OCHF$_2$ |
| — | 1 (mixt.) | K | OCHF$_2$ | OCHF$_2$ |
| — | 1 (mixt.) | ½Mg | OCHF$_2$ | OCHF$_2$ |
| — | 1 (mixt.) | ½Ca | OCHF$_2$ | OCHF$_2$ |
| — | 1 (mixt.) | MeNH$_3$ | OCHF$_2$ | OCHF$_2$ |
| — | 1 (mixt.) | EtNH$_3$ | OCHF$_2$ | OCHF$_2$ |
| — | 1 (mixt.) | PrNH$_3$ | OCHF$_2$ | OCHF$_2$ |
| — | 1 (mixt.) | $^{i}$PrNH$_3$ | OCHF$_2$ | OCHF$_2$ |
| — | 1 (mixt.) | NH$_2$CONH$_3$ | OCHF$_2$ | OCHF$_2$ |
| — | 1 (mixt.) | Me | OCHF$_2$ | OCHF$_2$ |
| — | 1 (mixt.) | Et | OCHF$_2$ | OCHF$_2$ |
| — | 1 (mixt.) | $^{i}$Pr | OCHF$_2$ | OCHF$_2$ |

TABLE 3-continued

A compound of the general formula:

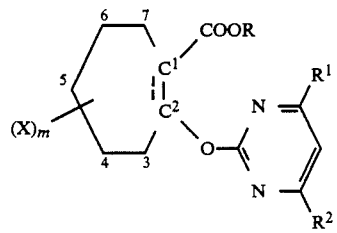

In the below-mentioned table, Me represents methyl group, Et represents ethyl group, Pr represents propyl group, $^{i}$Pr represents isopropyl group, Bu represents butyl group, $^{i}$Bu represents isobutyl group, $^{s}$Bu represents secondary butyl group, $^{t}$Bu represents tertiary butyl group, cis represents a cis-form, trans represents a trans-form, mix. represents a mixture of a cis-form and a trans-form, 1 represents a single bond and 2 represents a double bond

| $(X)_m$ | — | R | $R^1$ | $R^2$ |
|---|---|---|---|---|
| — | 1 (mixt.) | Pr | OCHF$_2$ | OCHF$_2$ |
| — | 1 (mixt.) | Bu | OCHF$_2$ | OCHF$_2$ |
| — | 1 (mixt.) | $^{i}$Bu | OCHF$_2$ | OCHF$_2$ |
| — | 1 (mixt.) | $^{s}$Bu | OCHF$_2$ | OCHF$_2$ |
| — | 1 (mixt.) | $^{t}$Bu | OCHF$_2$ | OCHF$_2$ |
| — | 1 (mixt.) | —CH$_2$OCH$_3$ | OCHF$_2$ | OCHF$_2$ |
| — | 1 (mixt.) | —CH$_2$CH$_2$OCH$_3$ | OCHF$_2$ | OCHF$_2$ |
| — | 1 (mixt.) | —CH$_2$SCH$_3$ | OCHF$_2$ | OCHF$_2$ |
| — | 1 (mixt.) | —CH$_2$CH=CH$_2$ | OCHF$_2$ | OCHF$_2$ |
| — | 1 (mixt.) | —C(CH$_3$)$_2$CH=CH$_2$ | OCHF$_2$ | OCHF$_2$ |
| — | 1 (mixt.) | —CH$_2$C≡CH$_2$ | OCHF$_2$ | OCHF$_2$ |
| — | 1 (mixt.) | —CH$_2$C$_6$H$_5$ | OCHF$_2$ | OCHF$_2$ |
| — | 1 (mixt.) | —CH$_2$C$_6$H$_4$—Cl-2 | OCHF$_2$ | OCHF$_2$ |
| — | 1 (mixt.) | —CH$_2$C$_6$H$_4$—Cl-3 | OCHF$_2$ | OCHF$_2$ |
| — | 1 (mixt.) | —CH$_2$C$_6$H$_4$—Cl-4 | OCHF$_2$ | OCHF$_2$ |
| — | 1 (mixt.) | —CH$_2$C$_6$H$_4$—Me-2 | OCHF$_2$ | OCHF$_2$ |
| — | 1 (mixt.) | —CH$_2$C$_6$H$_4$—Me-3 | OCHF$_2$ | OCHF$_2$ |
| — | 1 (mixt.) | —CH$_2$C$_6$H$_4$—Me-4 | OCHF$_2$ | OCHF$_2$ |
| — | 1 (mixt.) | —CH$_2$C$_6$H$_4$—OMe-2 | OCHF$_2$ | OCHF$_2$ |
| — | 1 (mixt.) | —CH$_2$C$_6$H$_4$—OMe-3 | OCHF$_2$ | OCHF$_2$ |
| — | 1 (mixt.) | —CH$_2$C$_6$H$_4$—OMe-4 | OCHF$_2$ | OCHF$_2$ |
| — | 1 (mixt.) | —CH$_2$CH$_2$C$_6$H$_5$ | OCHF$_2$ | OCHF$_2$ |
| — | 1 (mixt.) | H | SMe | OMe |
| — | 1 (mixt.) | Li | SMe | OMe |
| — | 1 (mixt.) | Na | SMe | OMe |
| — | 1 (mixt.) | K | SMe | OMe |
| — | 1 (mixt.) | ½Mg | SMe | OMe |
| — | 1 (mixt.) | ½Ca | SMe | OMe |
| — | 1 (mixt.) | MeNH$_3$ | SMe | OMe |
| — | 1 (mixt.) | EtNH$_3$ | SMe | OMe |
| — | 1 (mixt.) | PrNH$_3$ | SMe | OMe |
| — | 1 (mixt.) | $^{i}$PrNH$_3$ | SMe | OMe |
| — | 1 (mixt.) | NH$_2$CONH$_3$ | SMe | OMe |
| — | 1 (mixt.) | Me | SMe | OMe |
| — | 1 (mixt.) | Et | SMe | OMe |
| — | 1 (mixt.) | $^{i}$Pr | SMe | OMe |
| — | 1 (mixt.) | Pr | SMe | OMe |
| — | 1 (mixt.) | Bu | SMe | OMe |
| — | 1 (mixt.) | $^{i}$Bu | SMe | OMe |
| — | 1 (mixt.) | $^{s}$Bu | SMe | OMe |
| — | 1 (mixt.) | $^{t}$Bu | SMe | OMe |
| — | 1 (mixt.) | —CH$_2$OCH$_3$ | SMe | OMe |
| — | 1 (mixt.) | —CH$_2$CH$_2$OCH$_3$ | SMe | OMe |
| — | 1 (mixt.) | —CH$_2$SCH$_3$ | SMe | OMe |
| — | 1 (mixt.) | —CH$_2$CH=CH$_2$ | SMe | OMe |
| — | 1 (mixt.) | —C(CH$_3$)$_2$CH=CH$_2$ | SMe | OMe |
| — | 1 (mixt.) | —CH$_2$C≡CH$_2$ | SMe | OMe |
| — | 1 (mixt.) | —CH$_2$C$_6$H$_5$ | SMe | OMe |
| — | 1 (mixt.) | —CH$_2$C$_6$H$_4$—Cl-2 | SMe | OMe |
| — | 1 (mixt.) | —CH$_2$C$_6$H$_4$—Cl-3 | SMe | OMe |
| — | 1 (mixt.) | —CH$_2$C$_6$H$_4$—Cl-4 | SMe | OMe |
| — | 1 (mixt.) | —CH$_2$C$_6$H$_4$—Me-2 | SMe | OMe |
| — | 1 (mixt.) | —CH$_2$C$_6$H$_4$—Me-3 | SMe | OMe |
| — | 1 (mixt.) | —CH$_2$C$_6$H$_4$—Me-4 | SMe | OMe |
| — | 1 (mixt.) | —CH$_2$C$_6$H$_4$—OMe-2 | SMe | OMe |
| — | 1 (mixt.) | —CH$_2$C$_6$H$_4$—OMe-3 | SMe | OMe |
| — | 1 (mixt.) | —CH$_2$C$_6$H$_4$—OMe-4 | SMe | OMe |
| — | 1 (mixt.) | —CH$_2$CH$_2$C$_6$H$_5$ | SMe | OMe |

TABLE 3-continued

A compound of the general formula:

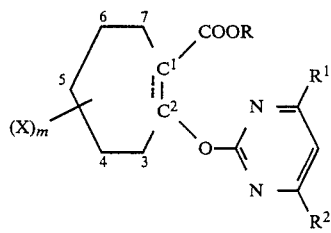

In the below-mentioned table, Me represents methyl group, Et represents ethyl group, Pr represents propyl group, $^i$Pr represents isopropyl group, Bu represents butyl group, $^i$Bu represents isobutyl group, $^s$Bu represents secondary butyl group, $^t$Bu represents tertiary butyl group, cis represents a cis-form, trans represents a trans-form, mix. represents a mixture of a cis-form and a trans-form, 1 represents a single bond and 2 represents a double bond

| $(X)_m$ | — | R | $R^1$ | $R^2$ |
|---|---|---|---|---|
| — | 1 (mixt.) | H | SMe | Me |
| — | 1 (mixt.) | Li | SMe | Me |
| — | 1 (mixt.) | Na | SMe | Me |
| — | 1 (mixt.) | K | SMe | Me |
| — | 1 (mixt.) | ½Mg | SMe | Me |
| — | 1 (mixt.) | ½Ca | SMe | Me |
| — | 1 (mixt.) | MeNH$_3$ | SMe | Me |
| — | 1 (mixt.) | EtNH$_3$ | SMe | Me |
| — | 1 (mixt.) | PrNH$_3$ | SMe | Me |
| — | 1 (mixt.) | $^i$PrNH$_3$ | SMe | Me |
| — | 1 (mixt.) | NH$_2$CONH$_3$ | SMe | Me |
| — | 1 (mixt.) | Me | SMe | Me |
| — | 1 (mixt.) | Et | SMe | Me |
| — | 1 (mixt.) | $^i$Pr | SMe | Me |
| — | 1 (mixt.) | Pr | SMe | Me |
| — | 1 (mixt.) | Bu | SMe | Me |
| — | 1 (mixt.) | $^i$Bu | SMe | Me |
| — | 1 (mixt.) | $^s$Bu | SMe | Me |
| — | 1 (mixt.) | $^t$Bu | SMe | Me |
| — | 1 (mixt.) | —CH$_2$OCH$_3$ | SMe | Me |
| — | 1 (mixt.) | —CH$_2$CH$_2$OCH$_3$ | SMe | Me |
| — | 1 (mixt.) | —CH$_2$SCH$_3$ | SMe | Me |
| — | 1 (mixt.) | —CH$_2$CH=CH$_2$ | SMe | Me |
| — | 1 (mixt.) | —C(CH$_3$)$_2$CH=CH$_2$ | SMe | Me |
| — | 1 (mixt.) | —CH$_2$C≡CH$_2$ | SMe | Me |
| — | 1 (mixt.) | —CH$_2$C$_6$H$_5$ | SMe | Me |
| — | 1 (mixt.) | —CH$_2$C$_6$H$_4$—Cl-2 | SMe | Me |
| — | 1 (mixt.) | —CH$_2$C$_6$H$_4$—Cl-3 | SMe | Me |
| — | 1 (mixt.) | —CH$_2$C$_6$H$_4$—Cl-4 | SMe | Me |
| — | 1 (mixt.) | —CH$_2$C$_6$H$_4$—Me-2 | SMe | Me |
| — | 1 (mixt.) | —CH$_2$C$_6$H$_4$—Me-3 | SMe | Me |
| — | 1 (mixt.) | —CH$_2$C$_6$H$_4$—Me-4 | SMe | Me |
| — | 1 (mixt.) | —CH$_2$C$_6$H$_4$—OMe-2 | SMe | Me |
| — | 1 (mixt.) | —CH$_2$C$_6$H$_4$—OMe-3 | SMe | Me |
| — | 1 (mixt.) | —CH$_2$C$_6$H$_4$—OMe-4 | SMe | Me |
| — | 1 (mixt.) | —CH$_2$CH$_2$C$_6$H$_5$ | SMe | Me |
| — | 2 (—) | H | Me | Me |
| — | 2 (—) | Li | Me | Me |
| — | 2 (—) | Na | Me | Me |
| — | 2 (—) | K | Me | Me |
| — | 2 (—) | ½Mg | Me | Me |
| — | 2 (—) | ½Ca | Me | Me |
| — | 2 (—) | MeNH$_3$ | Me | Me |
| — | 2 (—) | EtNH$_3$ | Me | Me |
| — | 2 (—) | PrNH$_3$ | Me | Me |
| — | 2 (—) | $^i$PrNH$_3$ | Me | Me |
| — | 2 (—) | NH$_2$CONH$_3$ | Me | Me |
| — | 2 (—) | Me | Me | Me |
| — | 2 (—) | Et | Me | Me |
| — | 2 (—) | $^i$Pr | Me | Me |
| — | 2 (—) | Pr | Me | Me |
| — | 2 (—) | Bu | Me | Me |
| — | 2 (—) | $^i$Bu | Me | Me |
| — | 2 (—) | $^s$Bu | Me | Me |
| — | 2 (—) | $^t$Bu | Me | Me |
| — | 2 (—) | —CH$_2$OCH$_3$ | Me | Me |
| — | 2 (—) | —CH$_2$CH$_2$OCH$_3$ | Me | Me |
| — | 2 (—) | —CH$_2$SCH$_3$ | Me | Me |
| — | 2 (—) | —CH$_2$CH=CH$_2$ | Me | Me |
| — | 2 (—) | —C(CH$_3$)$_2$CH=CH$_2$ | Me | Me |
| — | 2 (—) | —CH$_2$C≡CH$_2$ | Me | Me |
| — | 2 (—) | —CH$_2$C$_6$H$_5$ | Me | Me |
| — | 2 (—) | —CH$_2$C$_6$H$_4$—Cl-2 | Me | Me |
| — | 2 (—) | —CH$_2$C$_6$H$_4$—Cl-3 | Me | Me |
| — | 2 (—) | —CH$_2$C$_6$H$_4$—Cl-4 | Me | Me |
| — | 2 (—) | —CH$_2$C$_6$H$_4$—Me-2 | Me | Me |
| — | 2 (—) | —CH$_2$C$_6$H$_4$—Me-3 | Me | Me |
| — | 2 (—) | —CH$_2$C$_6$H$_4$—Me-4 | Me | Me |
| — | 2 (—) | —CH$_2$C$_6$H$_4$—OMe-2 | Me | Me |
| — | 2 (—) | —CH$_2$C$_6$H$_4$—OMe-3 | Me | Me |
| — | 2 (—) | —CH$_2$C$_6$H$_4$—OMe-4 | Me | Me |
| — | 2 (—) | —CH$_2$CH$_2$C$_6$H$_5$ | Me | Me |
| — | 2 (—) | H | OMe | Me |
| — | 2 (—) | Li | OMe | Me |
| — | 2 (—) | Na | OMe | Me |
| — | 2 (—) | K | OMe | Me |
| — | 2 (—) | ½Mg | OMe | Me |
| — | 2 (—) | ½Ca | OMe | Me |
| — | 2 (—) | MeNH$_3$ | OMe | Me |
| — | 2 (—) | EtNH$_3$ | OMe | Me |
| — | 2 (—) | PrNH$_3$ | OMe | Me |
| — | 2 (—) | $^i$PrNH$_3$ | OMe | Me |
| — | 2 (—) | NH$_2$CONH$_3$ | OMe | Me |
| — | 2 (—) | Me | OMe | Me |
| — | 2 (—) | Et | OMe | Me |
| — | 2 (—) | $^i$Pr | OMe | Me |
| — | 2 (—) | Pr | OMe | Me |
| — | 2 (—) | Bu | OMe | Me |
| — | 2 (—) | $^i$Bu | OMe | Me |
| — | 2 (—) | $^s$Bu | OMe | Me |
| — | 2 (—) | $^t$Bu | OMe | Me |
| — | 2 (—) | —CH$_2$OCH$_3$ | OMe | Me |
| — | 2 (—) | —CH$_2$CH$_2$OCH$_3$ | OMe | Me |
| — | 2 (—) | —CH$_2$SCH$_3$ | OMe | Me |
| — | 2 (—) | —CH$_2$CH=CH$_2$ | OMe | Me |
| — | 2 (—) | —C(CH$_3$)$_2$CH=CH$_2$ | OMe | Me |
| — | 2 (—) | —CH$_2$C≡CH$_2$ | OMe | Me |
| — | 2 (—) | —CH$_2$C$_6$H$_5$ | OMe | Me |
| — | 2 (—) | —CH$_2$C$_6$H$_4$—Cl-2 | OMe | Me |
| — | 2 (—) | —CH$_2$C$_6$H$_4$—Cl-3 | OMe | Me |
| — | 2 (—) | —CH$_2$C$_6$H$_4$—Cl-4 | OMe | Me |
| — | 2 (—) | —CH$_2$C$_6$H$_4$—Me-2 | OMe | Me |
| — | 2 (—) | —CH$_2$C$_6$H$_4$—Me-3 | OMe | Me |
| — | 2 (—) | —CH$_2$C$_6$H$_4$—Me-4 | OMe | Me |
| — | 2 (—) | —CH$_2$C$_6$H$_4$—OMe-2 | OMe | Me |
| — | 2 (—) | —CH$_2$C$_6$H$_4$—OMe-3 | OMe | Me |
| — | 2 (—) | —CH$_2$C$_6$H$_4$—OMe-4 | OMe | Me |
| — | 2 (—) | —CH$_2$CH$_2$C$_6$H$_5$ | OMe | Me |
| — | 2 (—) | H | OMe | OMe |
| — | 2 (—) | Li | OMe | OMe |
| — | 2 (—) | Na | OMe | OMe |
| — | 2 (—) | K | OMe | OMe |
| — | 2 (—) | ½Mg | OMe | OMe |
| — | 2 (—) | ½Ca | OMe | OMe |
| — | 2 (—) | MeNH$_3$ | OMe | OMe |
| — | 2 (—) | EtNH$_3$ | OMe | OMe |

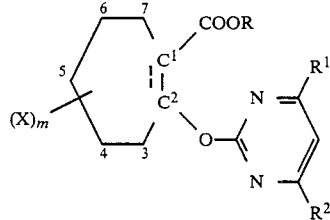

TABLE 3-continued

A compound of the general formula:

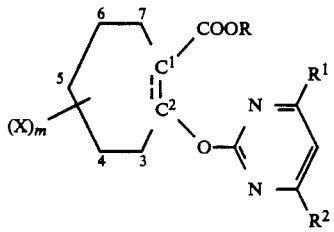

In the below-mentioned table, Me represents methyl group, Et represents ethyl group, Pr represents propyl group, $^i$Pr represents isopropyl group, Bu represents butyl group, $^i$Bu represents isobutyl group, $^s$Bu represents secondary butyl group, $^t$Bu represents tertiary butyl group, cis represents a cis-form, trans represents a trans-form, mix. represents a mixture of a cis-form and a trans-form, 1 represents a single bond and 2 represents a double bond

| $(X)_m$ | — | R | $R^1$ | $R^2$ |
|---|---|---|---|---|
| — | 2 (—) | PrNH$_3$ | OMe | OMe |
| — | 2 (—) | $^i$PrNH$_3$ | OMe | OMe |
| — | 2 (—) | NH$_2$CONH$_3$ | OMe | OMe |
| — | 2 (—) | Me | OMe | OMe |
| — | 2 (—) | Et | OMe | OMe |
| — | 2 (—) | $^i$Pr | OMe | OMe |
| — | 2 (—) | Pr | OMe | OMe |
| — | 2 (—) | Bu | OMe | OMe |
| — | 2 (—) | $^i$Bu | OMe | OMe |
| — | 2 (—) | $^s$Bu | OMe | OMe |
| — | 2 (—) | $^t$Bu | OMe | OMe |
| — | 2 (—) | —CH$_2$OCH$_3$ | OMe | OMe |
| — | 2 (—) | —CH$_2$CH$_2$OCH$_3$ | OMe | OMe |
| — | 2 (—) | —CH$_2$SCH$_3$ | OMe | OMe |
| — | 2 (—) | —CH$_2$CH=CH$_2$ | OMe | OMe |
| — | 2 (—) | —C(CH$_3$)$_2$CH=CH$_2$ | OMe | OMe |
| — | 2 (—) | —CH$_2$C≡CH | OMe | OMe |
| — | 2 (—) | —CH$_2$C$_6$H$_5$ | OMe | OMe |
| — | 2 (—) | —CH$_2$C$_6$H$_4$—Cl-2 | OMe | OMe |
| — | 2 (—) | —CH$_2$C$_6$H$_4$—Cl-3 | OMe | OMe |
| — | 2 (—) | —CH$_2$C$_6$H$_4$—Cl-4 | OMe | OMe |
| — | 2 (—) | —CH$_2$C$_6$H$_4$—Me-2 | OMe | OMe |
| — | 2 (—) | —CH$_2$C$_6$H$_4$—Me-3 | OMe | OMe |
| — | 2 (—) | —CH$_2$C$_6$H$_4$—Me-4 | OMe | OMe |
| — | 2 (—) | —CH$_2$C$_6$H$_4$—OMe-2 | OMe | OMe |
| — | 2 (—) | —CH$_2$C$_6$H$_4$—OMe-3 | OMe | OMe |
| — | 2 (—) | —CH$_2$C$_6$H$_4$—OMe-4 | OMe | OMe |
| — | 2 (—) | —CH$_2$CH$_2$C$_6$H$_5$ | OMe | OMe |
| — | 2 (—) | H | Cl | Me |
| — | 2 (—) | Li | Cl | Me |
| — | 2 (—) | Na | Cl | Me |
| — | 2 (—) | K | Cl | Me |
| — | 2 (—) | ½Mg | Cl | Me |
| — | 2 (—) | ½Ca | Cl | Me |
| — | 2 (—) | MeNH$_3$ | Cl | Me |
| — | 2 (—) | EtNH$_3$ | Cl | Me |
| — | 2 (—) | PrNH$_3$ | Cl | Me |
| — | 2 (—) | $^i$PrNH$_3$ | Cl | Me |
| — | 2 (—) | NH$_2$CONH$_3$ | Cl | Me |
| — | 2 (—) | Me | Cl | Me |
| — | 2 (—) | Et | Cl | Me |
| — | 2 (—) | $^i$Pr | Cl | Me |
| — | 2 (—) | Pr | Cl | Me |
| — | 2 (—) | Bu | Cl | Me |
| — | 2 (—) | $^i$Bu | Cl | Me |
| — | 2 (—) | $^s$Bu | Cl | Me |
| — | 2 (—) | $^t$Bu | Cl | Me |
| — | 2 (—) | —CH$_2$OCH$_3$ | Cl | Me |
| — | 2 (—) | —CH$_2$CH$_2$OCH$_3$ | Cl | Me |
| — | 2 (—) | —CH$_2$SCH$_3$ | Cl | Me |
| — | 2 (—) | —CH$_2$CH=CH$_2$ | Cl | Me |
| — | 2 (—) | —C(CH$_3$)$_2$CH=CH$_2$ | Cl | Me |
| — | 2 (—) | —CH$_2$C≡CH | Cl | Me |
| — | 2 (—) | —CH$_2$C$_6$H$_5$ | Cl | Me |
| — | 2 (—) | —CH$_2$C$_6$H$_4$—Cl-2 | Cl | Me |
| — | 2 (—) | —CH$_2$C$_6$H$_4$—Cl-3 | Cl | Me |
| — | 2 (—) | —CH$_2$C$_6$H$_4$—Cl-4 | Cl | Me |
| — | 2 (—) | —CH$_2$C$_6$H$_4$—Me-2 | Cl | Me |
| — | 2 (—) | —CH$_2$C$_6$H$_4$—Me-3 | Cl | Me |
| — | 2 (—) | —CH$_2$C$_6$H$_4$—Me-4 | Cl | Me |
| — | 2 (—) | —CH$_2$C$_6$H$_4$—OMe-2 | Cl | Me |
| — | 2 (—) | —CH$_2$C$_6$H$_4$—OMe-3 | Cl | Me |
| — | 2 (—) | —CH$_2$C$_6$H$_4$—OMe-4 | Cl | Me |
| — | 2 (—) | —CH$_2$C$_6$H$_5$ | Cl | Me |
| — | 2 (—) | H | Cl | Cl |
| — | 2 (—) | Li | Cl | Cl |
| — | 2 (—) | Na | Cl | Cl |
| — | 2 (—) | K | Cl | Cl |
| — | 2 (—) | ½Mg | Cl | Cl |
| — | 2 (—) | ½Ca | Cl | Cl |
| — | 2 (—) | MeNH$_3$ | Cl | Cl |
| — | 2 (—) | EtNH$_3$ | Cl | Cl |
| — | 2 (—) | PrNH$_3$ | Cl | Cl |
| — | 2 (—) | $^i$PrNH$_3$ | Cl | Cl |
| — | 2 (—) | NH$_2$CONH$_3$ | Cl | Cl |
| — | 2 (—) | Me | Cl | Cl |
| — | 2 (—) | Et | Cl | Cl |
| — | 2 (—) | $^i$Pr | Cl | Cl |
| — | 2 (—) | Pr | Cl | Cl |
| — | 2 (—) | Bu | Cl | Cl |
| — | 2 (—) | $^i$Bu | Cl | Cl |
| — | 2 (—) | $^s$Bu | Cl | Cl |
| — | 2 (—) | $^t$Bu | Cl | Cl |
| — | 2 (—) | —CH$_2$OCH$_3$ | Cl | Cl |
| — | 2 (—) | —CH$_2$CH$_2$OCH$_3$ | Cl | Cl |
| — | 2 (—) | —CH$_2$SCH$_3$ | Cl | Cl |
| — | 2 (—) | —CH$_2$CH=CH$_2$ | Cl | Cl |
| — | 2 (—) | —C(CH$_3$)$_2$CH=CH$_2$ | Cl | Cl |
| — | 2 (—) | —CH$_2$C≡CH | Cl | Cl |
| — | 2 (—) | —CH$_2$C$_6$H$_5$ | Cl | Cl |
| — | 2 (—) | —CH$_2$C$_6$H$_4$—Cl-2 | Cl | Cl |
| — | 2 (—) | —CH$_2$C$_6$H$_4$—Cl-3 | Cl | Cl |
| — | 2 (—) | —CH$_2$C$_6$H$_4$—Cl-4 | Cl | Cl |
| — | 2 (—) | —CH$_2$C$_6$H$_4$—Me-2 | Cl | Cl |
| — | 2 (—) | —CH$_2$C$_6$H$_4$—Me-3 | Cl | Cl |
| — | 2 (—) | —CH$_2$C$_6$H$_4$—Me-4 | Cl | Cl |
| — | 2 (—) | —CH$_2$C$_6$H$_4$—OMe-2 | Cl | Cl |
| — | 2 (—) | —CH$_2$C$_6$H$_4$—OMe-3 | Cl | Cl |
| — | 2 (—) | —CH$_2$C$_6$H$_4$—OMe-4 | Cl | Cl |
| — | 2 (—) | —CH$_2$CH$_2$C$_6$H$_5$ | Cl | Cl |
| — | 2 (—) | H | Cl | OMe |
| — | 2 (—) | Li | Cl | OMe |
| — | 2 (—) | Na | Cl | OMe |
| — | 2 (—) | K | Cl | OMe |
| — | 2 (—) | ½Mg | Cl | OMe |
| — | 2 (—) | ½Ca | Cl | OMe |
| — | 2 (—) | MeNH$_3$ | Cl | OMe |
| — | 2 (—) | EtNH$_3$ | Cl | OMe |
| — | 2 (—) | PrNH$_3$ | Cl | OMe |
| — | 2 (—) | $^i$PrNH$_3$ | Cl | OMe |
| — | 2 (—) | NH$_2$CONH$_3$ | Cl | OMe |
| — | 2 (—) | Me | Cl | OMe |
| — | 2 (—) | Et | Cl | OMe |
| — | 2 (—) | $^i$Pr | Cl | OMe |
| — | 2 (—) | Pr | Cl | OMe |
| — | 2 (—) | Bu | Cl | OMe |

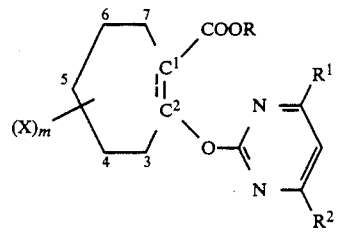

TABLE 3-continued

A compound of the general formula:

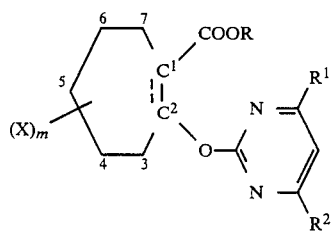

In the below-mentioned table, Me represents methyl group, Et represents ethyl group, Pr represents propyl group, $^iPr$ represents isopropyl group, Bu represents butyl group, $^iBu$ represents isobutyl group, $^sBu$ represents secondary butyl group, $^tBu$ represents tertiary butyl group, cis represents a cis-form, trans represents a trans-form, mix. represents a mixture of a cis-form and a trans-form, 1 represents a single bond and 2 represents a double bond

| $(X)_m$ | — | R | $R^1$ | $R^2$ |
|---|---|---|---|---|
| — | 2 (—) | $^iBu$ | Cl | OMe |
| — | 2 (—) | $^sBu$ | Cl | OMe |
| — | 2 (—) | $^tBu$ | Cl | OMe |
| — | 2 (—) | —CH$_2$OCH$_3$ | Cl | OMe |
| — | 2 (—) | —CH$_2$CH$_2$OCH$_3$ | Cl | OMe |
| — | 2 (—) | —CH$_2$SCH$_3$ | Cl | OMe |
| — | 2 (—) | —CH$_2$CH=CH$_2$ | Cl | OMe |
| — | 2 (—) | —C(CH$_3$)$_2$CH=CH$_2$ | Cl | OMe |
| — | 2 (—) | —CH$_2$C≡CH$_2$ | Cl | OMe |
| — | 2 (—) | —CH$_2$C$_6$H$_5$ | Cl | OMe |
| — | 2 (—) | —CH$_2$C$_6$H$_4$—Cl-2 | Cl | OMe |
| — | 2 (—) | —CH$_2$C$_6$H$_4$—Cl-3 | Cl | OMe |
| — | 2 (—) | —CH$_2$C$_6$H$_4$—Cl-4 | Cl | OMe |
| — | 2 (—) | —CH$_2$C$_6$H$_4$—Me-2 | Cl | OMe |
| — | 2 (—) | —CH$_2$C$_6$H$_4$—Me-3 | Cl | OMe |
| — | 2 (—) | —CH$_2$C$_6$H$_4$—Me-4 | Cl | OMe |
| — | 2 (—) | —CH$_2$C$_6$H$_4$—OMe-2 | Cl | OMe |
| — | 2 (—) | —CH$_2$C$_6$H$_4$—OMe-3 | Cl | OMe |
| — | 2 (—) | —CH$_2$C$_6$H$_4$—OMe-4 | Cl | OMe |
| — | 2 (—) | —CH$_2$CH$_2$C$_6$H$_5$ | Cl | OMe |
| — | 2 (—) | H | OCHF$_2$ | OMe |
| — | 2 (—) | Li | OCHF$_2$ | OMe |
| — | 2 (—) | Na | OCHF$_2$ | OMe |
| — | 2 (—) | K | OCHF$_2$ | OMe |
| — | 2 (—) | ½Mg | OCHF$_2$ | OMe |
| — | 2 (—) | ½Ca | OCHF$_2$ | OMe |
| — | 2 (—) | MeNH$_3$ | OCHF$_2$ | OMe |
| — | 2 (—) | EtNH$_3$ | OCHF$_2$ | OMe |
| — | 2 (—) | PrNH$_3$ | OCHF$_2$ | OMe |
| — | 2 (—) | $^iPrNH_3$ | OCHF$_2$ | OMe |
| — | 2 (—) | NH$_2$CONH$_3$ | OCHF$_2$ | OMe |
| — | 2 (—) | Me | OCHF$_2$ | OMe |
| — | 2 (—) | Et | OCHF$_2$ | OMe |
| — | 2 (—) | $^iPr$ | OCHF$_2$ | OMe |
| — | 2 (—) | Pr | OCHF$_2$ | OMe |
| — | 2 (—) | Bu | OCHF$_2$ | OMe |
| — | 2 (—) | $^iBu$ | OCHF$_2$ | OMe |
| — | 2 (—) | $^sBu$ | OCHF$_2$ | OMe |
| — | 2 (—) | $^tBu$ | OCHF$_2$ | OMe |
| — | 2 (—) | —CH$_2$OCH$_3$ | OCHF$_2$ | OMe |
| — | 2 (—) | —CH$_2$CH$_2$OCH$_3$ | OCHF$_2$ | OMe |
| — | 2 (—) | —CH$_2$SCH$_3$ | OCHF$_2$ | OMe |
| — | 2 (—) | —CH$_2$CH=CH$_2$ | OCHF$_2$ | OMe |
| — | 2 (—) | —C(CH$_3$)$_2$CH=CH$_2$ | OCHF$_2$ | OMe |
| — | 2 (—) | —CH$_2$C≡CH$_2$ | OCHF$_2$ | OMe |
| — | 2 (—) | —CH$_2$C$_6$H$_5$ | OCHF$_2$ | OMe |
| — | 2 (—) | —CH$_2$C$_6$H$_4$—Cl-2 | OCHF$_2$ | OMe |
| — | 2 (—) | —CH$_2$C$_6$H$_4$—Cl-3 | OCHF$_2$ | OMe |
| — | 2 (—) | —CH$_2$C$_6$H$_4$—Cl-4 | OCHF$_2$ | OMe |
| — | 2 (—) | —CH$_2$C$_6$H$_4$—Me-2 | OCHF$_2$ | OMe |
| — | 2 (—) | —CH$_2$C$_6$H$_4$—Me-3 | OCHF$_2$ | OMe |
| — | 2 (—) | —CH$_2$C$_6$H$_4$—Me-4 | OCHF$_2$ | OMe |
| — | 2 (—) | —CH$_2$C$_6$H$_4$—OMe-2 | OCHF$_2$ | OMe |
| — | 2 (—) | —CH$_2$C$_6$H$_4$—OMe-3 | OCHF$_2$ | OMe |
| — | 2 (—) | —CH$_2$C$_6$H$_4$—OMe-4 | OCHF$_2$ | OMe |
| — | 2 (—) | —CH$_2$CH$_2$C$_6$H$_5$ | OCHF$_2$ | OMe |
| — | 2 (—) | H | OCHF$_2$ | OCHF$_2$ |
| — | 2 (—) | Li | OCHF$_2$ | OCHF$_2$ |
| — | 2 (—) | Na | OCHF$_2$ | OCHF$_2$ |
| — | 2 (—) | K | OCHF$_2$ | OCHF$_2$ |
| — | 2 (—) | ½Mg | OCHF$_2$ | OCHF$_2$ |
| — | 2 (—) | ½Ca | OCHF$_2$ | OCHF$_2$ |
| — | 2 (—) | MeNH$_3$ | OCHF$_2$ | OCHF$_2$ |
| — | 2 (—) | EtNH$_3$ | OCHF$_2$ | OCHF$_2$ |
| — | 2 (—) | PrNH$_3$ | OCHF$_2$ | OCHF$_2$ |
| — | 2 (—) | $^iPrNH_3$ | OCHF$_2$ | OCHF$_2$ |
| — | 2 (—) | NH$_2$CONH$_3$ | OCHF$_2$ | OCHF$_2$ |
| — | 2 (—) | Me | OCHF$_2$ | OCHF$_2$ |
| — | 2 (—) | Et | OCHF$_2$ | OCHF$_2$ |
| — | 2 (—) | $^iPr$ | OCHF$_2$ | OCHF$_2$ |
| — | 2 (—) | Pr | OCHF$_2$ | OCHF$_2$ |
| — | 2 (—) | Bu | OCHF$_2$ | OCHF$_2$ |
| — | 2 (—) | $^iBu$ | OCHF$_2$ | OCHF$_2$ |
| — | 2 (—) | $^sBu$ | OCHF$_2$ | OCHF$_2$ |
| — | 2 (—) | $^tBu$ | OCHF$_2$ | OCHF$_2$ |
| — | 2 (—) | —CH$_2$OCH$_3$ | OCHF$_2$ | OCHF$_2$ |
| — | 2 (—) | —CH$_2$CH$_2$OCH$_3$ | OCHF$_2$ | OCHF$_2$ |
| — | 2 (—) | —CH$_2$SCH$_3$ | OCHF$_2$ | OCHF$_2$ |
| — | 2 (—) | —CH$_2$CH=CH$_2$ | OCHF$_2$ | OCHF$_2$ |
| — | 2 (—) | —C(CH$_3$)$_2$CH=CH$_2$ | OCHF$_2$ | OCHF$_2$ |
| — | 2 (—) | —CH$_2$C≡CH$_2$ | OCHF$_2$ | OCHF$_2$ |
| — | 2 (—) | —CH$_2$C$_6$H$_5$ | OCHF$_2$ | OCHF$_2$ |
| — | 2 (—) | —CH$_2$C$_6$H$_4$—Cl-2 | OCHF$_2$ | OCHF$_2$ |
| — | 2 (—) | —CH$_2$C$_6$H$_4$—Cl-3 | OCHF$_2$ | OCHF$_2$ |
| — | 2 (—) | —CH$_2$C$_6$H$_4$—Cl-4 | OCHF$_2$ | OCHF$_2$ |
| — | 2 (—) | —CH$_2$C$_6$H$_4$—Me-2 | OCHF$_2$ | OCHF$_2$ |
| — | 2 (—) | —CH$_2$C$_6$H$_4$—Me-3 | OCHF$_2$ | OCHF$_2$ |
| — | 2 (—) | —CH$_2$C$_6$H$_4$—Me-4 | OCHF$_2$ | OCHF$_2$ |
| — | 2 (—) | —CH$_2$C$_6$H$_4$—OMe-2 | OCHF$_2$ | OCHF$_2$ |
| — | 2 (—) | —CH$_2$C$_6$H$_4$—OMe-3 | OCHF$_2$ | OCHF$_2$ |
| — | 2 (—) | —CH$_2$C$_6$H$_4$—OMe-4 | OCHF$_2$ | OCHF$_2$ |
| — | 2 (—) | —CH$_2$CH$_2$C$_6$H$_5$ | OCHF$_2$ | OCHF$_2$ |
| — | 2 (—) | H | SMe | OMe |
| — | 2 (—) | Li | SMe | OMe |
| — | 2 (—) | Na | SMe | OMe |
| — | 2 (—) | K | SMe | OMe |
| — | 2 (—) | ½Mg | SMe | OMe |
| — | 2 (—) | ½Ca | SMe | OMe |
| — | 2 (—) | MeNH$_3$ | SMe | OMe |
| — | 2 (—) | EtNH$_3$ | SMe | OMe |
| — | 2 (—) | PrNH$_3$ | SMe | OMe |
| — | 2 (—) | $^iPrNH_3$ | SMe | OMe |
| — | 2 (—) | NH$_2$CONH$_3$ | SMe | OMe |
| — | 2 (—) | Me | SMe | OMe |
| — | 2 (—) | Et | SMe | OMe |
| — | 2 (—) | $^iPr$ | SMe | OMe |
| — | 2 (—) | Pr | SMe | OMe |
| — | 2 (—) | Bu | SMe | OMe |
| — | 2 (—) | $^iBu$ | SMe | OMe |
| — | 2 (—) | $^sBu$ | SMe | OMe |
| — | 2 (—) | $^tBu$ | SMe | OMe |
| — | 2 (—) | —CH$_2$OCH$_3$ | SMe | OMe |
| — | 2 (—) | —CH$_2$CH$_2$OCH$_3$ | SMe | OMe |
| — | 2 (—) | —CH$_2$SCH$_3$ | SMe | OMe |
| — | 2 (—) | —CH$_2$CH=CH$_2$ | SMe | OMe |
| — | 2 (—) | —C(CH$_3$)$_2$CH=CH$_2$ | SMe | OMe |

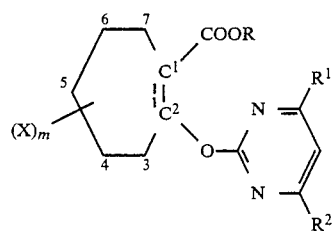

TABLE 3-continued

A compound of the general formula:

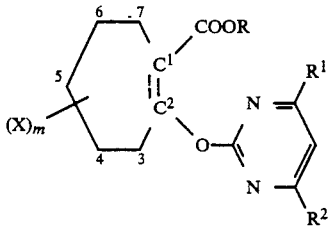 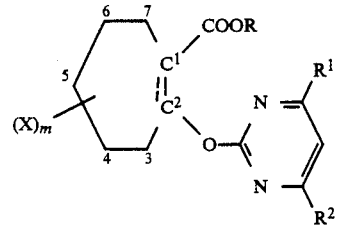

In the below-mentioned table, Me represents methyl group, Et represents ethyl group, Pr represents propyl group, $^i$Pr represents isopropyl group, Bu represents butyl group, $^i$Bu represents isobutyl group, $^s$Bu represents secondary butyl group, $^t$Bu represents tertiary butyl group, cis represents a cis-form, trans represents a trans-form, mix. represents a mixture of a cis-form and a trans-form, 1 represents a single bond and 2 represents a double bond

| $(X)_m$ | — | R | $R^1$ | $R^2$ |
|---|---|---|---|---|
| — | 2 (—) | —CH$_2$C≡CH$_2$ | SMe | OMe |
| — | 2 (—) | —CH$_2$C$_6$H$_5$ | SMe | OMe |
| — | 2 (—) | —CH$_2$C$_6$H$_4$—Cl-2 | SMe | OMe |
| — | 2 (—) | —CH$_2$C$_6$H$_4$—Cl-3 | SMe | OMe |
| — | 2 (—) | —CH$_2$C$_6$H$_4$—Cl-4 | SMe | OMe |
| — | 2 (—) | —CH$_2$C$_6$H$_4$—Me-2 | SMe | OMe |
| — | 2 (—) | —CH$_2$C$_6$H$_4$—Me-3 | SMe | OMe |
| — | 2 (—) | —CH$_2$C$_6$H$_4$—Me-4 | SMe | OMe |
| — | 2 (—) | —CH$_2$C$_6$H$_4$—OMe-2 | SMe | OMe |
| — | 2 (—) | —CH$_2$C$_6$H$_4$—OMe-3 | SMe | OMe |
| — | 2 (—) | —CH$_2$C$_6$H$_4$—OMe-4 | SMe | OMe |
| — | 2 (—) | —CH$_2$CH$_2$C$_6$H$_5$ | SMe | OMe |
| — | 2 (—) | H | SMe | Me |
| — | 2 (—) | Li | SMe | Me |
| — | 2 (—) | Na | SMe | Me |
| — | 2 (—) | K | SMe | Me |
| — | 2 (—) | ½Mg | SMe | Me |
| — | 2 (—) | ½Ca | SMe | Me |
| — | 2 (—) | MeNH$_3$ | SMe | Me |
| — | 2 (—) | EtNH$_3$ | SMe | Me |
| — | 2 (—) | PrNH$_3$ | SMe | Me |
| — | 2 (—) | $^i$PrNH$_3$ | SMe | Me |
| — | 2 (—) | NH$_2$CONH$_3$ | SMe | Me |
| — | 2 (—) | Me | SMe | Me |
| — | 2 (—) | Et | SMe | Me |
| — | 2 (—) | $^i$Pr | SMe | Me |
| — | 2 (—) | Pr | SMe | Me |
| — | 2 (—) | Bu | SMe | Me |
| — | 2 (—) | $^i$Bu | SMe | Me |
| — | 2 (—) | $^s$Bu | SMe | Me |
| — | 2 (—) | $^t$Bu | SMe | Me |
| — | 2 (—) | —CH$_2$OCH$_3$ | SMe | Me |
| — | 2 (—) | —CH$_2$CH$_2$OCH$_3$ | SMe | Me |
| — | 2 (—) | —CH$_2$SCH$_3$ | SMe | Me |
| — | 2 (—) | —CH$_2$CH=CH$_2$ | SMe | Me |
| — | 2 (—) | —C(CH$_3$)$_2$CH=CH$_2$ | SMe | Me |
| — | 2 (—) | —CH$_2$C≡CH$_2$ | SMe | Me |
| — | 2 (—) | —CH$_2$C$_6$H$_5$ | SMe | Me |
| — | 2 (—) | —CH$_2$C$_6$H$_4$—Cl-2 | SMe | Me |
| — | 2 (—) | —CH$_2$C$_6$H$_4$—Cl-3 | SMe | Me |
| — | 2 (—) | —CH$_2$C$_6$H$_4$—Cl-4 | SMe | Me |
| — | 2 (—) | —CH$_2$C$_6$H$_4$—Me-2 | SMe | Me |
| — | 2 (—) | —CH$_2$C$_6$H$_4$—Me-3 | SMe | Me |
| — | 2 (—) | —CH$_2$C$_6$H$_4$—Me-4 | SMe | Me |
| — | 2 (—) | —CH$_2$C$_6$H$_4$—OMe-2 | SMe | Me |
| — | 2 (—) | —CH$_2$C$_6$H$_4$—OMe-3 | SMe | Me |
| — | 2 (—) | —CH$_2$C$_6$H$_4$—OMe-4 | SMe | Me |
| — | 2 (—) | —CH$_2$CH$_2$C$_6$H$_5$ | SMe | Me |
| 5.5-(Me)$_2$ | 1 (cis) | H | OMe | OMe |
| 5.5-(Me)$_2$ | 1 (cis) | Na | OMe | OMe |
| 5.5-(Me)$_2$ | 1 (cis) | ½Ca | OMe | OMe |
| 5.5-(Me)$_2$ | 1 (cis) | $^i$PrNH$_3$ | OMe | OMe |
| 5.5-(Me)$_2$ | 1 (cis) | NH$_2$CONH$_3$ | OMe | OMe |
| 5.5-(Me)$_2$ | 1 (cis) | Me | OMe | OMe |
| 5.5-(Me)$_2$ | 1 (cis) | Et | OMe | OMe |
| 5.5-(Me)$_2$ | 1 (cis) | $^i$Pr | OMe | OMe |
| 5.5-(Me)$_2$ | 1 (cis) | Pr | OMe | OMe |
| 5.5-(Me)$_2$ | 1 (cis) | Bu | OMe | OMe |
| 5.5-(Me)$_2$ | 1 (cis) | $^i$Bu | OMe | OMe |
| 5.5-(Me)$_2$ | 1 (cis) | $^s$Bu | OMe | OMe |
| 5.5-(Me)$_2$ | 1 (cis) | —CH$_2$OCH$_3$ | OMe | OMe |
| 5.5-(Me)$_2$ | 1 (cis) | —CH$_2$CH$_2$OCH$_3$ | OMe | OMe |
| 5.5-(Me)$_2$ | 1 (cis) | —CH$_2$SCH$_3$ | OMe | OMe |
| 5.5-(Me)$_2$ | 1 (cis) | —CH$_2$CH=CH$_2$ | OMe | OMe |
| 5.5-(Me)$_2$ | 1 (cis) | —C(CH$_3$)$_2$CH=CH$_2$ | OMe | OMe |
| 5.5-(Me)$_2$ | 1 (cis) | —CH$_2$C≡CH$_2$ | OMe | OMe |
| 5.5-(Me)$_2$ | 1 (cis) | —CH$_2$C$_6$H$_5$ | OMe | OMe |
| 5.5-(Me)$_2$ | 1 (cis) | —CH$_2$C$_6$H$_4$—Cl-2 | OMe | OMe |
| 5.5-(Me)$_2$ | 1 (cis) | —CH$_2$C$_6$H$_4$—Cl-3 | OMe | OMe |
| 5.5-(Me)$_2$ | 1 (cis) | —CH$_2$C$_6$H$_4$—Cl-4 | OMe | OMe |
| 5.5-(Me)$_2$ | 1 (cis) | —CH$_2$C$_6$H$_4$—Me-2 | OMe | OMe |
| 5.5-(Me)$_2$ | 1 (cis) | —CH$_2$C$_6$H$_4$—Me-3 | OMe | OMe |
| 5.5-(Me)$_2$ | 1 (cis) | —CH$_2$C$_6$H$_4$—Me-4 | OMe | OMe |
| 5.5-(Me)$_2$ | 1 (cis) | —CH$_2$C$_6$H$_4$—OMe-2 | OMe | OMe |
| 5.5-(Me)$_2$ | 1 (cis) | —CH$_2$C$_6$H$_4$—OMe-3 | OMe | OMe |
| 5.5-(Me)$_2$ | 1 (cis) | —CH$_2$C$_6$H$_4$—OMe-4 | OMe | OMe |
| 5.5-(Me)$_2$ | 1 (cis) | —CH$_2$CH$_2$C$_6$H$_5$ | OMe | OMe |
| 5.5-(Me)$_2$ | 1 (trans) | H | OMe | OMe |
| 5.5-(Me)$_2$ | 1 (trans) | Na | OMe | OMe |
| 5.5-(Me)$_2$ | 1 (trans) | ½Ca | OMe | OMe |
| 5.5-(Me)$_2$ | 1 (trans) | $^i$PrNH$_3$ | OMe | OMe |
| 5.5-(Me)$_2$ | 1 (trans) | NH$_2$CONH$_3$ | OMe | OMe |
| 5.5-(Me)$_2$ | 1 (trans) | Me | OMe | OMe |
| 5.5-(Me)$_2$ | 1 (trans) | Et | OMe | OMe |
| 5.5-(Me)$_2$ | 1 (trans) | $^i$Pr | OMe | OMe |
| 5.5-(Me)$_2$ | 1 (trans) | Pr | OMe | OMe |
| 5.5-(Me)$_2$ | 1 (trans) | Bu | OMe | OMe |
| 5.5-(Me)$_2$ | 1 (trans) | $^i$Bu | OMe | OMe |
| 5.5-(Me)$_2$ | 1 (trans) | $^s$Bu | OMe | OMe |
| 5.5-(Me)$_2$ | 1 (trans) | —CH$_2$OCH$_3$ | OMe | OMe |
| 5.5-(Me)$_2$ | 1 (trans) | —CH$_2$CH$_2$OCH$_3$ | OMe | OMe |
| 5.5-(Me)$_2$ | 1 (trans) | —CH$_2$SCH$_3$ | OMe | OMe |
| 5.5-(Me)$_2$ | 1 (trans) | —CH$_2$CH=CH$_2$ | OMe | OMe |
| 5.5-(Me)$_2$ | 1 (trans) | —C(CH$_3$)$_2$CH=CH$_2$ | OMe | OMe |
| 5.5-(Me)$_2$ | 1 (trans) | —CH$_2$C≡CH$_2$ | OMe | OMe |
| 5.5-(Me)$_2$ | 1 (trans) | —CH$_2$C$_6$H$_5$ | OMe | OMe |
| 5.5-(Me)$_2$ | 1 (trans) | —CH$_2$C$_6$H$_4$—Cl-2 | OMe | OMe |
| 5.5-(Me)$_2$ | 1 (trans) | —CH$_2$C$_6$H$_4$—Cl-3 | OMe | OMe |
| 5.5-(Me)$_2$ | 1 (trans) | —CH$_2$C$_6$H$_4$—Cl-4 | OMe | OMe |
| 5.5-(Me)$_2$ | 1 (trans) | —CH$_2$C$_6$H$_4$—Me-2 | OMe | OMe |
| 5.5-(Me)$_2$ | 1 (trans) | —CH$_2$C$_6$H$_4$—Me-3 | OMe | OMe |
| 5.5-(Me)$_2$ | 1 (trans) | —CH$_2$C$_6$H$_4$—Me-4 | OMe | OMe |
| 5.5-(Me)$_2$ | 1 (trans) | —CH$_2$C$_6$H$_4$—OMe-2 | OMe | OMe |
| 5.5-(Me)$_2$ | 1 (trans) | —CH$_2$C$_6$H$_4$—OMe-3 | OMe | OMe |
| 5.5-(Me)$_2$ | 1 (trans) | —CH$_2$C$_6$H$_4$—OMe-4 | OMe | OMe |
| 5.5-(Me)$_2$ | 1 (trans) | —CH$_2$CH$_2$C$_6$H$_5$ | OMe | OMe |
| 5.5-(Me)$_2$ | 1 (mixt.) | H | OMe | OMe |
| 5.5-(Me)$_2$ | 1 (mixt.) | Na | OMe | OMe |
| 5.5-(Me)$_2$ | 1 (mixt.) | ½Ca | OMe | OMe |
| 5.5-(Me)$_2$ | 1 (mixt.) | $^i$PrNH$_3$ | OMe | OMe |
| 5.5-(Me)$_2$ | 1 (mixt.) | NH$_2$CONH$_3$ | OMe | OMe |
| 5.5-(Me)$_2$ | 1 (mixt.) | Me | OMe | OMe |
| 5.5-(Me)$_2$ | 1 (mixt.) | Et | OMe | OMe |
| 5.5-(Me)$_2$ | 1 (mixt.) | $^i$Pr | OMe | OMe |
| 5.5-(Me)$_2$ | 1 (mixt.) | Pr | OMe | OMe |
| 5.5-(Me)$_2$ | 1 (mixt.) | Bu | OMe | OMe |

TABLE 3-continued

A compound of the general formula:

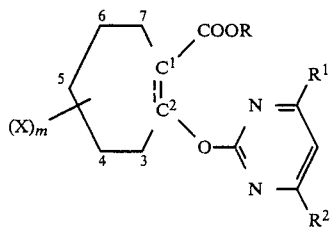

In the below-mentioned table, Me represents methyl group, Et represents ethyl group, Pr represents propyl group, $^i$Pr represents isopropyl group, Bu represents butyl group, $^i$Bu represents isobutyl group, $^s$Bu represents secondary butyl group, $^t$Bu represents tertiary butyl group, cis represents a cis-form, trans represents a trans-form, mix. represents a mixture of a cis-form and a trans-form, 1 represents a single bond and 2 represents a double bond

| (X)$_m$ | — | R | R$^1$ | R$^2$ |
|---|---|---|---|---|
| 5.5-(Me)$_2$ | 1 (mixt.) | $^i$Bu | OMe | OMe |
| 5.5-(Me)$_2$ | 1 (mixt.) | $^s$Bu | OMe | OMe |
| 5.5-(Me)$_2$ | 1 (mixt.) | —CH$_2$OCH$_3$ | OMe | OMe |
| 5.5-(Me)$_2$ | 1 (mixt.) | —CH$_2$CH$_2$OCH$_3$ | OMe | OMe |
| 5.5-(Me)$_2$ | 1 (mixt.) | —CH$_2$SCH$_3$ | OMe | OMe |
| 5.5-(Me)$_2$ | 1 (mixt.) | —CH$_2$CH=CH$_2$ | OMe | OMe |
| 5.5-(Me)$_2$ | 1 (mixt.) | —C(CH$_3$)$_2$CH=CH$_2$ | OMe | OMe |
| 5.5-(Me)$_2$ | 1 (mixt.) | —CH$_2$C≡CH$_2$ | OMe | OMe |
| 5.5-(Me)$_2$ | 1 (mixt.) | —CH$_2$C$_6$H$_5$ | OMe | OMe |
| 5.5-(Me)$_2$ | 1 (mixt.) | —CH$_2$C$_6$H$_4$—Cl-2 | OMe | OMe |
| 5.5-(Me)$_2$ | 1 (mixt.) | —CH$_2$C$_6$H$_4$—Cl-3 | OMe | OMe |
| 5.5-(Me)$_2$ | 1 (mixt.) | —CH$_2$C$_6$H$_4$—Cl-4 | OMe | OMe |
| 5.5-(Me)$_2$ | 1 (mixt.) | —CH$_2$C$_6$H$_4$—Me-2 | OMe | OMe |
| 5.5-(Me)$_2$ | 1 (mixt.) | —CH$_2$C$_6$H$_4$—Me-3 | OMe | OMe |
| 5.5-(Me)$_2$ | 1 (mixt.) | —CH$_2$C$_6$H$_4$—Me-4 | OMe | OMe |
| 5.5-(Me)$_2$ | 1 (mixt.) | —CH$_2$C$_6$H$_4$—OMe-2 | OMe | OMe |
| 5.5-(Me)$_2$ | 1 (mixt.) | —CH$_2$C$_6$H$_4$—OMe-3 | OMe | OMe |
| 5.5-(Me)$_2$ | 1 (mixt.) | —CH$_2$C$_6$H$_4$—OMe-4 | OMe | OMe |
| 5.5-(Me)$_2$ | 1 (mixt.) | —CH$_2$CH$_2$C$_6$H$_5$ | OMe | OMe |
| 5.5-(Me)$_2$ | 2 (—) | H | OMe | OMe |
| 5.5-(Me)$_2$ | 2 (—) | Na | OMe | OMe |
| 5.5-(Me)$_2$ | 2 (—) | ½Ca | OMe | OMe |
| 5.5-(Me)$_2$ | 2 (—) | $^i$PrNH$_3$ | OMe | OMe |
| 5.5-(Me)$_2$ | 2 (—) | NH$_2$CONH$_3$ | OMe | OMe |
| 5.5-(Me)$_2$ | 2 (—) | Me | OMe | OMe |
| 5.5-(Me)$_2$ | 2 (—) | Et | OMe | OMe |
| 5.5-(Me)$_2$ | 2 (—) | $^i$Pr | OMe | OMe |
| 5.5-(Me)$_2$ | 2 (—) | Pr | OMe | OMe |
| 5.5-(Me)$_2$ | 2 (—) | Bu | OMe | OMe |
| 5.5-(Me)$_2$ | 2 (—) | $^i$Bu | OMe | OMe |
| 5.5-(Me)$_2$ | 2 (—) | $^s$Bu | OMe | OMe |
| 5.5-(Me)$_2$ | 2 (—) | —CH$_2$OCH$_3$ | OMe | OMe |
| 5.5-(Me)$_2$ | 2 (—) | —CH$_2$CH$_2$OCH$_3$ | OMe | OMe |
| 5.5-(Me)$_2$ | 2 (—) | —CH$_2$SCH$_3$ | OMe | OMe |
| 5.5-(Me)$_2$ | 2 (—) | —CH$_2$CH=CH$_2$ | OMe | OMe |
| 5.5-(Me)$_2$ | 2 (—) | —C(CH$_3$)$_2$CH=CH$_2$ | OMe | OMe |
| 5.5-(Me)$_2$ | 2 (—) | —CH$_2$C≡CH$_2$ | OMe | OMe |
| 5.5-(Me)$_2$ | 2 (—) | —CH$_2$C$_6$H$_5$ | OMe | OMe |
| 5.5-(Me)$_2$ | 2 (—) | —CH$_2$C$_6$H$_4$—Cl-2 | OMe | OMe |
| 5.5-(Me)$_2$ | 2 (—) | —CH$_2$C$_6$H$_4$—Cl-3 | OMe | OMe |
| 5.5-(Me)$_2$ | 2 (—) | —CH$_2$C$_6$H$_4$—Cl-4 | OMe | OMe |
| 5.5-(Me)$_2$ | 2 (—) | —CH$_2$C$_6$H$_4$—Me-2 | OMe | OMe |
| 5.5-(Me)$_2$ | 2 (—) | —CH$_2$C$_6$H$_4$—Me-3 | OMe | OMe |
| 5.5-(Me)$_2$ | 2 (—) | —CH$_2$C$_6$H$_4$—Me-4 | OMe | OMe |
| 5.5-(Me)$_2$ | 2 (—) | —CH$_2$C$_6$H$_4$—OMe-2 | OMe | OMe |
| 5.5-(Me)$_2$ | 2 (—) | —CH$_2$C$_6$H$_4$—OMe-3 | OMe | OMe |
| 5.5-(Me)$_2$ | 2 (—) | —CH$_2$C$_6$H$_4$—OMe-4 | OMe | OMe |
| 5.5-(Me)$_2$ | 2 (—) | —CH$_2$CH$_2$C$_6$H$_5$ | OMe | OMe |
| 3.7-(Me)$_2$ | 1 (cis) | H | OMe | OMe |
| 3.7-(Me)$_2$ | 1 (cis) | Na | OMe | OMe |
| 3.7-(Me)$_2$ | 1 (cis) | ½Ca | OMe | OMe |
| 3.7-(Me)$_2$ | 1 (cis) | $^i$PrNH$_3$ | OMe | OMe |
| 3.7-(Me)$_2$ | 1 (cis) | NH$_2$CONH$_3$ | OMe | OMe |
| 3.7-(Me)$_2$ | 1 (cis) | Me | OMe | OMe |
| 3.7-(Me)$_2$ | 1 (cis) | Et | OMe | OMe |
| 3.7-(Me)$_2$ | 1 (cis) | $^i$Pr | OMe | OMe |
| 3.7-(Me)$_2$ | 1 (cis) | Pr | OMe | OMe |
| 3.7-(Me)$_2$ | 1 (cis) | Bu | OMe | OMe |
| 3.7-(Me)$_2$ | 1 (cis) | $^i$Bu | OMe | OMe |
| 3.7-(Me)$_2$ | 1 (cis) | $^s$Bu | OMe | OMe |
| 3.7-(Me)$_2$ | 1 (cis) | —CH$_2$OCH$_3$ | OMe | OMe |
| 3.7-(Me)$_2$ | 1 (cis) | —CH$_2$CH$_2$OCH$_3$ | OMe | OMe |
| 3.7-(Me)$_2$ | 1 (cis) | —CH$_2$SCH$_3$ | OMe | OMe |
| 3.7-(Me)$_2$ | 1 (cis) | —CH$_2$CH=CH$_2$ | OMe | OMe |
| 3.7-(Me)$_2$ | 1 (cis) | —C(CH$_3$)$_2$CH=CH$_2$ | OMe | OMe |
| 3.7-(Me)$_2$ | 1 (cis) | —CH$_2$C≡CH$_2$ | OMe | OMe |
| 3.7-(Me)$_2$ | 1 (cis) | —CH$_2$C$_6$H$_5$ | OMe | OMe |
| 3.7-(Me)$_2$ | 1 (cis) | —CH$_2$C$_6$H$_4$—Cl-2 | OMe | OMe |
| 3.7-(Me)$_2$ | 1 (cis) | —CH$_2$C$_6$H$_4$—Cl-3 | OMe | OMe |
| 3.7-(Me)$_2$ | 1 (cis) | —CH$_2$C$_6$H$_4$—Cl-4 | OMe | OMe |
| 3.7-(Me)$_2$ | 1 (cis) | —CH$_2$C$_6$H$_4$—Me-2 | OMe | OMe |
| 3.7-(Me)$_2$ | 1 (cis) | —CH$_2$C$_6$H$_4$—Me-3 | OMe | OMe |
| 3.7-(Me)$_2$ | 1 (cis) | —CH$_2$C$_6$H$_4$—Me-4 | OMe | OMe |
| 3.7-(Me)$_2$ | 1 (cis) | —CH$_2$C$_6$H$_4$—OMe-2 | OMe | OMe |
| 3.7-(Me)$_2$ | 1 (cis) | —CH$_2$C$_6$H$_4$—OMe-3 | OMe | OMe |
| 3.7-(Me)$_2$ | 1 (cis) | —CH$_2$C$_6$H$_4$—OMe-4 | OMe | OMe |
| 3.7-(Me)$_2$ | 1 (cis) | —CH$_2$CH$_2$C$_6$H$_5$ | OMe | OMe |
| 3.7-(Me)$_2$ | 1 (trans) | H | OMe | OMe |
| 3.7-(Me)$_2$ | 1 (trans) | Na | OMe | OMe |
| 3.7-(Me)$_2$ | 1 (trans) | ½Ca | OMe | OMe |
| 3.7-(Me)$_2$ | 1 (trans) | $^i$PrNH$_3$ | OMe | OMe |
| 3.7-(Me)$_2$ | 1 (trans) | NH$_2$CONH$_3$ | OMe | OMe |
| 3.7-(Me)$_2$ | 1 (trans) | Me | OMe | OMe |
| 3.7-(Me)$_2$ | 1 (trans) | Et | OMe | OMe |
| 3.7-(Me)$_2$ | 1 (trans) | $^i$Pr | OMe | OMe |
| 3.7-(Me)$_2$ | 1 (trans) | Pr | OMe | OMe |
| 3.7-(Me)$_2$ | 1 (trans) | Bu | OMe | OMe |
| 3.7-(Me)$_2$ | 1 (trans) | $^i$Bu | OMe | OMe |
| 3.7-(Me)$_2$ | 1 (trans) | $^s$Bu | OMe | OMe |
| 3.7-(Me)$_2$ | 1 (trans) | —CH$_2$OCH$_3$ | OMe | OMe |
| 3.7-(Me)$_2$ | 1 (trans) | —CH$_2$CH$_2$OCH$_3$ | OMe | OMe |
| 3.7-(Me)$_2$ | 1 (trans) | —CH$_2$SCH$_3$ | OMe | OMe |
| 3.7-(Me)$_2$ | 1 (trans) | —CH$_2$CH=CH$_2$ | OMe | OMe |
| 3.7-(Me)$_2$ | 1 (trans) | —C(CH$_3$)$_2$CH=CH$_2$ | OMe | OMe |
| 3.7-(Me)$_2$ | 1 (trans) | —CH$_2$C≡CH$_2$ | OMe | OMe |
| 3.7-(Me)$_2$ | 1 (trans) | —CH$_2$C$_6$H$_5$ | OMe | OMe |
| 3.7-(Me)$_2$ | 1 (trans) | —CH$_2$C$_6$H$_4$—Cl-2 | OMe | OMe |
| 3.7-(Me)$_2$ | 1 (trans) | —CH$_2$C$_6$H$_4$—Cl-3 | OMe | OMe |
| 3.7-(Me)$_2$ | 1 (trans) | —CH$_2$C$_6$H$_4$—Cl-4 | OMe | OMe |
| 3.7-(Me)$_2$ | 1 (trans) | —CH$_2$C$_6$H$_4$—Me-2 | OMe | OMe |
| 3.7-(Me)$_2$ | 1 (trans) | —CH$_2$C$_6$H$_4$—Me-3 | OMe | OMe |
| 3.7-(Me)$_2$ | 1 (trans) | —CH$_2$C$_6$H$_4$—Me-4 | OMe | OMe |
| 3.7-(Me)$_2$ | 1 (trans) | —CH$_2$C$_6$H$_4$—OMe-2 | OMe | OMe |
| 3.7-(Me)$_2$ | 1 (trans) | —CH$_2$C$_6$H$_4$—OMe-3 | OMe | OMe |
| 3.7-(Me)$_2$ | 1 (trans) | —CH$_2$C$_6$H$_4$—OMe-4 | OMe | OMe |
| 3.7-(Me)$_2$ | 1 (trans) | —CH$_2$CH$_2$C$_6$H$_5$ | OMe | OMe |
| 3.7-(Me)$_2$ | 1 (mixt.) | H | OMe | OMe |
| 3.7-(Me)$_2$ | 1 (mixt.) | Na | OMe | OMe |
| 3.7-(Me)$_2$ | 1 (mixt.) | ½Ca | OMe | OMe |
| 3.7-(Me)$_2$ | 1 (mixt.) | $^i$PrNH$_3$ | OMe | OMe |
| 3.7-(Me)$_2$ | 1 (mixt.) | NH$_2$CONH$_3$ | OMe | OMe |
| 3.7-(Me)$_2$ | 1 (mixt.) | Me | OMe | OMe |
| 3.7-(Me)$_2$ | 1 (mixt.) | Et | OMe | OMe |
| 3.7-(Me)$_2$ | 1 (mixt.) | $^i$Pr | OMe | OMe |
| 3.7-(Me)$_2$ | 1 (mixt.) | Pr | OMe | OMe |
| 3.7-(Me)$_2$ | 1 (mixt.) | Bu | OMe | OMe |

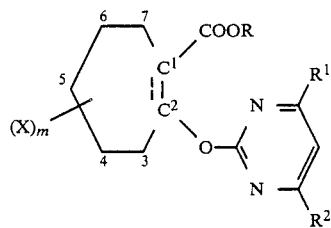

TABLE 3-continued

A compound of the general formula:

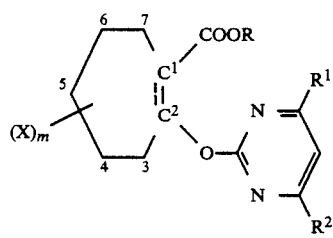

In the below-mentioned table, Me represents methyl group, Et represents ethyl group, Pr represents propyl group, $^i$Pr represents isopropyl group, Bu represents butyl group, $^i$Bu represents isobutyl group, $^s$Bu represents secondary butyl group, $^t$Bu represents tertiary butyl group, cis represents a cis-form, trans represents a trans-form, mix. represents a mixture of a cis-form and a trans-form, 1 represents a single bond and 2 represents a double bond

| (X)$_m$ | — | R | R$^1$ | R$^2$ |
|---|---|---|---|---|
| 3.7-(Me)$_2$ | 1 (mixt.) | $^i$Bu | OMe | OMe |
| 3.7-(Me)$_2$ | 1 (mixt.) | $^s$Bu | OMe | OMe |
| 3.7-(Me)$_2$ | 1 (mixt.) | —CH$_2$OCH$_3$ | OMe | OMe |
| 3.7-(Me)$_2$ | 1 (mixt.) | —CH$_2$CH$_2$OCH$_3$ | OMe | OMe |
| 3.7-(Me)$_2$ | 1 (mixt.) | —CH$_2$SCH$_3$ | OMe | OMe |
| 3.7-(Me)$_2$ | 1 (mixt.) | —CH$_2$CH=CH$_2$ | OMe | OMe |
| 3.7-(Me)$_2$ | 1 (mixt.) | —C(CH$_3$)$_2$CH=CH$_2$ | OMe | OMe |
| 3.7-(Me)$_2$ | 1 (mixt.) | —CH$_2$C≡CH$_2$ | OMe | OMe |
| 3.7-(Me)$_2$ | 1 (mixt.) | —CH$_2$C$_6$H$_5$ | OMe | OMe |
| 3.7-(Me)$_2$ | 1 (mixt.) | —CH$_2$C$_6$H$_4$—Cl-2 | OMe | OMe |
| 3.7-(Me)$_2$ | 1 (mixt.) | —CH$_2$C$_6$H$_4$—Cl-3 | OMe | OMe |
| 3.7-(Me)$_2$ | 1 (mixt.) | —CH$_2$C$_6$H$_4$—Cl-4 | OMe | OMe |
| 3.7-(Me)$_2$ | 1 (mixt.) | —CH$_2$C$_6$H$_4$—Me-2 | OMe | OMe |
| 3.7-(Me)$_2$ | 1 (mixt.) | —CH$_2$C$_6$H$_4$—Me-3 | OMe | OMe |
| 3.7-(Me)$_2$ | 1 (mixt.) | —CH$_2$C$_6$H$_4$—Me-4 | OMe | OMe |
| 3.7-(Me)$_2$ | 1 (mixt.) | —CH$_2$C$_6$H$_4$—OMe-2 | OMe | OMe |
| 3.7-(Me)$_2$ | 1 (mixt.) | —CH$_2$C$_6$H$_4$—OMe-3 | OMe | OMe |
| 3.7-(Me)$_2$ | 1 (mixt.) | —CH$_2$C$_6$H$_4$—OMe-4 | OMe | OMe |
| 3.7-(Me)$_2$ | 1 (mixt.) | —CH$_2$CH$_2$C$_6$H$_5$ | OMe | OMe |
| 3.7-(Me)$_2$ | 2 (—) | H | OMe | OMe |
| 3.7-(Me)$_2$ | 2 (—) | Na | OMe | OMe |
| 3.7-(Me)$_2$ | 2 (—) | ½Ca | OMe | OMe |
| 3.7-(Me)$_2$ | 2 (—) | $^i$PrNH$_3$ | OMe | OMe |
| 3.7-(Me)$_2$ | 2 (—) | NH$_2$CONH$_3$ | OMe | OMe |
| 3.7-(Me)$_2$ | 2 (—) | Me | OMe | OMe |
| 3.7-(Me)$_2$ | 2 (—) | Et | OMe | OMe |
| 3.7-(Me)$_2$ | 2 (—) | $^i$Pr | OMe | OMe |
| 3.7-(Me)$_2$ | 2 (—) | Pr | OMe | OMe |
| 3.7-(Me)$_2$ | 2 (—) | Bu | OMe | OMe |
| 3.7-(Me)$_2$ | 2 (—) | $^i$Bu | OMe | OMe |
| 3.7-(Me)$_2$ | 2 (—) | $^s$Bu | OMe | OMe |
| 3.7-(Me)$_2$ | 2 (—) | —CH$_2$OCH$_3$ | OMe | OMe |
| 3.7-(Me)$_2$ | 2 (—) | —CH$_2$CH$_2$OCH$_3$ | OMe | OMe |
| 3.7-(Me)$_2$ | 2 (—) | —CH$_2$SCH$_3$ | OMe | OMe |
| 3.7-(Me)$_2$ | 2 (—) | —CH$_2$CH=CH$_2$ | OMe | OMe |
| 3.7-(Me)$_2$ | 2 (—) | —C(CH$_3$)$_2$CH=CH$_2$ | OMe | OMe |
| 3.7-(Me)$_2$ | 2 (—) | —CH$_2$C≡CH$_2$ | OMe | OMe |
| 3.7-(Me)$_2$ | 2 (—) | —CH$_2$C$_6$H$_5$ | OMe | OMe |
| 3.7-(Me)$_2$ | 2 (—) | —CH$_2$C$_6$H$_4$—Cl-2 | OMe | OMe |
| 3.7-(Me)$_2$ | 2 (—) | —CH$_2$C$_6$H$_4$—Cl-3 | OMe | OMe |
| 3.7-(Me)$_2$ | 2 (—) | —CH$_2$C$_6$H$_4$—Cl-4 | OMe | OMe |
| 3.7-(Me)$_2$ | 2 (—) | —CH$_2$C$_6$H$_4$—Me-2 | OMe | OMe |
| 3.7-(Me)$_2$ | 2 (—) | —CH$_2$C$_6$H$_4$—Me-3 | OMe | OMe |
| 3.7-(Me)$_2$ | 2 (—) | —CH$_2$C$_6$H$_4$—Me-4 | OMe | OMe |
| 3.7-(Me)$_2$ | 2 (—) | —CH$_2$C$_6$H$_4$—OMe-2 | OMe | OMe |
| 3.7-(Me)$_2$ | 2 (—) | —CH$_2$C$_6$H$_4$—OMe-3 | OMe | OMe |
| 3.7-(Me)$_2$ | 2 (—) | —CH$_2$C$_6$H$_4$—OMe-4 | OMe | OMe |
| 3.7-(Me)$_2$ | 2 (—) | —CH$_2$CH$_2$C$_6$H$_5$ | OMe | OMe |

TABLE 4

A compound of the general formula:

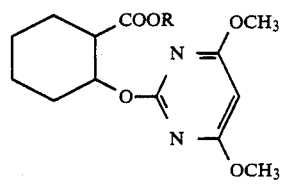

| R | | |
|---|---|---|
| H | cis | (+) |
| H | cis | (−) |
| H | trans | (+) |
| H | trans | (−) |
| Li | cis | (+) |
| Li | cis | (−) |
| Li | trans | (+) |
| Li | trans | (−) |
| Na | cis | (+) |
| Na | cis | (−) |
| Na | trans | (+) |
| Na | trans | (−) |
| K | cis | (+) |
| K | cis | (−) |
| K | trans | (+) |
| K | trans | (−) |
| ½Mg | cis | (+) |
| ½Mg | cis | (−) |
| ½Mg | trans | (+) |
| ½Mg | trans | (−) |
| NH$_4$ | cis | (±) |
| NH$_4$ | cis | (+) |
| NH$_4$ | cis | (−) |
| NH$_4$ | mixt. | |
| NH$_4$ | trans | (±) |
| NH$_4$ | trans | (+) |
| NH$_4$ | trans | (−) |
| MeNH$_3$ | cis | (+) |
| MeNH$_3$ | cis | (−) |
| MeNH$_3$ | trans | (+) |
| MeNH$_3$ | trans | (−) |
| $^i$PrNH$_3$ | cis | (+) |
| $^i$PrNH$_3$ | cis | (−) |
| $^i$PrNH$_3$ | trans | (+) |
| $^i$PrNH$_3$ | trans | (−) |
| Me | cis | (+) |
| Me | cis | (−) |
| Me | trans | (+) |
| Et | cis | (+) |
| Et | cis | (−) |
| Et | trans | (+) |
| Et | trans | (−) |
| $^i$Pr | cis | (+) |
| $^i$Pr | cis | (−) |
| $^i$Pr | trans | (+) |
| $^i$Pr | trans | (−) |
| —CH$_2$OMe | cis | (+) |
| —CH$_2$OMe | cis | (−) |
| —CH$_2$OMe | trans | (+) |
| —CH$_2$OMe | trans | (−) |
| —CH$_2$SMe | cis | (+) |
| —CH$_2$SMe | cis | (−) |
| —CH$_2$SMe | trans | (+) |
| —CH$_2$SMe | trans | (−) |
| —CH$_2$CH=CH$_2$ | cis | (+) |
| —CH$_2$CH=CH$_2$ | cis | (−) |
| —CH$_2$CH=CH$_2$ | trans | (+) |
| —CH$_2$CH=CH$_2$ | trans | (−) |
| —CH$_2$C≡CH | cis | (+) |
| —CH$_2$C≡CH | cis | (−) |
| —CH$_2$C≡CH | trans | (+) |
| —CH$_2$C≡CH | trans | (−) |
| —CH$_2$C$_6$H$_5$ | cis | (+) |
| —CH$_2$C$_6$H$_5$ | cis | (−) |
| —CH$_2$C$_6$H$_5$ | trans | (+) |
| —CH$_2$C$_6$H$_5$ | trans | (−) |
| —CH$_2$C$_6$H$_4$—Cl-2 | cis | (+) |
| —CH$_2$C$_6$H$_4$—Cl-2 | cis | (−) |
| —CH$_2$C$_6$H$_4$—Cl-2 | trans | (+) |
| —CH$_2$C$_6$H$_4$—Cl-2 | trans | (−) |

TABLE 4-continued

A compound of the general formula:

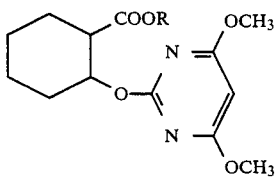

| R | | |
|---|---|---|
| —CH₂C₆H₄—Cl-3 | cis | (+) |
| —CH₂C₆H₄—Cl-3 | cis | (−) |
| —CH₂C₆H₄—Cl-3 | trans | (+) |
| —CH₂C₆H₄—Cl-3 | trans | (−) |
| —CH₂C₆H₄—Cl-4 | cis | (+) |
| —CH₂C₆H₄—Cl-4 | cis | (−) |
| —CH₂C₆H₄—Cl-4 | trans | (+) |
| —CH₂C₆H₄—Cl-4 | trans | (−) |
| —CH₂C₆H₄—Me-2 | cis | (+) |
| —CH₂C₆H₄—Me-2 | cis | (−) |
| —CH₂C₆H₄—Me-2 | trans | (+) |
| —CH₂C₆H₄—Me-2 | trans | (−) |
| —CH₂C₆H₄—Me-3 | cis | (+) |
| —CH₂C₆H₄—Me-3 | cis | (−) |
| —CH₂C₆H₄—Me-3 | trans | (+) |
| —CH₂C₆H₄—Me-3 | trans | (−) |
| —CH₂C₆H₄—Me-4 | cis | (+) |
| —CH₂C₆H₄—Me-4 | cis | (−) |
| —CH₂C₆H₄—Me-4 | trans | (+) |
| —CH₂C₆H₄—Me-4 | trans | (−) |
| —CH₂C₆H₄—OMe-2 | cis | (+) |
| —CH₂C₆H₄—OMe-2 | cis | (−) |
| —CH₂C₆H₄—OMe-2 | trans | (+) |
| —CH₂C₆H₄—OMe-2 | trans | (−) |
| —CH₂C₆H₄—OMe-3 | cis | (+) |
| —CH₂C₆H₄—OMe-3 | cis | (−) |
| —CH₂C₆H₄—OMe-3 | trans | (+) |
| —CH₂C₆H₄—OMe-3 | trans | (−) |
| —CH₂C₆H₄—OMe-4 | cis | (+) |
| —CH₂C₆H₄—OMe-4 | cis | (−) |
| —CH₂C₆H₄—OMe-4 | trans | (+) |
| —CH₂C₆H₄—OMe-4 | trans | (−) |
| —CH₂CH₂C₆H₅ | cis | (+) |
| —CH₂CH₂C₆H₅ | cis | (−) |
| —CH₂CH₂C₆H₅ | trans | (+) |
| —CH₂CH₂C₆H₅ | trans | (−) |

In the aforementioned Table 4, (±) represents non optical isomer, (+) represents dextro-rotatory optical isomer and (−) represents levo-rotatory optical isomer.
cis represents a cis-form, trans represents a trans-form and mix. represents a mixture of a cis-form and a trans-form.
Me represents methyl group, Et represents ethyl group and ⁱPr represents isopropyl group.

TABLE 5

A compound of the general formula:

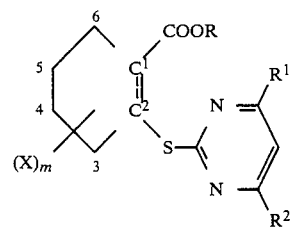

In the below-mentioned table, Me represents methyl group, Et represents ethyl group, Pr represents propyl group, ⁱPr represents isopropyl group, Bu represents butyl group, ⁱBu represents isobutyl group, ˢBu represents secondary butyl group, ᵗBu represents tertiary butyl group, cis represents a cis-form, trans represents a trans-form, mix. represents a mixture of a cis-form and a trans-form, 1 represents a single bond and 2 represents a double bond.

| (X)ₘ | === | R | R¹ | R² |
|---|---|---|---|---|
| — | 1 (cis) | H | Me | Me |
| — | 1 (cis) | Li | Me | Me |
| — | 1 (cis) | Na | Me | Me |
| — | 1 (cis) | K | Me | Me |
| — | 1 (cis) | ½Mg | Me | Me |
| — | 1 (cis) | ½Ca | Me | Me |
| — | 1 (cis) | MeNH₃ | Me | Me |
| — | 1 (cis) | EtNH₃ | Me | Me |
| — | 1 (cis) | PrNH₃ | Me | Me |
| — | 1 (cis) | ⁱPrNH₃ | Me | Me |
| — | 1 (cis) | NH₂CONH₃ | Me | Me |
| — | 1 (cis) | Me | Me | Me |
| — | 1 (cis) | Et | Me | Me |
| — | 1 (cis) | ⁱPr | Me | Me |
| — | 1 (cis) | Pr | Me | Me |
| — | 1 (cis) | Bu | Me | Me |
| — | 1 (cis) | ⁱBu | Me | Me |
| — | 1 (cis) | ˢBu | Me | Me |
| — | 1 (cis) | ᵗBu | Me | Me |
| — | 1 (cis) | —CH₂OCH₃ | Me | Me |
| — | 1 (cis) | —CH₂CH₂OCH₃ | Me | Me |
| — | 1 (cis) | —CH₂SCH₃ | Me | Me |
| — | 1 (cis) | —CH₂CH=CH₂ | Me | Me |
| — | 1 (cis) | —C(CH₃)₂CH=CH₂ | Me | Me |
| — | 1 (cis) | —CH₂C≡CH₂ | Me | Me |
| — | 1 (cis) | —CH₂C₆H₅ | Me | Me |
| — | 1 (cis) | —CH₂C₆H₄—Cl-2 | Me | Me |
| — | 1 (cis) | —CH₂C₆H₄—Cl-3 | Me | Me |
| — | 1 (cis) | —CH₂C₆H₄—Cl-4 | Me | Me |
| — | 1 (cis) | —CH₂C₆H₄—Me-2 | Me | Me |
| — | 1 (cis) | —CH₂C₆H₄—Me-3 | Me | Me |
| — | 1 (cis) | —CH₂C₆H₄—Me-4 | Me | Me |
| — | 1 (cis) | —CH₂C₆H₄—OMe-2 | Me | Me |
| — | 1 (cis) | —CH₂C₆H₄—OMe-3 | Me | Me |
| — | 1 (cis) | —CH₂C₆H₄—OMe-4 | Me | Me |
| — | 1 (cis) | —CH₂CH₂C₆H₅ | Me | Me |
| — | 1 (cis) | H | OMe | OMe |
| — | 1 (cis) | Li | OMe | OMe |
| — | 1 (cis) | Na | OMe | OMe |
| — | 1 (cis) | K | OMe | OMe |
| — | 1 (cis) | ½Mg | OMe | OMe |
| — | 1 (cis) | ½Ca | OMe | OMe |
| — | 1 (cis) | MeNH₃ | OMe | OMe |
| — | 1 (cis) | EtNH₃ | OMe | OMe |
| — | 1 (cis) | PrNH₃ | OMe | OMe |
| — | 1 (cis) | ⁱPrNH₃ | OMe | OMe |
| — | 1 (cis) | NH₂CONH₃ | OMe | OMe |
| — | 1 (cis) | Me | OMe | OMe |
| — | 1 (cis) | Et | OMe | OMe |
| — | 1 (cis) | ⁱPr | OMe | OMe |
| — | 1 (cis) | Pr | OMe | OMe |
| — | 1 (cis) | Bu | OMe | OMe |
| — | 1 (cis) | ⁱBu | OMe | OMe |
| — | 1 (cis) | ˢBu | OMe | OMe |
| — | 1 (cis) | ᵗBu | OMe | OMe |
| — | 1 (cis) | —CH₂OCH₃ | OMe | OMe |
| — | 1 (cis) | —CH₂CH₂OCH₃ | OMe | OMe |
| — | 1 (cis) | —CH₂SCH₃ | OMe | OMe |

TABLE 5-continued

A compound of the general formula:

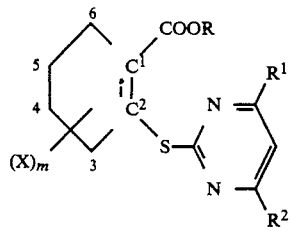

In the below-mentioned table, Me represents methyl group, Et represents ethyl group, Pr represents propyl group, $^i$Pr represents isopropyl group, Bu represents butyl group, $^i$Bu represents isobutyl group, $^s$Bu represents secondary butyl group, $^t$Bu represents tertiary butyl group, cis represents a cis-form, trans represents a trans-form, mix. represents a mixture of a cis-form and a trans-form, 1 represents a single bond and 2 represents a double bond.

| $(X)_m$ | === | R | $R^1$ | $R^2$ |
|---|---|---|---|---|
| — | 1 (cis) | —CH$_2$CH=CH$_2$ | OMe | OMe |
| — | 1 (cis) | —C(CH$_3$)$_2$CH=CH$_2$ | OMe | OMe |
| — | 1 (cis) | —CH$_2$C≡CH | OMe | OMe |
| — | 1 (cis) | —CH$_2$C$_6$H$_5$ | OMe | OMe |
| — | 1 (cis) | —CH$_2$C$_6$H$_4$—Cl-2 | OMe | OMe |
| — | 1 (cis) | —CH$_2$C$_6$H$_4$—Cl-3 | OMe | OMe |
| — | 1 (cis) | —CH$_2$C$_6$H$_4$—Cl-4 | OMe | OMe |
| — | 1 (cis) | —CH$_2$C$_6$H$_4$—Me-2 | OMe | OMe |
| — | 1 (cis) | —CH$_2$C$_6$H$_4$—Me-3 | OMe | OMe |
| — | 1 (cis) | —CH$_2$C$_6$H$_4$—Me-4 | OMe | OMe |
| — | 1 (cis) | —CH$_2$C$_6$H$_4$—OMe-2 | OMe | OMe |
| — | 1 (cis) | —CH$_2$C$_6$H$_4$—OMe-3 | OMe | OMe |
| — | 1 (cis) | —CH$_2$C$_6$H$_4$—OMe-4 | OMe | OMe |
| — | 1 (cis) | —CH$_2$CH$_2$C$_6$H$_5$ | OMe | OMe |
| — | 1 (trans) | H | Me | Me |
| — | 1 (trans) | Li | Me | Me |
| — | 1 (trans) | Na | Me | Me |
| — | 1 (trans) | K | Me | Me |
| — | 1 (trans) | ½Mg | Me | Me |
| — | 1 (trans) | ½Ca | Me | Me |
| — | 1 (trans) | MeNH$_3$ | Me | Me |
| — | 1 (trans) | EtNH$_3$ | Me | Me |
| — | 1 (trans) | PrNH$_3$ | Me | Me |
| — | 1 (trans) | $^i$PrNH$_3$ | Me | Me |
| — | 1 (trans) | NH$_2$CONH$_3$ | Me | Me |
| — | 1 (trans) | Me | Me | Me |
| — | 1 (trans) | Et | Me | Me |
| — | 1 (trans) | $^i$Pr | Me | Me |
| — | 1 (trans) | Pr | Me | Me |
| — | 1 (trans) | Bu | Me | Me |
| — | 1 (trans) | $^i$Bu | Me | Me |
| — | 1 (trans) | $^s$Bu | Me | Me |
| — | 1 (trans) | $^t$Bu | Me | Me |
| — | 1 (trans) | —CH$_2$OCH$_3$ | Me | Me |
| — | 1 (trans) | —CH$_2$CH$_2$OCH$_3$ | Me | Me |
| — | 1 (trans) | —CH$_2$SCH$_3$ | Me | Me |
| — | 1 (trans) | —CH$_2$CH=CH$_2$ | Me | Me |
| — | 1 (trans) | —C(CH$_3$)$_2$CH=CH$_2$ | Me | Me |
| — | 1 (trans) | —CH$_2$C≡CH$_2$ | Me | Me |
| — | 1 (trans) | —CH$_2$C$_6$H$_5$ | Me | Me |
| — | 1 (trans) | —CH$_2$C$_6$H$_4$—Cl-2 | Me | Me |
| — | 1 (trans) | —CH$_2$C$_6$H$_4$—Cl-3 | Me | Me |
| — | 1 (trans) | —CH$_2$C$_6$H$_4$—Cl-4 | Me | Me |
| — | 1 (trans) | —CH$_2$C$_6$H$_4$—Me-2 | Me | Me |
| — | 1 (trans) | —CH$_2$C$_6$H$_4$—Me-3 | Me | Me |
| — | 1 (trans) | —CH$_2$C$_6$H$_4$—Me-4 | Me | Me |
| — | 1 (trans) | —CH$_2$C$_6$H$_4$—OMe-2 | Me | Me |
| — | 1 (trans) | —CH$_2$C$_6$H$_4$—OMe-3 | Me | Me |
| — | 1 (trans) | —CH$_2$C$_6$H$_4$—OMe-4 | Me | Me |
| — | 1 (trans) | —CH$_2$CH$_2$C$_6$H$_5$ | Me | Me |
| — | 1 (trans) | H | OMe | OMe |
| — | 1 (trans) | Li | OMe | OMe |
| — | 1 (trans) | Na | OMe | OMe |
| — | 1 (trans) | K | OMe | OMe |
| — | 1 (trans) | ½Mg | OMe | OMe |
| — | 1 (trans) | ½Ca | OMe | OMe |
| — | 1 (trans) | MeNH$_3$ | OMe | OMe |
| — | 1 (trans) | EtNH$_3$ | OMe | OMe |

TABLE 5-continued

A compound of the general formula:

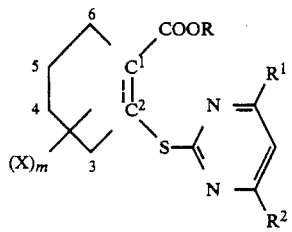

In the below-mentioned table, Me represents methyl group, Et represents ethyl group, Pr represents propyl group, $^i$Pr represents isopropyl group, Bu represents butyl group, $^i$Bu represents isobutyl group, $^s$Bu represents secondary butyl group, $^t$Bu represents tertiary butyl group, cis represents a cis-form, trans represents a trans-form, mix. represents a mixture of a cis-form and a trans-form, 1 represents a single bond and 2 represents a double bond.

| $(X)_m$ | === | R | $R^1$ | $R^2$ |
|---|---|---|---|---|
| — | 1 (trans) | PrNH$_3$ | OMe | OMe |
| — | 1 (trans) | $^i$PrNH$_3$ | OMe | OMe |
| — | 1 (trans) | NH$_2$CONH$_3$ | OMe | OMe |
| — | 1 (trans) | Me | OMe | OMe |
| — | 1 (trans) | Et | OMe | OMe |
| — | 1 (trans) | $^i$Pr | OMe | OMe |
| — | 1 (trans) | Pr | OMe | OMe |
| — | 1 (trans) | Bu | OMe | OMe |
| — | 1 (trans) | $^i$Bu | OMe | OMe |
| — | 1 (trans) | $^s$Bu | OMe | OMe |
| — | 1 (trans) | $^t$Bu | OMe | OMe |
| — | 1 (trans) | —CH$_2$OCH$_3$ | OMe | OMe |
| — | 1 (trans) | —CH$_2$CH$_2$OCH$_3$ | OMe | OMe |
| — | 1 (trans) | —CH$_2$SCH$_3$ | OMe | OMe |
| — | 1 (trans) | —CH$_2$CH=CH$_2$ | OMe | OMe |
| — | 1 (trans) | —C(CH$_3$)$_2$CH=CH$_2$ | OMe | OMe |
| — | 1 (trans) | —CH$_2$C≡CH$_2$ | OMe | OMe |
| — | 1 (trans) | —CH$_2$C$_6$H$_5$ | OMe | OMe |
| — | 1 (trans) | —CH$_2$C$_6$H$_4$—Cl-2 | OMe | OMe |
| — | 1 (trans) | —CH$_2$C$_6$H$_4$—Cl-3 | OMe | OMe |
| — | 1 (trans) | —CH$_2$C$_6$H$_4$—Cl-4 | OMe | OMe |
| — | 1 (trans) | —CH$_2$C$_6$H$_4$—Me-2 | OMe | OMe |
| — | 1 (trans) | —CH$_2$C$_6$H$_4$—Me-3 | OMe | OMe |
| — | 1 (trans) | —CH$_2$C$_6$H$_4$—Me-4 | OMe | OMe |
| — | 1 (trans) | —CH$_2$C$_6$H$_4$—OMe-2 | OMe | OMe |
| — | 1 (trans) | —CH$_2$C$_6$H$_4$—OMe-3 | OMe | OMe |
| — | 1 (trans) | —CH$_2$C$_6$H$_4$—OMe-4 | OMe | OMe |
| — | 1 (trans) | —CH$_2$CH$_2$C$_6$H$_5$ | OMe | OMe |
| — | 1 (mixt.) | H | Me | Me |
| — | 1 (mixt.) | Li | Me | Me |
| — | 1 (mixt.) | Na | Me | Me |
| — | 1 (mixt.) | K | Me | Me |
| — | 1 (mixt.) | ½Mg | Me | Me |
| — | 1 (mixt.) | ½Ca | Me | Me |
| — | 1 (mixt.) | MeNH$_3$ | Me | Me |
| — | 1 (mixt.) | EtNH$_3$ | Me | Me |
| — | 1 (mixt.) | PrNH$_3$ | Me | Me |
| — | 1 (mixt.) | $^i$PrNH$_3$ | Me | Me |
| — | 1 (mixt.) | NH$_2$CONH$_3$ | Me | Me |
| — | 1 (mixt.) | Me | Me | Me |
| — | 1 (mixt.) | Et | Me | Me |
| — | 1 (mixt.) | $^i$Pr | Me | Me |
| — | 1 (mixt.) | Pr | Me | Me |
| — | 1 (mixt.) | Bu | Me | Me |
| — | 1 (mixt.) | $^i$Bu | Me | Me |
| — | 1 (mixt.) | $^s$Bu | Me | Me |
| — | 1 (mixt.) | $^t$Bu | Me | Me |
| — | 1 (mixt.) | —CH$_2$OCH$_3$ | Me | Me |
| — | 1 (mixt.) | —CH$_2$CH$_2$OCH$_3$ | Me | Me |
| — | 1 (mixt.) | —CH$_2$SCH$_3$ | Me | Me |
| — | 1 (mixt.) | —CH$_2$CH=CH$_2$ | Me | Me |
| — | 1 (mixt.) | —C(CH$_3$)$_2$CH=CH$_2$ | Me | Me |
| — | 1 (mixt.) | —CH$_2$C≡CH$_2$ | Me | Me |
| — | 1 (mixt.) | —CH$_2$C$_6$H$_5$ | Me | Me |
| — | 1 (mixt.) | —CH$_2$C$_6$H$_4$—Cl-2 | Me | Me |
| — | 1 (mixt.) | —CH$_2$C$_6$H$_4$—Cl-3 | Me | Me |
| — | 1 (mixt.) | —CH$_2$C$_6$H$_4$—Cl-4 | Me | Me |
| — | 1 (mixt.) | —CH$_2$C$_6$H$_4$—Me-2 | Me | Me |

TABLE 5-continued

A compound of the general formula:

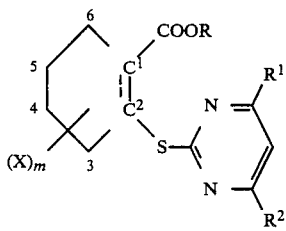

In the below-mentioned table, Me represents methyl group, Et represents ethyl group, Pr represents propyl group, $^i$Pr represents isopropyl group, Bu represents butyl group, $^i$Bu represents isobutyl group, $^s$Bu represents secondary butyl group, $^t$Bu represents tertiary butyl group, cis represents a cis-form, trans represents a trans-form, mix. represents a mixture of a cis-form and a trans-form, 1 represents a single bond and 2 represents a double bond.

| (X)$_m$ | === | R | R$^1$ | R$^2$ |
|---|---|---|---|---|
| — | 1 (mixt.) | —CH$_2$C$_6$H$_4$—Me-3 | Me | Me |
| — | 1 (mixt.) | —CH$_2$C$_6$H$_4$—Me-4 | Me | Me |
| — | 1 (mixt.) | —CH$_2$C$_6$H$_4$—OMe-2 | Me | Me |
| — | 1 (mixt.) | —CH$_2$C$_6$H$_4$—OMe-3 | Me | Me |
| — | 1 (mixt.) | —CH$_2$C$_6$H$_4$—OMe-4 | Me | Me |
| — | 1 (mixt.) | —CH$_2$CH$_2$C$_6$H$_5$ | Me | Me |
| — | 1 (mixt.) | H | OMe | OMe |
| — | 1 (mixt.) | Li | OMe | OMe |
| — | 1 (mixt.) | Na | OMe | OMe |
| — | 1 (mixt.) | K | OMe | OMe |
| — | 1 (mixt.) | ½Mg | OMe | OMe |
| — | 1 (mixt.) | ½Ca | OMe | OMe |
| — | 1 (mixt.) | MeNH$_3$ | OMe | OMe |
| — | 1 (mixt.) | EtNH$_3$ | OMe | OMe |
| — | 1 (mixt.) | PrNH$_3$ | OMe | OMe |
| — | 1 (mixt.) | $^i$PrNH$_3$ | OMe | OMe |
| — | 1 (mixt.) | NH$_2$CONH$_3$ | OMe | OMe |
| — | 1 (mixt.) | Me | OMe | OMe |
| — | 1 (mixt.) | Et | OMe | OMe |
| — | 1 (mixt.) | $^i$Pr | OMe | OMe |
| — | 1 (mixt.) | Pr | OMe | OMe |
| — | 1 (mixt.) | Bu | OMe | OMe |
| — | 1 (mixt.) | $^i$Bu | OMe | OMe |
| — | 1 (mixt.) | $^s$Bu | OMe | OMe |
| — | 1 (mixt.) | $^t$Bu | OMe | OMe |
| — | 1 (mixt.) | —CH$_2$OCH$_3$ | OMe | OMe |
| — | 1 (mixt.) | —CH$_2$CH$_2$OCH$_3$ | OMe | OMe |
| — | 1 (mixt.) | —CH$_2$SCH$_3$ | OMe | OMe |
| — | 1 (mixt.) | —CH$_2$CH=CH$_2$ | OMe | OMe |
| — | 1 (mixt.) | —C(CH$_3$)$_2$CH=CH$_2$ | OMe | OMe |
| — | 1 (mixt.) | —CH$_2$C≡CH$_2$ | OMe | OMe |
| — | 1 (mixt.) | —CH$_2$C$_6$H$_5$ | OMe | OMe |
| — | 1 (mixt.) | —CH$_2$C$_6$H$_4$—Cl-2 | OMe | OMe |
| — | 1 (mixt.) | —CH$_2$C$_6$H$_4$—Cl-3 | OMe | OMe |
| — | 1 (mixt.) | —CH$_2$C$_6$H$_4$—Cl-4 | OMe | OMe |
| — | 1 (mixt.) | —CH$_2$C$_6$H$_4$—Me-2 | OMe | OMe |
| — | 1 (mixt.) | —CH$_2$C$_6$H$_4$—Me-3 | OMe | OMe |
| — | 1 (mixt.) | —CH$_2$C$_6$H$_4$—Me-4 | OMe | OMe |
| — | 1 (mixt.) | —CH$_2$C$_6$H$_4$—OMe-2 | OMe | OMe |
| — | 1 (mixt.) | —CH$_2$C$_6$H$_4$—OMe-3 | OMe | OMe |
| — | 1 (mixt.) | —CH$_2$C$_6$H$_4$—OMe-4 | OMe | OMe |
| — | 1 (mixt.) | —CH$_2$CH$_2$C$_6$H$_5$ | OMe | OMe |
| — | 2 (—) | H | Me | Me |
| — | 2 (—) | Li | Me | Me |
| — | 2 (—) | Na | Me | Me |
| — | 2 (—) | K | Me | Me |
| — | 2 (—) | ½Mg | Me | Me |
| — | 2 (—) | ½Ca | Me | Me |
| — | 2 (—) | MeNH$_3$ | Me | Me |
| — | 2 (—) | EtNH$_3$ | Me | Me |
| — | 2 (—) | PrNH$_3$ | Me | Me |
| — | 2 (—) | $^i$PrNH$_3$ | Me | Me |
| — | 2 (—) | NH$_2$CONH$_3$ | Me | Me |
| — | 2 (—) | Me | Me | Me |
| — | 2 (—) | Et | Me | Me |
| — | 2 (—) | $^i$Pr | Me | Me |
| — | 2 (—) | Pr | Me | Me |
| — | 2 (—) | Bu | Me | Me |
| — | 2 (—) | $^i$Bu | Me | Me |
| — | 2 (—) | $^s$Bu | Me | Me |
| — | 2 (—) | $^t$Bu | Me | Me |
| — | 2 (—) | —CH$_2$OCH$_3$ | Me | Me |
| — | 2 (—) | —CH$_2$CH$_2$OCH$_3$ | Me | Me |
| — | 2 (—) | —CH$_2$SCH$_3$ | Me | Me |
| — | 2 (—) | —CH$_2$CH=CH$_2$ | Me | Me |
| — | 2 (—) | —C(CH$_3$)$_2$CH=CH$_2$ | Me | Me |
| — | 2 (—) | —CH$_2$C≡CH$_2$ | Me | Me |
| — | 2 (—) | —CH$_2$C$_6$H$_5$ | Me | Me |
| — | 2 (—) | —CH$_2$C$_6$H$_4$—Cl-2 | Me | Me |
| — | 2 (—) | —CH$_2$C$_6$H$_4$—Cl-3 | Me | Me |
| — | 2 (—) | —CH$_2$C$_6$H$_4$—Cl-4 | Me | Me |
| — | 2 (—) | —CH$_2$C$_6$H$_4$—Me-2 | Me | Me |
| — | 2 (—) | —CH$_2$C$_6$H$_4$—Me-3 | Me | Me |
| — | 2 (—) | —CH$_2$C$_6$H$_4$—Me-4 | Me | Me |
| — | 2 (—) | —CH$_2$C$_6$H$_4$—OMe-2 | Me | Me |
| — | 2 (—) | —CH$_2$C$_6$H$_4$—OMe-3 | Me | Me |
| — | 2 (—) | —CH$_2$C$_6$H$_4$—OMe-4 | Me | Me |
| — | 2 (—) | —CH$_2$CH$_2$C$_6$H$_5$ | Me | Me |
| — | 2 (—) | H | OMe | OMe |
| — | 2 (—) | Li | OMe | OMe |
| — | 2 (—) | Na | OMe | OMe |
| — | 2 (—) | K | OMe | OMe |
| — | 2 (—) | ½Mg | OMe | OMe |
| — | 2 (—) | ½Ca | OMe | OMe |
| — | 2 (—) | MeNH$_3$ | OMe | OMe |
| — | 2 (—) | EtNH$_3$ | OMe | OMe |
| — | 2 (—) | PrNH$_3$ | OMe | OMe |
| — | 2 (—) | $^i$PrNH$_3$ | OMe | OMe |
| — | 2 (—) | NH$_2$CONH$_3$ | OMe | OMe |
| — | 2 (—) | Me | OMe | OMe |
| — | 2 (—) | Et | OMe | OMe |
| — | 2 (—) | $^i$Pr | OMe | OMe |
| — | 2 (—) | Pr | OMe | OMe |
| — | 2 (—) | Bu | OMe | OMe |
| — | 2 (—) | $^i$Bu | OMe | OMe |
| — | 2 (—) | $^s$Bu | OMe | OMe |
| — | 2 (—) | $^t$Bu | OMe | OMe |
| — | 2 (—) | —CH$_2$OCH$_3$ | OMe | OMe |
| — | 2 (—) | —CH$_2$CH$_2$OCH$_3$ | OMe | OMe |
| — | 2 (—) | —CH$_2$SCH$_3$ | OMe | OMe |
| — | 2 (—) | —CH$_2$CH=CH$_2$ | OMe | OMe |
| — | 2 (—) | —C(CH$_3$)$_2$CH=CH$_2$ | OMe | OMe |
| — | 2 (—) | —CH$_2$C≡CH$_2$ | OMe | OMe |
| — | 2 (—) | —CH$_2$C$_6$H$_5$ | OMe | OMe |
| — | 2 (—) | —CH$_2$C$_6$H$_4$—Cl-2 | OMe | OMe |
| — | 2 (—) | —CH$_2$C$_6$H$_4$—Cl-3 | OMe | OMe |
| — | 2 (—) | —CH$_2$C$_6$H$_4$—Cl-4 | OMe | OMe |
| — | 2 (—) | —CH$_2$C$_6$H$_4$—Me-2 | OMe | OMe |
| — | 2 (—) | —CH$_2$C$_6$H$_4$—Me-3 | OMe | OMe |
| — | 2 (—) | —CH$_2$C$_6$H$_4$—Me-4 | OMe | OMe |
| — | 2 (—) | —CH$_2$C$_6$H$_4$—OMe-2 | OMe | OMe |
| — | 2 (—) | —CH$_2$C$_6$H$_4$—OMe-3 | OMe | OMe |
| — | 2 (—) | —CH$_2$C$_6$H$_4$—OMe-4 | OMe | OMe |
| — | 2 (—) | —CH$_2$CH$_2$C$_6$H$_5$ | OMe | OMe |

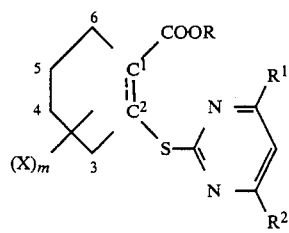

| Compound No. of the Invention | Formula | Physical data |
|---|---|---|
| 1 | [cyclopentene with COOCH₃; O-C(=N-)(-N=) linked to CH=C(OCH₃)-CH=C(OCH₃)] | Liquid $n_D^{20}$ 1.5303 |
| 2 | [cyclopentane with COOCH₃ and O-C(=N-)(-N=)-CH=C(OCH₃)-N=C(OCH₃)] (trans-form) | Liquid $n_D^{20}$ 1.5090 |
| 3 | [cyclopentane with COOCH₃ and O-linked pyrimidine-type group] (cis-form) | Liquid $n_D^{20}$ 1.5081 |
| 4 | [cyclopentane with CH₃, COOCH₃, and O-linked group with two OCH₃] | Liquid $n_D^{20}$ 1.5078 |
| 5 | [cyclohexene with COOCH₂CH₃ and O-linked group with two OCH₃] | Liquid |
| 6 | [cyclohexane with COOCH₂CH₃ and O-linked group with two OCH₃] (mixture of cis-form and trans-form) | Liquid |
| 7 | [cyclohexane with COOCH₃ and O-linked group with two OCH₃] (cis-form) | Liquid $n_D^{20}$ 1.5104 |

-continued

| Compound No. of the Invention | Formula | Physical data |
|---|---|---|
| 8 | (cis-form) cyclohexane with COOCH$_2$CH$_3$ and O-C(=N-)(N=) group with two OCH$_3$ substituents | Liquid $n_D^{19}$ 1.5052 |
| 9 | (trans-form) cyclohexane with COOCH$_3$ and O-C(=N-)(N=) group with two OCH$_3$ substituents | Liquid $n_D^{19.5}$ 1.5060 |
| 10 | (trans-form) cyclohexane with COOCH$_2$CH$_3$ and O-C(=N-)(N=) group with two OCH$_3$ substituents | Liquid $n_D^{19}$ 1.5035 |
| 11 | (cis(+)-form) cyclohexane with COOCH$_3$ and O-C(=N-)(N=) group with two OCH$_3$ substituents | Liquid $[\alpha]_D^{23.3}$ +8.34 (C = 1.030, CHCl$_3$) |
| 12 | (cis(−)-form) cyclohexane with COOCH$_3$ and O-C(=N-)(N=) group with two OCH$_3$ substituents | Liquid $[\alpha]_D^{23.3}$ −7.72 (C = 1.165, CHCl$_3$) |
| 13 | (trans(+)-form) cyclohexane with COOCH$_2$CH$_3$ and O-C(=N-)(N=) group with two OCH$_3$ substituents | Liquid $[\alpha]_D^{23.4}$ +17.94 (C = 1.287, CHCl$_3$) |
| 14 | (trans(−)-form) cyclohexane with COOCH$_2$CH$_3$ and O-C(=N-)(N=) group with two OCH$_3$ substituents | Liquid $[\alpha]_D^{23.4}$ −22.91 (C = 1.008, CHCl$_3$) |

-continued

| Compound No. of the Invention | Formula | Physical data |
|---|---|---|
| 15 | [cyclohexenyl-COOCH₃, S-C(=N-CH=C(OCH₃)-CH=N-OCH₃... pyrimidine with OCH₃ groups)] | Semi-crystal |
| 16 | [cyclohexyl-COOCH₂CH₃, S-pyrimidine(OCH₃)₂] | Liquid $n_D^{21.5}$ 1.5443 |
| 17 | [gem-dimethyl cyclohexyl with COOCH₃ and O-pyrimidine(OCH₃)₂] (cis-form) | Crystal m.p. 120.0~123.0° C. |
| 18 | [gem-dimethyl cyclohexyl with COOCH₃ and O-pyrimidine(OCH₃)₂] (trans-form) | Crystal m.p. 82.0~84.0° C. |
| 19 | [cyclohexyl with two COOCH₂CH₃ and O-pyrimidine(OCH₃)₂] | Liquid $n_D^{20}$ 1.4955 |
| 20 | [cyclohexyl with two COOCH₃ and O-pyrimidine(OCH₃)₂] | $n_D^{21}$ 1.4928 |
| 21 | [methyl-cyclohexyl with COOCH₃ and O-pyrimidine(OCH₃)₂] | Liquid $n_D^{21}$ 1.5048 |

-continued

| Compound No. of the Invention | Formula | Physical data |
|---|---|---|
| 22 | (cycloheptene with COOCH₃ and O-C(=N-CH(OCH₃)=CH-C(OCH₃)=N) group) | Liquid $n_D^{20}$ 1.5115 |
| 23 | (cycloheptane with COOCH₃ and O-C(=N-CH(OCH₃)=CH-C(OCH₃)=N) group) | Liquid $n_D^{20}$ 1.5128 |

TABLE 7

| No. | Application rate g/a | Echinochoa crus galli | Digitaria adscendens | Cyperus microiria | Solanum nigrum | Galinsoga ciliate | Rorippa indica | Cotton |
|---|---|---|---|---|---|---|---|---|
| 1 | 6.3 | 4 | 4 | 4 | 4 | 3 | 5 | 0 |
| 2 | 1.6 | 5 | 5 | 5 | 5 | 4 | 5 | 0 |
|   | 3.2 | 5 | 5 | 5 | 5 | 5 | 5 | 0 |
|   | 6.3 | 5 | 5 | 5 | 5 | 5 | 5 | 1 |
| 3 | 6.3 | 4 | 4 | 5 | 4 | 5 | 5 | 0 |
| 4 | 25  | 4 | 4 | 5 | 5 | 3 | 5 | 0 |
| 5 | 1.6 | 4 | 4 | 5 | 4 | 3 | 4 | 0 |
|   | 3.2 | 5 | 5 | 5 | 5 | 4 | 5 | 0 |
|   | 6.3 | 5 | 5 | 5 | 5 | 5 | 5 | 0 |
| 6 | 1.6 | 4 | 4 | 5 | 5 | 3 | 5 | 0 |
|   | 3.2 | 5 | 5 | 5 | 5 | 4 | 5 | 0 |
|   | 6.3 | 5 | 5 | 5 | 5 | 5 | 5 | 1 |
| 7 | 1.6 | 4 | 4 | 5 | 5 | 3 | 5 | — |
|   | 3.2 | 5 | 5 | 5 | 5 | 4 | 5 | — |
|   | 6.3 | 5 | 5 | 5 | 5 | 5 | 5 | — |
| 8 | 6.3 | 5 | 5 | 5 | 5 | 5 | 5 | 1 |
| 9 | 1.6 | 5 | 5 | 5 | 5 | 5 | 5 | 0 |
|   | 3.2 | 5 | 5 | 5 | 5 | 5 | 5 | 1 |
|   | 6.3 | 5 | 5 | 5 | 5 | 5 | 5 | 2 |
| 10 | 1.6 | 5 | 5 | 5 | 5 | 5 | 5 | 0 |
|   | 3.2 | 5 | 5 | 5 | 5 | 5 | 5 | 1 |
|   | 6.3 | 5 | 5 | 5 | 5 | 5 | 5 | 2 |
| 11 | 6.3 | 5 | 5 | 5 | 5 | 4 | 5 | 0 |
| 12 | 6.3 | 5 | 5 | 5 | 5 | 4 | 5 | 0 |
| 13 | 1.6 | 5 | 5 | 5 | 5 | 5 | 5 | 0 |
| 14 | 6.3 | 5 | 5 | 5 | 5 | 5 | 5 | 0 |
| 16 | 6.3 | 4 | 4 | 5 | 5 | 4 | 5 | 0 |
| 18 | 25 | 4 | 4 | 5 | 4 | 3 | 5 | 0 |
| 19 | 25 | 5 | 5 | 5 | 5 | 4 | 5 | 0 |
| 20 | 25 | 4 | 4 | 5 | 4 | 3 | 5 | 0 |
| 22 | 25 | 4 | 4 | 4 | 5 | 3 | 5 | 0 |
| 23 | 6.3 | 5 | 5 | 5 | 5 | 4 | 5 | 0 |

TABLE 8

| No. | Application rate g/a | Echinochoa crus galli | Digitaria adscendens | Cyperus microiria | Solanum nigrum | Galinsoga ciliate | Rorippa indica | Cotton |
|---|---|---|---|---|---|---|---|---|
| 1 | 6.3 | 3 | 4 | 5 | 5 | 2 | 5 | 1 |
| 2 | 6.3 | 4 | 4 | 5 | 5 | 3 | 5 | 0 |
| 3 | 6.3 | 3 | 3 | 4 | 5 | 2 | 5 | 0 |
| 4 | 25  | 3 | 4 | 5 | 5 | 2 | 5 | 0 |
| 5 | 6.3 | 4 | 4 | 4 | 5 | 4 | 5 | 0 |
| 6 | 1.6 | 4 | 4 | 5 | 5 | 2 | 5 | 0 |
|   | 3.2 | 5 | 5 | 5 | 5 | 3 | 5 | 1 |
|   | 6.3 | 5 | 5 | 5 | 5 | 4 | 5 | 2 |
| 7 | 1.6 | 5 | 4 | 5 | 5 | 3 | 5 | 0 |
|   | 3.2 | 5 | 5 | 5 | 5 | 4 | 5 | 1 |
|   | 6.3 | 5 | 5 | 5 | 5 | 5 | 5 | 2 |
| 8 | 6.3 | 5 | 4 | 5 | 5 | 4 | 5 | 0 |
| 9 | 1.6 | 5 | 5 | 5 | 5 | 4 | 5 | 1 |
|   | 3.2 | 5 | 5 | 5 | 5 | 5 | 5 | 2 |
|   | 6.3 | 5 | 5 | 5 | 5 | 5 | 5 | 3 |
| 10 | 1.6 | 5 | 5 | 5 | 5 | 4 | 5 | 1 |

TABLE 8-continued

| No. | Application rate g/a | Echinochoa crus galli | Digitaria adscendens | Cyperus microiria | Solanum nigrum | Galinsoga ciliate | Rorippa indica | Cotton |
|---|---|---|---|---|---|---|---|---|
|   | 3.2 | 5 | 5 | 5 | 5 | 5 | 5 | 2 |
|   | 6.3 | 5 | 5 | 5 | 5 | 5 | 5 | 3 |
| 11 | 6.3 | 5 | 5 | 5 | 5 | 4 | 5 | 0 |
| 12 | 6.3 | 5 | 5 | 5 | 5 | 4 | 5 | 0 |
| 13 | 1.6 | 5 | 5 | 5 | 5 | 5 | 5 | 0 |
| 14 | 6.3 | 5 | 5 | 5 | 5 | 5 | 5 | 0 |
| 16 | 6.3 | 4 | 3 | 5 | 5 | 3 | 4 | 0 |
| 18 | 25 | 3 | 4 | 4 | 5 | 2 | 4 | 0 |
| 19 | 25 | 5 | 5 | 5 | 5 | 5 | 5 | 0 |
| 20 | 25 | 3 | 4 | 5 | 5 | 3 | 4 | 0 |
| 22 | 25 | 4 | 4 | 5 | 5 | 3 | 4 | 0 |
| 23 | 6.3 | 5 | 4 | 5 | 5 | 3 | 5 | 0 |

What is claimed is:

1. A pyrimidine compound or an optical isomer thereof a formula (I):

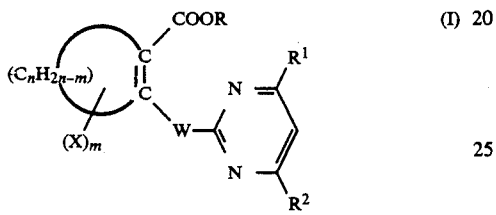

where

W represents an oxygen atom or a sulfur atom;

X represents a lower alkyl group or a lower alkoxycarbonyl group;

R represents a hydrogen atom; a lower alkyl group optionally substituted by at least one substituent selected from a halogen atom, a lower alkoxy group or a lower alkylthio group, or a phenyl group optionally substituted by a halogen atom, a lower alkyl group, a lower alkoxy group or a lower alkylthio group; a lower alkenyl group optionally substituted by at least one substituent selected from a halogen atom, a lower alkoxy group or a lower alkylthio group, or a phenyl group optionally substituted by a halogen atom, a lower alkyl group, a lower alkoxy group or a lower alkylthio group; a lower alkynyl group optionally substituted by at least one substituent selected from a halogen atom, a lower alkoxy group or a lower alkylthio group, or a phenyl group optionally substituted by a halogen atom, a lower alkyl group, a lower alkoxy group or a lower alkylthio group; an alkali metal, an alkaline earth metal or an optionally substituted ammonium cation;

$R^1$ and $R^2$ may be the same or different and each represents a halogen atom; a lower alkyl group optionally substituted by at least one substituent selected from a halogen atom, a lower alkoxy group or a lower alkylthio group; or a lower alkoxy group optionally substituted by at least one substituent selected from a halogen atom, a lower alkoxy group or a lower alkylthio group;

n represents an integer of from 3 to 5;

m represents an integer of from 0 to 2; and

═represents a single bond or a double bond.

2. A herbicidal composition comprising a herbicidally effective amount of a compound as claimed in claim 1, and a carrier.

* * * * *